US011912693B2

(12) United States Patent
Pitis et al.

(10) Patent No.: US 11,912,693 B2
(45) Date of Patent: Feb. 27, 2024

(54) COMPOUNDS FOR MODULATING S1P1 ACTIVITY AND METHODS OF USING THE SAME

(71) Applicant: TREVENA, INC., Chesterbrook, PA (US)

(72) Inventors: Philip Michael Pitis, Chesterbrook, PA (US); Robert Eugene Boyd, Chesterbrook, PA (US); Tamara Ann Miskowski Daubert, Chesterbrook, PA (US); Michael John Hawkins, Chesterbrook, PA (US); Guodong Liu, Chesterbrook, PA (US); Aimee Crombie Speerschneider, Chesterbrook, PA (US)

(73) Assignee: TREVENA, INC., Chesterbrook, PA (US)

( * ) Notice: Subject to any disclaimer, the term of this patent is extended or adjusted under 35 U.S.C. 154(b) by 90 days.

(21) Appl. No.: 16/613,152

(22) PCT Filed: Jun. 12, 2018

(86) PCT No.: PCT/US2018/036989
§ 371 (c)(1),
(2) Date: Nov. 13, 2019

(87) PCT Pub. No.: WO2018/231745
PCT Pub. Date: Dec. 20, 2018

(65) Prior Publication Data
US 2021/0188826 A1 Jun. 24, 2021

Related U.S. Application Data

(60) Provisional application No. 62/519,575, filed on Jun. 14, 2017.

(51) Int. Cl.
*A61P 25/02* (2006.01)
*A61P 35/00* (2006.01)
*C07D 413/14* (2006.01)
*C07D 413/04* (2006.01)
*C07D 405/14* (2006.01)

(52) U.S. Cl.
CPC ............ *C07D 413/04* (2013.01); *A61P 25/02* (2018.01); *A61P 35/00* (2018.01); *C07D 405/14* (2013.01); *C07D 413/14* (2013.01)

(58) Field of Classification Search
CPC ... C07D 413/04; C07D 413/14; C07D 405/14
See application file for complete search history.

(56) References Cited

U.S. PATENT DOCUMENTS

| | | | |
|---|---|---|---|
| 2011/0118231 A1* | 5/2011 | Akritopoulou-Zanze | C07D 487/04 514/211.1 |
| 2011/0212940 A1 | 9/2011 | Burli et al. | |
| 2012/0115849 A1 | 5/2012 | Demopulos et al. | |
| 2012/0129828 A1 | 5/2012 | Cee et al. | |
| 2013/0237566 A1 | 9/2013 | Cherney et al. | |
| 2014/0066427 A1 | 3/2014 | Gill et al. | |
| 2015/0359755 A1 | 12/2015 | Guy et al. | |
| 2016/0235718 A1 | 8/2016 | Baraban | |
| 2021/0147402 A1 | 5/2021 | Heasley et al. | |
| 2023/0114241 A1 | 4/2023 | Demitrack et al. | |
| 2023/0234946 A1 | 7/2023 | Pitis et al. | |

FOREIGN PATENT DOCUMENTS

| | | | |
|---|---|---|---|
| EP | 1247810 A1 | 10/2002 | |
| EP | 2003132 A1 | 12/2008 | |
| EP | 2671881 A1 | 12/2013 | |
| EP | 2853532 A1 | 4/2015 | |
| JP | 2008515985 A | 5/2008 | |
| JP | 2009520751 A | 5/2009 | |
| JP | 2011522818 A | 8/2011 | |
| JP | 2011530485 A | 12/2011 | |
| JP | 2019507185 A | 3/2019 | |
| TW | 201004944 A | 2/2010 | |
| WO | 20000003681 A2 | 1/2000 | |
| WO | 2004018462 A1 | 3/2004 | |
| WO | WO 2004/022554 | * | 3/2004 |
| WO | 2004026863 A1 | 4/2004 | |
| WO | 2006044456 A1 | 4/2006 | |
| WO | 2007071598 A1 | 6/2007 | |
| WO | 2007116866 A1 | 10/2007 | |
| WO | WO 2009133970 | * | 11/2009 |
| WO | 2009146343 A1 | 12/2009 | |
| WO | 2009148452 A1 | 12/2009 | |
| WO | 2011059619 A1 | 5/2011 | |
| WO | 2011126960 A1 | 10/2011 | |
| WO | 2012154760 A1 | 11/2012 | |
| WO | 2013053051 A1 | 4/2013 | |
| WO | 2013181931 A1 | 12/2013 | |
| WO | 2014029684 A1 | 2/2014 | |

(Continued)

OTHER PUBLICATIONS

Maha. Tetrahedron, 2016, 72, 2874-2879 (Year: 2016).*
Pubchem CID 43591546 Create Date: Jul. 21, 2009 Date Accessed; Oct. 2, 2018 p. 3.
International Preliminary Report on Patentability for International PCT Application No. PCT/US2018/036989 dated Dec. 17, 2019.
International Preliminary Report on Patentability for International PCT Application No. PCT/US2020/049147 dated Mar. 8, 2022.
International Preliminary Report on Patentability for International PCT Application No. PCT/US2020/060822 dated May 17, 2022.
Ex Parte Quayle, dated May 10, 2023, in U.S. Appl. No. 17/099,895.
Notice of Allowance, dated Jul. 27, 2023, issued in U.S. Appl. No. 17/099,895.

(Continued)

*Primary Examiner* — Noble E Jarrell

(74) *Attorney, Agent, or Firm* — Goodwin Procter LLP

(57) ABSTRACT

The present embodiments are directed, in part, to compounds, or pharmaceutically acceptable salts thereof, or pharmaceutical compositions thereof for modulating the activity of $S_1P_1$ receptor and methods of using the same.

8 Claims, No Drawings

(56) References Cited

FOREIGN PATENT DOCUMENTS

| WO | 2016028959 A1 | 2/2016 |
| WO | 2016209809 A1 | 12/2016 |
| WO | 2017136309 A1 | 8/2017 |
| WO | 2018231745 A1 | 12/2018 |
| WO | 2021046183 A1 | 3/2021 |
| WO | 2021101854 A1 | 5/2021 |

OTHER PUBLICATIONS

Ashok et al., "Synthesis of Novel 2,4,6-Trisubstituted Pyrimidine Derivatives and Their In Vitro Antimicrobial Activity," Russian Journal of General Chemistry, 2016, vol. 86, No. 6, pp. 1396-1404.

Birch et al., "Novel 7-methoxy-6-oxazol-5-yl-2,3-dihydro-1H-quinazolin-4-ones as IMPDH Inhibitors," Bioorganic & Medicinal Chemistry Letters, 2005, vol. 15, pp. 5335-5339.

Extended European Search Report for European Patent Application No. 18818411.3 dated May 11, 2021.

Hemalatha et al., "Binding Mode of Dihydroquinazolinones with Lysozyme and its Antifungal Activity Against Apergillus Species," Journal of Photochemistry & Photobiology, B: Biology, 2016, vol. 161, pp. 71-79.

International Search Report and Written Opinion for International PCT Application No. PCT/US2018/036989 dated Oct. 25, 2018.

International Search Report and Written Opinion dated Feb. 2, 2021 for PCT Application No. PCT/US2020/49147.

International Search Report and Written Opinion dated Mar. 17, 2021 for PCT Application No. PCT /US2020/60822.

Non-Final Office Action, dated Nov. 25, 2022, issued in U.S. Appl. No. 17/099,895.

PubChem CID 117960303 Create Date: Feb. 23, 2016 Date Accessed; Apr. 22, 2023 p. 2 formula.

Xu et al., "Discovery and Modification of In Vivo Active Nrf2 Activators with 1,2,4-Oxadiazole Core: Hits Identification and Structure-Activity Relationship Study," Journal of Medicinal Chemistry, 2015, vol. 58, pp. 5419-5436.

\* cited by examiner

COMPOUNDS FOR MODULATING S1P1 ACTIVITY AND METHODS OF USING THE SAME

CROSS-REFERENCE TO RELATED APPLICATIONS

This application is a National Phase Entry of International Patent Application No. PCT/US2018/036989 filed Jun. 12, 2018, which claims priority to U.S. Provisional Application No. 62/519,575, filed Jun. 14, 2017, each of which is hereby incorporated by reference in its entirety.

FIELD

Embodiments disclosed herein are directed, in part, to compounds, or pharmaceutically acceptable salts thereof, for modulating S1P1 receptor activity and/or methods for treating and/or preventing pain, such as neuropathic pain, chemotherapy induced neuropathic pain (CINP), chemotherapy induced peripheral neuropathy (CIPN), or treating cancer or inhibiting tumor growth, and the like as described herein.

BACKGROUND

Pain is still a prevalent and pervasive problem, especially neuropathic pain, which has few good treatments or preventive therapeutics. This is especially true in conditions such chemotherapy induced neuropathic pain (CINP) and chemotherapy induced peripheral neuropathy (CIPN). Thus, there is a need for new compounds and compositions for treating and/or preventing such conditions.

The compounds and compositions described herein fulfill these needs as well as others.

SUMMARY OF EMBODIMENTS

In some embodiments, compounds, or pharmaceutically acceptable salts thereof, are provided that, in part, modulate the activity of the S1P1 receptor. The compounds can have, for example, a formula as described herein. In some embodiments, the compound is selected form a compound described herein. In some embodiments, methods of treating the conditions described herein are provided. In some embodiments, the condition is CIPN, CINP, pain, neuropathy, and the like. In some embodiments, the condition is cancer and the like.

In some embodiments, the compound is a compound having a formula of Formula I or Formula II:

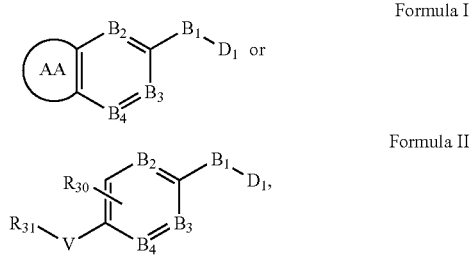

Formula I

Formula II or a pharmaceutically acceptable salt thereof, wherein AA, $B_1$, $B_2$, $B_3$, $B_4$, $D_1$, V, $R_{30}$, and $R_{31}$ are as provided for herein and, for example, can be selected from the respective groups of chemical moieties described herein. Also provided are processes for preparing these compounds.

In some embodiments, also provided are pharmaceutical compositions comprising one or more compounds as described herein, which can also comprise a pharmaceutically acceptable carrier.

In some embodiments, the compounds described herein can be provided in any form, such as a solid or solution (e.g., aqueous solution), such as is described herein. The compounds described herein, for example, can be obtained and employed in lyophilized form alone or with suitable additives.

Also provided are methods for treating and/or preventing pain such as neuropathic pain, chemotherapy induced neuropathic pain (CINP), chemotherapy induced peripheral neuropathy (CIPN), or treating cancer or inhibiting tumor growth, and the like as described herein. In some embodiments, the methods comprise administering a one or more compounds described herein to a subject or subject.

DESCRIPTION OF EMBODIMENTS

Unless defined otherwise, all technical and scientific terms have the same meaning as is commonly understood by one of ordinary skill in the art to which the embodiments disclosed belongs.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by +10% and remain within the scope of the disclosed embodiments.

As used herein, the term "acylamino" means an amino group substituted by an acyl group (e.g., —O—C(=O)—H or —O—C(=O)-alkyl). An example of an acylamino is —NHC(=O)H or —NHC(=O)CH$_3$. The term "lower acylamino" refers to an amino group substituted by a lower acyl group (e.g., —O—C(=O)—H or —O—C(=O)—C$_{1-6}$alkyl). An example of a lower acylamino is —NHC(=O)H or —NHC(=O)CH$_3$.

As used herein, the term "alkenyl" means a straight or branched alkyl group having one or more double carbon-carbon bonds and 2-20 carbon atoms, including, but not limited to, ethenyl, 1-propenyl, 2-propenyl, 2-methyl-1-propenyl, 1-butenyl, 2-butenyl, and the like. In some embodiments, the alkenyl chain is from 2 to 10 carbon atoms in length, from 2 to 8 carbon atoms in length, from 2 to 6 carbon atoms in length, or from 2 to 4 carbon atoms in length.

The terms "alkoxy", "phenyloxy", "benzoxy" and "pyrimidinyloxy" refer to an alkyl group, phenyl group, benzyl group, or pyrimidinyl group, respectively, each optionally substituted, that is bonded through an oxygen atom. For example, the term "alkoxy" means a straight or branched —O— alkyl group of 1 to 20 carbon atoms, including, but not limited to, methoxy, ethoxy, n-propoxy, isopropoxy, t-butoxy, and the like. In some embodiments, the alkoxy chain is from 1 to 10 carbon atoms in length, from 1 to 8 carbon atoms in length, from 1 to 6 carbon atoms in length, from 1 to 4 carbon atoms in length, from 2 to 10 carbon atoms in length, from 2 to 8 carbon atoms in length, from 2 to 6 carbon atoms in length, or from 2 to 4 carbon atoms in length.

As used herein, the term "alkyl" means a saturated hydrocarbon group which is straight-chained or branched. An alkyl group can contain from 1 to 20, from 2 to 20, from 1 to 10, from 2 to 10, from 1 to 8, from 2 to 8, from 1 to 6, from 2 to 6, from 1 to 4, from 2 to 4, from 1 to 3, or 2 or 3 carbon atoms. Examples of alkyl groups include, but are not limited to, methyl (Me), ethyl (Et), propyl (e.g., n-propyl and isopropyl), butyl (e.g., n-butyl, t-butyl, isobutyl), pentyl (e.g., n-pentyl, isopentyl, neopentyl), hexyl, isohexyl, heptyl, 4,4-dimethylpentyl, octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

As used herein, the term "allylamino" means an amino group substituted by an alkyl group having from 1 to 6 carbon atoms. An example of an alkylamino is —NHCH$_2$CH$_3$.

As used herein, the term "alkylene" or "alkylenyl" means a divalent alkyl linking group. An example of an alkylene (or alkylenyl) is methylene or methylenyl (—CH$_2$—).

As used herein, the term "alkylthio" means an —S-alkyl group having from 1 to 6 carbon atoms. An example of an alkylthio group is —SCH$_2$CH$_3$.

As used herein, the term "alkynyl" means a straight or branched alkyl group having one or more triple carbon-carbon bonds and 2-20 carbon atoms, including, but not limited to, acetylene, 1-propylene, 2-propylene, and the like. In some embodiments, the alkynyl chain is 2 to 10 carbon atoms in length, from 2 to 8 carbon atoms in length, from 2 to 6 carbon atoms in length, or from 2 to 4 carbon atoms in length.

As used herein, the term "amidino" means —C(=NH)NH$_2$.

As used herein, the term "amino" means —NH$_2$.

As used herein, the term "aminoalkoxy" means an alkoxy group substituted by an amino group. An example of an aminoalkoxy is —OCH$_2$CH$_2$NH$_2$.

As used herein, the term "aminoalkyl" means an alkyl group substituted by an amino group.

An example of an aminoalkyl is —CH$_2$CH$_2$NH$_2$.

As used herein, the term "aminosulfonyl" means —S(=O)$_2$NH$_2$.

As used herein, the term "aminoalkylthio" means an alkylthio group substituted by an amino group. An example of an aminoalkylthio is —SCH$_2$CH$_2$NH$_2$.

As used herein, the term "amphiphilic" means a three-dimensional structure having discrete hydrophobic and hydrophilic regions. An amphiphilic compound suitably has the presence of both hydrophobic and hydrophilic elements.

As used herein, the term "animal" includes, but is not limited to, humans and non-human vertebrates such as wild, domestic, and farm animals.

As used herein, the term "antagonize" or "antagonizing" means reducing or completely eliminating an effect, such as an activity of the S$_1$P$_1$ receptor.

As used herein, the phrase "anti-receptor effective amount" of a compound can be measured by the anti-receptor effectiveness of the compound. In some embodiments, an anti-receptor effective amount inhibits an activity of the receptor by at least 10%, by at least 20%, by at least 30%, by at least 40%, by at least 50%, by at least 60%, by at least 70%, by at least 80%, by at least 90%, or by at least 95%. In some embodiments, an "anti-receptor effective amount" is also a "therapeutically effective amount" whereby the compound reduces or eliminates at least one effect of a S$_1$P$_1$ receptor.

In some embodiments, the effect is the beta-arrestin effect. In some embodiments, the effect is the G-protein mediated effect.

As used herein, the term "aryl" means a monocyclic, bicyclic, or polycyclic (e.g., having 2, 3 or 4 fused rings) aromatic hydrocarbons. In some embodiments, aryl groups have from 6 to 20 carbon atoms or from 6 to 10 carbon atoms. Examples of aryl groups include, but are not limited to, phenyl, naphthyl, anthracenyl, phenanthrenyl, indanyl, indenyl, tetrahydronaphthyl, and the like.

Examples of aryl groups include, but are not limited to:

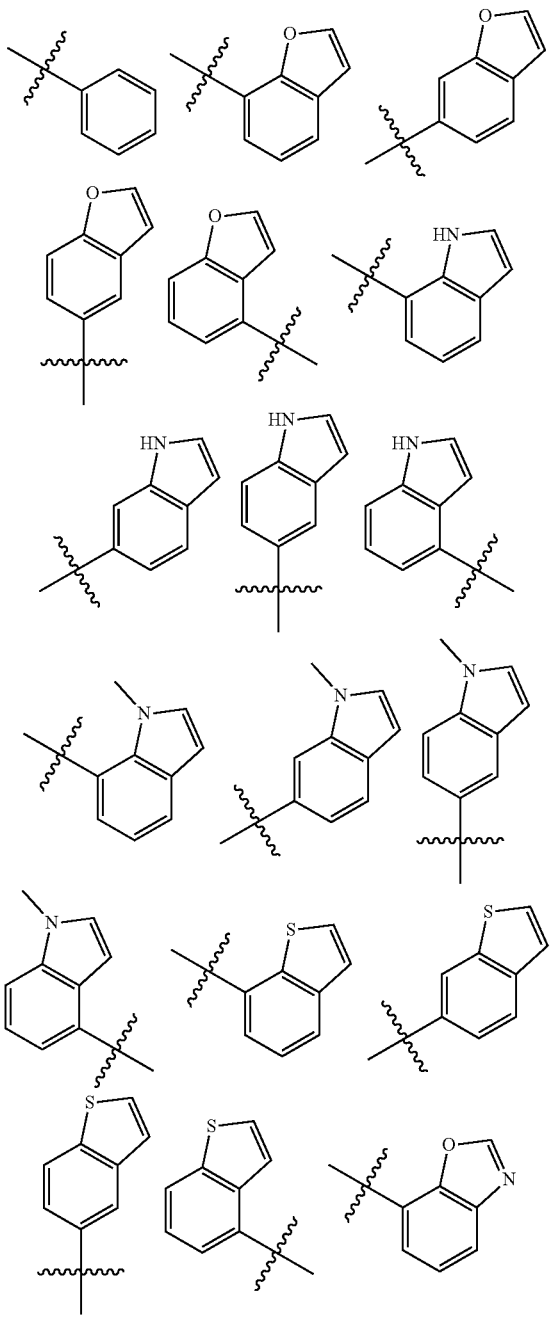

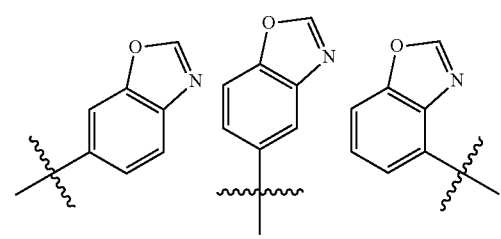
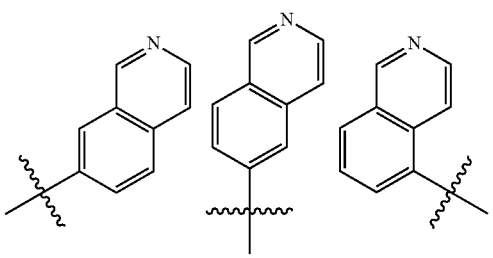
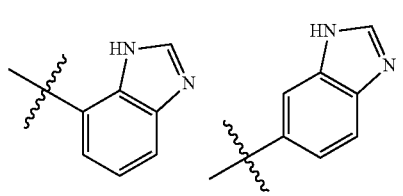
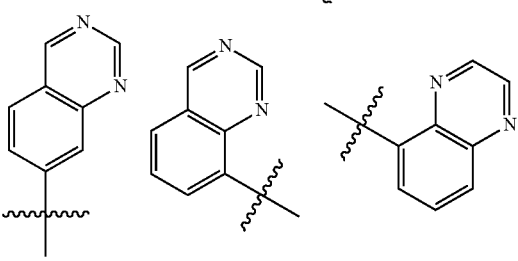
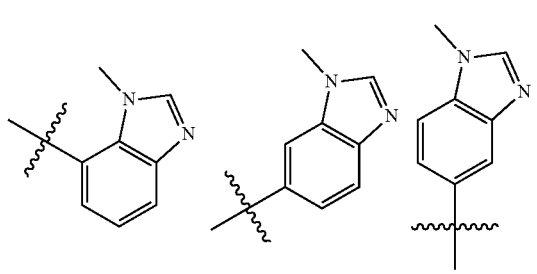
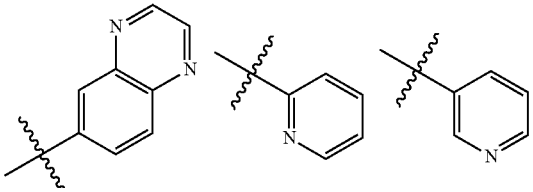
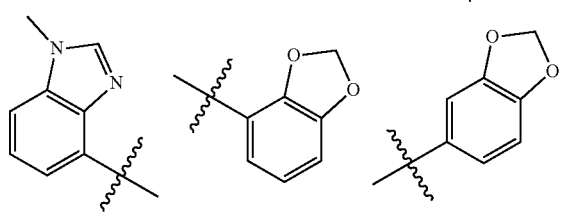
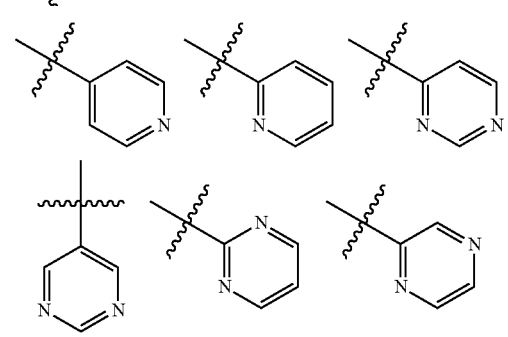
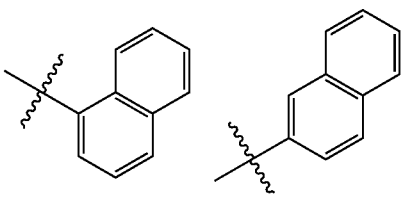
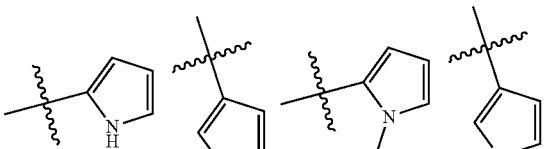
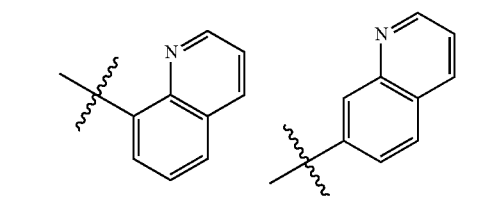
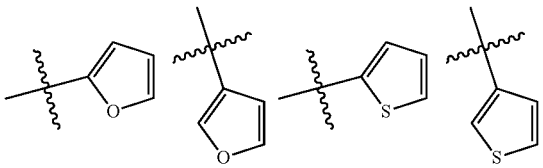
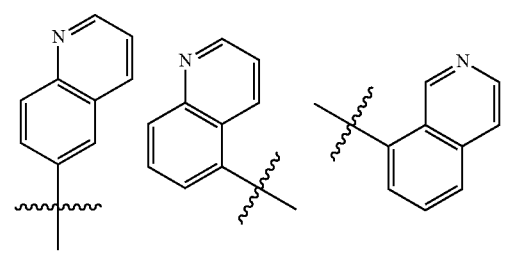

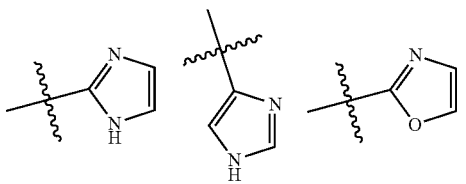
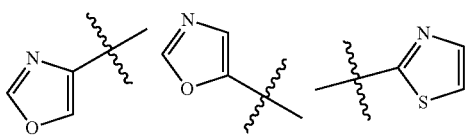
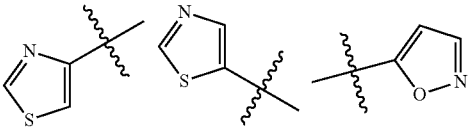
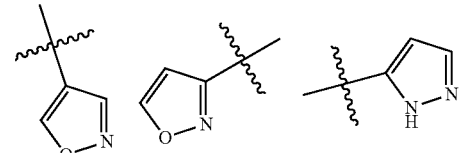
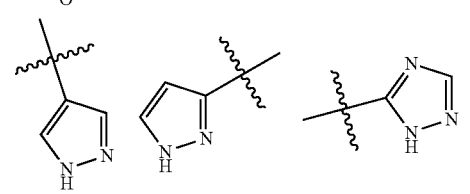
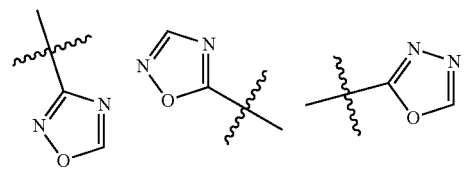
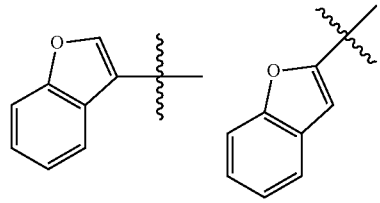
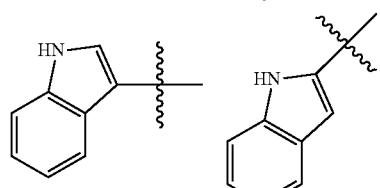
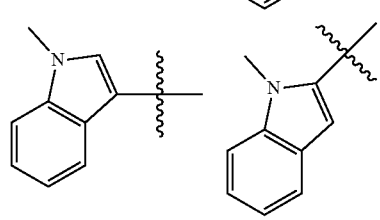
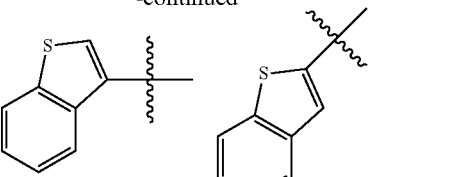
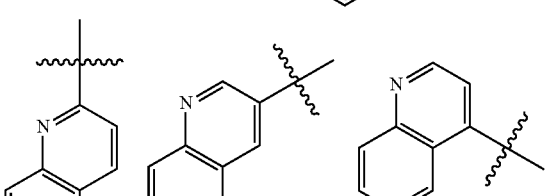
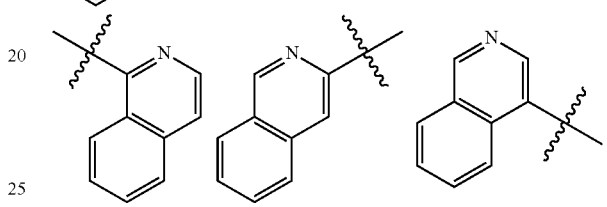
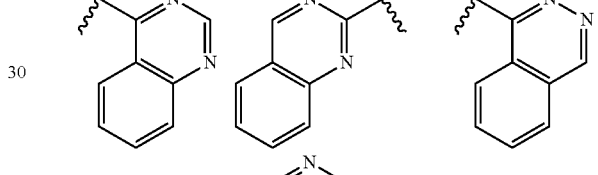

As used herein, the term "arylalkyl" means a $C_{1-6}$alkyl substituted by aryl.

As used herein, the term "arylamino" means an amino group substituted by an aryl group. An example of an arylamino is —NH(phenyl).

As used herein, the term "arylene" means an aryl linking group, i.e., an aryl group that links one group to another group in a molecule.

As used herein, the term "cancer" means a spectrum of pathological symptoms associated with the initiation or progression, as well as metastasis, of malignant tumors.

As used herein, the term "carbamoyl" means —C(=O)—NH$_2$.

As used herein, the term "carbocycle" means a 5- or 6-membered, saturated or unsaturated cyclic ring, optionally containing O, S, or N atoms as part of the ring. Examples of carbocycles include, but are not limited to, cyclopentyl, cyclohexyl, cyclopenta-1,3-diene, phenyl, and any of the heterocycles recited above.

As used herein, the term "carrier" means a diluent, adjuvant, or excipient with which a compound is administered. Pharmaceutical carriers can be liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used.

As used herein, the term, "compound" means all stereoisomers, tautomers, and isotopes of the compounds described herein.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "contacting" means bringing together of two elements in an in vitro system or an in vivo system. For example, "contacting" a $S_1P_1$ receptor compound with a $S_1P_1$ receptor with an individual or patient or cell includes the administration of the compound to an individual or patient, such as a human, as well as, for example, introducing a compound into a sample containing a cellular or purified preparation containing the $S_1P_1$ receptor.

As used herein, the term "cyano" means —CN.

As used herein, the term "cycloalkyl" means non-aromatic cyclic hydrocarbons including cyclized alkyl, alkenyl, and alkynyl groups that contain up to 20 ring-forming carbon atoms.

Cycloalkyl groups can include mono- or polycyclic ring systems such as fused ring systems, bridged ring systems, and spiro ring systems. In some embodiments, polycyclic ring systems include 2, 3, or 4 fused rings. A cycloalkyl group can contain from 3 to 15, from 3 to 10, from 3 to 8, from 3 to 6, from 4 to 6, from 3 to 5, or 5 or 6 ring-forming carbon atoms. Ring-forming carbon atoms of a cycloalkyl group can be optionally substituted by oxo or sulfido. Examples of cycloalkyl groups include, but are not limited to, cyclopropyl, cyclobutyl, cyclopentyl, cyclohexyl, cycloheptyl, cyclooctyl, cyclononyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (having a bond in common with) to the cycloalkyl ring, for example, benzo or thienyl derivatives of pentane, pentene, hexane, and the like (e.g., 2,3-dihydro-1H-indene-1-yl, or 1H-inden-2(3H)-one-1-yl).

As used herein, the term "cycloalkylalkyl" means a $C_{1-6}$alkyl substituted by cycloalkyl.

As used herein, the term "dialkylamino" means an amino group substituted by two alkyl groups, each having from 1 to 6 carbon atoms.

As used herein, the term "diazamino" means —N(NH$_2$)$_2$.

As used herein, the term "facially amphiphilic" or "facial amphiphilicity" means compounds with polar (hydrophilic) and nonpolar (hydrophobic) side chains that adopt conformation(s) leading to segregation of polar and nonpolar side chains to opposite faces or separate regions of the structure or molecule.

As used herein, the term "guanidino" means —NH(=NH)NH$_2$.

As used herein, the term "halo" means halogen groups including, but not limited to fluoro, chloro, bromo, and iodo.

As used herein, the term "haloalkoxy" means an —O-haloalkyl group. An example of an haloalkoxy group is OCF$_3$.

As used herein, the term "haloalkyl" means a $C_{1-6}$alkyl group having one or more halogen substituents. Examples of haloalkyl groups include, but are not limited to, CF$_3$, C$_2$F$_5$, CH$_2$F, CHF$_2$, CCl$_3$, CHCl$_2$, CH$_2$CF$_3$, and the like.

As used herein, the term "heteroaryl" means an aromatic heterocycle having up to 20 ring-forming atoms (e.g., C) and having at least one heteroatom ring member (ring-forming atom) such as sulfur, oxygen, or nitrogen. In some embodiments, the heteroaryl group has at least one or more heteroatom ring-forming atoms, each of which are, independently, sulfur, oxygen, or nitrogen. In some embodiments, the heteroaryl group has from 3 to 20 ring-forming atoms, from 3 to 10 ring-forming atoms, from 3 to 6 ring-forming atoms, or from 3 to 5 ring-forming atoms. In some embodiments, the heteroaryl group contains 2 to 14 carbon atoms, from 2 to 7 carbon atoms, or 5 or 6 carbon atoms. In some embodiments, the heteroaryl group has 1 to 4 heteroatoms, 1 to 3 heteroatoms, or 1 or 2 heteroatoms. Heteroaryl groups include monocyclic and polycyclic (e.g., having 2, 3 or 4 fused rings) systems. Examples of heteroaryl groups include, but are not limited to, pyridyl, pyrimidinyl, pyrazinyl, pyridazinyl, triazinyl, furyl, quinolyl, isoquinolyl, thienyl, imidazolyl, thiazolyl, indolyl (such as indol-3-yl), pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, pyranyl, oxadiazolyl, isoxazolyl, triazolyl, thianthrenyl, pyrazolyl, indolizinyl, isoindolyl, isobenzofuranyl, benzoxazolyl, xanthenyl, 2H-pyrrolyl, pyrrolyl, 3H-indolyl, 4H-quinolizinyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furanyl, phenoxazinyl groups, and the like. Suitable heteroaryl groups include 1,2,3-triazole, 1,2,4-triazole, 5-amino-1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, and 2-aminopyridine.

As used herein, the term "heteroarylalkyl" means a $C_{1-6}$alkyl group substituted by a heteroaryl group.

As used herein, the term "heteroarylamino" means an amino group substituted by a heteroaryl group. An example of a heteroarylamino is —NH-(2-pyridyl).

As used herein, the term "heteroarylene" means a heteroaryl linking group, i.e., a heteroaryl group that links one group to another group in a molecule.

As used herein, the term "heterocycle" or "heterocyclic ring" means a 5- to 7-membered mono- or bicyclic or 7- to 10-membered bicyclic heterocyclic ring system any ring of which may be saturated or unsaturated, and which consists of carbon atoms and from one to three heteroatoms chosen from N, O and S, and wherein the N and S heteroatoms may optionally be oxidized, and the N heteroatom may optionally be quaternized, and including any bicyclic group in which any of the above-defined heterocyclic rings is fused to a benzene ring. Particularly useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of heterocyclic groups include, but are not limited to, piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

As used herein, the term "heterocycloalkyl" means nonaromatic heterocycles having up to 20 ring-forming atoms including cyclized alkyl, alkenyl, and alkynyl groups, where one or more of the ring-forming carbon atoms is replaced by a heteroatom such as an O, N, or S atom. Hetercycloalkyl groups can be mono or polycyclic (e.g., fused, bridged, or spiro systems). In some embodiments, the heterocycloalkyl group has from 1 to 20 carbon atoms, or from 3 to 20 carbon atoms. In some embodiments, the heterocycloalkyl group contains 3 to 14 ring-forming atoms, 3 to 7 ring-forming atoms, or 5 or 6 ring-forming atoms. In some embodiments, the heterocycloalkyl group has 1 to 4 heteroatoms, 1 to 3 heteroatoms, or 1 or 2 heteroatoms. In some embodiments, the heterocycloalkyl group contains 0 to 3 double bonds. In some embodiments, the heterocycloalkyl group contains 0 to 2 triple bonds. Examples of heterocycloalkyl groups include, but are not limited to, morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, oxazolidinyl, isothiazolidinyl, pyrazolidinyl, thiazolidinyl, imidazolidinyl, pyrrolidin-2-one-3-yl, and the like. In addition, ring-forming carbon atoms and heteroatoms of a heterocycloalkyl group can be optionally substituted by oxo or sulfido. For example, a ring-forming S atom can be substituted by 1 or 2 oxo (form a S(O) or S(O)$_2$). For another example, a ring-forming C atom can be substituted by oxo (form carbonyl). Also included in the definition of heterocycloalkyl are moieties that have one or more aromatic rings fused (having a bond in common with) to the nonaromatic heterocyclic ring including, but not limited to, pyridinyl, thiophenyl, phthalimidyl, naphthalimidyl, and benzo derivatives of heterocycles such as indolene, isoindolene, 4,5,6,7-tetrahydrothieno[2,3-c]pyridine-5-yl, 5,6-dihydrothieno[2,3-c]pyridin-7(4H)-one-5-yl, isoindolin-1-one-3-yl, and 3,4-dihydroisoquinolin-1(2H)-one-3yl groups. Ring-forming carbon atoms and heteroatoms of the heterocycloalkyl group can be optionally substituted by oxo or sulfido.

As used herein, the term "heterocycloalkylalkyl" refers to a C$_{1-6}$alkyl substituted by heterocycloalkyl.

As used herein, the term "hydroxy" or "hydroxyl" means an —OH group.

As used herein, the term "hydroxyalkyl" or "hydroxylalkyl" means an alkyl group substituted by a hydroxyl group. Examples of a hydroxylalkyl include, but are not limited to, —CH$_2$OH and —CH$_2$CH$_2$OH.

As used herein, the term "individual" or "patient," used interchangeably, means any animal, including mammals, such as mice, rats, other rodents, rabbits, dogs, cats, swine, cattle, sheep, horses, or primates, such as humans.

As used herein, the phrase "inhibiting activity," such as enzymatic or receptor activity means reducing by any measurable amount the activity of an enzyme or receptor, such as the S$_1$P$_1$ receptor.

As used herein, the phrase "in need thereof" means that the animal or mammal has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent.

As used herein, the phrase "in situ gellable" means embracing not only liquids of low viscosity that form gels upon contact with the eye or with lacrimal fluid in the exterior of the eye, but also more viscous liquids such as semi-fluid and thixotropic gels that exhibit substantially increased viscosity or gel stiffness upon administration to the eye.

As used herein, the phrase "integer from X to Y" means any integer that includes the endpoints. For example, the phrase "integer from X to Y" means 1, 2, 3, 4, or 5.

As used herein, the term "isolated" means that the compounds described herein are separated from other components of either (a) a natural source, such as a plant or cell, or (b) a synthetic organic chemical reaction mixture, such as by conventional techniques.

As used herein, the term "mammal" means a rodent (i.e., a mouse, a rat, or a guinea pig), a monkey, a cat, a dog, a cow, a horse, a pig, or a human. In some embodiments, the mammal is a human.

As used herein, the term "N-alkyl" refers to a alkyl chain that is substituted with an amine group. Non-limiting examples, include, but are not limited to

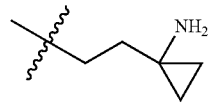 [SMILES: *CCC1(N)CC1]

and the like. The alkyl chain can be linear, branched, cyclic, or any combination thereof. In some embodiments, the alkyl comprises 1-10, 1-9, 1-8, 1-7, 1-6, 1-5, 1-4, 1-3, or 1-2 carbons.

As used herein, the term "nitro" means —NO$_2$.

As used herein, the term "n-membered", where n is an integer, typically describes the number of ring-forming atoms in a moiety, where the number of ring-forming atoms is n. For example, pyridine is an example of a 6-membered heteroaryl ring and thiophene is an example of a 5-membered heteroaryl ring.

As used herein, the phrase "ophthalmically acceptable" means having no persistent detrimental effect on the treated eye or the functioning thereof, or on the general health of the subject being treated. However, it will be recognized that transient effects such as minor irritation or a "stinging" sensation are common with topical ophthalmic administration of drugs and the existence of such transient effects is not inconsistent with the composition, formulation, or ingredient (e.g., excipient) in question being "ophthalmically acceptable" as herein defined.

As used herein, the phrase "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent groups, provided that the normal valency of the designated atom or moiety is not exceeded, and that the substitution results in a stable compound. For example, if a methyl group is optionally substituted, then 3 hydrogen atoms on the carbon atom can be replaced with substituent groups.

As used herein, the phrase "pharmaceutically acceptable" means those compounds, materials, compositions, and/or dosage forms which are, within the scope of sound medical judgment, suitable for use in contact with tissues of humans and animals. In some embodiments, "pharmaceutically acceptable" means approved by a regulatory agency of the Federal or a state government or listed in the U.S. Pharmacopeia or other generally recognized pharmacopeia for use in animals, and more particularly in humans.

In some embodiments, the salt of a compound described herein is a pharmaceutically acceptable salt thereof. As used herein, the phrase "pharmaceutically acceptable salt(s)," includes, but is not limited to, salts of acidic or basic groups. Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, thiosulfuric, citric, maleic, acetic, oxalic, hydrochloride, hydrobromide, hydroiodide, nitrate, sulfate, bisulfate, bisulfite, phosphate, acid phosphate, isonicotinate, borate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, bicarbonate, malonate, mesylate, esylate, napsydisylate, tosylate, besylate, orthophoshate, trifluoroacetate, and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, ammonium, sodium, lithium, zinc, potassium, and iron salts. The present embodiments also includes quaternary ammonium salts of the compounds described herein, where the compounds have one or more tertiary amine moiety.

As used herein, the term "phenyl" means —$C_6H_5$. A phenyl group can be unsubstituted or substituted with one, two, or three suitable substituents.

As used herein, the term "prodrug" means a derivative of a known direct acting drug, which derivative has enhanced delivery characteristics and therapeutic value as compared to the drug, and is transformed into the active drug by an enzymatic or chemical process.

As used herein, the term "purified" means that when isolated, the isolate contains at least 90%, at least 95%, at least 98%, or at least 99% of a compound described herein by weight of the isolate.

As used herein, the phrase "quaternary ammonium salts" means derivatives of the disclosed compounds with one or more tertiary amine moieties wherein at least one of the tertiary amine moieties in the parent compound is modified by converting the tertiary amine moiety to a quaternary ammonium cation via alkylation (and the cations are balanced by anions such as $C_1^-$, $CH_3COO^-$, and $CF_3COO^-$), for example methylation or ethylation.

As used herein, the term "semicarbazone" means=NNHC (=O)$NH_2$.

As used herein, the phrase "solubilizing agent" means agents that result in formation of a micellar solution or a true solution of the drug.

As used herein, the term "solution/suspension" means a liquid composition wherein a first portion of the active agent is present in solution and a second portion of the active agent is present in particulate form, in suspension in a liquid matrix.

As used herein, the phrase "substantially isolated" means a compound that is at least partially or substantially separated from the environment in which it is formed or detected.

As used herein, the phrase "suitable substituent" or "substituent" means a group that does not nullify the synthetic or pharmaceutical utility of the compounds described herein or the intermediates useful for preparing them. Examples of suitable substituents include, but are not limited to: $C_1$-$C_6$alkyl, $C_1$-$C_6$alkenyl, $C_1$-$C_6$alkynyl, $C_5$-$C_6$aryl, $C_1$-$C_6$alkoxy, $C_3$-$C_5$heteroaryl, $C_3$-$C_6$cycloalkyl, $C_5$-$C_6$aryloxy, —CN, —OH, oxo, halo, haloalkyl, —$NO_2$, —$CO_2H$, —$NH_2$, —NH($C_1$-$C_8$alkyl), —N($C_1$-$C_6$alkyl)$_2$, —NH($C_6$aryl), —N($C_5$-$C_6$aryl)$_2$, —CHO, —CO($C_1$-$C_6$alkyl), —CO(($C_5$-$C_6$)aryl), —$CO_2$(($C_1$-$C_6$)alkyl), and —$CO_2$(($C_5$-$C_6$)aryl). One of skill in art can readily choose a suitable substituent based on the stability and pharmacological and synthetic activity of the compounds described herein.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment.

As used herein, the terms "treat," "treated," or "treating" mean both therapeutic treatment and prophylactic measures wherein the object is to slow down (lessen) an undesired physiological condition, disorder or disease, or obtain beneficial or desired clinical results. Beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response without excessive levels of side effects. Treatment also includes prolonging survival as compared to expected survival if not receiving treatment. Thus, "treatment of pain" or "treating pain" means an activity that alleviates or ameliorates any of the primary phenomena or secondary symptoms associated with the pain or other condition described herein.

As used herein, the term "ureido" means —NHC(=O)—$NH_2$.

At various places in the present specification, substituents of compounds may be disclosed in groups or in ranges. It is specifically intended that embodiments include each and every individual subcombination of the members of such groups and ranges. For example, the term "$C_{1-6}$alkyl" is specifically intended to individually disclose methyl, ethyl, propyl, C$_4$alkyl, C$_5$alkyl, and C$_6$alkyl.

For compounds in which a variable appears more than once, each variable can be a different moiety selected from the Markush group defining the variable. For example, where a structure is described having two R groups that are simultaneously present on the same compound, the two R groups can represent different moieties selected from the Markush groups defined for R. In another example, when an optionally multiple substituent is designated in the form, for example, S(R)s

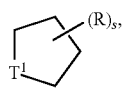

then it is understood that substituent R can occur s number of times on the ring, and R can be a different moiety at each occurrence. In the above example, where the variable T$^1$ is defined to include hydrogens, such as when T$^1$ is CH$_2$, NH, etc., any H can be replaced with a substituent.

It is further appreciated that certain features described herein, which are, for clarity, described in the context of separate embodiments, can also be provided in combination in a single embodiment.

Conversely, various features which are, for brevity, described in the context of a single embodiment, can also be provided separately or in any suitable subcombination.

It is understood that the present embodiments encompasses the use, where applicable, of stereoisomers, diastereomers and optical stereoisomers of the compounds, as well as mixtures thereof. Additionally, it is understood that stereoisomers, diastereomers, and optical stereoisomers of the compounds, and mixtures thereof, are within the scope of the embodiments. By way of non-limiting example, the mixture may be a racemate or the mixture may comprise unequal proportions of one particular stereoisomer over the other. Additionally, the compounds can be provided as a substantially pure stereoisomers, diastereomers and optical stereoisomers (such as epimers).

The compounds described herein can be asymmetric (e.g., having one or more stereocenters).

All stereoisomers, such as enantiomers and diastereomers, are intended to be included within the scope of the embodiments unless otherwise indicated. Compounds that contain asymmetrically substituted carbon atoms can be isolated in optically active or racemic forms. Methods of preparation of optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are provided herein. Cis and trans geometric isomers of the compounds are also included within the present embodiments and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

In some embodiments, the composition comprises a compound, or a pharmaceutically acceptable salt thereof, that is at least 90%, at least 95%, at least 98%, or at least 99%, or 100% enantiomeric pure, which means that the ratio of one enantiomer to the other in the composition is at least 90:1 at least 95:1, at least 98:1, or at least 99:1, or is completely in the form of one enantiomer over the other.

Resolution of racemic mixtures of compounds can be carried out by any of numerous methods known in the art, including, for example, chiral HPLC, fractional recrystallization using a chiral resolving acid which is an optically active, salt-forming organic acid. Suitable resolving agents for fractional recrystallization methods include, but are not limited to, optically active acids, such as the D and L forms of tartaric acid, diacetyltartaric acid, dibenzoyltartaric acid, mandelic acid, malic acid, lactic acid, and the various optically active camphorsulfonic acids such as 0-camphorsulfonic acid. Other resolving agents suitable for fractional crystallization methods include, but are not limited to, stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

Compounds may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds also include hydrates and solvates, as well as anhydrous and non-solvated forms.

Compounds can also include all isotopes of atoms occurring in the intermediates or final compounds. Isotopes include those atoms having the same atomic number but different mass numbers. For example, isotopes of hydrogen include tritium and deuterium.

In some embodiments, the compounds, or salts thereof, are substantially isolated. Partial separation can include, for example, a composition enriched in the compound. Substantial separation can include compositions containing at least about 50%, at least about 60%, at least about 70%, at least about 80%, at least about 90%, at least about 95%, at least about 97%, or at least about 99% by weight of the compound, or salt thereof. Methods for isolating compounds and their salts are routine in the art.

Although the disclosed compounds are suitable, other functional groups can be incorporated into the compound with an expectation of similar results. In particular, thioamides and thioesters are anticipated to have very similar properties. The distance between aromatic rings can impact the geometrical pattern of the compound and this distance can be altered by incorporating aliphatic chains of varying length, which can be optionally substituted or can comprise an amino acid, a dicarboxylic acid or a diamine. The distance between and the relative orientation of monomers within the compounds can also be altered by replacing the amide bond with a surrogate having additional atoms. Thus, replacing a carbonyl group with a dicarbonyl alters the distance between the monomers and the propensity of dicarbonyl unit to adopt an anti-arrangement of the two carbonyl moiety and alter the periodicity of the compound. Pyromellitic anhydride represents still another alternative to simple amide linkages which can alter the conformation and physical properties of the compound. Modern methods of solid phase organic chemistry (E. Atherton and R. C. Sheppard, Solid Phase Peptide Synthesis A Practical Approach IRL Press Oxford 1989) now allow the synthesis of homodisperse compounds with molecular weights approaching 5,000 Daltons. Other substitution patterns are equally effective.

The compounds also include derivatives referred to as prodrugs.

Compounds containing an amine function can also form N-oxides. A reference herein to a compound that contains an amine function also includes the N-oxide. Where a compound contains several amine functions, one or more than one nitrogen atom can be oxidized to form an N-oxide. Examples of N-oxides include N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g., a peroxycarboxylic acid) (see, Advanced Organic Chemistry, by Jerry March, 4th Edition, Wiley Interscience).

Embodiments of various compounds and salts thereof are provided. Where a variable is not specifically recited, the variable can be any option described herein, except as otherwise noted or dictated by context.

In some embodiments, the compound is as described in the appended exemplary, non-limiting claims, or a pharmaceutically acceptable salt thereof.

In some embodiments, compounds having Formula I or Formula II, or a pharmaceutically acceptable salt thereof, are provided:

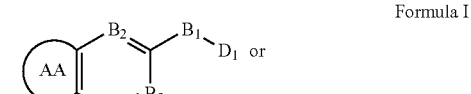

Formula I

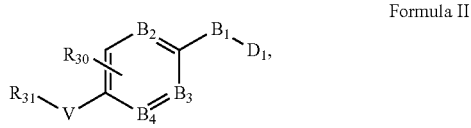

Formula II wherein:
AA is

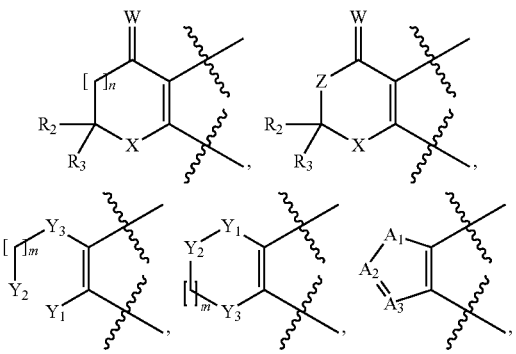

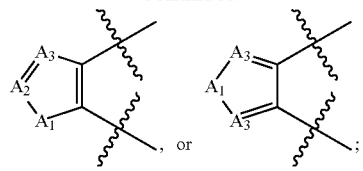

W is O, S, or NR1;
X is O, S, or NR4;
V is O, S, or NR$_{32}$;
Z is CHR$_{42}$ or NR$_{43}$;
n is 0, 1, 2, 3, or 4;
Y$_1$ and Y$_2$ are independently O, S, NR$_5$, C=O, C=S or C=NR$_6$;
Y$_3$ is O, S, CH$_2$, or NR$_{34}$;
m is 0, 1, 2, or 3;
A$_1$ is O, S, NR$_7$, C=O, or C=S;
A$_2$ and A$_3$ are independently CR$_{29}$ or N;

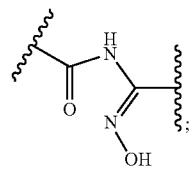 [SMILES: *C(=O)N/C(*)=N/O]

B$_1$ is an optionally substituted aryl or heteroaryl group, a carbocycle, or OH;
B$_2$, B$_3$, and B$_4$ are independently CR$_{38}$ or N;
D$_1$ is H, OH, NH$_2$, NO$_2$, cycle, optionally substituted aryl group, branched or unbranched alkyl alcohol, halo, branched or unbranched alkyl, amide, cyano, alkoxy, haloalkyl, aklylsulfonyl, nitrite, or alkylsulfanyl;
R$_2$ and R$_3$, are independently H, optionally substituted C$_1$-C$_6$ alkyl, optionally substituted C$_1$-C$_6$ hydroxyalkyl, optionally substituted C$_1$-C$_6$ alkoxy, optionally substituted cycloalkyl, or optionally substituted cycloheteroalkyl; or R$_2$ and R$_3$ are together optionally substituted cycloalkyl, or optionally substituted cycloheteroalkyl;
R$_1$, R$_4$, R$_5$, R$_6$, R$_7$, R$_{29}$, R$_{31}$, R$_{32}$, R$_{33}$, R$_{34}$, R$_{38}$, and R$_{43}$ are independently H, OH, NH$_2$, optionally substituted C$_1$-C$_6$ alkyl, optionally substituted C$_1$-C$_6$ hydroxyalkyl, optionally substituted C$_1$-C$_6$ alkoxy, optionally substituted cycloalkyl, or optionally substituted cycloheteroalkyl.
R$_{30}$ is independently H, CN, CF$_3$, optionally substituted C$_1$-C$_6$ alkyl, optionally substituted C$_1$-C$_6$ hydroxyalkyl, optionally substituted C$_1$-C$_6$ alkoxy, optionally substituted cycloalkyl, or optionally substituted cycloheteroalkyl; or optionally substituted haloalkyl; R$_{42}$ is independently Br, C$_1$, F, optionally substituted C$_1$-C$_6$ alkyl, optionally substituted C$_1$-C$_6$ hydroxyalkyl, optionally substituted C$_1$-C$_6$ alkoxy, optionally substituted cycloalkyl, or optionally substituted cycloheteroalkyl;
In some embodiments of compounds of Formula I or Formula II, D$_1$ and B$_1$ are:

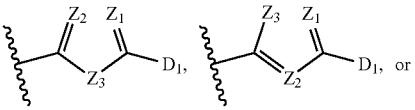

-continued

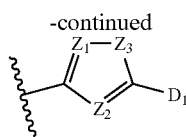

wherein:
$Z_1$ and $Z_2$ are independently N or $CR_{39}$;
$Z_3$ is O, S, or $NR_{27}$;
$R_{27}$ and $R_{39}$ are independently H, optionally substituted $C_1$-$C_6$ alkyl, optionally substituted $C_1$-$C_6$ hydroxyalkyl, optionally substituted $C_1$-$C_6$ alkoxy, optionally substituted cycloalkyl, or optionally substituted cycloheteroalkyl.

In some embodiments, one of $Z_1$ and $Z_2$ is N. In some embodiments, both $Z_1$ and $Z_2$ are N.

In some embodiments, $Z_3$ is O.

In some embodiments of compounds, or a pharmaceutically acceptable salt thereof, of Formula I or Formula II, $D_1$ and $B_1$ have a formula of:

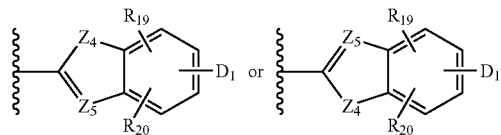

wherein:
$Z_4$ is O, S, or $NR_{28}$;
$Z_5$ is N or CH;
$R_{19}$, and $R_{20}$ are each independently H, OH, $NH_2$, $NO_2$, cycle, aryl, branched or unbranched alkyl alcohol, halo, branched or unbranched alkyl, amide, cyano, alkoxy, alkylthio, haloalkyl, aklylsulfonyl, nitrite, or alkylsulfanyl; or two of $R_{19}$, and $R_{20}$ together form an aryl or cycle that is attached to one or more of the atoms of $B_1$.

$R_{28}$ is H, optionally substituted $C_1$-$C_6$ alkyl, optionally substituted $C_1$-$C_6$ hydroxyalkyl, optionally substituted $C_1$-$C_6$ alkoxy, optionally substituted cycloalkyl, or optionally substituted cycloheteroalkyl.

In some embodiments, $Z_5$ is N. In some embodiments, $Z_4$ is O. In some embodiments, $Z_5$ is N and $Z_4$ is O.

In some embodiments of compounds of Formula I or Formula II, $D_1$ is

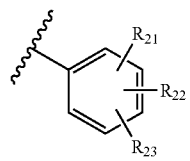

wherein $R_{21}$, $R_{22}$, and $R_{23}$ are each independently H, OH, $NH_2$, $NO_2$, cycle, aryl, branched or unbranched alkyl alcohol, halo, branched or unbranched alkyl, amide, cyano, alkoxy, haloalkyl, aklylsulfonyl, nitrite, or alkylsulfanyl; or two of $R_{21}$, $R_{22}$, and $R_{23}$ together form an aryl or cycle that is attached to one or more of the atoms of $D_1$.

In some embodiments, one of $R_{21}$, $R_{22}$, and $R_{23}$ is H. In some embodiments, two of $R_{21}$, $R_{22}$, and $R_{23}$ are H. In some embodiments, $R_{23}$ is Me, OH, $NH_2$, Cl, $NHSO_2Me$, $SO_2NH_2$, NH(CO)Me, or $(CO)NH_2$. In some embodiments, $R_{21}$ and $R_{22}$ are H and $R_{23}$ is Me, OH, $NH_2$, $C_1$, $NHSO_2Me$, $SO_2NH_2$, NH(CO)Me, or $(CO)NH_2$.

In some embodiments of compounds of Formula I or Formula II, $D_1$ is optionally substituted aryl or optionally substituted hetero aryl.

In some embodiments of compounds of Formula I or Formula II, $D_1$ is

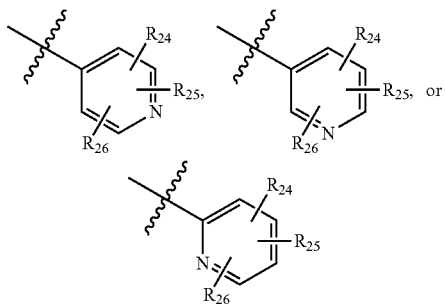

wherein $R_{24}$, $R_{25}$, and $R_{26}$ are each independently H, OH, $NH_2$, $NO_2$, cycle (e.g. carbocycle or heterocyle), aryl, branched or unbranched alkyl alcohol, halo, branched or unbranched alkyl, amide, cyano, alkoxy, haloalkyl, aklylsulfonyl, nitrite, or alkylsulfanyl; or two of $R_{24}$, $R_{25}$, and $R_{26}$ together form an aryl or cycle that is attached to one or more of the atoms of $D_1$.

In some embodiments, one of $R_{24}$, $R_{25}$, and $R_{26}$ is H. In some embodiments, two of $R_{24}$, $R_{25}$, and $R_{26}$ are H. In some embodiments, $R_{26}$ is H, Me, OH, $CF_3$, or OMe. In some embodiments, $R_{24}$ and $R_{25}$ are H and $R_{26}$ is H, Me, OH, $CF_3$, or OMe.

In some embodiments of compounds of Formula I or Formula II, AA is

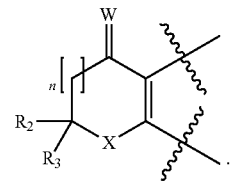

In some embodiments, W is O. In some embodiments, X is O. In some embodiments, $R_2$ and $R_3$ are independently H, optionally substituted $C_1$-$C_6$ alkyl, optionally substituted $C_1$-$C_6$ hydroxyalkyl, optionally substituted $C_1$-$C_6$ alkoxy, optionally substituted cycloalkyl, or optionally substituted cycloheteroalkyl. In some embodiments, $R_2$ and $R_3$ are the same. In some embodiments, $R_2$ and $R_3$ are ethyl.

In some embodiments, $D_1$ is

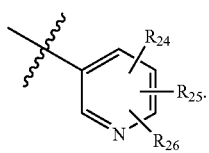

In some embodiments, one of $R_{24}$, $R_{25}$, and $R_{26}$ is H. In some embodiments, two of $R_{24}$, $R_{25}$, and $R_{26}$ are H and the other member is as defined herein. In some embodiments, $D_1$ is

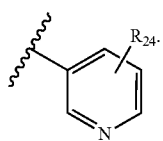

In some embodiments, $D_1$ is

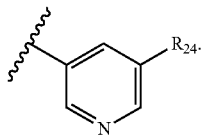

In some embodiments, $R_{24}$ is H. In some embodiments, $R_{24}$ is OH. In some embodiments, $D_1$ is

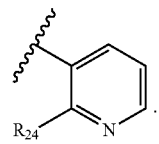

In some embodiments, $R_{24}$ is OMe.

In some embodiments, $D_1$ is

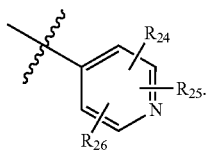

In some embodiments, one of $R_{24}$, $R_{25}$, and $R_{26}$ is H. In some embodiments, two of $R_{24}$, $R_{25}$, and $R_{26}$ are H and the other member is as defined herein.

In some embodiments, $D_1$ is

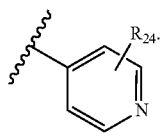

In some embodiments, $D_1$ is

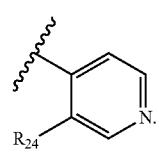

In some embodiments, $D_1$ is

In some embodiments, $R_{24}$ is halide. In some embodiments, $R_{24}$ is F.

In some embodiments, $R_{24}$ is Me. In some embodiments, $R_{24}$ is OMe. In some embodiments, $R_{24}$ is OH.

In some embodiments of compounds of Formula I or Formula II, $R_2$ and $R_3$ are together

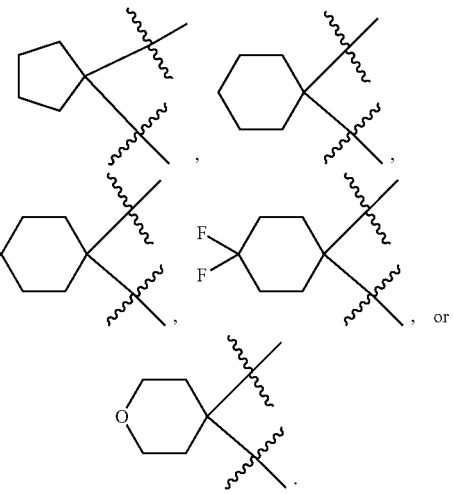

In some embodiments, n is 1.

In some embodiments of compounds of Formula I or Formula II, AA is

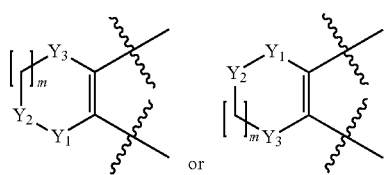

In some embodiments, $Y_1$ is $NR_6$. In some embodiments, $R_5$ is H.

In some embodiments, $Y_2$ is $C=NR_6$. In some embodiments, $R_6$ is H.

In some embodiments, $Y_2$ is $C=O$. In some embodiments, $Y_3$ is O. In some embodiments, $Y_3$ is $CH_2$. In some embodiments, m is 0. In some embodiments, m is 1.

In some embodiments of compounds of Formula I or Formula II, AA is

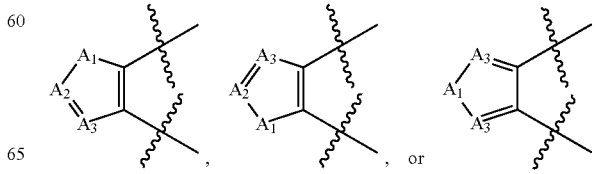

In some embodiments, $A_1$ is O. In some embodiments, $A_1$ is S. In some embodiments, $A_2$ is N. In some embodiments, $A_3$ is N. In some embodiments, $A_3$ is $CR_{29}$. In some embodiments, $R_{29}$ is H.

In some embodiments, $A_2$ is $CR_{29}$. In some embodiments, $R_{29}$ is H.

In some embodiments, $A_1$ is $NR_7$. In some embodiments, $R_7$ is Me

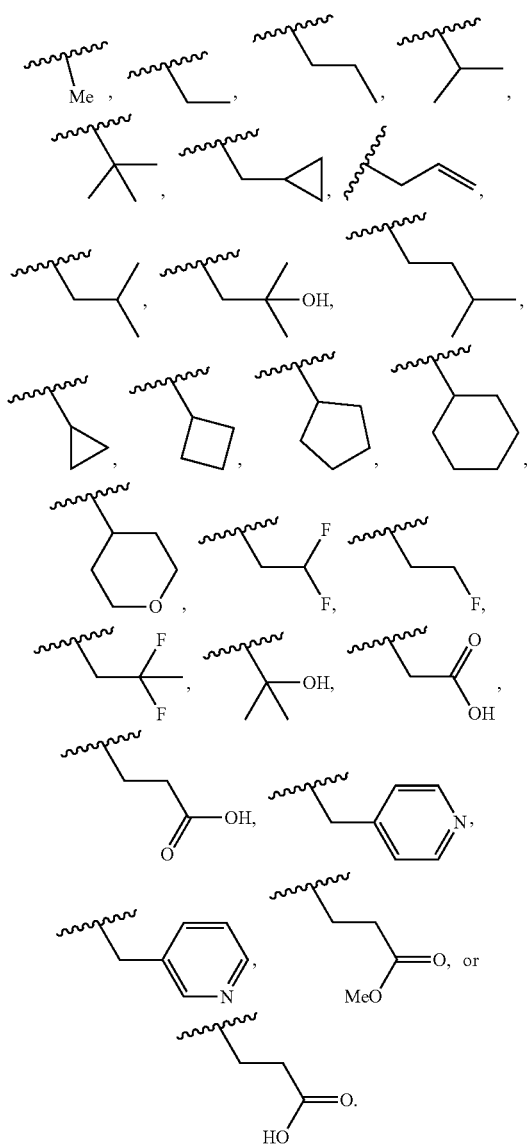

In some embodiments, $D_1$ is

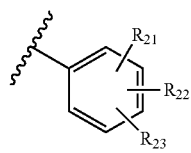

In some embodiments, $D_1$ is

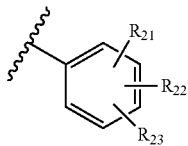

and two of $R_{21}$, $R_{22}$, and $R_{23}$ are H. In some embodiments, $D_1$ is

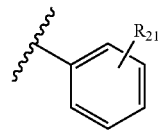

In some embodiments, $R_{21}$ is optionally substituted $C_1$-$C_6$ alkyl. In some embodiments, $R_{21}$ is ethyl or methyl. In some embodiments, $D_1$ is

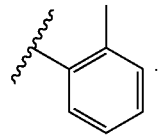 [SMILES: *c1ccccc1C ; "."]

In some embodiments of compounds of Formula I or Formula II, $D_1$ is

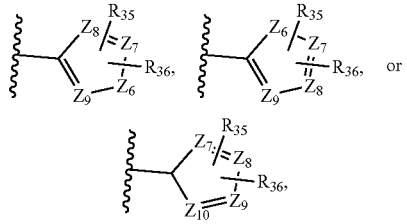

wherein:

$Z_6$ is O, S, $NR_{40}$, or $CHR_{37}$;

$Z_7$, $Z_8$, $Z_9$ and $Z_{10}$ are independently N or $CR_{41}$;

$R_{35}$, $R_{36}$, $R_{37}$, $R_{40}$, and $R_{41}$ are each independently H, OH, $NH_2$, cycle, aryl, branched or unbranched alkyl alcohol, halo, branched or unbranched alkyl, amide, cyano, alkoxy, haloalkyl, aklylsulfonyl, nitrite, or alkylsulfanyl; or $R_{35}$ and $R_{36}$ together form an aryl or cycle that is attached to one or more of the atoms of $D_1$.

In some embodiments, one of $R_{35}$ and $R_{36}$ is H. In some embodiments, both $R_{35}$ and $R_{36}$ are H. In some embodiments, $Z_6$ is NH. In some embodiments, one of $Z_7$, $Z_8$ and $Z_9$ is N.

In some embodiments, $Z_7$ is N. In some embodiments, $Z_8$ is CH. In some embodiments, $Z_9$ is CH. In some embodiments, both $Z_8$ and $Z_9$ are CH.

In some embodiments, AA is

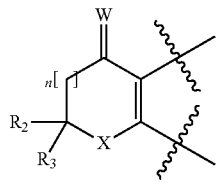

In some embodiments, W is O. In some embodiments, X is O. In some embodiments, $R_2$ and $R_3$ are independently H, optionally substituted $C_1$-$C_6$ alkyl, optionally substituted $C_1$-$C_6$ hydroxyalkyl, optionally substituted $C_1$-$C_6$ alkoxy, optionally substituted cycloalkyl, or optionally substituted cycloheteroalkyl. In some embodiments, both $R_2$ and $R_3$ are the same. In some embodiments, both $R_2$ and $R_3$ are methyl or ethyl. In some embodiments, n is 1. In some embodiments, $D_1$ is pyrazoly. In some embodiments, $D_1$ is

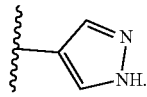

In some embodiments, the compound, or a pharmaceutically acceptable salt thereof, is a compound of Formula I having a formula of

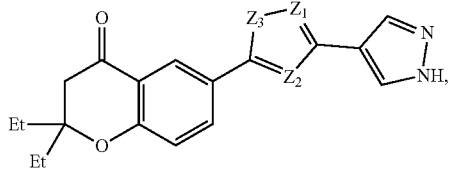

or a pharmaceutically acceptable salt thereof, wherein $Z_1$, $Z_2$, and $Z_3$ are as defined herein and above.

In some embodiments, $Z_2$ is N. In some embodiments, $Z_1$ is N. In some embodiments, $Z_3$ is O. In some embodiments, $Z_2$ and $Z_1$ are N and $Z_3$ is as defined herein. In some embodiments, $Z_2$ and $Z_1$ are N and $Z_3$ is O. In some embodiments, the compound is a compound of Formula I having a formula of

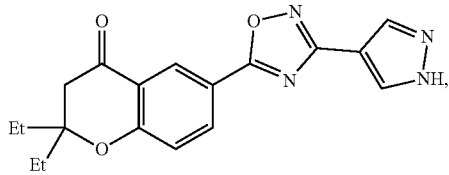 [SMILES: CCC1(CC)CC(=O)c2cc(-c3nc(-c4cn[nH]c4)no3)ccc2O1]

or a pharmaceutically acceptable salt thereof.

In some embodiments of compounds of Formula II, $D_1$ and $B_1$ is

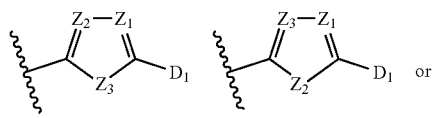

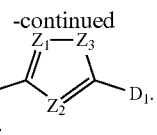

In some embodiments, $Z_3$ is O and $Z_1$ and $Z_2$ are independently N or $CR_{39}$.

In some embodiments, $Z_1$ is N, $Z_2$ is N or $CR_{39}$ and $Z_3$ is O, S, or $NR_{27}$. In some embodiments, $Z_1$ and $Z_2$ are N and $Z_3$ is O.

In some embodiments, the compound is a compounds of Formula II having a formula

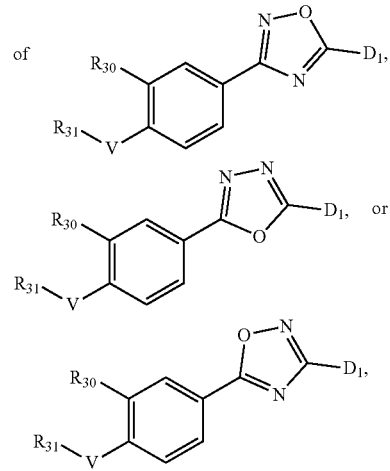

or a pharmaceutically acceptable salt thereof. In some embodiments, $R_{30}$ is CN. In some embodiments, V is NH. In some embodiments, $R_{31}$ is C—$C_5$ alkyl. In some embodiments, $R_{31}$ is

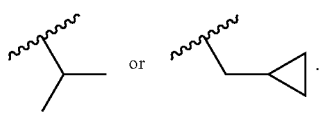

In some embodiments, $R_{31}$ is C—$C_5$ haloalkyl.
In some embodiments, $R_{31}$ is

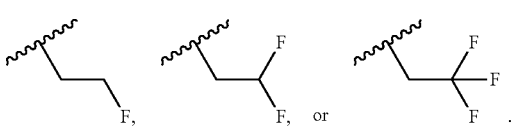

In some embodiments of compounds of Formula II, $D_1$, $B_1$, and AA together is

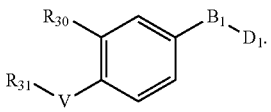

In some embodiments, $R_{30}$ is $CF_3$. In some embodiments, V is O or NH.

In some embodiments, $R_{30}$ is $CF_3$.
In some embodiments, $B_1$-$D_1$ is

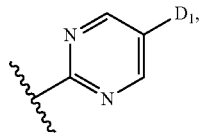

wherein $D_1$ is as defined herein and above.
In some embodiments, $D_1$ is

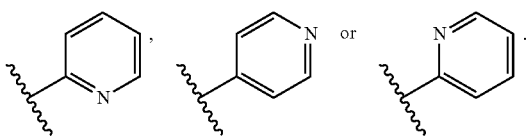 [SMILES: *c1ccccn1 ; "," ; *c1ccncc1 ; "or" ; *c1ccccn1 ; "."]

In some embodiments, $R_{31}$ is

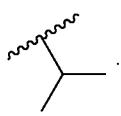

In the preceding embodiments, or as shown below, or as illustrated in the appending claims, if a variable (substituent) is not explicitly defined then the variable is as defined above, which would be readily apparent based upon the present embodiments.

In some embodiments, the compound has a formula of:

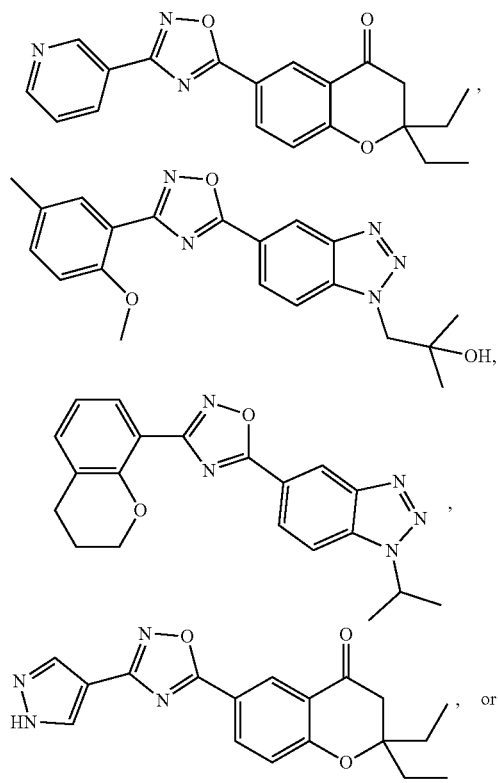

-continued

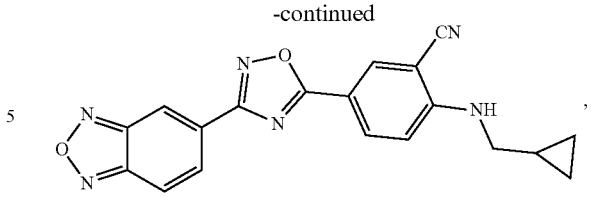

or a pharmaceutically acceptable salt thereof.

In some embodiments, the present embodiments provide a pharmaceutical composition comprising one or more compounds as provided or described herein, such as any compound of Formula I or Formula II, or a pharmaceutically acceptable salt thereof.

In some embodiments, the present embodiments provide methods of treating or preventing neuropathy, pain, inflammatory pain, cancer pain, bone cancer pain, tumor pain, pain or neuropathy resulting from disorders of the central or peripheral nervous system, neuropathic pain, pain associated with dysesthesia, allodynia or hypersensitivity, chemotherapy induced neuropathic pain, chemotherapy induced peripheral neuropathy, diabetic neuropathy or pain associated with diabetic neuropathy, post herpetic neuralgia or pain associated with post herpetic neuralgia, hiv-related neuropathy or pain associated with hiv-related neuropathy, pain or neuropathy resulting from spinal cord injury, nerve lesions, tissue injury, multiple sclerosis, stroke, nutritional deficiencies, or toxins, fibromyalgia or pain associated with fibromyalgia, phantom limb pain, complex regional pain syndrome, carpal tunnel syndrome, sciatica, pudendal neuralgia, back or neck pain, including those resulting from degenerative disk disease, trigeminal neuralgia, headache disorders including, but not limited to migraine and cluster headache, orofacial pain, odontalgia, temporomandibular joint pain, endometrial pain, osteoarthritis, rheumatoid arthritis, atypical odontalgia, interstitial cystitis, uveitis, or any combination thereof in a subject comprising administering to the subject one or more compounds described herein, or a pharmaceutically acceptable salt thereof, or a pharmaceutical composition comprising one or more compounds described herein.

In some embodiments, the present embodiments provide methods of treating or preventing neuropathy, chemotherapy induced neuropathic pain, chemotherapy induced peripheral neuropathy, diabetic neuropathy or pain associated with diabetic neuropathy in a subject, the method comprising administering to the subject one or more compounds described herein, or a pharmaceutically acceptable salt thereof, or a pharmaceutical composition comprising one or more compounds described herein.

In some embodiments, the present embodiments provide methods of treating cancer in a subject, the method comprising administering to the subject one or more compounds described herein, or a pharmaceutically acceptable salt thereof, or a pharmaceutical composition comprising one or more compounds described herein.

In some embodiments, the present embodiments provide methods of treating cancer in a subject, wherein the cancer is ovarian, breast, lung, brain, colon, prostate, esophageal, pancreatic, brain, glioblastoma, leukemia, multiple myeloma, lymphoma, skin cancer, acute Lymphoblastic Leukemia, acute myeloid leukemia, basal cell cancer, bile duct cancer, bladder cancer, bone cancer (Ewing sarcoma, osteosarcoma), CLL, CML, uterine cancer, cervical cancer, hairy cell leukemia, melanoma, thyroid cancer, rectal cancer, renal cell cancer, small cell lung cancer, non-small cell lung cancer, or stomach cancer.

In some embodiments, wherein the subject is a subject in need thereof. In some embodiments, wherein the cancer therapeutic is selected from those described herein.

In some embodiments, the condition is prevented.

In some embodiments, a compound, or a pharmaceutically acceptable salt thereof, is chosen from a compound of as shown in the following table and/or as described herein, including in the Examples section of the present disclosure. Any of the compounds provided for herein can be prepared as pharmaceutically acceptable salts and/or as part of a pharmaceutical composition as provided for herein. Examples of such salts are provided for herein. As described herein, the compounds can be prepared according to the schemes and methods described herein.

| Structure | Compound Number | Chemical Name |
|---|---|---|
| 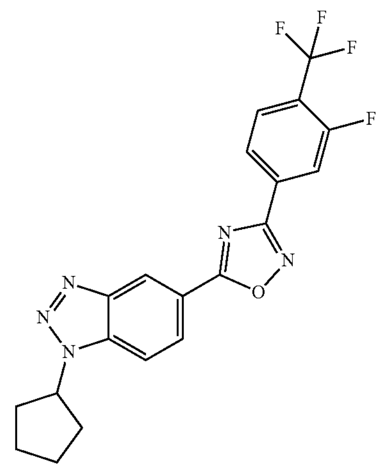 [SMILES: Fc1cc(-c2noc(-c3ccc4c(c3)nnn4C3CCCC3)n2)ccc1C(F)(F)F] | 1 | 1-cyclopentyl-5-{3-[3-fluoro-4-(trifluoromethyl)phenyl]-1,2,4-oxadiazol-5-yl}-1H-1,2,3-benzotriazole |
| 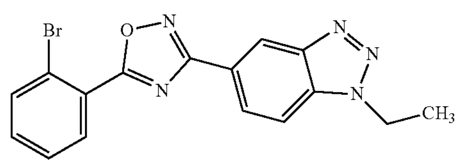 [SMILES: CCn1nnc2cc(-c3noc(-c4ccccc4Br)n3)ccc21] | 2 | 5-(2-bromophenyl)-3-(1-ethyl-1H-benzo[d][1,2,3]triazol-5-yl)-1,2,4-oxadiazole |
| 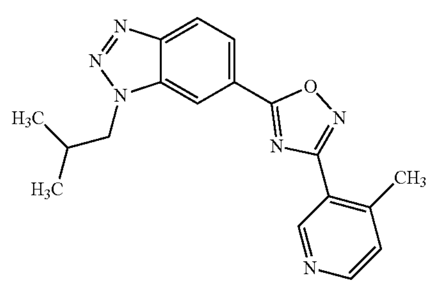 [SMILES: Cc1ccncc1-c1noc(-c2ccc3nnn(CC(C)C)c3c2)n1] | 3 | 1-(2-methylpropyl)-6-[3-(4-methylpyridin-3-yl)-1,2,4-oxadiazol-5-yl]-1H-1,2,3-benzotriazole |

-continued

| Structure | Compound Number | Chemical Name |
|---|---|---|
| 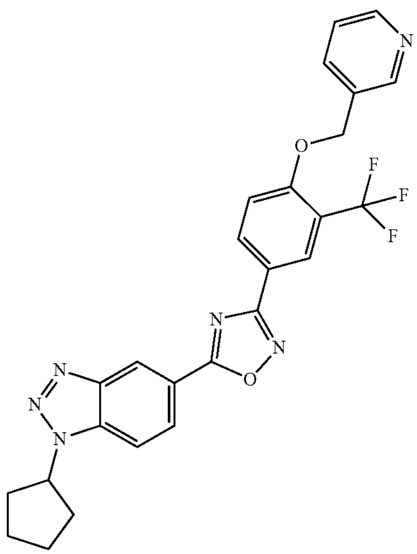 [SMILES: FC(F)(F)c1cc(-c2noc(-c3ccc4c(c3)nnn4C3CCCC3)n2)ccc1OCc1cccnc1] | 4 | 1-cyclopentyl-5-{3-[4-(pyridin-3-ylmethoxy)-3-(trifluoromethyl)phenyl]-1,2,4-oxadiazol-5-yl}-1H-1,2,3-benzotriazole |
| 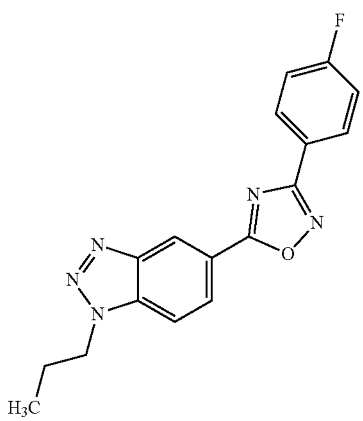 [SMILES: CCCn1nnc2cc(-c3nc(-c4ccc(F)cc4)no3)ccc21] | 5 | 5-[3-(4-fluorophenyl)-1,2,4-oxadiazol-5-yl]-1-propyl-1H-1,2,3-benzotriazole |
| 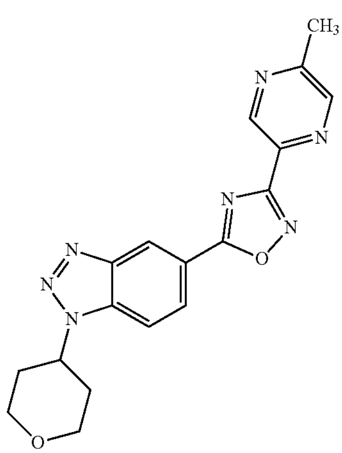 [SMILES: Cc1cnc(-c2noc(-c3ccc4c(c3)nnn4C3CCOCC3)n2)cn1] | 6 | 5-[3-(5-methylpyrazin-2-yl)-1,2,4-oxadiazol-5-yl]-1-(oxan-4-yl)-1H-1,2,3-benzotriazole |

-continued

| Structure | Compound Number | Chemical Name |
|---|---|---|
| 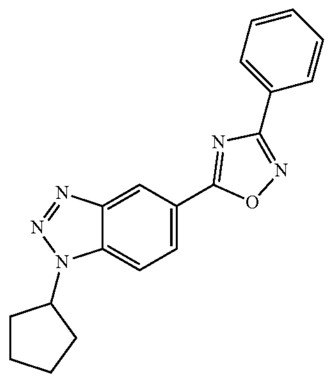 [SMILES: c1ccc(-c2noc(-c3ccc4c(c3)nnn4C3CCCC3)n2)cc1] | 7 | 1-cyclopentyl-5-(3-phenyl-1,2,4-oxadiazol-5-yl)-1H-1,2,3-benzotriazole |
| 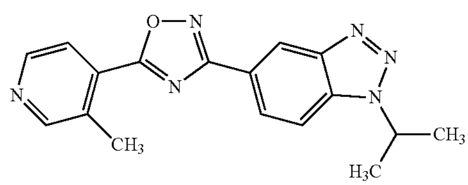 [SMILES: Cc1cnccc1-c1nc(-c2ccc3c(c2)nnn3C(C)C)no1] | 8 | 3-(1-isopropyl-1H-benzo[d][1,2,3]triazol-5-yl)-5-(3-methylpyridin-4-yl)-1,2,4-oxadiazole |
| 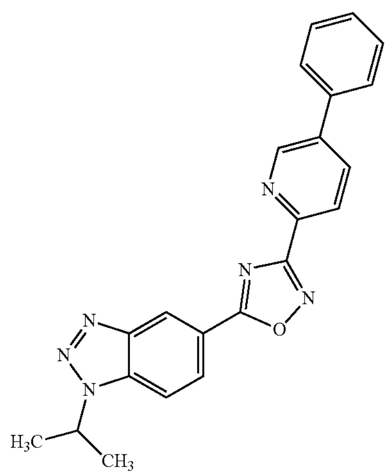 [SMILES: CC(C)n1nnc2cc(-c3nc(-c4ccc(-c5ccccc5)cn4)no3)ccc21] | 9 | 5-[3-(5-phenylpyridin-2-yl)-1,2,4-oxadiazol-5-yl]-1-(propan-2-yl)-1H-1,2,3-benzotriazole |
| 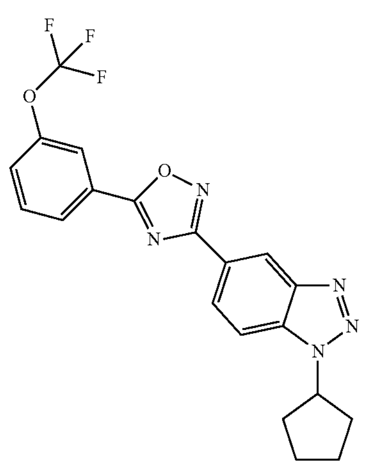 [SMILES: FC(F)(F)Oc1cccc(-c2nc(-c3ccc4c(c3)nnn4C3CCCC3)no2)c1] | 10 | 3-(1-cyclopentyl-1H-benzo[d][1,2,3]triazol-5-yl)-5-(3-(trifluoromethoxy)phenyl)-1,2,4-oxadiazole |

-continued

| Structure | Compound Number | Chemical Name |
|---|---|---|
| 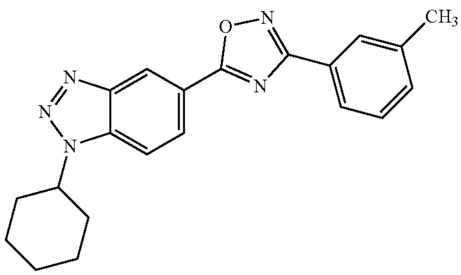 [SMILES: Cc1cccc(-c2noc(-c3ccc4c(c3)nnn4C3CCCCC3)n2)c1] | 11 | 1-cyclohexyl-5-[3-(3-methylphenyl)-1,2,4-oxadiazol-5-yl]-1H-1,2,3-benzotriazole |
| 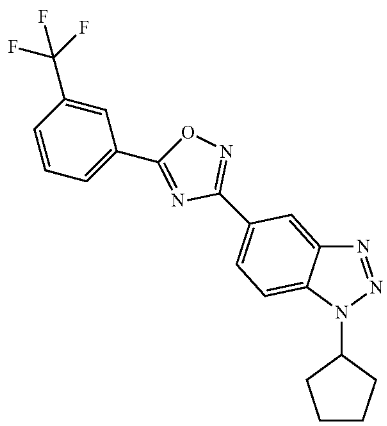 [SMILES: FC(F)(F)c1cccc(-c2nc(-c3ccc4c(c3)nnn4C3CCCC3)no2)c1] | 12 | 3-(1-cyclopentyl-1H-benzo[d][1,2,3]triazol-5-yl)-5-(3-(trifluoromethyl)phenyl)-1,2,4-oxadiazole |
| 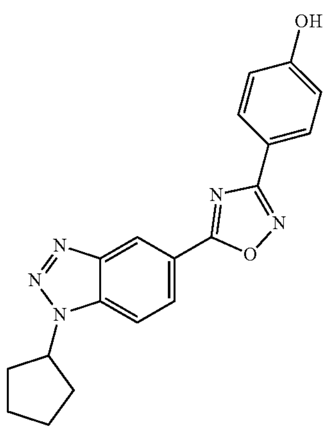 [SMILES: Oc1ccc(-c2noc(-c3ccc4c(c3)nnn4C3CCCC3)n2)cc1] | 13 | 4-[5-(1-cyclopentyl-1H-1,2,3-benzotriazol-5-yl)-1,2,4-oxadiazol-3-yl]phenol |
| 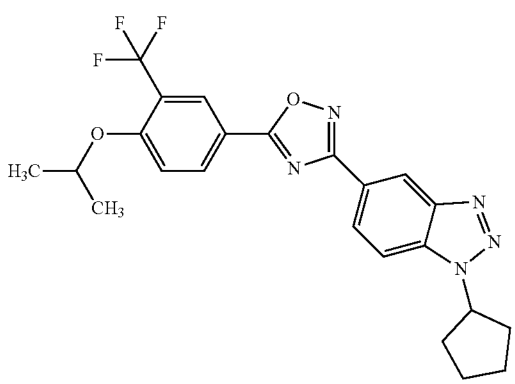 [SMILES: CC(C)Oc1ccc(-c2nc(-c3ccc4c(c3)nnn4C3CCCC3)no2)cc1C(F)(F)F] | 14 | 3-(1-cyclopentyl-1H-benzo[d][1,2,3]triazol-5-yl)-5-(4-isopropoxy-3-(trifluoromethyl)phenyl)-1,2,4-oxadiazole |

-continued

| Structure | Compound Number | Chemical Name |
|---|---|---|
| 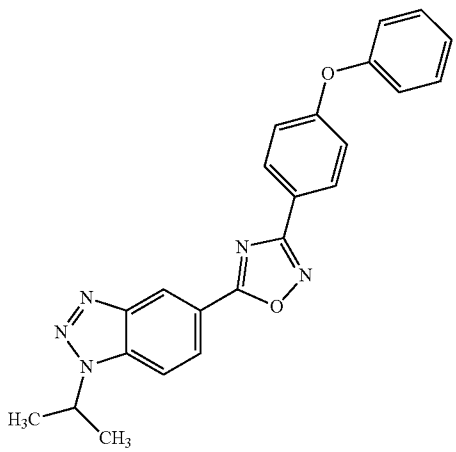 [SMILES: CC(C)n1nnc2cc(-c3nc(-c4ccc(Oc5ccccc5)cc4)no3)ccc21] | 15 | 5-[3-(4-phenoxyphenyl)-1,2,4-oxadiazol-5-yl]-1-(propan-2-yl)-1H-1,2,3-benzotriazole |
| 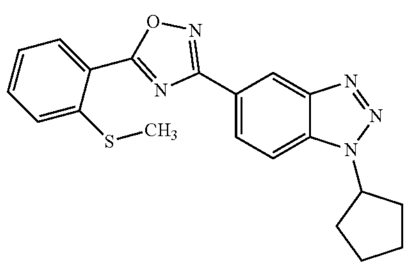 [SMILES: CSc1ccccc1-c1nc(-c2ccc3c(c2)nnn3C2CCCC2)no1] | 16 | 3-(1-cyclopentyl-1H-benzo[d][1,2,3]triazol-5-yl)-5-(2-(methylthio)phenyl)-1,2,4-oxadiazole |
| 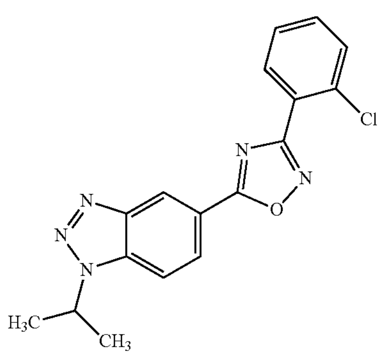 [SMILES: CC(C)n1nnc2cc(-c3nc(-c4ccccc4Cl)no3)ccc21] | 17 | 5-[3-(2-chlorophenyl)-1,2,4-oxadiazol-5-yl]-1-(propan-2-yl)-1H-1,2,3-benzotriazole |
| 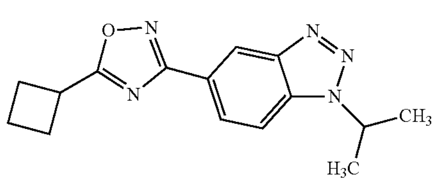 [SMILES: CC(C)n1nnc2cc(-c3noc(C4CCC4)n3)ccc21] | 18 | 5-(5-cyclobutyl-1,2,4-oxadiazol-3-yl)-1-(propan-2-yl)-1H-1,2,3-benzotriazole |

| Structure | Compound Number | Chemical Name |
|---|---|---|
| 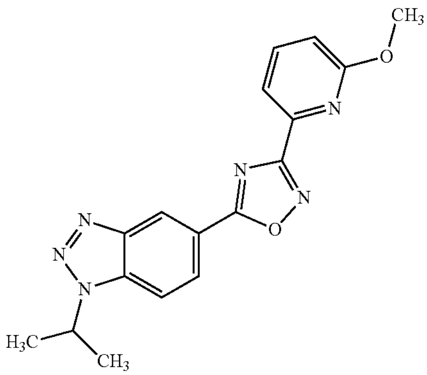 [SMILES: COc1cccc(-c2noc(-c3ccc4c(c3)nnn4C(C)C)n2)n1] | 19 | 5-[3-(6-methoxypyridin-2-yl)-1,2,4-oxadiazol-5-yl]-1-(propan-2-yl)-1H-1,2,3-benzotriazole |
| 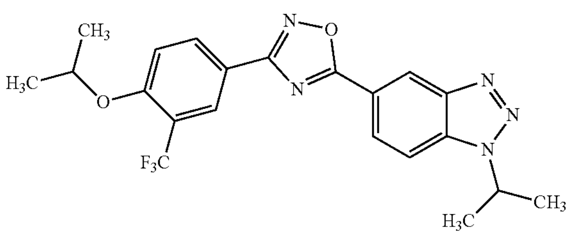 [SMILES: CC(C)Oc1ccc(-c2noc(-c3ccc4c(c3)nnn4C(C)C)n2)cc1C(F)(F)F] | 20 | 3-(4-isopropoxy-3-(trifluoromethyl)phenyl)-5-(1-isopropyl-1H-benzo[d][1,2,3]triazol-5-yl)-1,2,4-oxadiazole |
| 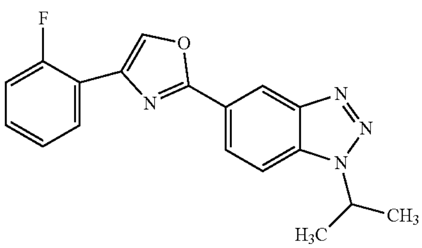 [SMILES: CC(C)n1nnc2cc(-c3nc(-c4ccccc4F)co3)ccc21] | 21 | 5-[4-(2-fluorophenyl)-1,3-oxazol-2-yl]-1-(propan-2-yl)-1H-1,2,3-benzotriazole |
| 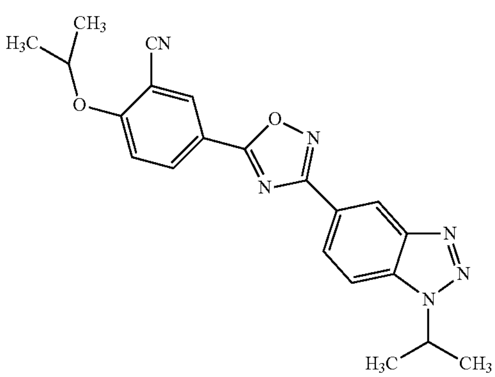 [SMILES: CC(C)Oc1ccc(-c2nc(-c3ccc4c(c3)nnn4C(C)C)no2)cc1C#N] | 22 | 2-isopropoxy-5-(3-(1-isopropyl-1H-benzo[d][1,2,3]triazol-5-yl)-1,2,4-oxadiazol-5-yl)benzonitrile |
| 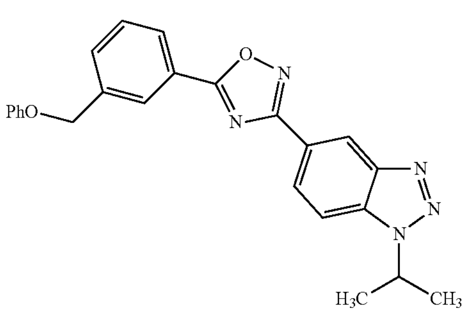 [SMILES: CC(C)n1nnc2cc(-c3noc(-c4cccc(COc5ccccc5)c4)n3)ccc21] | 23 | 3-(1-isopropyl-1H-benzo[d][1,2,3]triazol-5-yl)-5-(3-(phenoxymethyl)phenyl)-1,2,4-oxadiazole |

-continued

| Structure | Compound Number | Chemical Name |
|---|---|---|
| 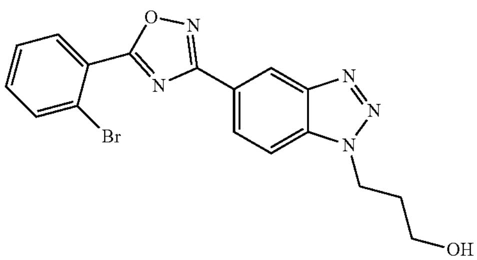 [SMILES: OCCCn1nnc2cc(-c3noc(-c4ccccc4Br)n3)ccc21] | 24 | 3-(5-(5-(2-bromophenyl)-1,2,4-oxadiazol-3-yl)-1H-benzo[d][1,2,3]triazol-1-yl)propan-1-ol |
| 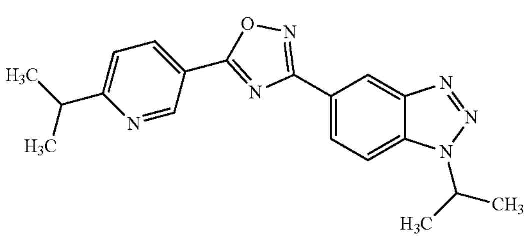 [SMILES: CC(C)c1ccc(-c2nc(-c3ccc4c(c3)nnn4C(C)C)no2)cn1] | 25 | 3-(1-isopropyl-1H-benzo[d][1,2,3]triazol-5-yl)-5-(6-isopropylpyridin-3-yl)-1,2,4-oxadiazole |
| 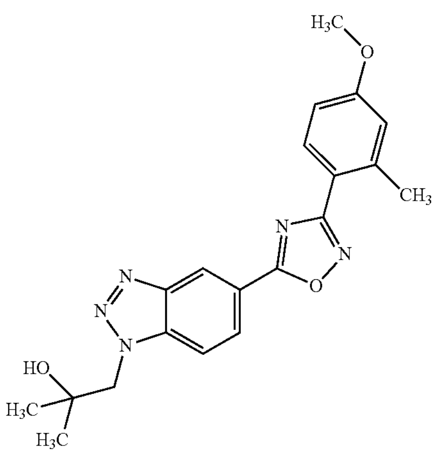 [SMILES: COc1ccc(-c2noc(-c3ccc4c(c3)nnn4CC(C)(C)O)n2)c(C)c1] | 26 | 1-{5-[3-(4-methoxy-2-methylphenyl)-1,2,4-oxadiazol-5-yl]-1H-1,2,3-benzotriazol-1-yl}-2-methylpropan-2-ol |
| 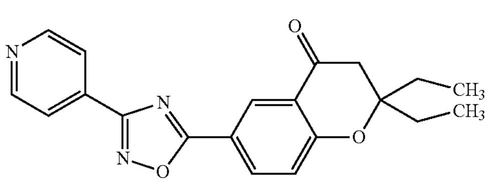 [SMILES: CCC1(CC)CC(=O)c2cc(-c3nc(-c4ccncc4)no3)ccc2O1] | 27 | 2,2-diethyl-6-[3-(pyridin-4-yl)-1,2,4-oxadiazol-5-yl]-3,4-dihydro-2H-1-benzopyran-4-one |
| 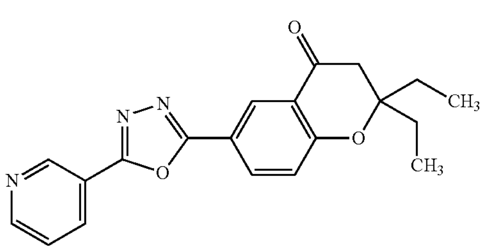 [SMILES: CCC1(CC)CC(=O)c2cc(-c3nnc(-c4cccnc4)o3)ccc2O1] | 28 | 2,2-diethyl-6-(5-(pyridin-3-yl)-1,3,4-oxadiazol-2-yl)chroman-4-one |

-continued

| Structure | Compound Number | Chemical Name |
|---|---|---|
| 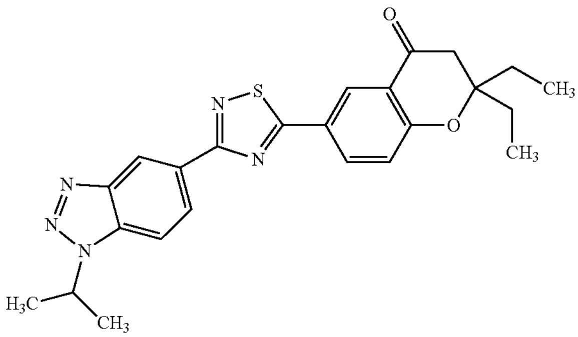 [SMILES: CCC1(CC)CC(=O)c2cc(-c3nc(-c4ccc5c(c4)nnn5C(C)C)ns3)ccc2O1] | 29 | 2,2-diethyl-6-(3-(1-isopropyl-1H-benzo[d][1,2,3]triazol-5-yl)-1,2,4-thiadiazol-5-yl)chroman-4-one |
| 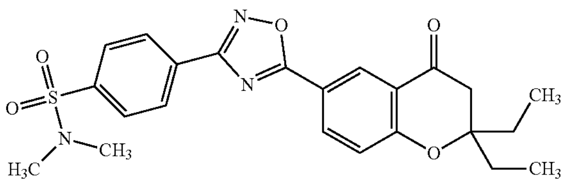 [SMILES: CCC1(CC)CC(=O)c2cc(-c3nc(-c4ccc(S(=O)(=O)N(C)C)cc4)no3)ccc2O1] | 30 | 4-(5-(2,2-diethyl-4-oxochroman-6-yl)-1,2,4-oxadiazol-3-yl)-N,N-dimethylbenzenesulfonamide |
| 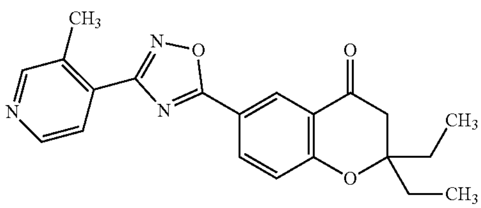 [SMILES: CCC1(CC)CC(=O)c2cc(-c3nc(-c4ccncc4C)no3)ccc2O1] | 31 | 2,2-diethyl-6-(3-(3-methylpyridin-4-yl)-1,2,4-oxadiazol-5-yl)chroman-4-one |
| 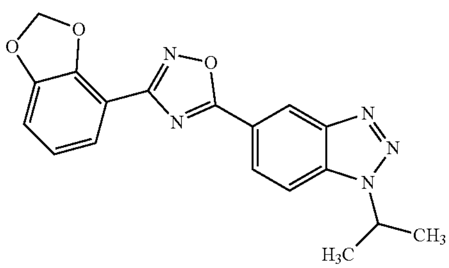 [SMILES: CC(C)n1nnc2cc(-c3nc(-c4cccc5c4OCO5)no3)ccc21] | 32 | 3-(benzo[d][1,3]dioxol-4-yl)-5-(1-isopropyl-1H-benzo[d][1,2,3]triazol-5-yl)-1,2,4-oxadiazole |
| 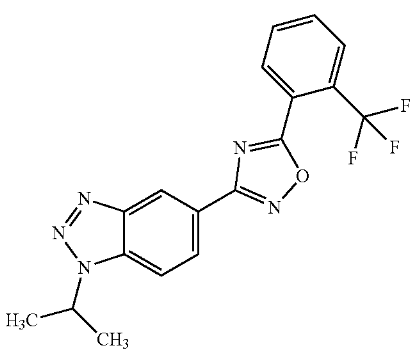 [SMILES: CC(C)n1nnc2cc(-c3noc(-c4ccccc4C(F)(F)F)n3)ccc21] | 33 | 3-(1-isopropylbenzotriazol-5-yl)-5-[2-(trifluoromethyl)phenyl]-1,2,4-oxadiazole |
| 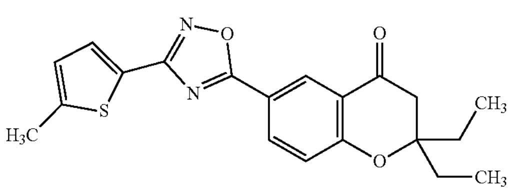 [SMILES: CCC1(CC)CC(=O)c2cc(-c3nc(-c4ccc(C)s4)no3)ccc2O1] | 34 | 2,2-diethyl-6-(3-(5-methylthiophen-2-yl)-1,2,4-oxadiazol-5-yl)chroman-4-one |

-continued

| Structure | Compound Number | Chemical Name |
|---|---|---|
| 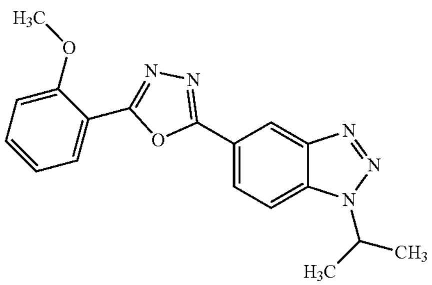 [SMILES: COc1ccccc1-c1nnc(-c2ccc3c(c2)nnn3C(C)C)o1] | 35 | 5-[5-(2-methoxyphenyl)-1,3,4-oxadiazol-2-yl]-1-(propan-2-yl)-1H-1,2,3-benzotriazole |
| 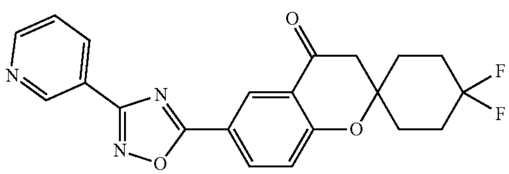 [SMILES: O=C1CC2(CCC(F)(F)CC2)Oc2ccc(-c3nc(-c4cccnc4)no3)cc21] | 36 | 4',4'-difluoro-6-[3-(pyridin-3-yl)-1,2,4-oxadiazol-5-yl]-3,4-dihydrospiro[1-benzopyran-2,1'-cyclohexane]-4-one |
| 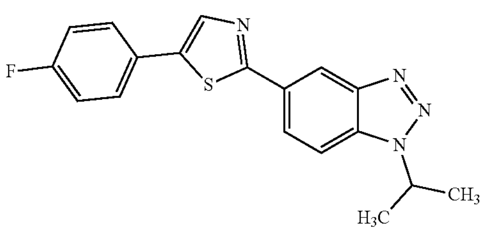 [SMILES: CC(C)n1nnc2cc(-c3ncc(-c4ccc(F)cc4)s3)ccc21] | 37 | 5-(4-fluorophenyl)-2-(1-isopropylbenzotriazol-5-yl)thiazole |
| 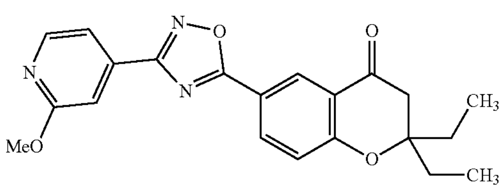 [SMILES: CCC1(CC)CC(=O)c2cc(-c3nc(-c4ccnc(OC)c4)no3)ccc2O1] | 38 | 2,2-diethyl-6-(3-(2-methoxypyridin-4-yl)-1,2,4-oxadiazol-5-yl)chroman-4-one |
| 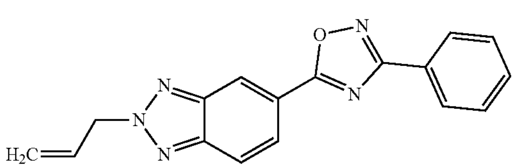 [SMILES: C=CCn1nc2ccc(-c3nc(-c4ccccc4)no3)cc2n1] | 39 | 5-(3-phenyl-1,2,4-oxadiazol-5-yl)-2-(prop-2-en-1-yl)-2H-1,2,3-benzotriazole |
| 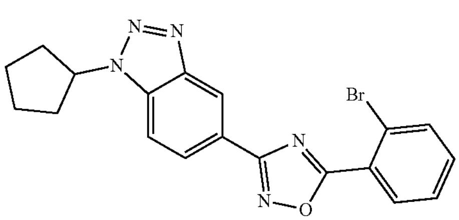 [SMILES: Brc1ccccc1-c1nc(-c2ccc3c(c2)nnn3C2CCCC2)no1] | 40 | 5-(2-bromophenyl)-3-(1-cyclopentyl-1H-benzo[d][1,2,3]triazol-5-yl)-1,2,4-oxadiazole |
| 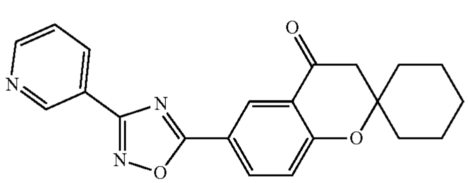 [SMILES: O=C1CC2(CCCCC2)Oc2ccc(-c3nc(-c4cccnc4)no3)cc21] | 41 | 6-[3-(pyridin-3-yl)-1,2,4-oxadiazol-5-yl]-3,4-dihydrospiro[1-benzopyran-2,1'-cyclohexane]-4-one |

-continued

| Structure | Compound Number | Chemical Name |
|---|---|---|
| 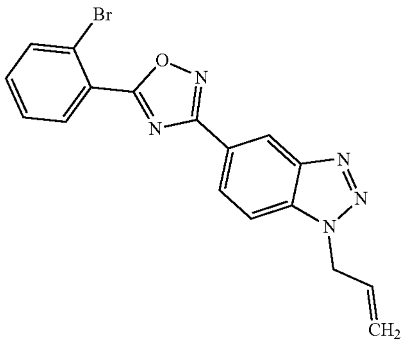 [SMILES: C=CCn1nnc2cc(-c3noc(-c4ccccc4Br)n3)ccc21] | 42 | 3-(1-allyl-1H-benzo[d][1,2,3]triazol-5-yl)-5-(2-bromophenyl)-1,2,4-oxadiazole |
| 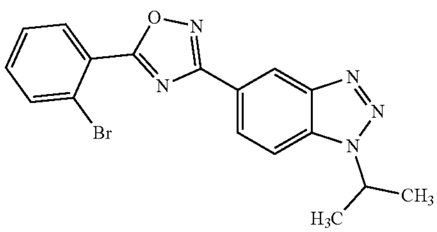 [SMILES: CC(C)n1nnc2cc(-c3noc(-c4ccccc4Br)n3)ccc21] | 43 | 5-(2-bromophenyl)-3-(1-isopropyl-1H-benzo[d][1,2,3]triazol-5-yl)-1,2,4-oxadiazole |
| 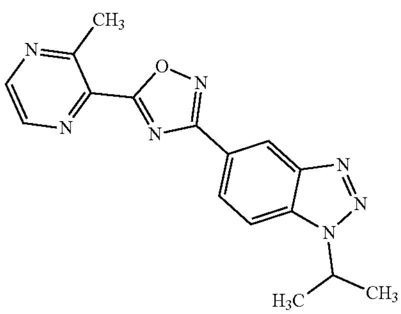 [SMILES: Cc1nccnc1-c1nc(-c2ccc3c(c2)nnn3C(C)C)no1] | 44 | 3-(1-isopropyl-1H-benzo[d][1,2,3]triazol-5-yl)-5-(3-methylpyrazin-2-yl)-1,2,4-oxadiazole |
| 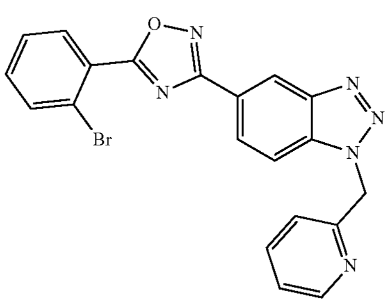 [SMILES: Brc1ccccc1-c1nc(-c2ccc3c(c2)nnn3Cc2ccccn2)no1] | 45 | 5-(2-bromophenyl)-3-(1-(pyridin-2-ylmethyl)-1H-benzo[d][1,2,3]triazol-5-yl)-1,2,4-oxadiazole |
| 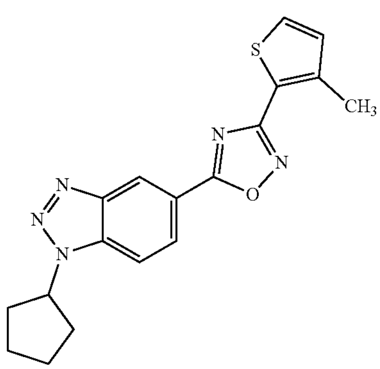 [SMILES: Cc1ccsc1-c1noc(-c2ccc3c(c2)nnn3C2CCCC2)n1] | 46 | 1-cyclopentyl-5-[3-(3-methylthiophen-2-yl)-1,2,4-oxadiazol-5-yl]-1H-1,2,3-benzotriazole |

-continued

| Structure | Compound Number | Chemical Name |
|---|---|---|
| 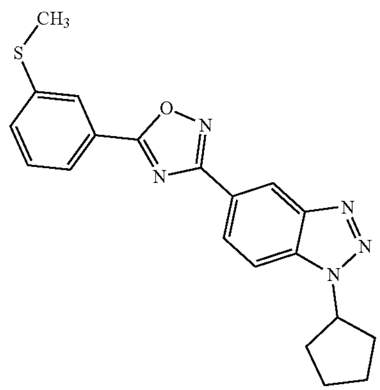 [SMILES: CSc1cccc(-c2nc(-c3ccc4c(c3)nnn4C3CCCC3)no2)c1] | 47 | 3-(1-cyclopentyl-1H-benzo[d][1,2,3]triazol-5-yl)-5-(3-(methylthio)phenyl)-1,2,4-oxadiazole |
| 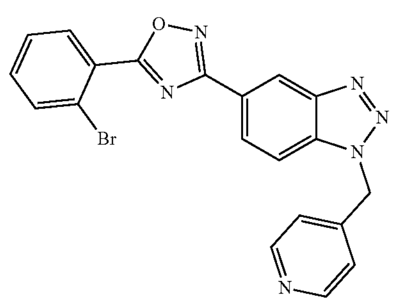 [SMILES: Brc1ccccc1-c1nc(-c2ccc3c(c2)nnn3Cc2ccncc2)no1] | 48 | 5-(2-bromophenyl)-3-(1-(pyridin-4-ylmethyl)-1H-benzo[d][1,2,3]triazol-5-yl)-1,2,4-oxadiazole |
| 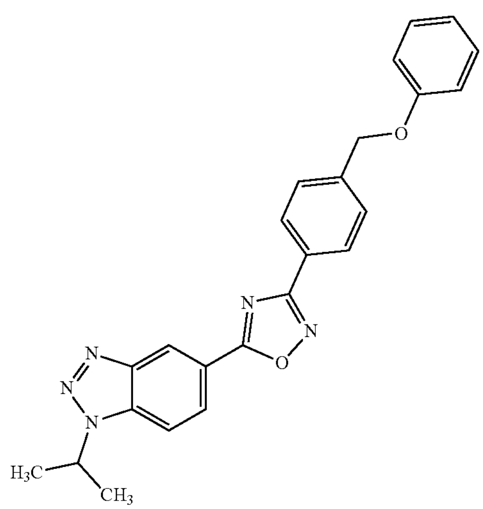 [SMILES: CC(C)n1nnc2cc(-c3nc(-c4ccc(COc5ccccc5)cc4)no3)ccc21] | 49 | 5-{3-[4-(phenoxymethyl)phenyl]-1,2,4-oxadiazol-5-yl}-1-(propan-2-yl)-1H-1,2,3-benzotriazole |
| 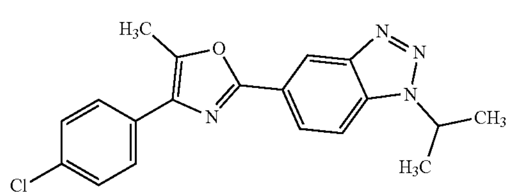 [SMILES: Cc1oc(-c2ccc3c(c2)nnn3C(C)C)nc1-c1ccc(Cl)cc1] | 50 | 5-[4-(4-chlorophenyl)-5-methyl-1,3-oxazol-2-yl]-1-(propan-2-yl)-1H-1,2,3-benzotriazole |

-continued

| Structure | Compound Number | Chemical Name |
|---|---|---|
| 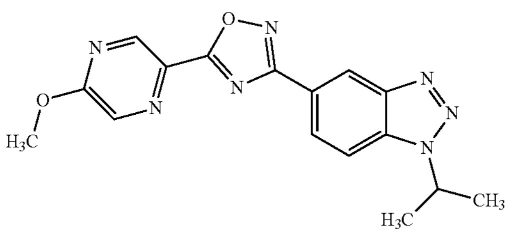 [SMILES: COc1cnc(-c2nc(-c3ccc4c(c3)nnn4C(C)C)no2)cn1] | 51 | 3-(1-isopropyl-1H-benzo[d][1,2,3]triazol-5-yl)-5-(5-methoxypyrazin-2-yl)-1,2,4-oxadiazole |
| 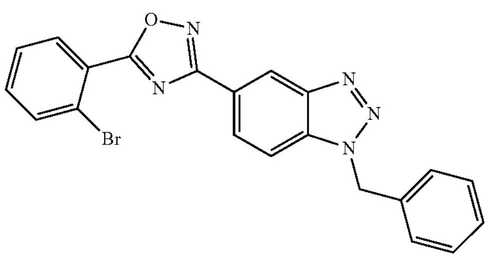 [SMILES: Brc1ccccc1-c1nc(-c2ccc3c(c2)nnn3Cc2ccccc2)no1] | 52 | 3-(1-benzyl-1H-benzo[d][1,2,3]triazol-5-yl)-5-(2-bromophenyl)-1,2,4-oxadiazole |
| 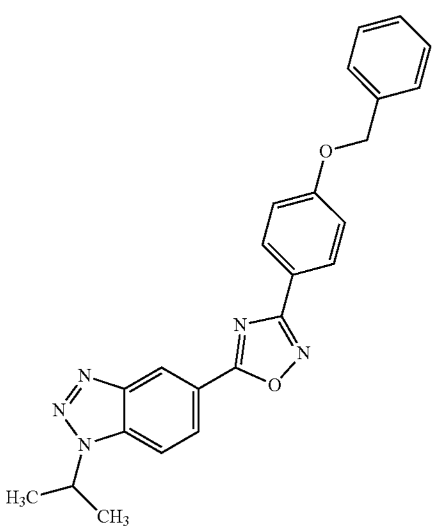 [SMILES: CC(C)n1nnc2cc(-c3nc(-c4ccc(OCc5ccccc5)cc4)no3)ccc21] | 53 | 5-{3-[4-(benzyloxy)phenyl]-1,2,4-oxadiazol-5-yl}-1-(propan-2-yl)-1H-1,2,3-benzotriazole |
| 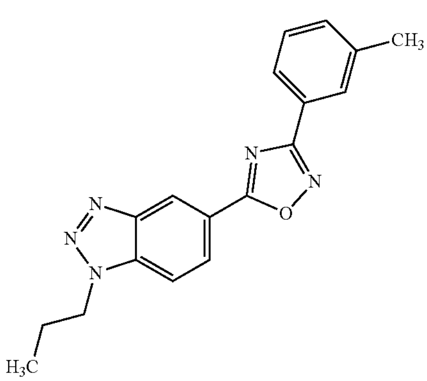 [SMILES: CCCn1nnc2cc(-c3nc(-c4cccc(C)c4)no3)ccc21] | 54 | 5-[3-(3-methylphenyl)-1,2,4-oxadiazol-5-yl]-1-propyl-1H-1,2,3-benzotriazole |

-continued

| Structure | Compound Number | Chemical Name |
|---|---|---|
| 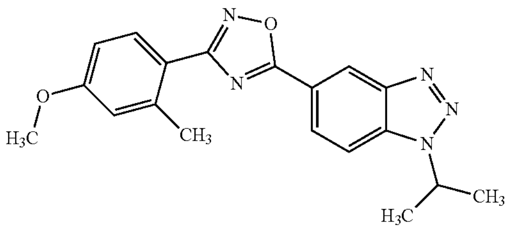 [SMILES: COc1ccc(-c2noc(-c3ccc4c(c3)nnn4C(C)C)n2)c(C)c1] | 55 | 5-(1-isopropyl-1H-benzo[d][1,2,3]triazol-5-yl)-3-(4-methoxy-2-methylphenyl)-1,2,4-oxadiazole |
| 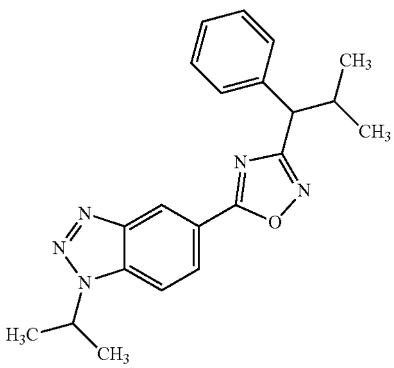 [SMILES: CC(C)C(c1ccccc1)c1noc(-c2ccc3c(c2)nnn3C(C)C)n1] | 56 | 5-[3-(2-methyl-1-phenylpropyl)-1,2,4-oxadiazol-5-yl]-1-(propan-2-yl)-1H-1,2,3-benzotriazole |
| 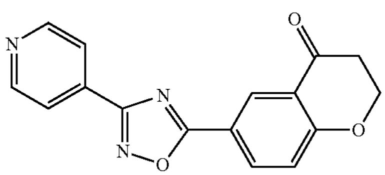 [SMILES: O=C1CCOc2ccc(-c3nc(-c4ccncc4)no3)cc21] | 57 | 6-[3-(pyridin-4-yl)-1,2,4-oxadiazol-5-yl]-3,4-dihydro-2H-1-benzopyran-4-one |
| 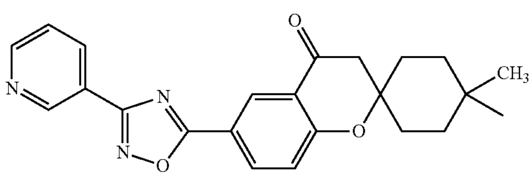 [SMILES: CC1(C)CCC2(CC1)CC(=O)c1cc(-c3nc(-c4cccnc4)no3)ccc1O2] | 58 | 4',4'-dimethyl-6-[3-(pyridin-3-yl)-1,2,4-oxadiazol-5-yl]-3,4-dihydrospiro[1-benzopyran-2,1'-cyclohexane]-4-one |
| 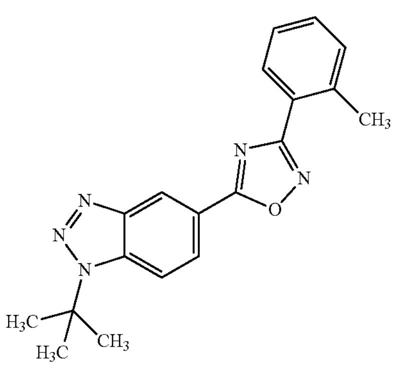 [SMILES: Cc1ccccc1-c1noc(-c2ccc3c(c2)nnn3C(C)(C)C)n1] | 59 | 1-tert-butyl-5-[3-(2-methylphenyl)-1,2,4-oxadiazol-5-yl]-1H-1,2,3-benzotriazole |
| 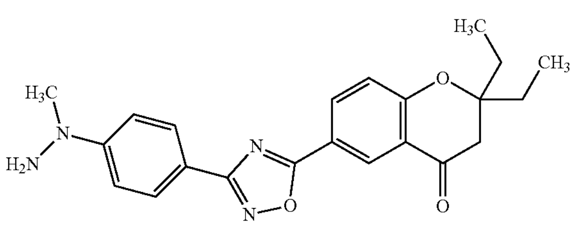 [SMILES: CCC1(CC)CC(=O)c2cc(-c3nc(-c4ccc(N(C)N)cc4)no3)ccc2O1] | 60 | 6-(3-(4-(dimethylamino)phenyl)-1,2,4-oxadiazol-5-yl)-2,2-diethylchroman-4-one |

-continued

| Structure | Compound Number | Chemical Name |
|---|---|---|
| 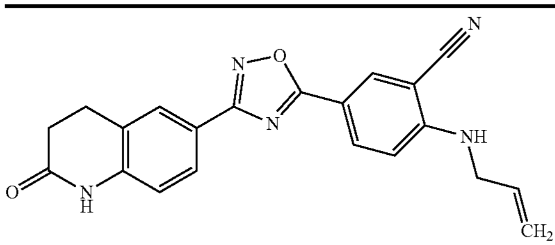 | 61 | 2-(allylamino)-5-(3-(2-oxo-1,2,3,4-tetrahydroquinolin-6-yl)-1,2,4-oxadiazol-5-yl)benzonitrile |
| 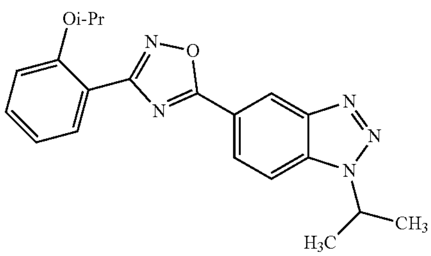 | 62 | 3-(2-isopropoxyphenyl)-5-(1-isopropyl-1H-benzo[d][1,2,3]triazol-5-yl)-1,2,4-oxadiazole |
| 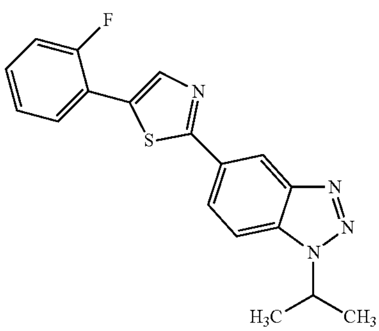 [SMILES: CC(C)n1nnc2cc(-c3ncc(-c4ccccc4F)s3)ccc21] | 63 | 5-(2-fluorophenyl)-2-(1-isopropyl-1H-benzo[d][1,2,3]triazol-5-yl)thiazole |
| 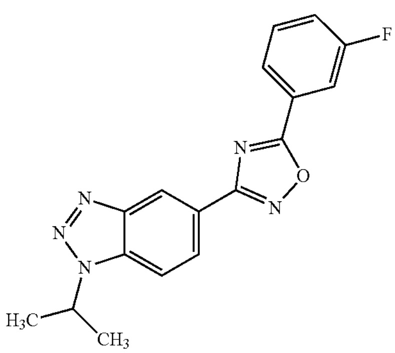 [SMILES: CC(C)n1nnc2cc(-c3noc(-c4cccc(F)c4)n3)ccc21] | 64 | 5-(3-fluorophenyl)-3-(1-isopropylbenzotriazol-5-yl)-1,2,4-oxadiazole |
| 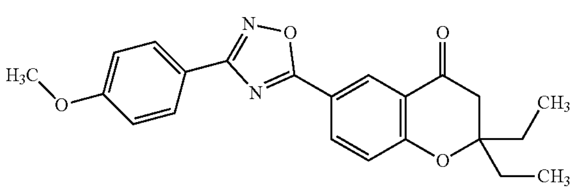 [SMILES: CCC1(CC)CC(=O)c2cc(-c3nc(-c4ccc(OC)cc4)no3)ccc2O1] | 65 | 2,2-diethyl-6-(3-(4-methoxyphenyl)-1,2,4-oxadiazol-5-yl)chroman-4-one |
| 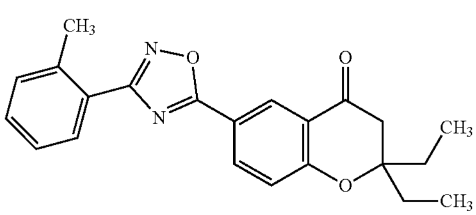 | 66 | 2,2-diethyl-6-(3-(o-tolyl)-1,2,4-oxadiazol-5-yl)chroman-4-one |

| Structure | Compound Number | Chemical Name |
|---|---|---|
| 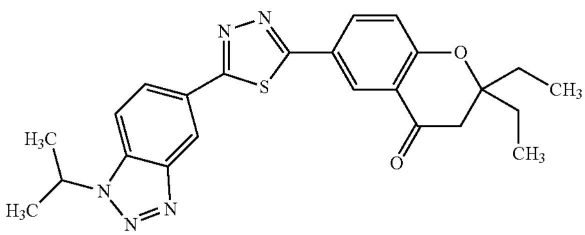 [SMILES: CCC1(CC)CC(=O)c2cc(-c3nnc(-c4ccc5c(c4)nnn5C(C)C)s3)ccc2O1] | 67 | 2,2-diethyl-6-(5-(1-isopropyl-1H-benzo[d][1,2,3]triazol-5-yl)-1,3,4-thiadiazol-2-yl)chroman-4-one |
| 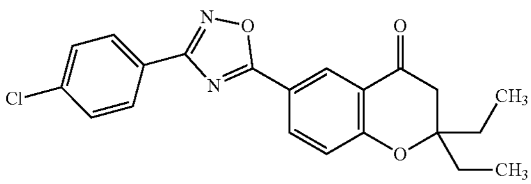 [SMILES: CCC1(CC)CC(=O)c2cc(-c3nc(-c4ccc(Cl)cc4)no3)ccc2O1] | 68 | 6-[3-(4-chlorophenyl)-1,2,4-oxadiazol-5-yl]-2,2-diethyl-chroman-4-one |
| 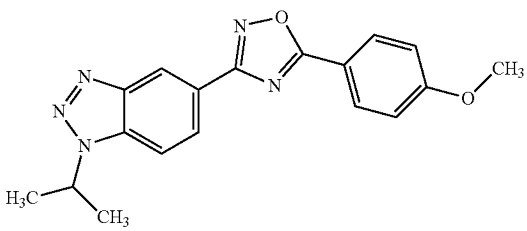 [SMILES: COc1ccc(-c2nc(-c3ccc4c(c3)nnn4C(C)C)no2)cc1] | 69 | 3-(1-isopropylbenzotriazol-5-yl)-5-(4-methoxyphenyl)-1,2,4-oxadiazole |
| 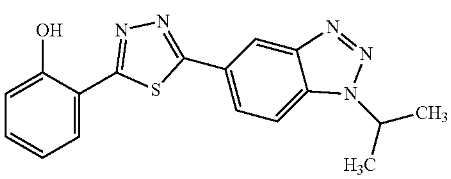 [SMILES: CC(C)n1nnc2cc(-c3nnc(-c4ccccc4O)s3)ccc21] | 70 | 2-{5-[1-(propan-2-yl)-1H-1,2,3-benzotriazol-5-yl]-1,3,4-thiadiazol-2-yl}phenol |
| 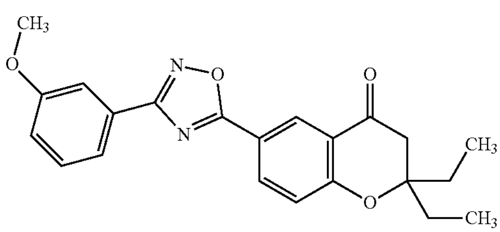 [SMILES: CCC1(CC)CC(=O)c2cc(-c3nc(-c4cccc(OC)c4)no3)ccc2O1] | 71 | 2,2-diethyl-6-(3-(3-methoxyphenyl)-1,2,4-oxadiazol-5-yl)chroman-4-one |
| 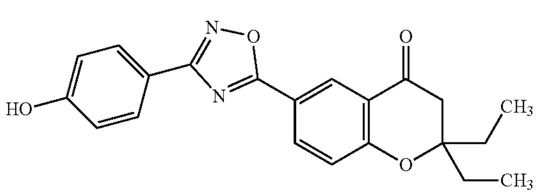 [SMILES: CCC1(CC)CC(=O)c2cc(-c3nc(-c4ccc(O)cc4)no3)ccc2O1] | 72 | 2,2-diethyl-6-[3-(4-hydroxyphenyl)-1,2,4-oxadiazol-5-yl]chroman-4-one |
| 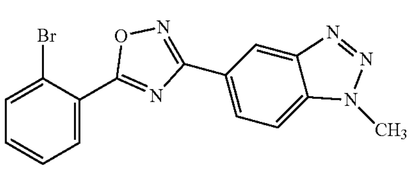 [SMILES: Cn1nnc2cc(-c3noc(-c4ccccc4Br)n3)ccc21] | 73 | 5-(2-bromophenyl)-3-(1-methyl-1H-benzo[d][1,2,3]triazol-5-yl)-1,2,4-oxadiazole |

-continued

| Structure | Compound Number | Chemical Name |
|---|---|---|
| 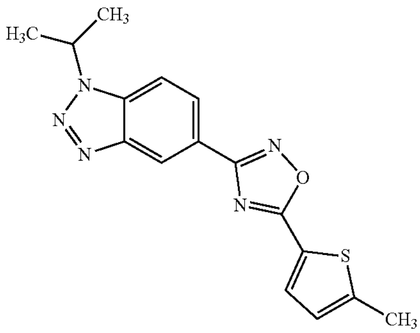 [SMILES: Cc1ccc(-c2nc(-c3ccc4c(c3)nnn4C(C)C)no2)s1] | 74 | 5-[5-(5-methylthiophen-2-yl)-1,2,4-oxadiazol-3-yl]-1-(propan-2-yl)-1H-1,2,3-benzotriazole |
| 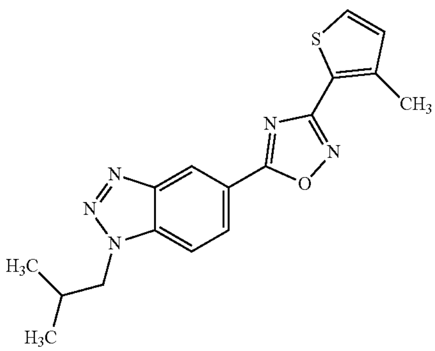 [SMILES: Cc1ccsc1-c1noc(-c2ccc3c(c2)nnn3CC(C)C)n1] | 75 | 1-(2-methylpropyl)-5-[3-(3-methylthiophen-2-yl)-1,2,4-oxadiazol-5-yl]-1H-1,2,3-benzotriazole |
| 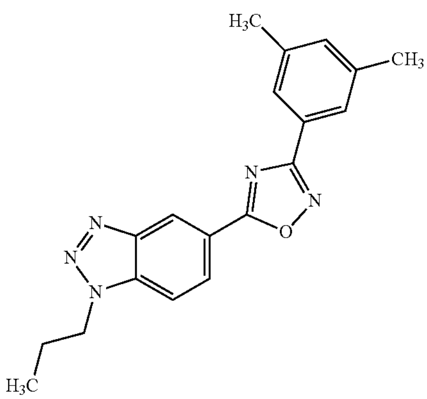 [SMILES: CCCn1nnc2cc(-c3nc(-c4cc(C)cc(C)c4)no3)ccc21] | 76 | 5-[3-(3,5-dimethylphenyl)-1,2,4-oxadiazol-5-yl]-1-propyl-1H-1,2,3-benzotriazole |
| 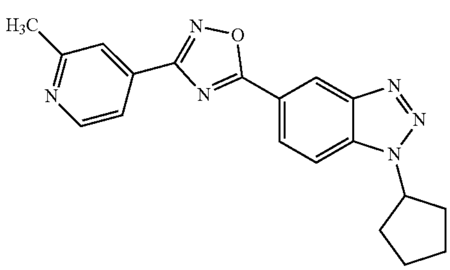 [SMILES: Cc1cc(-c2noc(-c3ccc4c(c3)nnn4C3CCCC3)n2)ccn1] | 77 | 5-[3-(2-methoxypyridin-4-yl)-1,2,4-oxadiazol-5-yl]-1-methyl-2,3-dihydro-1H-1,2,3-benzotriazole; cyclopentane |
| 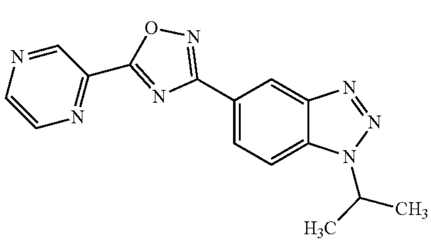 [SMILES: CC(C)n1nnc2cc(-c3noc(-c4cnccn4)n3)ccc21] | 78 | 3-(1-isopropyl-1H-benzo[d][1,2,3]triazol-5-yl)-5-(pyrazin-2-yl)-1,2,4-oxadiazole |

-continued

| Structure | Compound Number | Chemical Name |
|---|---|---|
| 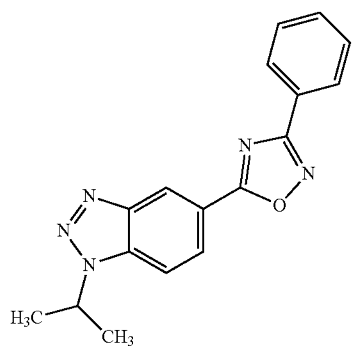 [SMILES: CC(C)n1nnc2cc(-c3nc(-c4ccccc4)no3)ccc21] | 79 | 5-(3-phenyl-1,2,4-oxadiazol-5-yl)-1-(propan-2-yl)-1H-1,2,3-benzotriazole |
| 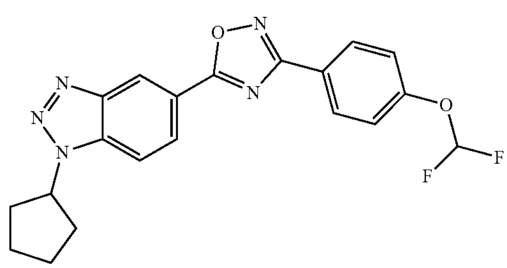 [SMILES: FC(F)Oc1ccc(-c2noc(-c3ccc4c(c3)nnn4C3CCCC3)n2)cc1] | 80 | 1-cyclopentyl-5-{3-[4-(difluoromethoxy)phenyl]-1,2,4-oxadiazol-5-yl}-1H-1,2,3-benzotriazole |
| 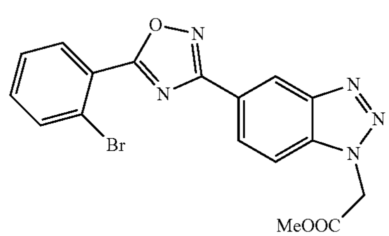 [SMILES: COC(=O)Cn1nnc2cc(-c3noc(-c4ccccc4Br)n3)ccc21] | 81 | methyl 2-(5-(5-(2-bromophenyl)-1,2,4-oxadiazol-3-yl)-1H-benzo[d][1,2,3]triazol-1-yl)acetate |
| 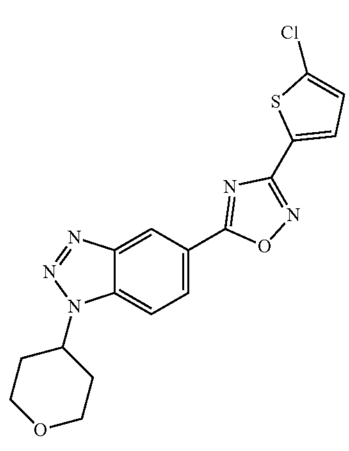 [SMILES: Clc1ccc(-c2noc(-c3ccc4c(c3)nnn4C3CCOCC3)n2)s1] | 82 | 5-[3-(5-chlorothiophen-2-yl)-1,2,4-oxadiazol-5-yl]-1-(oxan-4-yl)-1H-1,2,3-benzotriazole |

-continued
| Structure | Compound Number | Chemical Name |
|---|---|---|
| 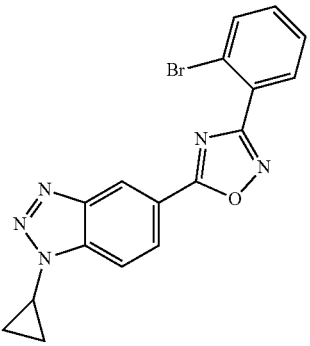 [SMILES: Brc1ccccc1-c1noc(-c2ccc3c(c2)nnn3C2CC2)n1] | 83 | 5-[3-(2-bromophenyl)-1,2,4-oxadiazol-5-yl]-1-cyclopropyl-1H-1,2,3-benzotriazole |
| 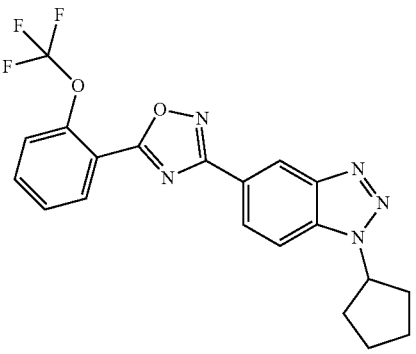 [SMILES: FC(F)(F)Oc1ccccc1-c1nc(-c2ccc3c(c2)nnn3C2CCCC2)no1] | 84 | 3-(1-cyclopentyl-1H-benzo[d][1,2,3]triazol-5-yl)-5-(2-(trifluoromethoxy)phenyl)-1,2,4-oxadiazole |
| 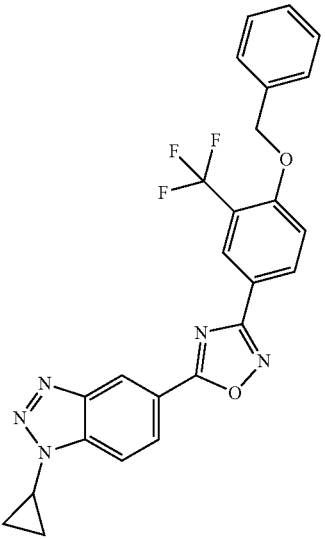 [SMILES: FC(F)(F)c1cc(-c2noc(-c3ccc4c(c3)nnn4C3CC3)n2)ccc1OCc1ccccc1] | 85 | 5-{3-[4-(benzyloxy)-3-(trifluoromethyl)phenyl]-1,2,4-oxadiazol-5-yl}-1-cyclopropyl-1H-1,2,3-benzotriazole |
| 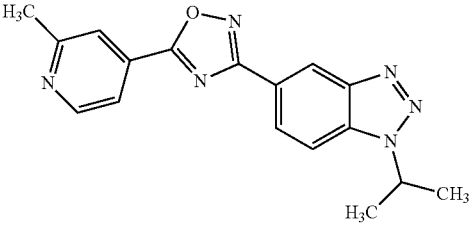 [SMILES: Cc1cc(-c2nc(-c3ccc4c(c3)nnn4C(C)C)no2)ccn1] | 86 | 3-(1-isopropyl-1H-benzo[d][1,2,3]triazol-5-yl)-5-(2-methylpyridin-4-yl)-1,2,4-oxadiazole |

-continued

| Structure | Compound Number | Chemical Name |
|---|---|---|
| 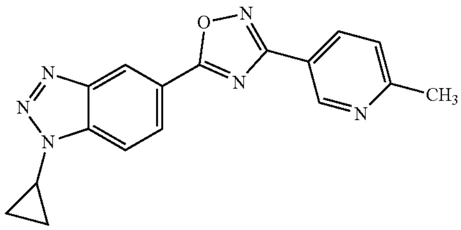 [SMILES: Cc1ccc(-c2noc(-c3ccc4c(c3)nnn4C3CC3)n2)cn1] | 87 | 1-cyclopropyl-5-[3-(6-methylpyridin-3-yl)-1,2,4-oxadiazol-5-yl]-1H-1,2,3-benzotriazole |
| 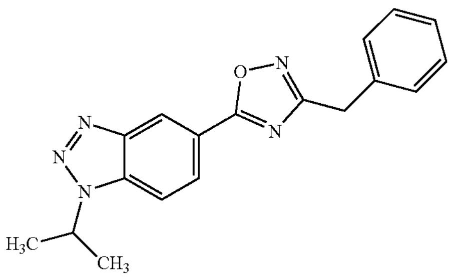 [SMILES: CC(C)n1nnc2cc(-c3nc(Cc4ccccc4)no3)ccc21] | 88 | 5-(3-benzyl-1,2,4-oxadiazol-5-yl)-1-(propan-2-yl)-1H-1,2,3-benzotriazole |
| 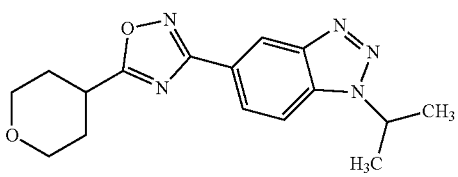 [SMILES: CC(C)n1nnc2cc(-c3noc(C4CCOCC4)n3)ccc21] | 89 | 5-[5-(oxan-4-yl)-1,2,4-oxadiazol-3-yl]-1-(propan-2-yl)-1H-1,2,3-benzotriazole |
| 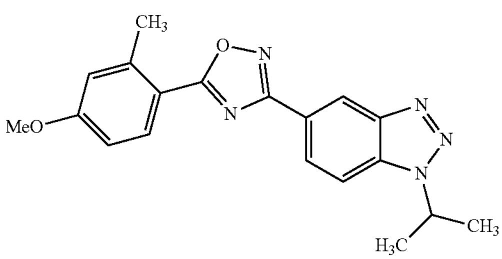 [SMILES: COc1ccc(-c2nc(-c3ccc4c(c3)nnn4C(C)C)no2)c(C)c1] | 90 | 3-(1-isopropyl-1H-benzo[d][1,2,3]triazol-5-yl)-5-(4-methoxy-2-methylphenyl)-1,2,4-oxadiazole |
| 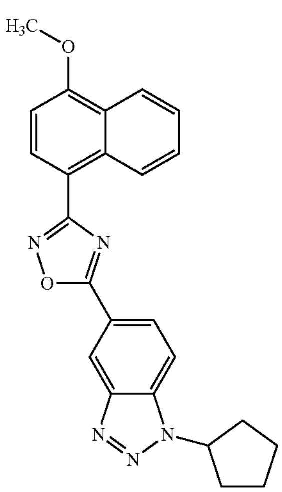 [SMILES: COc1ccc(-c2noc(-c3ccc4c(c3)nnn4C3CCCC3)n2)c2ccccc12] | 91 | 1-cyclopentyl-5-[3-(4-methoxynaphthalen-1-yl)-1,2,4-oxadiazol-5-yl]-1H-1,2,3-benzotriazole |

-continued

| Structure | Compound Number | Chemical Name |
|---|---|---|
| 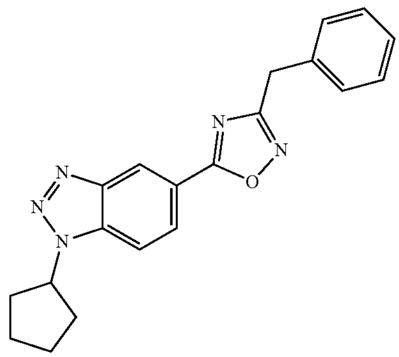 [SMILES: c1ccc(Cc2noc(-c3ccc4c(c3)nnn4C3CCCC3)n2)cc1] | 92 | 5-(3-benzyl-1,2,4-oxadiazol-5-yl)-1-cyclopentyl-1H-1,2,3-benzotriazole |
| 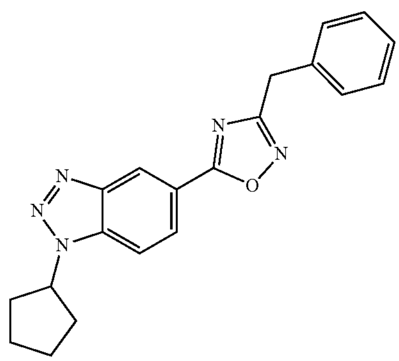 [SMILES: c1ccc(Cc2noc(-c3ccc4c(c3)nnn4C3CCCC3)n2)cc1] | 93 | 5-[3-(3,5-dimethylphenyl)-1,2,4-oxadiazol-5-yl]-1-(oxan-4-yl)-1H-1,2,3-benzotriazole |
| 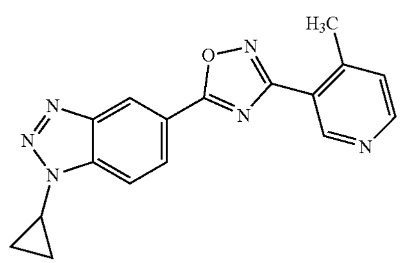 [SMILES: Cc1ccncc1-c1noc(-c2ccc3c(c2)nnn3C2CC2)n1] | 94 | 1-cyclopropyl-5-[3-(4-methylpyridin-3-yl)-1,2,4-oxadiazol-5-yl]-1H-1,2,3-benzotriazole |
| 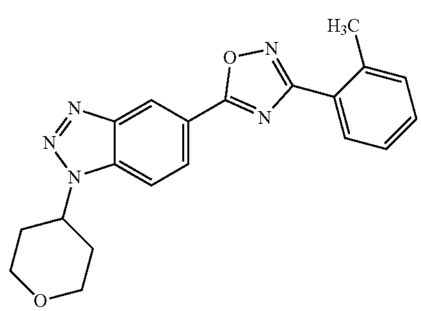 [SMILES: Cc1ccccc1-c1noc(-c2ccc3c(c2)nnn3C2CCOCC2)n1] | 95 | 5-[3-(2-methylphenyl)-1,2,4-oxadiazol-5-yl]-1-(oxan-4-yl)-1H-1,2,3-benzotriazole |
| 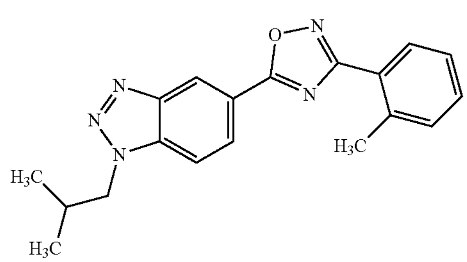 [SMILES: Cc1ccccc1-c1noc(-c2ccc3c(c2)nnn3CC(C)C)n1] | 96 | 5-[3-(2-methylphenyl)-1,2,4-oxadiazol-5-yl]-1-(2-methylpropyl)-1H-1,2,3-benzotriazole |

-continued

| Structure | Compound Number | Chemical Name |
|---|---|---|
| 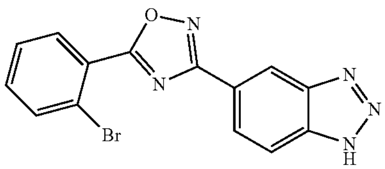 [SMILES: Brc1ccccc1-c1nc(-c2ccc3[nH]nnc3c2)no1] | 97 | 3-(1H-benzo[d][1,2,3]triazol-5-yl)-5-(2-bromophenyl)-1,2,4-oxadiazole |
| 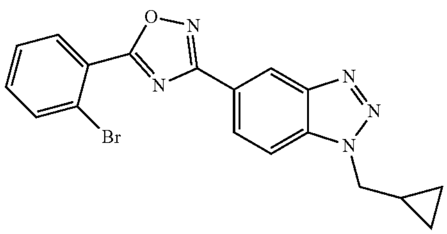 [SMILES: Brc1ccccc1-c1nc(-c2ccc3c(c2)nnn3CC2CC2)no1] | 98 | 5-(2-bromophenyl)-3-(1-(cyclopropylmethyl)-1H-benzo[d][1,2,3]triazol-5-yl)-1,2,4-oxadiazole |
| 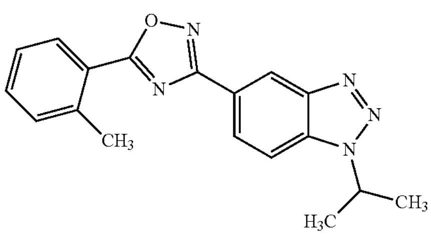 | 99 | 3-(1-isopropyl-1H-benzo[d][1,2,3]triazol-5-yl)-5-(o-tolyl)-1,2,4-oxadiazole |
| 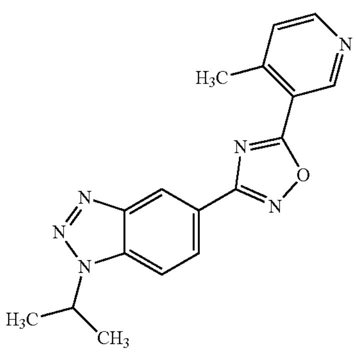 [SMILES: Cc1ccncc1-c1nc(-c2ccc3c(c2)nnn3C(C)C)no1] | 100 | 3-(1-isopropyl-1H-benzo[d][1,2,3]triazol-5-yl)-5-(4-methylpyridin-3-yl)-1,2,4-oxadiazole |
| 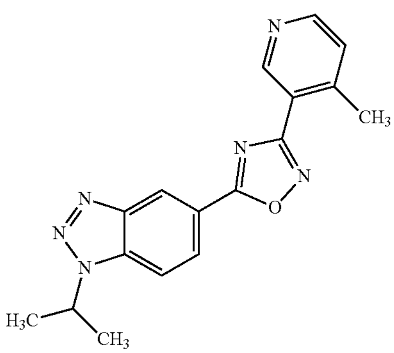 [SMILES: Cc1ccncc1-c1noc(-c2ccc3c(c2)nnn3C(C)C)n1] | 101 | 5-[3-(4-methylpyridin-3-yl)-1,2,4-oxadiazol-5-yl]-1-(propan-2-yl)-1H-1,2,3-benzotriazole |
| 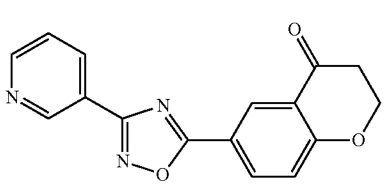 [SMILES: O=C1CCOc2ccc(-c3nc(-c4cccnc4)no3)cc21] | 102 | 6-[3-(pyridin-3-yl)-1,2,4-oxadiazol-5-yl]-3,4-dihydro-2H-1-benzopyran-4-one |

-continued

| Structure | Compound Number | Chemical Name |
|---|---|---|
| 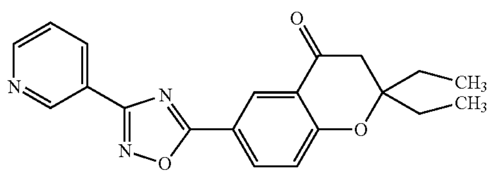 [SMILES: CCC1(CC)CC(=O)c2cc(-c3nc(-c4cccnc4)no3)ccc2O1] | 103 | 2,2-diethyl-6-[3-(pyridin-3-yl)-1,2,4-oxadiazol-5-yl]-3,4-dihydro-2H-1-benzopyran-4-one |
| 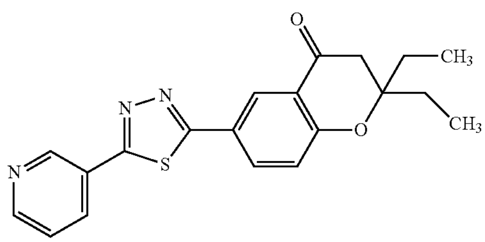 [SMILES: CCC1(CC)CC(=O)c2cc(-c3nnc(-c4cccnc4)s3)ccc2O1] | 104 | 2,2-diethyl-6-(5-(pyridin-3-yl)-1,3,4-thiadiazol-2-yl)chroman-4-one |
| 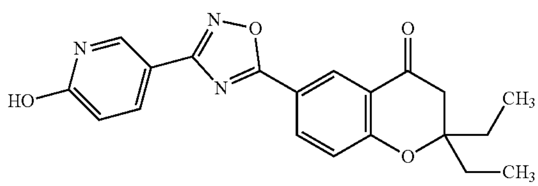 [SMILES: CCC1(CC)CC(=O)c2cc(-c3nc(-c4ccc(O)nc4)no3)ccc2O1] | 105 | 2,2-diethyl-6-[3-(6-hydroxy-3-pyridyl)-1,2,4-oxadiazol-5-yl]chroman-4-one |
| 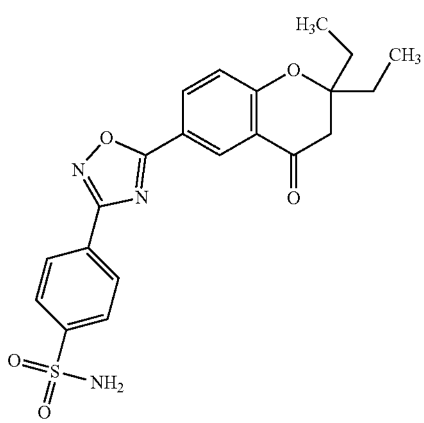 [SMILES: CCC1(CC)CC(=O)c2cc(-c3nc(-c4ccc(S(N)(=O)=O)cc4)no3)ccc2O1] | 106 | 4-(5-(2,2-diethyl-4-oxochroman-6-yl)-1,2,4-oxadiazol-3-yl)benzenesulfonamide |
| 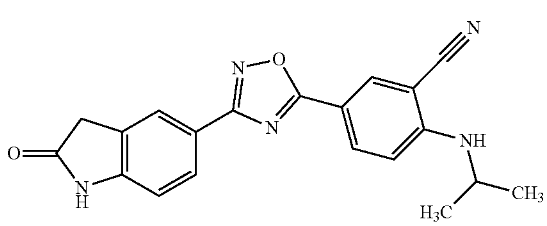 [SMILES: CC(C)Nc1ccc(-c2nc(-c3ccc4c(c3)CC(=O)N4)no2)cc1C#N] | 107 | 2-(isopropylamino)-5-(3-(2-oxoindolin-5-yl)-1,2,4-oxadiazol-5-yl)benzonitrile |

-continued
| Structure | Compound Number | Chemical Name |
|---|---|---|
| 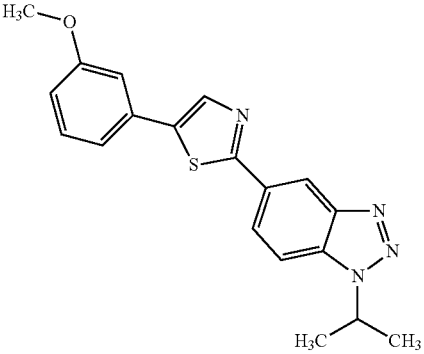 [SMILES: COc1cccc(-c2cnc(-c3ccc4c(c3)nnn4C(C)C)s2)c1] | 108 | 2-(1-isopropyl-1H-benzo[d][1,2,3]triazol-5-yl)-5-(3-methoxyphenyl)thiazole |
| 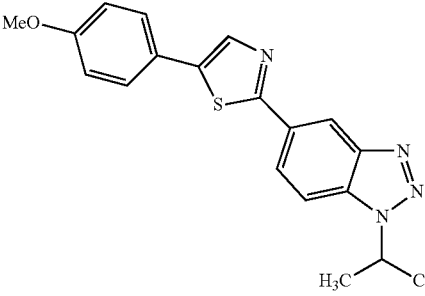 | 109 | 2-(1-isopropyl-1H-benzo[d][1,2,3]triazol-5-yl)-5-(4-methoxyphenyl)thiazole |
| 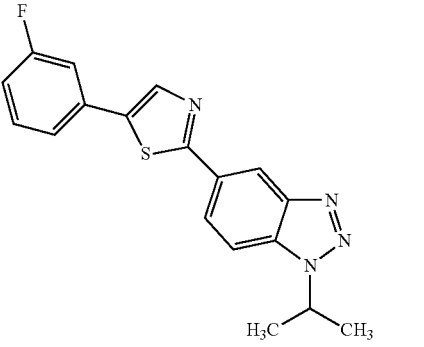 [SMILES: CC(C)n1nnc2cc(-c3ncc(-c4cccc(F)c4)s3)ccc21] | 110 | 5-(3-fluorophenyl)-2-(1-isopropyl-1H-benzo[d][1,2,3]triazol-5-yl)thiazole |
| 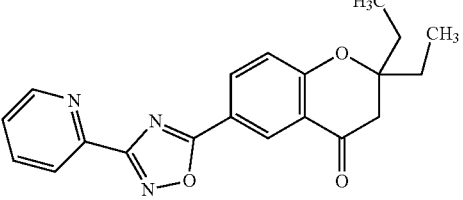 | 111 | 2,2-diethyl-6-[3-(2-pyridyl)-1,2,4-oxadiazol-5-yl]chroman-4-one |
| 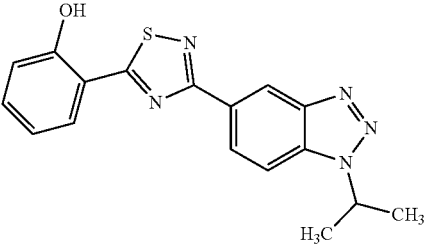 | 112 | 2-{3-[1-(propan-2-yl)-1H-1,2,3-benzotriazol-5-yl]-1,2,4-thiadiazol-5-yl}phenol |

-continued

| Structure | Compound Number | Chemical Name |
|---|---|---|
| 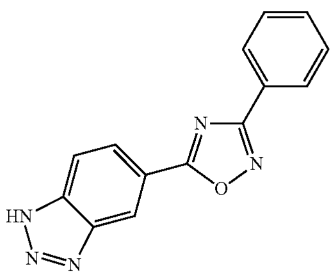 [SMILES: c1ccc(-c2noc(-c3ccc4[nH]nnc4c3)n2)cc1] | 113 | 5-(3-phenyl-1,2,4-oxadiazol-5-yl)-1H-1,2,3-benzotriazole |
| 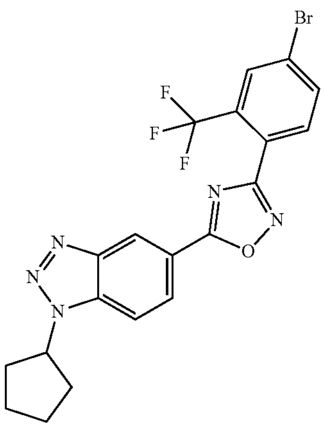 [SMILES: FC(F)(F)c1cc(Br)ccc1-c1noc(-c2ccc3c(c2)nnn3C2CCCC2)n1] | 114 | 5-{3-[4-bromo-2-(trifluoromethyl)phenyl]-1,2,4-oxadiazol-5-yl}-1-cyclopentyl-1H-1,2,3-benzotriazole |
| 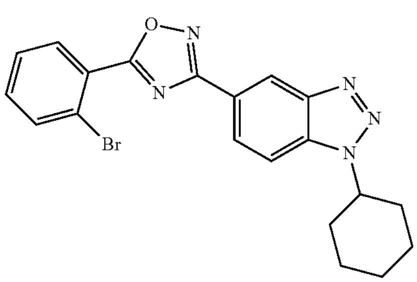 [SMILES: Brc1ccccc1-c1nc(-c2ccc3c(c2)nnn3C2CCCCC2)no1] | 115 | 5-(2-bromophenyl)-3-(1-cyclohexyl-1H-benzo[d][1,2,3]triazol-5-yl)-1,2,4-oxadiazole |
| 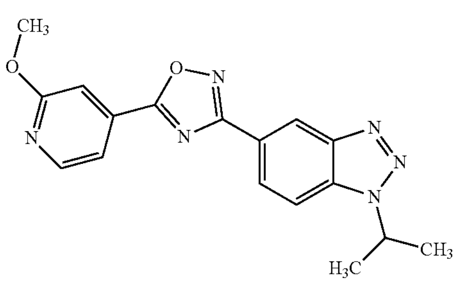 | 116 | 3-(1-isopropyl-1H-benzo[d][1,2,3]triazol-5-yl)-5-(2-methoxypyridin-4-yl)-1,2,4-oxadiazole |

-continued
| Structure | Compound Number | Chemical Name |
|---|---|---|
| 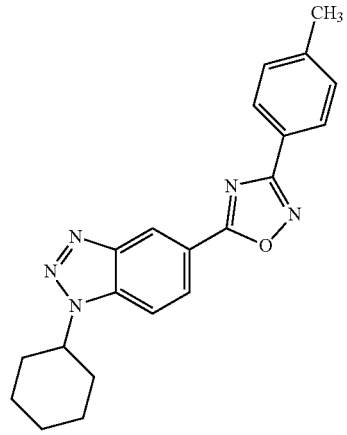 [SMILES: Cc1ccc(-c2noc(-c3ccc4c(c3)nnn4C3CCCCC3)n2)cc1] | 117 | 1-cyclohexyl-5-[3-(4-methylphenyl)-1,2,4-oxadiazol-5-yl]-1H-1,2,3-benzotriazole |
| 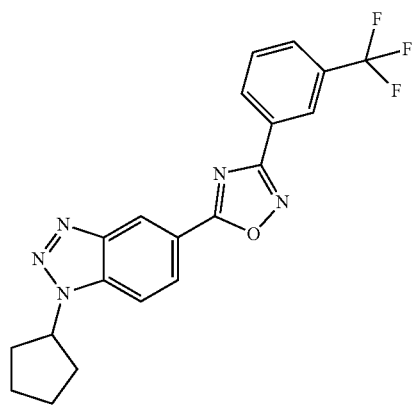 [SMILES: FC(F)(F)c1cccc(-c2noc(-c3ccc4c(c3)nnn4C3CCCC3)n2)c1] | 118 | 1-cyclopentyl-5-{3-[3-(trifluoromethyl)phenyl]-1,2,4-oxadiazol-5-yl}-1H-1,2,3-benzotriazole |
| 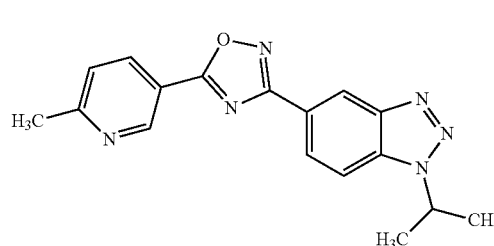 | 119 | 3-(1-isopropyl-1H-benzo[d][1,2,3]triazol-5-yl)-5-(6-methylpyridin-3-yl)-1,2,4-oxadiazole |
| 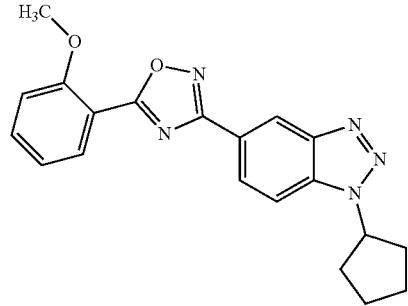 [SMILES: COc1ccccc1-c1nc(-c2ccc3c(c2)nnn3C2CCCC2)no1] | 120 | 3-(1-cyclopentyl-1H-benzo[d][1,2,3]triazol-5-yl)-5-(2-methoxyphenyl)-1,2,4-oxadiazole |

-continued

| Structure | Compound Number | Chemical Name |
|---|---|---|
| 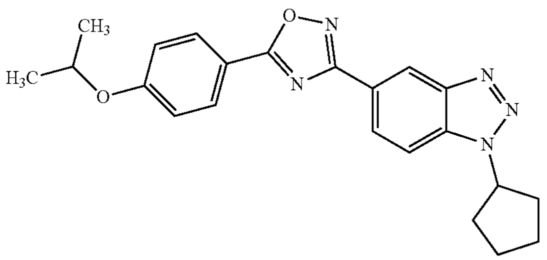 [SMILES: CC(C)Oc1ccc(-c2nc(-c3ccc4c(c3)nnn4C3CCCC3)no2)cc1] | 121 | 3-(1-cyclopentyl-1H-benzo[d][1,2,3]triazol-5-yl)-5-(4-isopropoxyphenyl)-1,2,4-oxadiazole |
| 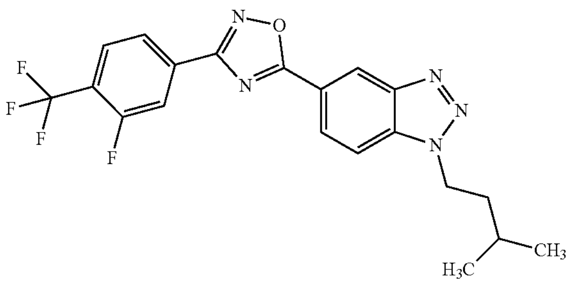 [SMILES: CC(C)CCn1nnc2cc(-c3nc(-c4ccc(C(F)(F)F)c(F)c4)no3)ccc21] | 122 | 5-{3-[3-fluoro-4-(trifluoromethyl)phenyl]-1,2,4-oxadiazol-5-yl}-1-(3-methylbutyl)-1H-1,2,3-benzotriazole |
| 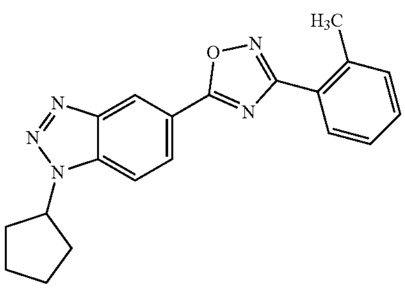 [SMILES: Cc1ccccc1-c1noc(-c2ccc3c(c2)nnn3C2CCCC2)n1] | 123 | 5-[3-(3,5-dimethylphenyl)-1,2,4-oxadiazol-5-yl]-1-(propan-2-yl)-1H-1,2,3-benzotriazole |
| 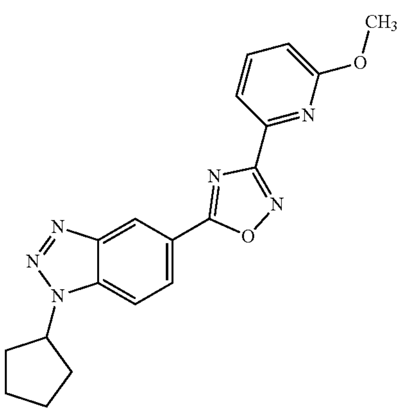 [SMILES: COc1cccc(-c2noc(-c3ccc4c(c3)nnn4C3CCCC3)n2)n1] | 124 | 1-cyclopentyl-5-[3-(6-methoxypyridin-2-yl)-1,2,4-oxadiazol-5-yl]-1H-1,2,3-benzotriazole |
| 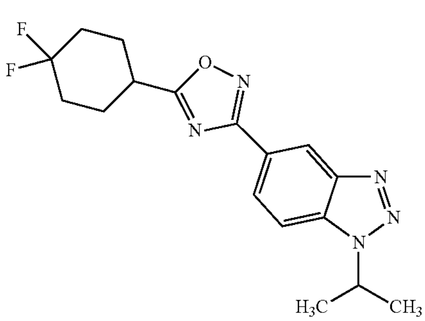 [SMILES: CC(C)n1nnc2cc(-c3noc(C4CCC(F)(F)CC4)n3)ccc21] | 125 | 5-[5-(4,4-difluorocyclohexyl)-1,2,4-oxadiazol-3-yl]-1-(propan-2-yl)-1H-1,2,3-benzotriazole |

| Structure | Compound Number | Chemical Name |
|---|---|---|
| 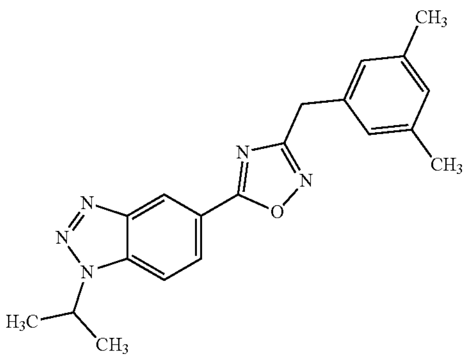 [SMILES: Cc1cc(C)cc(Cc2noc(-c3ccc4c(c3)nnn4C(C)C)n2)c1] | 126 | 5-{3-[(3,5-dimethylphenyl)methyl]-1,2,4-oxadiazol-5-yl}-1-(propan-2-yl)-1H-1,2,3-benzotriazole |
| 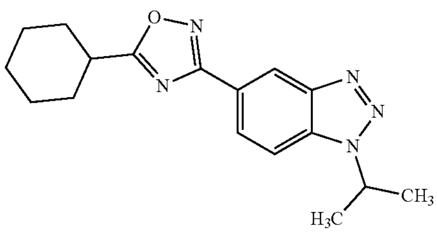 [SMILES: CC(C)n1nnc2cc(-c3noc(C4CCCCC4)n3)ccc21] | 127 | 5-(5-cyclohexyl-1,2,4-oxadiazol-3-yl)-1-(propan-2-yl)-1H-1,2,3-benzotriazole |
| 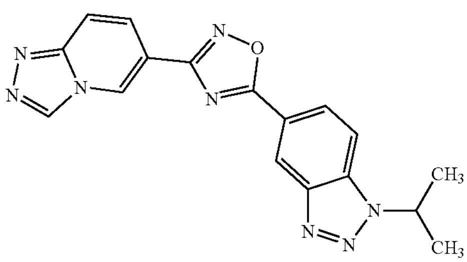 [SMILES: CC(C)n1nnc2cc(-c3nc(-c4ccc5nncn5c4)no3)ccc21] | 128 | 1-(propan-2-yl)-5-(3-{[1,2,4]triazolo[4,3-a]pyridin-6-yl}-1,2,4-oxadiazol-5-yl)-1H-1,2,3-benzotriazole |
| 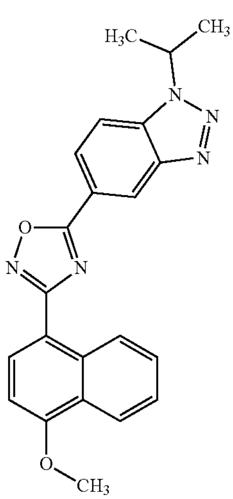 [SMILES: COc1ccc(-c2noc(-c3ccc4c(c3)nnn4C(C)C)n2)c2ccccc12] | 129 | 5-[3-(4-methoxynaphthalen-1-yl)-1,2,4-oxadiazol-5-yl]-1-(propan-2-yl)-1H-1,2,3-benzotriazole |

-continued

| Structure | Compound Number | Chemical Name |
|---|---|---|
| 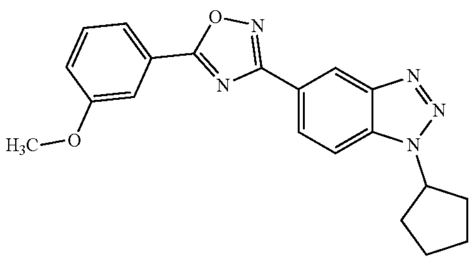 [SMILES: COc1cccc(-c2nc(-c3ccc4c(c3)nnn4C3CCCC3)no2)c1] | 130 | 3-(1-cyclopentyl-1H-benzo[d][1,2,3]triazol-5-yl)-5-(3-methoxyphenyl)-1,2,4-oxadiazole |
| 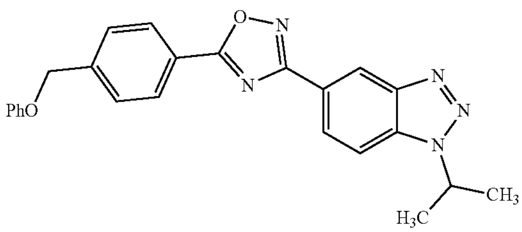 [SMILES: CC(C)n1nnc2cc(-c3noc(-c4ccc(COc5ccccc5)cc4)n3)ccc21] | 131 | 3-(1-isopropyl-1H-benzo[d][1,2,3]triazol-5-yl)-5-(4-(phenoxymethyl)phenyl)-1,2,4-oxadiazole |
| 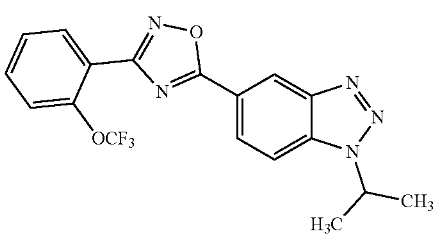 [SMILES: CC(C)n1nnc2cc(-c3nc(-c4ccccc4OC(F)(F)F)no3)ccc21] | 132 | 5-(1-isopropyl-1H-benzo[d][1,2,3]triazol-5-yl)-3-(2-(trifluoromethoxy)phenyl)-1,2,4-oxadiazole |
| 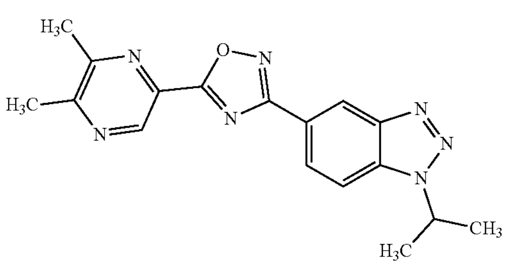 [SMILES: Cc1ncc(-c2nc(-c3ccc4c(c3)nnn4C(C)C)no2)nc1C] | 133 | 5-(5,6-dimethylpyrazin-2-yl)-3-(1-isopropyl-1H-benzo[d][1,2,3]triazol-5-yl)-1,2,4-oxadiazole |
| 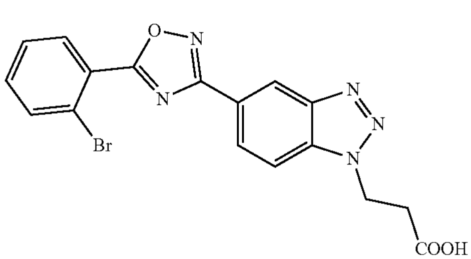 [SMILES: O=C(O)CCn1nnc2cc(-c3noc(-c4ccccc4Br)n3)ccc21] | 134 | 3-(5-(5-(2-bromophenyl)-1,2,4-oxadiazol-3-yl)-1H-benzo[d][1,2,3]triazol-1-yl)propanoic acid |

-continued

| Structure | Compound Number | Chemical Name |
|---|---|---|
| 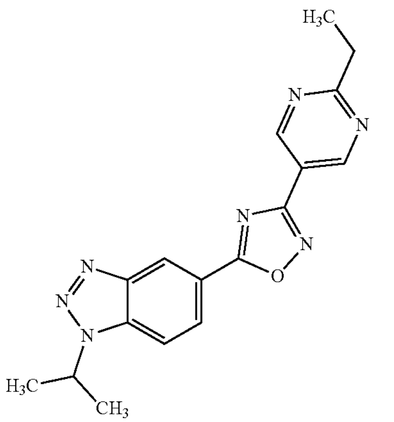 [SMILES: CCc1ncc(-c2noc(-c3ccc4c(c3)nnn4C(C)C)n2)cn1] | 135 | 5-[3-(2-ethylpyrimidin-5-yl)-1,2,4-oxadiazol-5-yl]-1-(propan-2-yl)-1H-1,2,3-benzotriazole |
| 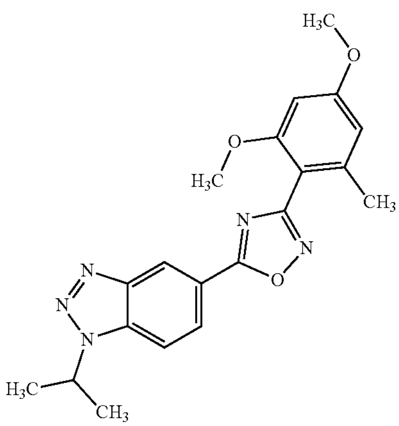 [SMILES: COc1cc(C)c(-c2noc(-c3ccc4c(c3)nnn4C(C)C)n2)c(OC)c1] | 136 | 5-[3-(2,4-dimethoxy-6-methylphenyl)-1,2,4-oxadiazol-5-yl]-1-(propan-2-yl)-1H-1,2,3-benzotriazole |
| 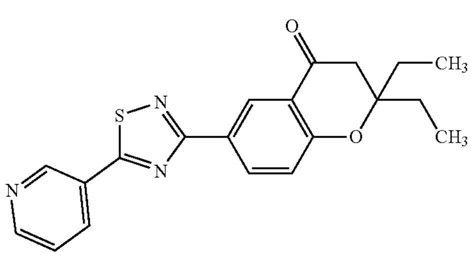 [SMILES: CCC1(CC)CC(=O)c2cc(-c3nsc(-c4cccnc4)n3)ccc2O1] | 137 | 2,2-diethyl-6-(5-(pyridin-3-yl)-1,2,4-thiadiazol-3-yl)chroman-4-one |
| 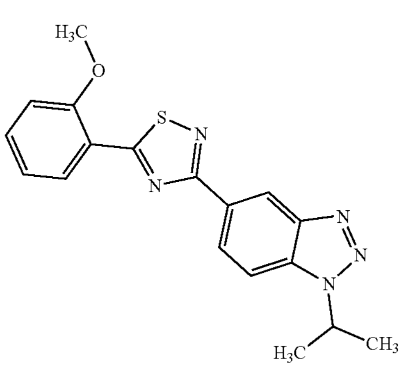 [SMILES: COc1ccccc1-c1nc(-c2ccc3c(c2)nnn3C(C)C)ns1] | 138 | 5-[5-(2-methoxyphenyl)-1,2,4-thiadiazol-3-yl]-1-(propan-2-yl)-1H-1,2,3-benzotriazole |

-continued
| Structure | Compound Number | Chemical Name |
|---|---|---|
| 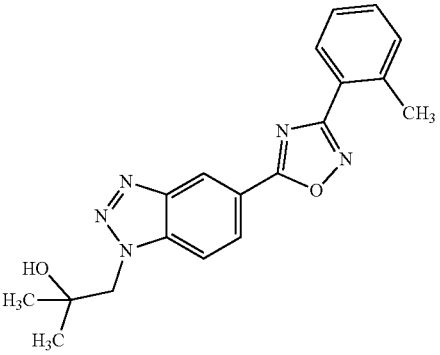 [SMILES: Cc1ccccc1-c1noc(-c2ccc3c(c2)nnn3CC(C)(C)O)n1] | 139 | 2-methyl-1-{5-[3-(2-methylphenyl)-1,2,4-oxadiazol-5-yl]-1H-1,2,3-benzotriazol-1-yl}propan-2-ol |
| 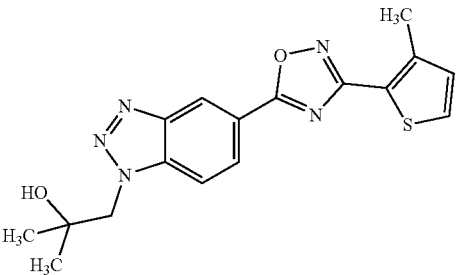 [SMILES: Cc1ccsc1-c1noc(-c2ccc3c(c2)nnn3CC(C)(C)O)n1] | 140 | 2-methyl-1-{5-[3-(3-methylthiophen-2-yl)-1,2,4-oxadiazol-5-yl]-1H-1,2,3-benzotriazol-1-yl}propan-2-ol |
| 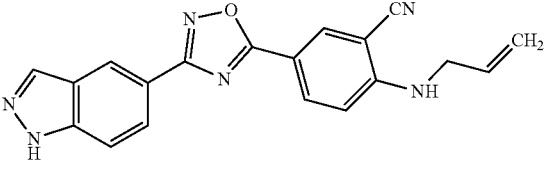 [SMILES: C=CCNc1ccc(-c2nc(-c3ccc4[nH]ncc4c3)no2)cc1C#N] | 141 | 5-(3-(1H-indazol-5-yl)-1,2,4-oxadiazol-5-yl)-2-(allylamino)benzonitrile |
| 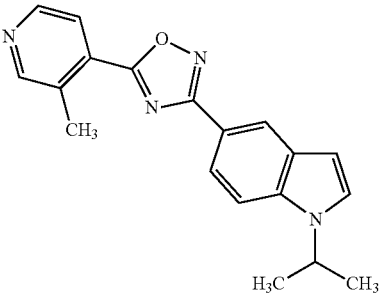 [SMILES: Cc1cnccc1-c1nc(-c2ccc3c(ccn3C(C)C)c2)no1] | 142 | 3-(1-isopropyl-1H-indol-5-yl)-5-(3-methylpyridin-4-yl)-1,2,4-oxadiazole |
| 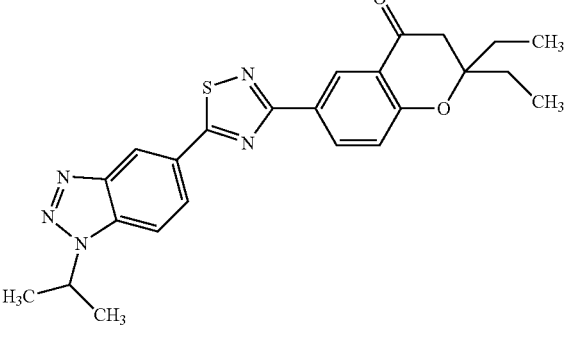 | 143 | 2,2-diethyl-6-(5-(1-isopropyl-1H-benzo[d][1,2,3]triazol-5-yl)-1,2,4-thiadiazol-3-yl)chroman-4-one |

-continued

| Structure | Compound Number | Chemical Name |
|---|---|---|
| 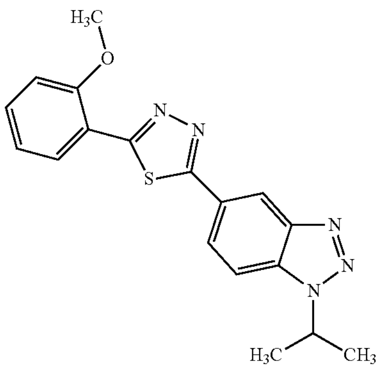 [SMILES: COc1ccccc1-c1nnc(-c2ccc3c(c2)nnn3C(C)C)s1] | 144 | 5-[5-(2-methoxyphenyl)-1,3,4-thiadiazol-2-yl]-1-(propan-2-yl)-1H-1,2,3-benzotriazole |
| 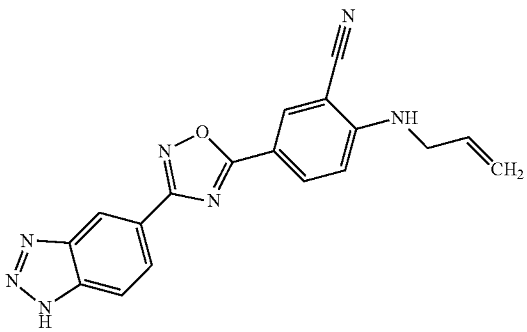 [SMILES: C=CCNc1ccc(-c2nc(-c3ccc4[nH]nnc4c3)no2)cc1C#N] | 145 | 5-(3-(1H-benzo[d][1,2,3]triazol-5-yl)-1,2,4-oxadiazol-5-yl)-2-(allylamino)benzonitrile |
| 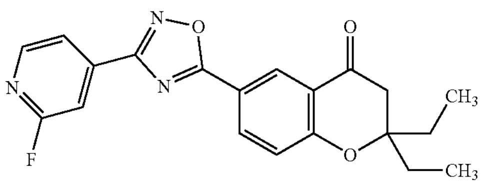 [SMILES: CCC1(CC)CC(=O)c2cc(-c3nc(-c4ccnc(F)c4)no3)ccc2O1] | 146 | 2,2-diethyl-6-(3-(2-fluoropyridin-4-yl)-1,2,4-oxadiazol-5-yl)chroman-4-one |
| 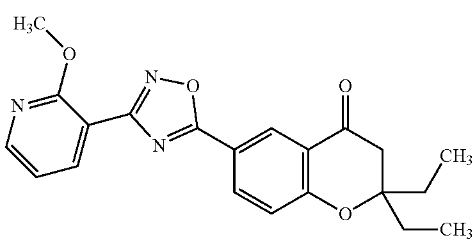 | 147 | 2,2-diethyl-6-(3-(2-methoxypyridin-3-yl)-1,2,4-oxadiazol-5-yl)chroman-4-one |
| 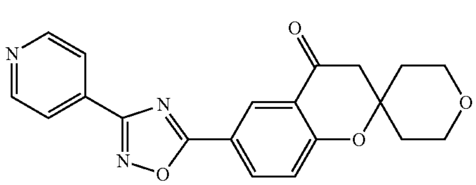 [SMILES: O=C1CC2(CCOCC2)Oc2ccc(-c3nc(-c4ccncc4)no3)cc21] | 148 | 6-[3-(pyridin-4-yl)-1,2,4-oxadiazol-5-yl]-3,4-dihydrospiro[1-benzopyran-2,4'-oxane]-4-one |
| 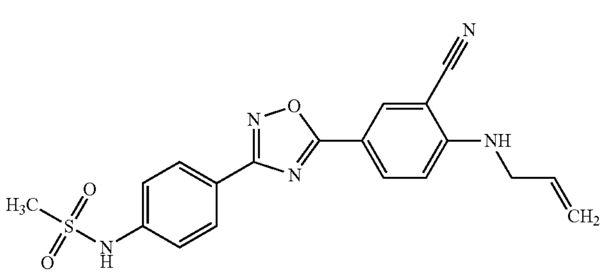 [SMILES: C=CCNc1ccc(-c2nc(-c3ccc(NS(C)(=O)=O)cc3)no2)cc1C#N] | 149 | N-(4-(5-(4-(allylamino)-3-cyanophenyl)-1,2,4-oxadiazol-3-yl)phenyl)methanesulfonamide |

| Structure | Compound Number | Chemical Name |
|---|---|---|
| 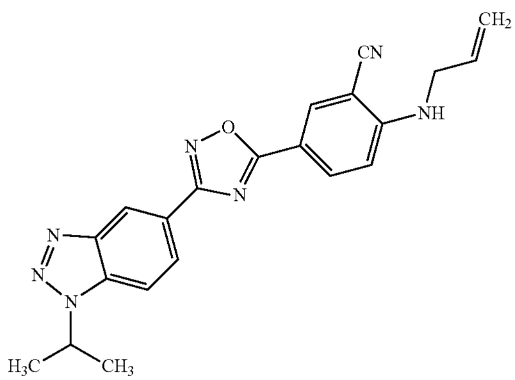 [SMILES: C=CCNc1ccc(-c2nc(-c3ccc4c(c3)nnn4C(C)C)no2)cc1C#N] | 150 | 2-(allylamino)-5-(3-(1-isopropyl-1H-benzo[d][1,2,3]triazol-5-yl)-1,2,4-oxadiazol-5-yl)benzonitrile |
| 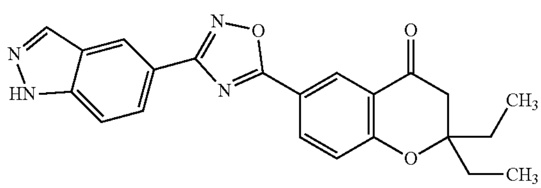 [SMILES: CCC1(CC)CC(=O)c2cc(-c3nc(-c4ccc5[nH]ncc5c4)no3)ccc2O1] | 151 | 4-(5-(2,2-diethyl-4-oxochroman-6-yl)-1,2,4-oxadiazol-3-yl)-N,N-dimethylbenzamide |
| 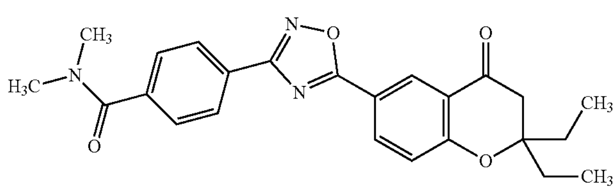 [SMILES: CCC1(CC)CC(=O)c2cc(-c3nc(-c4ccc(C(=O)N(C)C)cc4)no3)ccc2O1] | 152 | 6-(3-(1H-indazol-5-yl)-1,2,4-oxadiazol-5-yl)-2,2-diethylchroman-4-one |
| 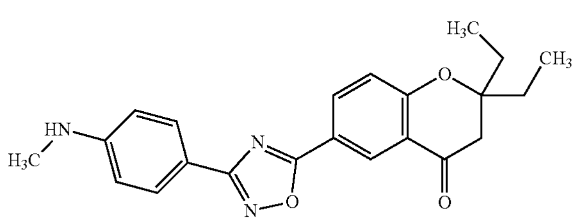 [SMILES: CCC1(CC)CC(=O)c2cc(-c3nc(-c4ccc(NC)cc4)no3)ccc2O1] | 153 | 2,2-diethyl-6-(3-(4-(methylamino)phenyl)-1,2,4-oxadiazol-5-yl)chroman-4-one |
| 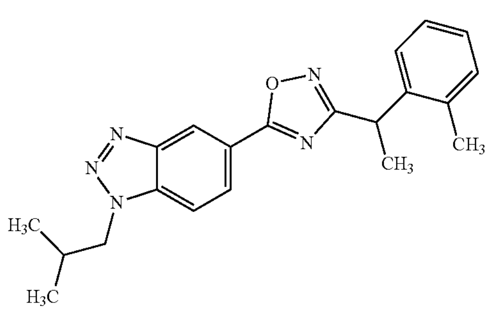 [SMILES: Cc1ccccc1C(C)c1noc(-c2ccc3c(c2)nnn3CC(C)C)n1] | 154 | 5-{3-[1-(2-methylphenyl)ethyl]-1,2,4-oxadiazol-5-yl}-1-(2-methylpropyl)-1H-1,2,3-benzotriazole |

-continued

| Structure | Compound Number | Chemical Name |
|---|---|---|
| 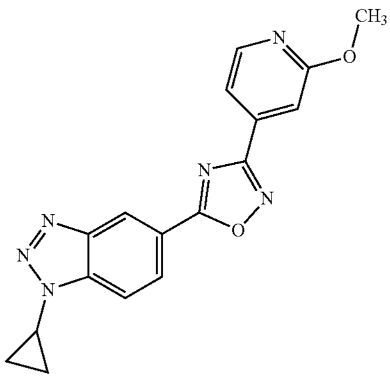 [SMILES: COc1cc(-c2noc(-c3ccc4c(c3)nnn4C3CC3)n2)ccn1] | 155 | 1-cyclopropyl-5-[3-(2-methoxypyridin-4-yl)-1,2,4-oxadiazol-5-yl]-1H-1,2,3-benzotriazole |
| 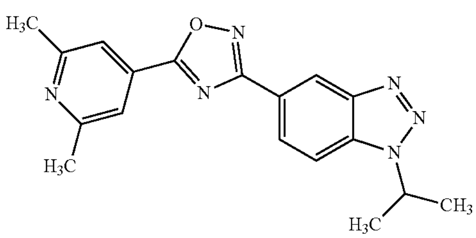 [SMILES: Cc1cc(-c2nc(-c3ccc4c(c3)nnn4C(C)C)no2)cc(C)n1] | 156 | 5-(2,6-dimethylpyridin-4-yl)-3-(1-isopropyl-1H-benzo[d][1,2,3]triazol-5-yl)-1,2,4-oxadiazole |
| 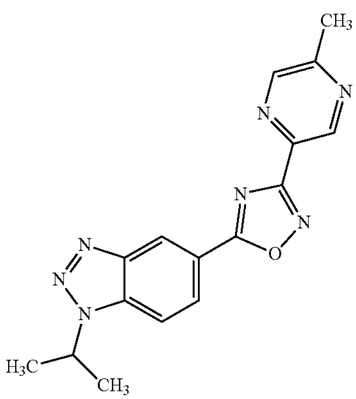 [SMILES: Cc1cnc(-c2noc(-c3ccc4c(c3)nnn4C(C)C)n2)cn1] | 157 | 5-[3-(5-methylpyrazin-2-yl)-1,2,4-oxadiazol-5-yl]-1-(propan-2-yl)-1H-1,2,3-benzotriazole |
| 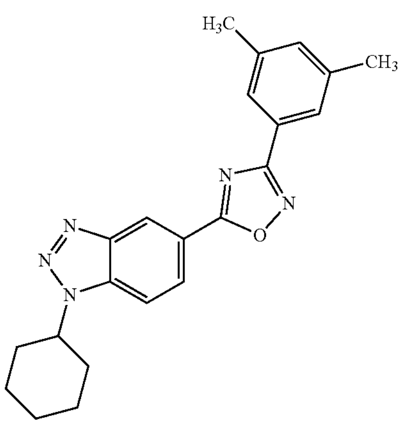 [SMILES: Cc1cc(C)cc(-c2noc(-c3ccc4c(c3)nnn4C3CCCCC3)n2)c1] | 158 | 1-cyclohexyl-5-[3-(3,5-dimethylphenyl)-1,2,4-oxadiazol-5-yl]-1H-1,2,3-benzotriazole |

-continued
| Structure | Compound Number | Chemical Name |
|---|---|---|
| 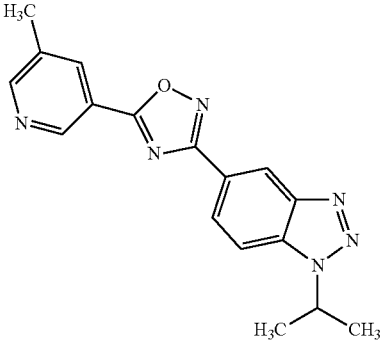 [SMILES: Cc1cncc(-c2nc(-c3ccc4c(c3)nnn4C(C)C)no2)c1] | 159 | 3-(1-isopropyl-1H-benzo[d][1,2,3]triazol-5-yl)-5-(5-methylpyridin-3-yl)-1,2,4-oxadiazole |
| 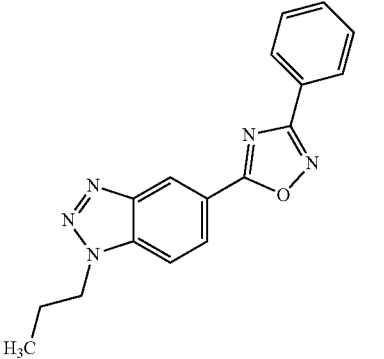 [SMILES: CCCn1nnc2cc(-c3nc(-c4ccccc4)no3)ccc21] | 160 | 5-(3-phenyl-1,2,4-oxadiazol-5-yl)-1-propyl-1H-1,2,3-benzotriazole |
| 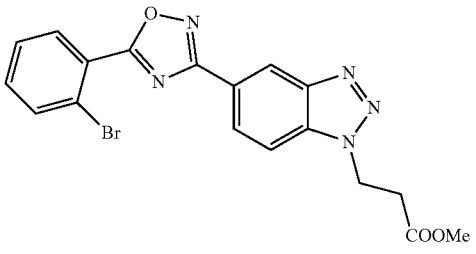 [SMILES: COC(=O)CCn1nnc2cc(-c3noc(-c4ccccc4Br)n3)ccc21] | 161 | methyl 3-(5-(5-(2-bromophenyl)-1,2,4-oxadiazol-3-yl)-1H-benzo[d][1,2,3]triazol-1-yl)propanoate |
| 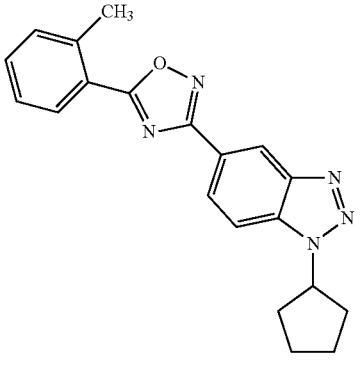 [SMILES: Cc1ccccc1-c1nc(-c2ccc3c(c2)nnn3C2CCCC2)no1] | 162 | 3-(1-cyclopentyl-1H-benzo[d][1,2,3]triazol-5-yl)-5-(o-tolyl)-1,2,4-oxadiazole |
| 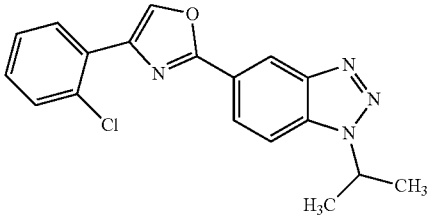 [SMILES: CC(C)n1nnc2cc(-c3nc(-c4ccccc4Cl)co3)ccc21] | 163 | 5-[4-(2-chlorophenyl)-2,3-dihydro-1,3-oxazol-2-yl]-1-(propan-2-yl)-1H-1,2,3-benzotriazole |

-continued
| Structure | Compound Number | Chemical Name |
|---|---|---|
| 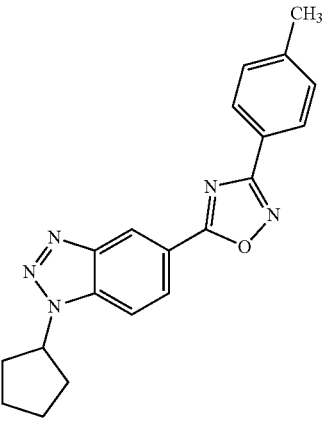 [SMILES: Cc1ccc(-c2noc(-c3ccc4c(c3)nnn4C3CCCC3)n2)cc1] | 164 | 1-cyclopentyl-5-[3-(4-methylphenyl)-1,2,4-oxadiazol-5-yl]-1H-1,2,3-benzotriazole |
| 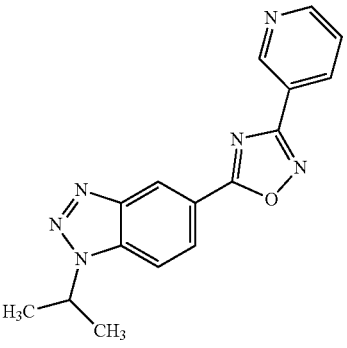 | 165 | 1-(propan-2-yl)-5-[3-(pyridin-3-yl)-1,2,4-oxadiazol-5-yl]-1H-1,2,3-benzotriazole |
| 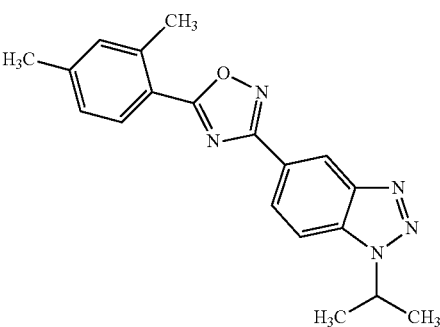 [SMILES: Cc1ccc(-c2nc(-c3ccc4c(c3)nnn4C(C)C)no2)c(C)c1] | 166 | 5-(2,4-dimethylphenyl)-3-(1-isopropyl-1H-benzo[d][1,2,3]triazol-5-yl)-1,2,4-oxadiazole |
| 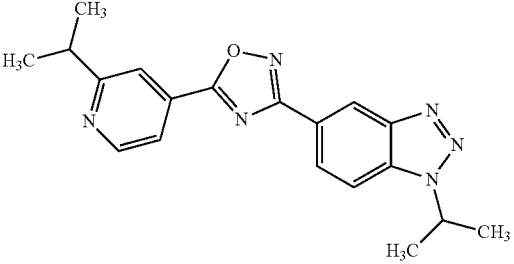 [SMILES: CC(C)c1cc(-c2nc(-c3ccc4c(c3)nnn4C(C)C)no2)ccn1] | 167 | 3-(1-isopropyl-1H-benzo[d][1,2,3]triazol-5-yl)-5-(2-isopropylpyridin-4-yl)-1,2,4-oxadiazole |

-continued

| Structure | Compound Number | Chemical Name |
|---|---|---|
| 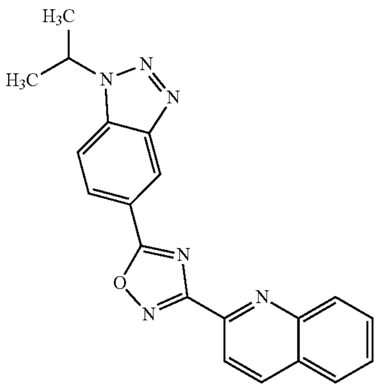 [SMILES: CC(C)n1nnc2cc(-c3nc(-c4ccc5ccccc5n4)no3)ccc21] | 168 | 2-{5-[1-(propan-2-yl)-1H-1,2,3-benzotriazol-5-yl]-1,2,4-oxadiazol-3-yl}quinoline |
| 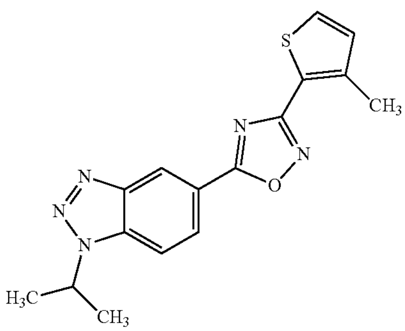 [SMILES: Cc1ccsc1-c1noc(-c2ccc3c(c2)nnn3C(C)C)n1] | 169 | 5-[3-(3-methylthiophen-2-yl)-1,2,4-oxadiazol-5-yl]-1-(propan-2-yl)-1H-1,2,3-benzotriazole |
| 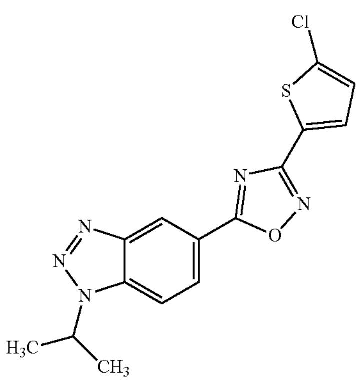 [SMILES: CC(C)n1nnc2cc(-c3nc(-c4ccc(Cl)s4)no3)ccc21] | 170 | 5-[3-(5-chlorothiophen-2-yl)-1,2,4-oxadiazol-5-yl]-1-(propan-2-yl)-1H-1,2,3-benzotriazole |
| 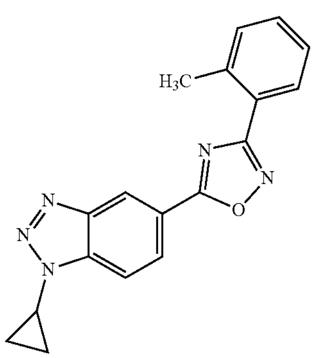 [SMILES: Cc1ccccc1-c1noc(-c2ccc3c(c2)nnn3C2CC2)n1] | 171 | 1-cyclopropyl-5-[3-(2-methylphenyl)-1,2,4-oxadiazol-5-yl]-1H-1,2,3-benzotriazole |

-continued

| Structure | Compound Number | Chemical Name |
|---|---|---|
| 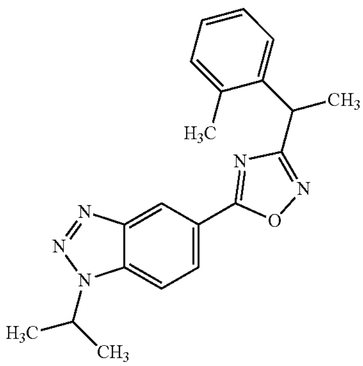 [SMILES: Cc1ccccc1C(C)c1noc(-c2ccc3c(c2)nnn3C(C)C)n1] | 172 | 5-{3-[1-(2-methylphenyl)ethyl]-1,2,4-oxadiazol-5-yl}-1-(propan-2-yl)-1H-1,2,3-benzotriazole |
| 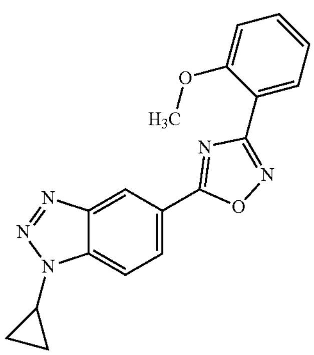 [SMILES: COc1ccccc1-c1noc(-c2ccc3c(c2)nnn3C2CC2)n1] | 173 | 1-cyclopropyl-5-[3-(2-methoxyphenyl)-1,2,4-oxadiazol-5-yl]-1H-1,2,3-benzotriazole |
| 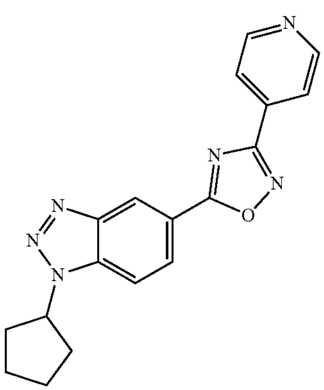 [SMILES: c1cc(-c2noc(-c3ccc4c(c3)nnn4C3CCCC3)n2)ccn1] | 174 | 1-cyclopentyl-5-[3-(pyridin-4-yl)-1,2,4-oxadiazol-5-yl]-1H-1,2,3-benzotriazole |
| 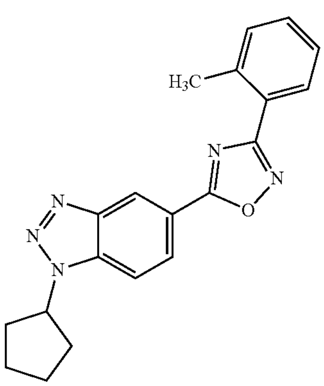 [SMILES: Cc1ccccc1-c1noc(-c2ccc3c(c2)nnn3C2CCCC2)n1] | 175 | 1-cyclopentyl-5-[3-(2-methylphenyl)-1,2,4-oxadiazol-5-yl]-1H-1,2,3-benzotriazole |

-continued

| Structure | Compound Number | Chemical Name |
|---|---|---|
| 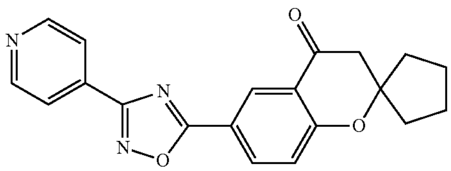 [SMILES: O=C1CC2(CCCC2)Oc2ccc(-c3nc(-c4ccncc4)no3)cc21] | 176 | 6-[3-(pyridin-4-yl)-1,2,4-oxadiazol-5-yl]-3,4-dihydrospiro[1-benzopyran-2,1'-cyclopentane]-4-one |
| 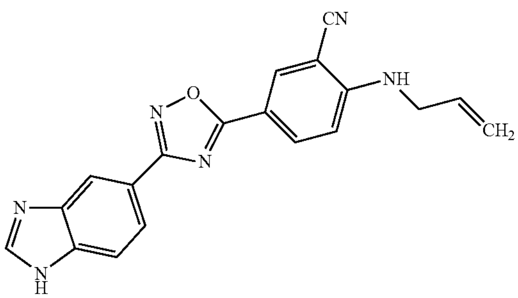 [SMILES: C=CCNc1ccc(-c2nc(-c3ccc4[nH]cnc4c3)no2)cc1C#N] | 177 | 5-(3-(1H-benzo[d]imidazol-5-yl)-1,2,4-oxadiazol-5-yl)-2-(allylamino)benzonitrile |
| 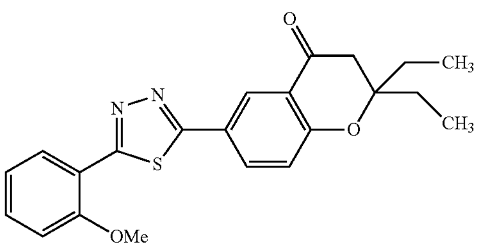 [SMILES: CCC1(CC)CC(=O)c2cc(-c3nnc(-c4ccccc4OC)s3)ccc2O1] | 178 | 2,2-diethyl-6-(5-(2-methoxyphenyl)-1,3,4-thiadiazol-2-yl)chroman-4-one |
| 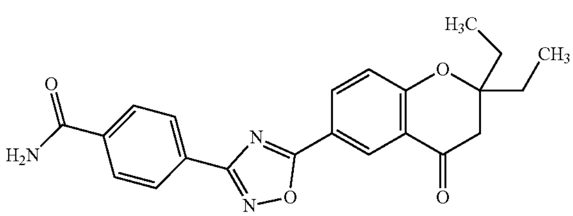 [SMILES: CCC1(CC)CC(=O)c2cc(-c3nc(-c4ccc(C(N)=O)cc4)no3)ccc2O1] | 179 | 4-(5-(2,2-diethyl-4-oxochroman-6-yl)-1,2,4-oxadiazol-3-yl)benzamide |
| 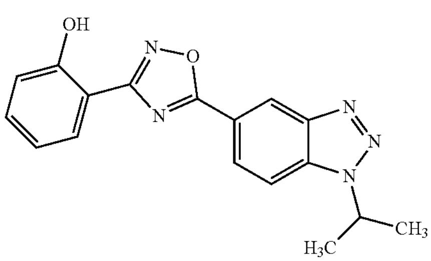 [SMILES: CC(C)n1nnc2cc(-c3nc(-c4ccccc4O)no3)ccc21] | 180 | 2-(5-(1-isopropyl-1H-benzo[d][1,2,3]triazol-5-yl)-1,2,4-oxadiazol-3-yl)phenol |
| 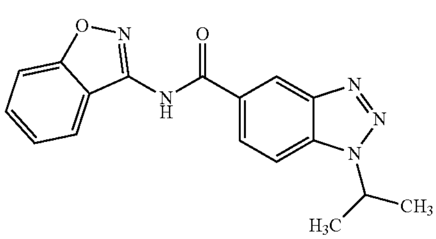 [SMILES: CC(C)n1nnc2cc(C(=O)Nc3noc4ccccc34)ccc21] | 181 | N-(benzo[d]isoxazol-3-yl)-1-isopropyl-1H-benzo[d][1,2,3]triazole-5-carboxamide |

-continued

| Structure | Compound Number | Chemical Name |
|---|---|---|
| 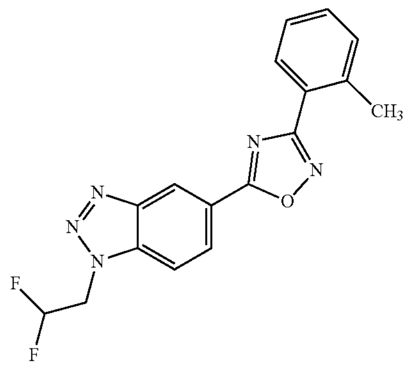 [SMILES: Cc1ccccc1-c1noc(-c2ccc3c(c2)nnn3CC(F)F)n1] | 182 | 1-(2,2-difluoroethyl)-5-[3-(2-methylphenyl)-1,2,4-oxadiazol-5-yl]-1H-1,2,3-benzotriazole |
| 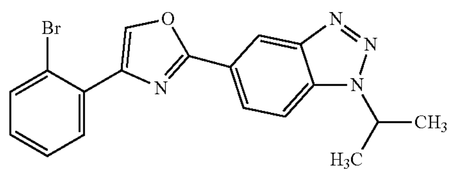 [SMILES: CC(C)n1nnc2cc(-c3nc(-c4ccccc4Br)co3)ccc21] | 183 | 5-[4-(2-bromophenyl)-1,3-oxazol-2-yl]-1-(propan-2-yl)-1H-1,2,3-benzotriazole |
| 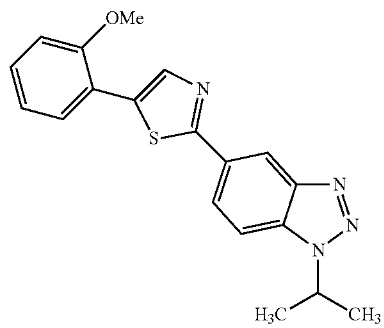 [SMILES: COc1ccccc1-c1cnc(-c2ccc3c(c2)nnn3C(C)C)s1] | 184 | 2-(1-isopropyl-1H-benzo[d][1,2,3]triazol-5-yl)-5-(2-methoxyphenyl)thiazole |
| 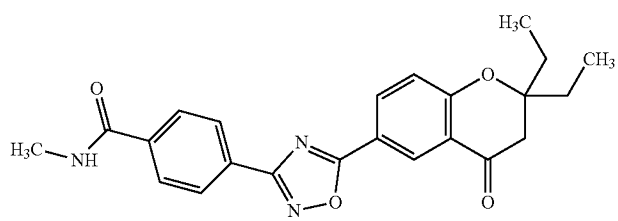 [SMILES: CCC1(CC)CC(=O)c2cc(-c3nc(-c4ccc(C(=O)NC)cc4)no3)ccc2O1] | 185 | 4-(5-(2,2-diethyl-4-oxochroman-6-yl)-1,2,4-oxadiazol-3-yl)-N-methylbenzamide |
| 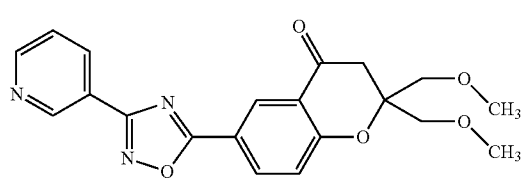 [SMILES: COCC1(COC)CC(=O)c2cc(-c3nc(-c4cccnc4)no3)ccc2O1] | 186 | 2,2-bis(methoxymethyl)-6-[3-(pyridin-3-yl)-1,2,4-oxadiazol-5-yl]-3,4-dihydro-2H-1-benzopyran-4-one |
| 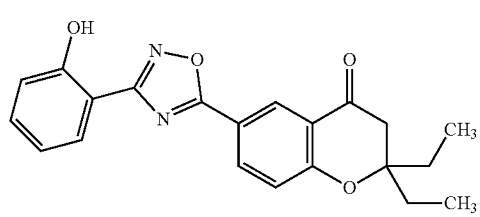 [SMILES: CCC1(CC)CC(=O)c2cc(-c3nc(-c4ccccc4O)no3)ccc2O1] | 187 | 2,2-diethyl-6-[3-(2-hydroxyphenyl)-1,2,4-oxadiazol-5-yl]chroman-4-one |

-continued

| Structure | Compound Number | Chemical Name |
|---|---|---|
| 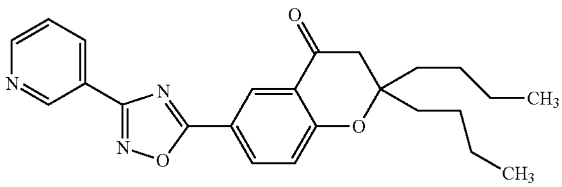 [SMILES: CCCCC1(CCCC)CC(=O)c2cc(-c3nc(-c4cccnc4)no3)ccc2O1] | 188 | 2,2-dibutyl-6-[3-(pyridin-3-yl)-1,2,4-oxadiazol-5-yl]-3,4-dihydro-2H-1-benzopyran-4-one |
| 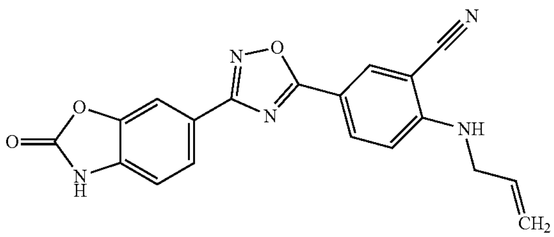 [SMILES: C=CCNc1ccc(-c2nc(-c3ccc4[nH]c(=O)oc4c3)no2)cc1C#N] | 189 | 2-(allylamino)-5-(3-(2-oxo-2,3-dihydrobenzo[d]oxazol-6-yl)-1,2,4-oxadiazol-5-yl)benzonitrile |
| 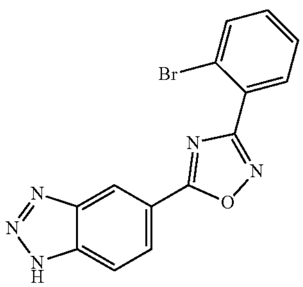 [SMILES: Brc1ccccc1-c1noc(-c2ccc3[nH]nnc3c2)n1] | 190 | 5-[3-(2-bromophenyl)-1,2,4-oxadiazol-5-yl]-1H-1,2,3-benzotriazole |
| 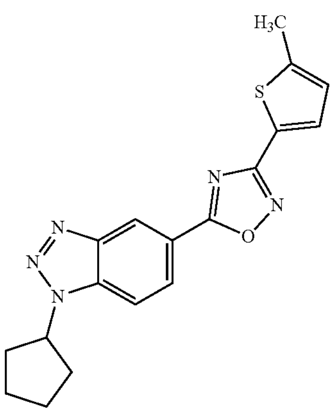 [SMILES: Cc1ccc(-c2noc(-c3ccc4c(c3)nnn4C3CCCC3)n2)s1] | 192 | 1-cyclopentyl-5-[3-(5-methylthiophen-2-yl)-1,2,4-oxadiazol-5-yl]-1H-1,2,3-benzotriazole |
| 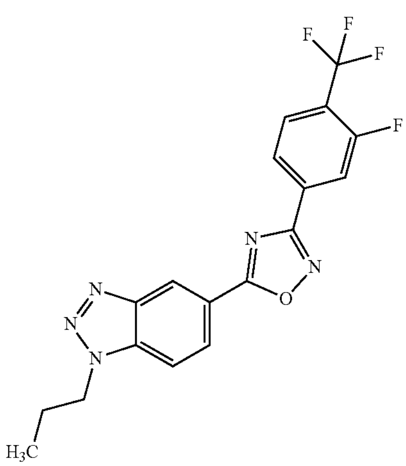 [SMILES: CCCn1nnc2cc(-c3nc(-c4ccc(C(F)(F)F)c(F)c4)no3)ccc21] | 193 | 5-{3-[3-fluoro-4-(trifluoromethyl)phenyl]-1,2,4-oxadiazol-5-yl}-1-propyl-1H-1,2,3-benzotriazole |

| Structure | Compound Number | Chemical Name |
|---|---|---|
| 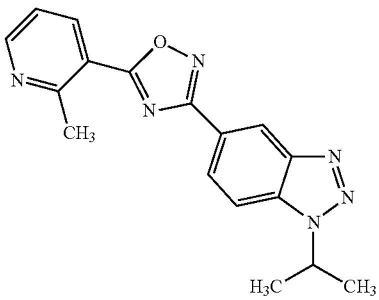 [SMILES: Cc1ncccc1-c1nc(-c2ccc3c(c2)nnn3C(C)C)no1] | 194 | 3-(1-isopropyl-1H-benzo[d][1,2,3]triazol-5-yl)-5-(2-methylpyridin-3-yl)-1,2,4-oxadiazole |
| 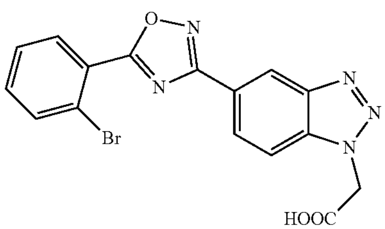 [SMILES: O=C(O)Cn1nnc2cc(-c3noc(-c4ccccc4Br)n3)ccc21] | 195 | 2-(5-(5-(2-bromophenyl)-1,2,4-oxadiazol-3-yl)-1H-benzo[d][1,2,3]triazol-1-yl)acetic acid |
| 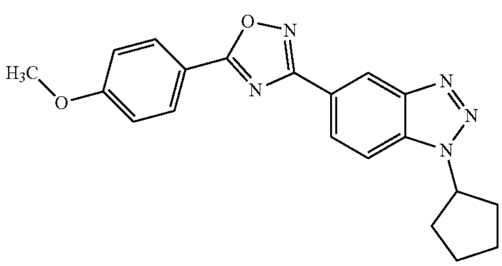 [SMILES: COc1ccc(-c2nc(-c3ccc4c(c3)nnn4C3CCCC3)no2)cc1] | 196 | 3-(1-cyclopentyl-1H-benzo[d][1,2,3]triazol-5-yl)-5-(4-methoxyphenyl)-1,2,4-oxadiazole |
| 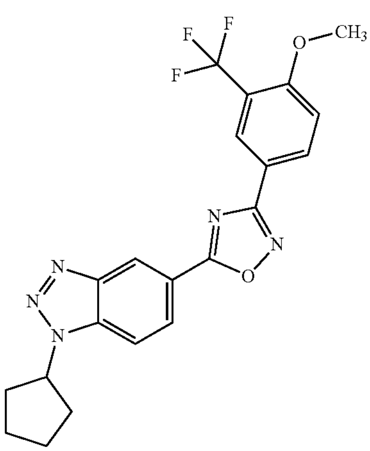 [SMILES: COc1ccc(-c2noc(-c3ccc4c(c3)nnn4C3CCCC3)n2)cc1C(F)(F)F] | 197 | 1-cyclopentyl-5-{3-[4-methoxy-3-(trifluoromethyl)phenyl]-1,2,4-oxadiazol-5-yl}-1H-1,2,3-benzotriazole |

-continued

| Structure | Compound Number | Chemical Name |
|---|---|---|
| 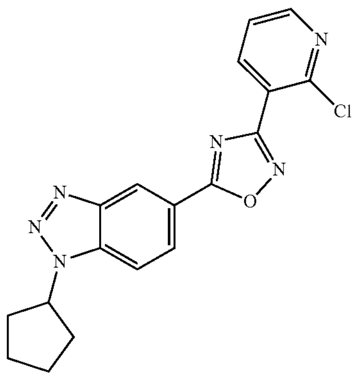 [SMILES: Clc1ncccc1-c1noc(-c2ccc3c(c2)nnn3C2CCCC2)n1] | 198 | 5-[3-(2-chloropyridin-3-yl)-1,2,4-oxadiazol-5-yl]-1-cyclopentyl-1H-1,2,3-benzotriazole |
| 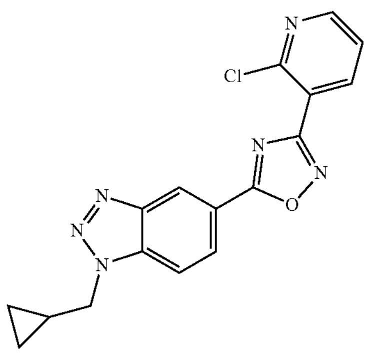 [SMILES: Clc1ncccc1-c1noc(-c2ccc3c(c2)nnn3CC2CC2)n1] | 199 | 5-[3-(2-chloropyridin-3-yl)-1,2,4-oxadiazol-5-yl]-1-(cyclopropylmethyl)-1H-1,2,3-benzotriazole |
| 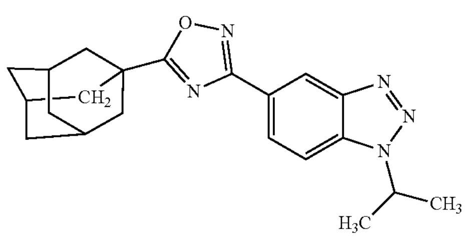 [SMILES: CC(C)n1nnc2cc(-c3noc(C45CC6CC(CC(C6)C4)C5)n3)ccc21] | 200 | 5-[5-(adamantan-1-yl)-1,2,4-oxadiazol-3-yl]-1-(propan-2-yl)-1H-1,2,3-benzotriazole |
| 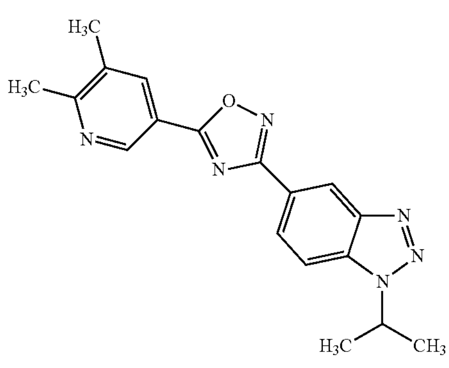 [SMILES: Cc1cc(-c2nc(-c3ccc4c(c3)nnn4C(C)C)no2)cnc1C] | 201 | 5-(5,6-dimethylpyridin-3-yl)-3-(1-isopropyl-1H-benzo[d][1,2,3]triazol-5-yl)-1,2,4-oxadiazole |

-continued

| Structure | Compound Number | Chemical Name |
|---|---|---|
| 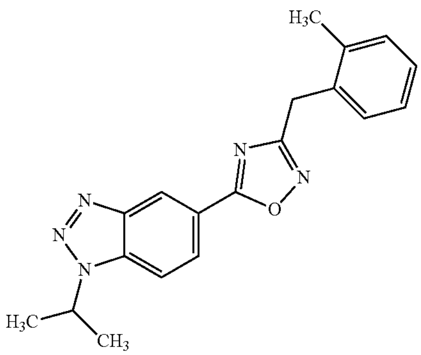 [SMILES: Cc1ccccc1Cc1noc(-c2ccc3c(c2)nnn3C(C)C)n1] | 202 | 5-{3-[(2-methylphenyl)methyl]-1,2,4-oxadiazol-5-yl}-1-(propan-2-yl)-1H-1,2,3-benzotriazole |
| 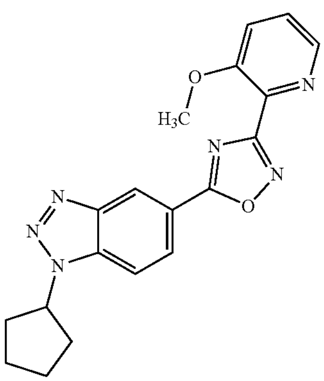 [SMILES: COc1cccnc1-c1noc(-c2ccc3c(c2)nnn3C2CCCC2)n1] | 203 | 1-cyclopentyl-5-[3-(3-methoxypyridin-2-yl)-1,2,4-oxadiazol-5-yl]-1H-1,2,3-benzotriazole |
| 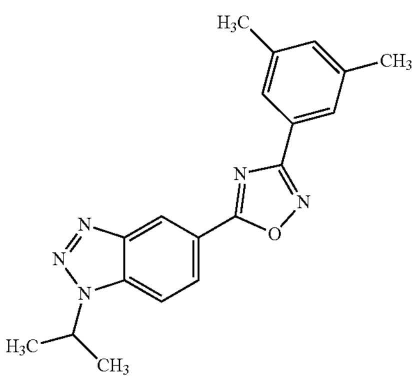 [SMILES: Cc1cc(C)cc(-c2noc(-c3ccc4c(c3)nnn4C(C)C)n2)c1] | 204 | 5-[3-(3,5-dimethylphenyl)-1,2,4-oxadiazol-5-yl]-1-(propan-2-yl)-1H-1,2,3-benzotriazole |
| 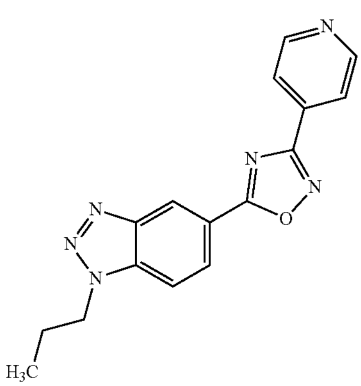 [SMILES: CCCn1nnc2cc(-c3nc(-c4ccncc4)no3)ccc21] | 205 | 1-propyl-5-[3-(pyridin-4-yl)-1,2,4-oxadiazol-5-yl]-1H-1,2,3-benzotriazole |

-continued

| Structure | Compound Number | Chemical Name |
|---|---|---|
| 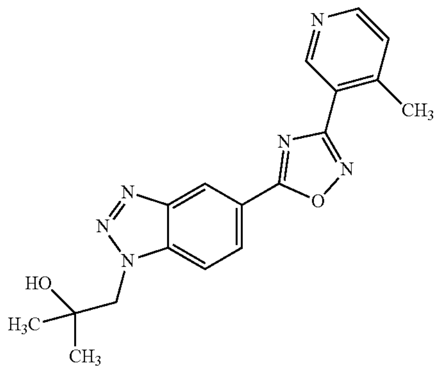 [SMILES: Cc1ccncc1-c1noc(-c2ccc3c(c2)nnn3CC(C)(C)O)n1] | 206 | 2-methyl-1-{5-[3-(4-methylpyridin-3-yl)-1,2,4-oxadiazol-5-yl]-1H-1,2,3-benzotriazol-1-yl}propan-2-ol |
| 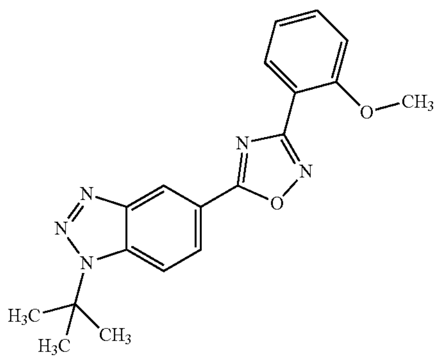 [SMILES: COc1ccccc1-c1noc(-c2ccc3c(c2)nnn3C(C)(C)C)n1] | 207 | 1-tert-butyl-5-[3-(2-methoxyphenyl)-1,2,4-oxadiazol-5-yl]-1H-1,2,3-benzotriazole |
| 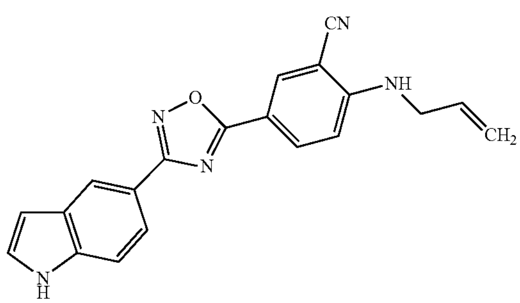 [SMILES: C=CCNc1ccc(-c2nc(-c3ccc4[nH]ccc4c3)no2)cc1C#N] | 208 | 5-(3-(1H-indol-5-yl)-1,2,4-oxadiazol-5-yl)-2-(allylamino)benzonitrile |
| 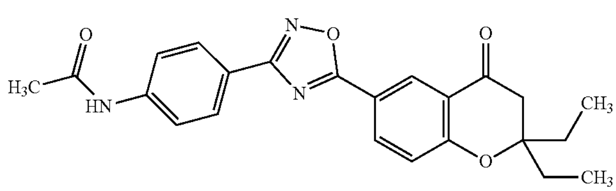 [SMILES: CCC1(CC)CC(=O)c2cc(-c3nc(-c4ccc(NC(C)=O)cc4)no3)ccc2O1] | 209 | N-(4-(5-(2,2-diethyl-4-oxochroman-6-yl)-1,2,4-oxadiazol-3-yl)phenyl)acetamide |
| 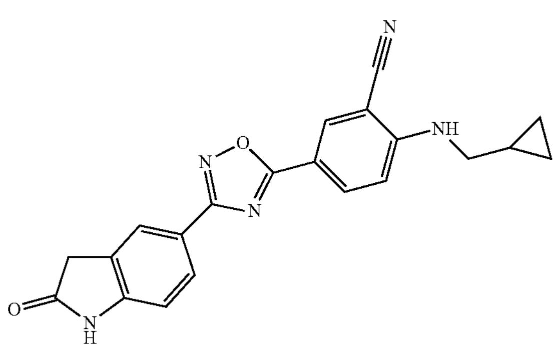 [SMILES: N#Cc1cc(-c2nc(-c3ccc4c(c3)CC(=O)N4)no2)ccc1NCC1CC1] | 210 | 2-((cyclopropylmethyl)amino)-5-(3-(2-oxoindolin-5-yl)-1,2,4-oxadiazol-5-yl)benzonitrile |

-continued

| Structure | Compound Number | Chemical Name |
|---|---|---|
| 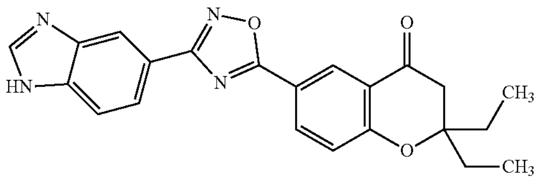 [SMILES: CCC1(CC)CC(=O)c2cc(-c3nc(-c4ccc5[nH]cnc5c4)no3)ccc2O1] | 211 | 6-(3-(1H-benzo[d]imidazol-5-yl)-1,2,4-oxadiazol-5-yl)-2,2-diethylchroman-4-one |
| 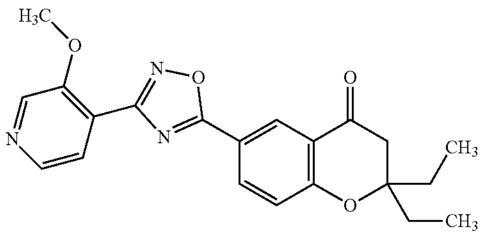 [SMILES: CCC1(CC)CC(=O)c2cc(-c3nc(-c4ccncc4OC)no3)ccc2O1] | 212 | 2,2-diethyl-6-(3-(3-methoxypyridin-4-yl)-1,2,4-oxadiazol-5-yl)chroman-4-one |
| 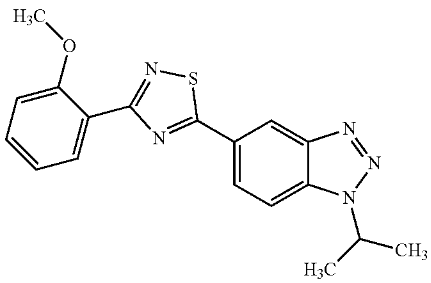 [SMILES: COc1ccccc1-c1nsc(-c2ccc3c(c2)nnn3C(C)C)n1] | 213 | 5-[3-(2-methoxyphenyl)-1,2,4-thiadiazol-5-yl]-1-(propan-2-yl)-1H-1,2,3-benzotriazole |
| 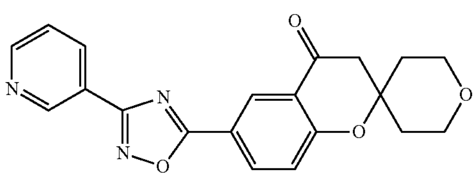 [SMILES: O=C1CC2(CCOCC2)Oc2ccc(-c3nc(-c4cccnc4)no3)cc21] | 214 | 6-[3-(pyridin-3-yl)-1,2,4-oxadiazol-5-yl]-3,4-dihydrospiro[1-benzopyran-2,4'-oxane]-4-one |
| 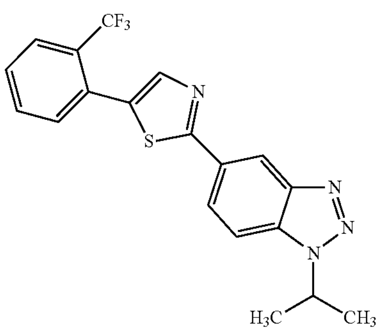 [SMILES: CC(C)n1nnc2cc(-c3ncc(-c4ccccc4C(F)(F)F)s3)ccc21] | 215 | 2-(1-isopropyl-1H-benzo[d][1,2,3]triazol-5-yl)-5-(2-(trifluoromethyl)phenyl)thiazole |
| 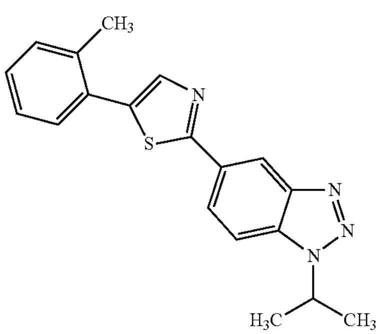 [SMILES: Cc1ccccc1-c1cnc(-c2ccc3c(c2)nnn3C(C)C)s1] | 216 | 2-(1-isopropylbenzotriazol-5-yl)-5-(o-tolyl)thiazole |

-continued

| Structure | Compound Number | Chemical Name |
|---|---|---|
| 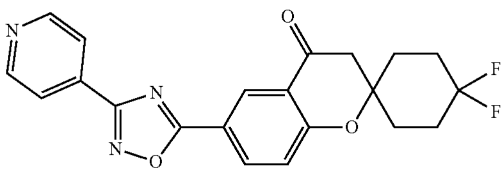 [SMILES: O=C1CC2(CCC(F)(F)CC2)Oc2ccc(-c3nc(-c4ccncc4)no3)cc21] | 217 | 4',4'-difluoro-6-[3-(pyridin-4-yl)-1,2,4-oxadiazol-5-yl]-3,4-dihydrospiro[1-benzopyran-2,1'-cyclohexane]-4-one |
| 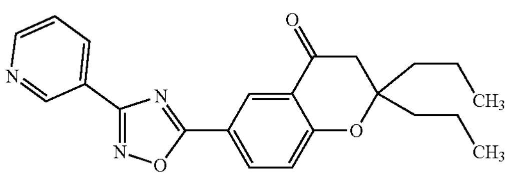 [SMILES: CCCC1(CCC)CC(=O)c2cc(-c3nc(-c4cccnc4)no3)ccc2O1] | 218 | 2,2-dipropyl-6-[3-(pyridin-3-yl)-1,2,4-oxadiazol-5-yl]-3,4-dihydro-2H-1-benzopyran-4-one |
| 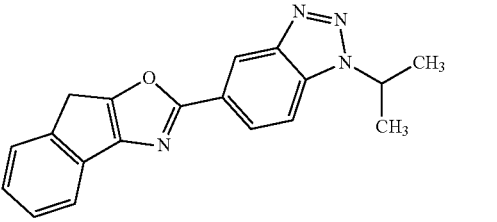 [SMILES: CC(C)n1nnc2cc(-c3nc4c(o3)Cc3ccccc3-4)ccc21] | 219 | 5-{8H-indeno[1,2-d][1,3]oxazol-2-yl}-1-(propan-2-yl)-1H-1,2,3-benzotriazole |
| 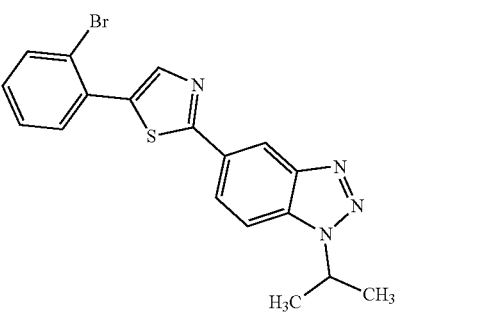 | 220 | 5-(2-bromophenyl)-2-(1-isopropylbenzotriazol-5-yl)thiazole |
| 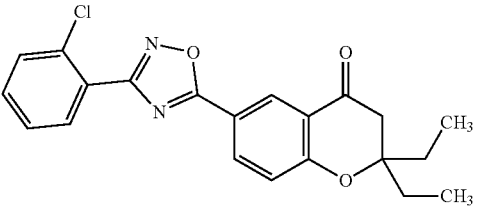 | 221 | 6-(3-(2-chlorophenyl)-1,2,4-oxadiazol-5-yl)-2,2-diethylchroman-4-one |
| 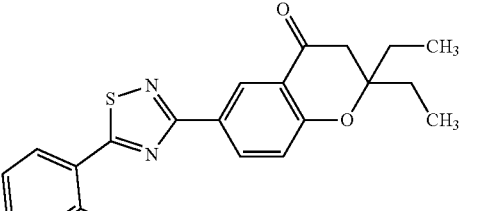 | 222 | 2,2-diethyl-6-(5-(2-methoxyphenyl)-1,2,4-thiadiazol-3-yl)chroman-4-one |

-continued

| Structure | Compound Number | Chemical Name |
|---|---|---|
| 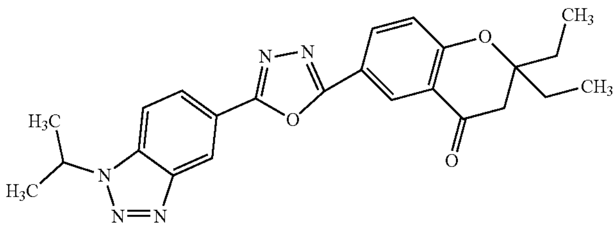 [SMILES: CCC1(CC)CC(=O)c2cc(-c3nnc(-c4ccc5c(c4)nnn5C(C)C)o3)ccc2O1] | 223 | 2,2-diethyl-6-(5-(1-isopropyl-1H-benzo[d][1,2,3]triazol-5-yl)-1,3,4-oxadiazol-2-yl)chroman-4-one |
| 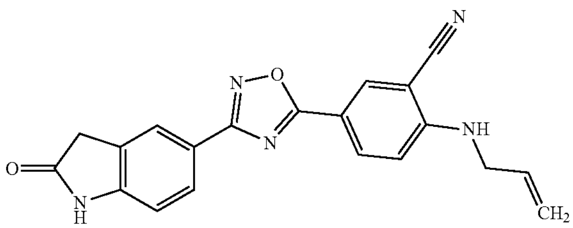 [SMILES: C=CCNc1ccc(-c2nc(-c3ccc4c(c3)CC(=O)N4)no2)cc1C#N] | 224 | 2-(allylamino)-5-(3-(2-oxoindolin-5-yl)-1,2,4-oxadiazol-5-yl)benzonitrile |
| 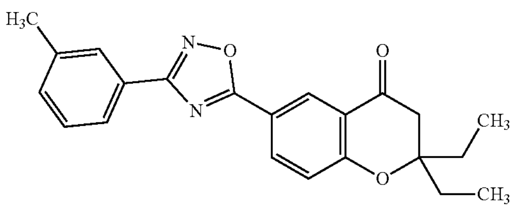 [SMILES: CCC1(CC)CC(=O)c2cc(-c3nc(-c4cccc(C)c4)no3)ccc2O1] | 225 | 2,2-diethyl-6-(3-(m-tolyl)-1,2,4-oxadiazol-5-yl)chroman-4-one |
| 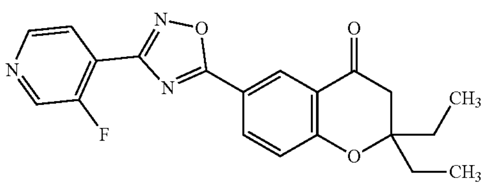 | 226 | 2,2-diethyl-6-(3-(3-fluoropyridin-4-yl)-1,2,4-oxadiazol-5-yl)chroman-4-one |
| 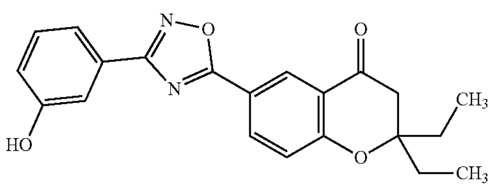 [SMILES: CCC1(CC)CC(=O)c2cc(-c3nc(-c4cccc(O)c4)no3)ccc2O1] | 227 | 2,2-diethyl-6-[3-(3-hydroxyphenyl)-1,2,4-oxadiazol-5-yl]chroman-4-one |
| 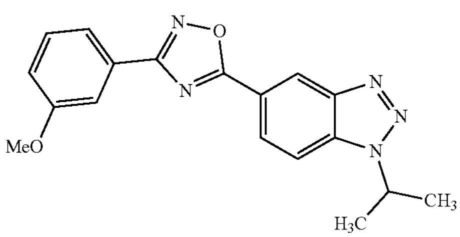 [SMILES: COc1cccc(-c2noc(-c3ccc4c(c3)nnn4C(C)C)n2)c1] | 228 | 5-(1-isopropyl-1H-benzo[d][1,2,3]triazol-5-yl)-3-(3-methoxyphenyl)-1,2,4-oxadiazole |
| 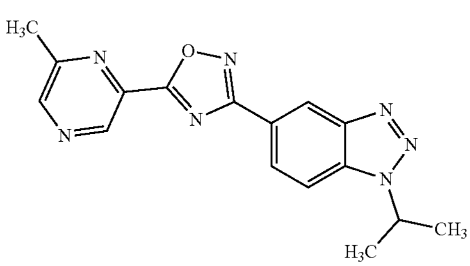 [SMILES: Cc1cncc(-c2nc(-c3ccc4c(c3)nnn4C(C)C)no2)n1] | 229 | 3-(1-isopropyl-1H-benzo[d][1,2,3]triazol-5-yl)-5-(6-methylpyrazin-2-yl)-1,2,4-oxadiazole |

-continued

| Structure | Compound Number | Chemical Name |
|---|---|---|
| 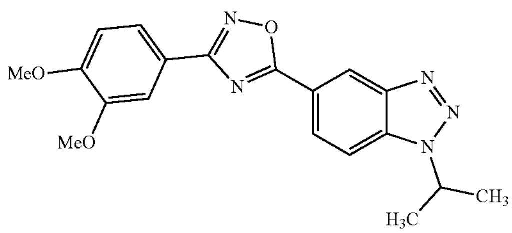 [SMILES: COc1ccc(-c2noc(-c3ccc4c(c3)nnn4C(C)C)n2)cc1OC] | 230 | 3-(3,4-dimethoxyphenyl)-5-(1-isopropyl-1H-benzo[d][1,2,3]triazol-5-yl)-1,2,4-oxadiazole |
| 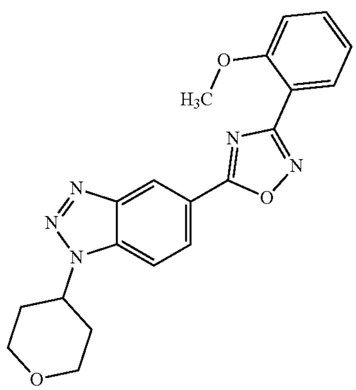 [SMILES: COc1ccccc1-c1noc(-c2ccc3c(c2)nnn3C2CCOCC2)n1] | 231 | 5-[3-(2-methoxyphenyl)-1,2,4-oxadiazol-5-yl]-1-(oxan-4-yl)-1H-1,2,3-benzotriazole |
| 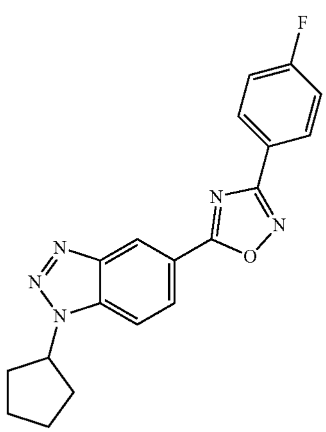 [SMILES: Fc1ccc(-c2noc(-c3ccc4c(c3)nnn4C3CCCC3)n2)cc1] | 232 | 1-cyclopentyl-5-[3-(4-fluorophenyl)-1,2,4-oxadiazol-5-yl]-1H-1,2,3-benzotriazole |
| 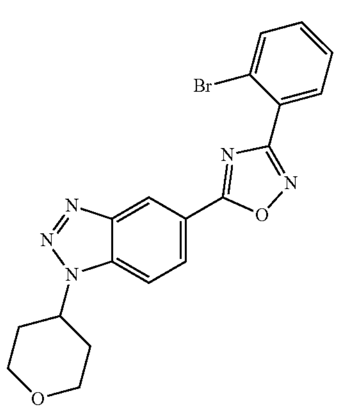 [SMILES: Brc1ccccc1-c1noc(-c2ccc3c(c2)nnn3C2CCOCC2)n1] | 233 | 5-[3-(2-bromophenyl)-1,2,4-oxadiazol-5-yl]-1-(oxan-4-yl)-1H-1,2,3-benzotriazole |

| Structure | Compound Number | Chemical Name |
|---|---|---|
| 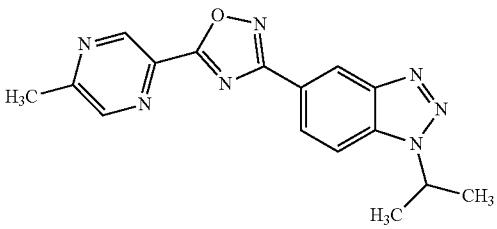 [SMILES: Cc1cnc(-c2nc(-c3ccc4c(c3)nnn4C(C)C)no2)cn1] | 234 | 3-(1-isopropyl-1H-benzo[d][1,2,3]triazol-5-yl)-5-(5-methylpyrazin-2-yl)-1,2,4-oxadiazole |
| 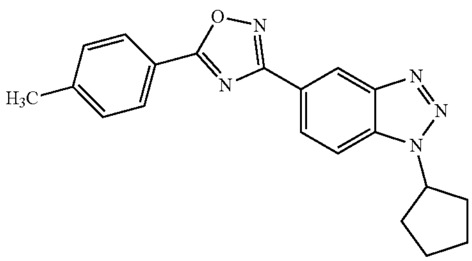 [SMILES: Cc1ccc(-c2nc(-c3ccc4c(c3)nnn4C3CCCC3)no2)cc1] | 235 | 3-(1-cyclopentyl-1H-benzo[d][1,2,3]triazol-5-yl)-5-(p-tolyl)-1,2,4-oxadiazole |
| 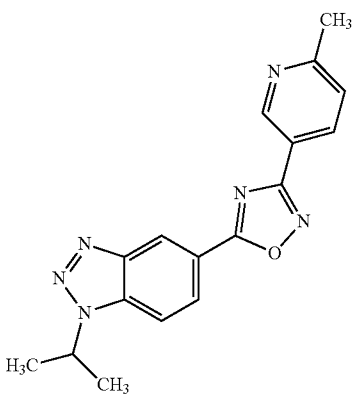 [SMILES: Cc1ccc(-c2noc(-c3ccc4c(c3)nnn4C(C)C)n2)cn1] | 236 | 5-[3-(6-methylpyridin-3-yl)-1,2,4-oxadiazol-5-yl]-1-(propan-2-yl)-1H-1,2,3-benzotriazole |
| 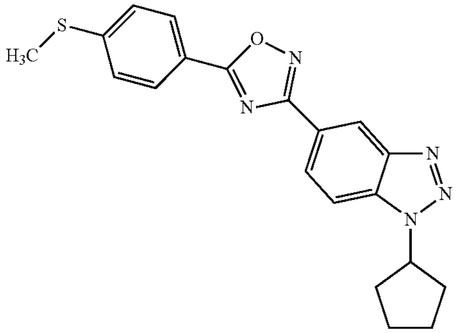 [SMILES: CSc1ccc(-c2nc(-c3ccc4c(c3)nnn4C3CCCC3)no2)cc1] | 237 | 3-(1-cyclopentyl-1H-benzo[d][1,2,3]triazol-5-yl)-5-(4-(methylthio)phenyl)-1,2,4-oxadiazole |
| 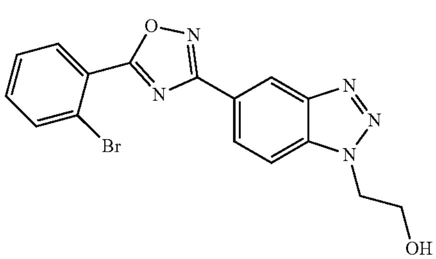 [SMILES: OCCn1nnc2cc(-c3noc(-c4ccccc4Br)n3)ccc21] | 238 | 2-(5-(5-(2-bromophenyl)-1,2,4-oxadiazol-3-yl)-1H-benzo[d][1,2,3]triazol-1-yl)ethanol |

-continued

| Structure | Compound Number | Chemical Name |
|---|---|---|
| 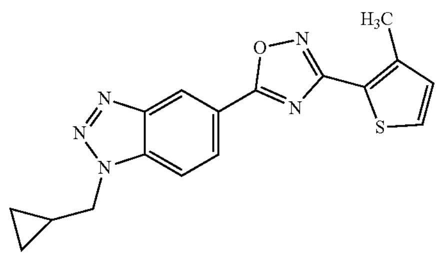 [SMILES: Cc1ccsc1-c1noc(-c2ccc3c(c2)nnn3CC2CC2)n1] | 239 | 1-(cyclopropylmethyl)-5-[3-(3-methylthiophen-2-yl)-1,2,4-oxadiazol-5-yl]-1H-1,2,3-benzotriazole |
| 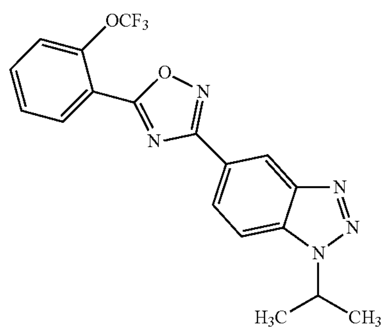 [SMILES: CC(C)n1nnc2cc(-c3noc(-c4ccccc4OC(F)(F)F)n3)ccc21] | 240 | 3-(1-isopropyl-1H-benzo[d][1,2,3]triazol-5-yl)-5-(2-(trifluoromethoxy)phenyl)-1,2,4-oxadiazole |
| 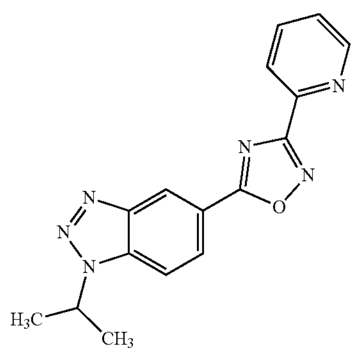 [SMILES: CC(C)n1nnc2cc(-c3nc(-c4ccccn4)no3)ccc21] | 241 | 1-(propan-2-yl)-5-[3-(pyridin-2-yl)-1,2,4-oxadiazol-5-yl]-1H-1,2,3-benzotriazole |
| 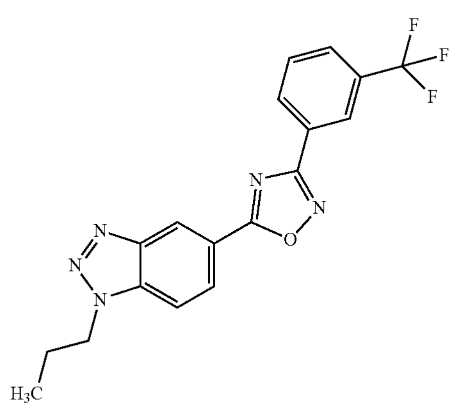 [SMILES: CCCn1nnc2cc(-c3nc(-c4cccc(C(F)(F)F)c4)no3)ccc21] | 242 | 1-propyl-5-{3-[3-(trifluoromethyl)phenyl]-1,2,4-oxadiazol-5-yl}-1H-1,2,3-benzotriazole |

-continued

| Structure | Compound Number | Chemical Name |
|---|---|---|
| 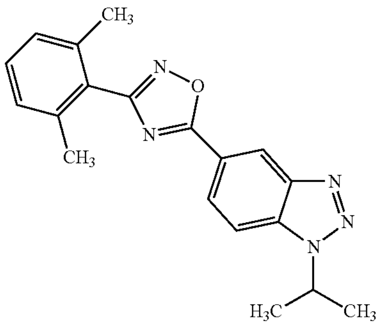 [SMILES: Cc1cccc(C)c1-c1noc(-c2ccc3c(c2)nnn3C(C)C)n1] | 243 | 3-(2,6-dimethylphenyl)-5-(1-isopropyl-1H-benzo[d][1,2,3]triazol-5-yl)-1,2,4-oxadiazole |
| 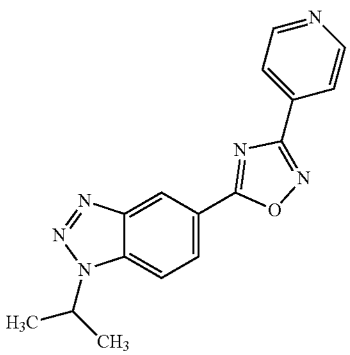 [SMILES: CC(C)n1nnc2cc(-c3nc(-c4ccncc4)no3)ccc21] | 244 | 1-(propan-2-yl)-5-[3-(pyridin-4-yl)-1,2,4-oxadiazol-5-yl]-1H-1,2,3-benzotriazole |
| 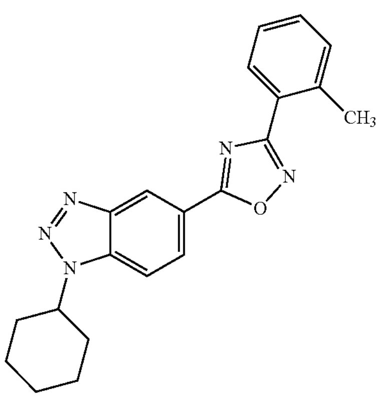 [SMILES: Cc1ccccc1-c1noc(-c2ccc3c(c2)nnn3C2CCCCC2)n1] | 245 | 1-cyclohexyl-5-[3-(2-methylphenyl)-1,2,4-oxadiazol-5-yl]-1H-1,2,3-benzotriazole |
| 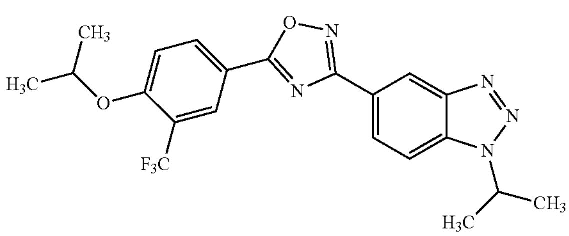 [SMILES: CC(C)Oc1ccc(-c2nc(-c3ccc4c(c3)nnn4C(C)C)no2)cc1C(F)(F)F] | 246 | 5-(4-isopropoxy-3-(trifluoromethyl)phenyl)-3-(1-isopropyl-1H-benzo[d][1,2,3]triazol-5-yl)-1,2,4-oxadiazole |
| 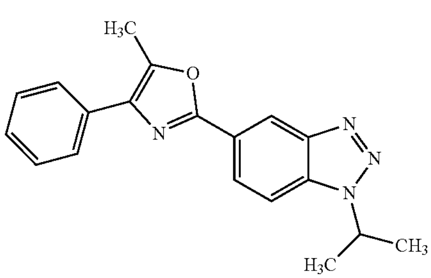 [SMILES: Cc1oc(-c2ccc3c(c2)nnn3C(C)C)nc1-c1ccccc1] | 247 | 5-(5-methyl-4-phenyl-1,3-oxazol-2-yl)-1-(propan-2-yl)-1H-1,2,3-benzotriazole |

-continued

| Structure | Compound Number | Chemical Name |
|---|---|---|
| 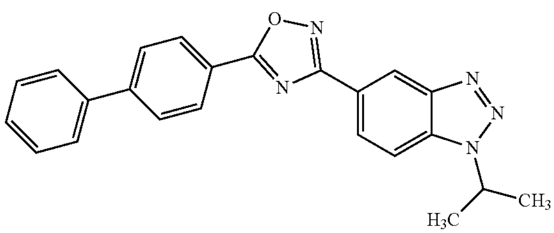 [SMILES: CC(C)n1nnc2cc(-c3noc(-c4ccc(-c5ccccc5)cc4)n3)ccc21] | 248 | 5-([1,1'-biphenyl]-4-yl)-3-(1-isopropyl-1H-benzo[d][1,2,3]triazol-5-yl)-1,2,4-oxadiazole |
| 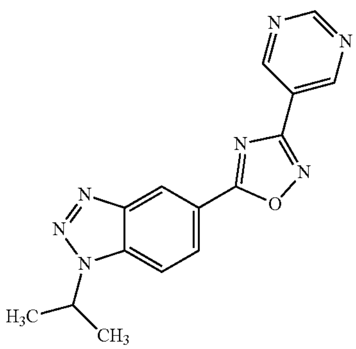 [SMILES: CC(C)n1nnc2cc(-c3nc(-c4cncnc4)no3)ccc21] | 249 | 1-(propan-2-yl)-5-[3-(pyrimidin-5-yl)-1,2,4-oxadiazol-5-yl]-1H-1,2,3-benzotriazole |
| 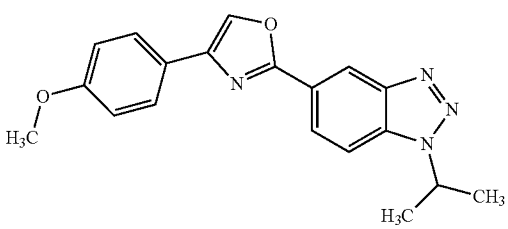 [SMILES: COc1ccc(-c2coc(-c3ccc4c(c3)nnn4C(C)C)n2)cc1] | 250 | 5-[4-(4-methoxyphenyl)-1,3-oxazol-2-yl]-1-(propan-2-yl)-1H-1,2,3-benzotriazole |
| 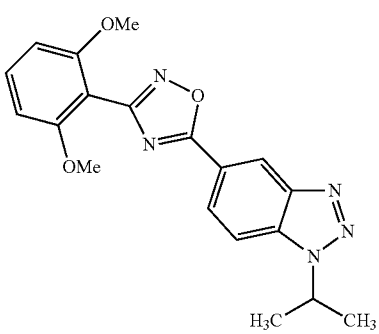 | 251 | 3-(2,6-dimethoxyphenyl)-5-(1-isopropylbenzotriazol-5-yl)-1,2,4-oxadiazole |
| 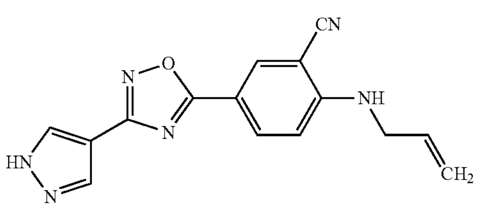 [SMILES: C=CCNc1ccc(-c2nc(-c3cn[nH]c3)no2)cc1C#N] | 252 | 5-(3-(1H-pyrazol-4-yl)-1,2,4-oxadiazol-5-yl)-2-(allylamino)benzonitrile |
| 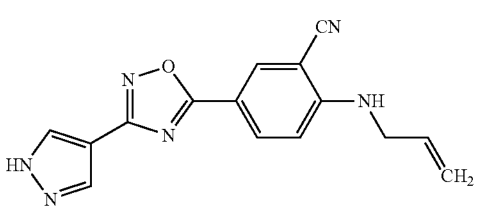 [SMILES: C=CCNc1ccc(-c2nc(-c3cn[nH]c3)no2)cc1C#N] | 253 | 1-tert-butyl-5-[3-(3-methylthiophen-2-yl)-1,2,4-oxadiazol-5-yl]-1H-1,2,3-benzotriazole |

-continued

| Structure | Compound Number | Chemical Name |
|---|---|---|
| 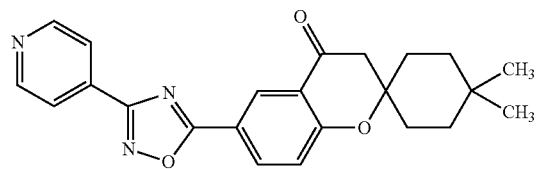 [SMILES: CC1(C)CCC2(CC1)CC(=O)c1cc(-c3nc(-c4ccncc4)no3)ccc1O2] | 254 | 4',4'-dimethyl-6-[3-(pyridin-4-yl)-1,2,4-oxadiazol-5-yl]-3,4-dihydrospiro[1-benzopyran-2,1'-cyclohexane]-4-one |
| 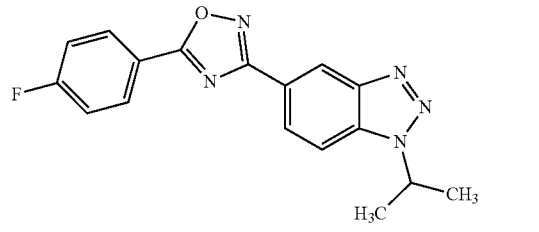 [SMILES: CC(C)n1nnc2cc(-c3noc(-c4ccc(F)cc4)n3)ccc21] | 255 | 5-(4-fluorophenyl)-3-(1-isopropylbenzotriazol-5-yl)-1,2,4-oxadiazole |
| 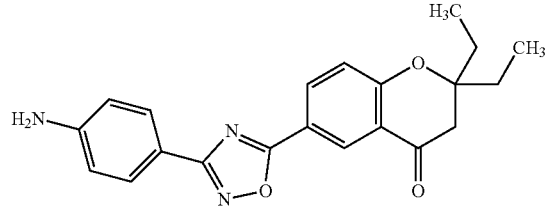 [SMILES: CCC1(CC)CC(=O)c2cc(-c3nc(-c4ccc(N)cc4)no3)ccc2O1] | 256 | 6-(3-(4-aminophenyl)-1,2,4-oxadiazol-5-yl)-2,2-diethylchroman-4-one |
| 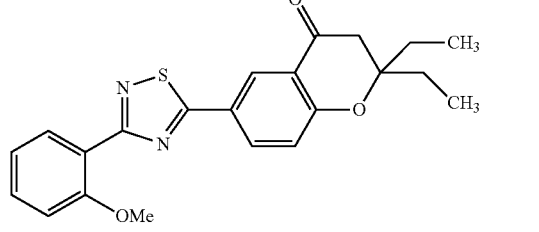 | 257 | 2,2-diethyl-6-(3-(2-methoxyphenyl)-1,2,4-thiadiazol-5-yl)chroman-4-one |
| 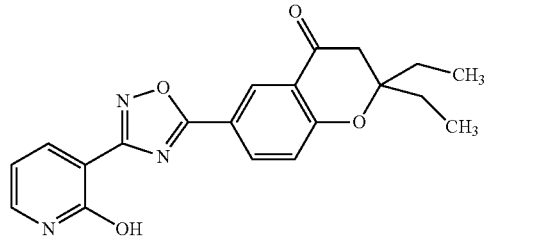 [SMILES: CCC1(CC)CC(=O)c2cc(-c3nc(-c4cccnc4O)no3)ccc2O1] | 258 | 2,2-diethyl-6-(3-(2-hydroxypyridin-3-yl)-1,2,4-oxadiazol-5-yl)chroman-4-one |
| 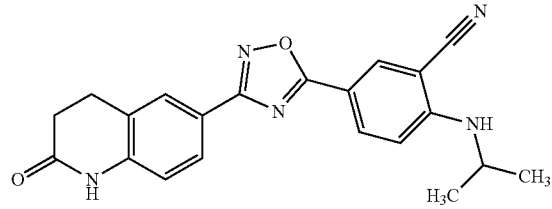 [SMILES: CC(C)Nc1ccc(-c2nc(-c3ccc4c(c3)CCC(=O)N4)no2)cc1C#N] | 259 | 2-(isopropylamino)-5-(3-(2-oxo-1,2,3,4-tetrahydroquinolin-6-yl)-1,2,4-oxadiazol-5-yl)benzonitrile |

-continued

| Structure | Compound Number | Chemical Name |
|---|---|---|
| 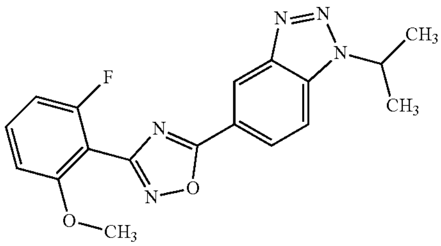 [SMILES: COc1cccc(F)c1-c1noc(-c2ccc3c(c2)nnn3C(C)C)n1] | 260 | 3-(2-fluoro-6-methoxy-phenyl)-5-(1-isopropylbenzotriazol-5-yl)-1,2,4-oxadiazole |
| 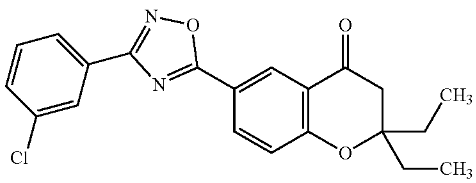 [SMILES: CCC1(CC)CC(=O)c2cc(-c3nc(-c4cccc(Cl)c4)no3)ccc2O1] | 261 | 6-[3-(3-chlorophenyl)-1,2,4-oxadiazol-5-yl]-2,2-diethyl-chroman-4-one |
| 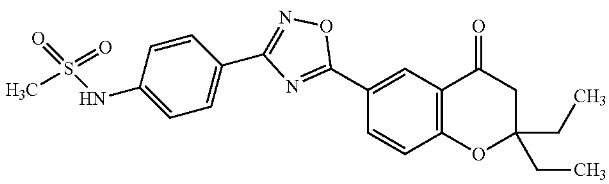 [SMILES: CCC1(CC)CC(=O)c2cc(-c3nc(-c4ccc(NS(C)(=O)=O)cc4)no3)ccc2O1] | 262 | N-(4-(5-(2,2-diethyl-4-oxochroman-6-yl)-1,2,4-oxadiazol-3-yl)phenyl)methanesulfonamide |
| 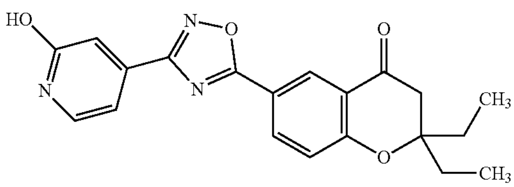 [SMILES: CCC1(CC)CC(=O)c2cc(-c3nc(-c4ccnc(O)c4)no3)ccc2O1] | 263 | 2,2-diethyl-6-[3-(2-hydroxy-4-pyridyl)-1,2,4-oxadiazol-5-yl]chroman-4-one |
| 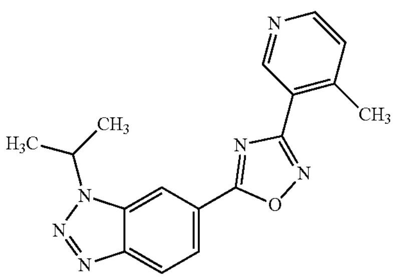 [SMILES: Cc1ccncc1-c1noc(-c2ccc3nnn(C(C)C)c3c2)n1] | 264 | 6-[3-(4-methylpyridin-3-yl)-1,2,4-oxadiazol-5-yl]-1-(propan-2-yl)-1H-1,2,3-benzotriazole |
| 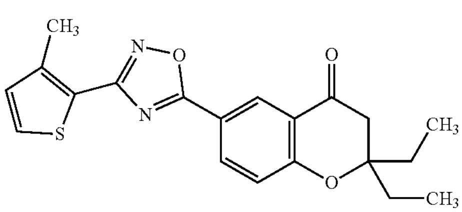 [SMILES: CCC1(CC)CC(=O)c2cc(-c3nc(-c4sccc4C)no3)ccc2O1] | 265 | 2,2-diethyl-6-(3-(3-methylthiophen-2-yl)-1,2,4-oxadiazol-5-yl)chroman-4-one |
| 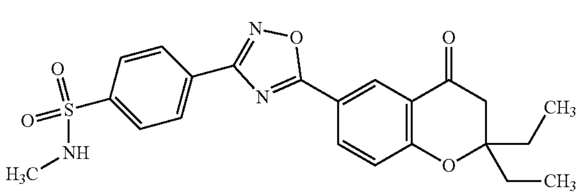 [SMILES: CCC1(CC)CC(=O)c2cc(-c3nc(-c4ccc(S(=O)(=O)NC)cc4)no3)ccc2O1] | 266 | 4-(5-(2,2-diethyl-4-oxochroman-6-yl)-1,2,4-oxadiazol-3-yl)-N-methylbenzenesulfonamide |

-continued

| Structure | Compound Number | Chemical Name |
|---|---|---|
| 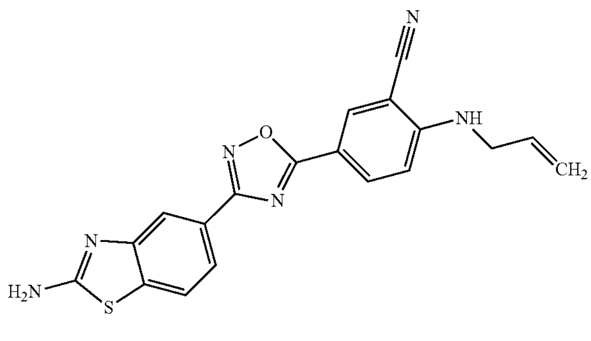 [SMILES: C=CCNc1ccc(-c2nc(-c3ccc4sc(N)nc4c3)no2)cc1C#N] | 267 | 2-(allylamino)-5-(3-(2-aminobenzo[d]thiazol-5-yl)-1,2,4-oxadiazol-5-yl)benzonitrile |
| 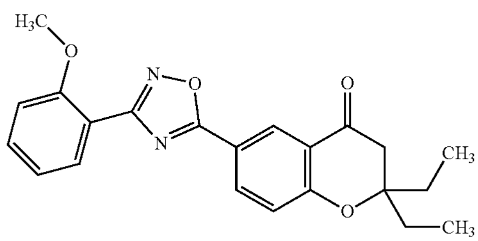 [SMILES: CCC1(CC)CC(=O)c2cc(-c3nc(-c4ccccc4OC)no3)ccc2O1] | 268 | 2,2-diethyl-6-[3-(2-methoxyphenyl)-1,2,4-oxadiazol-5-yl]chroman-4-one |
| 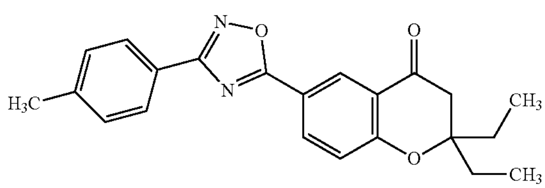 [SMILES: CCC1(CC)CC(=O)c2cc(-c3nc(-c4ccc(C)cc4)no3)ccc2O1] | 269 | 2,2-diethyl-6-[3-(p-tolyl)-1,2,4-oxadiazol-5-yl]chroman-4-one |
| 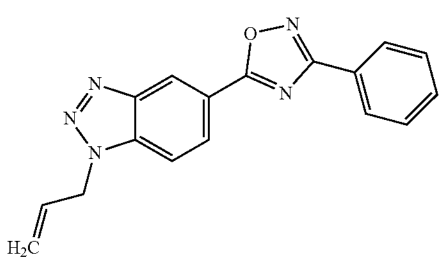 [SMILES: C=CCn1nnc2cc(-c3nc(-c4ccccc4)no3)ccc21] | 270 | 5-(3-phenyl-1,2,4-oxadiazol-5-yl)-1-(prop-2-en-1-yl)-1H-1,2,3-benzotriazole |
| 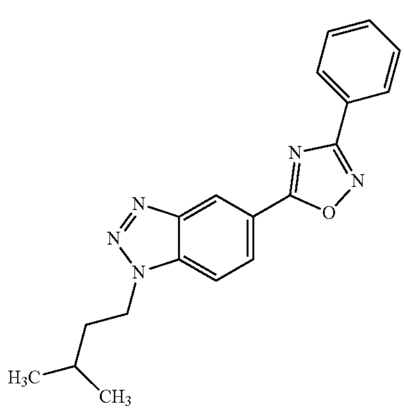 [SMILES: CC(C)CCn1nnc2cc(-c3nc(-c4ccccc4)no3)ccc21] | 271 | 1-(3-methylbutyl)-5-(3-phenyl-1,2,4-oxadiazol-5-yl)-1H-1,2,3-benzotriazole |

-continued

| Structure | Compound Number | Chemical Name |
|---|---|---|
| 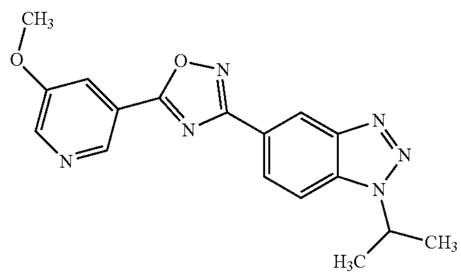 [SMILES: COc1cncc(-c2nc(-c3ccc4c(c3)nnn4C(C)C)no2)c1] | 272 | 3-(1-isopropyl-1H-benzo[d][1,2,3]triazol-5-yl)-5-(5-methoxypyridin-3-yl)-1,2,4-oxadiazole |
| 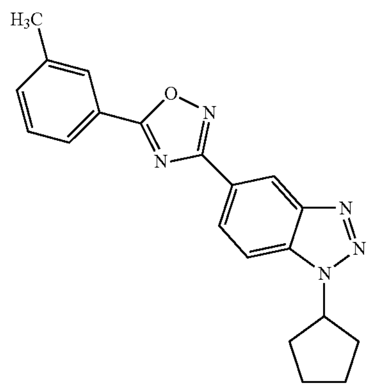 [SMILES: Cc1cccc(-c2nc(-c3ccc4c(c3)nnn4C3CCCC3)no2)c1] | 273 | 3-(1-cyclopentyl-1H-benzo[d][1,2,3]triazol-5-yl)-5-(m-tolyl)-1,2,4-oxadiazole |
| 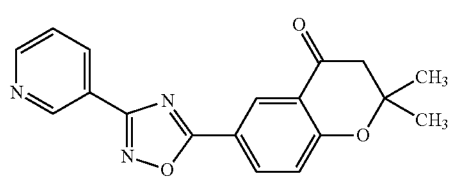 [SMILES: CC1(C)CC(=O)c2cc(-c3nc(-c4cccnc4)no3)ccc2O1] | 274 | 2,2-dimethyl-6-[3-(pyridin-3-yl)-1,2,4-oxadiazol-5-yl]-3,4-dihydro-2H-1-benzopyran-4-one |
| 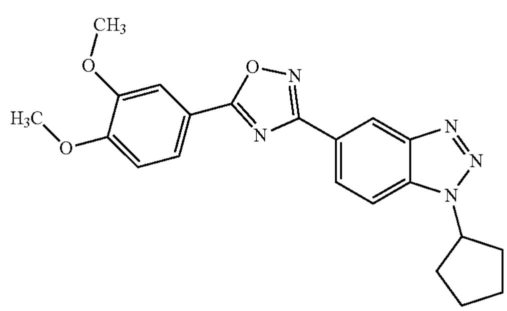 [SMILES: COc1ccc(-c2nc(-c3ccc4c(c3)nnn4C3CCCC3)no2)cc1OC] | 275 | 3-(1-cyclopentyl-1H-benzo[d][1,2,3]triazol-5-yl)-5-(3,4-dimethoxyphenyl)-1,2,4-oxadiazole |
| 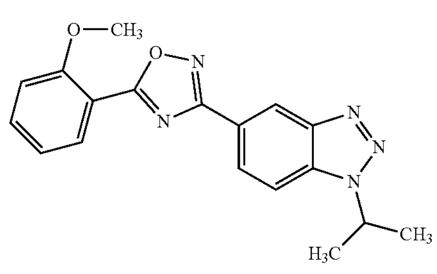 [SMILES: COc1ccccc1-c1nc(-c2ccc3c(c2)nnn3C(C)C)no1] | 276 | 3-(1-isopropyl-1H-benzo[d][1,2,3]triazol-5-yl)-5-(2-(methylthio)phenyl)-1,2,4-oxadiazole |

-continued

| Structure | Compound Number | Chemical Name |
|---|---|---|
| 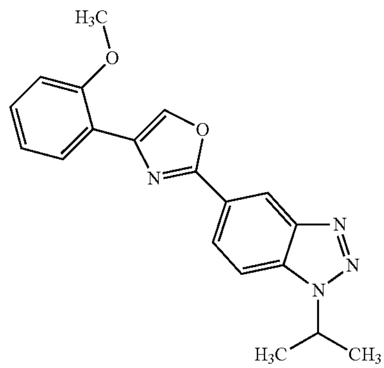 [SMILES: COc1ccccc1-c1coc(-c2ccc3c(c2)nnn3C(C)C)n1] | 277 | 5-[4-(2-methoxyphenyl)-1,3-oxazol-2-yl]-1-(propan-2-yl)-1H-1,2,3-benzotriazole |
| 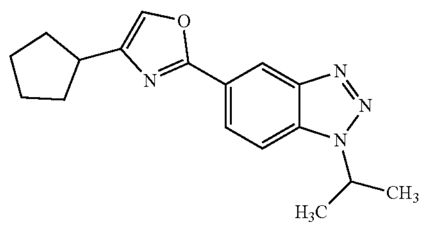 [SMILES: CC(C)n1nnc2cc(-c3nc(C4CCCC4)co3)ccc21] | 278 | 5-(5-cyclopentyl-1,2,4-oxadiazol-3-yl)-1-(propan-2-yl)-1H-1,2,3-benzotriazole5-(5-cyclopentyl-1,2,4-oxadiazol-3-yl)-1-(propan-2-yl)-1H-1,2,3-benzotriazole |
| 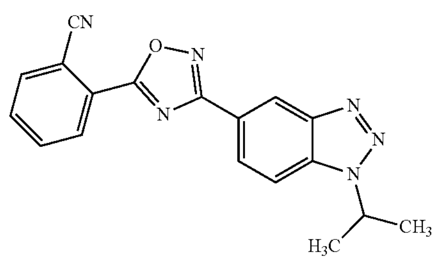 [SMILES: CC(C)n1nnc2cc(-c3noc(-c4ccccc4C#N)n3)ccc21] | 279 | 2-(3-(1-isopropyl-1H-benzo[d][1,2,3]triazol-5-yl)-1,2,4-oxadiazol-5-yl)benzonitrile |
| 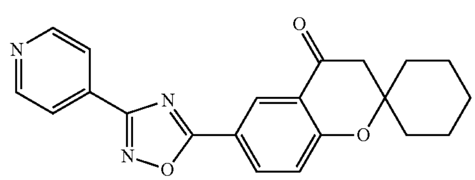 [SMILES: O=C1CC2(CCCCC2)Oc2ccc(-c3nc(-c4ccncc4)no3)cc21] | 280 | 6-[3-(pyridin-4-yl)-1,2,4-oxadiazol-5-yl]-3,4-dihydrospiro[1-benzopyran-2,1'-cyclohexane]-4-one |
| 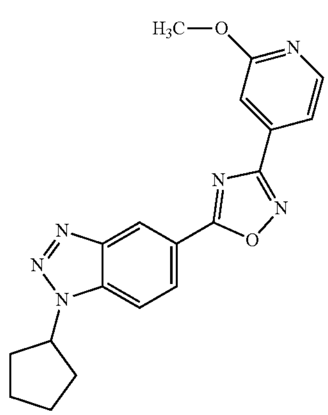 [SMILES: COc1cc(-c2noc(-c3ccc4c(c3)nnn4C3CCCC3)n2)ccn1] | 281 | 1-cyclopentyl-5-[3-(2-methoxypyridin-4-yl)-1,2,4-oxadiazol-5-yl]-1H-1,2,3-benzotriazole |

-continued

| Structure | Compound Number | Chemical Name |
|---|---|---|
| 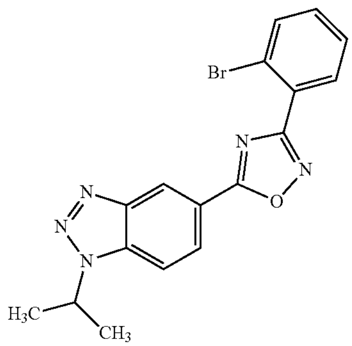 [SMILES: CC(C)n1nnc2cc(-c3nc(-c4ccccc4Br)no3)ccc21] | 282 | 5-[3-(2-bromophenyl)-1,2,4-oxadiazol-5-yl]-1-(propan-2-yl)-1H-1,2,3-benzotriazole |
| 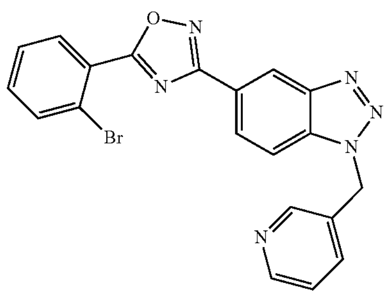 [SMILES: Brc1ccccc1-c1nc(-c2ccc3c(c2)nnn3Cc2cccnc2)no1] | 283 | 5-(2-bromophenyl)-3-(1-(pyridin-3-ylmethyl)-1H-benzo[d][1,2,3]triazol-5-yl)-1,2,4-oxadiazole |
| 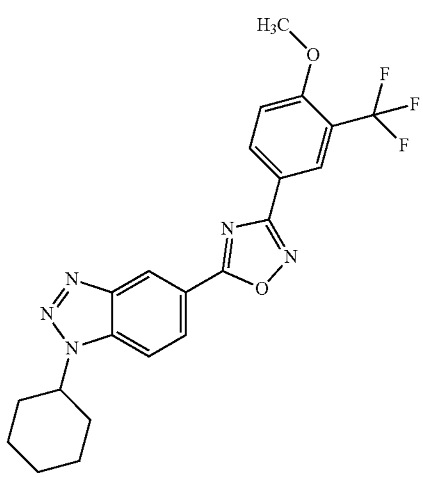 [SMILES: COc1ccc(-c2noc(-c3ccc4c(c3)nnn4C3CCCCC3)n2)cc1C(F)(F)F] | 284 | 1-cyclohexyl-5-{3-[4-methoxy-3-(trifluoromethyl)phenyl]-1,2,4-oxadiazol-5-yl}-1H-1,2,3-benzotriazole |
| 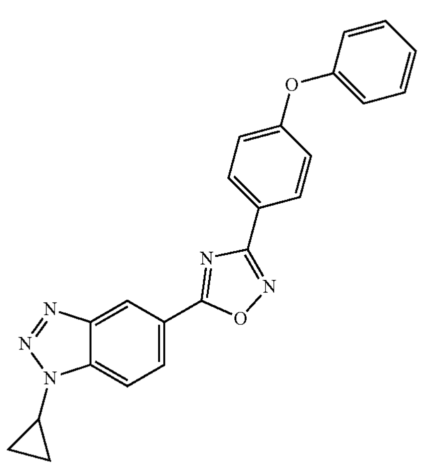 [SMILES: c1ccc(Oc2ccc(-c3noc(-c4ccc5c(c4)nnn5C4CC4)n3)cc2)cc1] | 285 | 1-cyclopropyl-5-[3-(4-phenoxyphenyl)-1,2,4-oxadiazol-5-yl]-1H-1,2,3-benzotriazole |

-continued

| Structure | Compound Number | Chemical Name |
|---|---|---|
| 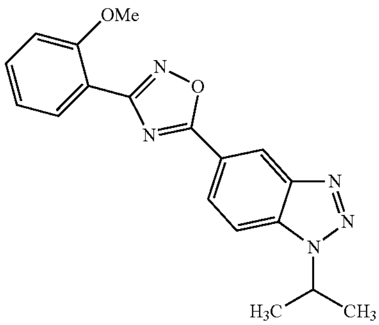 [SMILES: COc1ccccc1-c1noc(-c2ccc3c(c2)nnn3C(C)C)n1] | 286 | 5-(1-isopropyl-1H-benzo[d][1,2,3]triazol-5-yl)-3-(2-methoxyphenyl)-1,2,4-oxadiazole |
| 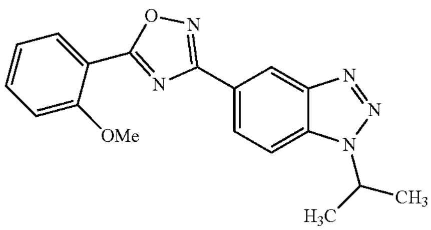 [SMILES: COc1ccccc1-c1nc(-c2ccc3c(c2)nnn3C(C)C)no1] | 287 | 3-(1-isopropyl-1H-benzo[d][1,2,3]triazol-5-yl)-5-(2-methoxyphenyl)-1,2,4-oxadiazole |
| 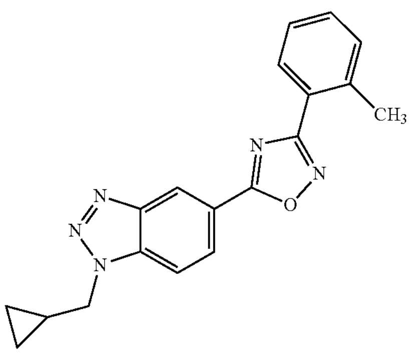 [SMILES: Cc1ccccc1-c1noc(-c2ccc3c(c2)nnn3CC2CC2)n1] | 288 | 1-(cyclopropylmethyl)-5-[3-(2-methylphenyl)-1,2,4-oxadiazol-5-yl]-1H-1,2,3-benzotriazole |
| 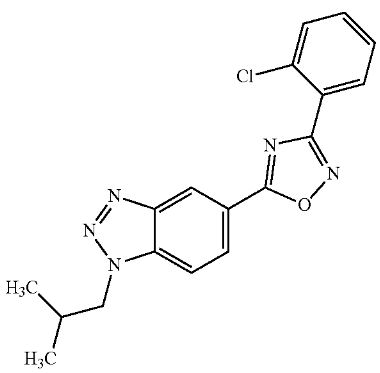 [SMILES: CC(C)Cn1nnc2cc(-c3nc(-c4ccccc4Cl)no3)ccc21] | 289 | 5-[3-(2-chlorophenyl)-1,2,4-oxadiazol-5-yl]-1-(2-methylpropyl)-1H-1,2,3-benzotriazole |
| 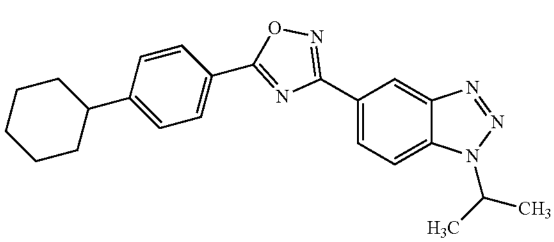 [SMILES: CC(C)n1nnc2cc(-c3noc(-c4ccc(C5CCCCC5)cc4)n3)ccc21] | 290 | 5-(4-cyclohexylphenyl)-3-(1-isopropyl-1H-benzo[d][1,2,3]triazol-5-yl)-1,2,4-oxadiazole |

-continued

| Structure | Compound Number | Chemical Name |
|---|---|---|
| 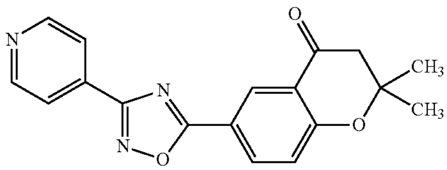 [SMILES: CC1(C)CC(=O)c2cc(-c3nc(-c4ccncc4)no3)ccc2O1] | 291 | 2,2-dimethyl-6-[3-(pyridin-4-yl)-1,2,4-oxadiazol-5-yl]-3,4-dihydro-2H-1-benzopyran-4-one |
| 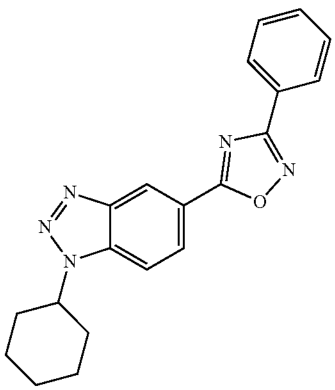 [SMILES: c1ccc(-c2noc(-c3ccc4c(c3)nnn4C3CCCCC3)n2)cc1] | 292 | 1-cyclohexyl-5-(3-phenyl-1,2,4-oxadiazol-5-yl)-1H-1,2,3-benzotriazole |
| 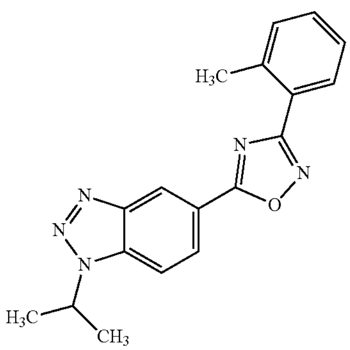 [SMILES: Cc1ccccc1-c1noc(-c2ccc3c(c2)nnn3C(C)C)n1] | 293 | 5-[3-(2-methylphenyl)-1,2,4-oxadiazol-5-yl]-1-(propan-2-yl)-1H-1,2,3-benzotriazole |
| 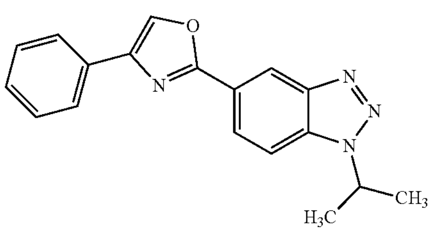 [SMILES: CC(C)n1nnc2cc(-c3nc(-c4ccccc4)co3)ccc21] | 294 | 5-(4-phenyl-1,3-oxazol-2-yl)-1-(propan-2-yl)-1H-1,2,3-benzotriazole |
| 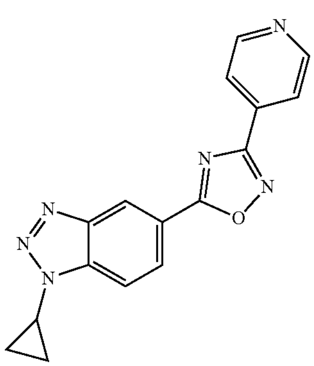 [SMILES: c1cc(-c2noc(-c3ccc4c(c3)nnn4C3CC3)n2)ccn1] | 295 | 1-cyclopropyl-5-[3-(pyridin-4-yl)-1,2,4-oxadiazol-5-yl]-1H-1,2,3-benzotriazole |

-continued

| Structure | Compound Number | Chemical Name |
|---|---|---|
| 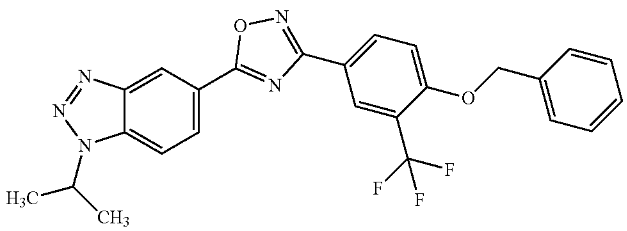 [SMILES: CC(C)n1nnc2cc(-c3nc(-c4ccc(OCc5ccccc5)c(C(F)(F)F)c4)no3)ccc21] | 296 | 5-{3-[4-(benzyloxy)-3-(trifluoromethyl)phenyl]-1,2,4-oxadiazol-5-yl}-1-(propan-2-yl)-1H-1,2,3-benzotriazole |
| 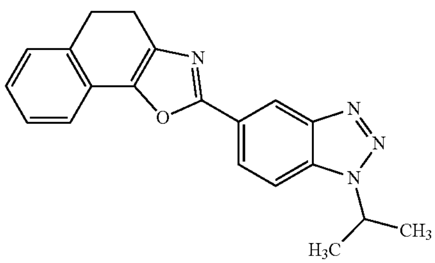 [SMILES: CC(C)n1nnc2cc(-c3nc4c(o3)-c3ccccc3CC4)ccc21] | 297 | 5-{4H,5H-naphtho[2,1-d][1,3]oxazol-2-yl}-1-(propan-2-yl)-1H-1,2,3-benzotriazole |
| 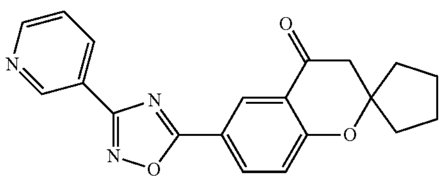 [SMILES: O=C1CC2(CCCC2)Oc2ccc(-c3nc(-c4cccnc4)no3)cc21] | 298 | 6-[3-(pyridin-3-yl)-1,2,4-oxadiazol-5-yl]-3,4-dihydrospiro[1-benzopyran-2,1'-cyclopentane]-4-one |
| 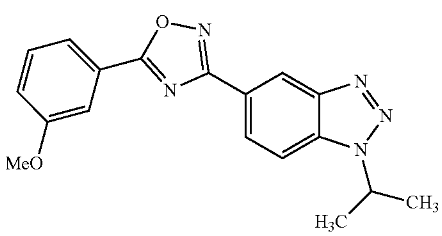 [SMILES: COc1cccc(-c2nc(-c3ccc4c(c3)nnn4C(C)C)no2)c1] | 299 | 3-(1-isopropylbenzotriazol-5-yl)-5-(3-methoxyphenyl)-1,2,4-oxadiazole |
| 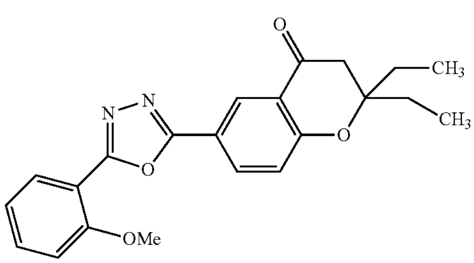 [SMILES: CCC1(CC)CC(=O)c2cc(-c3nnc(-c4ccccc4OC)o3)ccc2O1] | 300 | 2,2-diethyl-6-(5-(2-methoxyphenyl)-1,3,4-oxadiazol-2-yl)chroman-4-one |
| 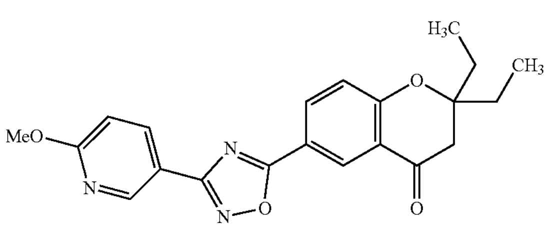 [SMILES: CCC1(CC)CC(=O)c2cc(-c3nc(-c4ccc(OC)nc4)no3)ccc2O1] | 301 | 2,2-diethyl-6-[3-(6-methoxy-3-pyridyl)-1,2,4-oxadiazol-5-yl]chroman-4-one |

-continued

| Structure | Compound Number | Chemical Name |
|---|---|---|
| 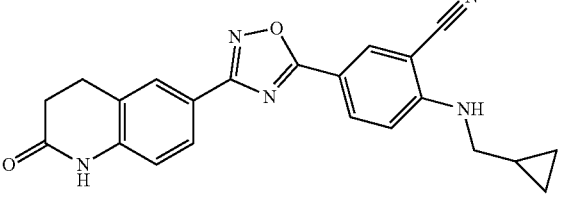 | 302 | 2-((cyclopropylmethyl)amino)-5-(3-(2-oxo-1,2,3,4-tetrahydroquinolin-6-yl)-1,2,4-oxadiazol-5-yl)benzonitrile |
| 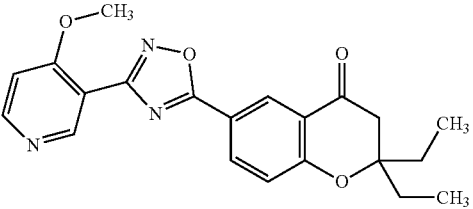 [SMILES: CCC1(CC)CC(=O)c2cc(-c3nc(-c4cnccc4OC)no3)ccc2O1] | 303 | 2,2-diethyl-6-(3-(4-methoxypyridin-3-yl)-1,2,4-oxadiazol-5-yl)chroman-4-one |
| 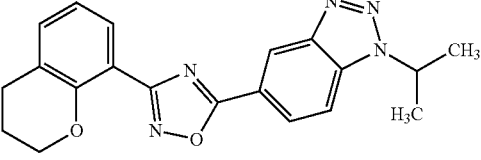 | 304 | 3-chroman-8-yl-5-(1-isopropylbenzotriazol-5-yl)-1,2,4-oxadiazole |
| 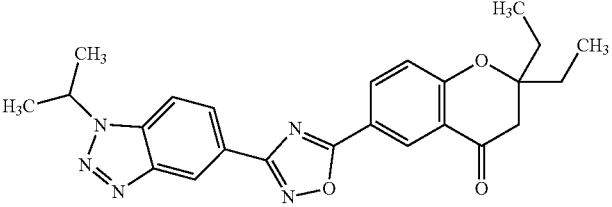 [SMILES: CCC1(CC)CC(=O)c2cc(-c3nc(-c4ccc5c(c4)nnn5C(C)C)no3)ccc2O1] | 305 | 2,2-diethyl-6-(3-(1-isopropyl-1H-benzo[d][1,2,3]triazol-5-yl)-1,2,4-oxadiazol-5-yl)chroman-4-one |
| 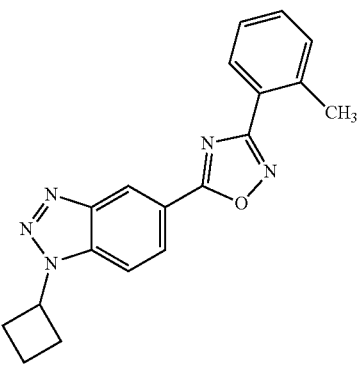 [SMILES: Cc1ccccc1-c1noc(-c2ccc3c(c2)nnn3C2CCC2)n1] | 306 | 1-cyclobutyl-5-[3-(2-methylphenyl)-1,2,4-oxadiazol-5-yl]-1H-1,2,3-benzotriazole |
| 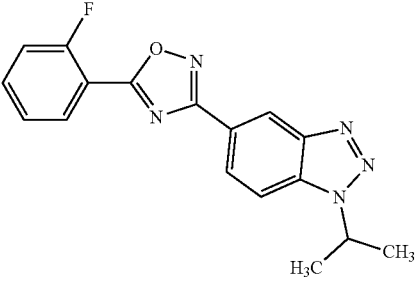 [SMILES: CC(C)n1nnc2cc(-c3noc(-c4ccccc4F)n3)ccc21] | 307 | 5-(2-fluorophenyl)-3-(1-isopropyl-1H-benzo[d][1,2,3]triazol-5-yl)-1,2,4-oxadiazole |

-continued

| Structure | Compound Number | Chemical Name |
|---|---|---|
| 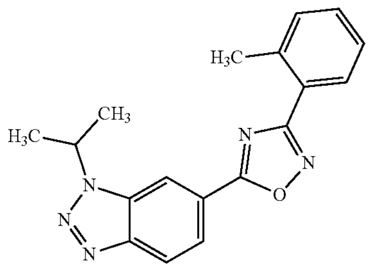 [SMILES: Cc1ccccc1-c1noc(-c2ccc3nnn(C(C)C)c3c2)n1] | 308 | 6-[3-(2-methylphenyl)-1,2,4-oxadiazol-5-yl]-1-(propan-2-yl)-1H-1,2,3-benzotriazole |
| 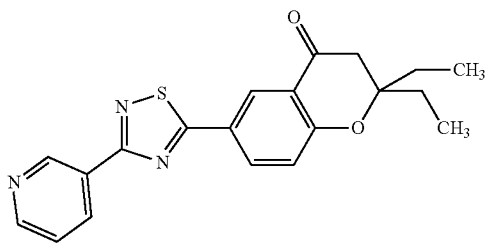 [SMILES: CCC1(CC)CC(=O)c2cc(-c3nc(-c4cccnc4)ns3)ccc2O1] | 309 | 2,2-diethyl-6-(3-(pyridin-3-yl)-1,2,4-thiadiazol-5-yl)chroman-4-one |
| 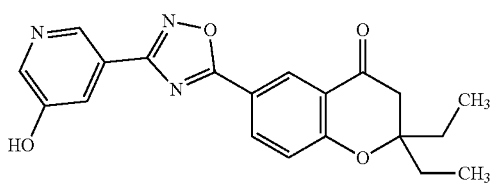 [SMILES: CCC1(CC)CC(=O)c2cc(-c3nc(-c4cncc(O)c4)no3)ccc2O1] | 310 | 2,2-diethyl-6-[3-(5-hydroxy-3-pyridyl)-1,2,4-oxadiazol-5-yl]chroman-4-one |
| 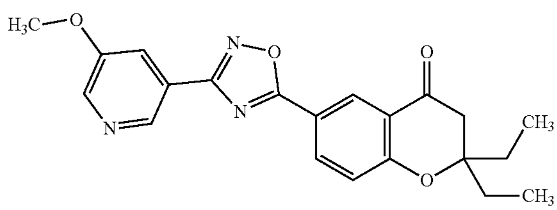 [SMILES: CCC1(CC)CC(=O)c2cc(-c3nc(-c4cncc(OC)c4)no3)ccc2O1] | 311 | 2,2-diethyl-6-(3-(5-methoxypyridin-3-yl)-1,2,4-oxadiazol-5-yl)chroman-4-one |
| 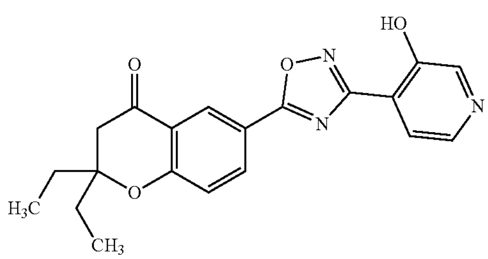 [SMILES: CCC1(CC)CC(=O)c2cc(-c3nc(-c4ccncc4O)no3)ccc2O1] | 312 | 2,2-diethyl-6-(3-(3-hydroxypyridin-4-yl)-1,2,4-oxadiazol-5-yl)chroman-4-one |
| 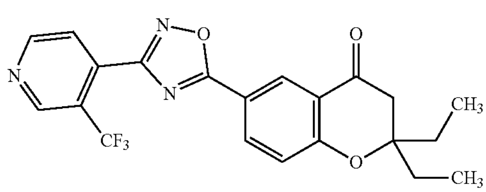 | 313 | 2,2-diethyl-6-(3-(3-(trifluoromethyl)pyridin-4-yl)-1,2,4-oxadiazol-5-yl)chroman-4-one |
| 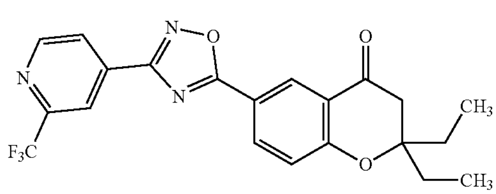 [SMILES: CCC1(CC)CC(=O)c2cc(-c3nc(-c4ccnc(C(F)(F)F)c4)no3)ccc2O1] | 314 | 2,2-diethyl-6-(3-(2-(trifluoromethyl)pyridin-4-yl)-1,2,4-oxadiazol-5-yl)chroman-4-one |

-continued

| Structure | Compound Number | Chemical Name |
|---|---|---|
| 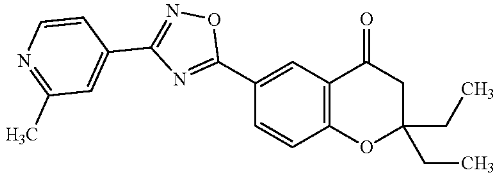 | 315 | 2,2-diethyl-6-(3-(2-methylpyridin-4-yl)-1,2,4-oxadiazol-5-yl)chroman-4-one |
| 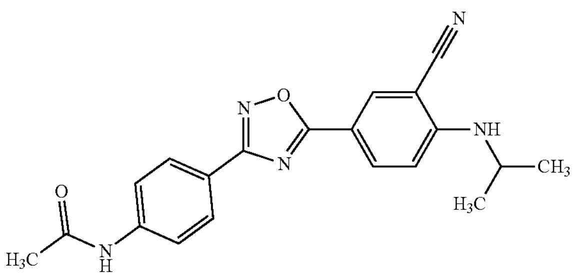 [SMILES: CC(=O)Nc1ccc(-c2noc(-c3ccc(NC(C)C)c(C#N)c3)n2)cc1] | 316 | N-(4-(5-(3-cyano-4-(isopropylamino)phenyl)-1,2,4-oxadiazol-3-yl)phenyl)acetamide |
| 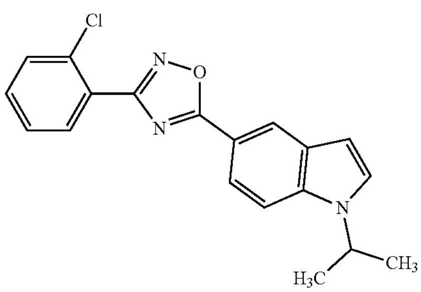 [SMILES: CC(C)n1ccc2cc(-c3nc(-c4ccccc4Cl)no3)ccc21] | 320 | 3-(2-chlorophenyl)-5-(1-isopropyl-1H-indol-5-yl)-1,2,4-oxadiazole |
| 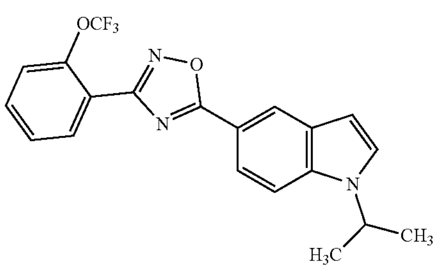 | 321 | 5-(1-isopropyl-1H-indol-5-yl)-3-(2-(trifluoromethoxy)phenyl)-1,2,4-oxadiazole |
| 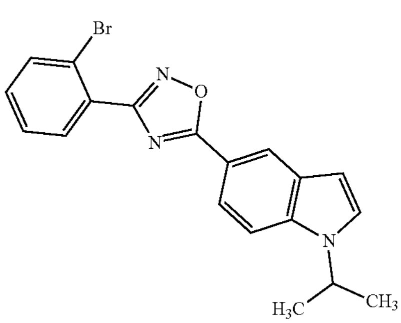 [SMILES: CC(C)n1ccc2cc(-c3nc(-c4ccccc4Br)no3)ccc21] | 322 | 3-(2-bromophenyl)-5-(1-isopropyl-1H-indol-5-yl)-1,2,4-oxadiazole |

-continued

| Structure | Compound Number | Chemical Name |
|---|---|---|
| 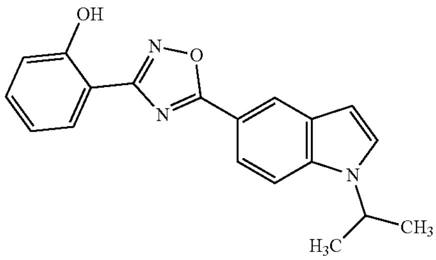 | 323 | 2-(5-(1-isopropyl-1H-indol-5-yl)-1,2,4-oxadiazol-3-yl)phenol |
| 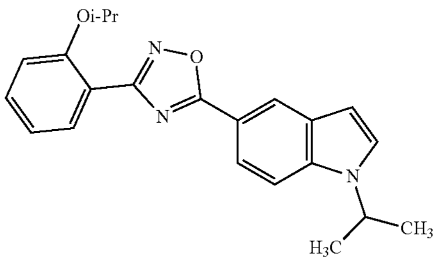 | 324 | 3-(2-isopropoxyphenyl)-5-(1-isopropyl-1H-indol-5-yl)-1,2,4-oxadiazole |
| 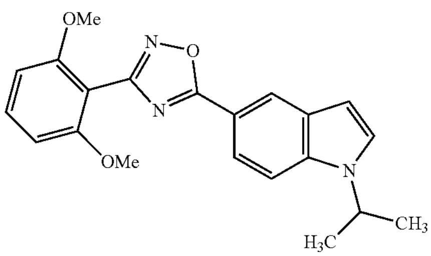 [SMILES: COc1cccc(OC)c1-c1noc(-c2ccc3c(ccn3C(C)C)c2)n1] | 325 | 3-(2,6-dimethoxyphenyl)-5-(1-isopropylindol-5-yl)-1,2,4-oxadiazole |
| 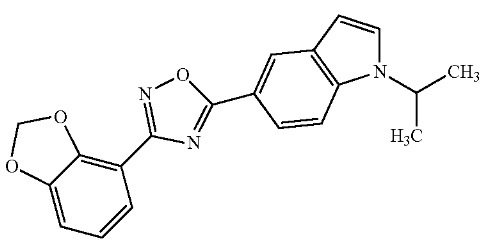 [SMILES: CC(C)n1ccc2cc(-c3nc(-c4cccc5c4OCO5)no3)ccc21] | 326 | 3-(benzo[d][1,3]dioxol-4-yl)-5-(1-isopropyl-1H-indol-5-yl)-1,2,4-oxadiazole |
| 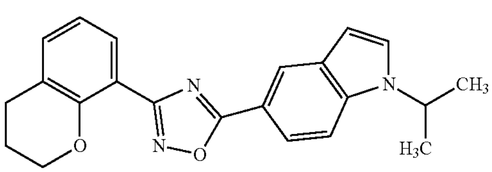 [SMILES: CC(C)n1ccc2cc(-c3nc(-c4cccc5c4OCCC5)no3)ccc21] | 327 | 3-chroman-8-yl-5-(1-isopropylindol-5-yl)-1,2,4-oxadiazole |
| 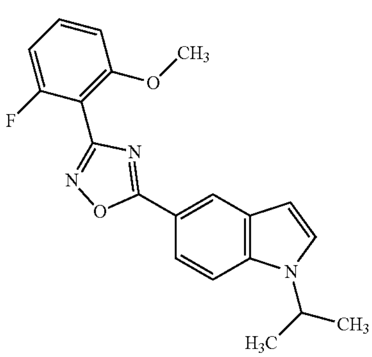 [SMILES: COc1cccc(F)c1-c1noc(-c2ccc3c(ccn3C(C)C)c2)n1] | 328 | 3-(2-fluoro-6-methoxy-phenyl)-5-(1-isopropylindol-5-yl)-1,2,4-oxadiazole |

-continued

| Structure | Compound Number | Chemical Name |
|---|---|---|
| 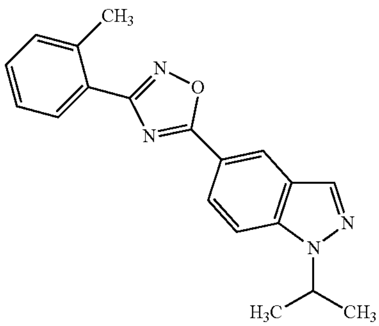 | 329 | 5-(1-isopropyl-1H-indazol-5-yl)-3-(o-tolyl)-1,2,4-oxadiazole |
| 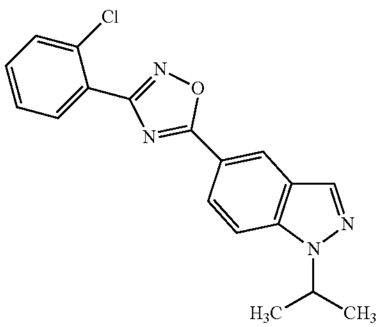 [SMILES: CC(C)n1ncc2cc(-c3nc(-c4ccccc4Cl)no3)ccc21] | 330 | 3-(2-chlorophenyl)-5-(1-isopropyl-1H-indazol-5-yl)-1,2,4-oxadiazole |
| 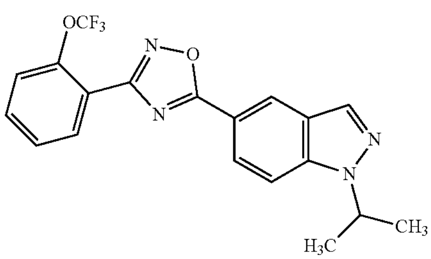 | 331 | 5-(1-isopropyl-1H-indazol-5-yl)-3-(2-(trifluoromethoxy)phenyl)-1,2,4-oxadiazole |
| 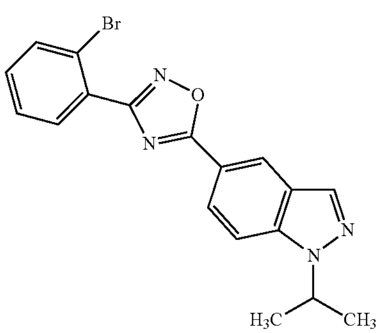 | 332 | 3-(2-bromophenyl)-5-(1-isopropyl-1H-indazol-5-yl)-1,2,4-oxadiazole |
| 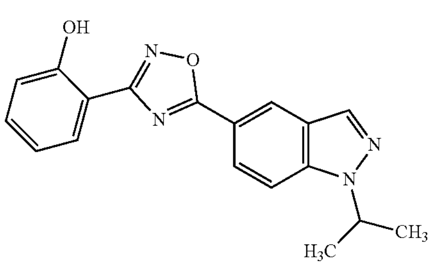 | 333 | 2-(5-(1-isopropyl-1H-indazol-5-yl)-1,2,4-oxadiazol-3-yl)phenol |

-continued

| Structure | Compound Number | Chemical Name |
|---|---|---|
| 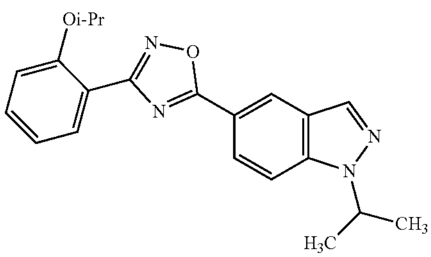 | 334 | 3-(2-isopropoxyphenyl)-5-(1-isopropyl-1H-indazol-5-yl)-1,2,4-oxadiazole |
| 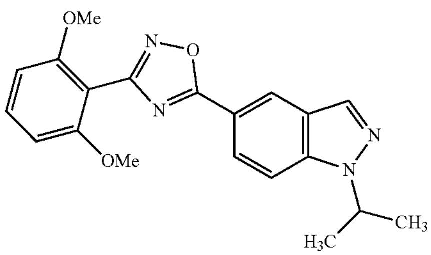 [SMILES: COc1cccc(OC)c1-c1noc(-c2ccc3c(cnn3C(C)C)c2)n1] | 335 | 3-(2,6-dimethoxyphenyl)-5-(1-isopropylindazol-5-yl)-1,2,4-oxadiazole |
| 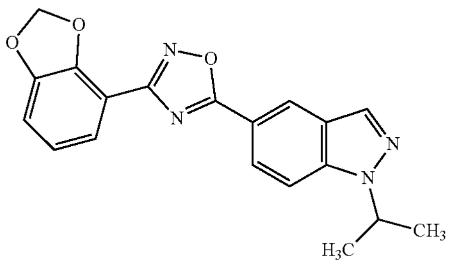 [SMILES: CC(C)n1ncc2cc(-c3nc(-c4cccc5c4OCO5)no3)ccc21] | 336 | 3-(benzo[d][1,3]dioxol-4-yl)-5-(1-isopropyl-1H-indazol-5-yl)-1,2,4-oxadiazole |
| 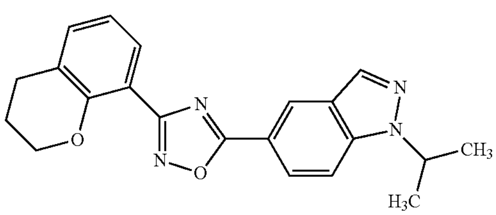 [SMILES: CC(C)n1ncc2cc(-c3nc(-c4cccc5c4OCCC5)no3)ccc21] | 337 | 3-chroman-8-yl-5-(1-isopropylindazol-5-yl)-1,2,4-oxadiazole |
| 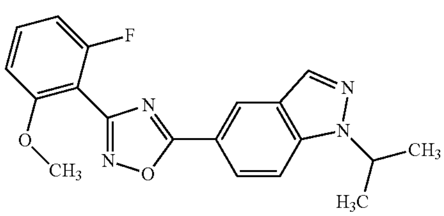 [SMILES: COc1cccc(F)c1-c1noc(-c2ccc3c(cnn3C(C)C)c2)n1] | 338 | 3-(2-fluoro-6-methoxy-phenyl)-5-(1-isopropylindazol-5-yl)-1,2,4-oxadiazole |
| 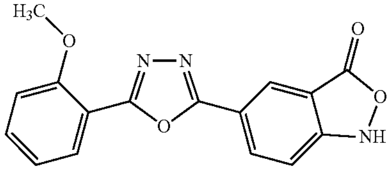 [SMILES: COc1ccccc1-c1nnc(-c2ccc3[nH]oc(=O)c3c2)o1] | 339 | 5-[5-(2-methoxyphenyl)-1,3,4-oxadiazol-2-yl]-1,3-dihydro-2,1-benzoxazol-3-one |

-continued

| Structure | Compound Number | Chemical Name |
|---|---|---|
| 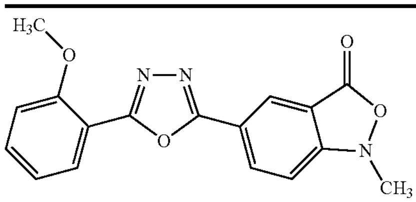 | 340 | 5-[5-(2-methoxyphenyl)-1,3,4-oxadiazol-2-yl]-1-methyl-1,3-dihydro-2,1-benzoxazol-3-one |
| 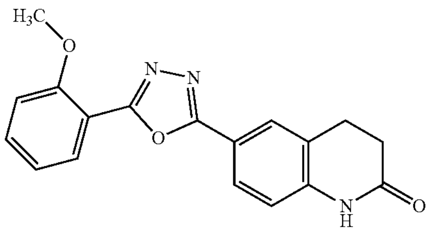 [SMILES: COc1ccccc1-c1nnc(-c2ccc3c(c2)CCC(=O)N3)o1] | 341 | 6-[5-(2-methoxyphenyl)-1,3,4-oxadiazol-2-yl]-1,2,3,4-tetrahydroquinolin-2-one |
| 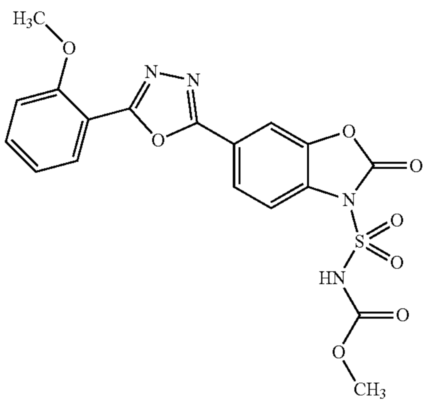 [SMILES: COC(=O)NS(=O)(=O)n1c(=O)oc2cc(-c3nnc(-c4ccccc4OC)o3)ccc21] | 342 | methyl N-({6-[5-(2-methoxyphenyl)-1,3,4-oxadiazol-2-yl]-2-oxo-2,3-dihydro-1,3-benzoxazol-3-yl}sulfonyl)carbamate |
| 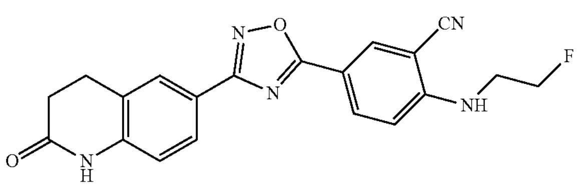 [SMILES: N#Cc1cc(-c2nc(-c3ccc4c(c3)CCC(=O)N4)no2)ccc1NCCF] | 343 | 2-[(2-fluoroethyl)amino]-5-[3-(2-oxo-1,2,3,4-tetrahydroquinolin-6-yl)-1,2,4-oxadiazol-5-yl]benzonitrile |
| 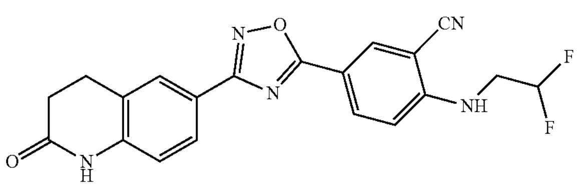 [SMILES: N#Cc1cc(-c2nc(-c3ccc4c(c3)CCC(=O)N4)no2)ccc1NCC(F)F] | 344 | 2-[(2,2-difluoroethyl)amino]-5-[3-(2-oxo-1,2,3,4-tetrahydroquinolin-6-yl)-1,2,4-oxadiazol-5-yl]benzonitrile |
| 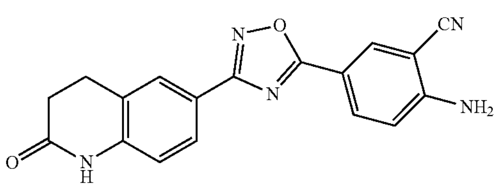 [SMILES: N#Cc1cc(-c2nc(-c3ccc4c(c3)CCC(=O)N4)no2)ccc1N] | 345 | 2-amino-5-[3-(2-oxo-1,2,3,4-tetrahydroquinolin-6-yl)-1,2,4-oxadiazol-5-yl]benzonitrile |
| 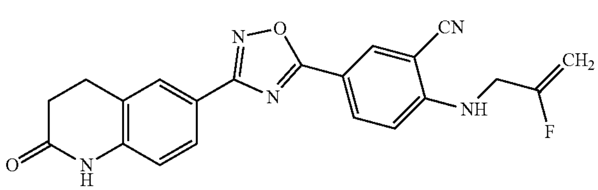 [SMILES: C=C(F)CNc1ccc(-c2nc(-c3ccc4c(c3)CCC(=O)N4)no2)cc1C#N] | 346 | 2-[(2-fluoroprop-2-en-1-yl)amino]-5-[3-(2-oxo-1,2,3,4-tetrahydroquinolin-6-yl)-1,2,4-oxadiazol-5-yl]benzonitrile |

-continued

| Structure | Compound Number | Chemical Name |
|---|---|---|
| 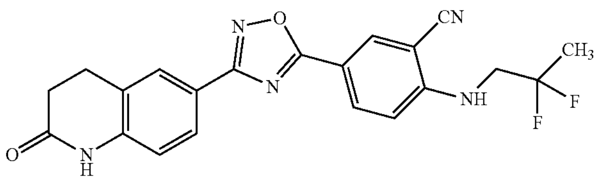 [SMILES: CC(F)(F)CNc1ccc(-c2nc(-c3ccc4c(c3)CCC(=O)N4)no2)cc1C#N] | 347 | 2-[(2,2-difluoropropyl)amino]-5-[3-(2-oxo-1,2,3,4-tetrahydroquinolin-6-yl)-1,2,4-oxadiazol-5-yl]benzonitrile |
| 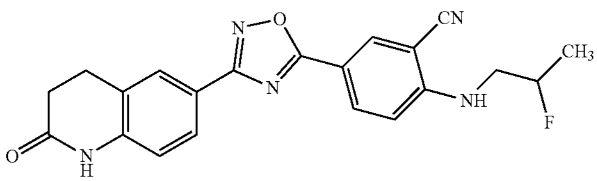 [SMILES: CC(F)CNc1ccc(-c2nc(-c3ccc4c(c3)CCC(=O)N4)no2)cc1C#N] | 348 | 2-[(2-fluoropropyl)amino]-5-[3-(2-oxo-1,2,3,4-tetrahydroquinolin-6-yl)-1,2,4-oxadiazol-5-yl]benzonitrile |
| 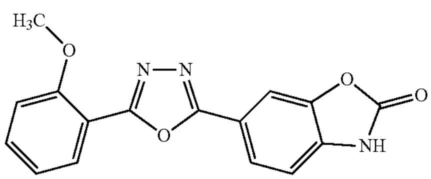 [SMILES: COc1ccccc1-c1nnc(-c2ccc3[nH]c(=O)oc3c2)o1] | 349 | 6-[5-(2-methoxyphenyl)-1,3,4-oxadiazol-2-yl]-2,3-dihydro-1,3-benzoxazol-2-one |
| 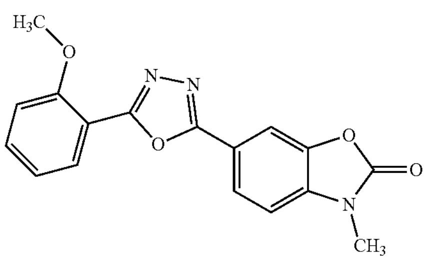 [SMILES: COc1ccccc1-c1nnc(-c2ccc3c(c2)oc(=O)n3C)o1] | 350 | 6-[5-(2-methoxyphenyl)-1,3,4-oxadiazol-2-yl]-3-methyl-2,3-dihydro-1,3-benzoxazol-2-one |
| 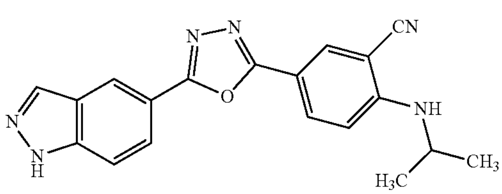 [SMILES: CC(C)Nc1ccc(-c2nnc(-c3ccc4[nH]ncc4c3)o2)cc1C#N] | 351 | 5-[5-(1H-indazol-5-yl)-1,3,4-oxadiazol-2-yl]-2-[(propan-2-yl)amino]benzonitrile |
| 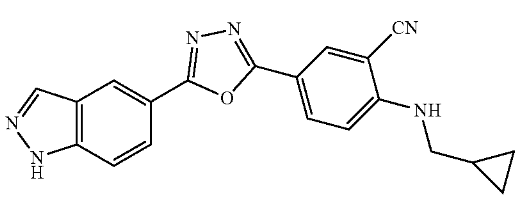 [SMILES: N#Cc1cc(-c2nnc(-c3ccc4[nH]ncc4c3)o2)ccc1NCC1CC1] | 352 | 2-[(cyclopropylmethyl)amino]-5-[5-(1H-indazol-5-yl)-1,3,4-oxadiazol-2-yl]benzonitrile |
| 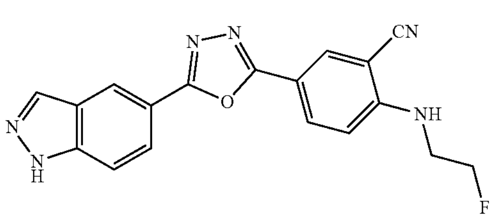 [SMILES: N#Cc1cc(-c2nnc(-c3ccc4[nH]ncc4c3)o2)ccc1NCCF] | 353 | 2-[(2-fluoroethyl)amino]-5-[5-(1H-indazol-5-yl)-1,3,4-oxadiazol-2-yl]benzonitrile |

-continued

| Structure | Compound Number | Chemical Name |
|---|---|---|
| 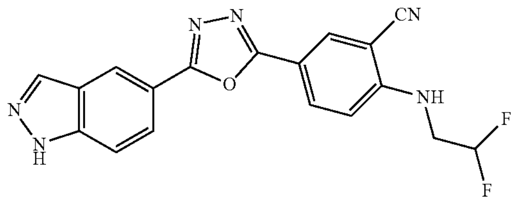 [SMILES: N#Cc1cc(-c2nnc(-c3ccc4[nH]ncc4c3)o2)ccc1NCC(F)F] | 354 | 2-[(2,2-difluoroethyl)amino]-5-[5-(1H-indazol-5-yl)-1,3,4-oxadiazol-2-yl]benzonitrile |
| 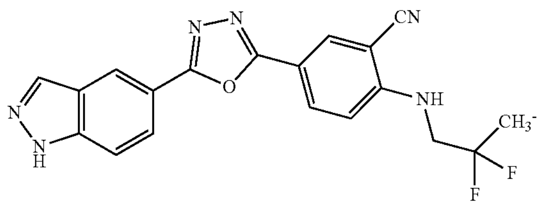 | 355 | 2-[(2,2-difluoropropyl)amino]-5-[5-(1H-indazol-5-yl)-1,3,4-oxadiazol-2-yl]benzonitrile |
| 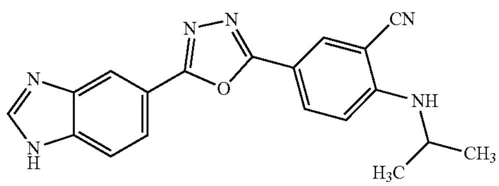 [SMILES: CC(C)Nc1ccc(-c2nnc(-c3ccc4[nH]cnc4c3)o2)cc1C#N] | 356 | 5-[5-(1H-1,3-benzodiazol-5-yl)-1,3,4-oxadiazol-2-yl]-2-[(propan-2-yl)amino]benzonitrile |
| 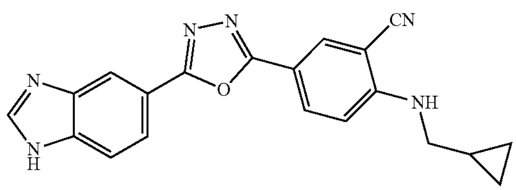 [SMILES: N#Cc1cc(-c2nnc(-c3ccc4[nH]cnc4c3)o2)ccc1NCC1CC1] | 357 | 5-[5-(1H-1,3-benzodiazol-5-yl)-1,3,4-oxadiazol-2-yl]-2-[(cyclopropylmethyl)amino]benzonitrile |
| 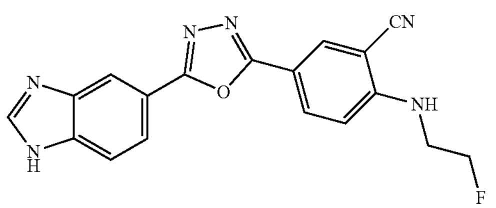 [SMILES: N#Cc1cc(-c2nnc(-c3ccc4[nH]cnc4c3)o2)ccc1NCCF] | 358 | 5-[5-(1H-1,3-benzodiazol-5-yl)-1,3,4-oxadiazol-2-yl]-2-[(2-fluoroethyl)amino]benzonitrile |
| 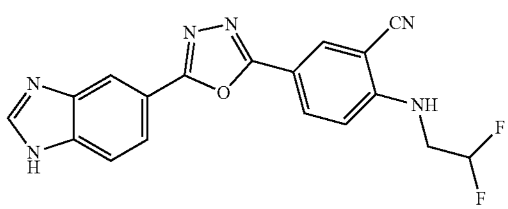 [SMILES: N#Cc1cc(-c2nnc(-c3ccc4[nH]cnc4c3)o2)ccc1NCC(F)F] | 359 | 5-[5-(1H-1,3-benzodiazol-5-yl)-1,3,4-oxadiazol-2-yl]-2-[(2,2-difluoroethyl)amino]benzonitrile |
| 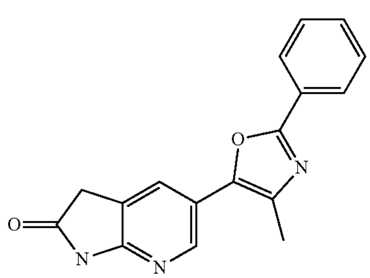 [SMILES: Cc1nc(-c2ccccc2)oc1-c1cnc2c(c1)CC(=O)N2] | 360 | 5-(4-methyl-2-phenyl-1,3-oxazol-5-yl)-1H,2H,3H-pyrrolo[2,3-b]pyridin-2-one |

-continued
| Structure | Compound Number | Chemical Name |
|---|---|---|
| 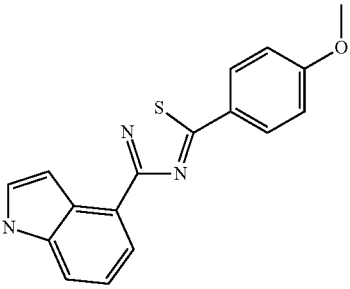 [SMILES: COc1ccc(/C(S)=N/C(=N)c2cccc3[nH]ccc23)cc1] | 361 | 4-[5-(4-methoxyphenyl)-1,2,4-thiadiazol-3-yl]-1H-indole |
| 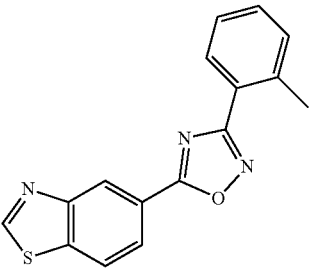 [SMILES: Cc1ccccc1-c1noc(-c2ccc3scnc3c2)n1] | 362 | 5-[3-(2-methylphenyl)-1,2,4-oxadiazol-5-yl]-1,3-benzothiazole |
| 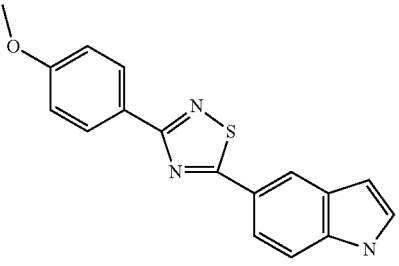 [SMILES: COc1ccc(-c2nsc(-c3ccc4[nH]ccc4c3)n2)cc1] | 363 | 5-[3-(4-methoxyphenyl)-1,2,4-thiadiazol-5-yl]-1H-indole |
| 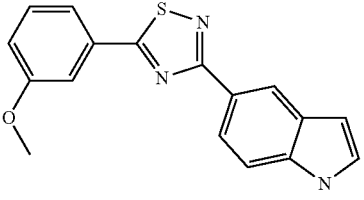 [SMILES: COc1cccc(-c2nc(-c3ccc4[nH]ccc4c3)ns2)c1] | 364 | 5-[5-(3-methoxyphenyl)-1,2,4-thiadiazol-3-yl]-1H-indole |
| 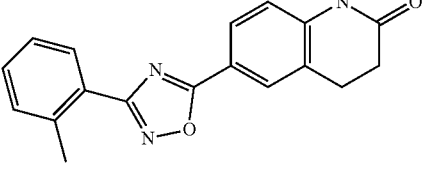 | 365 | 6-[3-(2-methylphenyl)-1,2,4-oxadiazol-5-yl]-1,2,3,4-tetrahydroquinolin-2-one |

-continued

| Structure | Compound Number | Chemical Name |
|---|---|---|
| 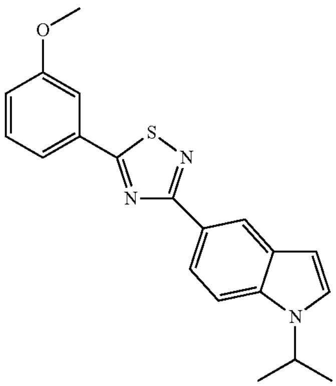 [SMILES: COc1cccc(-c2nc(-c3ccc4c(ccn4C(C)C)c3)ns2)c1] | 366 | 5-[5-(3-methoxyphenyl)-1,2,4-thiadiazol-3-yl]-1-(propan-2-yl)-1H-indole |
| 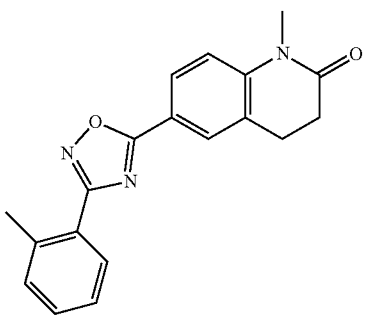 [SMILES: Cc1ccccc1-c1noc(-c2ccc3c(c2)CCC(=O)N3C)n1] | 367 | 1-methyl-6-[3-(2-methylphenyl)-1,2,4-oxadiazol-5-yl]-1,2,3,4-tetrahydroquinolin-2-one |
| 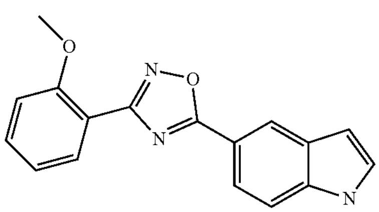 [SMILES: COc1ccccc1-c1noc(-c2ccc3[nH]ccc3c2)n1] | 368 | 5-(1H-indol-5-yl)-3-(2-methoxyphenyl)-1,2,4-oxadiazole |
| 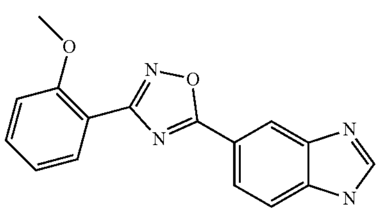 [SMILES: COc1ccccc1-c1noc(-c2ccc3[nH]cnc3c2)n1] | 369 | 5-(1H-benzo[d]imidazol-5-yl)-3-(2-methoxyphenyl)-1,2,4-oxadiazole |
| 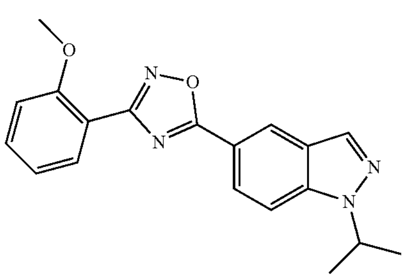 [SMILES: COc1ccccc1-c1noc(-c2ccc3c(cnn3C(C)C)c2)n1] | 370 | 5-(1-isopropyl-1H-indazol-5-yl)-3-(2-methoxyphenyl)-1,2,4-oxadiazole |

-continued
| Structure | Compound Number | Chemical Name |
|---|---|---|
| 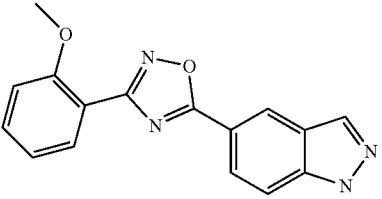 [SMILES: COc1ccccc1-c1noc(-c2ccc3[nH]ncc3c2)n1] | 371 | 5-(1H-indazol-5-yl)-3-(2-methoxyphenyl)-1,2,4-oxadiazole |
| 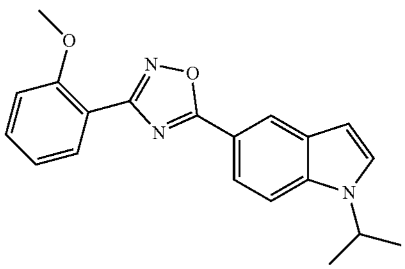 [SMILES: COc1ccccc1-c1noc(-c2ccc3c(ccn3C(C)C)c2)n1] | 372 | 5-(1-isopropyl-1H-indol-5-yl)-3-(2-methoxyphenyl)-1,2,4-oxadiazole |
| 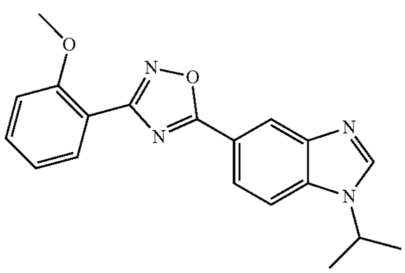 [SMILES: COc1ccccc1-c1noc(-c2ccc3c(c2)ncn3C(C)C)n1] | 373 | 5-(1-isopropyl-1H-benzo[d]imidazol-5-yl)-3-(2-methoxyphenyl)-1,2,4-oxadiazole |
| 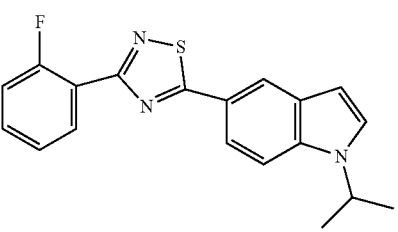 [SMILES: CC(C)n1ccc2cc(-c3nc(-c4ccccc4F)ns3)ccc21] | 374 | 5-[3-(2-fluorophenyl)-1,2,4-thiadiazol-5-yl]-1-(propan-2-yl)-1H-indole |
| 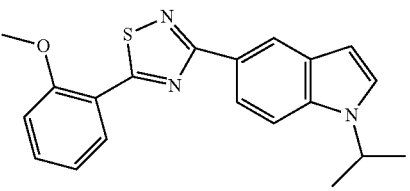 [SMILES: COc1ccccc1-c1nc(-c2ccc3c(ccn3C(C)C)c2)ns1] | 375 | 5-[5-(2-methoxyphenyl)-1,2,4-thiadiazol-3-yl]-1-(propan-2-yl)-1H-indole |
| 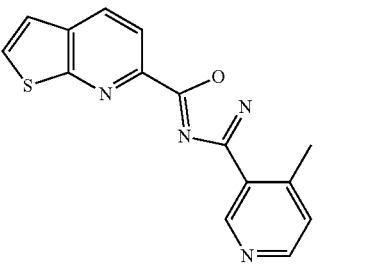 [SMILES: Cc1ccncc1C(=N)/N=C(\O)c1ccc2ccsc2n1] | 376 | 4-methyl-3-(5-{thieno[2,3-b]pyridin-6-yl}-1,2,4-oxadiazol-3-yl)pyridine |

-continued

| Structure | Compound Number | Chemical Name |
|---|---|---|
| 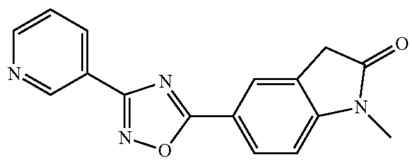 [SMILES: CN1C(=O)Cc2cc(-c3nc(-c4cccnc4)no3)ccc21] | 377 | 1-methyl-5-[3-(pyridin-3-yl)-1,2,4-oxadiazol-5-yl]-2,3-dihydro-1H-indol-2-one |
| 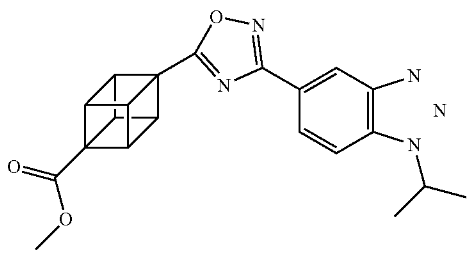 | 378 | 8-{3-[1-(propan-2-yl)-1H-1,2,3-benzotriazol-5-yl]-1,2,4-oxadiazol-5-yl}cubane-1-carboxylate |
| 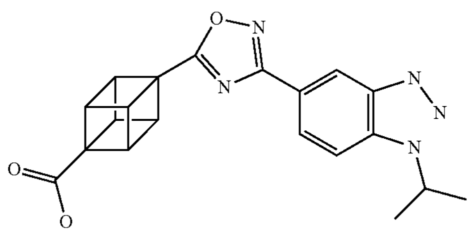 [SMILES: CC(C)Nc1ccc(-c2noc(C34C5C6C3C3C4C5C63C(=O)O)n2)cc1NN] | 379 | 8-{3-[1-(propan-2-yl)-1H-1,2,3-benzotriazol-5-yl]-1,2,4-oxadiazol-5-yl}cubane-1-carboxylic acid |
| 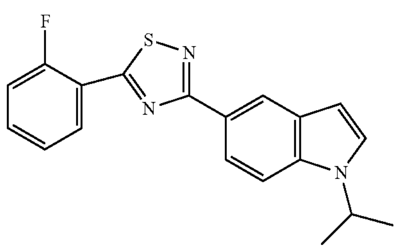 [SMILES: CC(C)n1ccc2cc(-c3nsc(-c4ccccc4F)n3)ccc21] | 380 | 5-[5-(2-fluorophenyl)-1,2,4-thiadiazol-3-yl]-1-(propan-2-yl)-1H-indole |
| 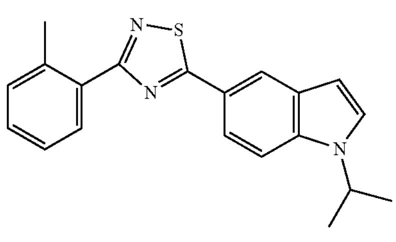 [SMILES: Cc1ccccc1-c1nsc(-c2ccc3c(ccn3C(C)C)c2)n1] | 381 | 5-[3-(2-methylphenyl)-1,2,4-thiadiazol-5-yl]-1-(propan-2-yl)-1H-indole |
| 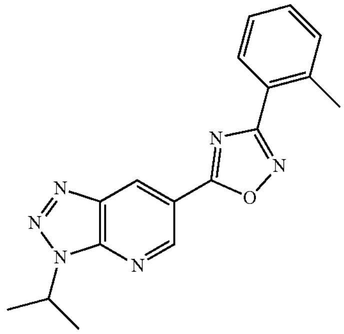 [SMILES: Cc1ccccc1-c1noc(-c2cnc3c(c2)nnn3C(C)C)n1] | 382 | 3-(2-methylphenyl)-5-[3-(propan-2-yl)-3H-[1,2,3]triazolo[4,5-b]pyridin-6-yl]-1,2,4-oxadiazole |

-continued

| Structure | Compound Number | Chemical Name |
|---|---|---|
| 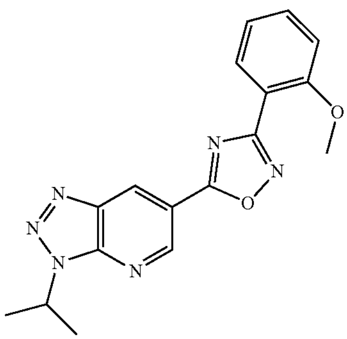 [SMILES: COc1ccccc1-c1noc(-c2cnc3c(c2)nnn3C(C)C)n1] | 383 | 3-(2-methoxyphenyl)-5-[3-(propan-2-yl)-3H-[1,2,3]triazolo[4,5-b]pyridin-6-yl]-1,2,4-oxadiazole |
| 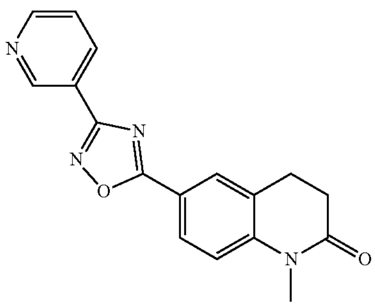 [SMILES: CN1C(=O)CCc2cc(-c3nc(-c4cccnc4)no3)ccc21] | 384 | 1-methyl-6-[3-(pyridin-3-yl)-1,2,4-oxadiazol-5-yl]-1,2,3,4-tetrahydroquinolin-2-one |
| 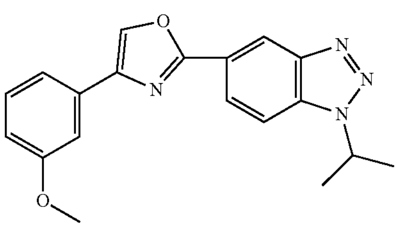 [SMILES: COc1cccc(-c2coc(-c3ccc4c(c3)nnn4C(C)C)n2)c1] | 385 | 5-[4-(3-methoxyphenyl)-1,3-oxazol-2-yl]-1-(propan-2-yl)-1H-1,2,3-benzotriazole |
| 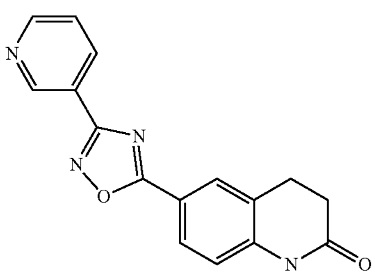 [SMILES: O=C1CCc2cc(-c3nc(-c4cccnc4)no3)ccc2N1] | 386 | 6-[3-(pyridin-3-yl)-1,2,4-oxadiazol-5-yl]-1,2,3,4-tetrahydroquinolin-2-one |
| 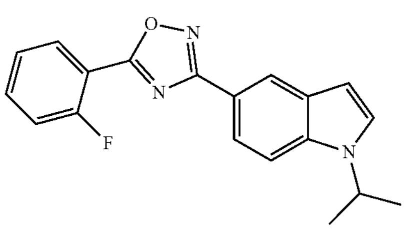 [SMILES: CC(C)n1ccc2cc(-c3noc(-c4ccccc4F)n3)ccc21] | 387 | 5-(2-fluorophenyl)-3-(1-isopropyl-1H-indol-5-yl)-1,2,4-oxadiazole |

-continued

| Structure | Compound Number | Chemical Name |
|---|---|---|
| 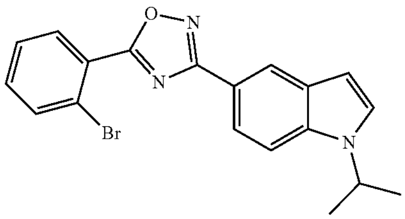 [SMILES: CC(C)n1ccc2cc(-c3noc(-c4ccccc4Br)n3)ccc21] | 388 | 5-(2-bromophenyl)-3-(1-isopropyl-1H-indol-5-yl)-1,2,4-oxadiazole |
| 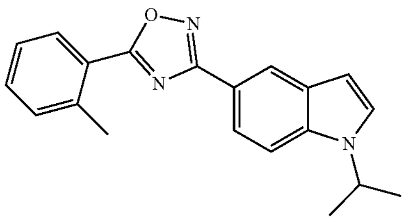 [SMILES: Cc1ccccc1-c1nc(-c2ccc3c(ccn3C(C)C)c2)no1] | 389 | 3-(1-isopropyl-1H-indol-5-yl)-5-(o-tolyl)-1,2,4-oxadiazole |
| 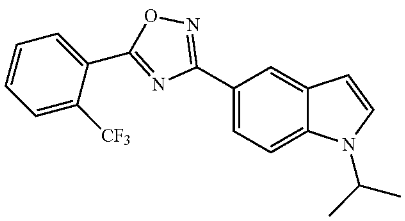 [SMILES: CC(C)n1ccc2cc(-c3noc(-c4ccccc4C(F)(F)F)n3)ccc21] | 390 | 3-(1-isopropyl-1H-indol-5-yl)-5-(2-(trifluoromethyl)phenyl)-1,2,4-oxadiazole |
| 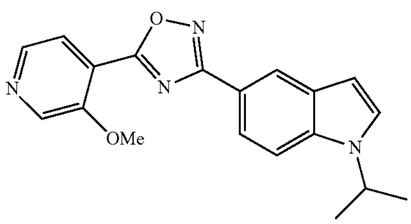 [SMILES: COc1cnccc1-c1nc(-c2ccc3c(ccn3C(C)C)c2)no1] | 391 | 3-(1-isopropyl-1H-indol-5-yl)-5-(3-methoxypyridin-4-yl)-1,2,4-oxadiazole |
| 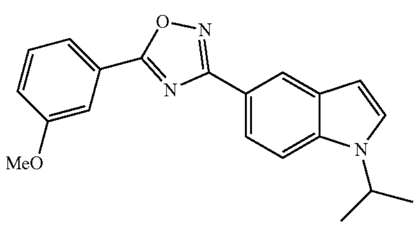 [SMILES: COc1cccc(-c2nc(-c3ccc4c(ccn4C(C)C)c3)no2)c1] | 392 | 3-(1-isopropyl-1H-indol-5-yl)-5-(3-methoxyphenyl)-1,2,4-oxadiazole |
| 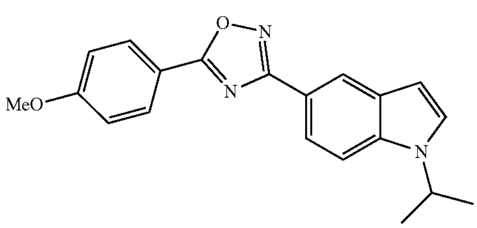 [SMILES: COc1ccc(-c2nc(-c3ccc4c(ccn4C(C)C)c3)no2)cc1] | 393 | 3-(1-isopropyl-1H-indol-5-yl)-5-(4-methoxyphenyl)-1,2,4-oxadiazole |
| 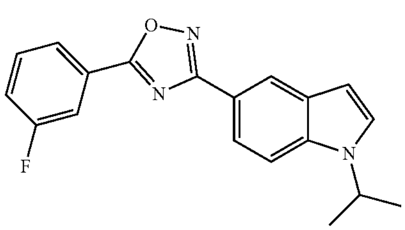 [SMILES: CC(C)n1ccc2cc(-c3noc(-c4cccc(F)c4)n3)ccc21] | 394 | 5-(3-fluorophenyl)-3-(1-isopropyl-1H-indol-5-yl)-1,2,4-oxadiazole |

-continued

| Structure | Compound Number | Chemical Name |
|---|---|---|
| 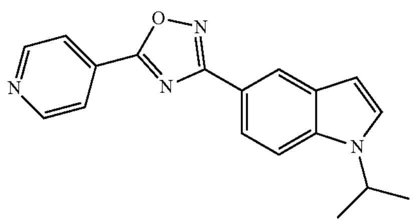 [SMILES: CC(C)n1ccc2cc(-c3noc(-c4ccncc4)n3)ccc21] | 395 | 3-(1-isopropyl-1H-indol-5-yl)-5-(pyridin-4-yl)-1,2,4-oxadiazole |
| 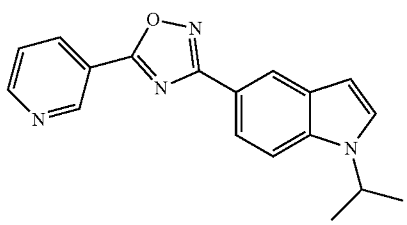 [SMILES: CC(C)n1ccc2cc(-c3noc(-c4cccnc4)n3)ccc21] | 396 | 3-(1-isopropyl-1H-indol-5-yl)-5-(pyridin-3-yl)-1,2,4-oxadiazole |
| 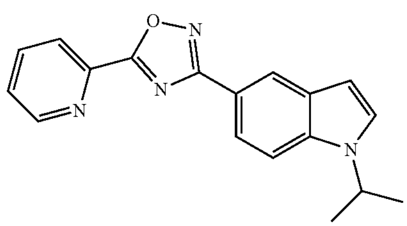 [SMILES: CC(C)n1ccc2cc(-c3noc(-c4ccccn4)n3)ccc21] | 397 | 3-(1-isopropyl-1H-indol-5-yl)-5-(pyridin-2-yl)-1,2,4-oxadiazole |
| 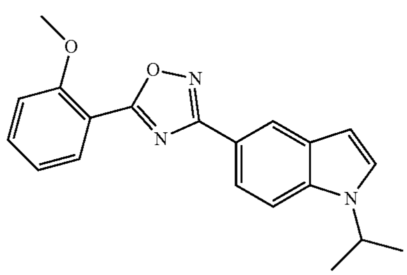 [SMILES: COc1ccccc1-c1nc(-c2ccc3c(ccn3C(C)C)c2)no1] | 398 | 3-(1-isopropyl-1H-indol-5-yl)-5-(2-methoxyphenyl)-1,2,4-oxadiazole |
| 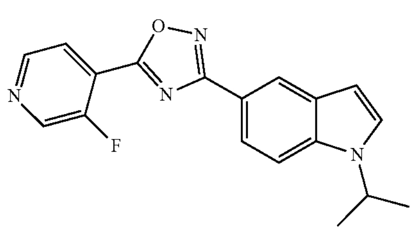 [SMILES: CC(C)n1ccc2cc(-c3noc(-c4ccncc4F)n3)ccc21] | 399 | 5-(3-fluoropyridin-4-yl)-3-(1-isopropyl-1H-indol-5-yl)-1,2,4-oxadiazole |
| 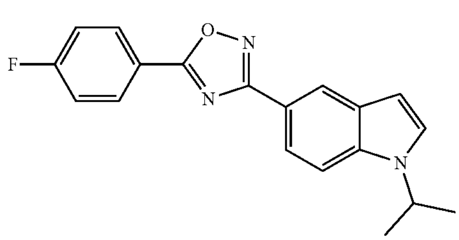 [SMILES: CC(C)n1ccc2cc(-c3noc(-c4ccc(F)cc4)n3)ccc21] | 400 | 5-(4-fluorophenyl)-3-(1-isopropyl-1H-indol-5-yl)-1,2,4-oxadiazole |

-continued

| Structure | Compound Number | Chemical Name |
|---|---|---|
| 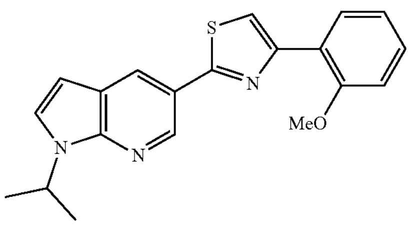 [SMILES: COc1ccccc1-c1csc(-c2cnc3c(ccn3C(C)C)c2)n1] | 401 | 2-(1-isopropyl-1H-pyrrolo[2,3-b]pyridin-5-yl)-4-(2-methoxyphenyl)thiazole |
| 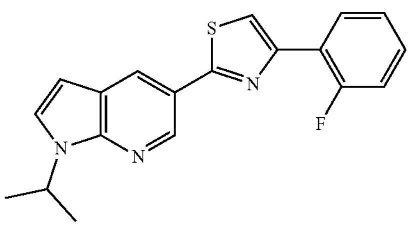 [SMILES: CC(C)n1ccc2cc(-c3nc(-c4ccccc4F)cs3)cnc21] | 402 | 4-(2-fluorophenyl)-2-(1-isopropyl-1H-pyrrolo[2,3-b]pyridin-5-yl)thiazole |
| 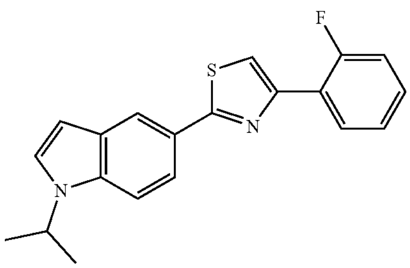 [SMILES: CC(C)n1ccc2cc(-c3nc(-c4ccccc4F)cs3)ccc21] | 403 | 4-(2-fluorophenyl)-2-(1-isopropylindol-5-yl)thiazole |
| 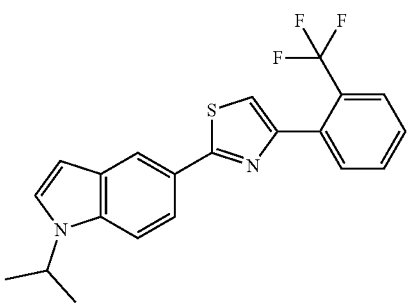 [SMILES: CC(C)n1ccc2cc(-c3nc(-c4ccccc4C(F)(F)F)cs3)ccc21] | 404 | 2-(1-isopropylindol-5-yl)-4-[2-(trifluoromethyl)phenyl]thiazole |
| 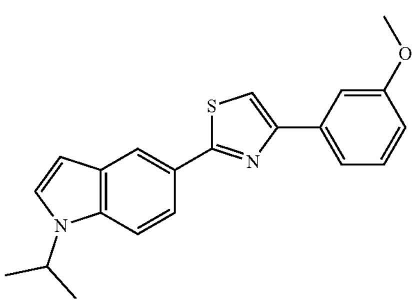 [SMILES: COc1cccc(-c2csc(-c3ccc4c(ccn4C(C)C)c3)n2)c1] | 405 | 2-(1-isopropylindol-5-yl)-4-(3-methoxyphenyl)thiazole |
| 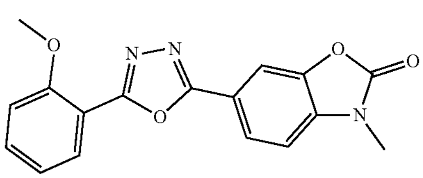 [SMILES: COc1ccccc1-c1nnc(-c2ccc3c(c2)oc(=O)n3C)o1] | 406 | 6-[5-(2-methoxyphenyl)-1,3,4-oxadiazol-2-yl]-3-methyl-2,3-dihydro-1,3-benzoxazol-2-one |

-continued

| Structure | Compound Number | Chemical Name |
|---|---|---|
| 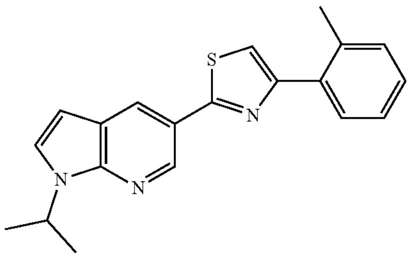 [SMILES: Cc1ccccc1-c1csc(-c2cnc3c(ccn3C(C)C)c2)n1] | 407 | 2-(1-isopropylpyrrolo[2,3-b]pyridin-5-yl)-4-(o-tolyl)thiazole |
| 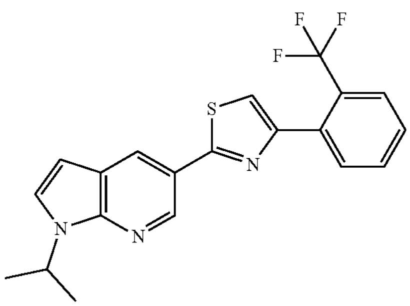 [SMILES: CC(C)n1ccc2cc(-c3nc(-c4ccccc4C(F)(F)F)cs3)cnc21] | 408 | 2-(1-isopropylpyrrolo[2,3-b]pyridin-5-yl)-4-[2-(trifluoromethyl)phenyl]thiazole |
| 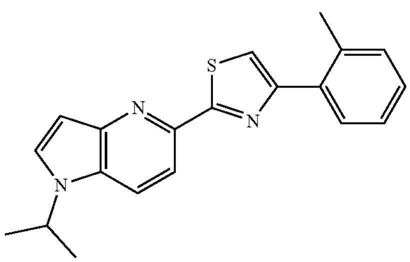 [SMILES: Cc1ccccc1-c1csc(-c2ccc3c(ccn3C(C)C)n2)n1] | 409 | 2-(1-isopropylpyrrolo[3,2-b]pyridin-5-yl)-4-(o-tolyl)thiazole |
| 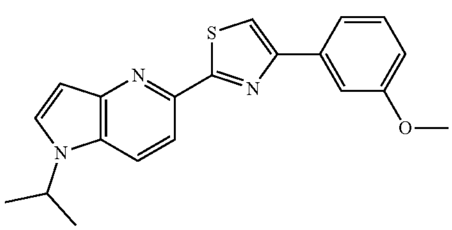 [SMILES: COc1cccc(-c2csc(-c3ccc4c(ccn4C(C)C)n3)n2)c1] | 410 | 2-(1-isopropylpyrrolo[3,2-b]pyridin-5-yl)-4-(3-methoxyphenyl)thiazole |
| 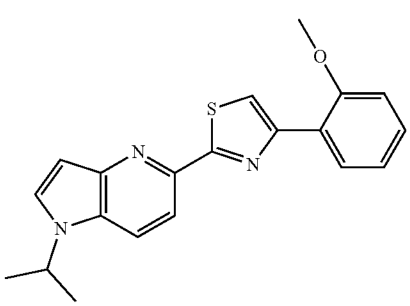 [SMILES: COc1ccccc1-c1csc(-c2ccc3c(ccn3C(C)C)n2)n1] | 411 | 2-(1-isopropyl-1H-pyrrolo[3,2-b]pyridin-5-yl)-4-(2-methoxyphenyl)thiazole |

-continued
| Structure | Compound Number | Chemical Name |
|---|---|---|
| 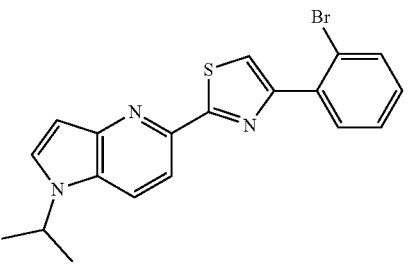 [SMILES: CC(C)n1ccc2nc(-c3nc(-c4ccccc4Br)cs3)ccc21] | 412 | 4-(2-bromophenyl)-2-(1-isopropyl-1H-pyrrolo[3,2-b]pyridin-5-yl)thiazole |
| 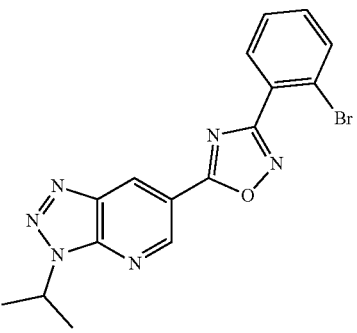 [SMILES: CC(C)n1nnc2cc(-c3nc(-c4ccccc4Br)no3)cnc21] | 413 | 3-(2-bromophenyl)-5-[3-(propan-2-yl)-3H-[1,2,3]triazolo[4,5-b]pyridin-6-yl]-1,2,4-oxadiazole |
| 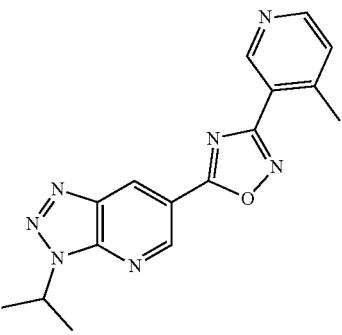 [SMILES: Cc1ccncc1-c1noc(-c2cnc3c(c2)nnn3C(C)C)n1] | 414 | 4-methyl-3-{5-[3-(propan-2-yl)-3H-[1,2,3]triazolo[4,5-b]pyridin-6-yl]-1,2,4-oxadiazol-3-yl}pyridine |
| 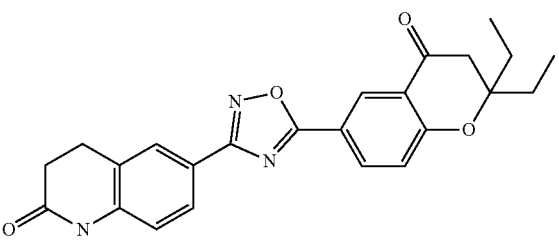 [SMILES: CCC1(CC)CC(=O)c2cc(-c3nc(-c4ccc5c(c4)CCC(=O)N5)no3)ccc2O1] | 415 | 6-(5-(2,2-diethyl-4-oxochroman-6-yl)-1,2,4-oxadiazol-3-yl)-3,4-dihydroquinolin-2(1H)-one |
| 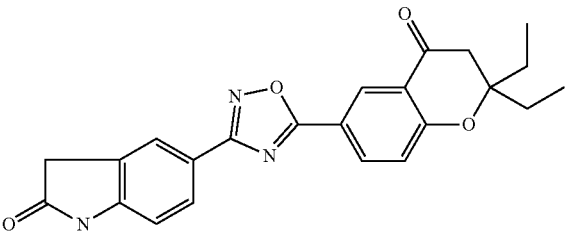 [SMILES: CCC1(CC)CC(=O)c2cc(-c3nc(-c4ccc5c(c4)CC(=O)N5)no3)ccc2O1] | 416 | 5-(5-(2,2-diethyl-4-oxochroman-6-yl)-1,2,4-oxadiazol-3-yl)indolin-2-one |

-continued
| Structure | Compound Number | Chemical Name |
|---|---|---|
| 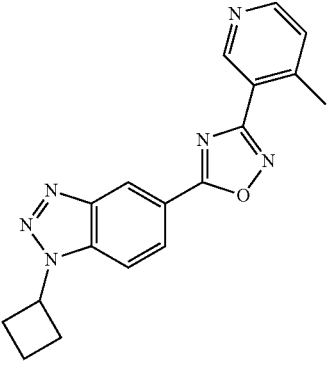 [SMILES: Cc1ccncc1-c1noc(-c2ccc3c(c2)nnn3C2CCC2)n1] | 417 | 1-cyclobutyl-5-[3-(4-methylpyridin-3-yl)-1,2,4-oxadiazol-5-yl]-1H-1,2,3-benzotriazole |
| 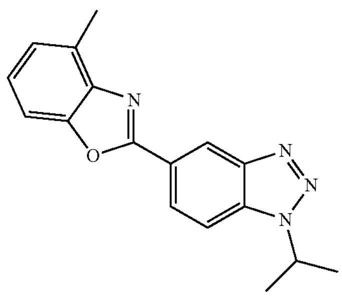 [SMILES: Cc1cccc2oc(-c3ccc4c(c3)nnn4C(C)C)nc12] | 418 | 2-(1-isopropyl-1H-benzo[d][1,2,3]triazol-5-yl)-4-methylbenzo[d]oxazole |
| 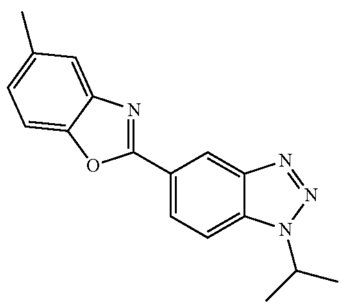 [SMILES: Cc1ccc2oc(-c3ccc4c(c3)nnn4C(C)C)nc2c1] | 419 | 2-(1-isopropyl-1H-benzo[d][1,2,3]triazol-5-yl)-5-methylbenzo[d]oxazole |
| 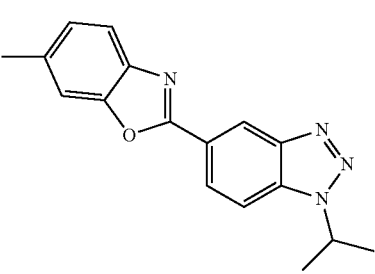 [SMILES: Cc1ccc2nc(-c3ccc4c(c3)nnn4C(C)C)oc2c1] | 420 | 2-(1-isopropyl-1H-benzo[d][1,2,3]triazol-5-yl)-6-methylbenzo[d]oxazole |
| 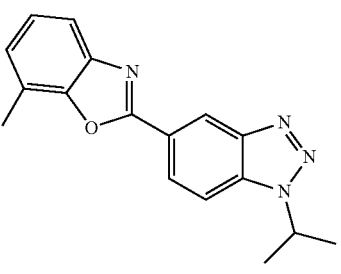 [SMILES: Cc1cccc2nc(-c3ccc4c(c3)nnn4C(C)C)oc12] | 421 | 2-(1-isopropyl-1H-benzo[d][1,2,3]triazol-5-yl)-7-methylbenzo[d]oxazole |

-continued

| Structure | Compound Number | Chemical Name |
|---|---|---|
| 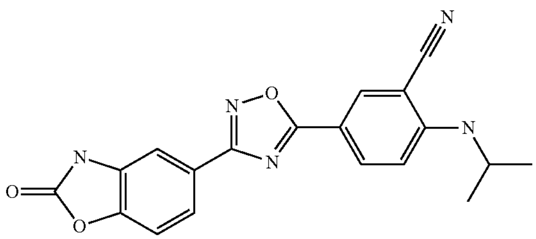 | 422 | 2-(isopropylamino)-5-(3-(2-oxo-2,3-dihydrobenzo[d]oxazol-5-yl)-1,2,4-oxadiazol-5-yl)benzonitrile |
| 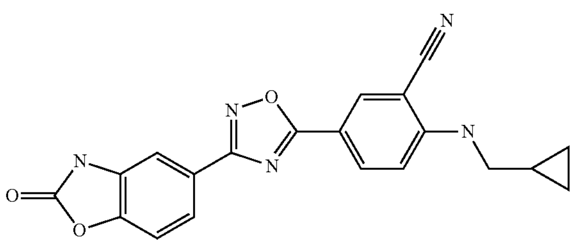 [SMILES: N#Cc1cc(-c2nc(-c3ccc4oc(=O)[nH]c4c3)no2)ccc1NCC1CC1] | 423 | 2-((cyclopropylmethyl)amino)-5-(3-(2-oxo-2,3-dihydrobenzo[d]oxazol-5-yl)-1,2,4-oxadiazol-5-yl)benzonitrile |
| 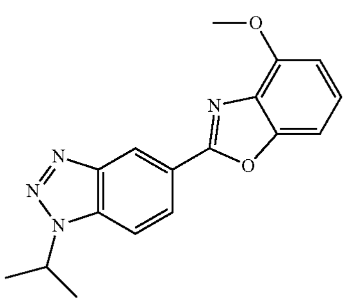 [SMILES: COc1cccc2oc(-c3ccc4c(c3)nnn4C(C)C)nc12] | 424 | 2-(1-isopropyl-1H-benzo[d][1,2,3]triazol-5-yl)-4-methoxybenzo[d]oxazole |
| 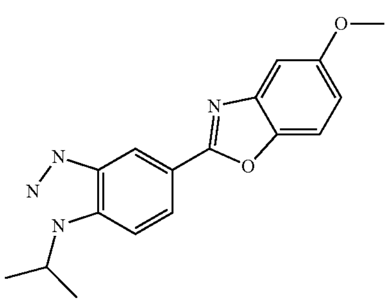 [SMILES: COc1ccc2oc(-c3ccc(NC(C)C)c(NN)c3)nc2c1] | 425 | 2-(1-isopropyl-1H-benzo[d][1,2,3]triazol-5-yl)-5-methoxybenzo[d]oxazole |
| 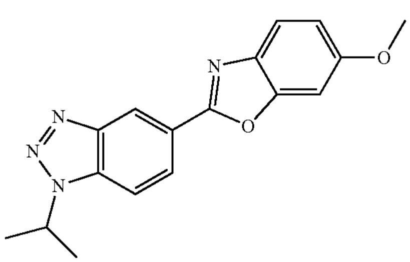 [SMILES: COc1ccc2nc(-c3ccc4c(c3)nnn4C(C)C)oc2c1] | 426 | 2-(1-isopropyl-1H-benzo[d][1,2,3]triazol-5-yl)-6-methoxybenzo[d]oxazole |

-continued

| Structure | Compound Number | Chemical Name |
|---|---|---|
| 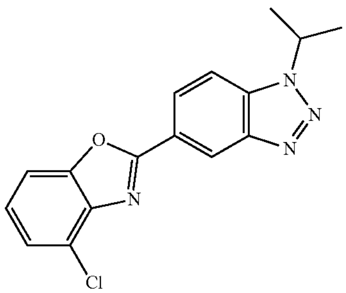 [SMILES: CC(C)n1nnc2cc(-c3nc4c(Cl)cccc4o3)ccc21] | 427 | 4-chloro-2-(1-isopropyl-1H-benzo[d][1,2,3]triazol-5-yl)benzo[d]oxazole |
| 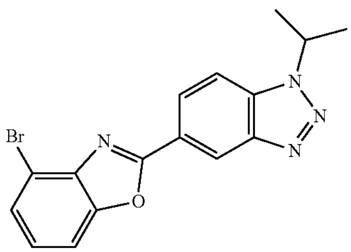 [SMILES: CC(C)n1nnc2cc(-c3nc4c(Br)cccc4o3)ccc21] | 428 | 4-bromo-2-(1-isopropylbenzotriazol-5-yl)-1,3-benzoxazole |
| 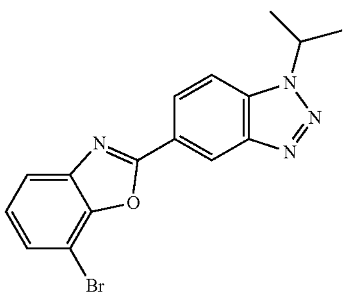 [SMILES: CC(C)n1nnc2cc(-c3nc4cccc(Br)c4o3)ccc21] | 429 | 7-bromo-2-(1-isopropyl-1H-benzo[d][1,2,3]triazol-5-yl)benzo[d]oxazole |
| 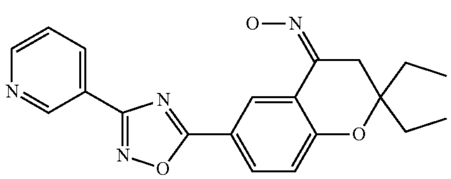 [SMILES: CCC1(CC)C/C(=N/O)c2cc(-c3nc(-c4cccnc4)no3)ccc2O1] | 430 | N-[(4Z)-2,2-diethyl-6-[3-(pyridin-3-yl)-1,2,4-oxadiazol-5-yl]-3,4-dihydro-2H-1-benzopyran-4-ylidene]hydroxylamine |
| 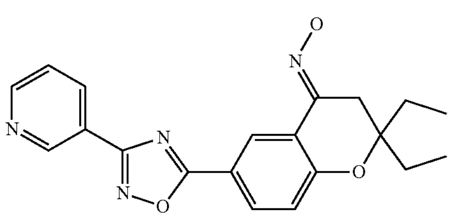 [SMILES: CCC1(CC)C/C(=N\O)c2cc(-c3nc(-c4cccnc4)no3)ccc2O1] | 431 | N-[(4E)-2,2-diethyl-6-[3-(pyridin-3-yl)-1,2,4-oxadiazol-5-yl]-3,4-dihydro-2H-1-benzopyran-4-ylidene]hydroxylamine |
| 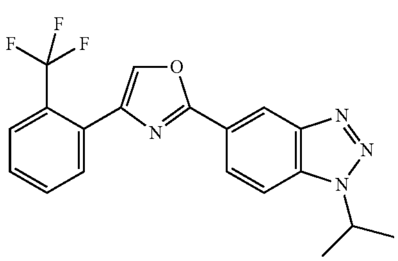 [SMILES: CC(C)n1nnc2cc(-c3nc(-c4ccccc4C(F)(F)F)co3)ccc21] | 432 | 1-(propan-2-yl)-5-{4-[2-(trifluoromethyl)phenyl]-1,3-oxazol-2-yl}-1H-1,2,3-benzotriazole |

-continued

| Structure | Compound Number | Chemical Name |
|---|---|---|
| 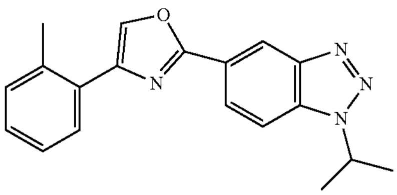 [SMILES: Cc1ccccc1-c1coc(-c2ccc3c(c2)nnn3C(C)C)n1] | 433 | 5-[4-(2-methylphenyl)-1,3-oxazol-2-yl]-1-(propan-2-yl)-1H-1,2,3-benzotriazole |
| 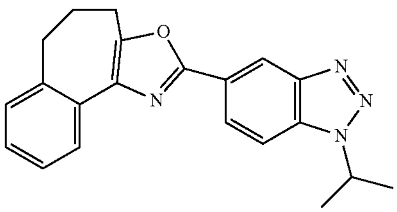 [SMILES: CC(C)n1nnc2cc(-c3nc4c(o3)CCCc3ccccc3-4)ccc21] | 434 | 4-[1-(propan-2-yl)-1H-1,2,3-benzotriazol-5-yl]-5-oxa-3-azatricyclo[8.4.0.0²,⁶]tetradeca-1(14),2(6),3,10,12-pentaene |
| 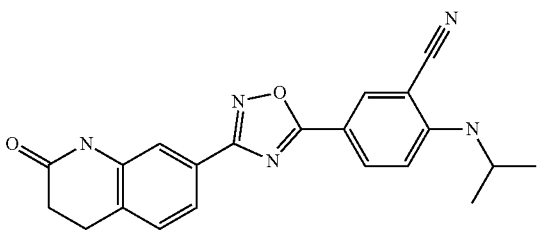 [SMILES: CC(C)Nc1ccc(-c2nc(-c3ccc4c(c3)NC(=O)CC4)no2)cc1C#N] | 435 | 2-(isopropylamino)-5-(3-(2-oxo-1,2,3,4-tetrahydroquinolin-7-yl)-1,2,4-oxadiazol-5-yl)benzonitrile |
| 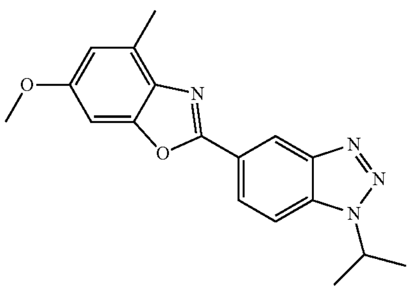 [SMILES: COc1cc(C)c2nc(-c3ccc4c(c3)nnn4C(C)C)oc2c1] | 436 | 2-(1-isopropyl-1H-benzo[d][1,2,3]triazol-5-yl)-6-methoxy-4-methylbenzo[d]oxazole |
| 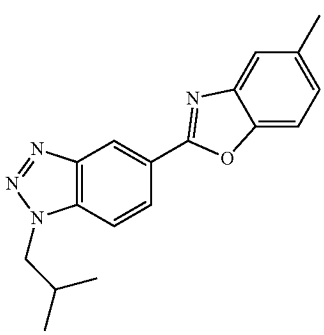 [SMILES: Cc1ccc2oc(-c3ccc4c(c3)nnn4CC(C)C)nc2c1] | 437 | 2-(1-isobutyl-1H-benzo[d][1,2,3]triazol-5-yl)-5-methylbenzo[d]oxazole |
| 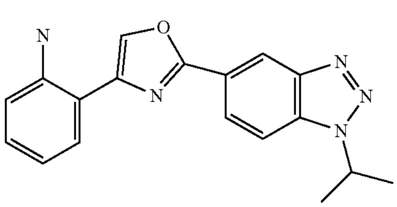 [SMILES: CC(C)n1nnc2cc(-c3nc(-c4ccccc4N)co3)ccc21] | 438 | 2-{2-[1-(propan-2-yl)-1H-1,2,3-benzotriazol-5-yl]-1,3-oxazol-4-yl}aniline |

-continued

| Structure | Compound Number | Chemical Name |
|---|---|---|
| 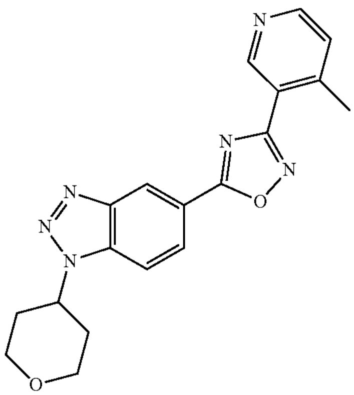 [SMILES: Cc1ccncc1-c1noc(-c2ccc3c(c2)nnn3C2CCOCC2)n1] | 439 | 5-[3-(4-methylpyridin-3-yl)-1,2,4-oxadiazol-5-yl]-1-(oxan-4-yl)-1H-1,2,3-benzotriazole |
| 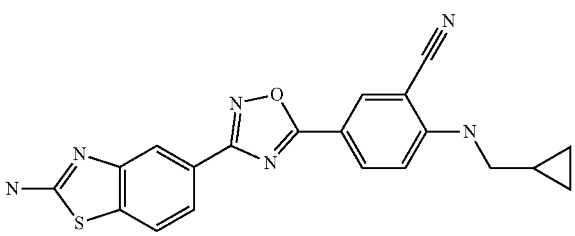 [SMILES: N#Cc1cc(-c2nc(-c3ccc4sc(N)nc4c3)no2)ccc1NCC1CC1] | 440 | 5-(3-(2-aminobenzo[d]thiazol-5-yl)-1,2,4-oxadiazol-5-yl)-2-((cyclopropylmethyl)amino)benzonitrile |
| 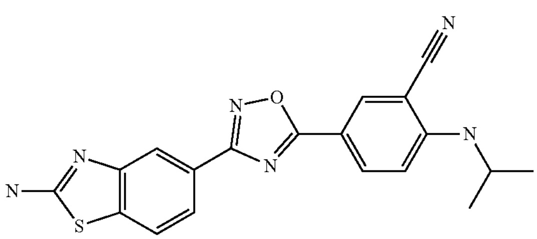 [SMILES: CC(C)Nc1ccc(-c2nc(-c3ccc4sc(N)nc4c3)no2)cc1C#N] | 441 | 5-(3-(2-aminobenzo[d]thiazol-5-yl)-1,2,4-oxadiazol-5-yl)-2-(isopropylamino)benzonitrile |
| 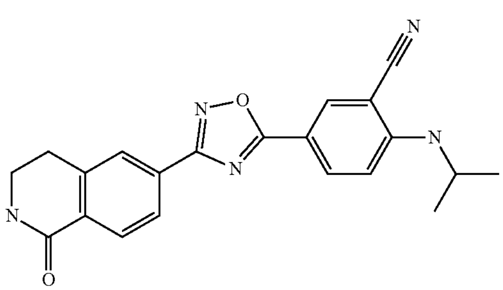 [SMILES: CC(C)Nc1ccc(-c2nc(-c3ccc4c(c3)CCNC4=O)no2)cc1C#N] | 442 | 2-(isopropylamino)-5-(3-(1-oxo-1,2,3,4-tetrahydroisoquinolin-6-yl)-1,2,4-oxadiazol-5-yl)benzonitrile |
| 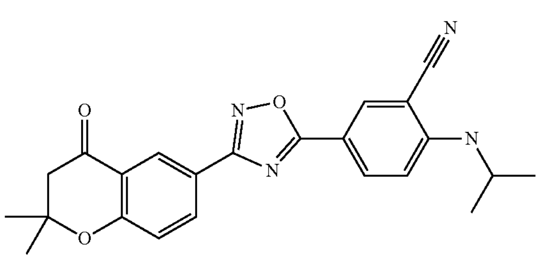 [SMILES: CC(C)Nc1ccc(-c2nc(-c3ccc4c(c3)C(=O)CC(C)(C)O4)no2)cc1C#N] | 443 | 5-(3-(2,2-diethyl-4-oxochroman-6-yl)-1,2,4-oxadiazol-5-yl)-2-(isopropylamino)benzonitrile |

-continued

| Structure | Compound Number | Chemical Name |
|---|---|---|
| 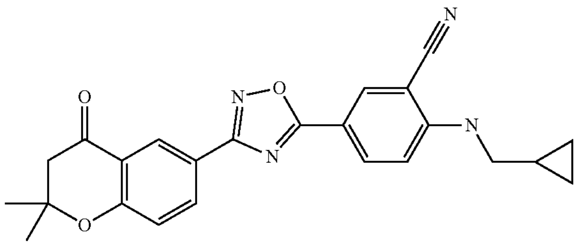 [SMILES: CC1(C)CC(=O)c2cc(-c3noc(-c4ccc(NCC5CC5)c(C#N)c4)n3)ccc2O1] | 444 | 2-((cyclopropylmethyl)amino)-5-(3-(2,2-diethyl-4-oxochroman-6-yl)-1,2,4-oxadiazol-5-yl)benzonitrile |
| 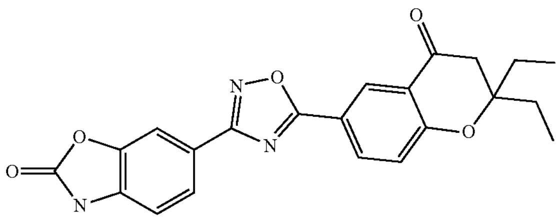 [SMILES: CCC1(CC)CC(=O)c2cc(-c3nc(-c4ccc5[nH]c(=O)oc5c4)no3)ccc2O1] | 445 | 6-(5-(2,2-diethyl-4-oxochroman-6-yl)-1,2,4-oxadiazol-3-yl)benzo[d]oxazol-2(3H)-one |
| 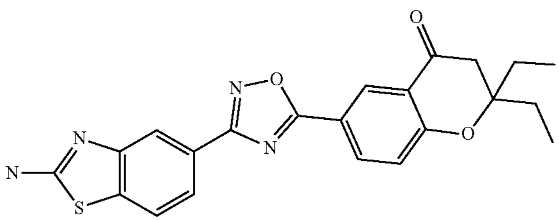 [SMILES: CCC1(CC)CC(=O)c2cc(-c3nc(-c4ccc5sc(N)nc5c4)no3)ccc2O1] | 446 | 6-(3-(2-aminobenzo[d]thiazol-5-yl)-1,2,4-oxadiazol-5-yl)-2,2-diethylchroman-4-one |
| 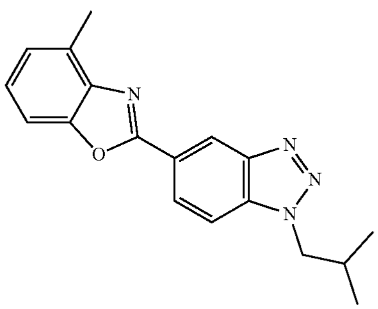 [SMILES: Cc1cccc2oc(-c3ccc4c(c3)nnn4CC(C)C)nc12] | 447 | 2-(1-isobutyl-1H-benzo[d][1,2,3]triazol-5-yl)-4-methylbenzo[d]oxazole |
| 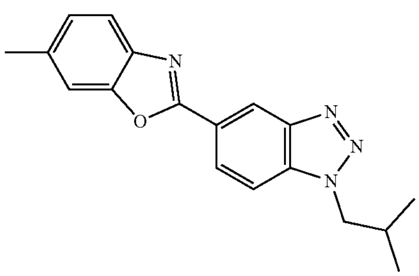 [SMILES: Cc1ccc2nc(-c3ccc4c(c3)nnn4CC(C)C)oc2c1] | 448 | 2-(1-isobutyl-1H-benzo[d][1,2,3]triazol-5-yl)-6-methylbenzo[d]oxazole |
| 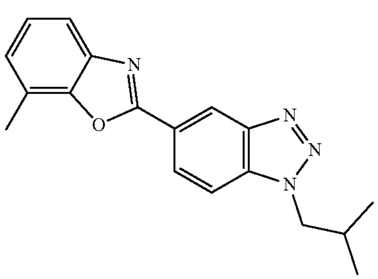 [SMILES: Cc1cccc2nc(-c3ccc4c(c3)nnn4CC(C)C)oc12] | 449 | 2-(1-isobutyl-1H-benzo[d][1,2,3]triazol-5-yl)-7-methylbenzo[d]oxazole |

-continued

| Structure | Compound Number | Chemical Name |
|---|---|---|
| 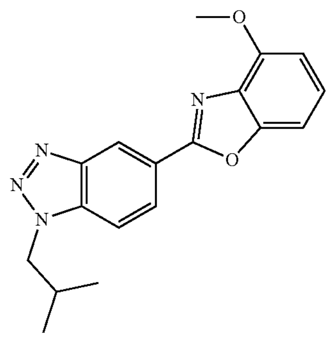 [SMILES: COc1cccc2oc(-c3ccc4c(c3)nnn4CC(C)C)nc12] | 450 | 2-(1-isobutyl-1H-benzo[d][1,2,3]triazol-5-yl)-4-methoxybenzo[d]oxazole |
| 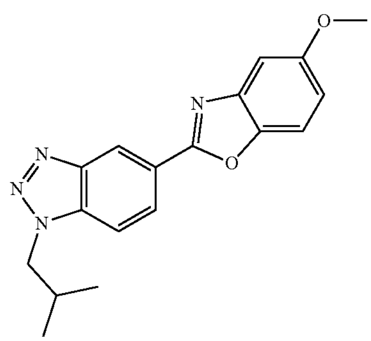 [SMILES: COc1ccc2oc(-c3ccc4c(c3)nnn4CC(C)C)nc2c1] | 451 | 2-(1-isobutyl-1H-benzo[d][1,2,3]triazol-5-yl)-5-methoxybenzo[d]oxazole |
| 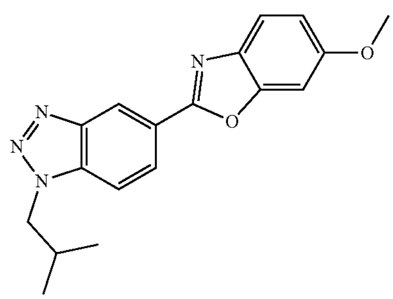 [SMILES: COc1ccc2nc(-c3ccc4c(c3)nnn4CC(C)C)oc2c1] | 452 | 2-(1-isobutyl-1H-benzo[d][1,2,3]triazol-5-yl)-6-methoxybenzo[d]oxazole |
| 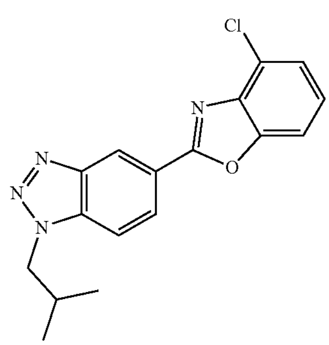 | 453 | 4-chloro-2-(1-isobutyl-1H-benzo[d][1,2,3]triazol-5-yl)benzo[d]oxazole |

-continued

| Structure | Compound Number | Chemical Name |
|---|---|---|
| 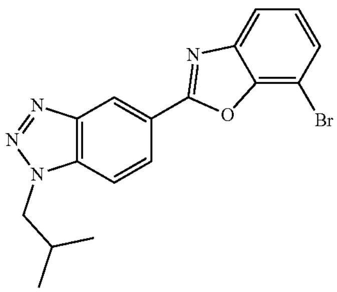 [SMILES: CC(C)Cn1nnc2cc(-c3nc4cccc(Br)c4o3)ccc21] | 454 | 7-bromo-2-(1-isobutyl-1H-benzo[d][1,2,3]triazol-5-yl)benzo[d]oxazole |
| 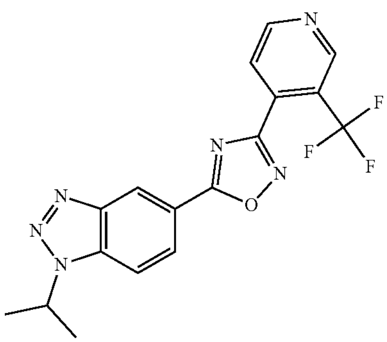 [SMILES: CC(C)n1nnc2cc(-c3nc(-c4ccncc4C(F)(F)F)no3)ccc21] | 455 | 1-(propan-2-yl)-5-{3-[3-(trifluoromethyl)pyridin-4-yl]-1,2,4-oxadiazol-5-yl}-1H-1,2,3-benzotriazole |
| 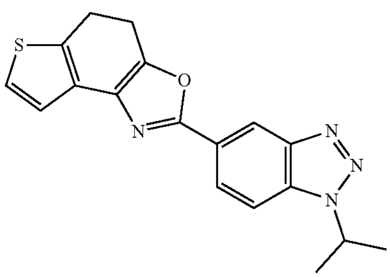 [SMILES: CC(C)n1nnc2cc(-c3nc4c(o3)CCc3sccc3-4)ccc21] | 456 | 4-[1-(propan-2-yl)-1H-1,2,3-benzotriazol-5-yl]-5-oxa-10-thia-3-azatricyclo[7.3.0.0²,⁶]dodeca-1(9),2(6),3,11-tetraene |
| 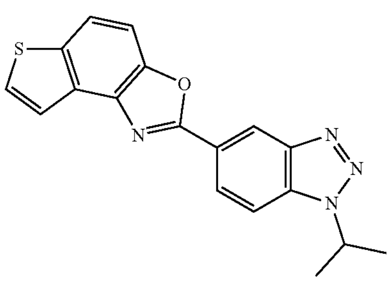 [SMILES: CC(C)n1nnc2cc(-c3nc4c(ccc5sccc54)o3)ccc21] | 457 | 4-[1-(propan-2-yl)-1H-1,2,3-benzotriazol-5-yl]-5-oxa-10-thia-3-azatricyclo[7.3.0.0²,⁶]dodeca-1(9),2(6),3,7,11-pentaene |
| 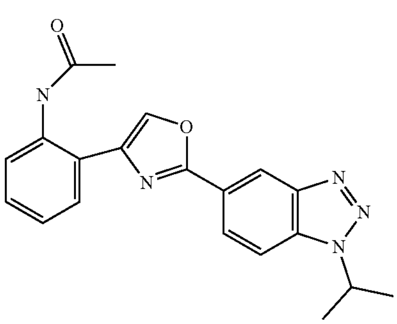 [SMILES: CC(=O)Nc1ccccc1-c1coc(-c2ccc3c(c2)nnn3C(C)C)n1] | 458 | N-(2-{2-[1-(propan-2-yl)-1H-1,2,3-benzotriazol-5-yl]-1,3-oxazol-4-yl}phenyl)acetamide |

-continued

| Structure | Compound Number | Chemical Name |
|---|---|---|
| 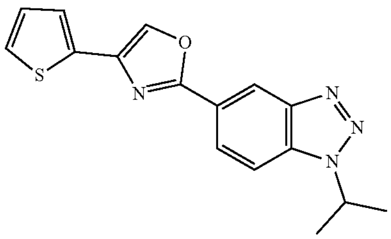 [SMILES: CC(C)n1nnc2cc(-c3nc(-c4cccs4)co3)ccc21] | 459 | 1-(propan-2-yl)-5-[4-(thiophen-2-yl)-1,3-oxazol-2-yl]-1H-1,2,3-benzotriazole |
| 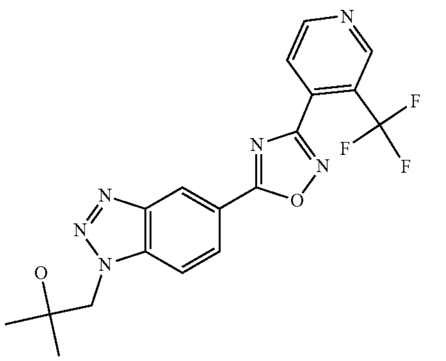 [SMILES: CC(C)(O)Cn1nnc2cc(-c3nc(-c4ccncc4C(F)(F)F)no3)ccc21] | 460 | 2-methyl-1-(5-{3-[3-(trifluoromethyl)pyridin-4-yl]-1,2,4-oxadiazol-5-yl}-1H-1,2,3-benzotriazol-1-yl)propan-2-ol |
| 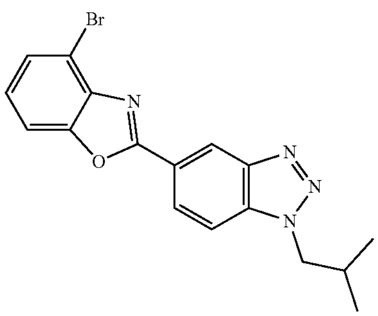 [SMILES: CC(C)Cn1nnc2cc(-c3nc4c(Br)cccc4o3)ccc21] | 461 | 4-bromo-2-(1-isobutyl-1H-benzo[d][1,2,3]triazol-5-yl)benzo[d]oxazole |
| 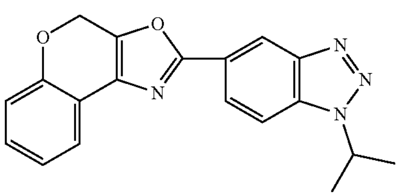 [SMILES: CC(C)n1nnc2cc(-c3nc4c(o3)COc3ccccc3-4)ccc21] | 462 | 5-{4H-chromeno[4,3-d][1,3]oxazol-2-yl}-1-(propan-2-yl)-1H-1,2,3-benzotriazole |
| 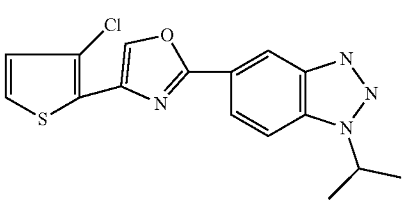 [SMILES: CC(C)N1NNc2cc(-c3nc(-c4sccc4Cl)co3)ccc21] | 463 | 5-[4-(3-chlorothiophen-2-yl)-1,3-oxazol-2-yl]-1-(propan-2-yl)-1H-1,2,3-benzotriazole |
| 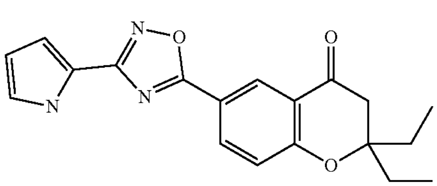 [SMILES: CCC1(CC)CC(=O)c2cc(-c3nc(-c4ccc[nH]4)no3)ccc2O1] | 464 | 6-(3-(1H-pyrrol-2-yl)-1,2,4-oxadiazol-5-yl)-2,2-diethylchroman-4-one |

-continued

| Structure | Compound Number | Chemical Name |
|---|---|---|
| 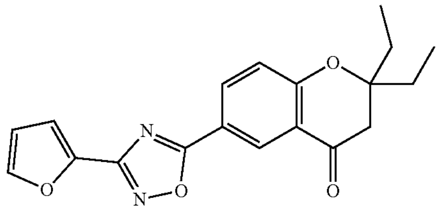 [SMILES: CCC1(CC)CC(=O)c2cc(-c3nc(-c4ccco4)no3)ccc2O1] | 465 | 2,2-diethyl-6-(3-(furan-2-yl)-1,2,4-oxadiazol-5-yl)chroman-4-one |
| 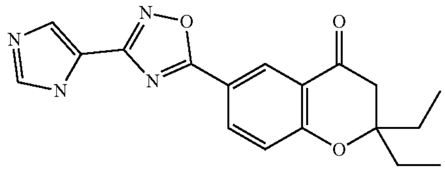 [SMILES: CCC1(CC)CC(=O)c2cc(-c3nc(-c4cnc[nH]4)no3)ccc2O1] | 466 | 6-(3-(1H-imidazol-5-yl)-1,2,4-oxadiazol-5-yl)-2,2-diethylchroman-4-one |
| 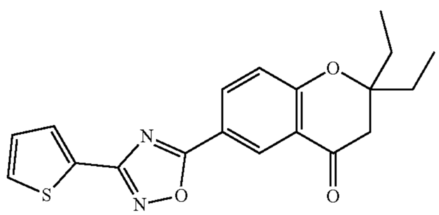 [SMILES: CCC1(CC)CC(=O)c2cc(-c3nc(-c4cccs4)no3)ccc2O1] | 467 | 2,2-diethyl-6-(3-(thiophen-2-yl)-1,2,4-oxadiazol-5-yl)chroman-4-one |
| 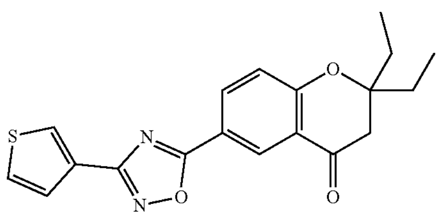 [SMILES: CCC1(CC)CC(=O)c2cc(-c3nc(-c4ccsc4)no3)ccc2O1] | 468 | 2,2-diethyl-6-(3-(thiophen-3-yl)-1,2,4-oxadiazol-5-yl)chroman-4-one |
| 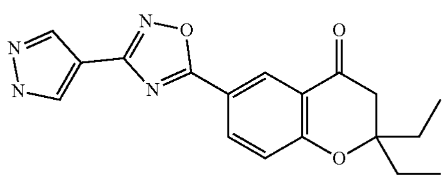 [SMILES: CCC1(CC)CC(=O)c2cc(-c3nc(-c4cn[nH]c4)no3)ccc2O1] | 469 | 6-(3-(1H-pyrazol-4-yl)-1,2,4-oxadiazol-5-yl)-2,2-diethylchroman-4-one |
| 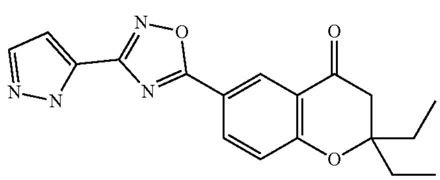 [SMILES: CCC1(CC)CC(=O)c2cc(-c3nc(-c4ccn[nH]4)no3)ccc2O1] | 470 | 6-(3-(1H-pyrazol-5-yl)-1,2,4-oxadiazol-5-yl)-2,2-diethylchroman-4-one |
| 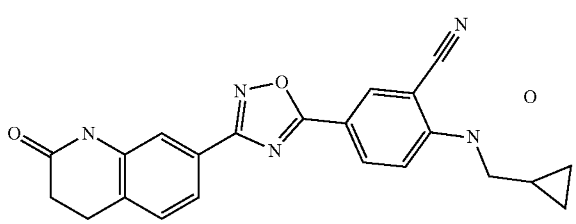 [SMILES: N#Cc1cc(-c2nc(-c3ccc4c(c3)NC(=O)CC4)no2)ccc1NCC1CC1 ; O] | 471 | 2-((cyclopropylmethyl)amino)-5-(3-(2-oxo-1,2,3,4-tetrahydroquinolin-7-yl)-1,2,4-oxadiazol-5-yl)benzonitrile |

-continued

| Structure | Compound Number | Chemical Name |
|---|---|---|
| 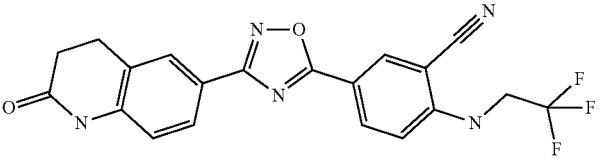 [SMILES: N#Cc1cc(-c2nc(-c3ccc4c(c3)CCC(=O)N4)no2)ccc1NCC(F)(F)F] | 472 | 5-[3-(2-oxo-1,2,3,4-tetrahydroquinolin-6-yl)-1,2,4-oxadiazol-5-yl]-2-[(2,2,2-trifluoroethyl)amino]benzonitrile |
| 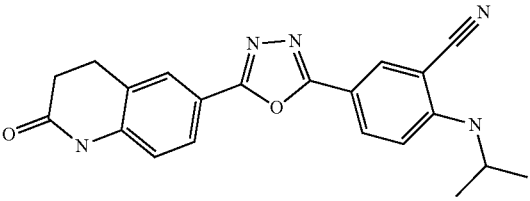 [SMILES: CC(C)Nc1ccc(-c2nnc(-c3ccc4c(c3)CCC(=O)N4)o2)cc1C#N] | 473 | 5-[5-(2-oxo-1,2,3,4-tetrahydroquinolin-6-yl)-1,3,4-oxadiazol-2-yl]-2-[(propan-2-yl)amino]benzonitrile |
| 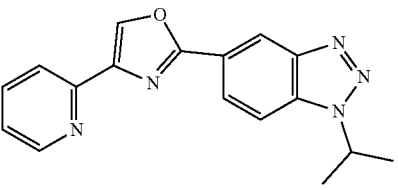 [SMILES: CC(C)n1nnc2cc(-c3nc(-c4ccccn4)co3)ccc21] | 474 | 1-(propan-2-yl)-5-[4-(pyridin-2-yl)-1,3-oxazol-2-yl]-1H-1,2,3-benzotriazole |
| 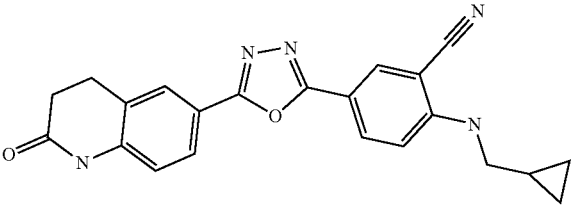 [SMILES: N#Cc1cc(-c2nnc(-c3ccc4c(c3)CCC(=O)N4)o2)ccc1NCC1CC1] | 475 | 2-[(cyclopropylmethyl)amino]-5-[5-(2-oxo-1,2,3,4-tetrahydroquinolin-6-yl)-1,3,4-oxadiazol-2-yl]benzonitrile |
| 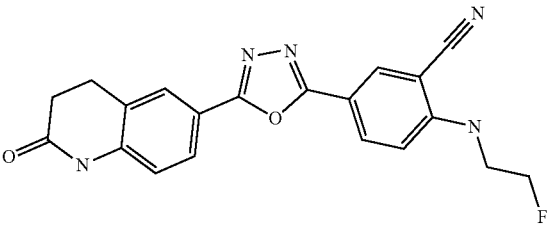 [SMILES: N#Cc1cc(-c2nnc(-c3ccc4c(c3)CCC(=O)N4)o2)ccc1NCCF] | 476 | 2-[(2-fluoroethyl)amino]-5-[5-(2-oxo-1,2,3,4-tetrahydroquinolin-6-yl)-1,3,4-oxadiazol-2-yl]benzonitrile |
| 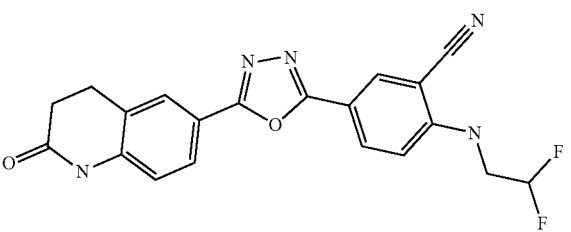 [SMILES: N#Cc1cc(-c2nnc(-c3ccc4c(c3)CCC(=O)N4)o2)ccc1NCC(F)F] | 477 | 2-[(2,2-difluoroethyl)amino]-5-[5-(2-oxo-1,2,3,4-tetrahydroquinolin-6-yl)-1,3,4-oxadiazol-2-yl]benzonitrile |
| 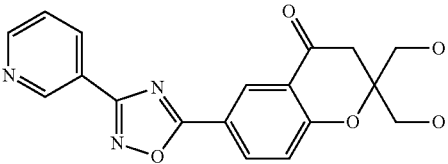 | 478 | 2,2-bis(hydroxymethyl)-6-[3-(pyridin-3-yl)-1,2,4-oxadiazol-5-yl]-3,4-dihydro-2H-1-benzopyran-4-one |

-continued

| Structure | Compound Number | Chemical Name |
|---|---|---|
| 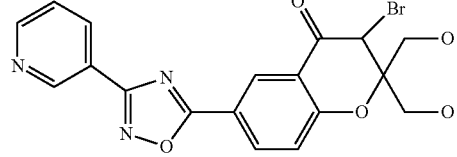 | 479 | 3-bromo-2,2-bis(hydroxymethyl)-6-[3-(pyridin-3-yl)-1,2,4-oxadiazol-5-yl]-3,4-dihydro-2H-1-benzopyran-4-one |
| 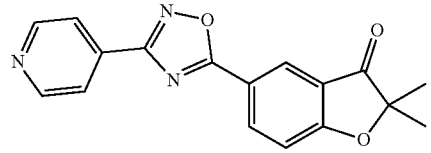 [SMILES: CC1(C)Oc2ccc(-c3nc(-c4ccncc4)no3)cc2C1=O] | 480 | 2,2-dimethyl-5-[3-(pyridin-4-yl)-1,2,4-oxadiazol-5-yl]-2,3-dihydro-1-benzofuran-3-one |
| 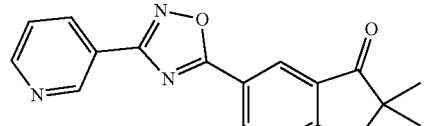 | 481 | 2,2-dimethyl-5-[3-(pyridin-3-yl)-1,2,4-oxadiazol-5-yl]-2,3-dihydro-1-benzofuran-3-one |
| 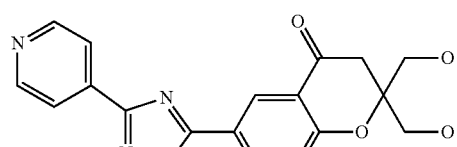 | 482 | 2,2-bis(hydroxymethyl)-6-[3-(pyridin-4-yl)-1,2,4-oxadiazol-5-yl]-3,4-dihydro-2H-1-benzopyran-4-one |
| 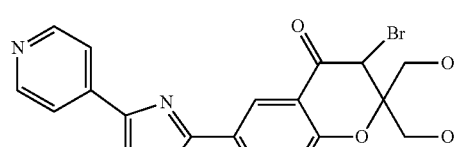 | 483 | 3-bromo-2,2-bis(hydroxymethyl)-6-[3-(pyridin-4-yl)-1,2,4-oxadiazol-5-yl]-3,4-dihydro-2H-1-benzopyran-4-one |
| 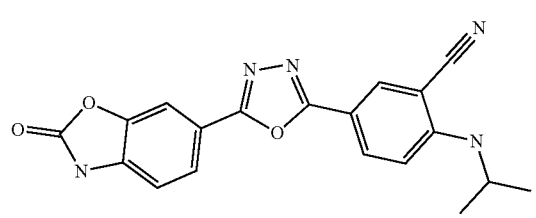 [SMILES: CC(C)Nc1ccc(-c2nnc(-c3ccc4[nH]c(=O)oc4c3)o2)cc1C#N] | 484 | 5-[5-(2-oxo-2,3-dihydro-1,3-benzoxazol-6-yl)-1,3,4-oxadiazol-2-yl]-2-[(propan-2-yl)amino]benzonitrile |
| 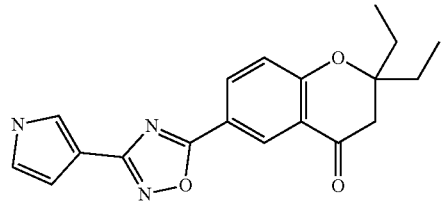 | 485 | 6-(3-(1H-pyrrol-3-yl)-1,2,4-oxadiazol-5-yl)-2,2-diethylchroman-4-one |
| 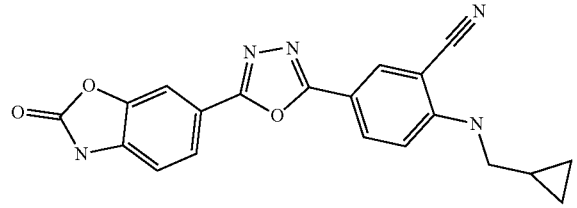 [SMILES: N#Cc1cc(-c2nnc(-c3ccc4[nH]c(=O)oc4c3)o2)ccc1NCC1CC1] | 486 | 2-[(cyclopropylmethyl)amino]-5-[5-(2-oxo-2,3-dihydro-1,3-benzoxazol-6-yl)-1,3,4-oxadiazol-2-yl]benzonitrile |

-continued

| Structure | Compound Number | Chemical Name |
|---|---|---|
| 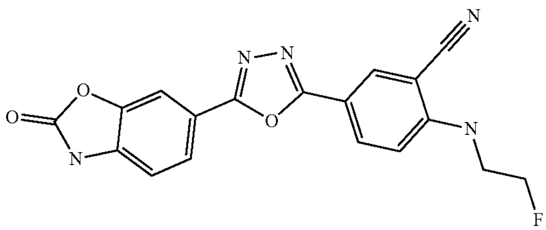 [SMILES: N#Cc1cc(-c2nnc(-c3ccc4[nH]c(=O)oc4c3)o2)ccc1NCCF] | 487 | 2-[(2-fluoroethyl)amino]-5-[5-(2-oxo-2,3-dihydro-1,3-benzoxazol-6-yl)-1,3,4-oxadiazol-2-yl]benzonitrile |
| 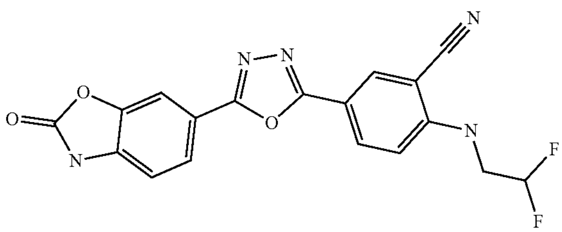 [SMILES: N#Cc1cc(-c2nnc(-c3ccc4[nH]c(=O)oc4c3)o2)ccc1NCC(F)F] | 488 | 2-[(2,2-difluoroethyl)amino]-5-[5-(2-oxo-2,3-dihydro-1,3-benzoxazol-6-yl)-1,3,4-oxadiazol-2-yl]benzonitrile |
| 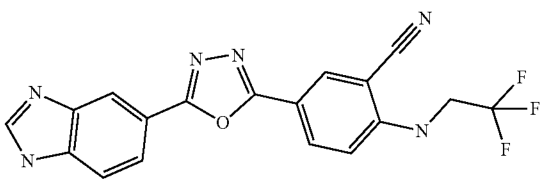 [SMILES: N#Cc1cc(-c2nnc(-c3ccc4[nH]cnc4c3)o2)ccc1NCC(F)(F)F] | 489 | 5-[3-(1H-1,3-benzodiazol-5-yl)-1,2,4-oxadiazol-5-yl]-2-[(2,2,2-trifluoroethyl)amino]benzonitrile |
| 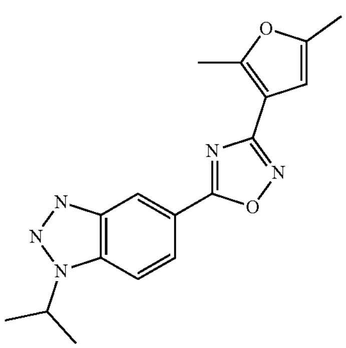 [SMILES: Cc1cc(-c2noc(-c3ccc4c(c3)NNN4C(C)C)n2)c(C)o1] | 490 | 5-[3-(2,5-dimethylfuran-3-yl)-1,2,4-oxadiazol-5-yl]-1-(propan-2-yl)-1H-1,2,3-benzotriazole |
| 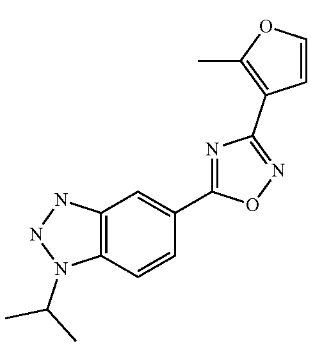 [SMILES: Cc1occc1-c1noc(-c2ccc3c(c2)NNN3C(C)C)n1] | 491 | 5-[3-(2-methylfuran-3-yl)-1,2,4-oxadiazol-5-yl]-1-(propan-2-yl)-1H-1,2,3-benzotriazole |

-continued

| Structure | Compound Number | Chemical Name |
|---|---|---|
| 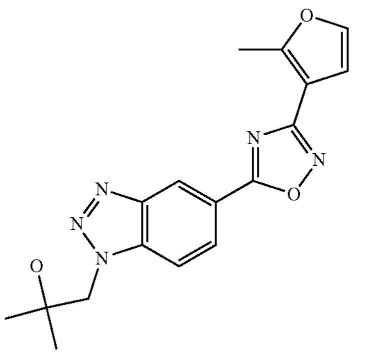 [SMILES: Cc1occc1-c1noc(-c2ccc3c(c2)nnn3CC(C)(C)O)n1] | 492 | 2-methyl-1-{5-[3-(2-methylfuran-3-yl)-1,2,4-oxadiazol-5-yl]-1H-1,2,3-benzotriazol-1-yl}propan-2-ol |
| 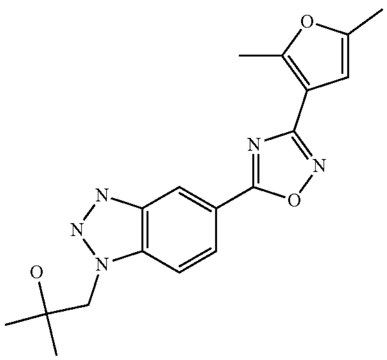 [SMILES: Cc1cc(-c2noc(-c3ccc4c(c3)NNN4CC(C)(C)O)n2)c(C)o1] | 493 | 1-{5-[3-(2,5-dimethylfuran-3-yl)-1,2,4-oxadiazol-5-yl]-1H-1,2,3-benzotriazol-1-yl}-2-methylpropan-2-ol |
| 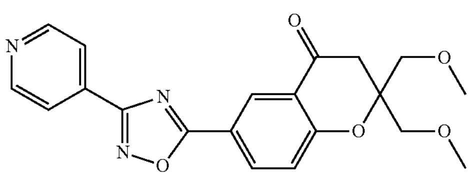 [SMILES: COCC1(COC)CC(=O)c2cc(-c3nc(-c4ccncc4)no3)ccc2O1] | 494 | 2,2-bis(methoxymethyl)-6-[3-(pyridin-4-yl)-1,2,4-oxadiazol-5-yl]-3,4-dihydro-2H-1-benzopyran-4-one |
| 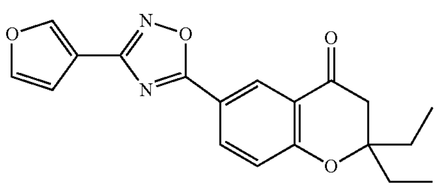 [SMILES: CCC1(CC)CC(=O)c2cc(-c3nc(-c4ccoc4)no3)ccc2O1] | 495 | 2,2-diethyl-6-(3-(furan-3-yl)-1,2,4-oxadiazol-5-yl)chroman-4-one |
| 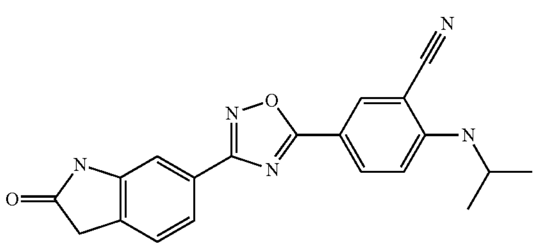 | 496 | 2-(isopropylamino)-5-(3-(2-oxoindolin-6-yl)-1,2,4-oxadiazol-5-yl)benzonitrile |
| 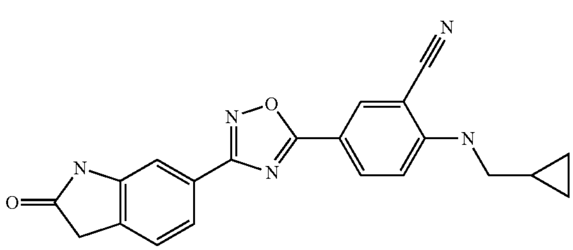 [SMILES: N#Cc1cc(-c2nc(-c3ccc4c(c3)NC(=O)C4)no2)ccc1NCC1CC1] | 497 | 2-((cyclopropylmethyl)amino)-5-(3-(2-oxoindolin-6-yl)-1,2,4-oxadiazol-5-yl)benzonitrile |

-continued

| Structure | Compound Number | Chemical Name |
|---|---|---|
| 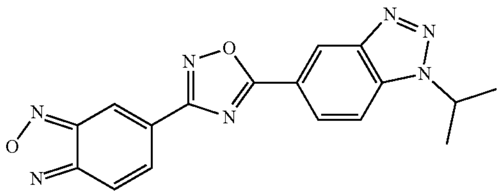 [SMILES: CC(C)n1nnc2cc(-c3nc(C4=C/C(=N/O)C(=N)C=C4)no3)ccc21] | 498 | 5-{5-[1-(propan-2-yl)-1H-1,2,3-benzotriazol-5-yl]-1,2,4-oxadiazol-3-yl}-2,1,3-benzoxadiazole |
| 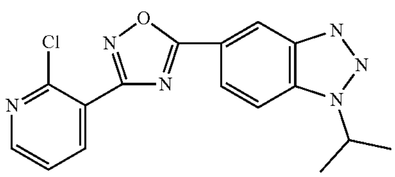 [SMILES: CC(C)N1NNc2cc(-c3nc(-c4cccnc4Cl)no3)ccc21] | 499 | 5-[3-(2-chloropyridin-3-yl)-1,2,4-oxadiazol-5-yl]-1-(propan-2-yl)-1H-1,2,3-benzotriazole |
| 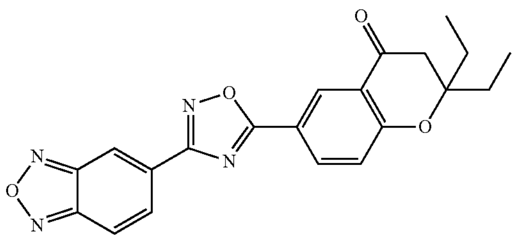 [SMILES: CCC1(CC)CC(=O)c2cc(-c3nc(-c4ccc5nonc5c4)no3)ccc2O1] | 500 | 6-[3-(2,1,3-benzoxadiazol-5-yl)-1,2,4-oxadiazol-5-yl]-2,2-diethyl-3,4-dihydro-2H-1-benzopyran-4-one |
| 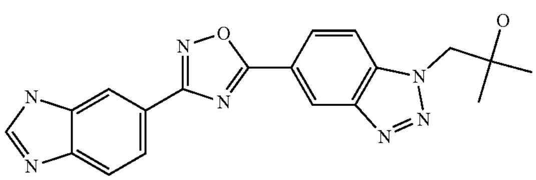 [SMILES: CC(C)(O)Cn1nnc2cc(-c3nc(-c4ccc5nc[nH]c5c4)no3)ccc21] | 501 | 1-{5-[3-(1H-1,3-benzodiazol-6-yl)-1,2,4-oxadiazol-5-yl]-1H-1,2,3-benzotriazol-1-yl}-2-methylpropan-2-ol |
| 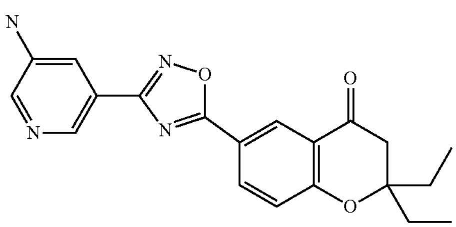 [SMILES: CCC1(CC)CC(=O)c2cc(-c3nc(-c4cncc(N)c4)no3)ccc2O1] | 502 | 6-(3-(5-aminopyridin-3-yl)-1,2,4-oxadiazol-5-yl)-2,2-diethylchroman-4-one |
| 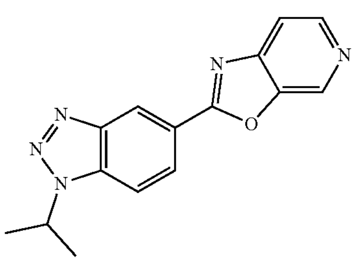 [SMILES: CC(C)n1nnc2cc(-c3nc4ccncc4o3)ccc21] | 503 | 2-(1-isopropyl-1H-benzo[d][1,2,3]triazol-5-yl)oxazolo[5,4-c]pyridine |
| 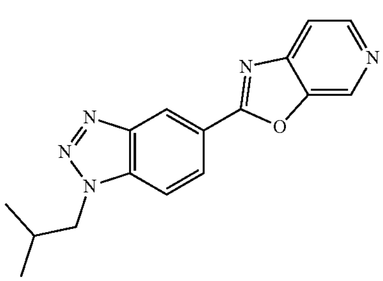 [SMILES: CC(C)Cn1nnc2cc(-c3nc4ccncc4o3)ccc21] | 504 | 2-(1-isobutyl-1H-benzo[d][1,2,3]triazol-5-yl)oxazolo[5,4-c]pyridine |

-continued

| Structure | Compound Number | Chemical Name |
|---|---|---|
| 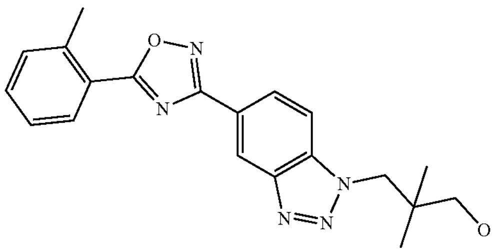 [SMILES: Cc1ccccc1-c1nc(-c2ccc3c(c2)nnn3CC(C)(C)CO)no1] | 505 | 2,2-dimethyl-3-(5-(5-(o-tolyl)-1,2,4-oxadiazol-3-yl)-1H-benzo[d][1,2,3]triazol-1-yl)propan-1-ol |
| 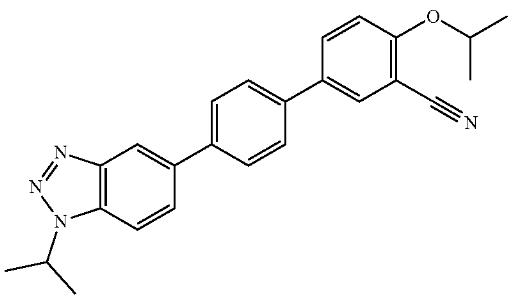 | 506 | 4-isopropoxy-4'-(1-isopropyl-1H-benzo[d][1,2,3]triazol-5-yl)-[1,1'-biphenyl]-3-carbonitrile |
| 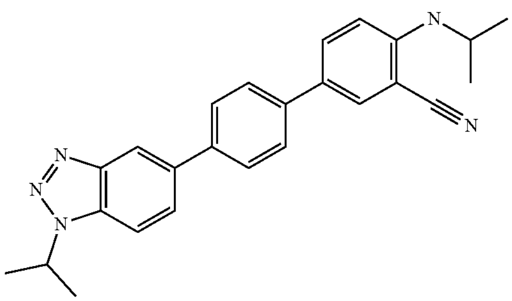 [SMILES: CC(C)Nc1ccc(-c2ccc(-c3ccc4c(c3)nnn4C(C)C)cc2)cc1C#N] | 507 | 4'-(1-isopropyl-1H-benzo[d][1,2,3]triazol-5-yl)-4-(isopropylamino)-[1,1'-biphenyl]-3-carbonitrile |
| 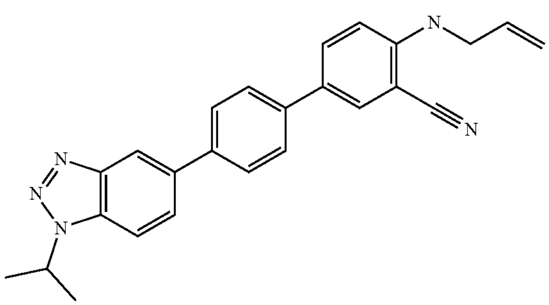 [SMILES: C=CCNc1ccc(-c2ccc(-c3ccc4c(c3)nnn4C(C)C)cc2)cc1C#N] | 508 | 4-(allylamino)-4'-(1-isopropyl-1H-benzo[d][1,2,3]triazol-5-yl)-[1,1'-biphenyl]-3-carbonitrile |
| 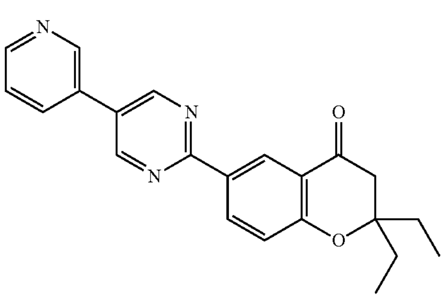 [SMILES: CCC1(CC)CC(=O)c2cc(-c3ncc(-c4cccnc4)cn3)ccc2O1] | 509 | 2,2-diethyl-6-(5-(pyridin-3-yl)pyrimidin-2-yl)chroman-4-one |

-continued

| Structure | Compound Number | Chemical Name |
|---|---|---|
| 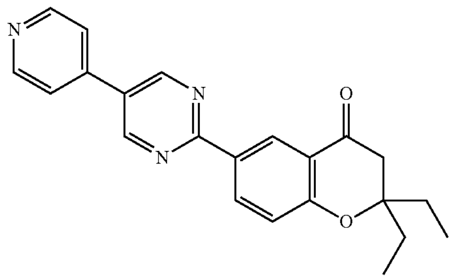 [SMILES: CCC1(CC)CC(=O)c2cc(-c3ncc(-c4ccncc4)cn3)ccc2O1] | 510 | 2,2-diethyl-6-(5-(pyridin-4-yl)pyrimidin-2-yl)chroman-4-one |
| 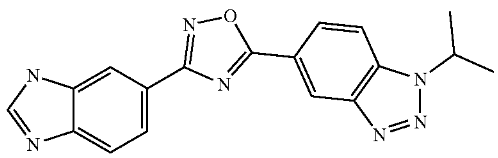 [SMILES: CC(C)n1nnc2cc(-c3nc(-c4ccc5nc[nH]c5c4)no3)ccc21] | 511 | 5-[3-(1H-1,3-benzodiazol-6-yl)-1,2,4-oxadiazol-5-yl]-1-(propan-2-yl)-1H-1,2,3-benzotriazole |
| 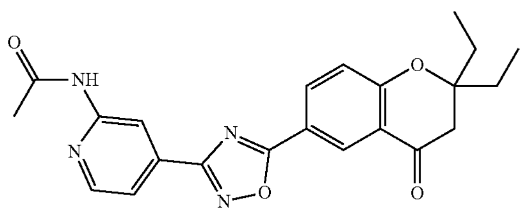 [SMILES: CCC1(CC)CC(=O)c2cc(-c3nc(-c4ccnc(NC(C)=O)c4)no3)ccc2O1] | 512 | N-(4-(5-(2,2-diethyl-4-oxochroman-6-yl)-1,2,4-oxadiazol-3-yl)pyridin-2-yl)acetamide |
| 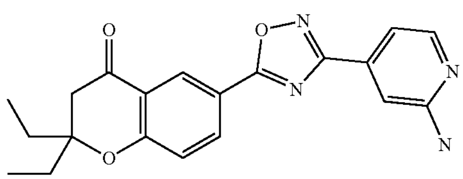 [SMILES: CCC1(CC)CC(=O)c2cc(-c3nc(-c4ccnc(N)c4)no3)ccc2O1] | 513 | 6-(3-(2-aminopyridin-4-yl)-1,2,4-oxadiazol-5-yl)-2,2-diethylchroman-4-one |
| 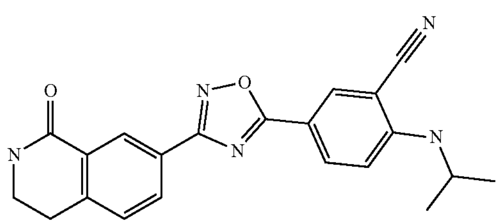 [SMILES: CC(C)Nc1ccc(-c2nc(-c3ccc4c(c3)C(=O)NCC4)no2)cc1C#N] | 514 | 2-(isopropylamino)-5-(3-(1-oxo-1,2,3,4-tetrahydroisoquinolin-7-yl)-1,2,4-oxadiazol-5-yl)benzonitrile |
| 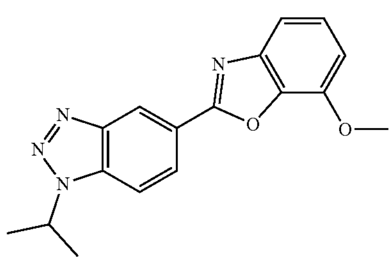 [SMILES: COc1cccc2nc(-c3ccc4c(c3)nnn4C(C)C)oc12] | 515 | 2-(1-isopropyl-1H-benzo[d][1,2,3]triazol-5-yl)-7-methoxybenzo[d]oxazole |
| 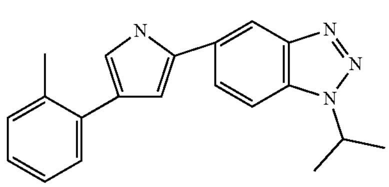 [SMILES: Cc1ccccc1-c1c[nH]c(-c2ccc3c(c2)nnn3C(C)C)c1] | 516 | 5-[4-(2-methylphenyl)-1H-pyrrol-2-yl]-1-(propan-2-yl)-1H-1,2,3-benzotriazole |

-continued

| Structure | Compound Number | Chemical Name |
|---|---|---|
| 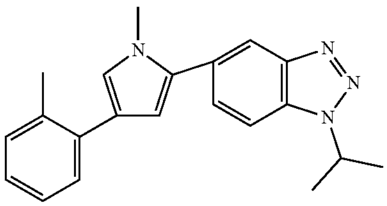 [SMILES: Cc1ccccc1-c1cc(-c2ccc3c(c2)nnn3C(C)C)n(C)c1] | 517 | 5-[1-methyl-4-(2-methylphenyl)-1H-pyrrol-2-yl]-1-(propan-2-yl)-1H-1,2,3-benzotriazole |
| 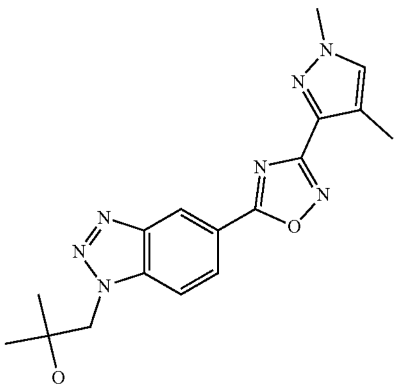 [SMILES: Cc1cn(C)nc1-c1noc(-c2ccc3c(c2)nnn3CC(C)(C)O)n1] | 518 | 1-{5-[3-(1,4-dimethyl-1H-pyrazol-3-yl)-1,2,4-oxadiazol-5-yl]-1H-1,2,3-benzotriazol-1-yl}-2-methylpropan-2-ol |
| 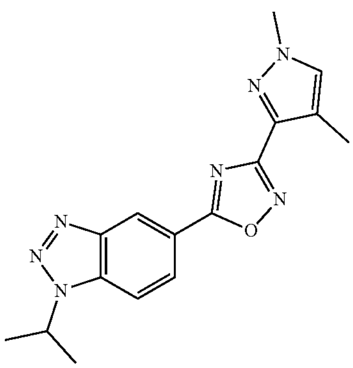 [SMILES: Cc1cn(C)nc1-c1noc(-c2ccc3c(c2)nnn3C(C)C)n1] | 519 | 5-[3-(1,4-dimethyl-1H-pyrazol-3-yl)-1,2,4-oxadiazol-5-yl]-1-(propan-2-yl)-1H-1,2,3-benzotriazole |
| 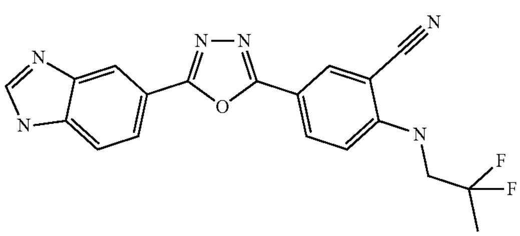 [SMILES: CC(F)(F)CNc1ccc(-c2nnc(-c3ccc4[nH]cnc4c3)o2)cc1C#N] | 520 | 5-[5-(1H-1,3-benzodiazol-5-yl)-1,3,4-oxadiazol-2-yl]-2-[(2,2-difluoropropyl)amino]benzonitrile |
| 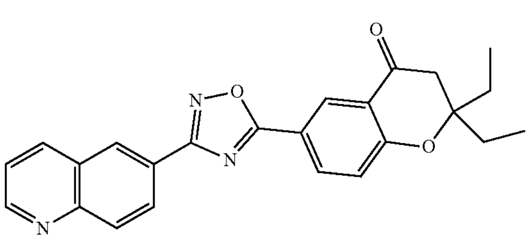 [SMILES: CCC1(CC)CC(=O)c2cc(-c3nc(-c4ccc5ncccc5c4)no3)ccc2O1] | 521 | 2,2-diethyl-6-(3-(quinolin-6-yl)-1,2,4-oxadiazol-5-yl)chroman-4-one |

-continued

| Structure | Compound Number | Chemical Name |
|---|---|---|
| 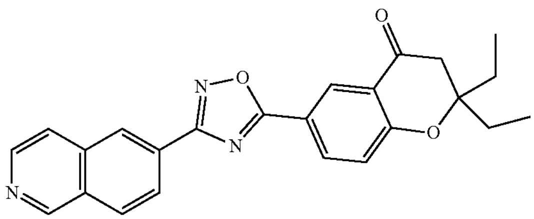 [SMILES: CCC1(CC)CC(=O)c2cc(-c3nc(-c4ccc5cnccc5c4)no3)ccc2O1] | 522 | 2,2-diethyl-6-(3-(isoquinolin-6-yl)-1,2,4-oxadiazol-5-yl)chroman-4-one |
| 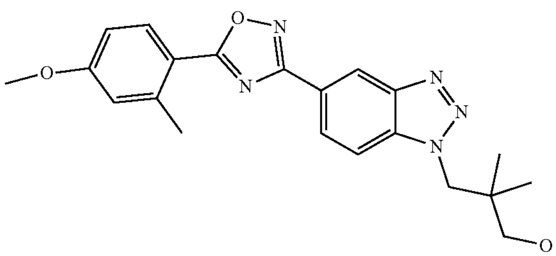 [SMILES: COc1ccc(-c2nc(-c3ccc4c(c3)nnn4CC(C)(C)CO)no2)c(C)c1] | 523 | 3-(5-(5-(4-methoxy-2-methylphenyl)-1,2,4-oxadiazol-3-yl)-1H-benzo[d][1,2,3]triazol-1-yl)-2,2-dimethylpropan-1-ol |
| 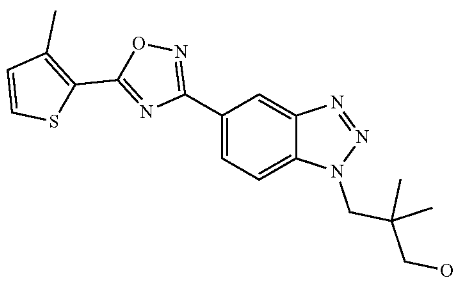 [SMILES: Cc1ccsc1-c1nc(-c2ccc3c(c2)nnn3CC(C)(C)CO)no1] | 524 | 2,2-dimethyl-3-(5-(5-(3-methylthiophen-2-yl)-1,2,4-oxadiazol-3-yl)-1H-benzo[d][1,2,3]triazol-1-yl)propan-1-ol |
| 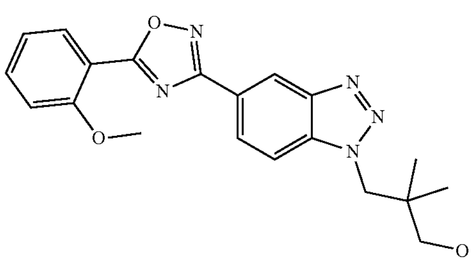 [SMILES: COc1ccccc1-c1nc(-c2ccc3c(c2)nnn3CC(C)(C)CO)no1] | 525 | 3-(5-(5-(2-methoxyphenyl)-1,2,4-oxadiazol-3-yl)-1H-benzo[d][1,2,3]triazol-1-yl)-2,2-dimethylpropan-1-ol |
| 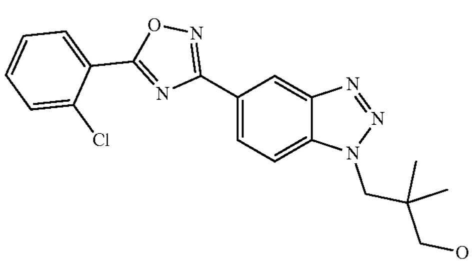 [SMILES: CC(C)(CO)Cn1nnc2cc(-c3noc(-c4ccccc4Cl)n3)ccc21] | 526 | 3-(5-(5-(2-chlorophenyl)-1,2,4-oxadiazol-3-yl)-1H-benzo[d][1,2,3]triazol-1-yl)-2,2-dimethylpropan-1-ol |
| 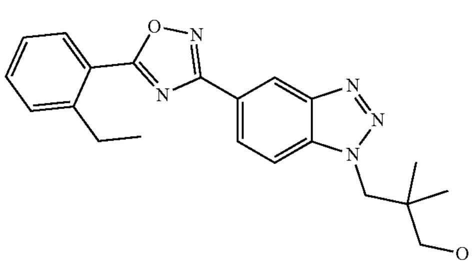 [SMILES: CCc1ccccc1-c1nc(-c2ccc3c(c2)nnn3CC(C)(C)CO)no1] | 527 | 3-(5-(5-(2-ethylphenyl)-1,2,4-oxadiazol-3-yl)-1H-benzo[d][1,2,3]triazol-1-yl)-2,2-dimethylpropan-1-ol |

-continued

| Structure | Compound Number | Chemical Name |
|---|---|---|
| 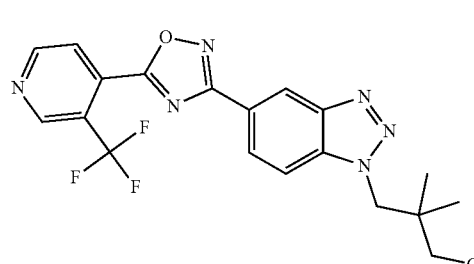 | 528 | 2,2-dimethyl-3-(5-(5-(3-(trifluoromethyl)pyridin-4-yl)-1,2,4-oxadiazol-3-yl)-1H-benzo[d][1,2,3]triazol-1-yl)propan-1-ol |
| 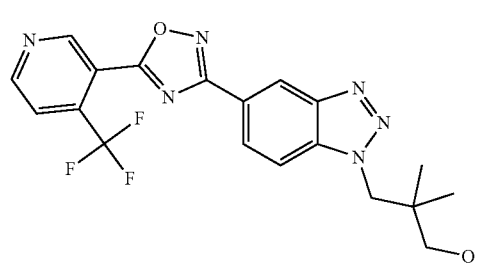 [SMILES: CC(C)(CO)Cn1nnc2cc(-c3noc(-c4cnccc4C(F)(F)F)n3)ccc21] | 529 | 2,2-dimethyl-3-(5-(5-(4-(trifluoromethyl)pyridin-3-yl)-1,2,4-oxadiazol-3-yl)-1H-benzo[d][1,2,3]triazol-1-yl)propan-1-ol |
| 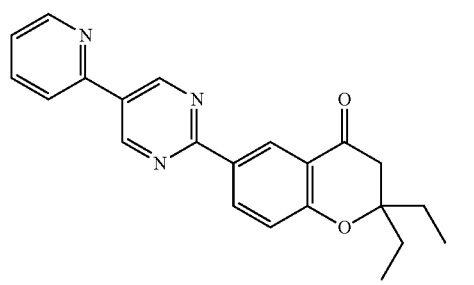 [SMILES: CCC1(CC)CC(=O)c2cc(-c3ncc(-c4ccccn4)cn3)ccc2O1] | 530 | 2,2-diethyl-6-(5-(pyridin-2-yl)pyrimidin-2-yl)chroman-4-one |
| 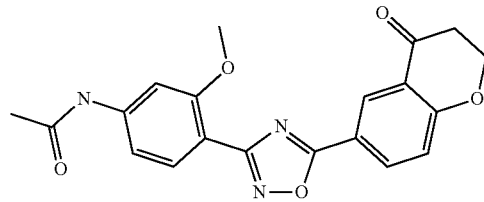 | 531 | N-{4-[5-(2,2-diethyl-4-oxo-3,4-dihydro-2H-1-benzopyran-6-yl)-1,2,4-oxadiazol-3-yl]-3-methoxyphenyl}acetamide |
| 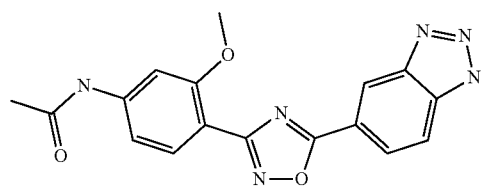 | 532 | N-(3-methoxy-4-{5-[1-(propan-2-yl)-1H-1,2,3-benzotriazol-5-yl]-1,2,4-oxadiazol-3-yl}phenyl)acetamide |
| 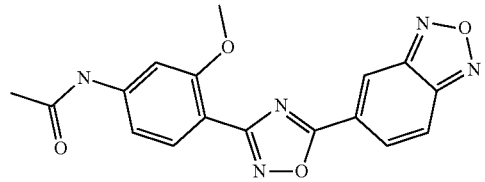 [SMILES: COc1cc(NC(C)=O)ccc1-c1noc(-c2ccc3nonc3c2)n1] | 533 | N-{4-[5-(2,1,3-benzoxadiazol-5-yl)-1,2,4-oxadiazol-3-yl]-3-methoxyphenyl}acetamide |

-continued

| Structure | Compound Number | Chemical Name |
|---|---|---|
| 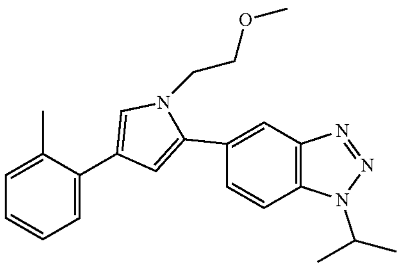 [SMILES: COCCn1cc(-c2ccccc2C)cc1-c1ccc2c(c1)nnn2C(C)C] | 534 | 5-[1-(2-methoxyethyl)-4-(2-methylphenyl)-1H-pyrrol-2-yl]-1-(propan-2-yl)-1H-1,2,3-benzotriazole |
| 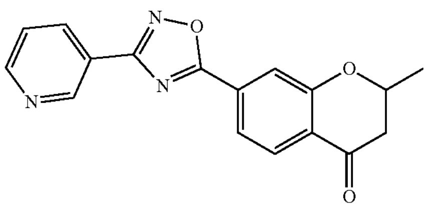 [SMILES: CC1CC(=O)c2ccc(-c3nc(-c4cccnc4)no3)cc2O1] | 535 | 2-methyl-7-[3-(pyridin-3-yl)-1,2,4-oxadiazol-5-yl]-3,4-dihydro-2H-1-benzopyran-4-one |
| 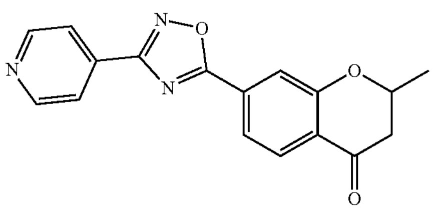 [SMILES: CC1CC(=O)c2ccc(-c3nc(-c4ccncc4)no3)cc2O1] | 536 | 2-methyl-7-[3-(pyridin-4-yl)-1,2,4-oxadiazol-5-yl]-3,4-dihydro-2H-1-benzopyran-4-one |
| 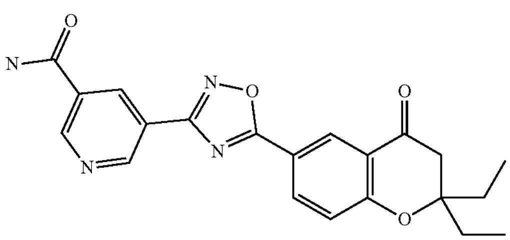 [SMILES: CCC1(CC)CC(=O)c2cc(-c3nc(-c4cncc(C(N)=O)c4)no3)ccc2O1] | 537 | 5-(5-(2,2-diethyl-4-oxochroman-6-yl)-1,2,4-oxadiazol-3-yl)nicotinamide |
| 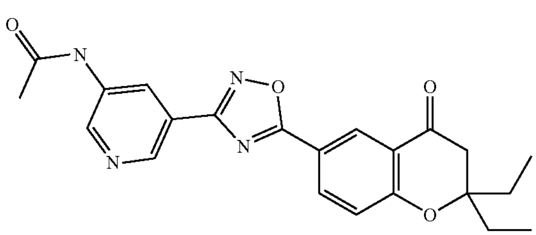 [SMILES: CCC1(CC)CC(=O)c2cc(-c3nc(-c4cncc(NC(C)=O)c4)no3)ccc2O1] | 538 | N-(5-(5-(2,2-diethyl-4-oxochroman-6-yl)-1,2,4-oxadiazol-3-yl)pyridin-3-yl)acetamide |
| 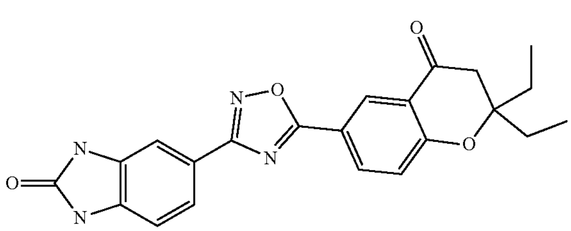 [SMILES: CCC1(CC)CC(=O)c2cc(-c3nc(-c4ccc5[nH]c(=O)[nH]c5c4)no3)ccc2O1] | 539 | 5-(5-(2,2-diethyl-4-oxochroman-6-yl)-1,2,4-oxadiazol-3-yl)-1H-benzo[d]imidazol-2(3H)-one |

-continued

| Structure | Compound Number | Chemical Name |
|---|---|---|
| 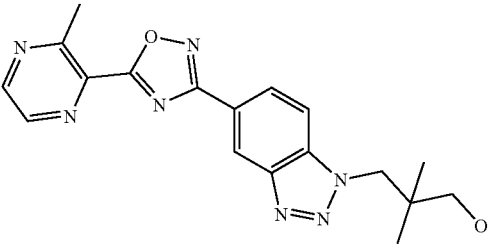 [SMILES: Cc1nccnc1-c1nc(-c2ccc3c(c2)nnn3CC(C)(C)CO)no1] | 540 | 2,2-dimethyl-3-(5-(5-(3-methylpyrazin-2-yl)-1,2,4-oxadiazol-3-yl)-1H-benzo[d][1,2,3]triazol-1-yl)propan-1-ol |
| 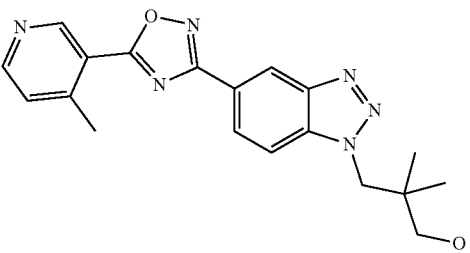 [SMILES: Cc1ccncc1-c1nc(-c2ccc3c(c2)nnn3CC(C)(C)CO)no1] | 541 | 2,2-dimethyl-3-(5-(5-(4-methylpyridin-3-yl)-1,2,4-oxadiazol-3-yl)-1H-benzo[d][1,2,3]triazol-1-yl)propan-1-ol |
| 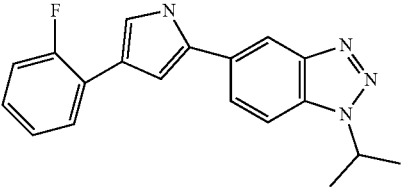 [SMILES: CC(C)n1nnc2cc(-c3cc(-c4ccccc4F)c[nH]3)ccc21] | 542 | 5-[4-(2-fluorophenyl)-1H-pyrrol-2-yl]-1-(propan-2-yl)-1H-1,2,3-benzotriazole |
| 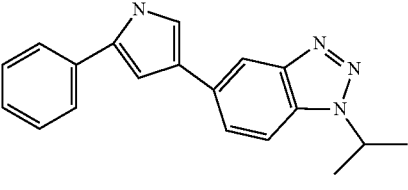 [SMILES: CC(C)n1nnc2cc(-c3c[nH]c(-c4ccccc4)c3)ccc21] | 543 | 5-(5-phenyl-1H-pyrrol-3-yl)-1-(propan-2-yl)-1H-1,2,3-benzotriazole |
| 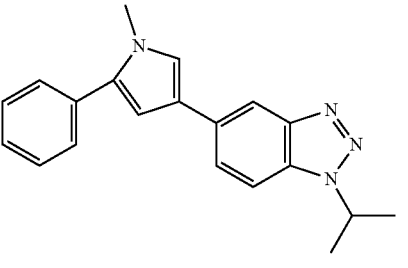 [SMILES: CC(C)n1nnc2cc(-c3cc(-c4ccccc4)n(C)c3)ccc21] | 544 | 5-(1-methyl-5-phenyl-1H-pyrrol-3-yl)-1-(propan-2-yl)-1H-1,2,3-benzotriazole |
| 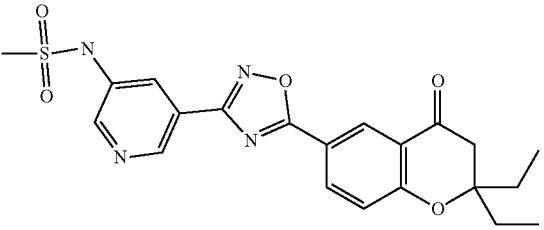 [SMILES: CCC1(CC)CC(=O)c2cc(-c3nc(-c4cncc(NS(C)(=O)=O)c4)no3)ccc2O1] | 545 | N-(5-(5-(2,2-diethyl-4-oxochroman-6-yl)-1,2,4-oxadiazol-3-yl)pyridin-3-yl)methanesulfonamide |

-continued

| Structure | Compound Number | Chemical Name |
|---|---|---|
| 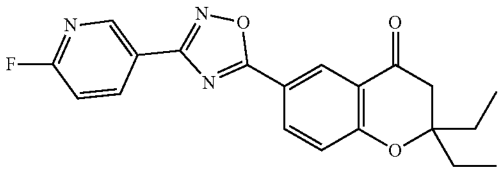 [SMILES: CCC1(CC)CC(=O)c2cc(-c3nc(-c4ccc(F)nc4)no3)ccc2O1] | 546 | 2,2-diethyl-6-(3-(6-fluoropyridin-3-yl)-1,2,4-oxadiazol-5-yl)chroman-4-one |
| 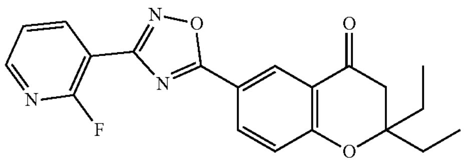 [SMILES: CCC1(CC)CC(=O)c2cc(-c3nc(-c4cccnc4F)no3)ccc2O1] | 547 | 2,2-diethyl-6-(3-(2-fluoropyridin-3-yl)-1,2,4-oxadiazol-5-yl)chroman-4-one |
| 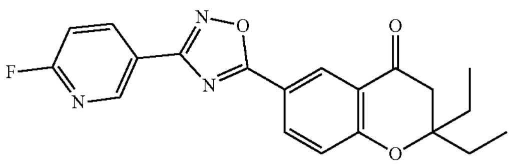 [SMILES: CCC1(CC)CC(=O)c2cc(-c3nc(-c4ccc(F)nc4)no3)ccc2O1] | 548 | 2,2-diethyl-6-(3-(6-(trifluoromethyl)pyridin-3-yl)-1,2,4-oxadiazol-5-yl)chroman-4-one |
| 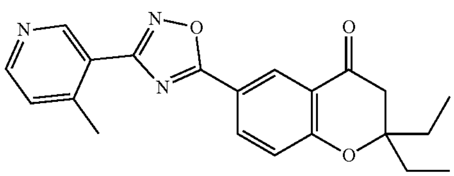 [SMILES: CCC1(CC)CC(=O)c2cc(-c3nc(-c4cnccc4C)no3)ccc2O1] | 549 | 2,2-diethyl-6-(3-(4-methylpyridin-3-yl)-1,2,4-oxadiazol-5-yl)chroman-4-one |
| 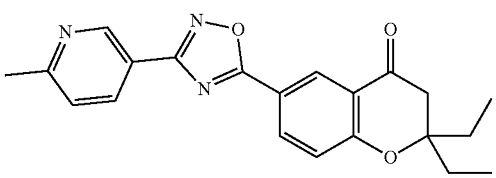 [SMILES: CCC1(CC)CC(=O)c2cc(-c3nc(-c4ccc(C)nc4)no3)ccc2O1] | 550 | 2,2-diethyl-6-(3-(6-methylpyridin-3-yl)-1,2,4-oxadiazol-5-yl)chroman-4-one |
| 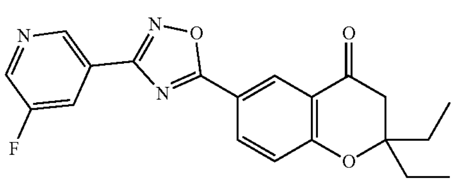 [SMILES: CCC1(CC)CC(=O)c2cc(-c3nc(-c4cncc(F)c4)no3)ccc2O1] | 551 | 2,2-diethyl-6-(3-(5-fluoropyridin-3-yl)-1,2,4-oxadiazol-5-yl)chroman-4-one |
| 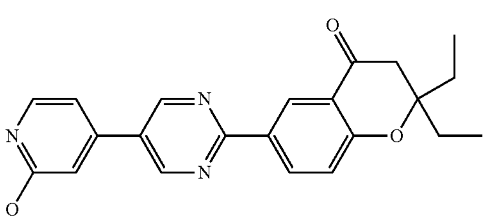 [SMILES: CCC1(CC)CC(=O)c2cc(-c3ncc(-c4ccnc(O)c4)cn3)ccc2O1] | 552 | 2,2-diethyl-6-(5-(2-hydroxypyridin-4-yl)pyrimidin-2-yl)chroman-4-one |
| 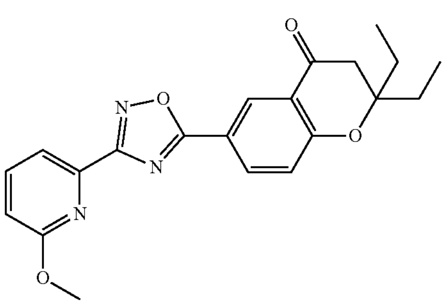 [SMILES: CCC1(CC)CC(=O)c2cc(-c3nc(-c4cccc(OC)n4)no3)ccc2O1] | 553 | 2,2-diethyl-6-[3-(6-methoxypyridin-2-yl)-1,2,4-oxadiazol-5-yl]-3,4-dihydro-2H-1-benzopyran-4-one |

| Structure | Compound Number | Chemical Name |
|---|---|---|
| 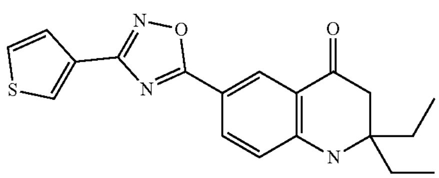 [SMILES: CCC1(CC)CC(=O)c2cc(-c3nc(-c4ccsc4)no3)ccc2N1] | 554 | 2,2-diethyl-6-(3-(thiophen-3-yl)-1,2,4-oxadiazol-5-yl)-2,3-dihydroquinolin-4(1H)-one |
| 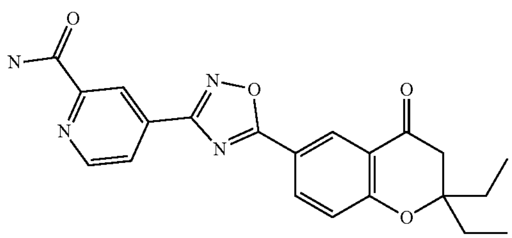 [SMILES: CCC1(CC)CC(=O)c2cc(-c3nc(-c4ccnc(C(N)=O)c4)no3)ccc2O1] | 555 | 4-(5-(2,2-diethyl-4-oxochroman-6-yl)-1,2,4-oxadiazol-3-yl)picolinamide |
| 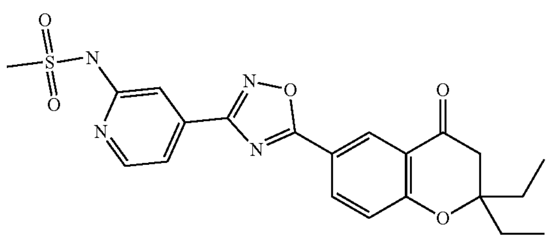 [SMILES: CCC1(CC)CC(=O)c2cc(-c3nc(-c4ccnc(NS(C)(=O)=O)c4)no3)ccc2O1] | 556 | N-(4-(5-(2,2-diethyl-4-oxochroman-6-yl)-1,2,4-oxadiazol-3-yl)pyridin-2-yl)methanesulfonamide |
| 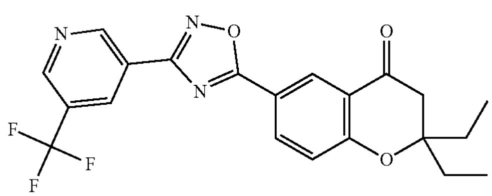 [SMILES: CCC1(CC)CC(=O)c2cc(-c3nc(-c4cncc(C(F)(F)F)c4)no3)ccc2O1] | 557 | 2,2-diethyl-6-(3-(5-(trifluoromethyl)pyridin-3-yl)-1,2,4-oxadiazol-5-yl)chroman-4-one |
| 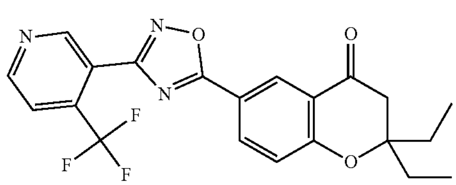 [SMILES: CCC1(CC)CC(=O)c2cc(-c3nc(-c4cnccc4C(F)(F)F)no3)ccc2O1] | 558 | 2,2-diethyl-6-(3-(4-(trifluoromethyl)pyridin-3-yl)-1,2,4-oxadiazol-5-yl)chroman-4-one |
| 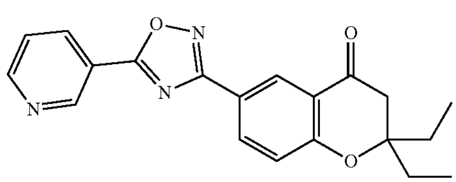 [SMILES: CCC1(CC)CC(=O)c2cc(-c3noc(-c4cccnc4)n3)ccc2O1] | 559 | 2,2-diethyl-6-(5-(pyridin-3-yl)-1,2,4-oxadiazol-3-yl)chroman-4-one |
| 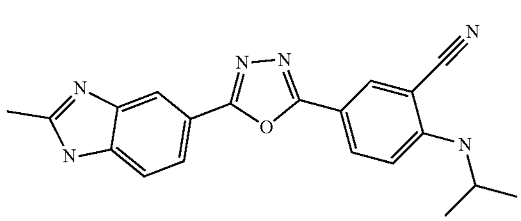 [SMILES: Cc1nc2cc(-c3nnc(-c4ccc(NC(C)C)c(C#N)c4)o3)ccc2[nH]1] | 560 | 5-[5-(2-methyl-1H-1,3-benzodiazol-5-yl)-1,3,4-oxadiazol-2-yl]-2-[(propan-2-yl)amino]benzonitrile |

-continued

| Structure | Compound Number | Chemical Name |
|---|---|---|
| 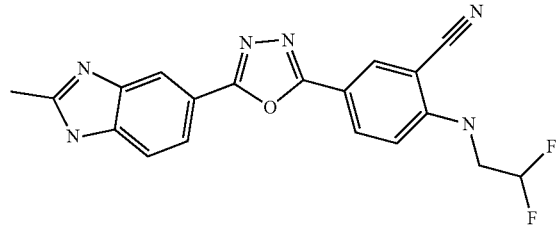 [SMILES: Cc1nc2cc(-c3nnc(-c4ccc(NCC(F)F)c(C#N)c4)o3)ccc2[nH]1] | 561 | 2-[(2,2-difluoroethyl)amino]-5-[5-(2-methyl-1H-1,3-benzodiazol-5-yl)-1,3,4-oxadiazol-2-yl]benzonitrile |
| 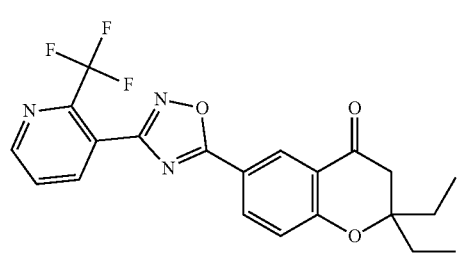 [SMILES: CCC1(CC)CC(=O)c2cc(-c3nc(-c4cccnc4C(F)(F)F)no3)ccc2O1] | 562 | 2,2-diethyl-6-(3-(2-(trifluoromethyl)pyridin-3-yl)-1,2,4-oxadiazol-5-yl)chroman-4-one |
| 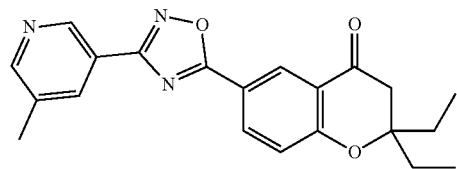 [SMILES: CCC1(CC)CC(=O)c2cc(-c3nc(-c4cncc(C)c4)no3)ccc2O1] | 563 | 2,2-diethyl-6-(3-(5-methylpyridin-3-yl)-1,2,4-oxadiazol-5-yl)chroman-4-one |
| 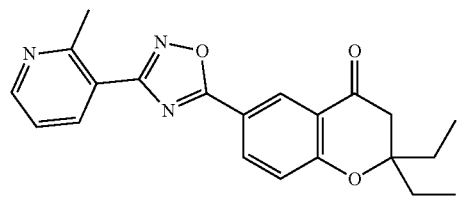 [SMILES: CCC1(CC)CC(=O)c2cc(-c3nc(-c4cccnc4C)no3)ccc2O1] | 564 | 2,2-diethyl-6-(3-(2-methylpyridin-3-yl)-1,2,4-oxadiazol-5-yl)chroman-4-one |
| 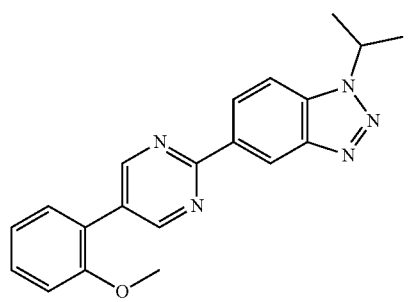 [SMILES: COc1ccccc1-c1cnc(-c2ccc3c(c2)nnn3C(C)C)nc1] | 565 | 1-isopropyl-5-(5-(2-methoxyphenyl)pyrimidin-2-yl)-1H-benzo[d][1,2,3]triazole |
| 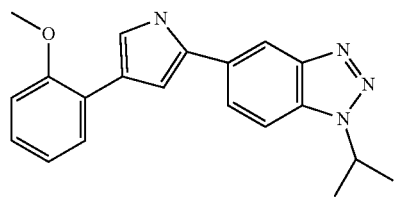 [SMILES: COc1ccccc1-c1c[nH]c(-c2ccc3c(c2)nnn3C(C)C)c1] | 566 | 5-[4-(2-methoxyphenyl)-1H-pyrrol-2-yl]-1-(propan-2-yl)-1H-1,2,3-benzotriazole |

-continued

| Structure | Compound Number | Chemical Name |
|---|---|---|
| 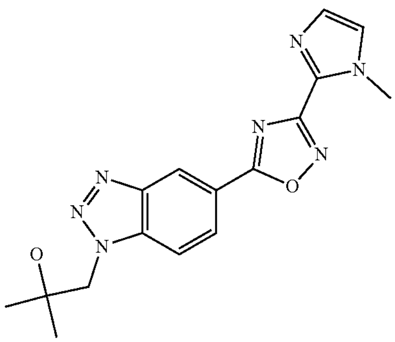 [SMILES: Cn1ccnc1-c1noc(-c2ccc3c(c2)nnn3CC(C)(C)O)n1] | 567 | 2-methyl-1-{5-[3-(1-methyl-1H-imidazol-2-yl)-1,2,4-oxadiazol-5-yl]-1H-1,2,3-benzotriazol-1-yl}propan-2-ol |
| 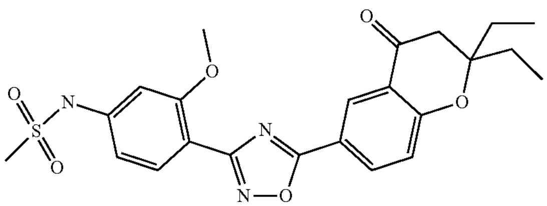 [SMILES: CCC1(CC)CC(=O)c2cc(-c3nc(-c4ccc(NS(C)(=O)=O)cc4OC)no3)ccc2O1] | 568 | N-{4-[5-(2,2-diethyl-4-oxo-3,4-dihydro-2H-1-benzopyran-6-yl)-1,2,4-oxadiazol-3-yl]-3-methoxyphenyl}methanesulfonamide |
| 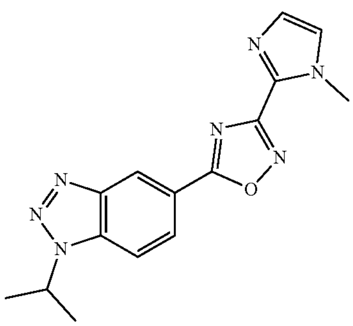 [SMILES: CC(C)n1nnc2cc(-c3nc(-c4nccn4C)no3)ccc21] | 569 | 5-[3-(1-methyl-1H-imidazol-2-yl)-1,2,4-oxadiazol-5-yl]-1-(propan-2-yl)-1H-1,2,3-benzotriazole |
| 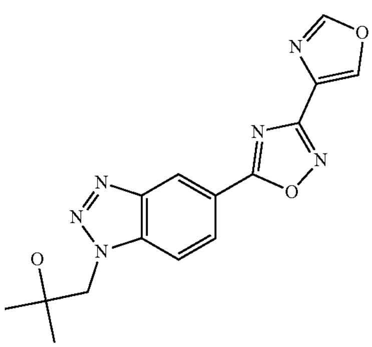 [SMILES: CC(C)(O)Cn1nnc2cc(-c3nc(-c4cocn4)no3)ccc21] | 570 | 2-methyl-1-{5-[3-(1,3-oxazol-4-yl)-1,2,4-oxadiazol-5-yl]-1H-1,2,3-benzotriazol-1-yl}propan-2-ol |
| 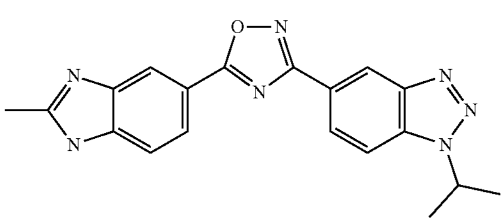 [SMILES: Cc1nc2cc(-c3nc(-c4ccc5c(c4)nnn5C(C)C)no3)ccc2[nH]1] | 571 | 5-[5-(2-methyl-1H-1,3-benzodiazol-5-yl)-1,2,4-oxadiazol-3-yl]-1-(propan-2-yl)-1H-1,2,3-benzotriazole |

-continued

| Structure | Compound Number | Chemical Name |
|---|---|---|
| 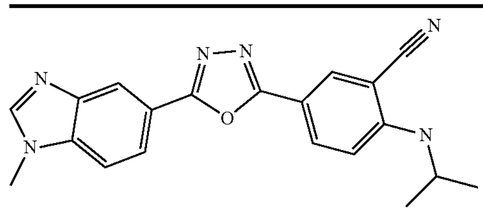 | 572 | 5-[5-(1-methyl-1H-1,3-benzodiazol-5-yl)-1,3,4-oxadiazol-2-yl]-2-[(propan-2-yl)amino]benzonitrile |
| 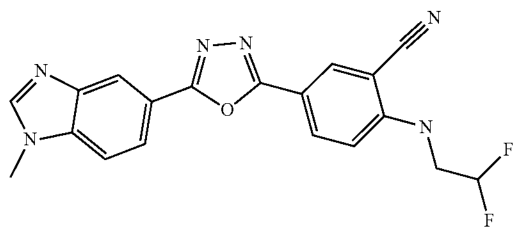 [SMILES: Cn1cnc2cc(-c3nnc(-c4ccc(NCC(F)F)c(C#N)c4)o3)ccc21] | 573 | 2-[(2,2-difluoroethyl)amino]-5-[5-(1-methyl-1H-1,3-benzodiazol-5-yl)-1,3,4-oxadiazol-2-yl]benzonitrile |
| 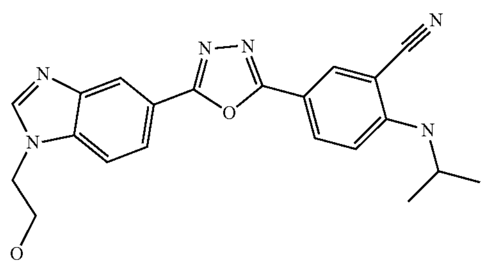 [SMILES: CC(C)Nc1ccc(-c2nnc(-c3ccc4c(c3)ncn4CCO)o2)cc1C#N] | 574 | 5-{5-[1-(2-hydroxyethyl)-1H-1,3-benzodiazol-5-yl]-1,3,4-oxadiazol-2-yl}-2-[(propan-2-yl)amino]benzonitrile |
| 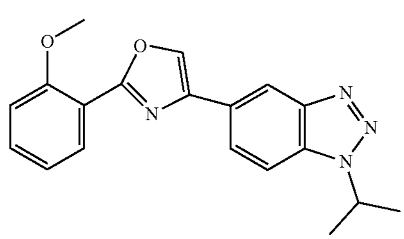 [SMILES: COc1ccccc1-c1nc(-c2ccc3c(c2)nnn3C(C)C)co1] | 575 | 5-[2-(2-methoxyphenyl)-1,3-oxazol-4-yl]-1-(propan-2-yl)-1H-1,2,3-benzotriazole |
| 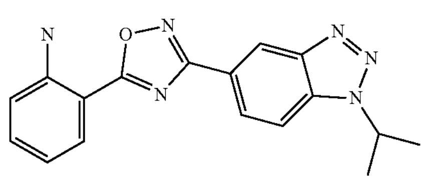 [SMILES: CC(C)n1nnc2cc(-c3noc(-c4ccccc4N)n3)ccc21] | 576 | 2-{3-[1-(propan-2-yl)-1H-1,2,3-benzotriazol-5-yl]-1,2,4-oxadiazol-5-yl}aniline |
| 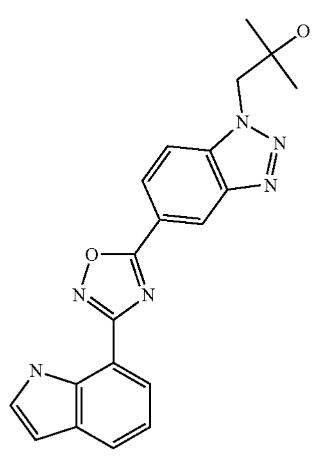 [SMILES: CC(C)(O)Cn1nnc2cc(-c3nc(-c4cccc5cc[nH]c45)no3)ccc21] | 577 | 1-{5-[3-(1H-indol-7-yl)-1,2,4-oxadiazol-5-yl]-1H-1,2,3-benzotriazol-1-yl}-2-methylpropan-2-ol |

| Structure | Compound Number | Chemical Name |
|---|---|---|
| 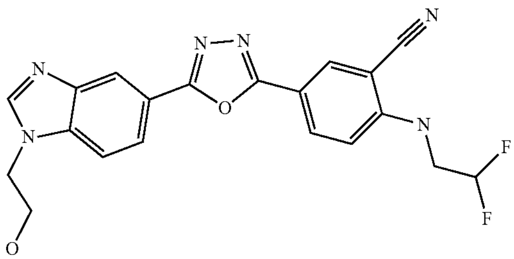 [SMILES: N#Cc1cc(-c2nnc(-c3ccc4c(c3)ncn4CCO)o2)ccc1NCC(F)F] | 578 | 2-[(2,2-difluoroethyl)amino]-5-{5-[1-(2-hydroxyethyl)-1H-1,3-benzodiazol-5-yl]-1,3,4-oxadiazol-2-yl}benzonitrile |
| 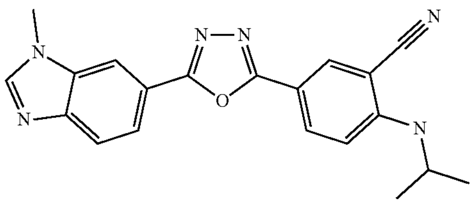 [SMILES: CC(C)Nc1ccc(-c2nnc(-c3ccc4ncn(C)c4c3)o2)cc1C#N] | 579 | 5-[5-(1-methyl-1H-1,3-benzodiazol-6-yl)-1,3,4-oxadiazol-2-yl]-2-[(propan-2-yl)amino]benzonitrile |
| 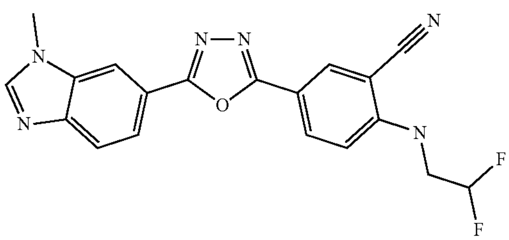 [SMILES: Cn1cnc2ccc(-c3nnc(-c4ccc(NCC(F)F)c(C#N)c4)o3)cc21] | 580 | 2-[(2,2-difluoroethyl)amino]-5-[5-(1-methyl-1H-1,3-benzodiazol-6-yl)-1,3,4-oxadiazol-2-yl]benzonitrile |
| 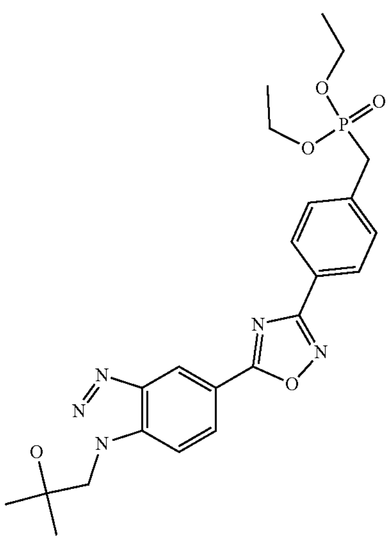 [SMILES: CCOP(=O)(Cc1ccc(-c2noc(-c3ccc(NCC(C)(C)O)c(N=N)c3)n2)cc1)OCC] | 581 | [(4-{5-[1-(2-hydroxy-2-methylpropyl)-1H-1,2,3-benzotriazol-5-yl]-1,2,4-oxadiazol-3-yl}phenyl)methyl]phosphonate |
| 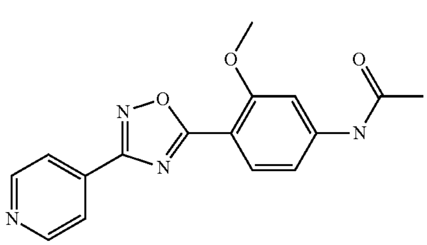 [SMILES: COc1cc(NC(C)=O)ccc1-c1nc(-c2ccncc2)no1] | 582 | N-{3-methoxy-4-[3-(pyridin-4-yl)-1,2,4-oxadiazol-5-yl]phenyl}acetamide |

-continued

| Structure | Compound Number | Chemical Name |
|---|---|---|
| 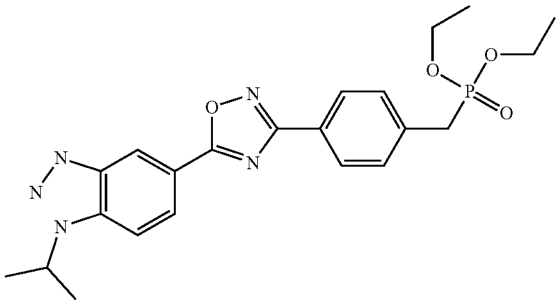 [SMILES: CCOP(=O)(Cc1ccc(-c2noc(-c3ccc(NC(C)C)c(NN)c3)n2)cc1)OCC] | 583 | diethyl [(4-{5-[1-(propan-2-yl)-1H-1,2,3-benzotriazol-5-yl]-1,2,4-oxadiazol-3-yl}phenyl)methyl]phosphonate |
| 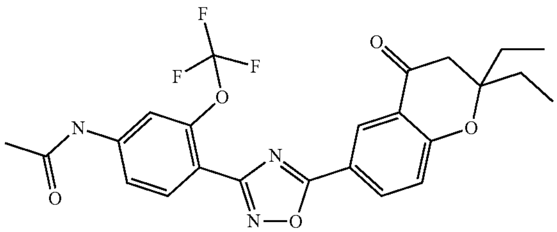 [SMILES: CCC1(CC)CC(=O)c2cc(-c3nc(-c4ccc(NC(C)=O)cc4OC(F)(F)F)no3)ccc2O1] | 584 | N-{4-[5-(2,2-diethyl-4-oxo-3,4-dihydro-2H-1-benzopyran-6-yl)-1,2,4-oxadiazol-3-yl]-3-(trifluoromethoxy)phenyl}acetamide |
| 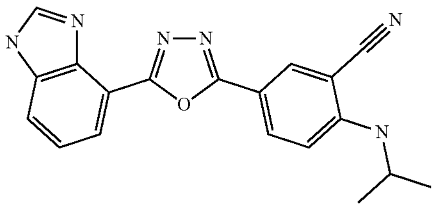 [SMILES: CC(C)Nc1ccc(-c2nnc(-c3cccc4[nH]cnc34)o2)cc1C#N] | 585 | 5-[5-(1H-1,3-benzodiazol-4-yl)-1,3,4-oxadiazol-2-yl]-2-[(propan-2-yl)amino]benzonitrile |
| 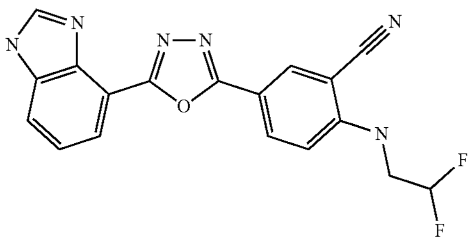 [SMILES: N#Cc1cc(-c2nnc(-c3cccc4[nH]cnc34)o2)ccc1NCC(F)F] | 586 | 5-[5-(1H-1,3-benzodiazol-4-yl)-1,3,4-oxadiazol-2-yl]-2-[(2,2-difluoroethyl)amino]benzonitrile |
| 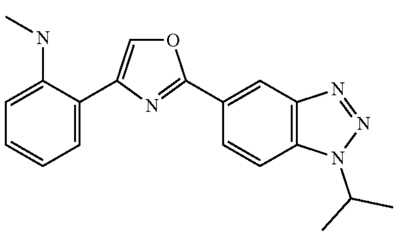 [SMILES: CNc1ccccc1-c1coc(-c2ccc3c(c2)nnn3C(C)C)n1] | 587 | N-methyl-2-{2-[1-(propan-2-yl)-1H-1,2,3-benzotriazol-5-yl]-1,3-oxazol-4-yl}aniline |
| 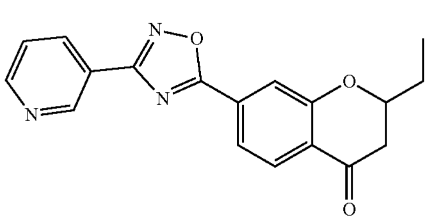 [SMILES: CCC1CC(=O)c2ccc(-c3nc(-c4cccnc4)no3)cc2O1] | 588 | 2-ethyl-7-[3-(pyridin-3-yl)-1,2,4-oxadiazol-5-yl]-3,4-dihydro-2H-1-benzopyran-4-one |

-continued

| Structure | Compound Number | Chemical Name |
|---|---|---|
| 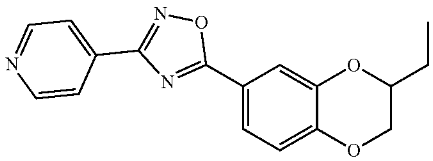 [SMILES: CCC1COc2ccc(-c3nc(-c4ccncc4)no3)cc2O1] | 589 | 2-ethyl-7-[3-(pyridin-4-yl)-1,2,4-oxadiazol-5-yl]-3,4-dihydro-2H-1-benzopyran-4-one |
| 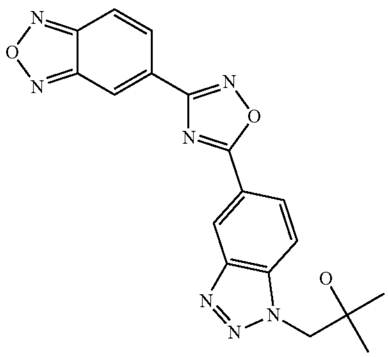 [SMILES: CC(C)(O)Cn1nnc2cc(-c3nc(-c4ccc5nonc5c4)no3)ccc21] | 590 | 1-{5-[3-(2,1,3-benzoxadiazol-5-yl)-1,2,4-oxadiazol-5-yl]-1H-1,2,3-benzotriazol-1-yl}-2-methylpropan-2-ol |
| 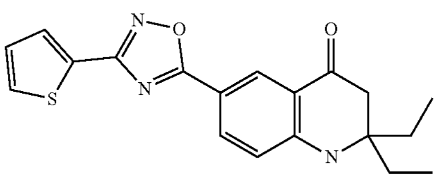 | 591 | 2,2-diethyl-6-(3-(thiophen-2-yl)-1,2,4-oxadiazol-5-yl)-2,3-dihydroquinolin-4(1H)-one |
| 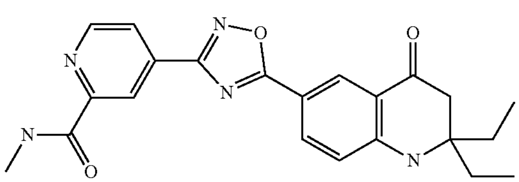 [SMILES: CCC1(CC)CC(=O)c2cc(-c3nc(-c4ccnc(C(=O)NC)c4)no3)ccc2N1] | 592 | 4-(5-(2,2-diethyl-4-oxochroman-6-yl)-1,2,4-oxadiazol-3-yl)-N-methylpicolinamide |
| 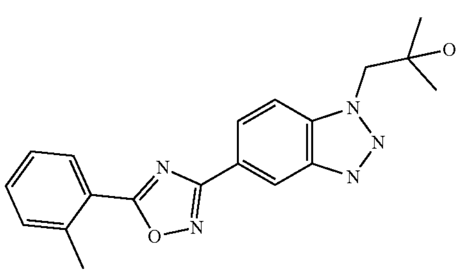 [SMILES: Cc1ccccc1-c1nc(-c2ccc3c(c2)NNN3CC(C)(C)O)no1] | 593 | 2-methyl-1-(5-(5-(o-tolyl)-1,2,4-oxadiazol-3-yl)-1H-benzo[d][1,2,3]triazol-1-yl)propan-2-ol |
| 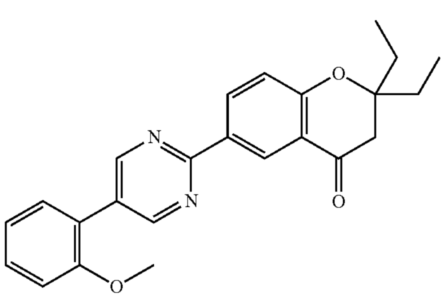 [SMILES: CCC1(CC)CC(=O)c2cc(-c3ncc(-c4ccccc4OC)cn3)ccc2O1] | 594 | 2,2-diethyl-6-(5-(2-methoxyphenyl)pyrimidin-2-yl)chroman-4-one |

-continued

| Structure | Compound Number | Chemical Name |
|---|---|---|
| 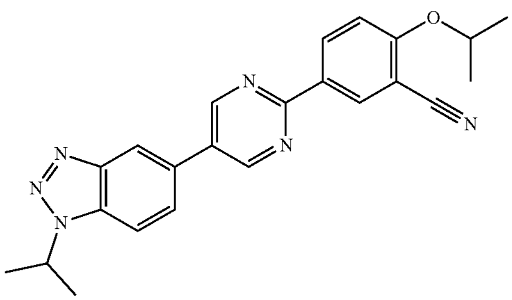 [SMILES: CC(C)Oc1ccc(-c2ncc(-c3ccc4c(c3)nnn4C(C)C)cn2)cc1C#N] | 595 | 2-isopropoxy-5-(5-(1-isopropyl-1H-benzo[d][1,2,3]triazol-5-yl)pyrimidin-2-yl)benzonitrile |
| 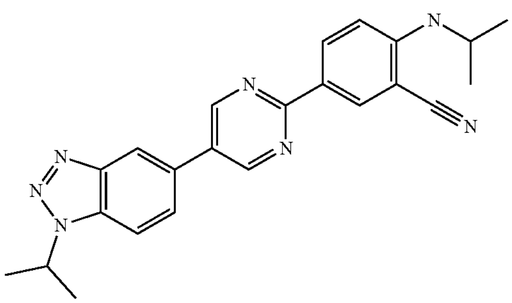 [SMILES: CC(C)Nc1ccc(-c2ncc(-c3ccc4c(c3)nnn4C(C)C)cn2)cc1C#N] | 596 | 5-(5-(1-isopropyl-1H-benzo[d][1,2,3]triazol-5-yl)pyrimidin-2-yl)-2-(isopropylamino)benzonitrile |
| 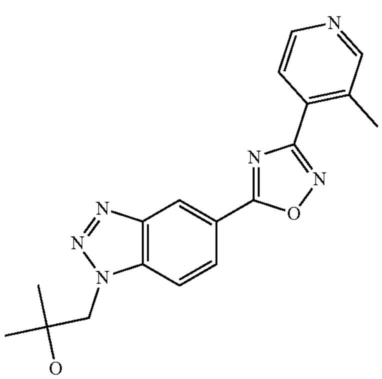 [SMILES: Cc1cnccc1-c1noc(-c2ccc3c(c2)nnn3CC(C)(C)O)n1] | 597 | 2-methyl-1-{5-[3-(3-methylpyridin-4-yl)-1,2,4-oxadiazol-5-yl]-1H-1,2,3-benzotriazol-1-yl}propan-2-ol |
| 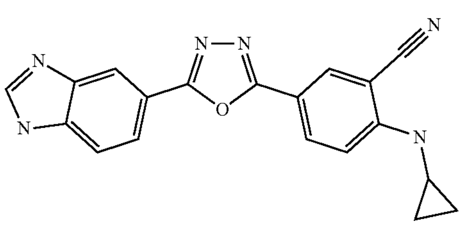 [SMILES: N#Cc1cc(-c2nnc(-c3ccc4[nH]cnc4c3)o2)ccc1NC1CC1] | 598 | 5-[5-(1H-1,3-benzodiazol-5-yl)-1,3,4-oxadiazol-2-yl]-2-(cyclopropylamino)benzonitrile |
| 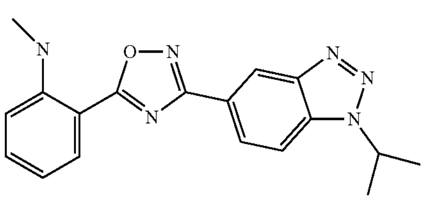 [SMILES: CNc1ccccc1-c1nc(-c2ccc3c(c2)nnn3C(C)C)no1] | 599 | N-methyl-2-{3-[1-(propan-2-yl)-1H-1,2,3-benzotriazol-5-yl]-1,2,4-oxadiazol-5-yl}aniline |

-continued

| Structure | Compound Number | Chemical Name |
|---|---|---|
| 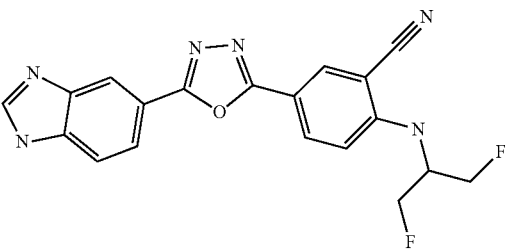 [SMILES: N#Cc1cc(-c2nnc(-c3ccc4[nH]cnc4c3)o2)ccc1NC(CF)CF] | 600 | 5-[5-(1H-1,3-benzodiazol-5-yl)-1,3,4-oxadiazol-2-yl]-2-[(1,3-difluoropropan-2-yl)amino]benzonitrile |
| 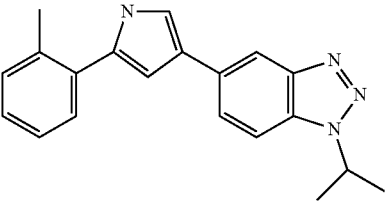 [SMILES: Cc1ccccc1-c1cc(-c2ccc3c(c2)nnn3C(C)C)c[nH]1] | 601 | 5-[5-(2-methylphenyl)-1H-pyrrol-3-yl]-1-(propan-2-yl)-1H-1,2,3-benzotriazole |
| 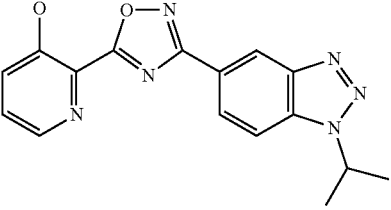 [SMILES: CC(C)n1nnc2cc(-c3noc(-c4ncccc4O)n3)ccc21] | 602 | 2-{3-[1-(propan-2-yl)-1H-1,2,3-benzotriazol-5-yl]-1,2,4-oxadiazol-5-yl}pyridin-3-ol |
| 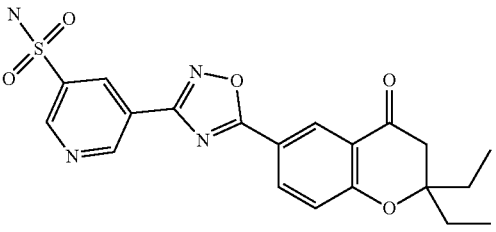 [SMILES: CCC1(CC)CC(=O)c2cc(-c3nc(-c4cncc(S(N)(=O)=O)c4)no3)ccc2O1] | 603 | 5-(5-(2,2-diethyl-4-oxochroman-6-yl)-1,2,4-oxadiazol-3-yl)pyridine-3-sulfonamide |
| 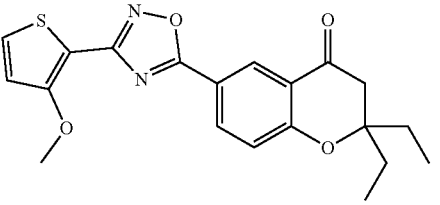 [SMILES: CCC1(CC)CC(=O)c2cc(-c3nc(-c4sccc4OC)no3)ccc2O1] | 604 | 2,2-diethyl-6-(3-(3-methoxythiophen-2-yl)-1,2,4-oxadiazol-5-yl)chroman-4-one |
| 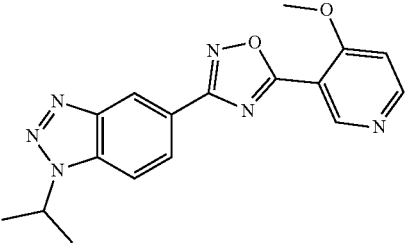 [SMILES: COc1ccncc1-c1nc(-c2ccc3c(c2)nnn3C(C)C)no1] | 605 | 3-(1-isopropyl-1H-benzo[d][1,2,3]triazol-5-yl)-5-(4-methoxypyridin-3-yl)-1,2,4-oxadiazole |

-continued

| Structure | Compound Number | Chemical Name |
|---|---|---|
| 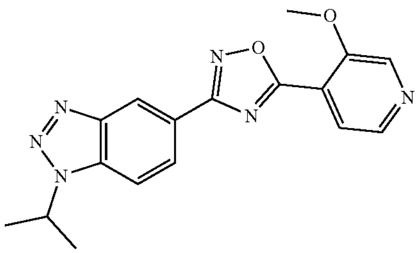 [SMILES: COc1cnccc1-c1nc(-c2ccc3c(c2)nnn3C(C)C)no1] | 606 | 3-(1-isopropyl-1H-benzo[d][1,2,3]triazol-5-yl)-5-(3-methoxypyridin-4-yl)-1,2,4-oxadiazole |
| 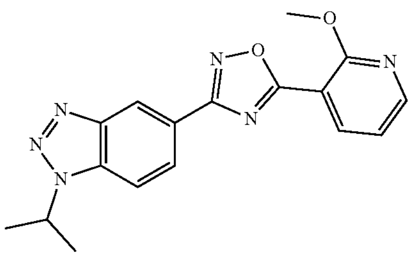 [SMILES: COc1ncccc1-c1nc(-c2ccc3c(c2)nnn3C(C)C)no1] | 607 | 3-(1-isopropyl-1H-benzo[d][1,2,3]triazol-5-yl)-5-(2-methoxypyridin-3-yl)-1,2,4-oxadiazole |
| 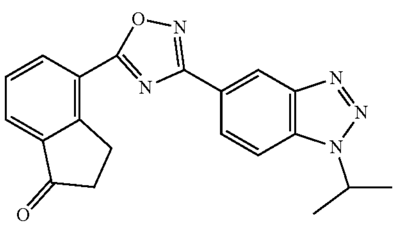 [SMILES: CC(C)n1nnc2cc(-c3noc(-c4cccc5c4CCC5=O)n3)ccc21] | 608 | 4-{3-[1-(propan-2-yl)-1H-1,2,3-benzotriazol-5-yl]-1,2,4-oxadiazol-5-yl}-2,3-dihydro-1H-inden-1-one |
| 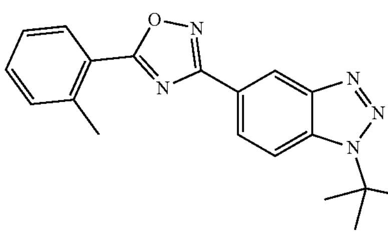 | 609 | 2-methyl-2-(5-(5-(o-tolyl)-1,2,4-oxadiazol-3-yl)-1H-benzo[d][1,2,3]triazol-1-yl)propan-1-ol |
| 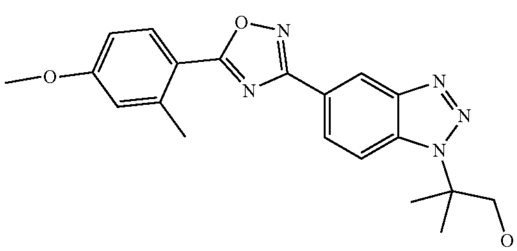 [SMILES: COc1ccc(-c2nc(-c3ccc4c(c3)nnn4C(C)(C)CO)no2)c(C)c1] | 610 | 2-(5-(5-(4-methoxy-2-methylphenyl)-1,2,4-oxadiazol-3-yl)-1H-benzo[d][1,2,3]triazol-1-yl)-2-methylpropan-1-ol |
| 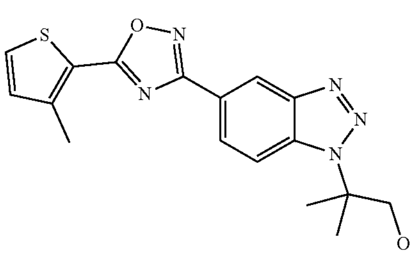 [SMILES: Cc1ccsc1-c1nc(-c2ccc3c(c2)nnn3C(C)(C)CO)no1] | 611 | 2-methyl-2-(5-(5-(3-methylthiophen-2-yl)-1,2,4-oxadiazol-3-yl)-1H-benzo[d][1,2,3]triazol-1-yl)propan-1-ol |

-continued

| Structure | Compound Number | Chemical Name |
|---|---|---|
| 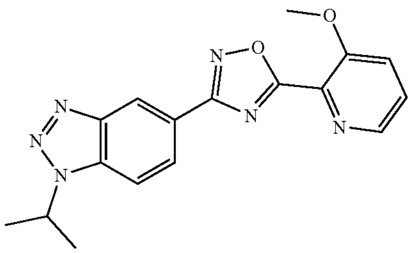 [SMILES: COc1cccnc1-c1nc(-c2ccc3c(c2)nnn3C(C)C)no1] | 612 | 3-(1-isopropyl-1H-benzo[d][1,2,3]triazol-5-yl)-5-(3-methoxypyridin-2-yl)-1,2,4-oxadiazole |
| 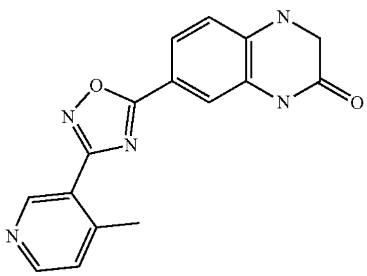 [SMILES: Cc1ccncc1-c1noc(-c2ccc3c(c2)NC(=O)CN3)n1] | 613 | 7-[3-(4-methylpyridin-3-yl)-1,2,4-oxadiazol-5-yl]-1,2,3,4-tetrahydroquinoxalin-2-one |
| 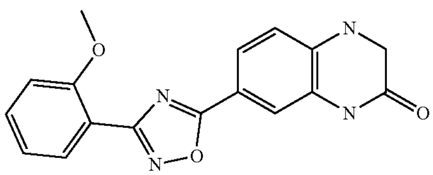 [SMILES: COc1ccccc1-c1noc(-c2ccc3c(c2)NC(=O)CN3)n1] | 614 | 7-[3-(2-methoxyphenyl)-1,2,4-oxadiazol-5-yl]-1,2,3,4-tetrahydroquinoxalin-2-one |
| 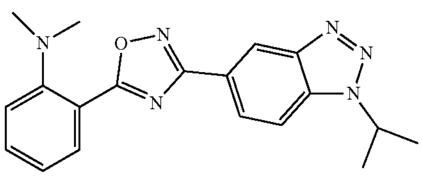 [SMILES: CC(C)n1nnc2cc(-c3noc(-c4ccccc4N(C)C)n3)ccc21] | 615 | N,N-dimethyl-2-{3-[1-(propan-2-yl)-1H-1,2,3-benzotriazol-5-yl]-1,2,4-oxadiazol-5-yl}aniline |
| 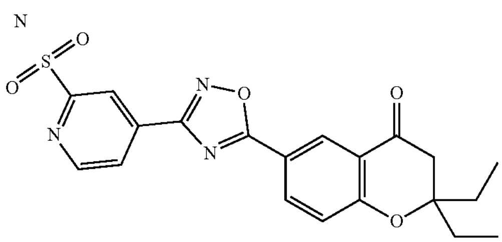 | 616 | 4-(5-(2,2-diethyl-4-oxochroman-6-yl)-1,2,4-oxadiazol-3-yl)pyridine-2-sulfonamide |
| 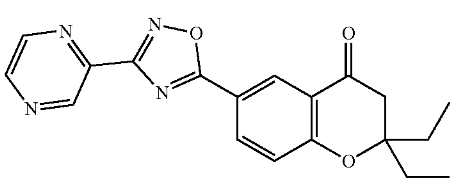 [SMILES: CCC1(CC)CC(=O)c2cc(-c3nc(-c4cnccn4)no3)ccc2O1] | 617 | 2,2-diethyl-6-(3-(pyrazin-2-yl)-1,2,4-oxadiazol-5-yl)chroman-4-one |
| 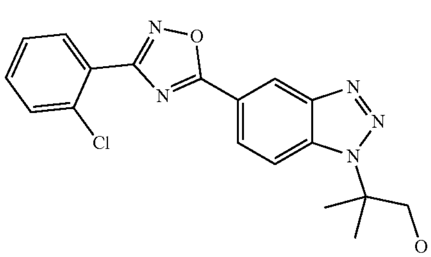 [SMILES: CC(C)(CO)n1nnc2cc(-c3nc(-c4ccccc4Cl)no3)ccc21] | 618 | 2-(5-(5-(2-chlorophenyl)-1,2,4-oxadiazol-3-yl)-1H-benzo[d][1,2,3]triazol-1-yl)-2-methylpropan-1-ol |

-continued

| Structure | Compound Number | Chemical Name |
|---|---|---|
| 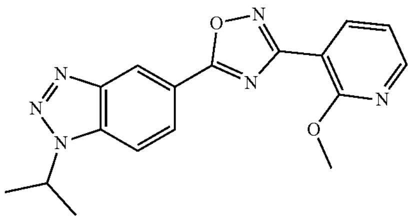 [SMILES: COc1ncccc1-c1noc(-c2ccc3c(c2)nnn3C(C)C)n1] | 619 | 5-(1-isopropyl-1H-benzo[d][1,2,3]triazol-5-yl)-3-(2-methoxypyridin-3-yl)-1,2,4-oxadiazole |
| 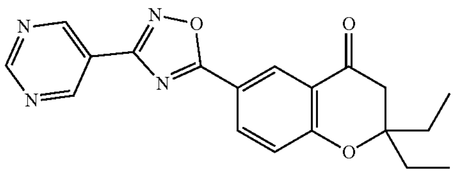 [SMILES: CCC1(CC)CC(=O)c2cc(-c3nc(-c4cncnc4)no3)ccc2O1] | 620 | 2,2-diethyl-6-(3-(pyrimidin-5-yl)-1,2,4-oxadiazol-5-yl)chroman-4-one |
| 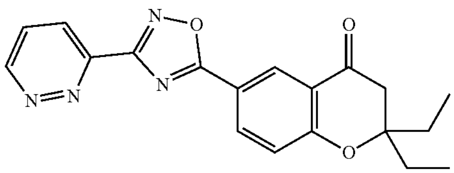 [SMILES: CCC1(CC)CC(=O)c2cc(-c3nc(-c4cccnn4)no3)ccc2O1] | 621 | 2,2-diethyl-6-(3-(pyridazin-3-yl)-1,2,4-oxadiazol-5-yl)chroman-4-one |
| 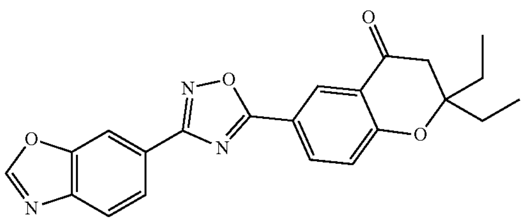 [SMILES: CCC1(CC)CC(=O)c2cc(-c3nc(-c4ccc5ncoc5c4)no3)ccc2O1] | 622 | 6-(3-(benzo[d]oxazol-6-yl)-1,2,4-oxadiazol-5-yl)-2,2-diethylchroman-4-one |
| 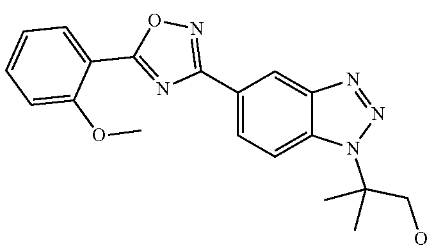 [SMILES: COc1ccccc1-c1nc(-c2ccc3c(c2)nnn3C(C)(C)CO)no1] | 623 | 2-(5-(5-(2-methoxyphenyl)-1,2,4-oxadiazol-3-yl)-1H-benzo[d][1,2,3]triazol-1-yl)-2-methylpropan-1-ol |
| 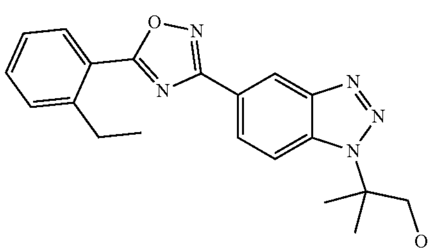 | 624 | 2-(5-(5-(2-ethylphenyl)-1,2,4-oxadiazol-3-yl)-1H-benzo[d][1,2,3]triazol-1-yl)-2-methylpropan-1-ol |
| 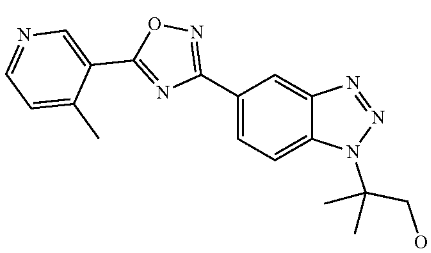 [SMILES: Cc1ccncc1-c1nc(-c2ccc3c(c2)nnn3C(C)(C)CO)no1] | 625 | 2-methyl-2-(5-(5-(4-methylpyridin-3-yl)-1,2,4-oxadiazol-3-yl)-1H-benzo[d][1,2,3]triazol-1-yl)propan-1-ol |

| Structure | Compound Number | Chemical Name |
|---|---|---|
| 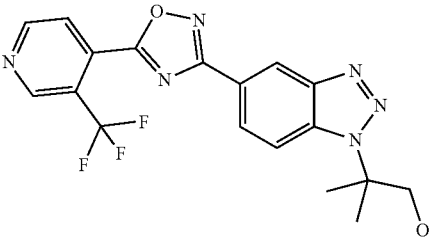 [SMILES: CC(C)(CO)n1nnc2cc(-c3noc(-c4ccncc4C(F)(F)F)n3)ccc21] | 626 | 2-methyl-2-(5-(5-(3-(trifluoromethyl)pyridin-4-yl)-1,2,4-oxadiazol-3-yl)-1H-benzo[d][1,2,3]triazol-1-yl)propan-1-ol |
| 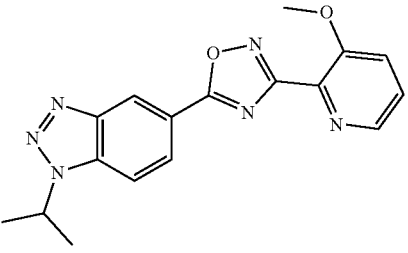 | 627 | 5-(1-isopropyl-1H-benzo[d][1,2,3]triazol-5-yl)-3-(3-methoxypyridin-2-yl)-1,2,4-oxadiazole |
| 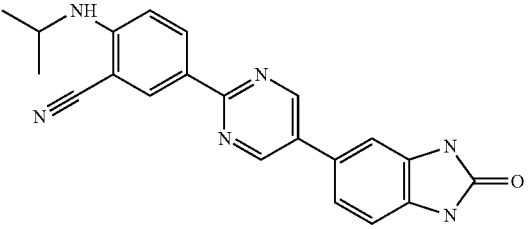 [SMILES: CC(C)Nc1ccc(-c2ncc(-c3ccc4[nH]c(=O)[nH]c4c3)cn2)cc1C#N] | 628 | 2-(isopropylamino)-5-(5-(2-oxo-2,3-dihydro-1H-benzo[d]imidazol-5-yl)pyrimidin-2-yl)benzonitrile |
| 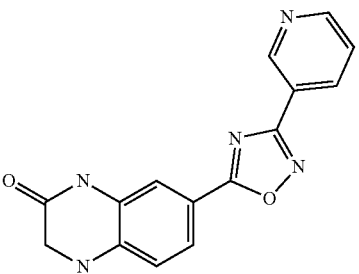 [SMILES: O=C1CNc2ccc(-c3nc(-c4cccnc4)no3)cc2N1] | 629 | 7-[3-(pyridin-3-yl)-1,2,4-oxadiazol-5-yl]-1,2,3,4-tetrahydroquinoxalin-2-one |
| 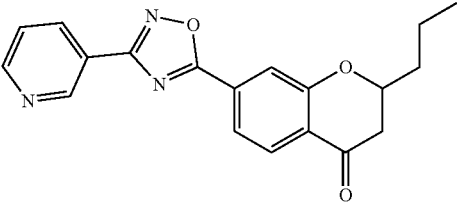 [SMILES: CCCC1CC(=O)c2ccc(-c3nc(-c4cccnc4)no3)cc2O1] | 630 | 2-propyl-7-[3-(pyridin-3-yl)-1,2,4-oxadiazol-5-yl]-3,4-dihydro-2H-1-benzopyran-4-one |
| 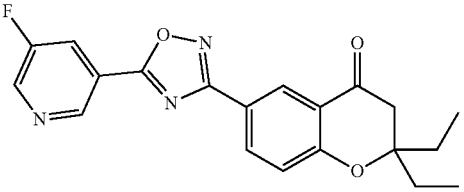 | 631 | 2,2-diethyl-6-[5-(5-fluoropyridin-3-yl)-1,2,4-oxadiazol-3-yl]-3,4-dihydro-2H-1-benzopyran-4-one |

-continued

| Structure | Compound Number | Chemical Name |
|---|---|---|
| 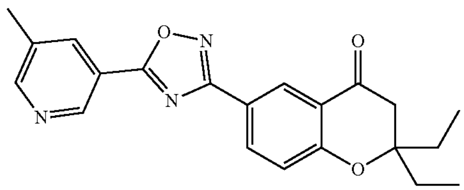 [SMILES: CCC1(CC)CC(=O)c2cc(-c3noc(-c4cncc(C)c4)n3)ccc2O1] | 632 | 2,2-diethyl-6-[5-(5-methylpyridin-3-yl)-1,2,4-oxadiazol-3-yl]-3,4-dihydro-2H-1-benzopyran-4-one |
| 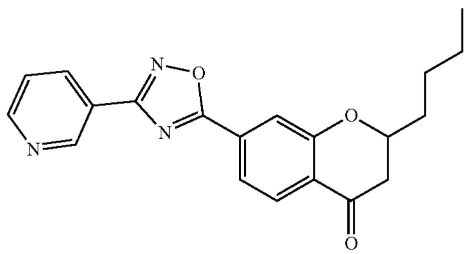 [SMILES: CCCCC1CC(=O)c2ccc(-c3nc(-c4cccnc4)no3)cc2O1] | 633 | 2-butyl-7-[3-(pyridin-3-yl)-1,2,4-oxadiazol-5-yl]-3,4-dihydro-2H-1-benzopyran-4-one |
| 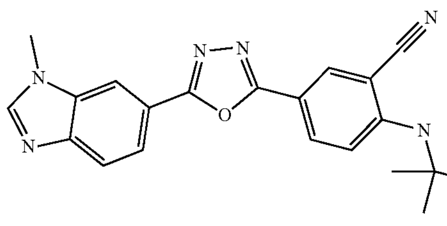 | 634 | 2-[(1-hydroxy-2-methylpropan-2-yl)amino]-5-[5-(1-methyl-1H-1,3-benzodiazol-6-yl)-1,3,4-oxadiazol-2-yl]benzonitrile |
| 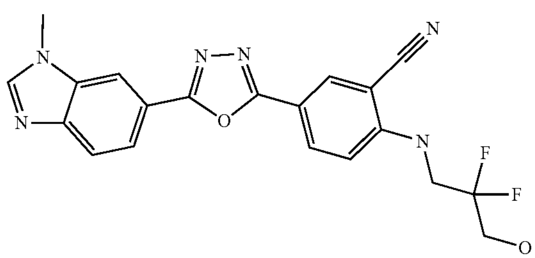 [SMILES: Cn1cnc2ccc(-c3nnc(-c4ccc(NCC(F)(F)CO)c(C#N)c4)o3)cc21] | 635 | 2-[(2,2-difluoro-3-hydroxypropyl)amino]-5-[5-(1-methyl-1H-1,3-benzodiazol-6-yl)-1,3,4-oxadiazol-2-yl]benzonitrile |
| 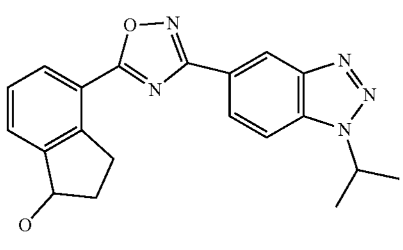 [SMILES: CC(C)n1nnc2cc(-c3noc(-c4cccc5c4CCC5O)n3)ccc21] | 636 | 4-{3-[1-(propan-2-yl)-1H-1,2,3-benzotriazol-5-yl]-1,2,4-oxadiazol-5-yl}-2,3-dihydro-1H-inden-1-ol |
| 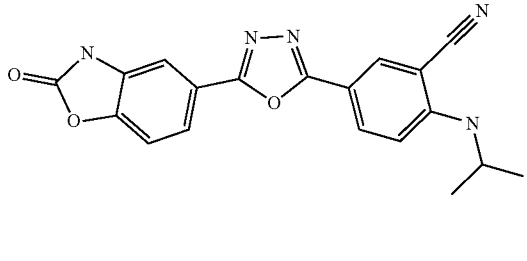 [SMILES: CC(C)Nc1ccc(-c2nnc(-c3ccc4oc(=O)[nH]c4c3)o2)cc1C#N] | 637 | 5-[5-(2-oxo-2,3-dihydro-1,3-benzoxazol-5-yl)-1,3,4-oxadiazol-2-yl]-2-[(propan-2-yl)amino]benzonitrile |

-continued

| Structure | Compound Number | Chemical Name |
|---|---|---|
| 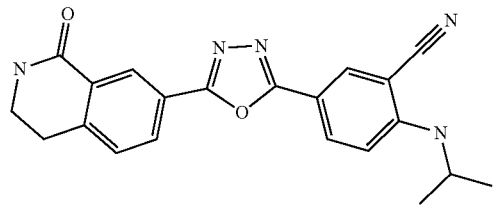 [SMILES: CC(C)Nc1ccc(-c2nnc(-c3ccc4c(c3)C(=O)NCC4)o2)cc1C#N] | 638 | 5-[5-(1-oxo-1,2,3,4-tetrahydroisoquinolin-7-yl)-1,3,4-oxadiazol-2-yl]-2-[(propan-2-yl)amino]benzonitrile |
| 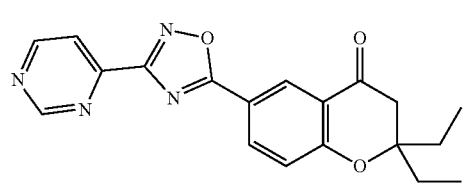 [SMILES: CCC1(CC)CC(=O)c2cc(-c3nc(-c4ccncn4)no3)ccc2O1] | 639 | 2,2-diethyl-6-(3-(pyrimidin-4-yl)-1,2,4-oxadiazol-5-yl)chroman-4-one |
| 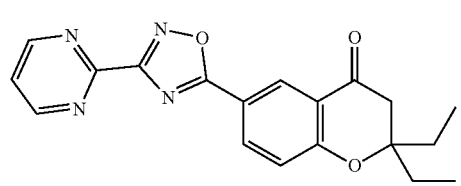 [SMILES: CCC1(CC)CC(=O)c2cc(-c3nc(-c4ncccn4)no3)ccc2O1] | 640 | 2,2-diethyl-6-(3-(pyrimidin-2-yl)-1,2,4-oxadiazol-5-yl)chroman-4-one |
| 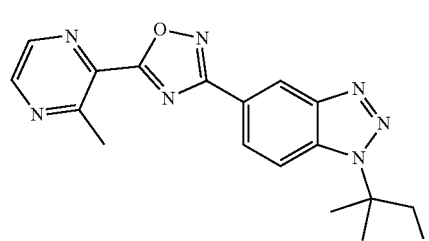 | 641 | 2-methyl-2-(5-(5-(3-methylpyrazin-2-yl)-1,2,4-oxadiazol-3-yl)-1H-benzo[d][1,2,3]triazol-1-yl)propan-1-ol |
| 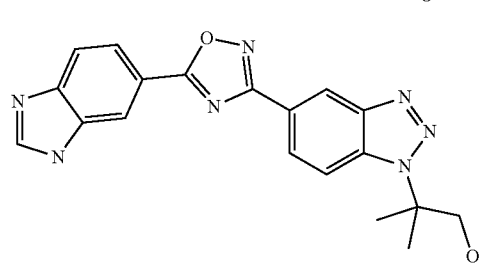 | 642 | 2-(5-(5-(1H-benzo[d]imidazol-6-yl)-1,2,4-oxadiazol-3-yl)-1H-benzo[d][1,2,3]triazol-1-yl)-2-methylpropan-1-ol |
| 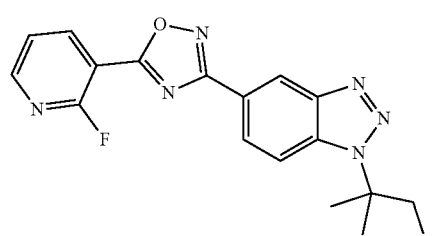 | 643 | 2-(5-(5-(2-fluoropyridin-3-yl)-1,2,4-oxadiazol-3-yl)-1H-benzo[d][1,2,3]triazol-1-yl)-2-methylpropan-1-ol |
| 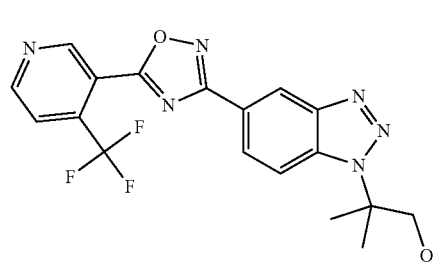 [SMILES: CC(C)(CO)n1nnc2cc(-c3noc(-c4cnccc4C(F)(F)F)n3)ccc21] | 644 | 2-methyl-2-(5-(5-(4-(trifluoromethyl)pyridin-3-yl)-1,2,4-oxadiazol-3-yl)-1H-benzo[d][1,2,3]triazol-1-yl)propan-1-ol |

-continued

| Structure | Compound Number | Chemical Name |
|---|---|---|
| 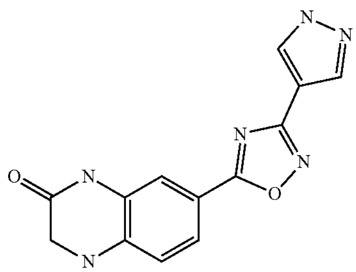 [SMILES: O=C1CNc2ccc(-c3nc(-c4cn[nH]c4)no3)cc2N1] | 645 | 7-[3-(1H-pyrazol-4-yl)-1,2,4-oxadiazol-5-yl]-1,2,3,4-tetrahydroquinoxalin-2-one |
| 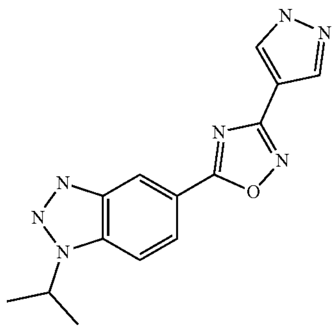 [SMILES: CC(C)N1NNc2cc(-c3nc(-c4cn[nH]c4)no3)ccc21] | 646 | 1-(propan-2-yl)-5-[3-(1H-pyrazol-4-yl)-1,2,4-oxadiazol-5-yl]-1H-1,2,3-benzotriazole |
| 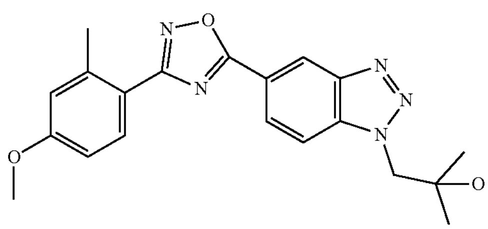 [SMILES: COc1ccc(-c2noc(-c3ccc4c(c3)nnn4CC(C)(C)O)n2)c(C)c1] | 647 | 1-{5-[3-(4-methoxy-2-methylphenyl)-1,2,4-oxadiazol-5-yl]-1H-1,2,3-benzotriazol-1-yl}-2-methylpropan-2-ol |
| 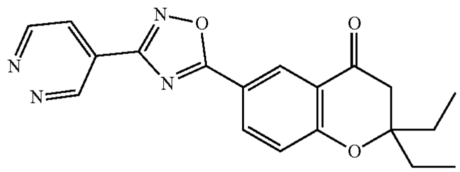 [SMILES: CCC1(CC)CC(=O)c2cc(-c3nc(/C(C=N)=C/C=N)no3)ccc2O1] | 648 | 2,2-diethyl-6-(3-(pyridazin-4-yl)-1,2,4-oxadiazol-5-yl)chroman-4-one |
| 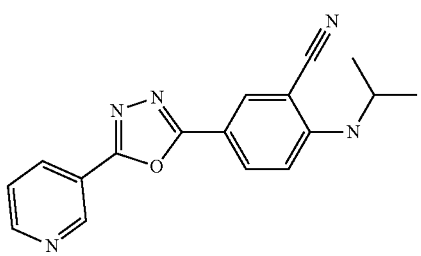 [SMILES: CC(C)Nc1ccc(-c2nnc(-c3cccnc3)o2)cc1C#N] | 649 | 2-(isopropylamino)-5-(5-(pyridin-3-yl)-1,3,4-oxadiazol-2-yl)benzonitrile |
| 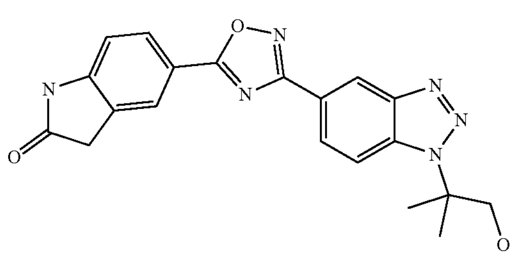 [SMILES: CC(C)(CO)n1nnc2cc(-c3noc(-c4ccc5c(c4)CC(=O)N5)n3)ccc21] | 650 | 5-(3-(1-(1-hydroxy-2-methylpropan-2-yl)-1H-benzo[d][1,2,3]triazol-5-yl)-1,2,4-oxadiazol-5-yl)indolin-2-one |

-continued

| Structure | Compound Number | Chemical Name |
|---|---|---|
| 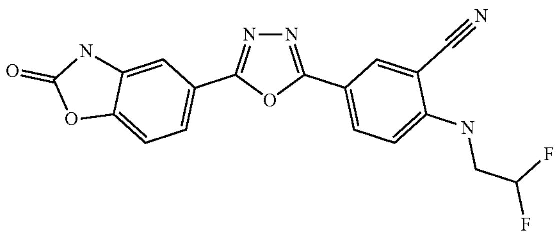 [SMILES: N#Cc1cc(-c2nnc(-c3ccc4oc(=O)[nH]c4c3)o2)ccc1NCC(F)F] | 651 | 2-[(2,2-difluoroethyl)amino]-5-[5-(2-oxo-2,3-dihydro-1,3-benzoxazol-5-yl)-1,3,4-oxadiazol-2-yl]benzonitrile |
| 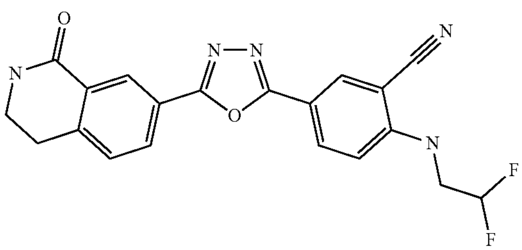 [SMILES: N#Cc1cc(-c2nnc(-c3ccc4c(c3)C(=O)NCC4)o2)ccc1NCC(F)F] | 652 | 2-[(2,2-difluoroethyl)amino]-5-[5-(1-oxo-1,2,3,4-tetrahydroisoquinolin-7-yl)-1,3,4-oxadiazol-2-yl]benzonitrile |
| 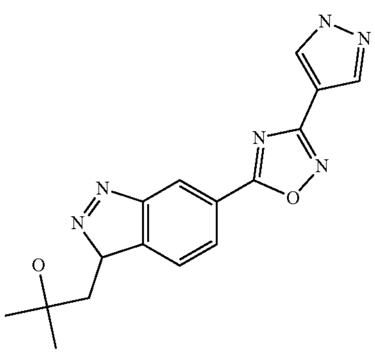 [SMILES: CC(C)(O)CC1N=Nc2cc(-c3nc(-c4cn[nH]c4)no3)ccc21] | 653 | 2-methyl-1-{6-[3-(1H-pyrazol-4-yl)-1,2,4-oxadiazol-5-yl]-3H-indazol-3-yl}propan-2-ol |
| 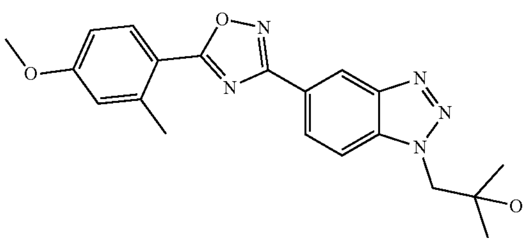 [SMILES: COc1ccc(-c2nc(-c3ccc4c(c3)nnn4CC(C)(C)O)no2)c(C)c1] | 654 | 1-(5-(5-(4-methoxy-2-methylphenyl)-1,2,4-oxadiazol-3-yl)-1H-benzo[d][1,2,3]triazol-1-yl)-2-methylpropan-2-ol |
| 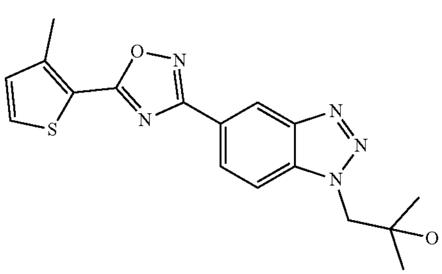 [SMILES: Cc1ccsc1-c1nc(-c2ccc3c(c2)nnn3CC(C)(C)O)no1] | 655 | 2-methyl-1-(5-(5-(3-methylthiophen-2-yl)-1,2,4-oxadiazol-3-yl)-1H-benzo[d][1,2,3]triazol-1-yl)propan-2-ol |

-continued

| Structure | Compound Number | Chemical Name |
|---|---|---|
| 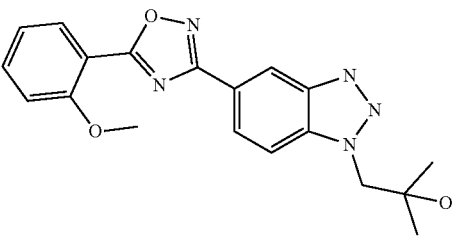 [SMILES: COc1ccccc1-c1nc(-c2ccc3c(c2)NNN3CC(C)(C)O)no1] | 656 | 1-(5-(5-(2-methoxyphenyl)-1,2,4-oxadiazol-3-yl)-1H-benzo[d][1,2,3]triazol-1-yl)-2-methylpropan-2-ol |
| 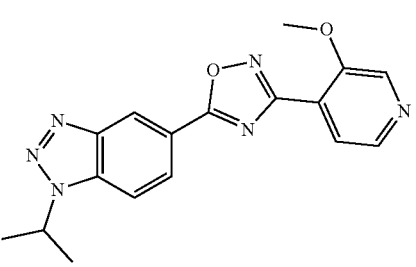 [SMILES: COc1cnccc1-c1noc(-c2ccc3c(c2)nnn3C(C)C)n1] | 657 | 5-(1-isopropyl-1H-benzo[d][1,2,3]triazol-5-yl)-3-(3-methoxypyridin-4-yl)-1,2,4-oxadiazole |
| 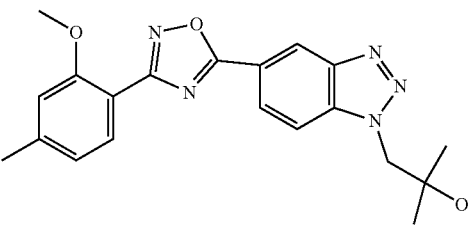 [SMILES: COc1cc(C)ccc1-c1noc(-c2ccc3c(c2)nnn3CC(C)(C)O)n1] | 662 | 1-{5-[3-(2-methoxy-4-methylphenyl)-1,2,4-oxadiazol-5-yl]-1H-1,2,3-benzotriazol-1-yl}-2-methylpropan-2-ol |
| 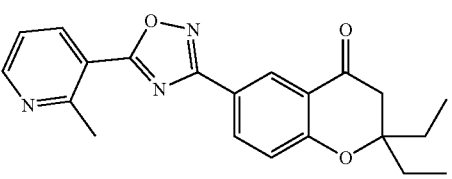 [SMILES: CCC1(CC)CC(=O)c2cc(-c3noc(-c4cccnc4C)n3)ccc2O1] | 663 | 2,2-diethyl-6-[5-(2-methylpyridin-3-yl)-1,2,4-oxadiazol-3-yl]-3,4-dihydro-2H-1-benzopyran-4-one |
| 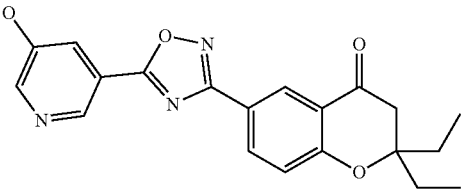 | 664 | 2,2-diethyl-6-[5-(5-hydroxypyridin-3-yl)-1,2,4-oxadiazol-3-yl]-3,4-dihydro-2H-1-benzopyran-4-one |
| 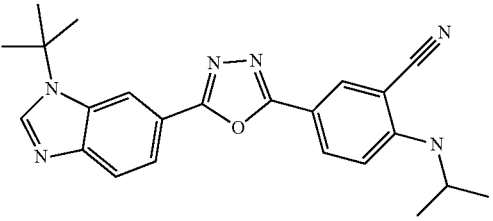 [SMILES: CC(C)Nc1ccc(-c2nnc(-c3ccc4ncn(C(C)(C)C)c4c3)o2)cc1C#N] | 665 | 5-[5-(1-tert-butyl-1H-1,3-benzodiazol-6-yl)-1,3,4-oxadiazol-2-yl]-2-[(propan-2-yl)amino]benzonitrile |

-continued

| Structure | Compound Number | Chemical Name |
|---|---|---|
| 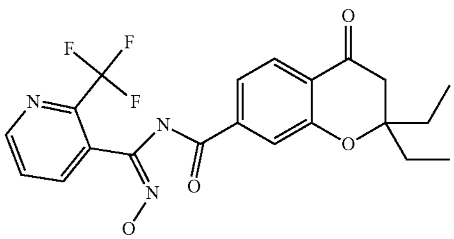 [SMILES: CCC1(CC)CC(=O)c2ccc(C(=O)N/C(=N/O)c3cccnc3C(F)(F)F)cc2O1] | 666 | 2,2-diethyl-N-[(1E)-(hydroxyimino)[2-(trifluoromethyl)pyridin-3-yl]methyl]-4-oxo-3,4-dihydro-2H-1-benzopyran-7-carboxamide |
| 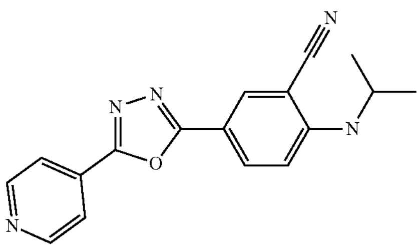 [SMILES: CC(C)Nc1ccc(-c2nnc(-c3ccncc3)o2)cc1C#N] | 667 | 2-(isopropylamino)-5-(5-(pyridin-4-yl)-1,3,4-oxadiazol-2-yl)benzonitrile |
| 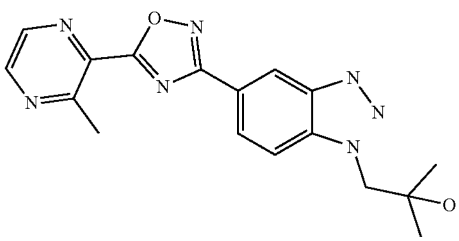 [SMILES: Cc1nccnc1-c1nc(-c2ccc(NCC(C)(C)O)c(NN)c2)no1] | 668 | 2-methyl-1-(5-(5-(3-methylpyrazin-2-yl)-1,2,4-oxadiazol-3-yl)-1H-benzo[d][1,2,3]triazol-1-yl)propan-2-ol |
| 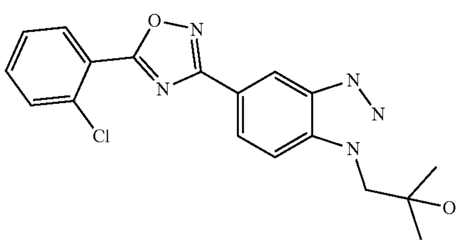 [SMILES: CC(C)(O)CNc1ccc(-c2noc(-c3ccccc3Cl)n2)cc1NN] | 669 | 1-(5-(5-(2-chlorophenyl)-1,2,4-oxadiazol-3-yl)-1H-benzo[d][1,2,3]triazol-1-yl)-2-methylpropan-2-ol |
| 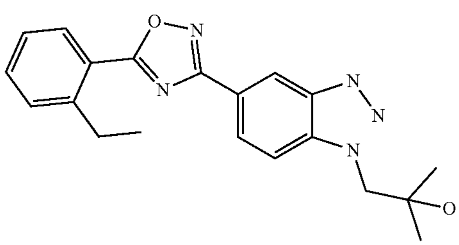 [SMILES: CCc1ccccc1-c1nc(-c2ccc(NCC(C)(C)O)c(NN)c2)no1] | 670 | 1-(5-(5-(2-ethylphenyl)-1,2,4-oxadiazol-3-yl)-1H-benzo[d][1,2,3]triazol-1-yl)-2-methylpropan-2-ol |
| 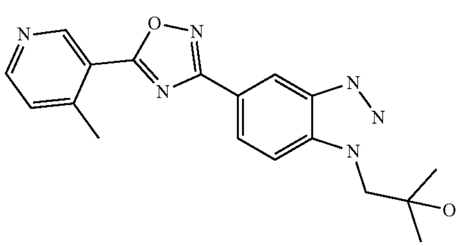 [SMILES: Cc1ccncc1-c1nc(-c2ccc(NCC(C)(C)O)c(NN)c2)no1] | 671 | 2-methyl-1-(5-(5-(4-methylpyridin-3-yl)-1,2,4-oxadiazol-3-yl)-1H-benzo[d][1,2,3]triazol-1-yl)propan-2-ol |

-continued

| Structure | Compound Number | Chemical Name |
|---|---|---|
| 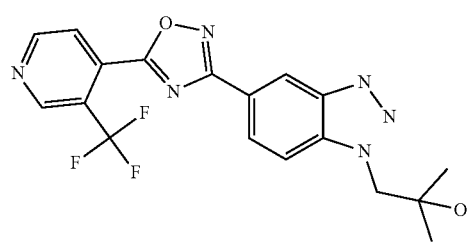 [SMILES: CC(C)(O)CNc1ccc(-c2noc(-c3ccncc3C(F)(F)F)n2)cc1NN] | 672 | 2-methyl-1-(5-(5-(3-(trifluoromethyl)pyridin-4-yl)-1,2,4-oxadiazol-3-yl)-1H-benzo[d][1,2,3]triazol-1-yl)propan-2-ol |
| 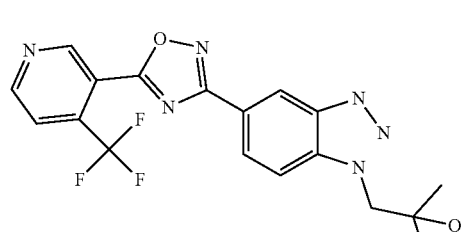 | 673 | 2-methyl-1-(5-(5-(4-(trifluoromethyl)pyridin-3-yl)-1,2,4-oxadiazol-3-yl)-1H-benzo[d][1,2,3]triazol-1-yl)propan-2-ol |
| 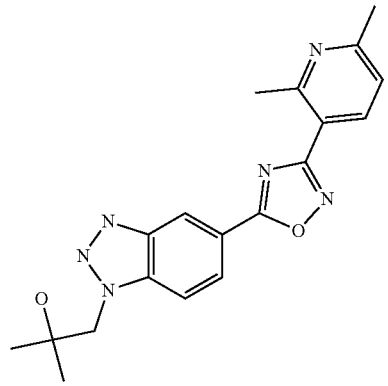 [SMILES: Cc1ccc(-c2noc(-c3ccc4c(c3)NNN4CC(C)(C)O)n2)c(C)n1] | 675 | 1-{5-[3-(2,6-dimethylpyridin-3-yl)-1,2,4-oxadiazol-5-yl]-1H-1,2,3-benzotriazol-1-yl}-2-methylpropan-2-ol |
| 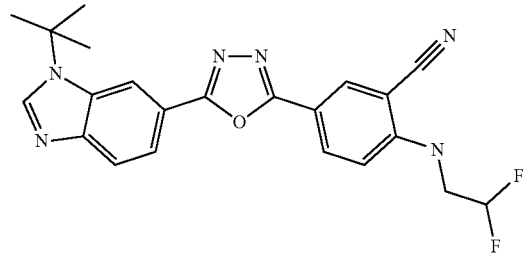 [SMILES: CC(C)(C)n1cnc2ccc(-c3nnc(-c4ccc(NCC(F)F)c(C#N)c4)o3)cc21] | 676 | 5-[5-(1-tert-butyl-1H-1,3-benzodiazol-6-yl)-1,3,4-oxadiazol-2-yl]-2-[(2,2-difluoroethyl)amino]benzonitrile |
| 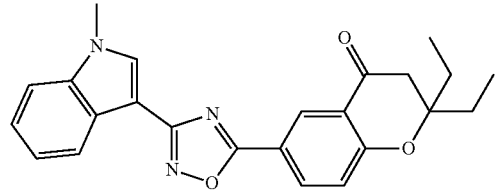 [SMILES: CCC1(CC)CC(=O)c2cc(-c3nc(-c4cn(C)c5ccccc45)no3)ccc2O1] | 677 | 2,2-diethyl-6-[3-(1-methyl-1H-indol-3-yl)-1,2,4-oxadiazol-5-yl]-3,4-dihydro-2H-1-benzopyran-4-one |

-continued

| Structure | Compound Number | Chemical Name |
|---|---|---|
| 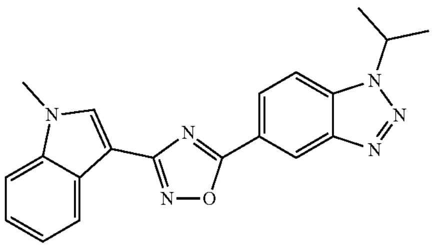 [SMILES: CC(C)n1nnc2cc(-c3nc(-c4cn(C)c5ccccc45)no3)ccc21] | 678 | 5-[3-(1-methyl-1H-indol-3-yl)-1,2,4-oxadiazol-5-yl]-1-(propan-2-yl)-1H-1,2,3-benzotriazole |
| 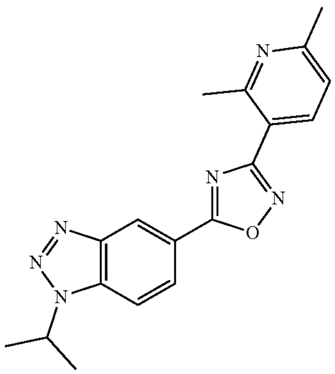 [SMILES: Cc1ccc(-c2noc(-c3ccc4c(c3)nnn4C(C)C)n2)c(C)n1] | 679 | 5-[3-(2,6-dimethylpyridin-3-yl)-1,2,4-oxadiazol-5-yl]-1-(propan-2-yl)-1H-1,2,3-benzotriazole |
| 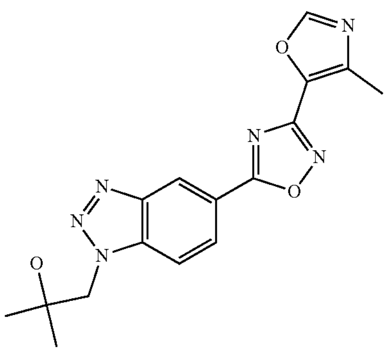 [SMILES: Cc1ncoc1-c1noc(-c2ccc3c(c2)nnn3CC(C)(C)O)n1] | 680 | 2-methyl-1-{5-[3-(4-methyl-1,3-oxazol-5-yl)-1,2,4-oxadiazol-5-yl]-1H-1,2,3-benzotriazol-1-yl}propan-2-ol |
| 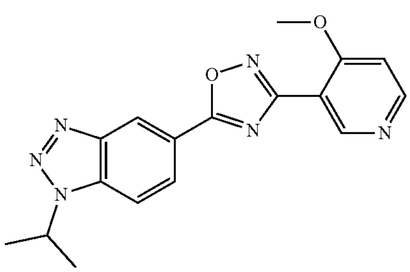 [SMILES: COc1ccncc1-c1noc(-c2ccc3c(c2)nnn3C(C)C)n1] | 681 | 5-(1-isopropyl-1H-benzo[d][1,2,3]triazol-5-yl)-3-(4-methoxypyridin-3-yl)-1,2,4-oxadiazole |
| 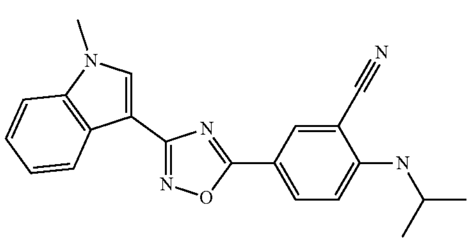 [SMILES: CC(C)Nc1ccc(-c2nc(-c3cn(C)c4ccccc34)no2)cc1C#N] | 682 | 5-[3-(1-methyl-1H-indol-3-yl)-1,2,4-oxadiazol-5-yl]-2-[(propan-2-yl)amino]benzonitrile |

-continued

| Structure | Compound Number | Chemical Name |
|---|---|---|
| 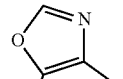 | 683 | 5-[3-(4-methyl-1,3-oxazol-5-yl)-1,2,4-oxadiazol-5-yl]-1-(propan-2-yl)-1H-1,2,3-benzotriazole |
| 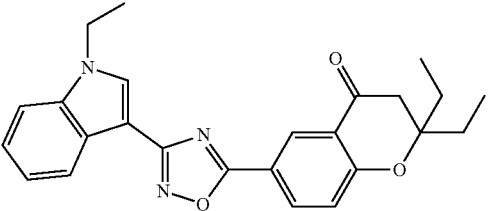 [SMILES: CCn1cc(-c2noc(-c3ccc4c(c3)C(=O)CC(CC)(CC)O4)n2)c2ccccc21] | 684 | 2,2-diethyl-6-[3-(1-ethyl-1H-indol-3-yl)-1,2,4-oxadiazol-5-yl]-3,4-dihydro-2H-1-benzopyran-4-one |
| 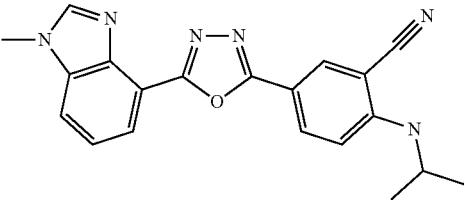 [SMILES: CC(C)Nc1ccc(-c2nnc(-c3cccc4c3ncn4C)o2)cc1C#N] | 685 | 5-[5-(1-methyl-1H-1,3-benzodiazol-4-yl)-1,3,4-oxadiazol-2-yl]-2-[(propan-2-yl)amino]benzonitrile |
| 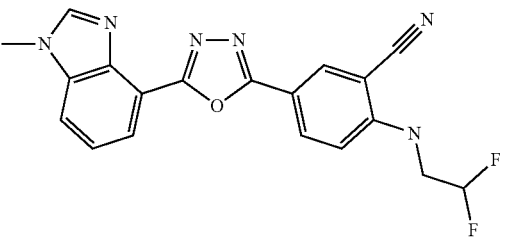 [SMILES: Cn1cnc2c(-c3nnc(-c4ccc(NCC(F)F)c(C#N)c4)o3)cccc21] | 686 | 2-[(2,2-difluoroethyl)amino]-5-[5-(1-methyl-1H-1,3-benzodiazol-4-yl)-1,3,4-oxadiazol-2-yl]benzonitrile |
| 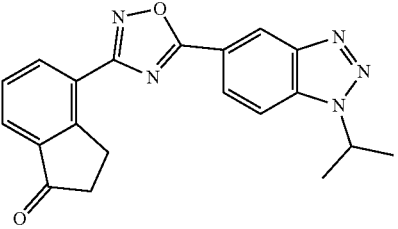 [SMILES: CC(C)n1nnc2cc(-c3nc(-c4cccc5c4CCC5=O)no3)ccc21] | 687 | 4-{5-[1-(propan-2-yl)-1H-1,2,3-benzotriazol-5-yl]-1,2,4-oxadiazol-3-yl}-2,3-dihydro-1H-inden-1-one |
| 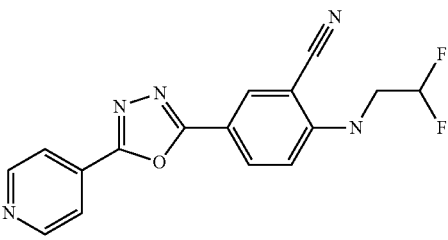 [SMILES: N#Cc1cc(-c2nnc(-c3ccncc3)o2)ccc1NCC(F)F] | 688 | 2-((2,2-difluoroethyl)amino)-5-(5-(pyridin-4-yl)-1,3,4-oxadiazol-2-yl)benzonitrile |

-continued

| Structure | Compound Number | Chemical Name |
|---|---|---|
| 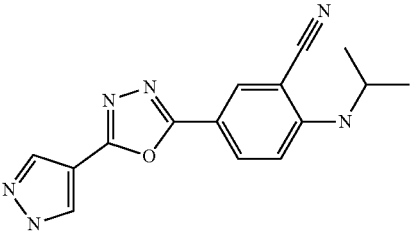 [SMILES: CC(C)Nc1ccc(-c2nnc(-c3cn[nH]c3)o2)cc1C#N] | 689 | 5-(5-(1H-pyrazol-4-yl)-1,3,4-oxadiazol-2-yl)-2-(isopropylamino)benzonitrile |
| 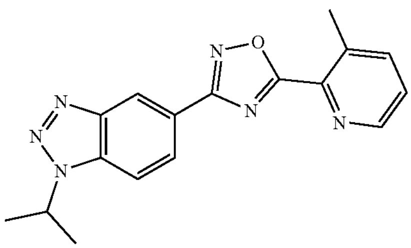 [SMILES: Cc1cccnc1-c1nc(-c2ccc3c(c2)nnn3C(C)C)no1] | 690 | 3-(1-isopropyl-1H-benzo[d][1,2,3]triazol-5-yl)-5-(3-methylpyridin-2-yl)-1,2,4-oxadiazole |
| 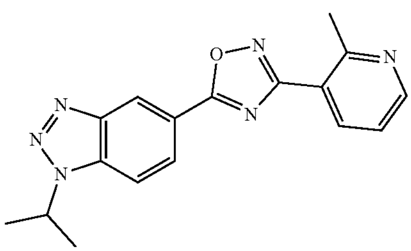 [SMILES: Cc1ncccc1-c1noc(-c2ccc3c(c2)nnn3C(C)C)n1] | 691 | 5-(1-isopropyl-1H-benzo[d][1,2,3]triazol-5-yl)-3-(2-methylpyridin-3-yl)-1,2,4-oxadiazole |
| 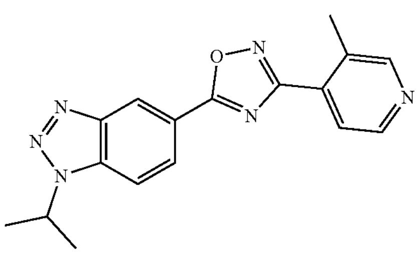 [SMILES: Cc1cnccc1-c1noc(-c2ccc3c(c2)nnn3C(C)C)n1] | 692 | 5-(1-isopropyl-1H-benzo[d][1,2,3]triazol-5-yl)-3-(3-methylpyridin-4-yl)-1,2,4-oxadiazole |
| 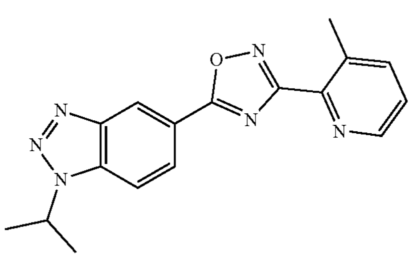 [SMILES: Cc1cccnc1-c1noc(-c2ccc3c(c2)nnn3C(C)C)n1] | 693 | 5-(1-isopropyl-1H-benzo[d][1,2,3]triazol-5-yl)-3-(3-methylpyridin-2-yl)-1,2,4-oxadiazole |
| 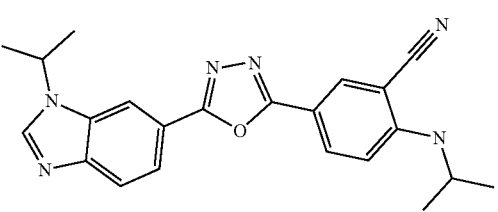 [SMILES: CC(C)Nc1ccc(-c2nnc(-c3ccc4ncn(C(C)C)c4c3)o2)cc1C#N] | 694 | 5-{5-[1-(propan-2-yl)-1H-1,3-benzodiazol-6-yl]-1,3,4-oxadiazol-2-yl}-2-[(propan-2-yl)amino]benzonitrile |

-continued

| Structure | Compound Number | Chemical Name |
|---|---|---|
| 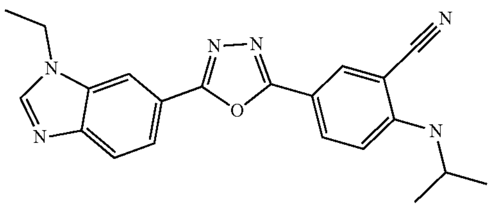 [SMILES: CCn1cnc2ccc(-c3nnc(-c4ccc(NC(C)C)c(C#N)c4)o3)cc21] | 695 | 5-[5-(1-ethyl-1H-1,3-benzodiazol-6-yl)-1,3,4-oxadiazol-2-yl]-2-[(propan-2-yl)amino]benzonitrile |
| 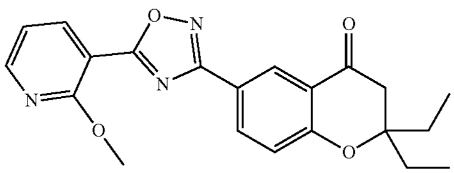 [SMILES: CCC1(CC)CC(=O)c2cc(-c3noc(-c4cccnc4OC)n3)ccc2O1] | 696 | 2,2-diethyl-6-[5-(2-methoxypyridin-3-yl)-1,2,4-oxadiazol-3-yl]-3,4-dihydro-2H-1-benzopyran-4-one |
| 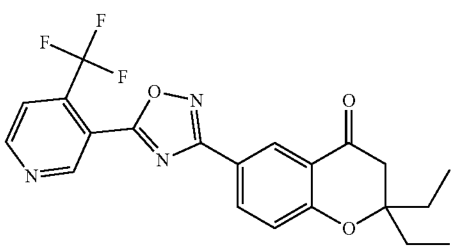 [SMILES: CCC1(CC)CC(=O)c2cc(-c3noc(-c4cnccc4C(F)(F)F)n3)ccc2O1] | 697 | 2,2-diethyl-6-{5-[4-(trifluoromethyl)pyridin-3-yl]-1,2,4-oxadiazol-3-yl}-3,4-dihydro-2H-1-benzopyran-4-one |
| 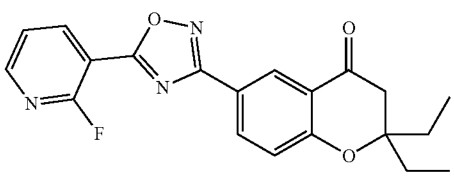 | 698 | 2,2-diethyl-6-[5-(2-fluoropyridin-3-yl)-1,2,4-oxadiazol-3-yl]-3,4-dihydro-2H-1-benzopyran-4-one |
| 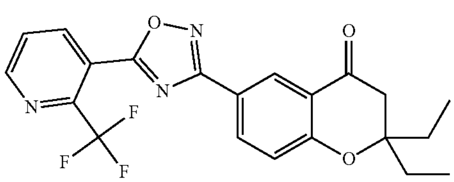 [SMILES: CCC1(CC)CC(=O)c2cc(-c3noc(-c4cccnc4C(F)(F)F)n3)ccc2O1] | 699 | 2,2-diethyl-6-{5-[2-(trifluoromethyl)pyridin-3-yl]-1,2,4-oxadiazol-3-yl}-3,4-dihydro-2H-1-benzopyran-4-one |
| 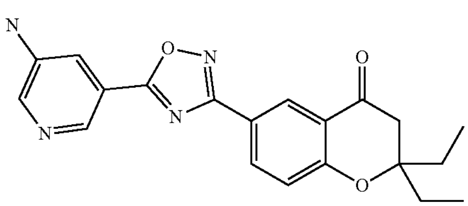 | 700 | 6-[5-(5-aminopyridin-3-yl)-1,2,4-oxadiazol-3-yl]-2,2-diethyl-3,4-dihydro-2H-1-benzopyran-4-one |
| 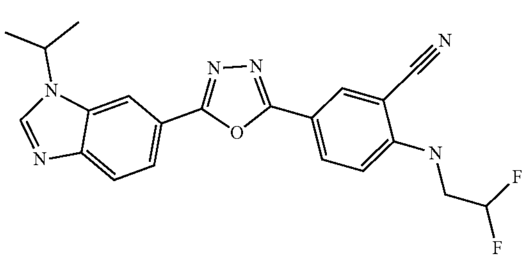 [SMILES: CC(C)n1cnc2ccc(-c3nnc(-c4ccc(NCC(F)F)c(C#N)c4)o3)cc21] | 701 | 2-[(2,2-difluoroethyl)amino]-5-{5-[1-(propan-2-yl)-1H-1,3-benzodiazol-6-yl]-1,3,4-oxadiazol-2-yl}benzonitrile |

-continued

| Structure | Compound Number | Chemical Name |
|---|---|---|
| 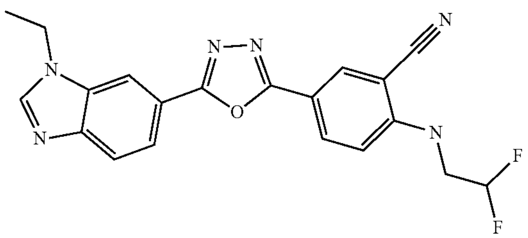 [SMILES: CCn1cnc2ccc(-c3nnc(-c4ccc(NCC(F)F)c(C#N)c4)o3)cc21] | 702 | 2-[(2,2-difluoroethyl)amino]-5-[5-(1-ethyl-1H-1,3-benzodiazol-6-yl)-1,3,4-oxadiazol-2-yl]benzonitrile |
| 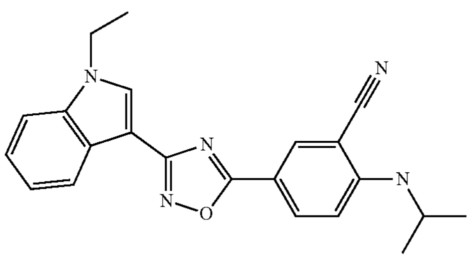 [SMILES: CCn1cc(-c2noc(-c3ccc(NC(C)C)c(C#N)c3)n2)c2ccccc21] | 703 | 5-[3-(1-ethyl-1H-indol-3-yl)-1,2,4-oxadiazol-5-yl]-2-[(propan-2-yl)amino]benzonitrile |
| 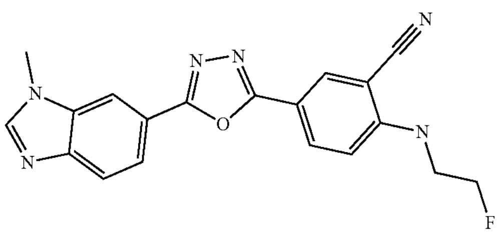 [SMILES: Cn1cnc2ccc(-c3nnc(-c4ccc(NCCF)c(C#N)c4)o3)cc21] | 704 | 2-[(2-fluoroethyl)amino]-5-[5-(1-methyl-1H-1,3-benzodiazol-6-yl)-1,3,4-oxadiazol-2-yl]benzonitrile |
| 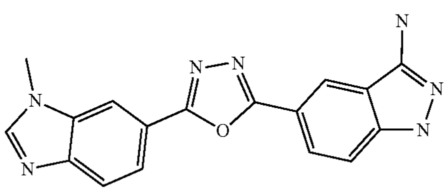 [SMILES: Cn1cnc2ccc(-c3nnc(-c4ccc5[nH]nc(N)c5c4)o3)cc21] | 705 | 5-[5-(1-methyl-1H-1,3-benzodiazol-6-yl)-1,3,4-oxadiazol-2-yl]-1H-indazol-3-amine |
| 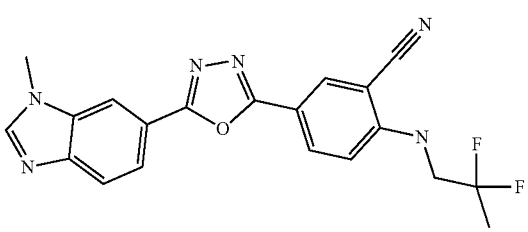 [SMILES: Cn1cnc2ccc(-c3nnc(-c4ccc(NCC(C)(F)F)c(C#N)c4)o3)cc21] | 706 | 2-[(2,2-difluoropropyl)amino]-5-[5-(1-methyl-1H-1,3-benzodiazol-6-yl)-1,3,4-oxadiazol-2-yl]benzonitrile |
| 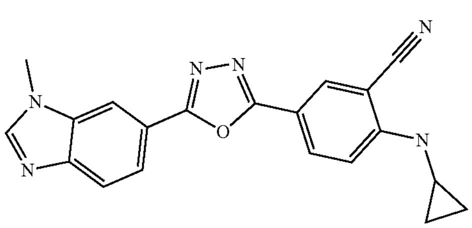 [SMILES: Cn1cnc2ccc(-c3nnc(-c4ccc(NC5CC5)c(C#N)c4)o3)cc21] | 707 | 2-(cyclopropylamino)-5-[5-(1-methyl-1H-1,3-benzodiazol-6-yl)-1,3,4-oxadiazol-2-yl]benzonitrile |

-continued

| Structure | Compound Number | Chemical Name |
|---|---|---|
| 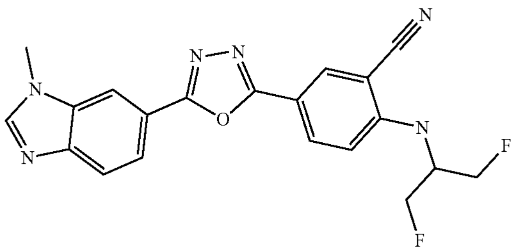 [SMILES: Cn1cnc2ccc(-c3nnc(-c4ccc(NC(CF)CF)c(C#N)c4)o3)cc21] | 708 | 2-[(1,3-difluoropropan-2-yl)amino]-5-[5-(1-methyl-1H-1,3-benzodiazol-6-yl)-1,3,4-oxadiazol-2-yl]benzonitrile |
| 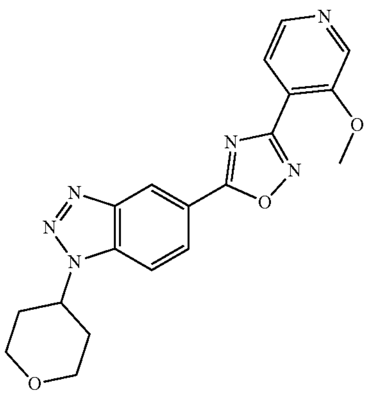 [SMILES: COc1cnccc1-c1noc(-c2ccc3c(c2)nnn3C2CCOCC2)n1] | 709 | 5-[3-(3-methoxypyridin-4-yl)-1,2,4-oxadiazol-5-yl]-1-(oxan-4-yl)-1H-1,2,3-benzotriazole |
| 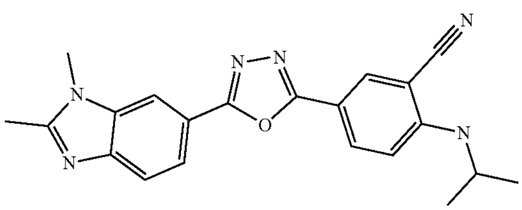 [SMILES: Cc1nc2ccc(-c3nnc(-c4ccc(NC(C)C)c(C#N)c4)o3)cc2n1C] | 710 | 5-[5-(1,2-dimethyl-1H-1,3-benzodiazol-6-yl)-1,3,4-oxadiazol-2-yl]-2-[(propan-2-yl)amino]benzonitrile |
| 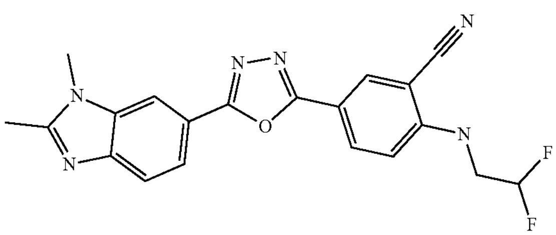 [SMILES: Cc1nc2ccc(-c3nnc(-c4ccc(NCC(F)F)c(C#N)c4)o3)cc2n1C] | 711 | 2-[(2,2-difluoroethyl)amino]-5-[5-(1,2-dimethyl-1H-1,3-benzodiazol-6-yl)-1,3,4-oxadiazol-2-yl]benzonitrile |
| 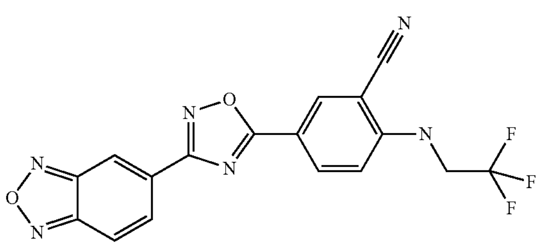 [SMILES: N#Cc1cc(-c2nc(-c3ccc4nonc4c3)no2)ccc1NCC(F)(F)F] | 712 | 5-[3-(2,1,3-benzoxadiazol-5-yl)-1,2,4-oxadiazol-5-yl]-2-[(2,2,2-trifluoroethyl)amino]benzonitrile |
| 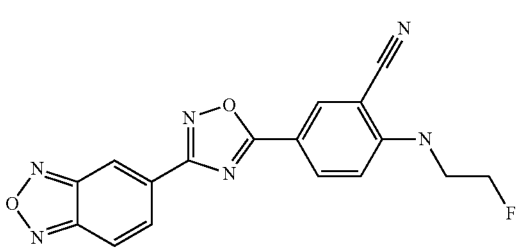 [SMILES: N#Cc1cc(-c2nc(-c3ccc4nonc4c3)no2)ccc1NCCF] | 713 | 5-[3-(2,1,3-benzoxadiazol-5-yl)-1,2,4-oxadiazol-5-yl]-2-[(2-fluoroethyl)amino]benzonitrile |

-continued

| Structure | Compound Number | Chemical Name |
|---|---|---|
| 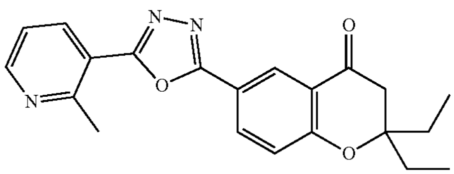 | 718 | 2,2-diethyl-6-(5-(2-methylpyridin-3-yl)-1,3,4-oxadiazol-2-yl)chroman-4-one |
| 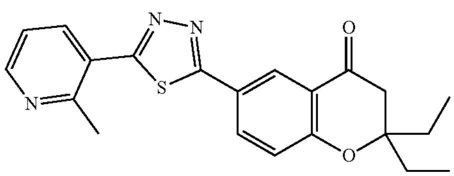 | 719 | 2,2-diethyl-6-(5-(2-methylpyridin-3-yl)-1,3,4-thiadiazol-2-yl)chroman-4-one |
| 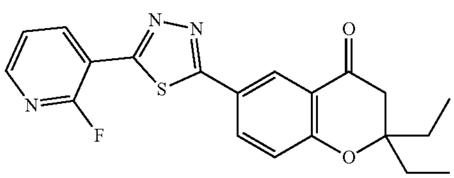 | 720 | 2,2-diethyl-6-(5-(2-fluoropyridin-3-yl)-1,3,4-thiadiazol-2-yl)chroman-4-one |
| 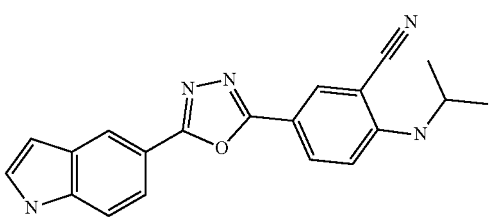 [SMILES: CC(C)Nc1ccc(-c2nnc(-c3ccc4[nH]ccc4c3)o2)cc1C#N] | 721 | 5-(5-(1H-indol-5-yl)-1,3,4-oxadiazol-2-yl)-2-(isopropylamino)benzonitrile |
| 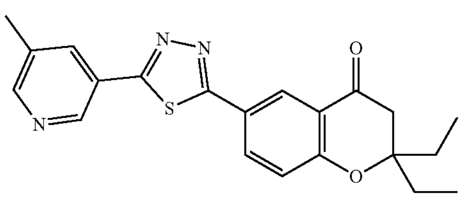 [SMILES: CCC1(CC)CC(=O)c2cc(-c3nnc(-c4cncc(C)c4)s3)ccc2O1] | 724 | 2,2-diethyl-6-(5-(5-methylpyridin-3-yl)-1,3,4-thiadiazol-2-yl)chroman-4-one |
| 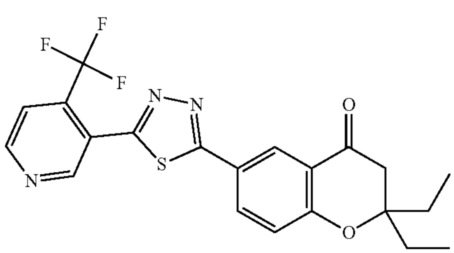 [SMILES: CCC1(CC)CC(=O)c2cc(-c3nnc(-c4cnccc4C(F)(F)F)s3)ccc2O1] | 725 | 2,2-diethyl-6-(5-(4-(trifluoromethyl)pyridin-3-yl)-1,3,4-thiadiazol-2-yl)chroman-4-one |
| 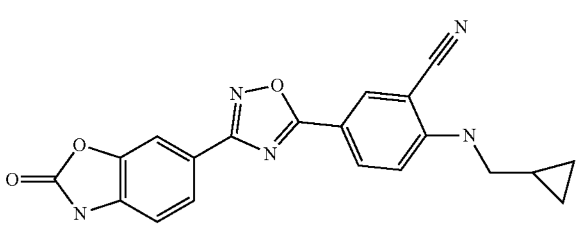 [SMILES: N#Cc1cc(-c2nc(-c3ccc4[nH]c(=O)oc4c3)no2)ccc1NCC1CC1] | 726 | 2-(cyclopropylmethylamino)-5-[3-(2-oxo-3H-1,3-benzoxazol-6-yl)-1,2,4-oxadiazol-5-yl]benzonitrile |

-continued

| Structure | Compound Number | Chemical Name |
|---|---|---|
| 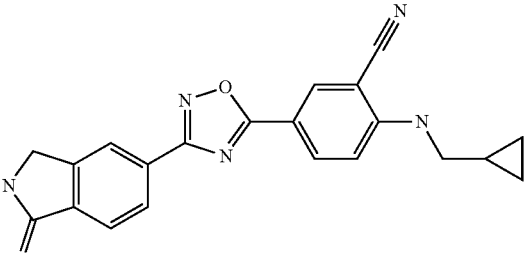 | 727 | 2-((cyclopropylmethyl)amino)-5-(3-(1-oxoisoindolin-5-yl)-1,2,4-oxadiazol-5-yl)benzonitrile |
| 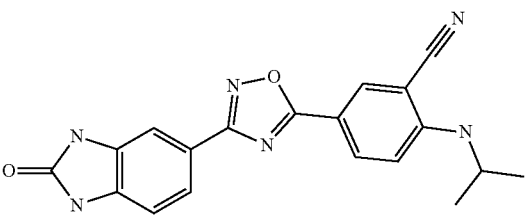 | 728 | 2-(isopropylamino)-5-(3-(2-oxo-2,3-dihydro-1H-benzo[d]imidazol-5-yl)-1,2,4-oxadiazol-5-yl)benzonitrile |
| 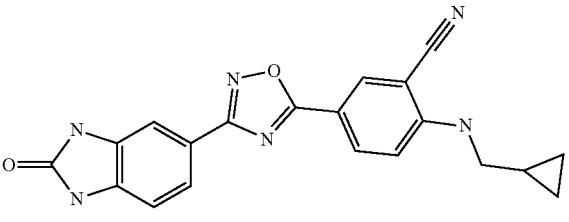 [SMILES: N#Cc1cc(-c2nc(-c3ccc4[nH]c(=O)[nH]c4c3)no2)ccc1NCC1CC1] | 729 | 2-((cyclopropylmethyl)amino)-5-(3-(2-oxo-2,3-dihydro-1H-benzo[d]imidazol-5-yl)-1,2,4-oxadiazol-5-yl)benzonitrile |
| 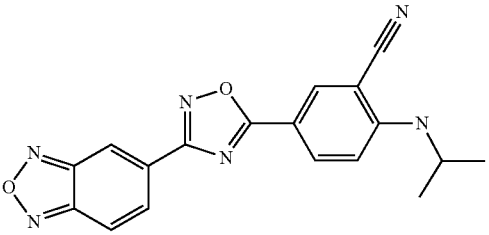 [SMILES: CC(C)Nc1ccc(-c2nc(-c3ccc4nonc4c3)no2)cc1C#N] | 730 | 5-[3-(2,1,3-benzoxadiazol-5-yl)-1,2,4-oxadiazol-5-yl]-2-[(propan-2-yl)amino]benzonitrile |
| 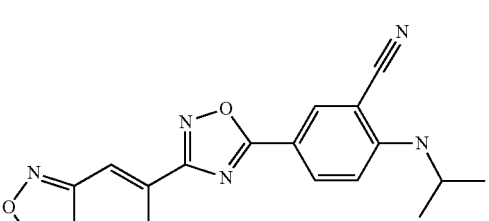 | 730 | 5-[3-(2,1,3-benzoxadiazol-5-yl)-1,2,4-oxadiazol-5-yl]-2-[(propan-2-yl)amino]benzonitrile |
| 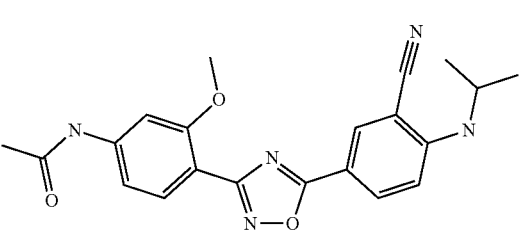 [SMILES: COc1cc(NC(C)=O)ccc1-c1noc(-c2ccc(NC(C)C)c(C#N)c2)n1] | 731 | N-[4-(5-{3-cyano-4-[(propan-2-yl)amino]phenyl}-1,2,4-oxadiazol-3-yl)-3-methoxyphenyl]acetamide |

| Structure | Compound Number | Chemical Name |
|---|---|---|
| 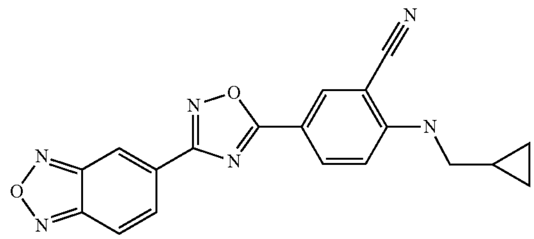 [SMILES: N#Cc1cc(-c2nc(-c3ccc4nonc4c3)no2)ccc1NCC1CC1] | 732 | 5-[3-(2,1,3-benzoxadiazol-5-yl)-1,2,4-oxadiazol-5-yl]-2-[(2,2-difluoroethyl)amino]benzonitrile |
| 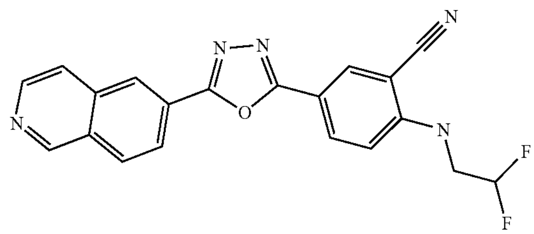 [SMILES: N#Cc1cc(-c2nnc(-c3ccc4cnccc4c3)o2)ccc1NCC(F)F] | 733 | 2-[(2,2-difluoroethyl)amino]-5-[5-(isoquinolin-6-yl)-1,3,4-oxadiazol-2-yl]benzonitrile |
| 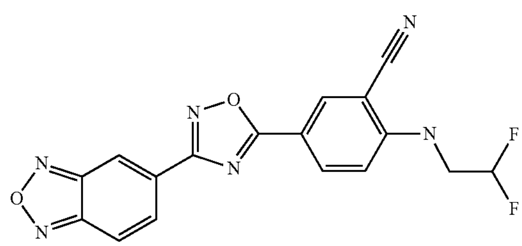 [SMILES: N#Cc1cc(-c2nc(-c3ccc4nonc4c3)no2)ccc1NCC(F)F] | 734 | 5-[3-(2,1,3-benzoxadiazol-5-yl)-1,2,4-oxadiazol-5-yl]-2-[(cyclopropylmethyl)amino]benzonitrile |
| 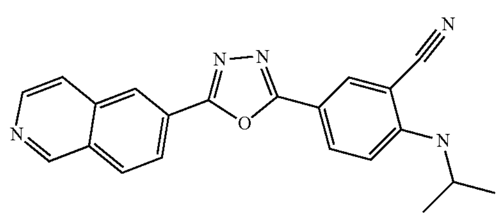 [SMILES: CC(C)Nc1ccc(-c2nnc(-c3ccc4cnccc4c3)o2)cc1C#N] | 735 | 5-[5-(isoquinolin-6-yl)-1,3,4-oxadiazol-2-yl]-2-[(propan-2-yl)amino]benzonitrile |
| | 736 | 2-[(propan-2-yl)amino]-5-[5-(quinolin-6-yl)-1,3,4-oxadiazol-2-yl]benzonitrile |
| | 736 | 2-[(propan-2-yl)amino]-5-[5-(quinolin-6-yl)-1,3,4-oxadiazol-2-yl]benzonitrile |

-continued

| Structure | Compound Number | Chemical Name |
|---|---|---|
| 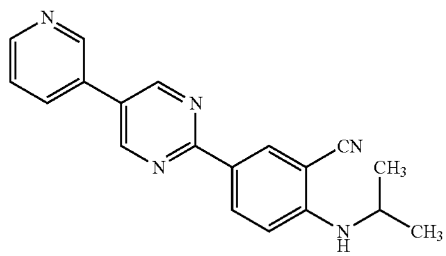 [SMILES: CC(C)Nc1ccc(-c2ncc(-c3cccnc3)cn2)cc1C#N] | 737 | 2-(isopropylamino)-5-(5-(pyridin-3-yl)pyrimidin-2-yl)benzonitrile |
| 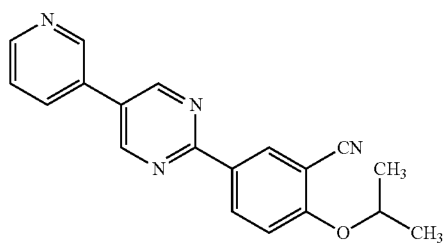 [SMILES: CC(C)Oc1ccc(-c2ncc(-c3cccnc3)cn2)cc1C#N] | 738 | 2-isopropoxy-5-(5-(pyridin-3-yl)pyrimidin-2-yl)benzonitrile |
| 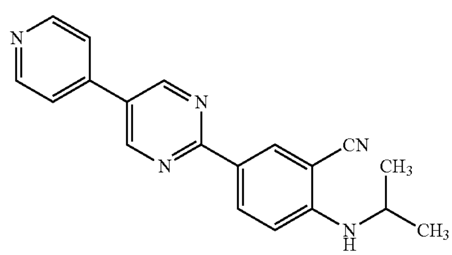 [SMILES: CC(C)Nc1ccc(-c2ncc(-c3ccncc3)cn2)cc1C#N] | 739 | 2-(isopropylamino)-5-(5-(pyridin-4-yl)pyrimidin-2-yl)benzonitrile |
| 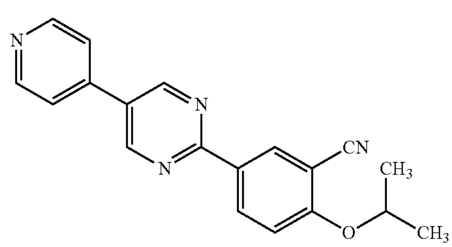 | 740 | 2-isopropoxy-5-(5-(pyridin-4-yl)pyrimidin-2-yl)benzonitrile |
| 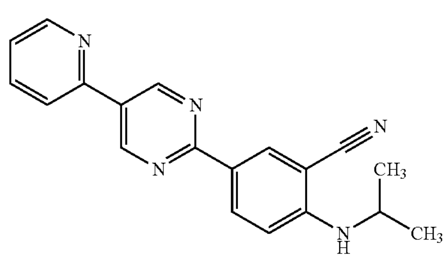 [SMILES: CC(C)Nc1ccc(-c2ncc(-c3ccccn3)cn2)cc1C#N] | 741 | 2-(isopropylamino)-5-(5-(pyridin-2-yl)pyrimidin-2-yl)benzonitrile |
| 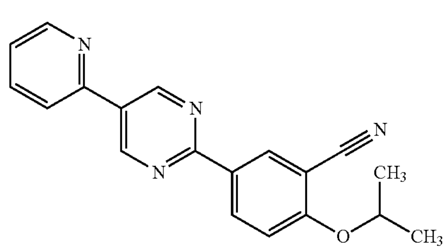 [SMILES: CC(C)Oc1ccc(-c2ncc(-c3ccccn3)cn2)cc1C#N] | 742 | 2-isopropoxy-5-(5-(pyridin-2-yl)pyrimidin-2-yl)benzonitrile |

-continued

| Structure | Compound Number | Chemical Name |
|---|---|---|
| 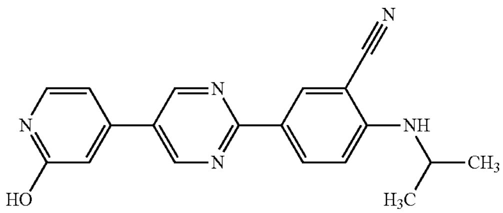 | 743 | 5-(5-(2-hydroxypyridin-4-yl)pyrimidin-2-yl)-2-(isopropylamino)benzonitrile |
| 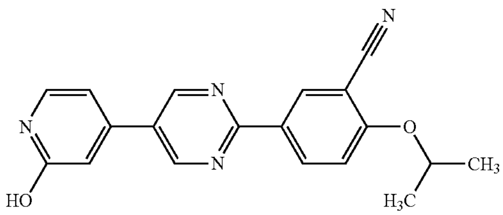 [SMILES: CC(C)Oc1ccc(-c2ncc(-c3ccnc(O)c3)cn2)cc1C#N] | 744 | 5-(5-(2-hydroxypyridin-4-yl)pyrimidin-2-yl)-2-isopropoxybenzonitrile |
| 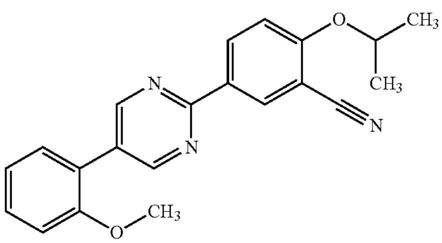 [SMILES: COc1ccccc1-c1cnc(-c2ccc(OC(C)C)c(C#N)c2)nc1] | 745 | 2-isopropoxy-5-(5-(2-methoxyphenyl)pyrimidin-2-yl)benzonitrile |
| 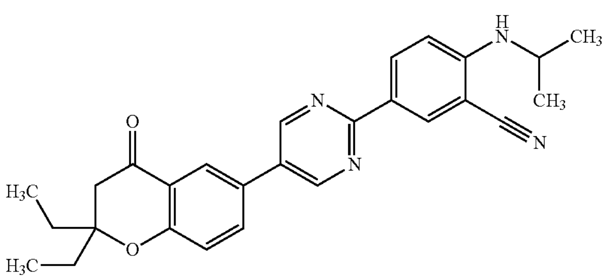 [SMILES: CCC1(CC)CC(=O)c2cc(-c3cnc(-c4ccc(NC(C)C)c(C#N)c4)nc3)ccc2O1] | 746 | 5-(5-(2,2-diethyl-4-oxochroman-6-yl)pyrimidin-2-yl)-2-(isopropylamino)benzonitrile |
| 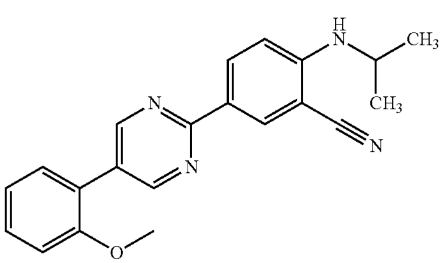 [SMILES: COc1ccccc1-c1cnc(-c2ccc(NC(C)C)c(C#N)c2)nc1] | 747 | 2-(isopropylamino)-5-(5-(2-methoxyphenyl)pyrimidin-2-yl)benzonitrile |
| 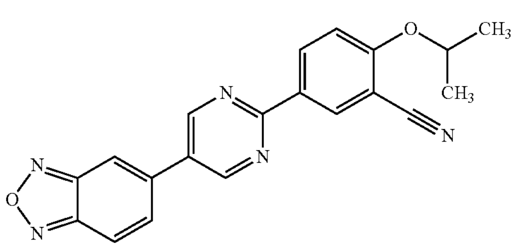 [SMILES: CC(C)Oc1ccc(-c2ncc(-c3ccc4nonc4c3)cn2)cc1C#N] | 748 | 5-(5-(benzo[c][1,2,5]oxadiazol-5-yl)pyrimidin-2-yl)-2-isopropoxybenzonitrile |

-continued

| Structure | Compound Number | Chemical Name |
|---|---|---|
| 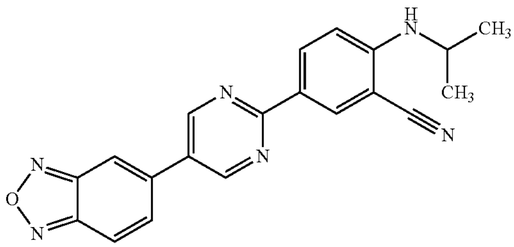 [SMILES: CC(C)Nc1ccc(-c2ncc(-c3ccc4nonc4c3)cn2)cc1C#N] | 749 | 5-(5-(benzo[c][1,2,5]oxadiazol-5-yl)pyrimidin-2-yl)-2-(isopropylamino)benzonitrile |
| 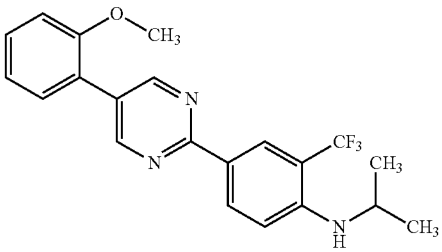 [SMILES: COc1ccccc1-c1cnc(-c2ccc(NC(C)C)c(C(F)(F)F)c2)nc1] | 750 | N-isopropyl-4-(5-(2-methoxyphenyl)pyrimidin-2-yl)-2-(trifluoromethyl)aniline |
| 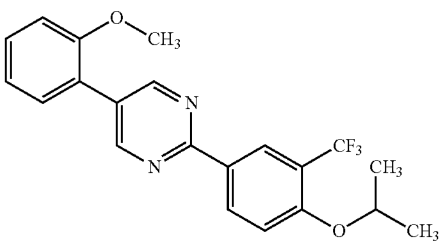 [SMILES: COc1ccccc1-c1cnc(-c2ccc(OC(C)C)c(C(F)(F)F)c2)nc1] | 751 | 2-(4-isopropoxy-3-(trifluoromethyl)phenyl)-5-(2-methoxyphenyl)pyrimidine |
| 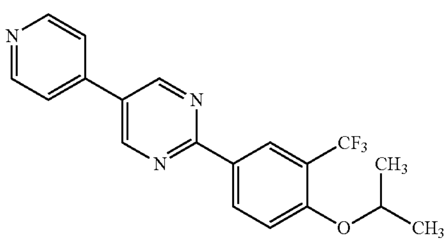 | 752 | 2-(4-isopropoxy-3-(trifluoromethyl)phenyl)-5-(pyridin-4-yl)pyrimidine |

Although the compounds described herein may be shown with specific stereochemistries around certain atoms, such as cis or trans, the compounds can also be made in the opposite orientation or in a racemic mixture. Such isomers or racemic mixtures are encompassed by the present disclosure. Additionally, although the compounds are shown collectively in a table, any compounds, or a pharmaceutically acceptable salt thereof, can be chosen from the table and used in the embodiments provided for herein.

In some embodiments, pharmaceutical compositions comprising a compound or pharmaceutically salt thereof of any compound described herein are provided.

The compounds described herein can be made by can be made according to the methods described herein and in the examples. The methods described herein can be adapted based upon the compounds desired and described herein. In some embodiments, the method is made according to the following schemes, wherein Q and L are the substituents as shown and described herein and would be apparent to one of skill in the art based upon the present disclosure. In some embodiments, this method can be used to make one or more compounds as described herein and will be apparent to one of skill in the art which compounds can be made according to the methods described herein.

The conditions and temperatures can be varied, such as shown in the examples described herein. These schemes are non-limiting synthetic schemes and the synthetic routes can be modified as would be apparent to one of skill in the art reading the present specification. The compounds can also be prepared according to the schemes described in the Examples.

The compounds can be used to modulate the $S_1P_1$ receptor. Thus, in some embodiments, the compounds can be referred to as $S_1P_1$ receptor modulating compounds Although the compounds in the tables above or in the examples section are shown with specific stereochemistries around certain atoms, such as cis or trans, the compounds can also be made in the opposite orientation or in a racemic mixture.

In some embodiments, the present embodiments provide pharmaceutical compositions comprising a compound or pharmaceutically salt thereof any compound described herein.

The compounds described herein can be made according to the methods described herein and in the examples. The methods described herein can be adapted based upon the compounds desired and described herein. In some embodiments, the method is made according to the following schemes, wherein Q and L are the substituents as shown and described herein and would be apparent to one of skill in the art based upon the present disclosure. In some embodiments, this method can be used to make one or more compounds as described herein and will be apparent to one of skill in the art which compounds can be made according to the methods described herein.

In some embodiments, the compounds are made according to schemes described in the examples. The schemes can be used to prepare the compounds and compositions described herein.

The conditions and temperatures can be varied, or the synthesis can be performed according to the examples described herein with modifications that are readily apparent based upon the compound being synthesized.

The conditions and temperatures can be varied, such as shown in the examples described herein. These schemes are non-limiting synthetic schemes and the synthetic routes can be modified as would be apparent to one of skill in the art reading the present specification.

The compounds described herein can be administered in any conventional manner by any route where they are active. Administration can be systemic, topical, or oral. For example, administration can be, but is not limited to, parenteral, subcutaneous, intravenous, intramuscular, intraperitoneal, transdermal, oral, buccal, sublingual, or ocular routes, or intravaginal, by inhalation, by depot injections, or by implants. The mode of administration can depend on the conditions or disease to be targeted or treated. The selection of the specific route of administration can be selected or adjusted by the clinician according to methods known to the clinician to obtain the desired clinical response.

In some embodiments, it may be desirable to administer one or more compounds, or a pharmaceutically acceptable salt thereof, locally to an area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, wherein the implant is of a porous, non-porous, or gelatinous material, including membranes, such as sialastic membranes, or fibers.

The compounds described herein can be administered either alone or in combination (concurrently or serially) with other pharmaceuticals. For example, the compounds can be administered in combination with other analgesics, antidepressants, anti-anxiety compounds, anti-overactive bladder compounds, compounds for the treatment of cancer, and the like. Examples of other pharmaceuticals or medicaments are known to one of skill in the art and include, but are not limited to those described herein.

The means and methods for administration are known in the art and an artisan can refer to various pharmacologic references for guidance (see, for example, Modem Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980)).

The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). The standard dosing for protamine can be used and adjusted (i.e., increased or decreased) depending upon the factors described above. The selection of the specific dose regimen can be selected or adjusted or titrated by the clinician according to methods known to the clinician to obtain the desired clinical response.

The amount of a compound described herein that will be effective in the treatment and/or prevention of a particular disease, condition, or disorder will depend on the nature and extent of the disease, condition, or disorder, and can be determined by standard clinical techniques. In addition, in vitro or in vivo assays may optionally be employed to help identify optimal dosage ranges. The precise dose to be employed in the compositions will also depend on the route of administration, and the seriousness of the disorder, and should be decided according to the judgment of the practitioner and each patient's circumstances. However, a suitable dosage range for oral administration is, generally, from about 0.001 milligram to about 200 milligrams per kilogram body weight, from about 0.01 milligram to about 100 milligrams per kilogram body weight, from about 0.01 milligram to about 70 milligrams per kilogram body weight, from about 0.1 milligram to about 50 milligrams per kilogram body weight, from 0.5 milligram to about 20 milligrams per kilogram body weight, or from about 1 milligram to about 10 milligrams per kilogram body weight. In some embodiments, the oral dose is about 5 milligrams per kilogram body weight.

In some embodiments, suitable dosage ranges for intravenous (i.v.) administration are from about 0.01 mg to about 500 mg per kg body weight, from about 0.1 mg to about 100 mg per kg body weight, from about 1 mg to about 50 mg per kg body weight, or from about 10 mg to about 35 mg per kg body weight. Suitable dosage ranges for other modes of administration can be calculated based on the forgoing dosages as known by those skilled in the art. For example, recommended dosages for intranasal, transmucosal, intradermal, intramuscular, intraperitoneal, subcutaneous, epidural, sublingual, intracerebral, intravaginal, transdermal administration or administration by inhalation are in the range of from about 0.001 mg to about 200 mg per kg of body weight, from about 0.01 mg to about 100 mg per kg of body weight, from about 0.1 mg to about 50 mg per kg of body weight, or from about 1 mg to about 20 mg per kg of body weight. Effective doses may be extrapolated from dose-response curves derived from in vitro or animal model test systems. Such animal models and systems are well known in the art.

The compounds described herein can be formulated for parenteral administration by injection, such as by bolus injection or continuous infusion. The compounds can be administered by continuous infusion subcutaneously over a period of about 15 minutes to about 24 hours.

Formulations for injection can be presented in unit dosage form, such as in ampoules or in multi-dose containers, with an optionally added preservative. The compositions can take such forms as suspensions, solutions or emulsions in oily or aqueous vehicles, and can contain formulatory agents such as suspending, stabilizing and/or dispersing agents. In some embodiments, the injectable is in the form of short-acting, depot, or implant and pellet forms injected subcutaneously or intramuscularly. In some embodiments, the parenteral dosage form is the form of a solution, suspension, emulsion, or dry powder.

For oral administration, the compounds described herein can be formulated by combining the compounds with pharmaceutically acceptable carriers well known in the art. Such carriers enable the compounds to be formulated as tablets, pills, dragees, capsules, emulsions, liquids, gels, syrups, caches, pellets, powders, granules, slurries, lozenges, aqueous or oily suspensions, and the like, for oral ingestion by a patient to be treated. Pharmaceutical preparations for oral use can be obtained by, for example, adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethylcellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds. Oral compositions can include standard vehicles such as mannitol, lactose, starch, magnesium stearate, sodium saccharine, cellulose, magnesium carbonate, etc. Such vehicles are suitably of pharmaceutical grade.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added.

For buccal administration, the compositions can take the form of, such as, tablets or lozenges formulated in a conventional manner.

For administration by inhalation, the compounds described herein can be delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, such as gelatin for use in an inhaler or insufflator can be formulated containing a powder mix of the compound and a suitable powder base such as lactose or starch.

The compounds described herein can also be formulated in rectal compositions such as suppositories or retention enemas, such as containing conventional suppository bases such as cocoa butter or other glycerides. The compounds described herein can also be formulated in vaginal compositions such as vaginal creams, suppositories, pessaries, vaginal rings, and intrauterine devices.

In transdermal administration, the compounds can be applied to a plaster, or can be applied by transdermal, therapeutic systems that are consequently supplied to the organism. In some embodiments, the compounds are present in creams, solutions, powders, fluid emulsions, fluid suspensions, semi-solids, ointments, pastes, gels, jellies, and foams, or in patches containing any of the same.

The compounds described herein can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In some embodiments, the compounds can be delivered in a controlled release system. In one embodiment, a pump may be used (see Langer, supra; Sefton, CRC Crit. Ref. Biomed. Eng., 1987, 14, 201; Buchwald et al., Surgery, 1980, 88, 507 Saudek et al., N. Engl. J. Med., 1989, 321, 574). In some embodiments, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger et al., J. Macromol. Sci. Rev. Macromol. Chem., 1983, 23, 61; see, also Levy et al., Science, 1985, 228, 190; During et al., Ann. Neurol., 1989, 25, 351; Howard et al., J. Neurosurg., 1989, 71, 105). In yet another embodiment, a controlled-release system can be placed in proximity of the target of the compounds described herein, such as the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, Science, 1990, 249, 1527-1533) may be used.

It is also known in the art that the compounds can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols. In some embodiments, the compounds described herein can be used with agents including, but not limited to, topical analgesics (e.g., lidocaine), barrier devices (e.g., GelClair), or rinses (e.g., Caphosol).

In some embodiments, the compounds described herein can be delivered in a vesicle, in particular a liposome (see, Langer, Science, 1990, 249, 1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

Suitable compositions include, but are not limited to, oral non-absorbed compositions. Suitable compositions also include, but are not limited to saline, water, cyclodextrin solutions, and buffered solutions of pH 3-9.

The compounds described herein, or pharmaceutically acceptable salts thereof, can be formulated with numerous excipients including, but not limited to, purified water, propylene glycol, PEG 400, glycerin, DMA, ethanol, benzyl alcohol, citric acid/sodium citrate (pH3), citric acid/sodium citrate (pH5), tris(hydroxymethyl)amino methane HCl (pH7.0), 0.9% saline, and 1.2% saline, and any combination thereof. In some embodiments, excipient is chosen from propylene glycol, purified water, and glycerin.

In some embodiments, the formulation can be lyophilized to a solid and reconstituted with, for example, water prior to use.

When administered to a mammal (e.g., to an animal for veterinary use or to a human for clinical use) the compounds can be administered in isolated form.

When administered to a human, the compounds can be sterile. Water is a suitable carrier when the compound of Formula I is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can take the form of a solution, suspension, emulsion, tablet, pill, pellet, capsule, capsule containing a liquid, powder, sustained-release formulation, suppository, aerosol, spray, or any other form suitable for use. Examples of suitable pharmaceutical carriers are described in Remington's Pharmaceutical Sciences, A. R. Gennaro (Editor) Mack Publishing Co.

In some embodiments, the compounds are formulated in accordance with routine procedures as a pharmaceutical composition adapted for administration to humans. Typically, compounds are solutions in sterile isotonic aqueous buffer. Where necessary, the compositions can also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound is to be administered by infusion, it can be dispensed, for example, with an infusion bottle containing sterile pharmaceutical grade water or saline. Where the compound is administered by injection, an ampoule of sterile water for injection or saline can be provided so that the ingredients may be mixed prior to administration.

The pharmaceutical compositions can be in unit dosage form. In such form, the composition can be divided into unit doses containing appropriate quantities of the active component. The unit dosage form can be a packaged preparation, the package containing discrete quantities of the preparations, for example, packeted tablets, capsules, and powders in vials or ampules. The unit dosage form can also be a capsule, cachet, or tablet itself, or it can be the appropriate number of any of these packaged forms.

In some embodiments, a composition is in the form of a liquid wherein the active agent (i.e., one of the facially amphiphilic polymers or oligomers disclosed herein) is present in solution, in suspension, as an emulsion, or as a solution/suspension. In some embodiments, the liquid composition is in the form of a gel. In other embodiments, the liquid composition is aqueous. In other embodiments, the composition is in the form of an ointment.

In some embodiments, the composition is in the form of a solid article. For example, in some embodiments, the ophthalmic composition is a solid article that can be inserted in a suitable location in the eye, such as between the eye and eyelid or in the conjunctival sac, where it releases the active agent as described, for example, U.S. Pat. Nos. 3,863,633; 3,867,519; 3,868,445; 3,960,150; 3,963,025; 4,186,184; 4,303,637; 5,443,505; and 5,869,079. Release from such an article is usually to the cornea, either via the lacrimal fluid that bathes the surface of the cornea, or directly to the cornea itself, with which the solid article is generally in intimate contact. Solid articles suitable for implantation in the eye in such fashion are generally composed primarily of polymers and can be bioerodible or non-bioerodible. Bioerodible polymers that can be used in the preparation of ocular implants carrying one or more of compounds include, but are not limited to, aliphatic polyesters such as polymers and copolymers of poly(glycolide), poly(lactide), poly(epsilon-caprolactone), poly-(hydroxybutyrate) and poly(hydroxyvalerate), polyamino acids, polyorthoesters, polyanhydrides, aliphatic polycarbonates and polyether lactones. Suitable non-bioerodible polymers include silicone elastomers.

The compositions described herein can contain preservatives. Suitable preservatives include, but are not limited to, mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

Optionally one or more stabilizers can be included in the compositions to enhance chemical stability where required. Suitable stabilizers include, but are not limited to, chelating agents or complexing agents, such as, for example, the calcium complexing agent ethylene diamine tetraacetic acid (EDTA). For example, an appropriate amount of EDTA or a salt thereof, e.g., the disodium salt, can be included in the composition to complex excess calcium ions and prevent gel formation during storage. EDTA or a salt thereof can suitably be included in an amount of about 0.01% to about 0.5%.

In those embodiments containing a preservative other than EDTA, the EDTA or a salt thereof, more particularly disodium EDTA, can be present in an amount of about 0.025% to about 0.1% by weight.

One or more antioxidants can also be included in the compositions. Suitable antioxidants include, but are not limited to, ascorbic acid, sodium metabisulfite, sodium bisulfite, acetylcysteine, polyquaternium-1, benzalkonium chloride, thimerosal, chlorobutanol, methyl paraben, propyl paraben, phenylethyl alcohol, edetate disodium, sorbic acid, or other agents know to those of skill in the art. Such preservatives are typically employed at a level of from about 0.001% to about 1.0% by weight.

In some embodiments, the compounds are solubilized at least in part by an acceptable solubilizing agent. Certain acceptable nonionic surfactants, for example polysorbate 80, can be useful as solubilizing agents, as can ophthalmically acceptable glycols, polyglycols, e.g., polyethylene glycol 400 (PEG-400), and glycol ethers.

Suitable solubilizing agents for solution and solution/suspension compositions are cyclodextrins. Suitable cyclodextrins can be chosen from α-cyclodextrin, β-cyclodextrin, γ-cyclodextrin, alkylcyclodextrins (e.g., methyl-β-cyclodextrin, dimethyl-β-cyclodextrin, diethyl-β-cyclodextrin), hydroxyalkylcyclodextrins (e.g., hydroxyethyl-β-cyclodextrin, hydroxypropyl-β-cyclodextrin), carboxy-alkylcyclodextrins (e.g., carboxymethyl-β-cyclodextrin), sulfoalkylether cyclodextrins (e.g., sulfobutylether-β-cyclodextrin), and the like. Ophthalmic applications of cyclodextrins have been reviewed in Rajewski et al., Journal of Pharmaceutical Sciences, 1996, 85, 1155-1159.

In some embodiments, the composition optionally contains a suspending agent. For example, in those embodiments in which the composition is an aqueous suspension or solution/suspension, the composition can contain one or more polymers as suspending agents. Useful polymers include, but are not limited to, water-soluble polymers such as cellulosic polymers, for example, hydroxypropyl methylcellulose, and water-insoluble polymers such as cross-linked carboxyl-containing polymers.

One or more acceptable pH adjusting agents and/or buffering agents can be included in the compositions, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

One or more acceptable salts can be included in the compositions in an amount required to bring osmolality of the composition into an acceptable range. Such salts include, but are not limited to, those having sodium, potassium or ammonium cations and chloride, citrate, ascorbate, borate, phosphate, bicarbonate, sulfate, thiosulfate or bisulfite anions. In some embodiments, salts include sodium chloride, potassium chloride, sodium thiosulfate, sodium bisulfite and ammonium sulfate. In some embodiments, the salt is sodium chloride.

Optionally one or more acceptable surfactants, preferably nonionic surfactants, or co-solvents can be included in the compositions to enhance solubility of the components of the compositions or to impart physical stability, or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40; polysorbate 20, 60 and 80; polyoxyethylene/polyoxypropylene surfactants (e.g., Pluronic® F-68, $F_{84}$ and P-103); cyclodextrin; or other agents known to those of skill in the art. Typically, such co-solvents or surfactants are employed in the compositions at a level of from about 0.01% to about 2% by weight.

In some embodiments, pharmaceutical packs or kits comprising one or more containers filled with one or more compounds described herein are provided. Optionally associated with such container(s) can be a notice in the form prescribed by a governmental agency regulating the manufacture, use or sale of pharmaceuticals or biological products, which notice reflects approval by the agency of manufacture, use or sale for human administration for treating a condition, disease, or disorder described herein. In some embodiments, the kit contains more than one compound described herein. In some embodiments, the kit comprises a compound described herein in a single injectable dosage form, such as a single dose within an injectable device such as a syringe with a needle.

Modulation of the $S_1P_1$ receptor has been found to be a target for the treatment of certain disorders. The compounds described herein can be used in the preparation of a medicament or pharmaceutical composition to treat and/or prevent neuropathy, pain, inflammatory pain, cancer pain, bone cancer pain, tumor pain, pain or neuropathy resulting from disorders of the central or peripheral nervous system, neuropathic pain, pain associated with dysesthesia, allodynia or hypersensitivity, chemotherapy induced neuropathic pain, chemotherapy induced peripheral neuropathy, diabetic neuropathy or pain associated with diabetic neuropathy, post herpetic neuralgia or pain associated with post herpetic neuralgia, hiv-related neuropathy or pain associated with hiv-related neuropathy, pain or neuropathy resulting from spinal cord injury, nerve lesions, tissue injury, ms, stroke, nutritional deficiencies, or toxins, fibromyalgia or pain associated with fibromyalgia, phantom limb pain, complex regional pain syndrome, carpal tunnel syndrome, sciatica, pudendal neuralgia, back or neck pain, including those resulting from degenerative disk disease, trigeminal neuralgia, headache disorders including, but not limited to migraine and cluster headache, orofacial pain, odontalgia, temporomandibular joint pain, endometrial pain, osteoarthritis, rheumatoid arthritis, atypical odontalgia, interstitial cystitis, uveitis, or any combination thereof.

Embodiments disclosed herein also provide for the compounds for the use of treating or preventing neuropathy, pain, inflammatory pain, cancer pain, bone cancer pain, tumor pain, pain or neuropathy resulting from disorders of the central or peripheral nervous system, neuropathic pain, pain associated with dysesthesia, allodynia or hypersensitivity, chemotherapy induced neuropathic pain, chemotherapy induced peripheral neuropathy, diabetic neuropathy or pain associated with diabetic neuropathy, post herpetic neuralgia or pain associated with post herpetic neuralgia, hiv-related neuropathy or pain associated with hiv-related neuropathy, pain or neuropathy resulting from spinal cord injury, nerve lesions, tissue injury, ms, stroke, nutritional deficiencies, or toxins, fibromyalgia or pain associated with fibromyalgia, phantom limb pain, complex regional pain syndrome, carpal tunnel syndrome, sciatica, pudendal neuralgia, back or neck pain, including those resulting from degenerative disk disease, trigeminal neuralgia, headache disorders including, but not limited to migraine and cluster headache, orofacial pain, odontalgia, temporomandibular joint pain, endometrial pain, osteoarthritis, rheumatoid arthritis, atypical odontalgia, interstitial cystitis, uveitis, or any combination thereof.

In some embodiments, methods of treating and/or preventing neuropathy, pain, inflammatory pain, cancer pain, bone cancer pain, tumor pain, pain or neuropathy resulting from disorders of the central or peripheral nervous system, neuropathic pain, pain associated with dysesthesia, allodynia or hypersensitivity, chemotherapy induced neuropathic pain, chemotherapy induced peripheral neuropathy, diabetic neuropathy or pain associated with diabetic neuropathy, post herpetic neuralgia or pain associated with post herpetic neuralgia, hiv-related neuropathy or pain associated with hiv-related neuropathy, pain or neuropathy resulting from spinal cord injury, nerve lesions, tissue injury, ms, stroke, nutritional deficiencies, or toxins, fibromyalgia or pain associated with fibromyalgia, phantom limb pain, complex regional pain syndrome, carpal tunnel syndrome, sciatica, pudendal neuralgia, back or neck pain, including those resulting from degenerative disk disease, trigeminal neuralgia, headache disorders including, but not limited to migraine and cluster headache, orofacial pain, odontalgia, temporomandibular joint pain, endometrial pain, osteoarthritis, rheumatoid arthritis, atypical odontalgia, interstitial cystitis, uveitis, or any combination thereof. In some embodiments, the methods comprise administering one or more of the compounds described herein, or pharmaceutically acceptable salts thereof, to the subject to treat or prevent such conditions. In some embodiments, the condition is CINP and CIPN, or other types of neuropathic pain or neuropathy. In some embodiments, the methods are performed without causing significant lymphopenia or immunosuppression. In some embodiments, the methods are performed without causing lymphopenia or immunosuppression.

In some embodiments, the compounds, or pharmaceutically acceptable salts thereof, are administered to the subject for any condition or indication provided for herein without causing significant lymphopenia or immunosuppression. In some embodiments, the methods are performed without causing lymphopenia or immunosuppression.

In some embodiments, the methods comprise administering to the subject one or more compounds described herein or a pharmaceutically acceptable salt thereof, or a pharmaceutical composition of the same. In some embodiments, the subject is a subject in need of such treatment.

As described herein, in some embodiments, the subject is a mammal, such as, but not limited to, a human.

In some embodiments, also provided are one or more compounds described above, or a pharmaceutically acceptable salt thereof, or a pharmaceutical composition comprising one or more compounds described above, for use in the manufacture of a medicament for the treatment of methods of treating and/or preventing pain, including, but not limited to the conditions described herein, in a subject, such as those described herein. In some embodiments, the subject is a subject in need thereof.

The present embodiments also provides the use of one or more compounds described above, or a pharmaceutically acceptable salt thereof, or a pharmaceutical composition comprising one or more compounds described above, in the modulation of a $S_1P_1$ receptor activity, such as the presence on the surface of the cell. In some embodiments, the compounds, pharmaceutically acceptable salt thereof, or a pharmaceutical composition of the same modulate the internalization, trafficking, and/or degradation of the $S_1P_1$ receptor. In some embodiments, the compounds, pharmaceutically acceptable salt thereof, or a pharmaceutical composition of the same modulate the G-protein modulated pathway of the $S_1P_1$ receptor.

As used herein, "modulation" can refer to either inhibition or enhancement of a specific activity. For example, the modulation of the $S_1P_1$ receptor can refer to the inhibition and/or activation of the G-protein mediated pathway of the $S_1P_1$ receptor. In some embodiments, the modulation refers to the inhibition or activation of the β-arrestin mediated pathway of the $S_1P_1$ receptor. In some embodiments, the modulation refers to the inhibition or activation of the internalization of the $S_1P_1$ receptor. The activity of a $S_1P_1$ receptor can be measured by any method including but not limited to the methods described herein.

The compounds described herein are agonists or antagonists of the $S_1P_1$ receptor. The ability of the compounds to stimulate or inhibit $S_1P_1$ receptor signaling may be measured using any assay known in the art used to detect $S_1P_1$ receptor mediated signaling or $S_1P_1$ receptor activity, or the absence of such signaling/activity. "$S_1P_1$ receptor activity" refers to the ability of a $S_1P_1$ receptor to transduce a signal. Such activity can be measured, e.g., in a heterologous cell, by coupling an $S_1P_1$ receptor (or a chimeric $S_1P_1$ receptor) to a downstream effector such as adenylate cyclase.

A "natural ligand-induced activity" as used herein, refers to activation of the $S_1P_1$ receptor by a natural ligand of the $S_1P_1$ receptor. Activity can be assessed using any number of endpoints to measure $S_1P_1$ receptor activity.

Generally, assays for testing compounds that modulate $S_1P_1$ receptor-mediated signal transduction include the determination of any parameter that is indirectly or directly under the influence of a $S_1P_1$ receptor, e.g., a functional, physical, or chemical effect.

Samples or assays comprising $S_1P_1$ receptors that are treated with a potential activator, inhibitor, or modulator are compared to control samples without the inhibitor, activator, or modulator to examine the extent of inhibition. Control samples (untreated with inhibitors) are assigned a relative $S_1P_1$ receptor activity value of 100%. Inhibition of a $S_1P_1$ receptor is achieved when the $S_1P_1$ receptor activity value relative to the control is about 80%, 50%, or 25%. Activation of a $S_1P_1$ receptor is achieved when the $S_1P_1$ receptor activity value relative to the control (untreated with activators) is 110%, 150%, or 200-500% (i.e., two to five fold higher relative to the control), or 1000-3000% or higher.

The effects of the compounds upon the function of an $S_1P_1$ receptor can be measured by examining any of the parameters described above. Any suitable physiological change that affects $S_1P_1$ receptor activity can be used to assess the influence of a compound on the $S_1P_1$ receptors and natural ligand-mediated $S_1P_1$ receptor activity. When the functional consequences are determined using intact cells or animals, one can also measure a variety of effects such as changes in intracellular second messengers such as cAMP.

Modulators of $S_1P_1$ receptor activity can be tested using $S_1P_1$ receptor polypeptides as described herein, either recombinant or naturally occurring. The protein can be isolated, expressed in a cell, expressed in a membrane derived from a cell, expressed in tissue or in an animal. For example, neuronal cells, cells of the immune system, transformed cells, or membranes can be used to test the $S_1P_1$ receptor polypeptides described herein. Modulation is tested using one of the in vitro or in vivo assays described herein. Signal transduction and cellular trafficking can also be examined in vitro with soluble or solid state reactions, using a chimeric molecule such as an extracellular domain of a receptor covalently linked to a heterologous signal transduction domain, or a heterologous extracellular domain covalently linked to the transmembrane and or cytoplasmic domain of a receptor. Furthermore, ligand-binding domains of the protein of interest can be used in vitro in soluble or solid state reactions to assay for ligand binding.

Ligand binding to an $S_1P_1$ receptor, a domain, or chimeric protein can be tested in a number of formats. Binding can be performed in solution, in a bilayer membrane, attached to a solid phase, in a lipid monolayer, or in vesicles. For example, in an assay, the binding of the natural ligand to its receptor is measured in the presence of a candidate modulator, such as the compound described herein. Alternatively, the binding of the candidate modulator may be measured in the presence of the natural ligand. Often, competitive assays that measure the ability of a compound to compete with binding of the natural ligand to the receptor are used. Binding can be tested by measuring, e.g., changes in spectroscopic characteristics (e.g., fluorescence, absorbance, refractive index), hydrodynamic (e.g., shape) changes, or changes in chromatographic or solubility properties. Another technology that can be used to evaluate SiPi receptor-protein interactions in living cells involves bioluminescence resonance energy transfer (BRET). A detailed discussion regarding BRET can be found in Kroeger et al., J. Biol. Chem., 276(16):12736 43 (2001).

After the receptor is expressed in a cell the cells can be grown in appropriate media in the appropriate cell plate. The cells can be plated, for example at 5000-10000 cells per well in a 384 well plate. In some embodiments, the cells are plated at about 1000, 2000, 3000, 4000, 5000, 6000, 7000, 8000, 9000, or 10000 cells/per well. The plates can have any number of wells and the number of cells can be modified accordingly.

Any medicament having utility in an application described herein can be used in co-therapy, co-administration or co-formulation with a composition as described above. Such additional medicaments include, medicines for cancer. Many medicines that are used to treat cancer cause CIPN or CINP. Therefore, the compounds described herein can be administered either before, concurrently with, or after such therapeutics are administered to a subject. Non-limiting examples of such therapeutics include, but are not limited to: Platinum-based drugs, such as but not limited to, carboplatin (Paraplatin), cisplatin, oxaliplatin; taxanes: paclitaxel (Taxol), paclitaxel nanoparticle albumin-bound (Abraxane), docetaxel (Taxotere), and cabazitaxel (Jevtana); Epothilones, such as ixabepilone (Ixempra); Plant alkaloids: vinblastine (Velban, Alkaban-AQ), vincristine (Oncovin, Vincasar PES, Vincrex), vinorelbine (Navelbine), and etoposide (Toposar, VePesid, Etopophos); halidomide (Thalomid), lenalidomide (Revlimid), and pomalidomide (Pomalyst), Bortezomib (Velcade); carfilzomib (Kyprolis), and Eribulin (Halaven). Other examples of therapeutics that the presently described compounds can be combined with include, but are not limited to, Abitrexate (Methotrexate Injection), Abraxane (Paclitaxel Injection), Adcetris (Brentuximab Vedotin Injection), Adriamycin (Doxorubicin), Adrucil Injection (5-FU (fluorouracil)), Afinitor (Everolimus), Afinitor Disperz (Everolimus), Alimta (PEMETREXED), Alkeran Injection (Melphalan Injection), Alkeran Tablets (Melphalan), Aredia (Pamidronate), Arimidex (Anastrozole), Aromasin (Exemestane), Arranon (Nelarabine), Arzerra (Ofatumumab Injection), Avastin (Bevacizumab), Beleodaq (Belinostat Injection), Bexxar (Tositumomab), BiCNU (Carmustine), Blenoxane (Bleomycin), Blincyto (Blinatumomab Injection), Bosulif (Bosutinib), Busulfex Injection (Busulfan Injection), Campath (Alemtuzumab), Camptosar (Irinotecan), Caprelsa (Vandetanib), Casodex (Bicalutamide), CeeNU (Lomustine), CeeNU Dose Pack (Lomustine), Cerubidine (Daunorubicin), Clolar (Clofarabine Injection), Cometriq (Cabozantinib), Cosmegen (Dactinomycin), Cotellic (Cobimetinib), Cyramza (Ramucirumab Injection), CytosarU (Cytarabine), Cytoxan (Cytoxan), Cytoxan Injection (Cyclophosphamide Injection), Dacogen (Decitabine), DaunoXome (Daunorubicin Lipid Complex Injection), Decadron (Dexamethasone), DepoCyt (Cytarabine Lipid Complex Injection), Dexamethasone Intensol (Dexamethasone), Dexpak Taperpak (Dexamethasone), Docefrez (Docetaxel), Doxil (Doxorubicin Lipid Complex Injection), Droxia (Hydroxyurea), DTIC (Decarbazine), Eligard (Leuprolide), Ellence (Ellence (epirubicin)), Eloxatin (Eloxatin (oxaliplatin)), Elspar (Asparaginase), Emcyt (Estramustine), Erbitux (Cetuximab), Erivedge (Vismodegib), Erwinaze (Asparaginase *Erwinia chrysanthemi*), Ethyol (Amifostine), Etopophos (Etoposide Injection), Eulexin (Flutamide), Fareston (Toremifene), Farydak (Panobinostat), Faslodex (Fulvestrant), Femara (Letrozole), Firmagon (Degarelix Injection), Fludara (Fludarabine), Folex (Methotrexate Injection), Folotyn (Pralatrexate Injection), FUDR (FUDR (floxuridine)), Gazyva (Obinutuzumab Injection), Gemzar (Gemcitabine), Gilotrif (Afatinib), Gleevec (Imatinib Mesylate), Gliadel Wafer (Carmustine wafer), Used to treat, Brain Tumors Halaven (Eribulin Injection), Herceptin (Trastuzumab), Hexalen (Altretamine), Hycamtin (Topotecan), Hycamtin (Topotecan), Hydrea (Hydroxyurea), Ibrance (Palbociclib), Iclusig (Ponatinib), Idamycin PFS (Idarubicin), Ifex (Ifosfamide), Imbruvica (Ibrutinib), Inlyta (Axitinib), Intron A alfab (Interferon alfa-2a), Iressa (Gefitinib), Istodax (Romidepsin Injection), Ixempra (Ixabepilone Injection), Jakafi (Ruxolitinib), Jevtana (Cabazitaxel Injection), Kadcyla (Ado-trastuzumab Emtansine), Keytruda (Pembrolizumab Injection), Kyprolis (Carfilzomib), Lanvima (Lenvatinib), Leukeran (Chlorambucil), Leukine (Sargramostim), Leustatin (Cladribine), Lonsurf (Trifluridine and Tipiracil), Lupron (Leuprolide), Lupron Depot (Leuprolide), Lupron DepotPED (Leuprolide), Lynparza (Olaparib), Lysodren (Mitotane), Marqibo Kit (Vincristine Lipid Complex Injection), Matulane (Procarbazine), Megace (Megestrol), Mekinist (Trametinib), Mesnex (Mesna), Mesnex (Mesna Injection), Metastron (Strontium-89 Chloride), Mexate (Methotrexate Injection), Mustargen (Mechlorethamine), Mutamycin (Mitomycin), Myleran (Busulfan), Mylotarg (Gemtuzumab Ozogamicin), Navelbine (Vinorelbine), Neosar Injection (Cyclophosphamide Injection), Neulasta (filgrastim), Neulasta (pegfilgrastim), Neupogen (filgrastim), Nexavar (Sorafenib), Nilandron (Nilandron (nilutamide)), Nipent (Pentostatin), Nolvadex (Tamoxifen), Novantrone (Mitoxantrone), Odomzo (Sonidegib), Oncaspar (Pegaspargase), Oncovin (Vincristine), Ontak (Denileukin Diftitox), Onxol (Paclitaxel Injection), Opdivo (Nivolumab Injection), Paraplatin (Carboplatin), Perjeta (Pertuzumab Injection), Platinol (Cisplatin), Platinol (Cisplatin Injection), PlatinolAQ (Cisplatin), PlatinolAQ (Cisplatin Injection), Pomalyst (Pomalidomide), Prednisone Intensol (Prednisone), Proleukin (Aldesleukin), Purinethol (Mercaptopurine), Reclast (Zoledronic acid), Revlimid (Lenalidomide), Rheumatrex (Methotrexate), Rituxan (Rituximab), RoferonA alfaa (Interferon alfa-2a), Rubex (Doxorubicin), Sandostatin (Octreotide), Sandostatin LAR Depot (Octreotide), Soltamox (Tamoxifen), Sprycel (Dasatinib), Sterapred (Prednisone), Sterapred DS (Prednisone), Stivarga (Regorafenib), Supprelin LA (Histrelin Implant), Sutent (Sunitinib), Sylatron (Peginterferon Alfa-2b Injection (Sylatron)), Sylvant (Siltuximab Injection), Synribo (Omacetaxine Injection), Tabloid (Thioguanine), Taflinar (Dabrafenib), Tarceva (Erlotinib), Targretin Capsules (Bexarotene), Tasigna (Decarbazine), Taxol (Paclitaxel Injection), Taxotere (Docetaxel), Temodar (Temozolomide), Temodar (Temozolomide Injection), Tepadina (Thiotepa), Thalomid (Thalidomide), TheraCys BCG (BCG), Thioplex (Thiotepa), TICE BCG (BCG), Toposar (Etoposide Injection), Torisel (Temsirolimus), Treanda (Bendamustine hydrochloride), Trelstar (Triptorelin Injection), Trexall (Methotrexate), Trisenox (Arsenic trioxide), Tykerb (lapatinib), Unituxin (Dinutuximab Injection), Valstar (Valrubicin Intravesical), Vantas (Histrelin Implant), Vectibix (Panitumumab), Velban (Vinblastine), Velcade (Bortezomib), Vepesid (Etoposide), Vepesid (Etoposide Injection), Vesanoid (Tretinoin), Vidaza (Azacitidine), Vincasar PFS (Vincristine), Vincrex (Vincristine), Votrient (Pazopanib), Vumon (Teniposide), Wellcovorin IV (Leucovorin Injection), Xalkori (Crizotinib), Xeloda (Capecitabine), Xtandi (Enzalutamide), Yervoy (Ipilimumab Injection), Yondelis (Trabectedin Injection), Zaltrap (Ziv-aflibercept Injection), Zanosar (Streptozocin), Zelboraf (Vemurafenib), Zevalin (Ibritumomab Tiuxetan), Zoladex (Goserelin), Zolinza (Vorinostat), Zometa (Zoledronic acid), Zortress (Everolimus), Zydelig (Idelalisib), Zykadia (Ceritinib), Zytiga (Abiraterone), or any combination thereof. Other examples include, but are not limited to, PD-1 antibodies, such as Nivolumab or Pembrolizumab. In some embodiments, the compounds, or pharmaceutically acceptable salts thereof, provided herein can be administered with, either concurrently or sequentially, or as part of a cancer treatment protocol, the additional therapeutics provided for herein.

In some embodiments, the compounds provided herein can also be used to treat cancer. In some embodiments, the compounds, or pharmaceutically acceptable salts thereof, can be used to inhibit tumor growth. In some embodiments, the compounds, or pharmaceutically acceptable salts thereof, are used to treat cancers, such as, but not limited to, ovarian cancer, breast cancer, lung cancer, brain cancer, colon cancer, prostate cancer, esophageal cancer, pancreatic cancer, brain cancer, glioblastoma cancer, leukemia, multiple myeloma, lymphoma, skin cancer, acute Lymphoblastic Leukemia, acute myeloid leukemia, basal cell cancer, bile duct cancer, bladder cancer, bone cancer (Ewing sarcoma, osteosarcoma), CLL, CML, uterine cancer, cervical cancer, hairy cell leukemia, melanoma, thyroid cancer, rectal cancer, renal cell cancer, small cell lung cancer, non-small cell lung cancer, or stomach cancer. In some embodiments, the cancer is breast or ovarian cancer. In some embodiments, the compounds, or pharmaceutically acceptable salts thereof, provided herein are combined with a taxane, such as paclitaxel.

The additional medicament can be administered in co-therapy (including co-formulation) with the one or more of the compounds described herein.

In some embodiments, the response of the disease or disorder to the treatment is monitored and the treatment regimen is adjusted if necessary in light of such monitoring.

Frequency of administration is typically such that the dosing interval, for example, the period of time between one dose and the next, during waking hours is from about 2 to about 12 hours, from about 3 to about 8 hours, or from about 4 to about 6 hours. It will be understood by those of skill in the art that an appropriate dosing interval is dependent to some degree on the length of time for which the selected composition is capable of maintaining a concentration of the compound(s) in the subject and/or in the target tissue (e.g., above the $EC_{50}$ (the minimum concentration of the compound which modulates the receptor's activity by 90%). Ideally the concentration remains above the $EC_{50}$ for at least 100% of the dosing interval. Where this is not achievable it is desired that the concentration should remain above the $EC_{50}$ for at least about 60% of the dosing interval, or should remain above the $EC_{50}$ for at least about 40% of the dosing interval.

The present disclosure also provides the following non-limiting embodiments: In order that the embodiments disclosed herein may be more efficiently understood, examples are provided below. It should be understood that these examples are for illustrative purposes only and are not to be construed as limiting the embodiments in any manner. Throughout these examples, there may be molecular cloning reactions, and other standard recombinant DNA techniques described and these were carried out according to methods described in Maniatis et al., Molecular Cloning—A Laboratory Manual, 2nd ed., Cold Spring Harbor Press (1989), using commercially available reagents, except where otherwise noted.

The following examples are illustrative, but not limiting, of the methods and compositions described herein. Other suitable modifications and adaptations of the variety of conditions and parameters normally encountered in therapy, synthesis, and other embodiments disclosed herein are within the spirit and scope of the embodiments.

EXAMPLES

Example 1: Synthesis of Compounds

Certain synthetic schemes, both general and specific, are provided herein. The compounds disclosed herein can be made according to the methods described herein or intermediates that lead to the compounds disclosed herein can be made according to the methods described herein. The substitutions can be varied according to the compound or intermediate being made based upon the following examples and other modifications known to one of skill in the art.

The following compounds were prepared according to the following examples or the examples were varied according to one of skill in the art to prepare the compounds.

| Structure | Compound Number | Chemical Name | Exact Mass | Actual Peak |
|---|---|---|---|---|
| 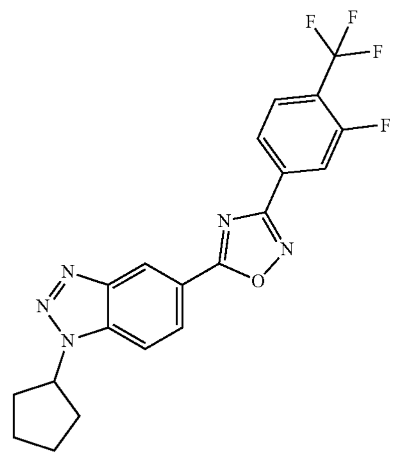 [SMILES: Fc1cc(-c2noc(-c3ccc4c(c3)nnn4C3CCCC3)n2)ccc1C(F)(F)F] | 1 | 1-cyclopentyl-5-{3-[3-fluoro-4-(trifluoromethyl)phenyl]-1,2,4-oxadiazol-5-yl}-1H-1,2,3-benzotriazole | 417.37 | 418.1 |
| 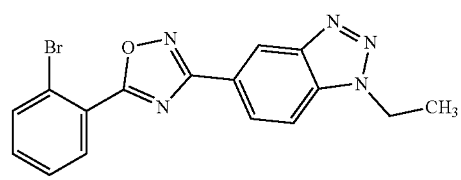 [SMILES: CCn1nnc2cc(-c3noc(-c4ccccc4Br)n3)ccc21] | 2 | 5-(2-bromophenyl)-3-(1-ethyl-1H-benzo[d][1,2,3]triazol-5-yl)-1,2,4-oxadiazole | 370.21 | 371 |
| 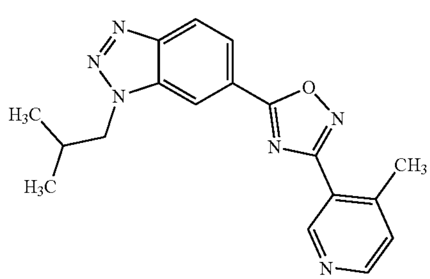 [SMILES: Cc1ccncc1-c1noc(-c2ccc3nnn(CC(C)C)c3c2)n1] | 3 | 1-(2-methylpropyl)-6-[3-(4-methylpyridin-3-yl)-1,2,4-oxadiazol-5-yl]-1H-1,2,3-benzotriazole | 334.38 | 355.2 |
| 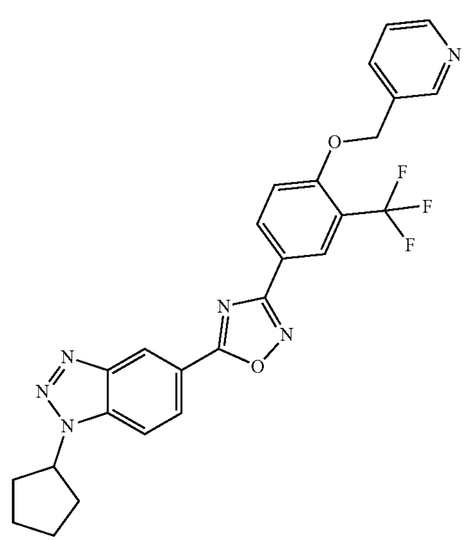 [SMILES: FC(F)(F)c1cc(-c2noc(-c3ccc4c(c3)nnn4C3CCCC3)n2)ccc1OCc1cccnc1] | 4 | 1-cyclopentyl-5-{3-[4-(pyridin-3-ylmethoxy)-3-(trifluoromethyl)phenyl]-1,2,4-oxadiazol-5-yl}-1H-1,2,3-benzotriazole | 506.49 | 507.2 |

-continued

| Structure | Compound Number | Chemical Name | Exact Mass | Actual Peak |
|---|---|---|---|---|
| 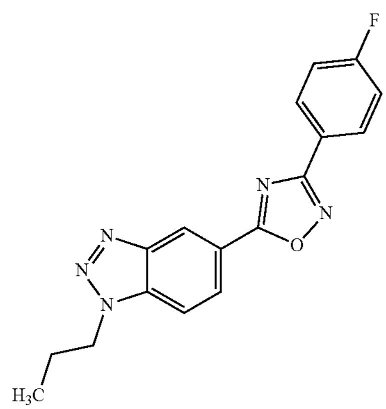 [SMILES: CCCn1nnc2cc(-c3nc(-c4ccc(F)cc4)no3)ccc21] | 5 | 5-[3-(4-fluorophenyl)-1,2,4-oxadiazol-5-yl]-1-propyl-1H-1,2,3-benzotriazole | 323.33 | 324.2 |
| 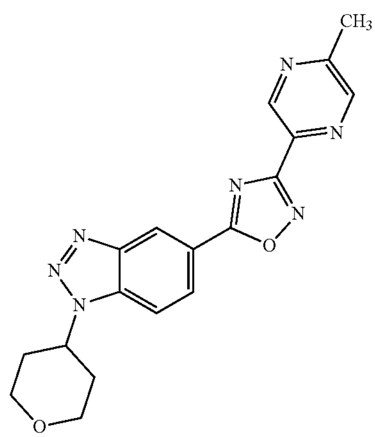 [SMILES: Cc1cnc(-c2noc(-c3ccc4c(c3)nnn4C3CCOCC3)n2)cn1] | 6 | 5-[3-(5-methylpyrazin-2-yl)-1,2,4-oxadiazol-5-yl]-1-(oxan-4-yl)-1H-1,2,3-benzotriazole | 363.38 | 364.1 |
| 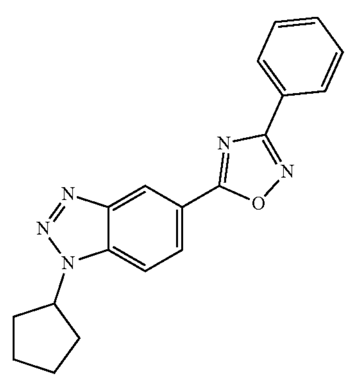 [SMILES: c1ccc(-c2noc(-c3ccc4c(c3)nnn4C3CCCC3)n2)cc1] | 7 | 1-cyclopentyl-5-(3-phenyl-1,2,4-oxadiazol-5-yl)-1H-1,2,3-benzotriazole | 331.38 | 332.1 |
| 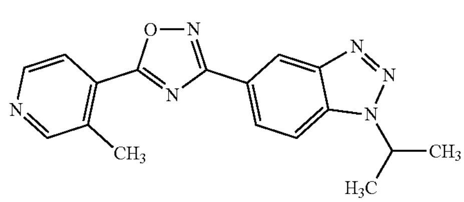 [SMILES: Cc1cnccc1-c1nc(-c2ccc3c(c2)nnn3C(C)C)no1] | 8 | 3-(1-isopropyl-1H-benzo[d][1,2,3]triazol-5-yl)-5-(3-methylpyridin-4-yl)-1,2,4-oxadiazole | 320.36 | 321 |

-continued
| Structure | Compound Number | Chemical Name | Exact Mass | Actual Peak |
|---|---|---|---|---|
| 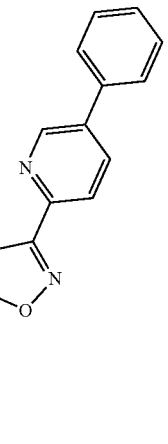 | 9 | 5-[3-(5-phenylpyridin-2-yl)-1,2,4-oxadiazol-5-yl]-1-(propan-2-yl)-1H-1,2,3-benzotriazole | 382.43 | 383.1 |
| 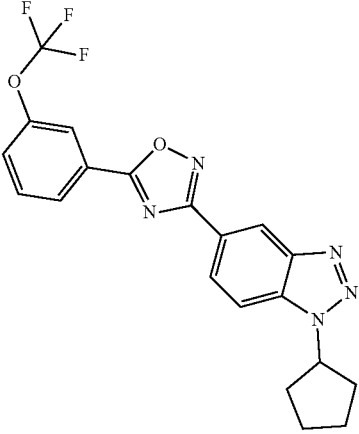 [SMILES: FC(F)(F)Oc1cccc(-c2nc(-c3ccc4c(c3)nnn4C3CCCC3)no2)c1] | 10 | 3-(1-cyclopentyl-1H-benzo[d][1,2,3]triazol-5-yl)-5-(3-(trifluoromethoxy)phenyl)-1,2,4-oxadiazole | 415.38 | 416.1 |
| 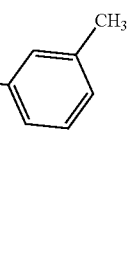 | 11 | 1-cyclohexyl-5-[3-(3-methylphenyl)-1,2,4-oxadiazol-5-yl]-1H-1,2,3-benzotriazole | 359.43 | 360.2 |

-continued

| Structure | Compound Number | Chemical Name | Exact Mass | Actual Peak |
|---|---|---|---|---|
| 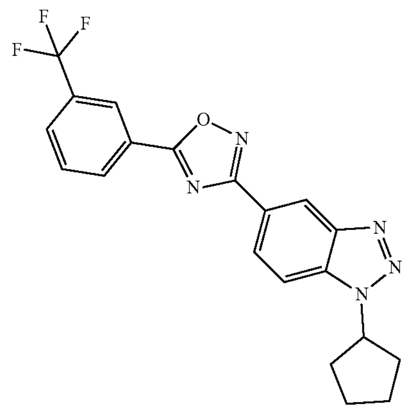 [SMILES: FC(F)(F)c1cccc(-c2nc(-c3ccc4c(c3)nnn4C3CCCC3)no2)c1] | 12 | 3-(1-cyclopentyl-1H-benzo[d][1,2,3]triazol-5-yl)-5-(3-(trifluoromethyl)phenyl)-1,2,4-oxadiazole | 399.38 | 400.1 |
| 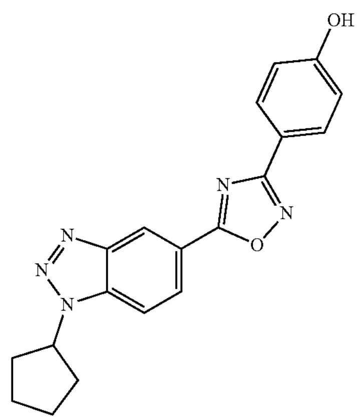 [SMILES: Oc1ccc(-c2noc(-c3ccc4c(c3)nnn4C3CCCC3)n2)cc1] | 13 | 4-[5-(1-cyclopentyl-1H-1,2,3-benzotriazol-5-yl)-1,2,4-oxadiazol-3-yl]phenol | 347.38 | 348.1 |
| 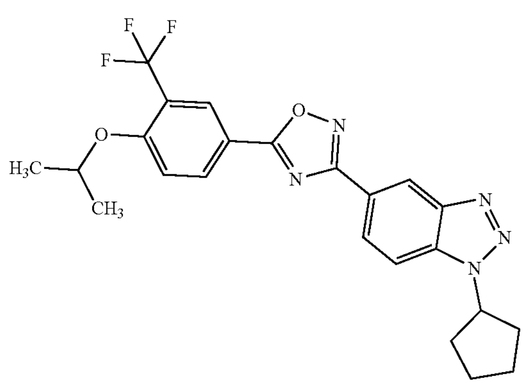 [SMILES: CC(C)Oc1ccc(-c2nc(-c3ccc4c(c3)nnn4C3CCCC3)no2)cc1C(F)(F)F] | 14 | 3-(1-cyclopentyl-1H-benzo[d][1,2,3]triazol-5-yl)-5-(4-isopropoxy-3-(trifluoromethyl)phenyl)-1,2,4-oxadiazole | 457.46 | 458.1 |

-continued

| Structure | Compound Number | Chemical Name | Exact Mass | Actual Peak |
|---|---|---|---|---|
| 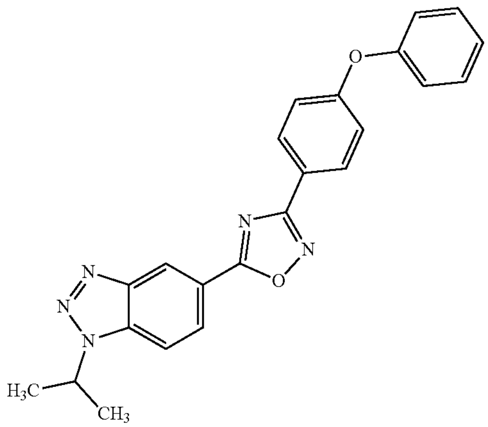 [SMILES: CC(C)n1nnc2cc(-c3nc(-c4ccc(Oc5ccccc5)cc4)no3)ccc21] | 15 | 5-[3-(4-phenoxyphenyl)-1,2,4-oxadiazol-5-yl]-1-(propan-2-yl)-1H-1,2,3-benzotriazole | 397.44 | 398.2 |
| 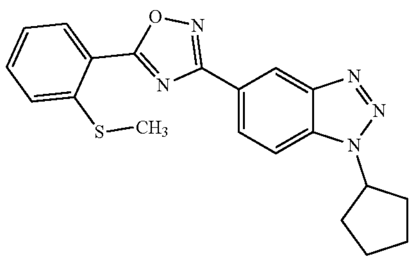 [SMILES: CSc1ccccc1-c1nc(-c2ccc3c(c2)nnn3C2CCCC2)no1] | 16 | 3-(1-cyclopentyl-1H-benzo[d][1,2,3]triazol-5-yl)-5-(2-(methylthio)phenyl)-1,2,4-oxadiazole | 377.47 | 378.1 |
| 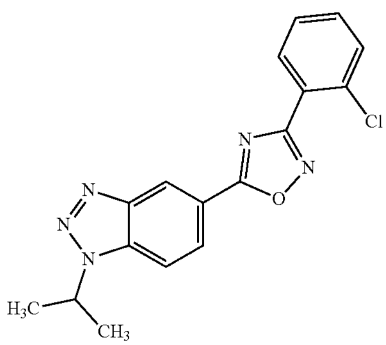 [SMILES: CC(C)n1nnc2cc(-c3nc(-c4ccccc4Cl)no3)ccc21] | 17 | 5-[3-(2-chlorophenyl)-1,2,4-oxadiazol-5-yl]-1-(propan-2-yl)-1H-1,2,3-benzotriazole | 339.78 | 340.1 |
| 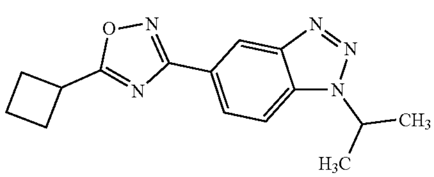 [SMILES: CC(C)n1nnc2cc(-c3noc(C4CCC4)n3)ccc21] | 18 | 5-(5-cyclobutyl-1,2,4-oxadiazol-3-yl)-1-(propan-2-yl)-1H-1,2,3-benzotriazole | 283.34 | 284 |
| 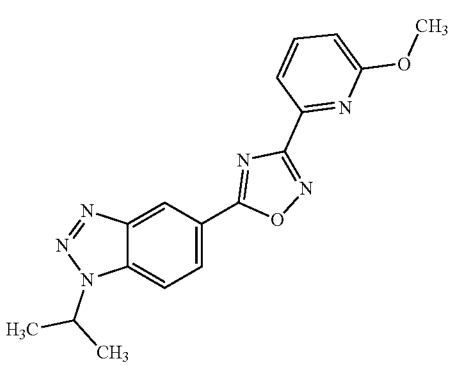 [SMILES: COc1cccc(-c2noc(-c3ccc4c(c3)nnn4C(C)C)n2)n1] | 19 | 5-[3-(6-methoxypyridin-2-yl)-1,2,4-oxadiazol-5-yl]-1-(propan-2-yl)-1H-1,2,3-benzotriazole | 336.36 | 337.1 |

-continued

| Structure | Compound Number | Chemical Name | Exact Mass | Actual Peak |
|---|---|---|---|---|
| 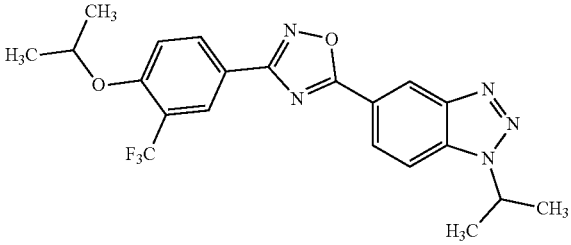 [SMILES: CC(C)Oc1ccc(-c2noc(-c3ccc4c(c3)nnn4C(C)C)n2)cc1C(F)(F)F] | 20 | 3-(4-isopropoxy-3-(trifluoromethyl)phenyl)-5-(1-isopropyl-1H-benzo[d][1,2,3]triazol-5-yl)-1,2,4-oxadiazole | 431.42 | 432 |
| 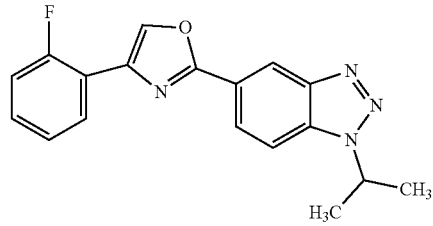 [SMILES: CC(C)n1nnc2cc(-c3nc(-c4ccccc4F)co3)ccc21] | 21 | 5-[4-(2-fluorophenyl)-1,3-oxazol-2-yl]-1-(propan-2-yl)-1H-1,2,3-benzotriazole | 322.34 | 323 |
| 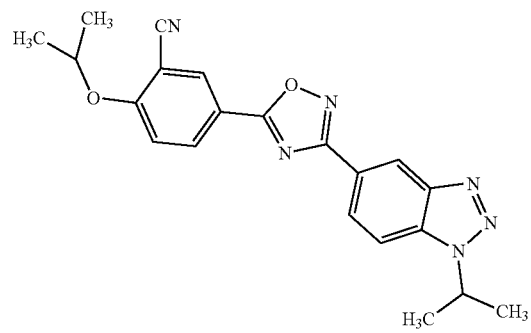 [SMILES: CC(C)Oc1ccc(-c2nc(-c3ccc4c(c3)nnn4C(C)C)no2)cc1C#N] | 22 | 2-isopropoxy-5-(3-(1-isopropyl-1H-benzo[d][1,2,3]triazol-5-yl)-1,2,4-oxadiazol-5-yl)benzonitrile | 388.43 | 389 |
| 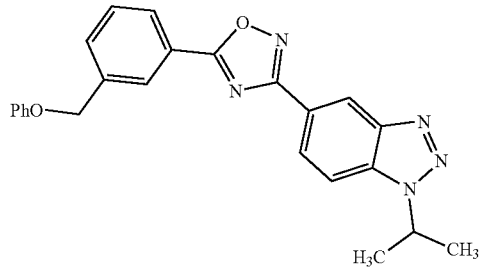 [SMILES: CC(C)n1nnc2cc(-c3noc(-c4cccc(COc5ccccc5)c4)n3)ccc21] | 23 | 3-(1-isopropyl-1H-benzo[d][1,2,3]triazol-5-yl)-5-(3-(phenoxymethyl)phenyl)-1,2,4-oxadiazole | 411.47 | 412 |
| 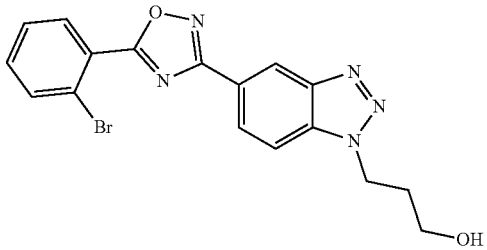 [SMILES: OCCCn1nnc2cc(-c3noc(-c4ccccc4Br)n3)ccc21] | 24 | 3-(5-(5-(2-bromophenyl)-1,2,4-oxadiazol-3-yl)-1H-benzo[d][1,2,3]triazol-1-yl)propan-1-ol | 400.24 | 400 |

-continued

| Structure | Compound Number | Chemical Name | Exact Mass | Actual Peak |
|---|---|---|---|---|
| 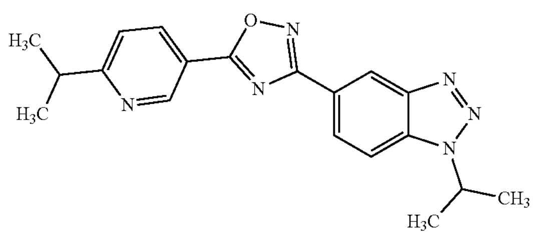 [SMILES: CC(C)c1ccc(-c2nc(-c3ccc4c(c3)nnn4C(C)C)no2)cn1] | 25 | 3-(1-isopropyl-1H-benzo[d][1,2,3]triazol-5-yl)-5-(6-isopropylpyridin-3-yl)-1,2,4-oxadiazole | 348.41 | 349.3 |
| 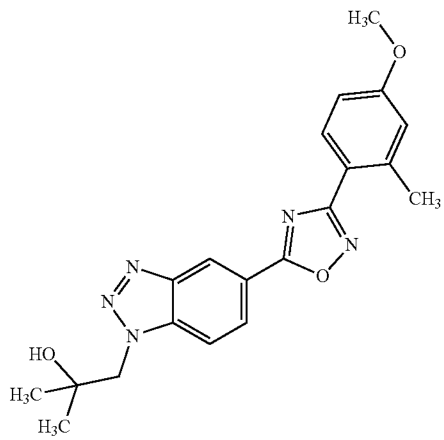 [SMILES: COc1ccc(-c2noc(-c3ccc4c(c3)nnn4CC(C)(C)O)n2)c(C)c1] | 26 | 1-{5-[3-(4-methoxy-2-methylphenyl)-1,2,4-oxadiazol-5-yl]-1H-1,2,3-benzotriazol-1-yl}-2-methylpropan-2-ol | 379.42 | 380.1 |
| 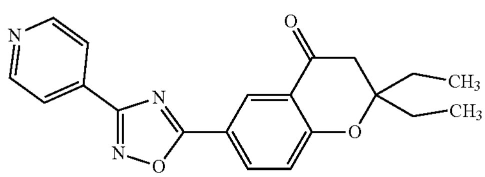 [SMILES: CCC1(CC)CC(=O)c2cc(-c3nc(-c4ccncc4)no3)ccc2O1] | 27 | 2,2-diethyl-6-[3-(pyridin-4-yl)-1,2,4-oxadiazol-5-yl]-3,4-dihydro-2H-1-benzopyran-4-one | 349.39 | 350.1 |
| 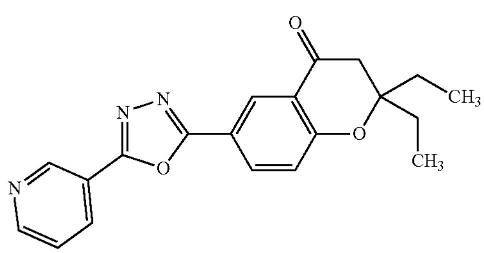 [SMILES: CCC1(CC)CC(=O)c2cc(-c3nnc(-c4cccnc4)o3)ccc2O1] | 28 | 2,2-diethyl-6-(5-(pyridin-3-yl)-1,3,4-oxadiazol-2-yl)chroman-4-one | 349.39 | 350.1 |
| 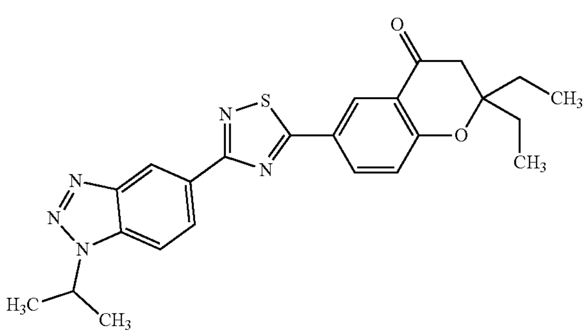 [SMILES: CCC1(CC)CC(=O)c2cc(-c3nc(-c4ccc5c(c4)nnn5C(C)C)ns3)ccc2O1] | 29 | 2,2-diethyl-6-(3-(1-isopropyl-1H-benzo[d][1,2,3]triazol-5-yl)-1,2,4-thiadiazol-5-yl)chroman-4-one | 447.56 | 448.2 |

-continued

| Structure | Compound Number | Chemical Name | Exact Mass | Actual Peak |
|---|---|---|---|---|
| 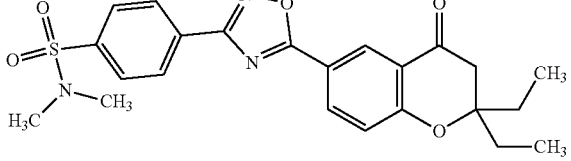 | 30 | 4-(5-(2,2-diethyl-4-oxochroman-6-yl)-1,2,4-oxadiazol-3-yl)-N,N-dimethylbenzenesulfonamide | 455.53 | 456.1 |
| 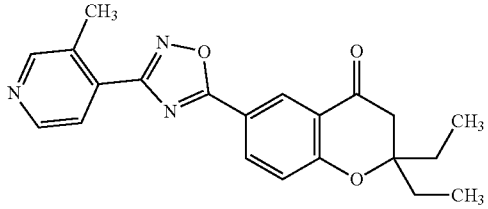 [SMILES: CCC1(CC)CC(=O)c2cc(-c3nc(-c4ccncc4C)no3)ccc2O1] | 31 | 2,2-diethyl-6-(3-(3-methylpyridin-4-yl)-1,2,4-oxadiazol-5-yl)chroman-4-one | 363.42 | 364.2 |
| 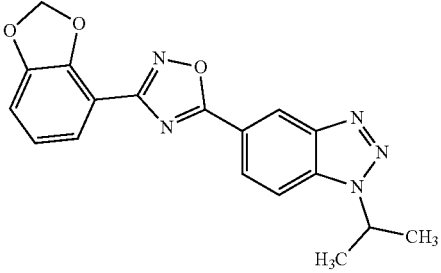 [SMILES: CC(C)n1nnc2cc(-c3nc(-c4cccc5c4OCO5)no3)ccc21] | 32 | 3-(benzo[d][1,3]dioxol-4-yl)-5-(1-isopropyl-1H-benzo[d][1,2,3]triazol-5-yl)-1,2,4-oxadiazole | 349.35 | 350.1 |
| 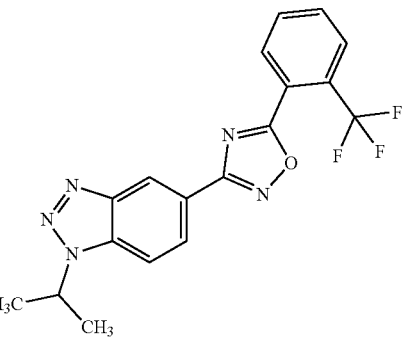 | 33 | 3-(1-isopropylbenzotriazol-5-yl)-5-{2-(trifluoromethyl)phenyl]-1,2,4-oxadiazole | 373.34 | 374.1 |
| 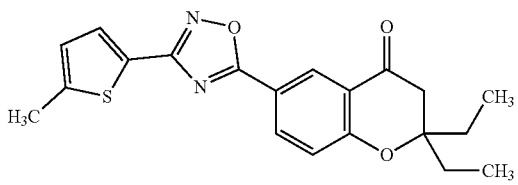 [SMILES: CCC1(CC)CC(=O)c2cc(-c3nc(-c4ccc(C)s4)no3)ccc2O1] | 34 | 2,2-diethyl-6-(3-(5-methylthiophen-2-yl)-1,2,4-oxadiazol-5-yl)chroman-4-one | 368.45 | 369.3 |
| 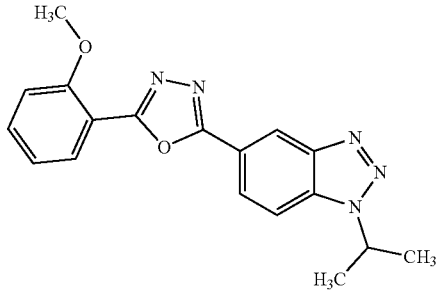 [SMILES: COc1ccccc1-c1nnc(-c2ccc3c(c2)nnn3C(C)C)o1] | 35 | 5-[5-(2-methoxyphenyl)-1,3,4-oxadiazol-2-yl]-1-(propan-2-yl)-1H-1,2,3-benzotriazole | 335.37 | 336 |

-continued

| Structure | Compound Number | Chemical Name | Exact Mass | Actual Peak |
|---|---|---|---|---|
| 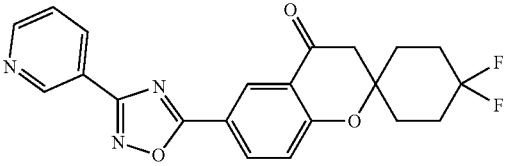 [SMILES: O=C1CC2(CCC(F)(F)CC2)Oc2ccc(-c3nc(-c4cccnc4)no3)cc21] | 36 | 4',4'-difluoro-6-[3-(pyridin-3-yl)-1,2,4-oxadiazol-5-yl]-3,4-dihydrospiro[1-benzopyran-2,1'-cyclohexane]-4-one | 397.38 | 298.1 |
| 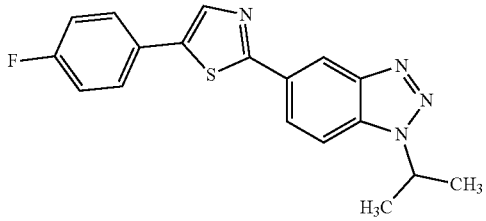 [SMILES: CC(C)n1nnc2cc(-c3ncc(-c4ccc(F)cc4)s3)ccc21] | 37 | 5-(4-fluorophenyl)-2-(1-isopropylbenzotriazol-5-yl)thiazole | 338.40 | 339.2 |
| 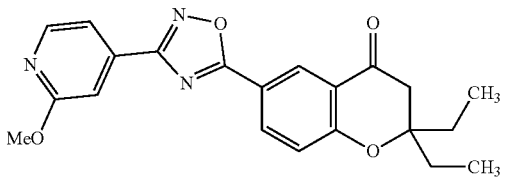 [SMILES: CCC1(CC)CC(=O)c2cc(-c3nc(-c4ccnc(OC)c4)no3)ccc2O1] | 38 | 2,2-diethyl-6-(3-(2-methoxypyridin-4-yl)-1,2,4-oxadiazol-5-yl)chroman-4-one | 379.42 | 380.1 |
| 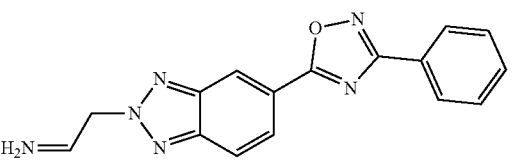 | 39 | 5-(3-phenyl-1,2,4-oxadiazol-5-yl)-2-(prop-2-en-1-yl)-2H-1,2,3-benzotriazole | 303.33 | 304.3 |
| 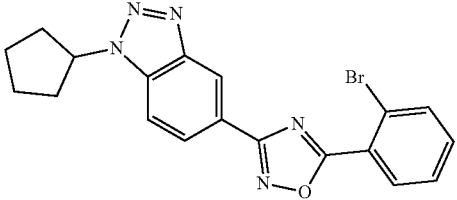 [SMILES: Brc1ccccc1-c1nc(-c2ccc3c(c2)nnn3C2CCCC2)no1] | 40 | 5-(2-bromophenyl)-3-(1-cyclopentyl-1H-benzo[d][1,2,3]triazol-5-yl)-1,2,4-oxadiazole | 410.28 | 409.9 |
| 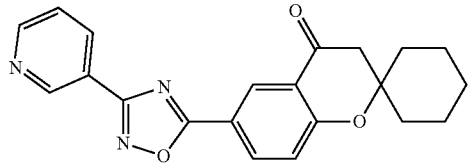 [SMILES: O=C1CC2(CCCCC2)Oc2ccc(-c3nc(-c4cccnc4)no3)cc21] | 41 | 6-[3-(pyridin-3-yl)-1,2,4-oxadiazol-5-yl]-3,4-dihydrospiro[1-benzopyran-2,1'-cyclohexane]-4-one | 361.40 | 362.1 |
| 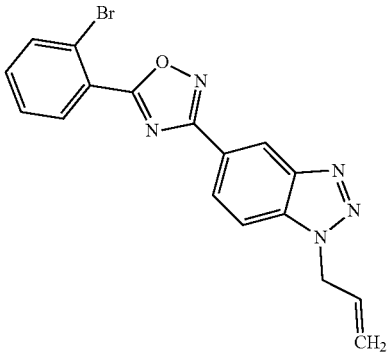 [SMILES: C=CCn1nnc2cc(-c3noc(-c4ccccc4Br)n3)ccc21] | 42 | 3-(1-allyl-1H-benzo[d][1,2,3]triazol-5-yl)-5-(2-bromophenyl)-1,2,4-oxadiazole | 382.22 | 382 |

-continued

| Structure | Compound Number | Chemical Name | Exact Mass | Actual Peak |
|---|---|---|---|---|
| 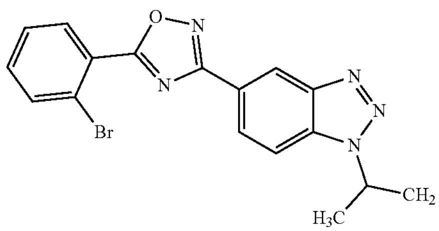 | 43 | 5-(2-bromophenyl)-3-(1-isopropyl-1H-benzo[d][1,2,3]triazol-5-yl)-1,2,4-oxadiazole | 384.24 | 384 |
| 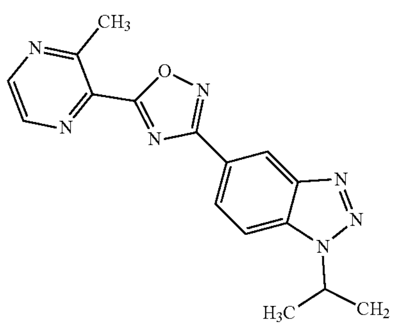 [SMILES: Cc1nccnc1-c1nc(-c2ccc3c(c2)nnn3C(C)C)no1] | 44 | 3-(1-isopropyl-1H-benzo[d][1,2,3]triazol-5-yl)-5-(3-methylpyrazin-2-yl)-1,2,4-oxadiazole | 321.34 | 322.1 |
| 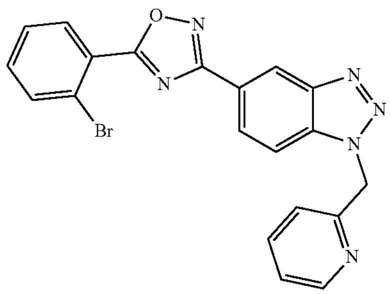 [SMILES: Brc1ccccc1-c1nc(-c2ccc3c(c2)nnn3Cc2ccccn2)no1] | 45 | 5-(2-bromophenyl)-3-(1-(pyridin-2-ylmethyl)-1H-benzo[d][1,2,3]triazol-5-yl)-1,2,4-oxadiazole | 433.27 | 435.1 |
| 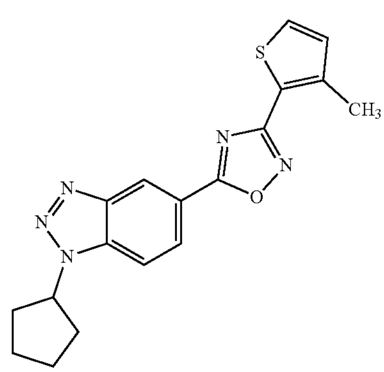 [SMILES: Cc1ccsc1-c1noc(-c2ccc3c(c2)nnn3C2CCCC2)n1] | 46 | 1-cyclopentyl-5-[3-(3-methylthiophen-2-yl)-1,2,4-oxadiazol-5-yl]-1H-1,2,3-benzotriazole | 351.43 | 352.1 |

-continued

| Structure | Compound Number | Chemical Name | Exact Mass | Actual Peak |
|---|---|---|---|---|
| 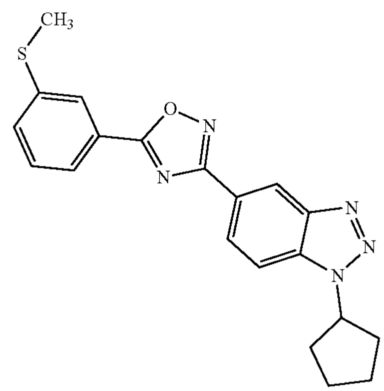 [SMILES: CSc1cccc(-c2nc(-c3ccc4c(c3)nnn4C3CCCC3)no2)c1] | 47 | 3-(1-cyclopentyl-1H-benzo[d][1,2,3]triazol-5-yl)-5-(3-(methylthio)phenyl)-1,2,4-oxadiazole | 377.47 | 378.1 |
| 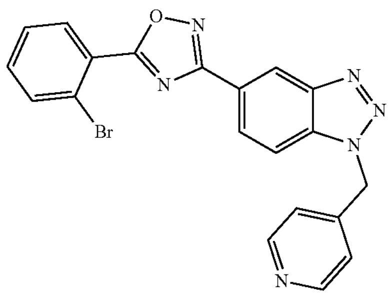 [SMILES: Brc1ccccc1-c1nc(-c2ccc3c(c2)nnn3Cc2ccncc2)no1] | 48 | 5-(2-bromophenyl)-3-(1-(pyridin-4-ylmethyl)-1H-benzo[d][1,2,3]triazol-5-yl)-1,2,4-oxadiazole | 433.27 | 435 |
| 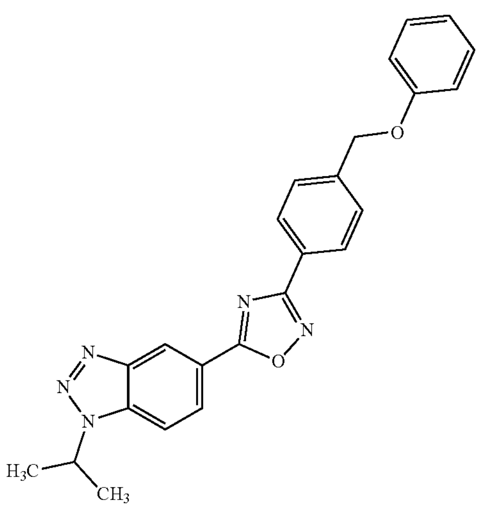 [SMILES: CC(C)n1nnc2cc(-c3nc(-c4ccc(COc5ccccc5)cc4)no3)ccc21] | 49 | 5-{3-[4-(phenoxymethyl)phenyl]-1,2,4-oxadiazol-5-yl}-1-(propan-2-yl)-1H-1,2,3-benzotriazole | 411.47 | 412.3 |
| 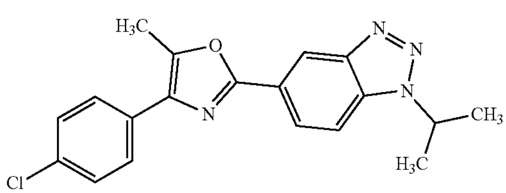 [SMILES: Cc1oc(-c2ccc3c(c2)nnn3C(C)C)nc1-c1ccc(Cl)cc1] | 50 | 5-[4-(4-chlorophenyl)-5-methyl-1,3-oxazol-2-yl]-1-(propan-2-yl)-1H-1,2,3-benzotriazole | 352.82 | 353 |

-continued

| Structure | Compound Number | Chemical Name | Exact Mass | Actual Peak |
|---|---|---|---|---|
| 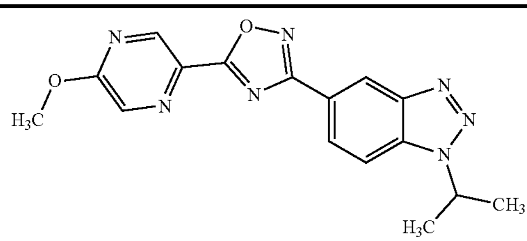 | 51 | 3-(1-isopropyl-1H-benzo[d][1,2,3]triazol-5-yl)-5-(5-methoxypyrazin-2-yl)-1,2,4-oxadiazole | 337.34 | 338 |
| 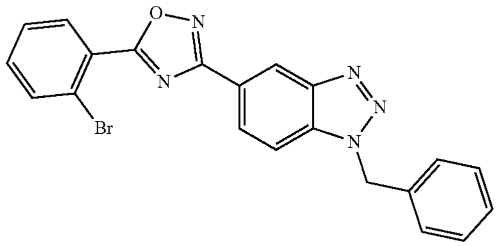 [SMILES: Brc1ccccc1-c1nc(-c2ccc3c(c2)nnn3Cc2ccccc2)no1] | 52 | 3-(1-benzyl-1H-benzo[d][1,2,3]triazol-5-yl)-5-(2-bromophenyl)-1,2,4-oxadiazole | 432.28 | 432 |
| 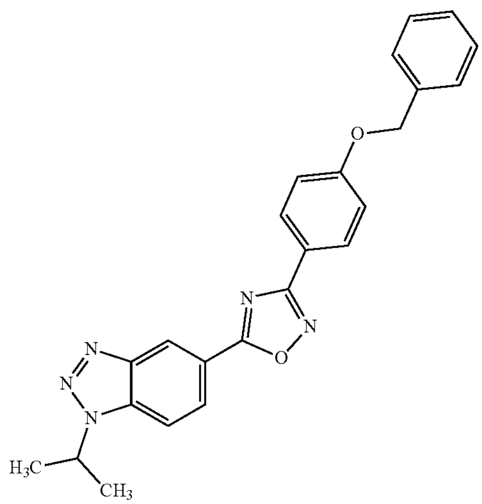 | 53 | 5-{3-[4-(benzyloxy)phenyl]-1,2,4-oxadiazol-5-yl}-1-(propan-2-yl)-1H-1,2,3-benzotriazole | 411.47 | 412.3 |
| 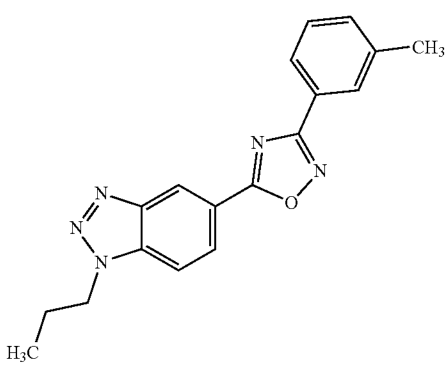 [SMILES: CCCn1nnc2cc(-c3nc(-c4cccc(C)c4)no3)ccc21] | 54 | 5-[3-(3-methylphenyl)-1,2,4-oxadiazol-5-yl]-1-propyl-1H-1,2,3-benzotriazole | 319.37 | 320.2 |
| 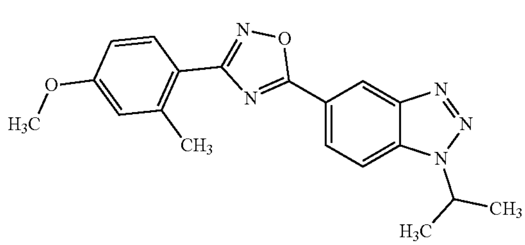 [SMILES: COc1ccc(-c2noc(-c3ccc4c(c3)nnn4C(C)C)n2)c(C)c1] | 55 | 5-(1-isopropyl-1H-benzo[d][1,2,3]triazol-5-yl)-3-(4-methoxy-2-methylphenyl)-1,2,4-oxadiazole | 349.39 | 350 |

-continued

| Structure | Compound Number | Chemical Name | Exact Mass | Actual Peak |
|---|---|---|---|---|
| 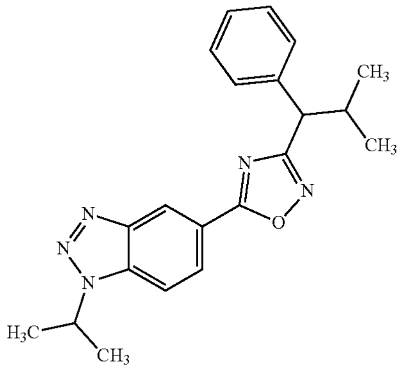 [SMILES: CC(C)C(c1ccccc1)c1noc(-c2ccc3c(c2)nnn3C(C)C)n1] | 56 | 5-[3-(2-methyl-1-phenylpropyl)-1,2,4-oxadiazol-5-yl]-1-(propan-2-yl)-1H-1,2,3-benzotriazole | 361.45 | 362.1 |
| 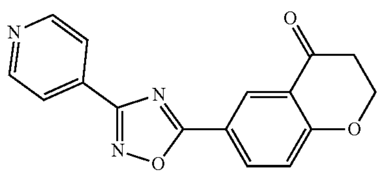 [SMILES: O=C1CCOc2ccc(-c3nc(-c4ccncc4)no3)cc21] | 57 | 6-[3-(pyridin-4-yl)-1,2,4-oxadiazol-5-yl]-3,4-dihydro-2H-1-benzopyran-4-one | 293.28 | 294.1 |
| 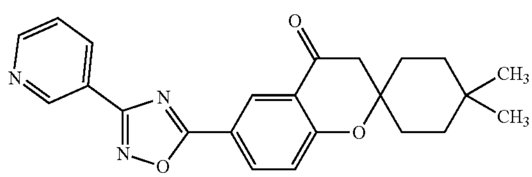 [SMILES: CC1(C)CCC2(CC1)CC(=O)c1cc(-c3nc(-c4cccnc4)no3)ccc1O2] | 58 | 4',4'-dimethyl-6-[3-(pyridin-3-yl)-1,2,4-oxadiazol-5-yl]-3,4-dihydrospiro[1-benzopyran-2,1'-cyclohexane]-4-one | 389.46 | 390.2 |
| 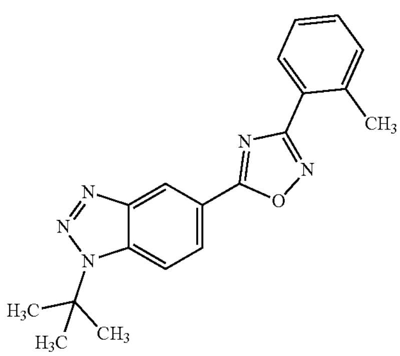 [SMILES: Cc1ccccc1-c1noc(-c2ccc3c(c2)nnn3C(C)(C)C)n1] | 59 | 1-tert-butyl-5-[3-(2-methylphenyl)-1,2,4-oxadiazol-5-yl]-1H-1,2,3-benzotriazole | 333.40 | 334.1 |
| 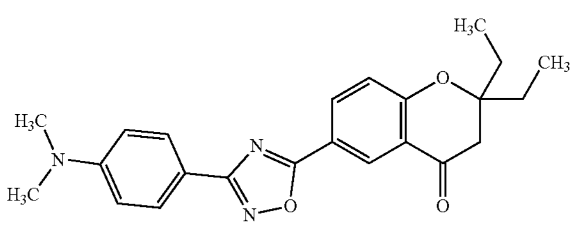 [SMILES: CCC1(CC)CC(=O)c2cc(-c3nc(-c4ccc(N(C)C)cc4)no3)ccc2O1] | 60 | 6-(3-(4-(dimethylamino)phenyl)-1,2,4-oxadiazol-5-yl)-2,2-diethylchroman-4-one | 391.47 | 392.3 |
| 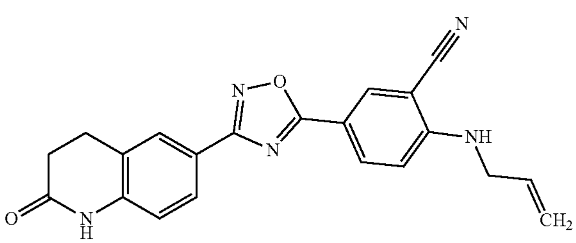 [SMILES: C=CCNc1ccc(-c2nc(-c3ccc4c(c3)CCC(=O)N4)no2)cc1C#N] | 61 | 2-(allylamino)-5-(3-(2-oxo-1,2,3,4-tetrahydroquinolin-6-yl)-1,2,4-oxadiazol-5-yl)benzonitrile | 371.40 | 372.1 |

-continued

| Structure | Compound Number | Chemical Name | Exact Mass | Actual Peak |
|---|---|---|---|---|
| 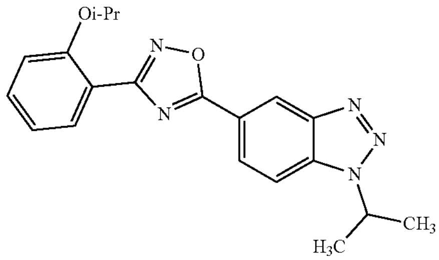 | 62 | 3-(2-isopropoxyphenyl)-5-(1-isopropyl-1H-benzo[d][1,2,3]triazol-5-yl)-1,2,4-oxadiazole | 363.42 | 364.1 |
| 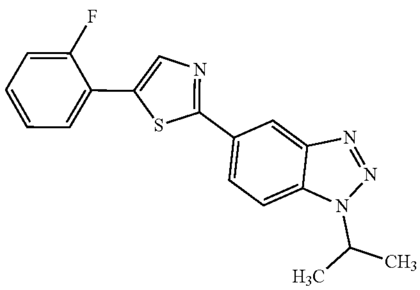 [SMILES: CC(C)n1nnc2cc(-c3ncc(-c4ccccc4F)s3)ccc21] | 63 | 5-(2-fluorophenyl)-2-(1-isopropyl-1H-benzo[d][1,2,3]triazol-5-yl)thiazole | 338.40 | 339.1 |
| 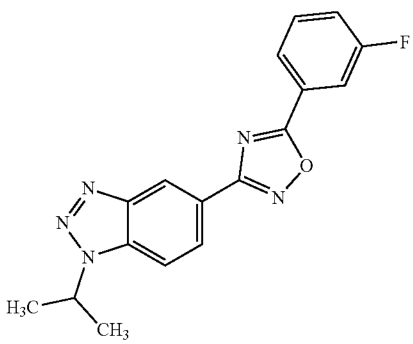 [SMILES: CC(C)n1nnc2cc(-c3noc(-c4cccc(F)c4)n3)ccc21] | 64 | 5-(3-fluorophenyl)-3-(1-isopropylbenzotriazol-5-yl)-1,2,4-oxadiazole | 323.33 | 324.1 |
| 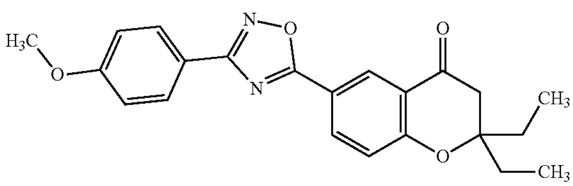 [SMILES: CCC1(CC)CC(=O)c2cc(-c3nc(-c4ccc(OC)cc4)no3)ccc2O1] | 65 | 2,2-diethyl-6-(3-(4-methoxyphenyl)-1,2,4-oxadiazol-5-yl)chroman-4-one | 378.43 | 379.1 |
| 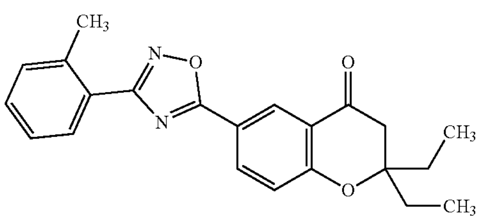 | 66 | 2,2-diethyl-6-(3-(o-tolyl)-1,2,4-oxadiazol-5-yl)chroman-4-one | 362.43 | 363.1 |
| 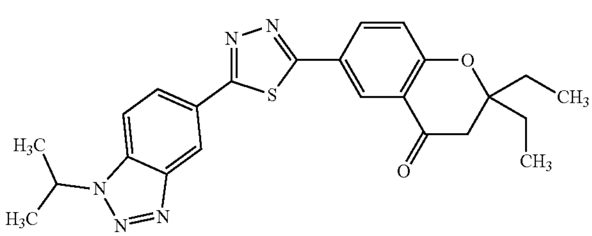 [SMILES: CCC1(CC)CC(=O)c2cc(-c3nnc(-c4ccc5c(c4)nnn5C(C)C)s3)ccc2O1] | 67 | 2,2-diethyl-6-(5-(1-isopropyl-1H-benzo[d][1,2,3]triazol-5-yl)-1,3,4-thiadiazol-2-yl)chroman-4-one | 447.56 | 448.1 |

-continued

| Structure | Compound Number | Chemical Name | Exact Mass | Actual Peak |
|---|---|---|---|---|
| 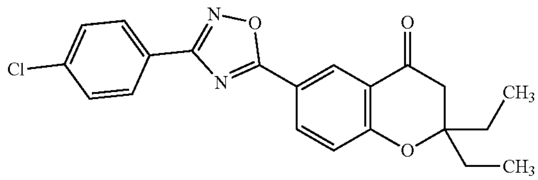 [SMILES: CCC1(CC)CC(=O)c2cc(-c3nc(-c4ccc(Cl)cc4)no3)ccc2O1] | 68 | 6-[3-(4-chlorophenyl)-1,2,4-oxadiazol-5-yl]-2,2-diethyl-chroman-4-one | 382.84 | 383.1 |
| 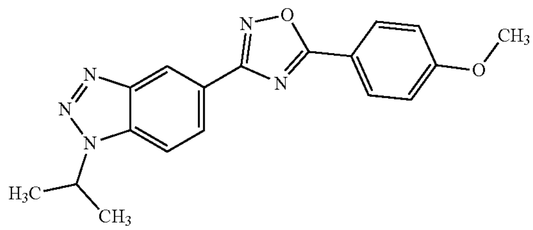 [SMILES: COc1ccc(-c2nc(-c3ccc4c(c3)nnn4C(C)C)no2)cc1] | 69 | 3-(1-isopropylbenzotriazol-5-yl)-5-(4-methoxyphenyl)-1,2,4-oxadiazole | 335.37 | 336.1 |
| 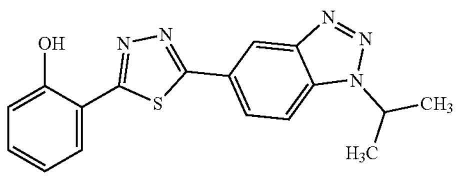 [SMILES: CC(C)n1nnc2cc(-c3nnc(-c4ccccc4O)s3)ccc21] | 70 | 2-{5-[1-(propan-2-yl)-1H-1,2,3-benzotriazol-5-yl]-1,3,4-thiadiazol-2-yl}phenol | 337.40 | 338 |
| 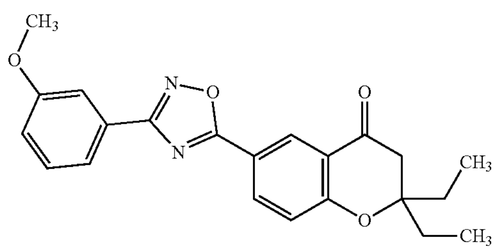 [SMILES: CCC1(CC)CC(=O)c2cc(-c3nc(-c4cccc(OC)c4)no3)ccc2O1] | 71 | 2,2-diethyl-6-(3-(3-methoxyphenyl)-1,2,4-oxadiazol-5-yl)chroman-4-one | 378.43 | 379.1 |
| 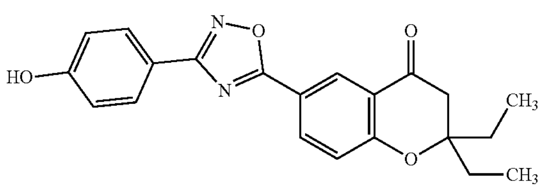 [SMILES: CCC1(CC)CC(=O)c2cc(-c3nc(-c4ccc(O)cc4)no3)ccc2O1] | 72 | 2,2-diethyl-6-[3-(4-hydroxyphenyl)-1,2,4-oxadiazol-5-yl]chroman-4-one | 364.40 | 365.1 |
| 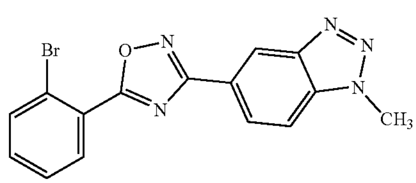 [SMILES: Cn1nnc2cc(-c3noc(-c4ccccc4Br)n3)ccc21] | 73 | 5-(2-bromophenyl)-3-(1-methyl-1H-benzo[d][1,2,3]triazol-5-yl)-1,2,4-oxadiazole | 356.18 | 356 |
| 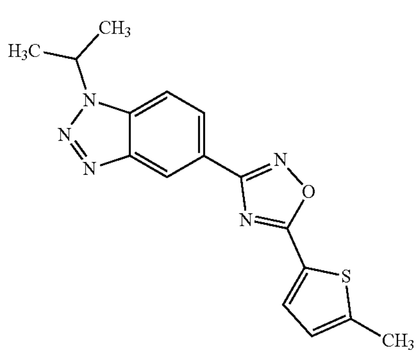 [SMILES: Cc1ccc(-c2nc(-c3ccc4c(c3)nnn4C(C)C)no2)s1] | 74 | 5-[5-(5-methylthiophen-2-yl)-1,2,4-oxadiazol-3-yl]-1-(propan-2-yl)-1H-1,2,3-benzotriazole | 325.39 | 326.1 |

-continued

| Structure | Compound Number | Chemical Name | Exact Mass | Actual Peak |
|---|---|---|---|---|
| 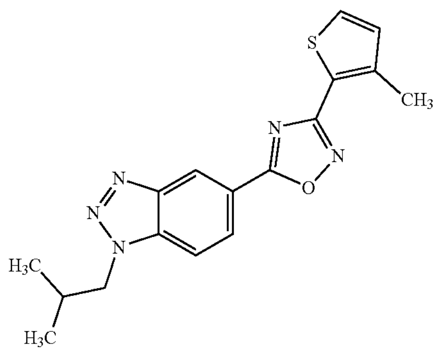 [SMILES: Cc1ccsc1-c1noc(-c2ccc3c(c2)nnn3CC(C)C)n1] | 75 | 1-(2-methylpropyl)-5-[3-(3-methylthiophen-2-yl)-1,2,4-oxadiazol-5-yl]-1H-1,2,3-benzotriazole | 339.42 | 340.1 |
| 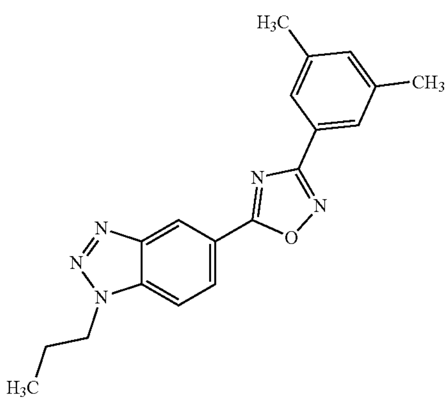 [SMILES: CCCn1nnc2cc(-c3nc(-c4cc(C)cc(C)c4)no3)ccc21] | 76 | 5-[3-(3,5-dimethylphenyl)-1,2,4-oxadiazol-5-yl]-1-propyl-1H-1,2,3-benzotriazole | 333.40 | 334.3 |
| 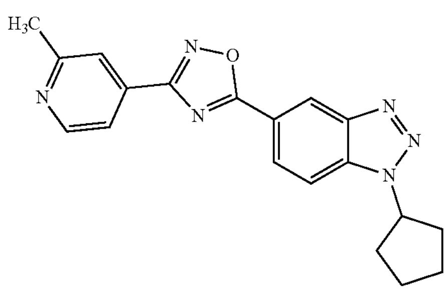 [SMILES: Cc1cc(-c2noc(-c3ccc4c(c3)nnn4C3CCCC3)n2)ccn1] | 77 | 5-[3-(2-methoxypyridin-4-yl)-1,2,4-oxadiazol-5-yl]-1-methyl-2,3-dihydro-1H-1,2,3-benzotriazole; cyclopentane | 346.39 | 347.1 |
| 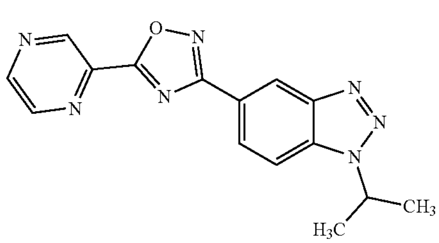 [SMILES: CC(C)n1nnc2cc(-c3noc(-c4cnccn4)n3)ccc21] | 78 | 3-(1-isopropyl-1H-benzo[d][1,2,3]triazol-5-yl)-5-(pyrazin-2-yl)-1,2,4-oxadiazole | 307.32 | 308 |

-continued

| Structure | Compound Number | Chemical Name | Exact Mass | Actual Peak |
|---|---|---|---|---|
| 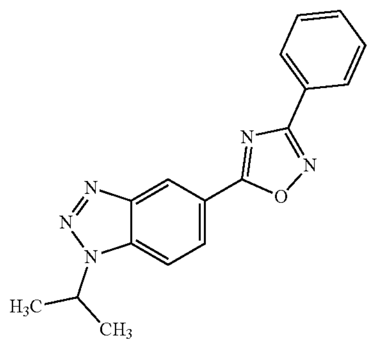 [SMILES: CC(C)n1nnc2cc(-c3nc(-c4ccccc4)no3)ccc21] | 79 | 5-(3-phenyl-1,2,4-oxadiazol-5-yl)-1-(propan-2-yl)-1H-1,2,3-benzotriazole | 305.34 | 306.3 |
| 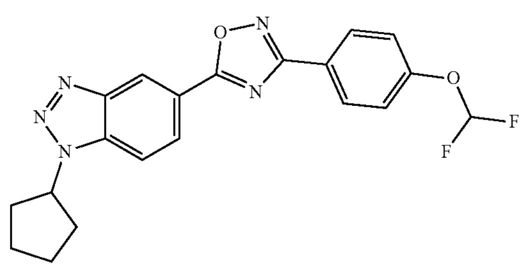 [SMILES: FC(F)Oc1ccc(-c2noc(-c3ccc4c(c3)nnn4C3CCCC3)n2)cc1] | 80 | 1-cyclopentyl-5-{3-[4-(difluoromethoxy)phenyl]-1,2,4-oxadiazol-5-yl}-1H-1,2,3-benzotriazole | 397.39 | 398.1 |
| 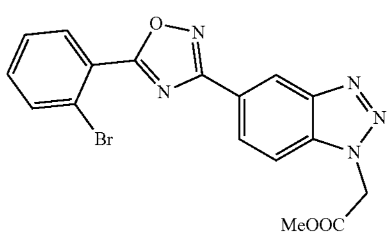 [SMILES: COC(=O)Cn1nnc2cc(-c3noc(-c4ccccc4Br)n3)ccc21] | 81 | methyl 2-(5-(5-(2-bromophenyl)-1,2,4-oxadiazol-3-yl)-1H-benzo[d][1,2,3]triazol-1-yl)acetate | 414.22 | 414.1 |
| 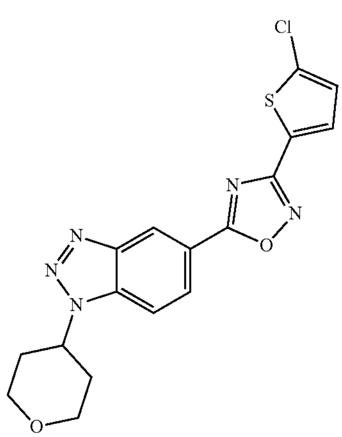 [SMILES: Clc1ccc(-c2noc(-c3ccc4c(c3)nnn4C3CCOCC3)n2)s1] | 82 | 5-[3-(5-chlorothiophen-2-yl)-1,2,4-oxadiazol-5-yl]-1-(oxan-4-yl)-1H-1,2,3-benzotriazole | 387.84 | 388 |

-continued

| Structure | Compound Number | Chemical Name | Exact Mass | Actual Peak |
|---|---|---|---|---|
| 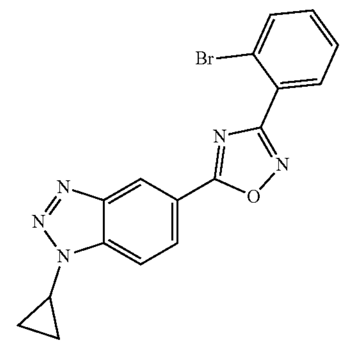 [SMILES: Brc1ccccc1-c1noc(-c2ccc3c(c2)nnn3C2CC2)n1] | 83 | 5-[3-(2-bromophenyl)-1,2,4-oxadiazol-5-yl]-1-cyclopropyl-1H-1,2,3-benzotriazole | 382.22 | 382.2 |
| 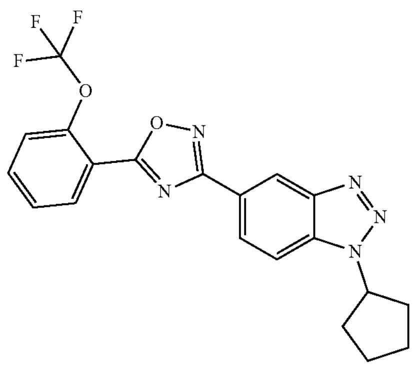 [SMILES: FC(F)(F)Oc1ccccc1-c1nc(-c2ccc3c(c2)nnn3C2CCCC2)no1] | 84 | 3-(1-cyclopentyl-1H-benzo[d][1,2,3]triazol-5-yl)-5-(2-(trifluoromethoxy)phenyl)-1,2,4-oxadiazole | 415.38 | 416 |
| 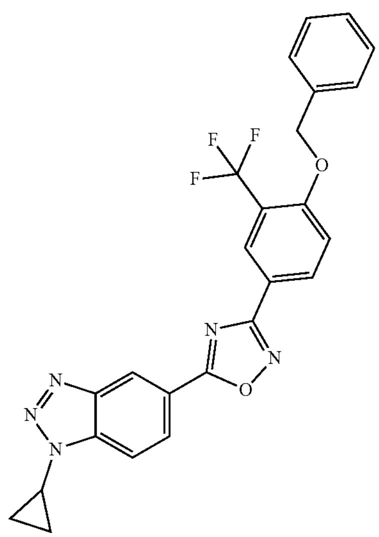 [SMILES: FC(F)(F)c1cc(-c2noc(-c3ccc4c(c3)nnn4C3CC3)n2)ccc1OCc1ccccc1] | 85 | 5-{3-[4-(benzyloxy)-3-(trifluoromethyl)phenyl]-1,2,4-oxadiazol-5-yl}-1-cyclopropyl-1H-1,2,3-benzotriazole | 477.45 | 478.2 |
| 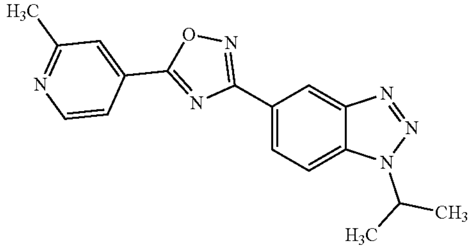 [SMILES: Cc1cc(-c2nc(-c3ccc4c(c3)nnn4C(C)C)no2)ccn1] | 86 | 3-(1-isopropyl-1H-benzo[d][1,2,3]triazol-5-yl)-5-(2-methylpyridin-4-yl)-1,2,4-oxadiazole | 322.37 | 321.1 |

-continued

| Structure | Compound Number | Chemical Name | Exact Mass | Actual Peak |
|---|---|---|---|---|
| 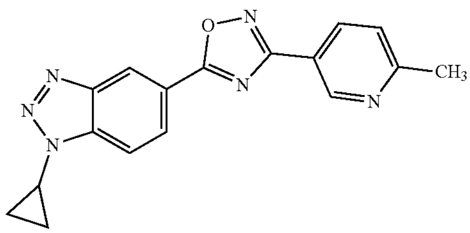 [SMILES: Cc1ccc(-c2noc(-c3ccc4c(c3)nnn4C3CC3)n2)cn1] | 87 | 1-cyclopropyl-5-[3-(6-methylpyridin-3-yl)-1,2,4-oxadiazol-5-yl]-1H-1,2,3-benzotriazole | 318.34 | 319.1 |
| 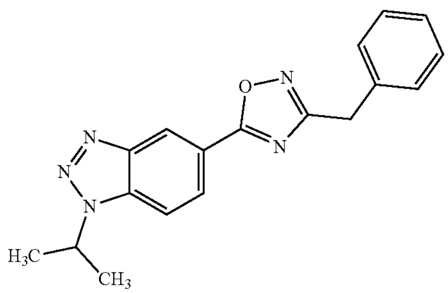 [SMILES: CC(C)n1nnc2cc(-c3nc(Cc4ccccc4)no3)ccc21] | 88 | 5-(3-benzyl-1,2,4-oxadiazol-5-yl)-1-(propan-2-yl)-1H-1,2,3-benzotriazole | 319.37 | 320.1 |
| 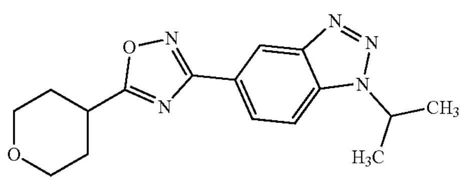 [SMILES: CC(C)n1nnc2cc(-c3noc(C4CCOCC4)n3)ccc21] | 89 | 5-[5-(oxan-4-yl)-1,2,4-oxadiazol-3-yl]-1-(propan-2-yl)-1H-1,2,3-benzotriazole | 313.36 | 314 |
| 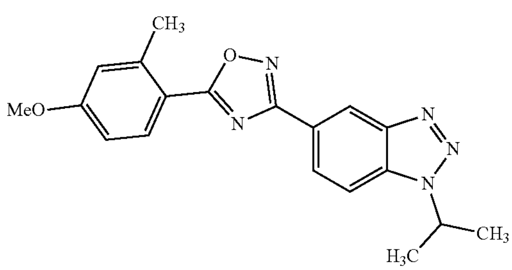 [SMILES: COc1ccc(-c2nc(-c3ccc4c(c3)nnn4C(C)C)no2)c(C)c1] | 90 | 3-(1-isopropyl-1H-benzo[d][1,2,3]triazol-5-yl)-5-(4-methoxy-2-methylphenyl)-1,2,4-oxadiazole | 349.39 | 350.1 |
| 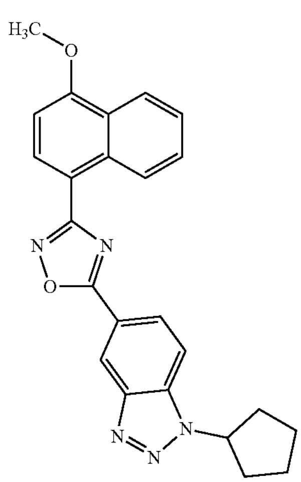 [SMILES: COc1ccc(-c2noc(-c3ccc4c(c3)nnn4C3CCCC3)n2)c2ccccc12] | 91 | 1-cyclopentyl-5-[3-(4-methoxynaphthalen-1-yl)-1,2,4-oxadiazol-5-yl]-1H-1,2,3-benzotriazole | 411.47 | 412.2 |

-continued

| Structure | Compound Number | Chemical Name | Exact Mass | Actual Peak |
|---|---|---|---|---|
| 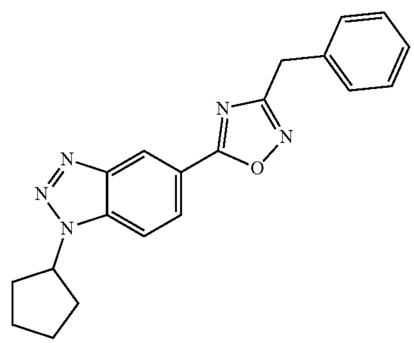 [SMILES: c1ccc(Cc2noc(-c3ccc4c(c3)nnn4C3CCCC3)n2)cc1] | 92 | 5-(3-benzyl-1,2,4-oxadiazol-5-yl)-1-cyclopentyl-1H-1,2,3-benzotriazole | 345.41 | 346.1 |
| 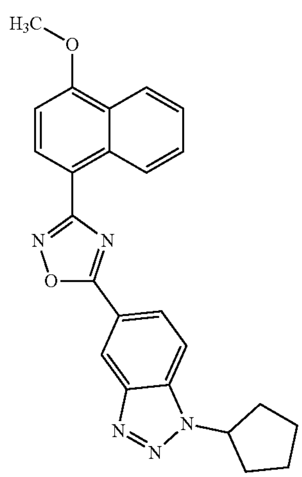 [SMILES: COc1ccc(-c2noc(-c3ccc4c(c3)nnn4C3CCCC3)n2)c2ccccc12] | 93 | 5-[3-(3,5-dimethylphenyl)-1,2,4-oxadiazol-5-yl]-1-(oxan-4-yl)-1H-1,2,3-benzotriazole | 375.43 | 376.2 |
| 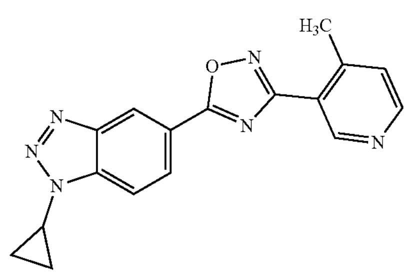 [SMILES: Cc1ccncc1-c1noc(-c2ccc3c(c2)nnn3C2CC2)n1] | 94 | 1-cyclopropyl-5-[3-(4-methylpyridin-3-yl)-1,2,4-oxadiazol-5-yl]-1H-1,2,3-benzotriazole | 318.34 | 319.3 |
| 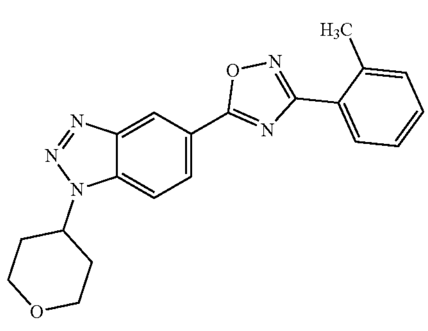 [SMILES: Cc1ccccc1-c1noc(-c2ccc3c(c2)nnn3C2CCOCC2)n1] | 95 | 5-[3-(2-methylphenyl)-1,2,4-oxadiazol-5-yl]-1-(oxan-4-yl)-1H-1,2,3-benzotriazole | 361.41 | 362.1 |

-continued

| Structure | Compound Number | Chemical Name | Exact Mass | Actual Peak |
|---|---|---|---|---|
| 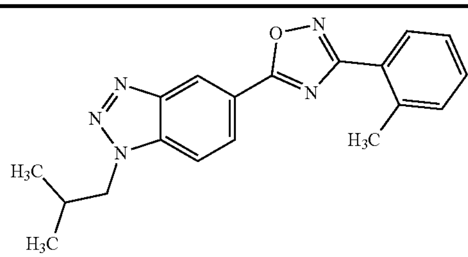 | 96 | 5-[3-(2-methylphenyl)-1,2,4-oxadiazol-5-yl]-1-(2-methylpropyl)-1H-1,2,3-benzotriazole | 333.40 | 334.2 |
| 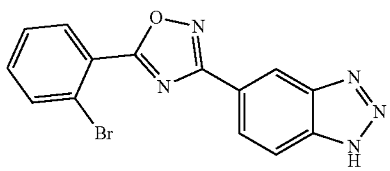 [SMILES: Brc1ccccc1-c1nc(-c2ccc3[nH]nnc3c2)no1] | 97 | 3-(1H-benzo[d][1,2,3]triazol-5-yl)-5-(2-bromophenyl)-1,2,4-oxadiazole | 342.16 | 343.9 |
| 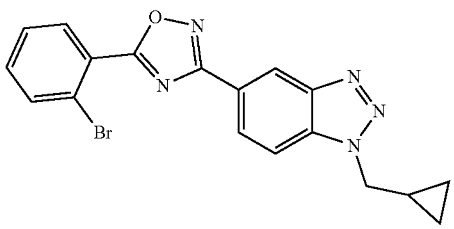 [SMILES: Brc1ccccc1-c1nc(-c2ccc3c(c2)nnn3CC2CC2)no1] | 98 | 5-(2-bromophenyl)-3-(1-(cyclopropylmethyl)-1H-benzo[d][1,2,3]triazol-5-yl)-1,2,4-oxadiazole | 396.25 | 396 |
| 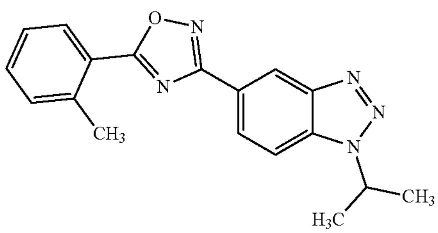 | 99 | 3-(1-isopropyl-1H-benzo[d][1,2,3]triazol-5-yl)-5-(o-tolyl)-1,2,4-oxadiazole | 319.37 | 320 |
| 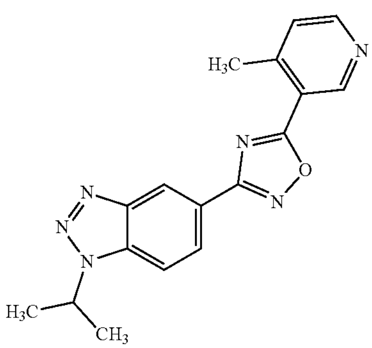 [SMILES: Cc1ccncc1-c1nc(-c2ccc3c(c2)nnn3C(C)C)no1] | 100 | 3-(1-isopropyl-1H-benzo[d][1,2,3]triazol-5-yl)-5-(4-methylpyridin-3-yl)-1,2,4-oxadiazole | 320.36 | 321.1 |
| 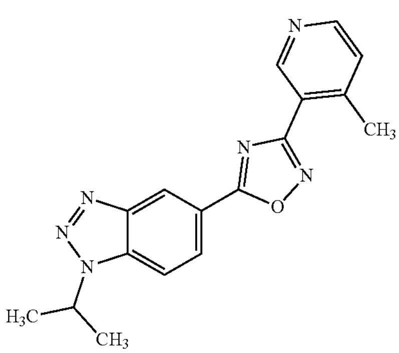 [SMILES: Cc1ccncc1-c1noc(-c2ccc3c(c2)nnn3C(C)C)n1] | 101 | 5-[3-(4-methylpyridin-3-yl)-1,2,4-oxadiazol-5-yl]-1-(propan-2-yl)-1H-1,2,3-benzotriazole | 320.36 | 321.1 |

-continued

| Structure | Compound Number | Chemical Name | Exact Mass | Actual Peak |
|---|---|---|---|---|
| 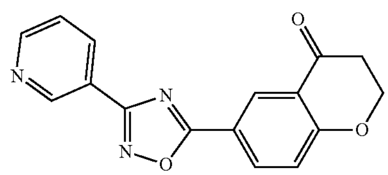 [SMILES: O=C1CCOc2ccc(-c3nc(-c4cccnc4)no3)cc21] | 102 | 6-[3-(pyridin-3-yl)-1,2,4-oxadiazol-5-yl]-3,4-dihydro-2H-1-benzopyran-4-one | 293.28 | 294.1 |
| 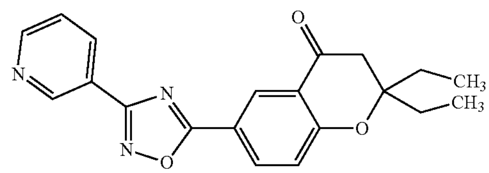 [SMILES: CCC1(CC)CC(=O)c2cc(-c3nc(-c4cccnc4)no3)ccc2O1] | 103 | 2,2-diethyl-6-[3-(pyridin-3-yl)-1,2,4-oxadiazol-5-yl]-3,4-dihydro-2H-1-benzopyran-4-one | 349.39 | 350.2 |
| 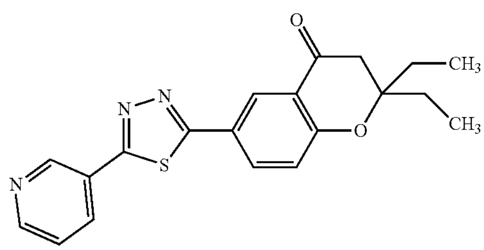 [SMILES: CCC1(CC)CC(=O)c2cc(-c3nnc(-c4cccnc4)s3)ccc2O1] | 104 | 2,2-diethyl-6-(5-(pyridin-3-yl)-1,3,4-thiadiazol-2-yl)chroman-4-one | 365.45 | 366.1 |
| 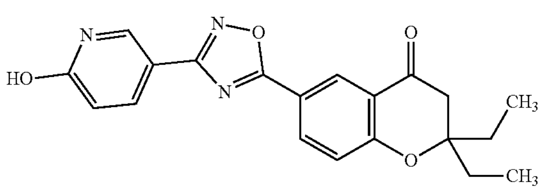 [SMILES: CCC1(CC)CC(=O)c2cc(-c3nc(-c4ccc(O)nc4)no3)ccc2O1] | 105 | 2,2-diethyl-6-[3-(6-hydroxy-3-pyridyl)-1,2,4-oxadiazol-5-yl]chroman-4-one | 365.39 | 366.1 |
| 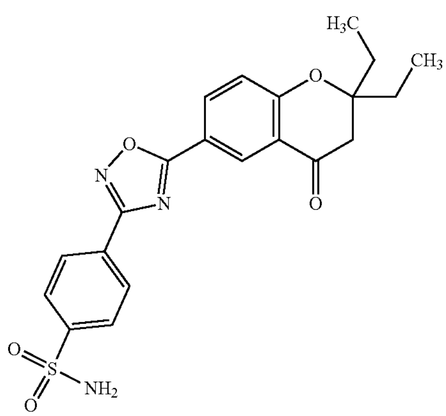 [SMILES: CCC1(CC)CC(=O)c2cc(-c3nc(-c4ccc(S(N)(=O)=O)cc4)no3)ccc2O1] | 106 | 4-(5-(2,2-diethyl-4-oxochroman-6-yl)-1,2,4-oxadiazol-3-yl)benzenesulfonamide | 427.48 | 428.1 |
| 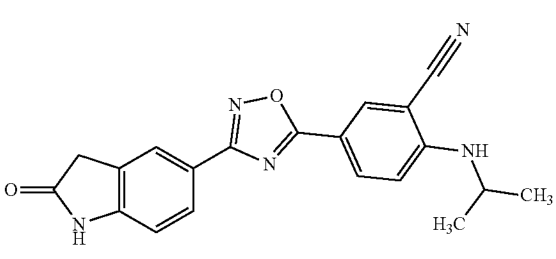 [SMILES: CC(C)Nc1ccc(-c2nc(-c3ccc4c(c3)CC(=O)N4)no2)cc1C#N] | 107 | 2-(isopropylamino)-5-(3-(2-oxoindolin-5-yl)-1,2,4-oxadiazol-5-yl)benzonitrile | 359.39 | 360.1 |

-continued

| Structure | Compound Number | Chemical Name | Exact Mass | Actual Peak |
|---|---|---|---|---|
| 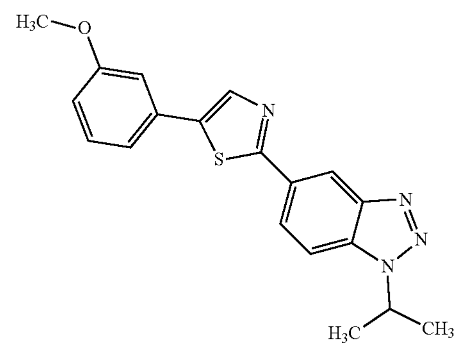 [SMILES: COc1cccc(-c2cnc(-c3ccc4c(c3)nnn4C(C)C)s2)c1] | 108 | 2-(1-isopropyl-1H-benzo[d][1,2,3]triazol-5-yl)-5-(3-methoxyphenyl)thiazole | 350.44 | 351.2 |
| 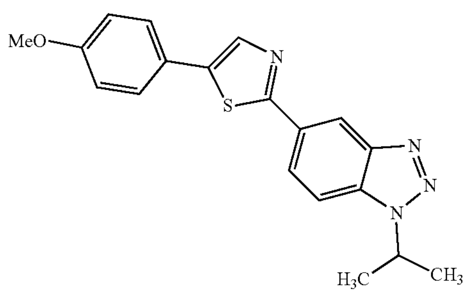 [SMILES: COc1ccc(-c2cnc(-c3ccc4c(c3)nnn4C(C)C)s2)cc1] | 109 | 2-(1-isopropyl-1H-benzo[d][1,2,3]triazol-5-yl)-5-(4-methoxyphenyl)thiazole | 350.44 | 351.1 |
| 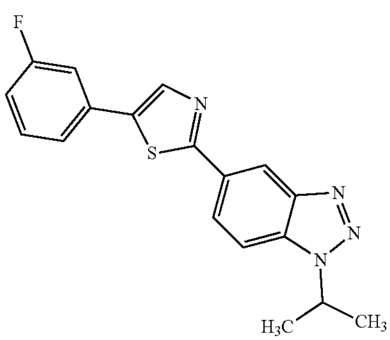 [SMILES: CC(C)n1nnc2cc(-c3ncc(-c4cccc(F)c4)s3)ccc21] | 110 | 5-(3-fluorophenyl)-2-(1-isopropyl-1H-benzo[d][1,2,3]triazol-5-yl)thiazole | 338.40 | 339.1 |
| 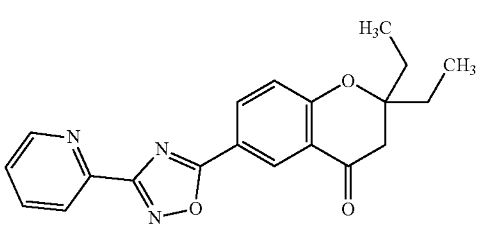 [SMILES: CCC1(CC)CC(=O)c2cc(-c3nc(-c4ccccn4)no3)ccc2O1] | 111 | 2,2-diethyl-6-[3-(2-pyridyl)-1,2,4-oxadiazol-5-yl]chroman-4-one | 349.39 | 350.1 |
| 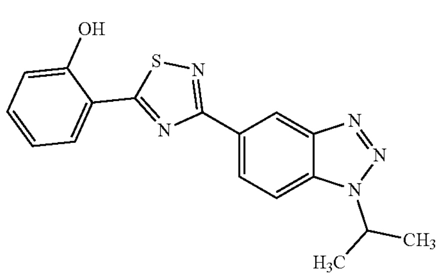 [SMILES: CC(C)n1nnc2cc(-c3nsc(-c4ccccc4O)n3)ccc21] | 112 | 2-{3-[1-(propan-2-yl)-1H-1,2,3-benzotriazol-5-yl]-1,2,4-thiadiazol-5-yl}phenol | 337.40 | 338 |

-continued

| Structure | Compound Number | Chemical Name | Exact Mass | Actual Peak |
|---|---|---|---|---|
| 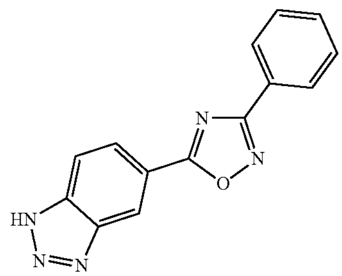 [SMILES: c1ccc(-c2noc(-c3ccc4[nH]nnc4c3)n2)cc1] | 113 | 5-(3-phenyl-1,2,4-oxadiazol-5-yl)-1H-1,2,3-benzotriazole | 263.26 | 264.1 |
| 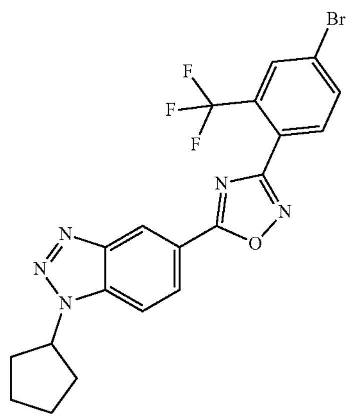 [SMILES: FC(F)(F)c1cc(Br)ccc1-c1noc(-c2ccc3c(c2)nnn3C2CCCC2)n1] | 114 | 5-{3-[4-bromo-2-(trifluoromethyl)phenyl]-1,2,4-oxadiazol-5-yl}-1-cyclopentyl-1H-1,2,3-benzotriazole | 478.27 | 478.1 |
| 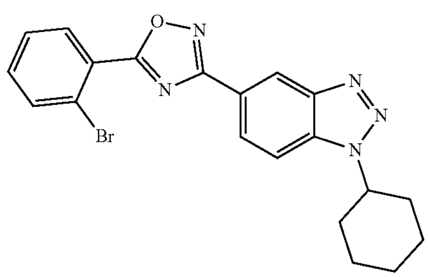 [SMILES: Brc1ccccc1-c1nc(-c2ccc3c(c2)nnn3C2CCCCC2)no1] | 115 | 5-(2-bromophenyl)-3-(1-cyclohexyl-1H-benzo[d][1,2,3]triazol-5-yl)-1,2,4-oxadiazole | 424.30 | 426 |
| 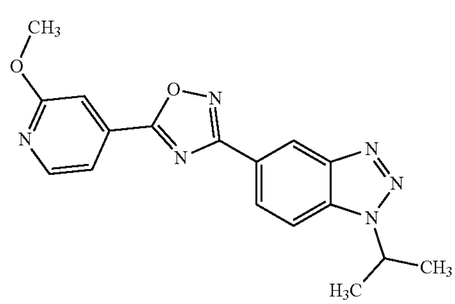 | 116 | 3-(1-isopropyl-1H-benzo[d][1,2,3]triazol-5-yl)-5-(2-methoxypyridin-4-yl)-1,2,4-oxadiazole | 336.36 | 337 |

-continued

| Structure | Compound Number | Chemical Name | Exact Mass | Actual Peak |
|---|---|---|---|---|
| 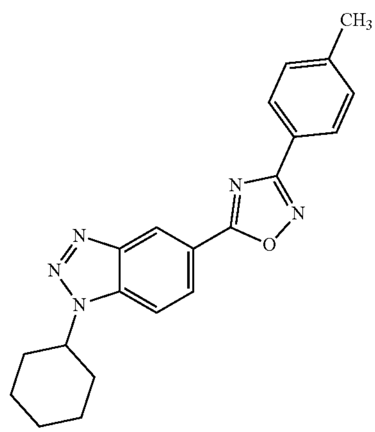 [SMILES: Cc1ccc(-c2noc(-c3ccc4c(c3)nnn4C3CCCCC3)n2)cc1] | 117 | 1-cyclohexyl-5-[3-(4-methylphenyl)-1,2,4-oxadiazol-5-yl]-1H-1,2,3-benzotriazole | 359.43 | 360.1 |
| 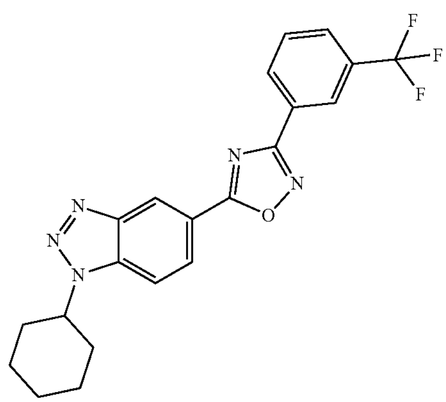 [SMILES: FC(F)(F)c1cccc(-c2noc(-c3ccc4c(c3)nnn4C3CCCCC3)n2)c1] | 118 | 1-cyclopentyl-5-{3-[3-(trifluoromethyl)phenyl]-1,2,4-oxadiazol-5-yl}-1H-1,2,3-benzotriazole | 399.38 | 400.1 |
| 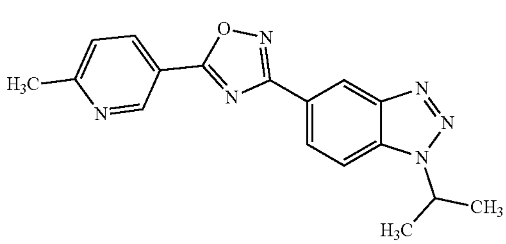 [SMILES: Cc1ccc(-c2nc(-c3ccc4c(c3)nnn4C(C)C)no2)cn1] | 119 | 3-(1-isopropyl-1H-benzo[d][1,2,3]triazol-5-yl)-5-(6-methylpyridin-3-yl)-1,2,4-oxadiazole | 320.36 | 321.1 |
| 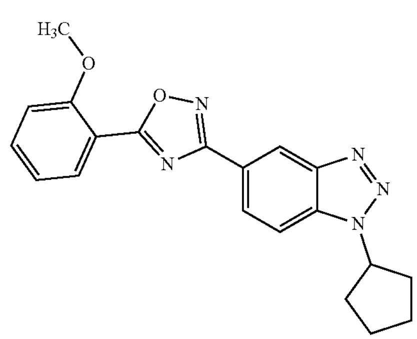 [SMILES: COc1ccccc1-c1nc(-c2ccc3c(c2)nnn3C2CCCC2)no1] | 120 | 3-(1-cyclopentyl-1H-benzo[d][1,2,3]triazol-5-yl)-5-(2-methoxyphenyl)-1,2,4-oxadiazole | 361.41 | 362 |

-continued

| Structure | Compound Number | Chemical Name | Exact Mass | Actual Peak |
|---|---|---|---|---|
| 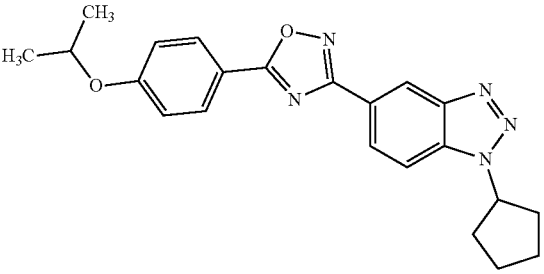 [SMILES: CC(C)Oc1ccc(-c2nc(-c3ccc4c(c3)nnn4C3CCCC3)no2)cc1] | 121 | 3-(1-cyclopentyl-1H-benzo[d][1,2,3]triazol-5-yl)-5-(4-isopropoxyphenyl)-1,2,4-oxadiazole | 389.46 | 390.3 |
| 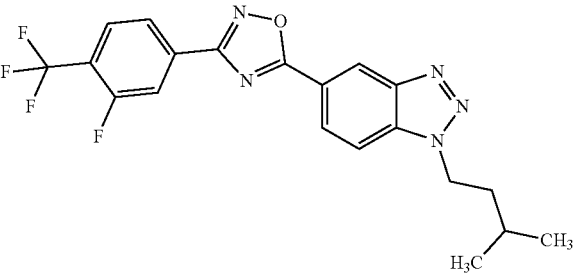 [SMILES: CC(C)CCn1nnc2cc(-c3nc(-c4ccc(C(F)(F)F)c(F)c4)no3)ccc21] | 122 | 5-{3-[3-fluoro-4-(trifluoromethyl)phenyl]-1,2,4-oxadiazol-5-yl}-1-(3-methylbutyl)-1H-1,2,3-benzotriazole | 419.38 | 420.2 |
| 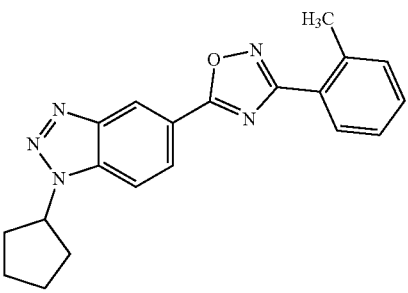 [SMILES: Cc1ccccc1-c1noc(-c2ccc3c(c2)nnn3C2CCCC2)n1] | 123 | 5-[3-(3,5-dimethylphenyl)-1,2,4-oxadiazol-5-yl]-1-(propan-2-yl)-1H-1,2,3-benzotriazole | 345.41 | 346.2 |
| 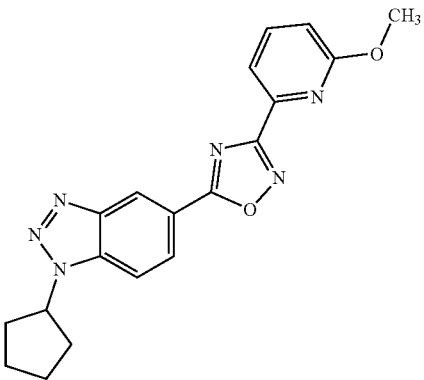 [SMILES: COc1cccc(-c2noc(-c3ccc4c(c3)nnn4C3CCCC3)n2)n1] | 124 | 1-cyclopentyl-5-[3-(6-methoxypyridin-2-yl)-1,2,4-oxadiazol-5-yl]-1H-1,2,3-benzotriazole | 362.39 | 363.1 |
| 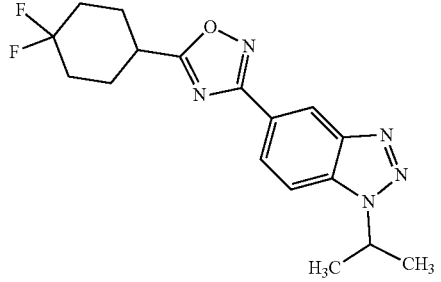 [SMILES: CC(C)n1nnc2cc(-c3noc(C4CCC(F)(F)CC4)n3)ccc21] | 125 | 5-[5-(4,4-difluorocyclohexyl)-1,2,4-oxadiazol-3-yl]-1-(propan-2-yl)-1H-1,2,3-benzotriazole | 347.37 | 348 |

-continued

| Structure | Compound Number | Chemical Name | Exact Mass | Actual Peak |
|---|---|---|---|---|
| 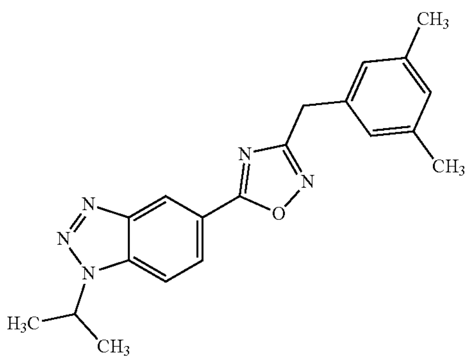 [SMILES: Cc1cc(C)cc(Cc2noc(-c3ccc4c(c3)nnn4C(C)C)n2)c1] | 126 | 5-{3-[(3,5-dimethylphenyl)methyl]-1,2,4-oxadiazol-5-yl}-1-(propan-2-yl)-1H-1,2,3-benzotriazole | 347.42 | 348.3 |
| 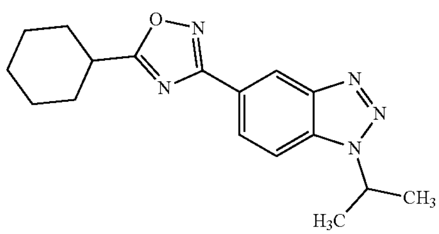 [SMILES: CC(C)n1nnc2cc(-c3noc(C4CCCCC4)n3)ccc21] | 127 | 5-(5-cyclohexyl-1,2,4-oxadiazol-3-yl)-1-(propan-2-yl)-1H-1,2,3-benzotriazole | 311.39 | 312 |
| 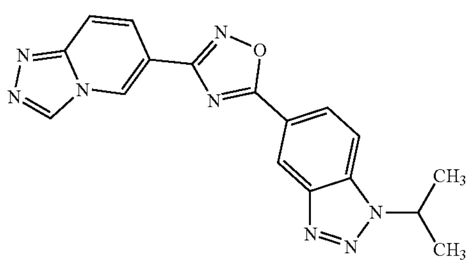 [SMILES: CC(C)n1nnc2cc(-c3nc(-c4ccc5nncn5c4)no3)ccc21] | 128 | 1-(propan-2-yl)-5-(3-{[1,2,4]triazolo[4,3-a]pyridin-6-yl}-1,2,4-oxadiazol-5-yl)-1H-1,2,3-benzotriazole | 346.35 | 347.1 |
| 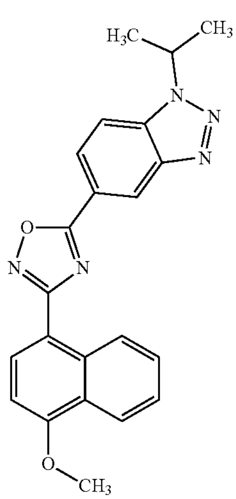 [SMILES: COc1ccc(-c2noc(-c3ccc4c(c3)nnn4C(C)C)n2)c2ccccc12] | 129 | 5-[3-(4-methoxynaphthalen-1-yl)-1,2,4-oxadiazol-5-yl]-1-(propan-2-yl)-1H-1,2,3-benzotriazole | 385.43 | 386.2 |

-continued

| Structure | Compound Number | Chemical Name | Exact Mass | Actual Peak |
|---|---|---|---|---|
| 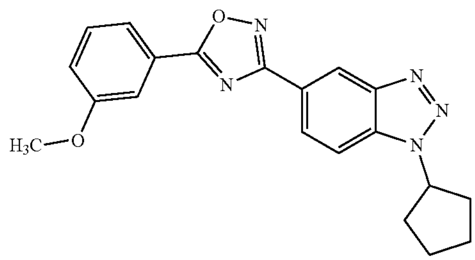 [SMILES: COc1cccc(-c2nc(-c3ccc4c(c3)nnn4C3CCCC3)no2)c1] | 130 | 3-(1-cyclopentyl-1H-benzo[d][1,2,3]triazol-5-yl)-5-(3-methoxyphenyl)-1,2,4-oxadiazole | 361.41 | 362 |
| 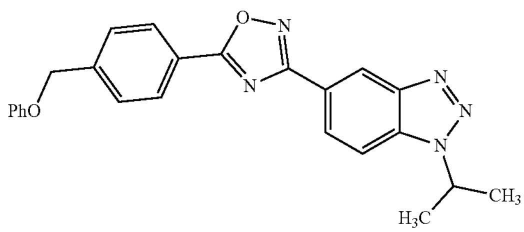 [SMILES: CC(C)n1nnc2cc(-c3noc(-c4ccc(COc5ccccc5)cc4)n3)ccc21] | 131 | 3-(1-isopropyl-1H-benzo[d][1,2,3]triazol-5-yl)-5-(4-(phenoxymethyl)phenyl)-1,2,4-oxadiazole | 411.47 | 412 |
| 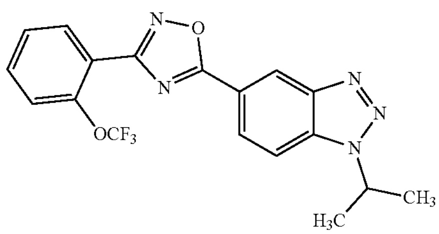 [SMILES: CC(C)n1nnc2cc(-c3nc(-c4ccccc4OC(F)(F)F)no3)ccc21] | 132 | 5-(1-isopropyl-1H-benzo[d][1,2,3]triazol-5-yl)-3-(2-(trifluoromethoxy)phenyl)-1,2,4-oxadiazole | 389.34 | 390 |
| 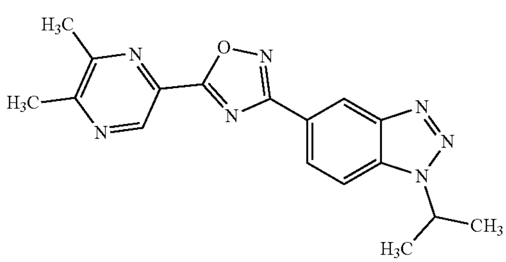 [SMILES: Cc1ncc(-c2nc(-c3ccc4c(c3)nnn4C(C)C)no2)nc1C] | 133 | 5-(5,6-dimethylpyrazin-2-yl)-3-(1-isopropyl-1H-benzo[d][1,2,3]triazol-5-yl)-1,2,4-oxadiazole | 335.37 | 356.1 |
| 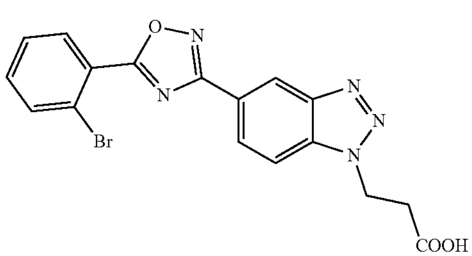 [SMILES: O=C(O)CCn1nnc2cc(-c3noc(-c4ccccc4Br)n3)ccc21] | 134 | 3-(5-(5-(2-bromophenyl)-1,2,4-oxadiazol-3-yl)-1H-benzo[d][1,2,3]triazol-1-yl)propanoic acid | 414.22 | 413.9 |

| Structure | Compound Number | Chemical Name | Exact Mass | Actual Peak |
|---|---|---|---|---|
| 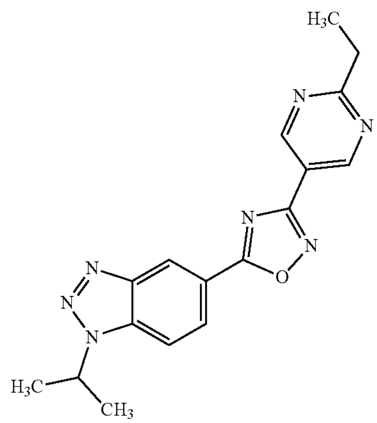 [SMILES: CCc1ncc(-c2noc(-c3ccc4c(c3)nnn4C(C)C)n2)cn1] | 135 | 5-[3-(2-ethylpyrimidin-5-yl)-1,2,4-oxadiazol-5-yl]-1-(propan-2-yl)-1H-1,2,3-benzotriazole | 335.37 | 336.1 |
| 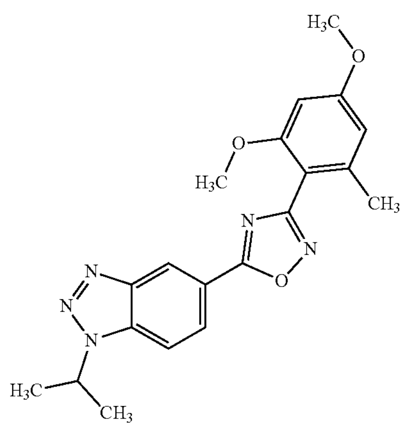 [SMILES: COc1cc(C)c(-c2noc(-c3ccc4c(c3)nnn4C(C)C)n2)c(OC)c1] | 136 | 5-[3-(2,4-dimethoxy-6-methylphenyl)-1,2,4-oxadiazol-5-yl]-1-(propan-2-yl)-1H-1,2,3-benzotriazole | 379.42 | 380.3 |
| 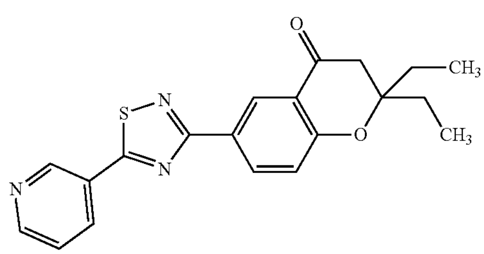 [SMILES: CCC1(CC)CC(=O)c2cc(-c3nsc(-c4cccnc4)n3)ccc2O1] | 137 | 2,2-diethyl-6-(5-(pyridin-3-yl)-1,2,4-thiadiazol-3-yl)chroman-4-one | 365.45 | 366 |
| 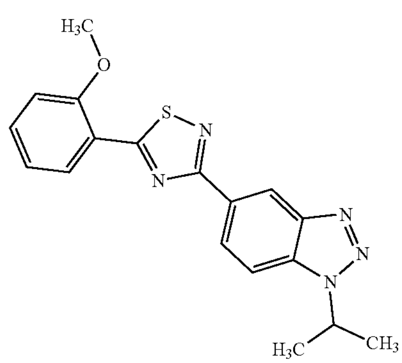 [SMILES: COc1ccccc1-c1nc(-c2ccc3c(c2)nnn3C(C)C)ns1] | 138 | 5-[5-(2-methoxyphenyl)-1,2,4-thiadiazol-3-yl]-1-(propan-2-yl)-1H-1,2,3-benzotriazole | 351.43 | 302 |

-continued

| Structure | Compound Number | Chemical Name | Exact Mass | Actual Peak |
|---|---|---|---|---|
| 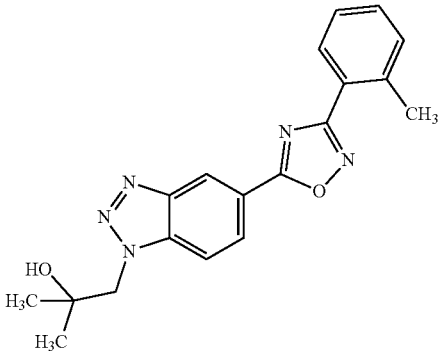 [SMILES: Cc1ccccc1-c1noc(-c2ccc3c(c2)nnn3CC(C)(C)O)n1] | 139 | 2-methyl-1-{5-[3-(2-methylphenyl)-1,2,4-oxadiazol-5-yl]-1H-1,2,3-benzotriazol-1-yl}propan-2-ol | 349.39 | 350.1 |
| 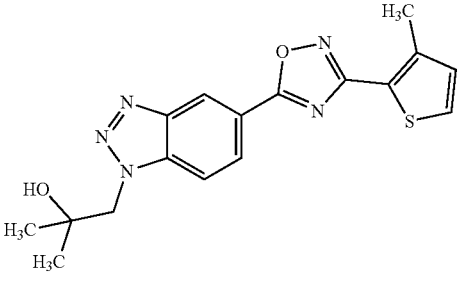 [SMILES: Cc1ccsc1-c1noc(-c2ccc3c(c2)nnn3CC(C)(C)O)n1] | 140 | 2-methyl-1-{5-[3-(3-methylthiophen-2-yl)-1,2,4-oxadiazol-5-yl]-1H-1,2,3-benzotriazol-1-yl}propan-2-ol | 355.42 | 356.1 |
| 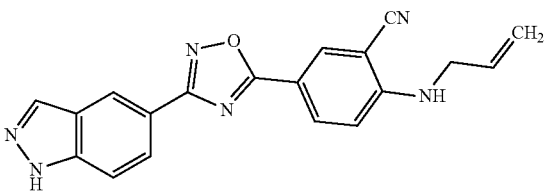 [SMILES: C=CCNc1ccc(-c2nc(-c3ccc4[nH]ncc4c3)no2)cc1C#N] | 141 | 5-(3-(1H-indazol-5-yl)-1,2,4-oxadiazol-5-yl)-2-(allylamino)benzonitrile | 342.36 | 343.1 |
| 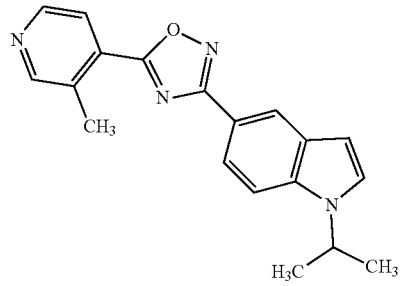 [SMILES: Cc1cnccc1-c1nc(-c2ccc3c(ccn3C(C)C)c2)no1] | 142 | 3-(1-isopropyl-1H-indol-5-yl)-5-(3-methylpyridin-4-yl)-1,2,4-oxadiazole | 318.38 | 318.15 |
| 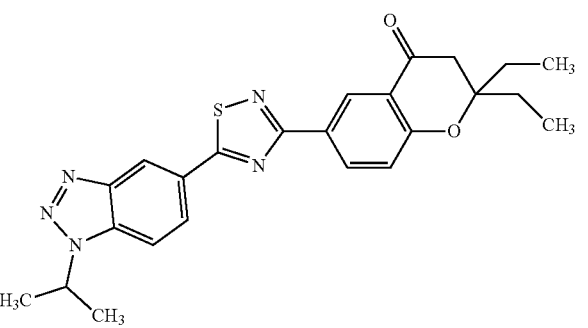 [SMILES: CCC1(CC)CC(=O)c2cc(-c3nsc(-c4ccc5c(c4)nnn5C(C)C)n3)ccc2O1] | 143 | 2,2-diethyl-6-(5-(1-isopropyl-1H-benzo[d][1,2,3]triazol-5-yl)-1,2,4-thiadiazol-3-yl)chroman-4-one | 447.56 | 448.1 |

-continued

| Structure | Compound Number | Chemical Name | Exact Mass | Actual Peak |
|---|---|---|---|---|
| 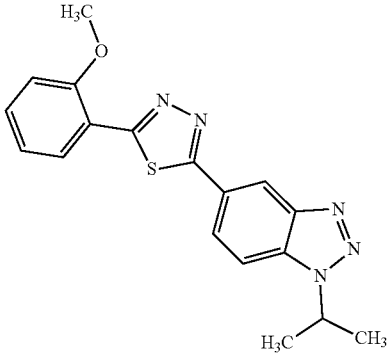 [SMILES: COc1ccccc1-c1nnc(-c2ccc3c(c2)nnn3C(C)C)s1] | 144 | 5-[5-(2-methoxyphenyl)-1,3,4-thiadiazol-2-yl]-1-(propan-2-yl)-1H-1,2,3-benzotriazole | 351.43 | 352 |
| 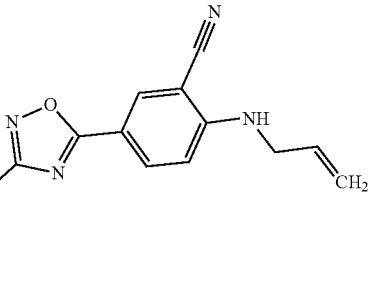 | 145 | 5-(3-(1H-benzo[d][1,2,3]triazol-5-yl)-1,2,4-oxadiazol-5-yl)-2-(allylamino)benzonitrile | 343.35 | 344.1 |
| 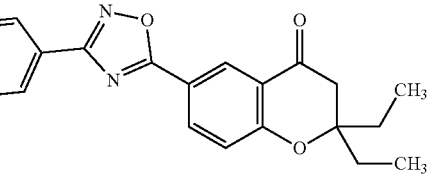 | 146 | 2,2-diethyl-6-(3-(2-fluoropyridin-4-yl)-1,2,4-oxadiazol-5-yl)chroman-4-one | 367.38 | 368.1 |
| 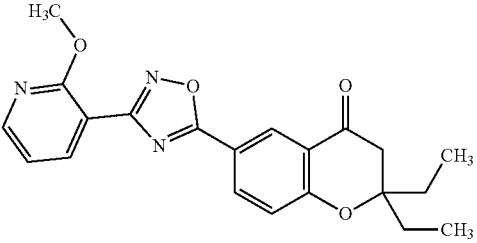 | 147 | 2,2-diethyl-6-(3-(2-methoxypyridin-3-yl)-1,2,4-oxadiazol-5-yl)chroman-4-one | 379.42 | 380.2 |
| 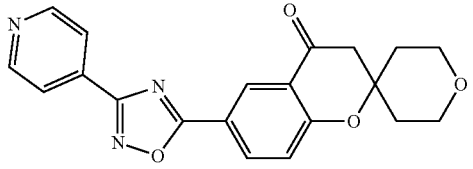 [SMILES: O=C1CC2(CCOCC2)Oc2ccc(-c3nc(-c4ccncc4)no3)cc21] | 148 | 6-[3-(pyridin-4-yl)-1,2,4-oxadiazol-5-yl]-3,4-dihydrospiro[1-benzopyran-2,4'-oxane]-4-one | 363.37 | 364.1 |
| 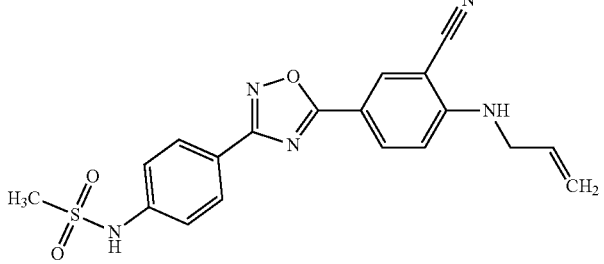 | 149 | N-(4-(5-(4-(allylamino)-3-cyanophenyl)-1,2,4-oxadiazol-3-yl)phenyl)methanesulfonamide | 395.44 | 396.1 |

| Structure | Compound Number | Chemical Name | Exact Mass | Actual Peak |
|---|---|---|---|---|
| 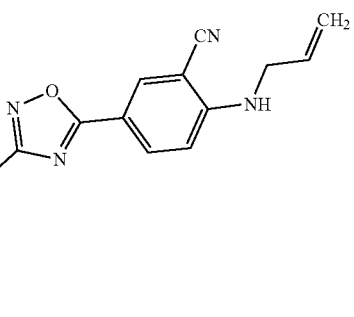 | 150 | 2-(allylamino)-5-(3-(1-isopropyl-1H-benzo[d][1,2,3]triazol-5-yl)-1,2,4-oxadiazol-5-yl)benzonitrile | 385.43 | 386.3 |
| 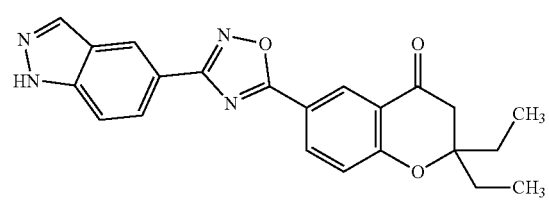 [SMILES: CCC1(CC)CC(=O)c2cc(-c3nc(-c4ccc5[nH]ncc5c4)no3)ccc2O1] | 151 | 4-(5-(2,2-diethyl-4-oxochroman-6-yl)-1,2,4-oxadiazol-3-yl)-N,N-dimethylbenzamide | 419.48 | 420.2 |
| 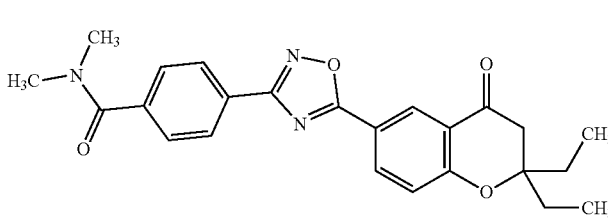 | 152 | 6-(3-(1H-indazol-5-yl)-1,2,4-oxadiazol-5-yl)-2,2-diethylchroman-4-one | 388.43 | 389.2 |
| 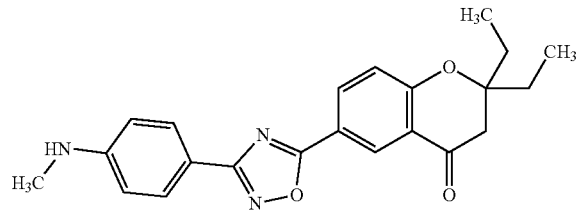 [SMILES: CCC1(CC)CC(=O)c2cc(-c3nc(-c4ccc(NC)cc4)no3)ccc2O1] | 153 | 2,2-diethyl-6-(3-(4-(methylamino)phenyl)-1,2,4-oxadiazol-5-yl)chroman-4-one | 377.44 | 378.2 |
| 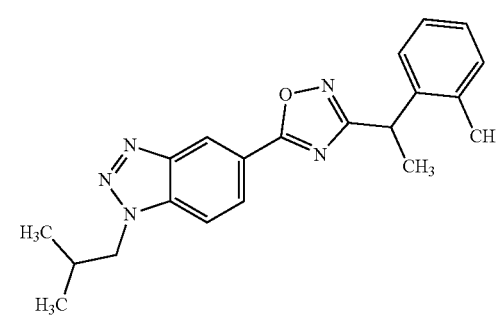 | 154 | 5-{3-[1-(2-methylphenyl)ethyl]-1,2,4-oxadiazol-5-yl}-1-(2-methylpropyl)-1H-1,2,3-benzotriazole | 361.45 | 362.2 |

-continued

| Structure | Compound Number | Chemical Name | Exact Mass | Actual Peak |
|---|---|---|---|---|
| 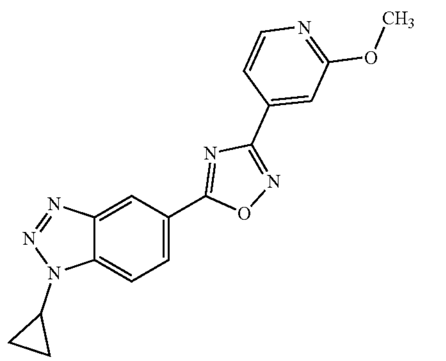 [SMILES: COc1cc(-c2noc(-c3ccc4c(c3)nnn4C3CC3)n2)ccn1] | 155 | 1-cyclopropyl-5-[3-(2-methoxypyridin-4-yl)-1,2,4-oxadiazol-5-yl]-1H-1,2,3-benzotriazole | 334.34 | 335.1 |
| 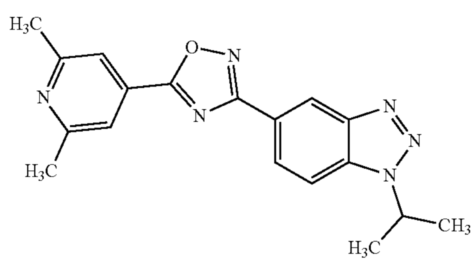 [SMILES: Cc1cc(-c2nc(-c3ccc4c(c3)nnn4C(C)C)no2)cc(C)n1] | 156 | 5-(2,6-dimethylpyridin-4-yl)-3-(1-isopropyl-1H-benzo[d][1,2,3]triazol-5-yl)-1,2,4-oxadiazole | 334.38 | 335.2 |
| 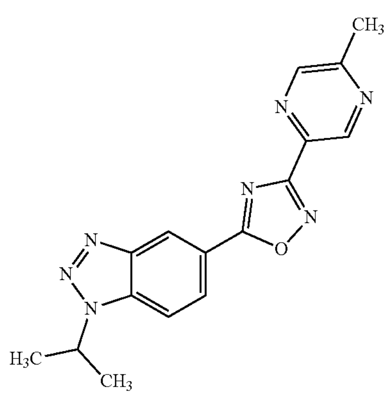 [SMILES: Cc1cnc(-c2noc(-c3ccc4c(c3)nnn4C(C)C)n2)cn1] | 157 | 5-[3-(5-methylpyrazin-2-yl)-1,2,4-oxadiazol-5-yl]-1-(propan-2-yl)-1H-1,2,3-benzotriazole | 321.34 | 322.1 |
| 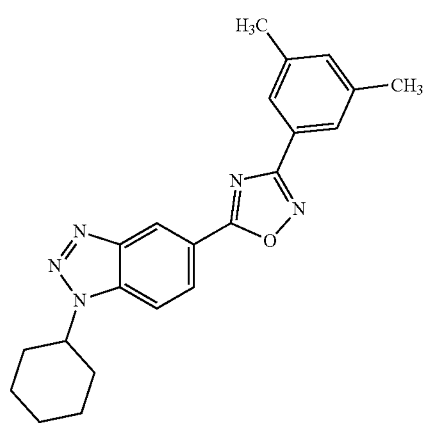 [SMILES: Cc1cc(C)cc(-c2noc(-c3ccc4c(c3)nnn4C3CCCCC3)n2)c1] | 158 | 1-cyclohexyl-5-[3-(3,5-dimethylphenyl)-1,2,4-oxadiazol-5-yl]-1H-1,2,3-benzotriazole | 373.46 | 374.2 |

-continued

| Structure | Compound Number | Chemical Name | Exact Mass | Actual Peak |
|---|---|---|---|---|
| 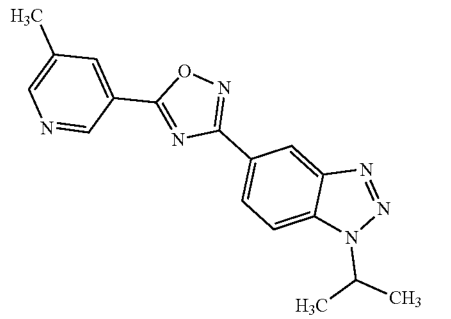 [SMILES: Cc1cncc(-c2nc(-c3ccc4c(c3)nnn4C(C)C)no2)c1] | 159 | 3-(1-isopropyl-1H-benzo[d][1,2,3]triazol-5-yl)-5-(5-methylpyridin-3-yl)-1,2,4-oxadiazole | 320.36 | 321.1 |
| 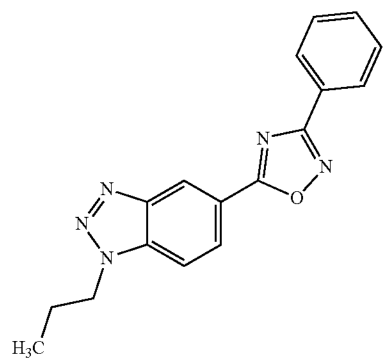 [SMILES: CCCn1nnc2cc(-c3nc(-c4ccccc4)no3)ccc21] | 160 | 5-(3-phenyl-1,2,4-oxadiazol-5-yl)-1-propyl-1H-1,2,3-benzotriazole | 305.34 | 306.1 |
| 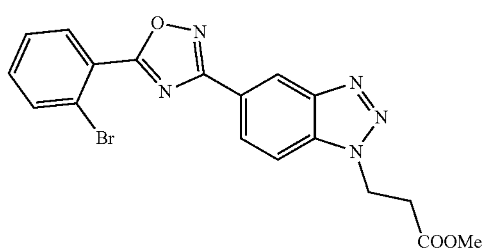 [SMILES: COC(=O)CCn1nnc2cc(-c3noc(-c4ccccc4Br)n3)ccc21] | 161 | methyl 3-(5-(5-(2-bromophenyl)-1,2,4-oxadiazol-3-yl)-1H-benzo[d][1,2,3]triazol-1-yl)propanoate | 428.25 | 429.9 |
| 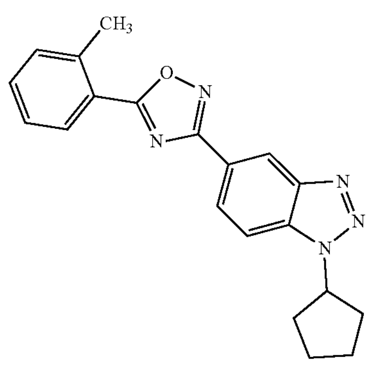 [SMILES: Cc1ccccc1-c1nc(-c2ccc3c(c2)nnn3C2CCCC2)no1] | 162 | 3-(1-cyclopentyl-1H-benzo[d][1,2,3]triazol-5-yl)-5-(o-tolyl)-1,2,4-oxadiazole | 345.41 | 346.1 |
| 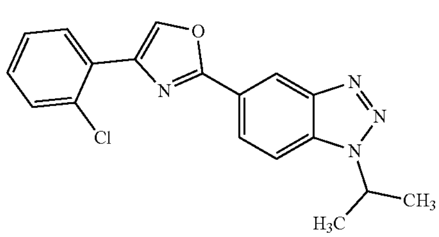 [SMILES: CC(C)n1nnc2cc(-c3nc(-c4ccccc4Cl)co3)ccc21] | 163 | 5-[4-(2-chlorophenyl)-2,3-dihydro-1,3-oxazol-2-yl]-1-(propan-2-yl)-1H-1,2,3-benzotriazole | 338.80 | 339 |

-continued
| Structure | Compound Number | Chemical Name | Exact Mass | Actual Peak |
|---|---|---|---|---|
| 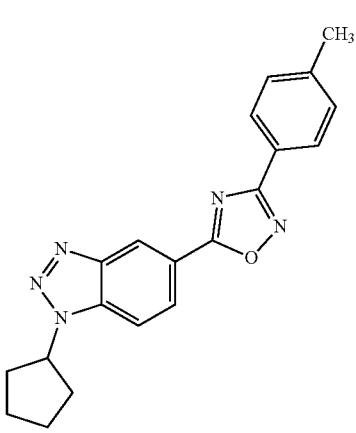 [SMILES: Cc1ccc(-c2noc(-c3ccc4c(c3)nnn4C3CCCC3)n2)cc1] | 164 | 1-cyclopentyl-5-[3-(4-methylphenyl)-1,2,4-oxadiazol-5-yl]-1H-1,2,3-benzotriazole | 345.41 | 346.3 |
| 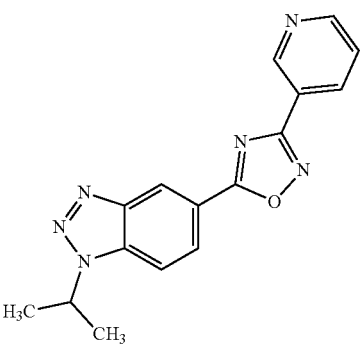 [SMILES: CC(C)n1nnc2cc(-c3nc(-c4cccnc4)no3)ccc21] | 165 | 1-(propan-2-yl)-5-[3-(pyridin-3-yl)-1,2,4-oxadiazol-5-yl]-1H-1,2,3-benzotriazole | 306.33 | 307.3 |
| 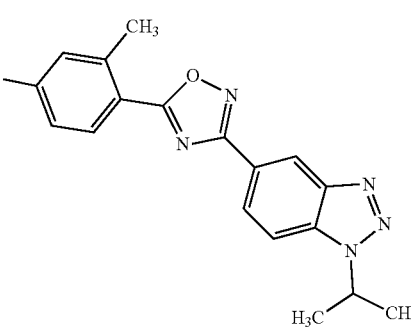 | 166 | 5-(2,4-dimethylphenyl)-3-(1-isopropyl-1H-benzo[d][1,2,3]triazol-5-yl)-1,2,4-oxadiazole | 333.40 | 334.2 |
| 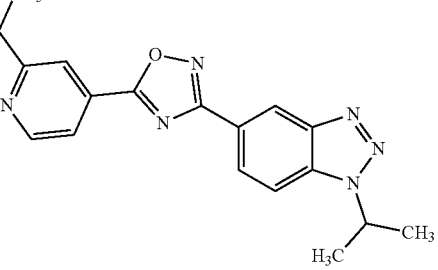 | 167 | 3-(1-isopropyl-1H-benzo[d][1,2,3]triazol-5-yl)-5-(2-isopropylpyridin-4-yl)-1,2,4-oxadiazole | 348.41 | 349.1 |

-continued

| Structure | Compound Number | Chemical Name | Exact Mass | Actual Peak |
|---|---|---|---|---|
| 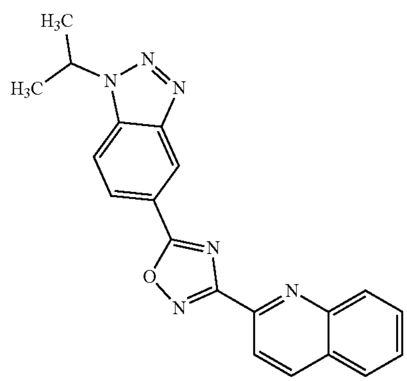 [SMILES: CC(C)n1nnc2cc(-c3nc(-c4ccc5ccccc5n4)no3)ccc21] | 168 | 2-{5-[1-(propan-2-yl)-1H-1,2,3-benzotriazol-5-yl]-1,2,4-oxadiazol-3-yl}quinoline | 356.39 | 357.1 |
| 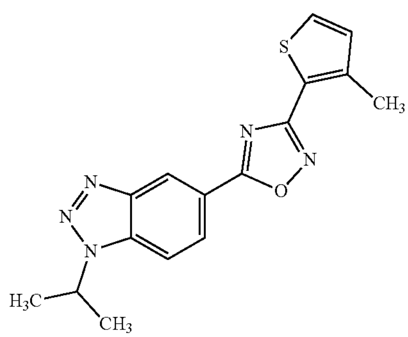 [SMILES: Cc1ccsc1-c1noc(-c2ccc3c(c2)nnn3C(C)C)n1] | 169 | 5-[3-(3-methylthiophen-2-yl)-1,2,4-oxadiazol-5-yl]-1-(propan-2-yl)-1H-1,2,3-benzotriazole | 325.39 | 326.1 |
| 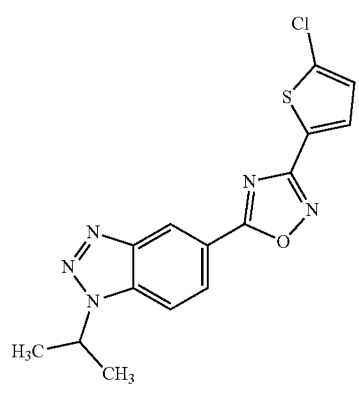 [SMILES: CC(C)n1nnc2cc(-c3nc(-c4ccc(Cl)s4)no3)ccc21] | 170 | 5-[3-(5-chlorothiophen-2-yl)-1,2,4-oxadiazol-5-yl]-1-(propan-2-yl)-1H-1,2,3-benzotriazole | 345.81 | 346.1 |
| 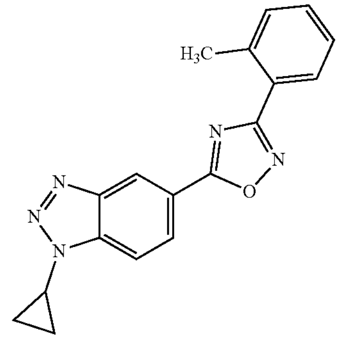 | 171 | 1-cyclopropyl-5-[3-(2-methylphenyl)-1,2,4-oxadiazol-5-yl]-1H-1,2,3-benzotriazole | 317.35 | 318.3 |

-continued

| Structure | Compound Number | Chemical Name | Exact Mass | Actual Peak |
|---|---|---|---|---|
| 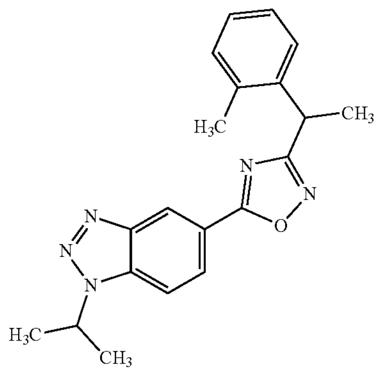 [SMILES: Cc1ccccc1C(C)c1noc(-c2ccc3c(c2)nnn3C(C)C)n1] | 172 | 5-{3-[1-(2-methylphenyl)ethyl]-1,2,4-oxadiazol-5-yl}-1-(propan-2-yl)-1H-1,2,3-benzotriazole | 347.42 | 348.1 |
| 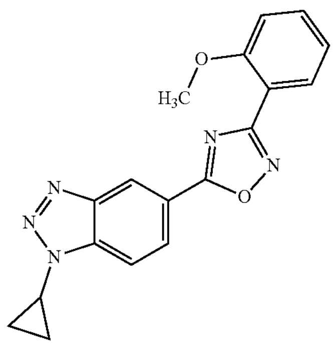 [SMILES: COc1ccccc1-c1noc(-c2ccc3c(c2)nnn3C2CC2)n1] | 173 | 1-cyclopropyl-5-[3-(2-methoxyphenyl)-1,2,4-oxadiazol-5-yl]-1H-1,2,3-benzotriazole | 333.35 | 334.2 |
| 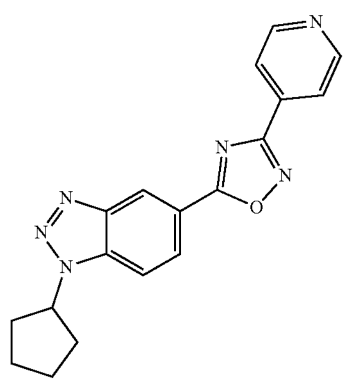 [SMILES: c1cc(-c2noc(-c3ccc4c(c3)nnn4C3CCCC3)n2)ccn1] | 174 | 1-cyclopentyl-5-[3-(pyridin-4-yl)-1,2,4-oxadiazol-5-yl]-1H-1,2,3-benzotriazole | 332.37 | 333.1 |
| 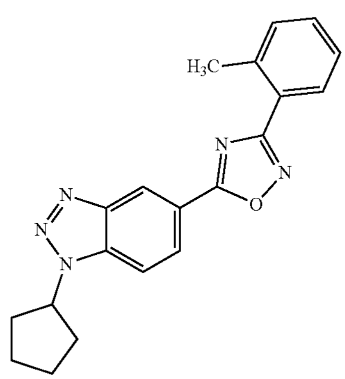 [SMILES: Cc1ccccc1-c1noc(-c2ccc3c(c2)nnn3C2CCCC2)n1] | 175 | 1-cyclopentyl-5-[3-(2-methylphenyl)-1,2,4-oxadiazol-5-yl]-1H-1,2,3-benzotriazole | 345.41 | 346.2 |

-continued

| Structure | Compound Number | Chemical Name | Exact Mass | Actual Peak |
|---|---|---|---|---|
| 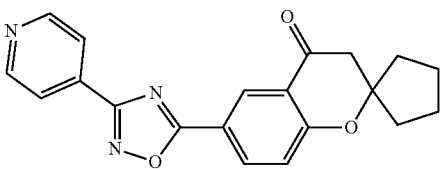 [SMILES: O=C1CC2(CCCC2)Oc2ccc(-c3nc(-c4ccncc4)no3)cc21] | 176 | 6-[3-(pyridin-4-yl)-1,2,4-oxadiazol-5-yl]-3,4-dihydrospiro[1-benzopyran-2,1'-cyclopentane]-4-one | 347.37 | 348.1 |
| 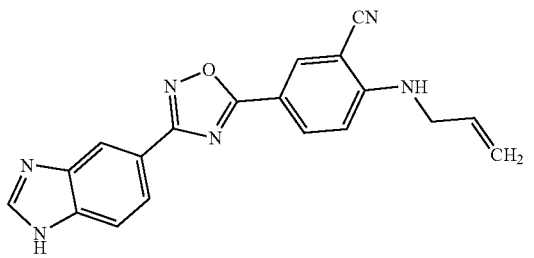 [SMILES: C=CCNc1ccc(-c2nc(-c3ccc4[nH]cnc4c3)no2)cc1C#N] | 177 | 5-(3-(1H-benzo[d]imidazol-5-yl)-1,2,4-oxadiazol-5-yl)-2-(allylamino)benzonitrile | 342.36 | 343.1 |
| 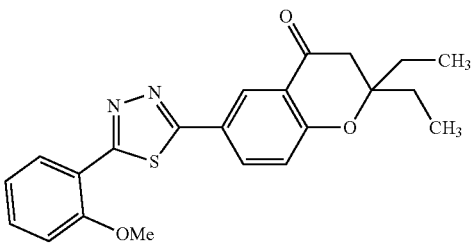 [SMILES: CCC1(CC)CC(=O)c2cc(-c3nnc(-c4ccccc4OC)s3)ccc2O1] | 178 | 2,2-diethyl-6-(5-(2-methoxyphenyl)-1,3,4-thiadiazol-2-yl)chroman-4-one | 394.49 | 395.2 |
| 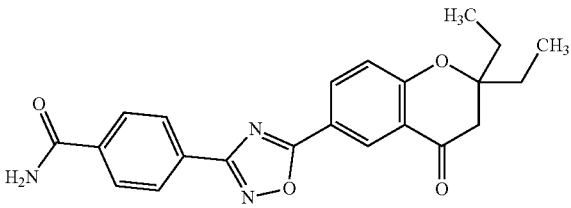 [SMILES: CCC1(CC)CC(=O)c2cc(-c3nc(-c4ccc(C(N)=O)cc4)no3)ccc2O1] | 179 | 4-(5-(2,2-diethyl-4-oxochroman-6-yl)-1,2,4-oxadiazol-3-yl)benzamide | 391.43 | 392.1 |
| 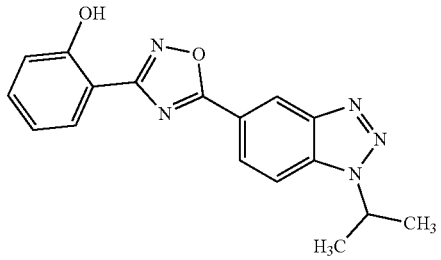 [SMILES: CC(C)n1nnc2cc(-c3nc(-c4ccccc4O)no3)ccc21] | 180 | 2-(5-(1-isopropyl-1H-benzo[d][1,2,3]triazol-5-yl)-1,2,4-oxadiazol-3-yl)phenol | 321.34 | 322.1 |
| 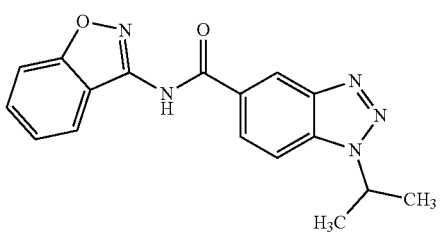 [SMILES: CC(C)n1nnc2cc(C(=O)Nc3noc4ccccc34)ccc21] | 181 | N-(benzo[d]isoxazol-3-yl)-1-isopropyl-1H-benzo[d][1,2,3]triazole-5-carboxamide | 321.34 | 322.1 |

-continued

| Structure | Compound Number | Chemical Name | Exact Mass | Actual Peak |
|---|---|---|---|---|
| 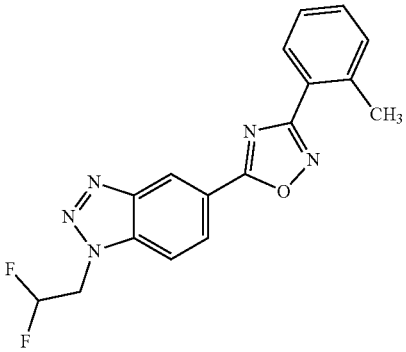 [SMILES: Cc1ccccc1-c1noc(-c2ccc3c(c2)nnn3CC(F)F)n1] | 182 | 1-(2,2-difluoroethyl)-5-[3-(2-methylphenyl)-1,2,4-oxadiazol-5-yl]-1H-1,2,3-benzotriazole | 341.32 | 342.1 |
| 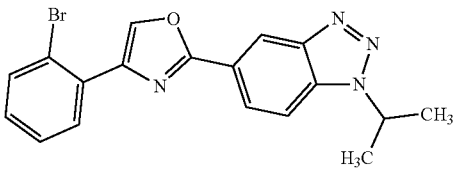 [SMILES: CC(C)n1nnc2cc(-c3nc(-c4ccccc4Br)co3)ccc21] | 183 | 5-[4-(2-bromophenyl)-1,3-oxazol-2-yl]-1-(propan-2-yl)-1H-1,2,3-benzotriazole | 383.25 | 383 |
| 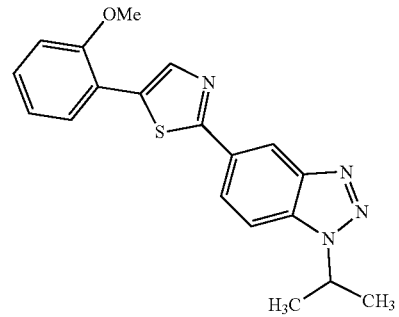 [SMILES: COc1ccccc1-c1cnc(-c2ccc3c(c2)nnn3C(C)C)s1] | 184 | 2-(1-isopropyl-1H-benzo[d][1,2,3]triazol-5-yl)-5-(2-methoxyphenyl)thiazole | 350.44 | 351 |
| 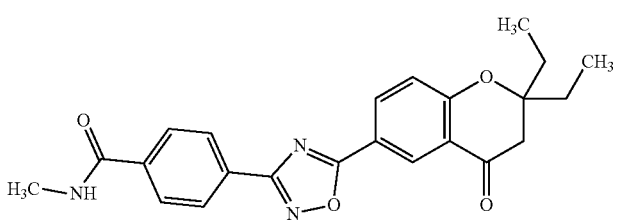 [SMILES: CCC1(CC)CC(=O)c2cc(-c3nc(-c4ccc(C(=O)NC)cc4)no3)ccc2O1] | 185 | 4-(5-(2,2-diethyl-4-oxochroman-6-yl)-1,2,4-oxadiazol-3-yl)-N-methylbenzamide | 405.45 | 406.1 |
| 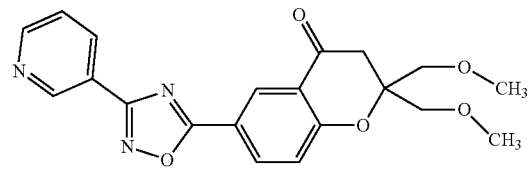 [SMILES: COCC1(COC)CC(=O)c2cc(-c3nc(-c4cccnc4)no3)ccc2O1] | 186 | 2,2-bis(methoxymethyl)-6-[3-(pyridin-3-yl)-1,2,4-oxadiazol-5-yl]-3,4-dihydro-2H-1-benzopyran-4-one | 381.39 | 282.2 |
| 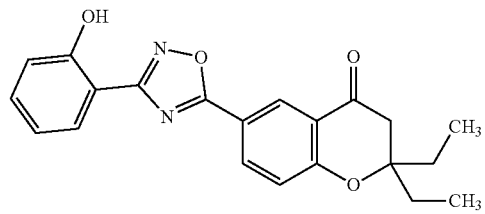 | 187 | 2,2-diethyl-6-[3-(2-hydroxyphenyl)-1,2,4-oxadiazol-5-yl]chroman-4-one | 364.40 | 365.1 |

-continued

| Structure | Compound Number | Chemical Name | Exact Mass | Actual Peak |
|---|---|---|---|---|
| 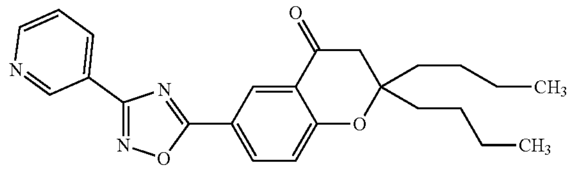 [SMILES: CCCCC1(CCCC)CC(=O)c2cc(-c3nc(-c4cccnc4)no3)ccc2O1] | 188 | 2,2-dibutyl-6-[3-(pyridin-3-yl)-1,2,4-oxadiazol-5-yl]-3,4-dihydro-2H-1-benzopyran-4-one | 405.50 | 406.2 |
| 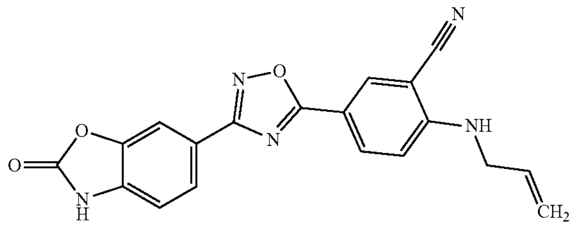 [SMILES: C=CCNc1ccc(-c2nc(-c3ccc4[nH]c(=O)oc4c3)no2)cc1C#N] | 189 | 2-(allylamino)-5-(3-(2-oxo-2,3-dihydrobenzo[d]oxazol-6-yl)-1,2,4-oxadiazol-5-yl)benzonitrile | 359.35 | 360.1 |
| 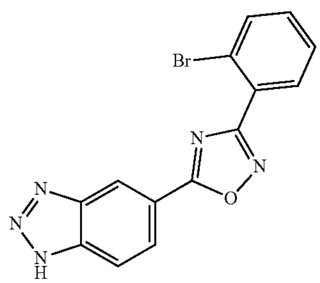 [SMILES: Brc1ccccc1-c1noc(-c2ccc3[nH]nnc3c2)n1] | 190 | 5-[3-(2-bromophenyl)-1,2,4-oxadiazol-5-yl]-1H-1,2,3-benzotriazole | 342.16 | 342 |
| 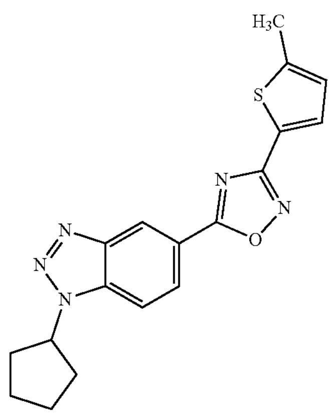 [SMILES: Cc1ccc(-c2noc(-c3ccc4c(c3)nnn4C3CCCC3)n2)s1] | 192 | 1-cyclopentyl-5-[3-(5-methylthiophen-2-yl)-1,2,4-oxadiazol-5-yl]-1H-1,2,3-benzotriazole | 351.43 | 352.1 |
| 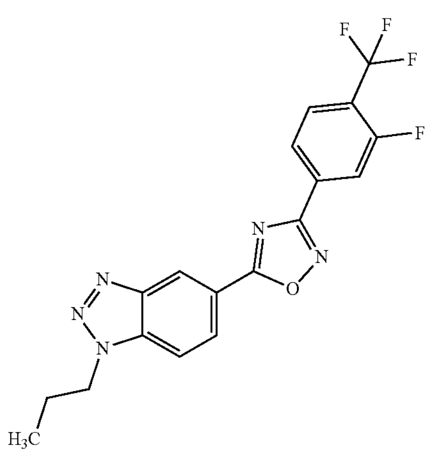 [SMILES: CCCn1nnc2cc(-c3nc(-c4ccc(C(F)(F)F)c(F)c4)no3)ccc21] | 193 | 5-{3-[3-fluoro-4-(trifluoromethyl)phenyl]-1,2,4-oxadiazol-5-yl}-1-propyl-1H-1,2,3-benzotriazole | 391.33 | 392.1 |

-continued

| Structure | Compound Number | Chemical Name | Exact Mass | Actual Peak |
|---|---|---|---|---|
| 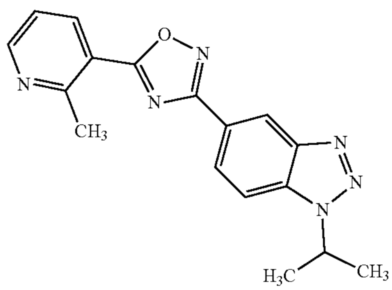 [SMILES: Cc1ncccc1-c1nc(-c2ccc3c(c2)nnn3C(C)C)no1] | 194 | 3-(1-isopropyl-1H-benzo[d][1,2,3]triazol-5-yl)-5-(2-methylpyridin-3-yl)-1,2,4-oxadiazole | 320.36 | 321 |
| 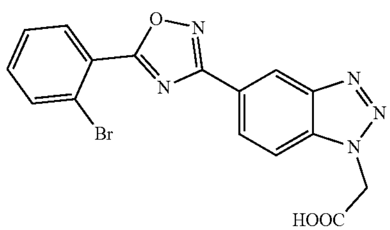 [SMILES: O=C(O)Cn1nnc2cc(-c3noc(-c4ccccc4Br)n3)ccc21] | 195 | 2-(5-(5-(2-bromophenyl)-1,2,4-oxadiazol-3-yl)-1H-benzo[d][1,2,3]triazol-1-yl)acetic acid | 400.19 | 400 |
| 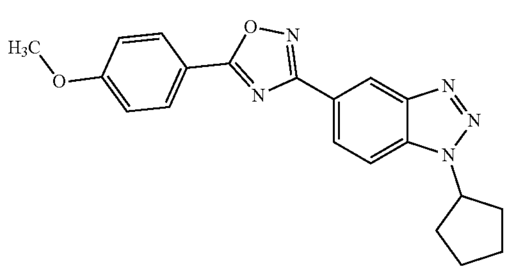 [SMILES: COc1ccc(-c2nc(-c3ccc4c(c3)nnn4C3CCCC3)no2)cc1] | 196 | 3-(1-cyclopentyl-1H-benzo[d][1,2,3]triazol-5-yl)-5-(4-methoxyphenyl)-1,2,4-oxadiazole | 361.41 | 362 |
| 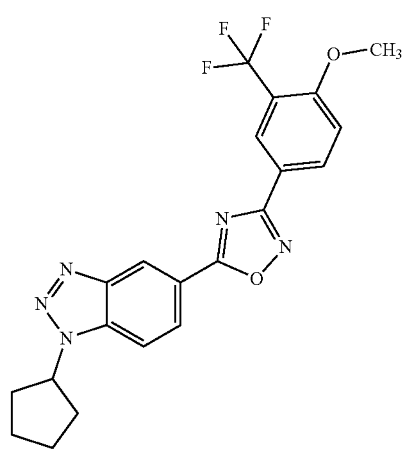 [SMILES: COc1ccc(-c2noc(-c3ccc4c(c3)nnn4C3CCCC3)n2)cc1C(F)(F)F] | 197 | 1-cyclopentyl-5-{3-[4-methoxy-3-(trifluoromethyl)phenyl]-1,2,4-oxadiazol-5-yl}-1H-1,2,3-benzotriazole | 429.40 | 430.1 |

-continued

| Structure | Compound Number | Chemical Name | Exact Mass | Actual Peak |
|---|---|---|---|---|
| 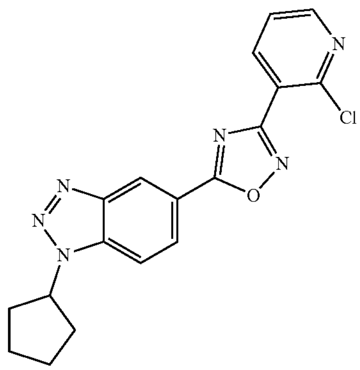 [SMILES: Clc1ncccc1-c1noc(-c2ccc3c(c2)nnn3C2CCCC2)n1] | 198 | 5-[3-(2-chloropyridin-3-yl)-1,2,4-oxadiazol-5-yl]-1-cyclopentyl-1H-1,2,3-benzotriazole | 366.81 | 367.1 |
| 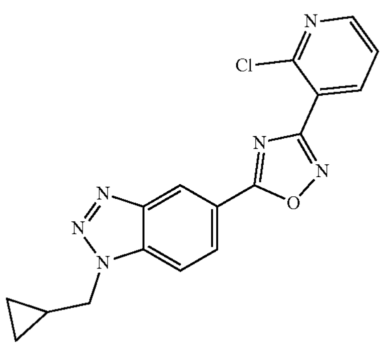 [SMILES: Clc1ncccc1-c1noc(-c2ccc3c(c2)nnn3CC2CC2)n1] | 199 | 5-[3-(2-chloropyridin-3-yl)-1,2,4-oxadiazol-5-yl]-1-(cyclopropylmethyl)-1H-1,2,3-benzotriazole | 352.78 | 353.1 |
| 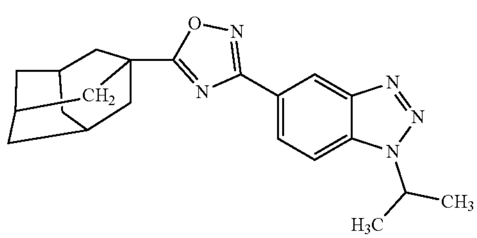 [SMILES: CC(C)n1nnc2cc(-c3noc(C45CC6CC(CC(C6)C4)C5)n3)ccc21] | 200 | 5-[5-(adamantan-1-yl)-1,2,4-oxadiazol-3-yl]-1-(propan-2-yl)-1H-1,2,3-benzotriazole | 363.47 | 364 |
| 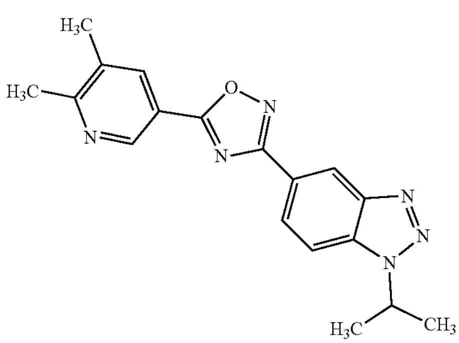 [SMILES: Cc1cc(-c2nc(-c3ccc4c(c3)nnn4C(C)C)no2)cnc1C] | 201 | 5-(5,6-dimethylpyridin-3-yl)-3-(1-isopropyl-1H-benzo[d][1,2,3]triazol-5-yl)-1,2,4-oxadiazole | 334.38 | 335.1 |

-continued

| Structure | Compound Number | Chemical Name | Exact Mass | Actual Peak |
|---|---|---|---|---|
| 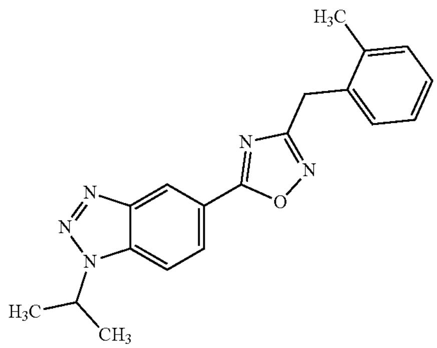 [SMILES: Cc1ccccc1Cc1noc(-c2ccc3c(c2)nnn3C(C)C)n1] | 202 | 5-{3-[(2-methylphenyl)methyl]-1,2,4-oxadiazol-5-yl}-1-(propan-2-yl)-1H-1,2,3-benzotriazole | 333.40 | 334.1 |
| 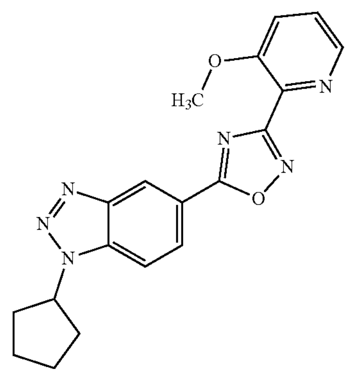 [SMILES: COc1cccnc1-c1noc(-c2ccc3c(c2)nnn3C2CCCC2)n1] | 203 | 1-cyclopentyl-5-[3-(3-methoxypyridin-2-yl)-1,2,4-oxadiazol-5-yl]-1H-1,2,3-benzotriazole | 362.39 | 363.1 |
| 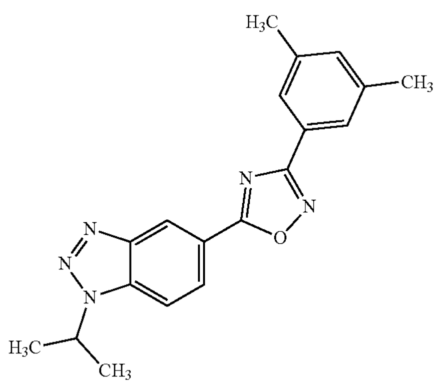 [SMILES: Cc1cc(C)cc(-c2noc(-c3ccc4c(c3)nnn4C(C)C)n2)c1] | 204 | 5-[3-(3,5-dimethylphenyl)-1,2,4-oxadiazol-5-yl]-1-(propan-2-yl)-1H-1,2,3-benzotriazole | 333.40 | 334.1 |
| 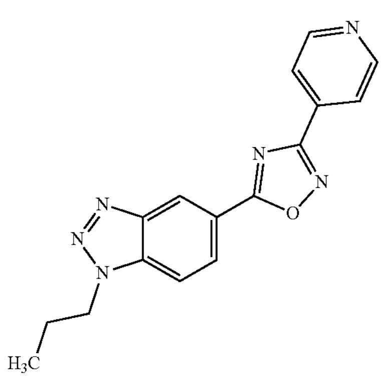 [SMILES: CCCn1nnc2cc(-c3nc(-c4ccncc4)no3)ccc21] | 205 | 1-propyl-5-[3-(pyridin-4-yl)-1,2,4-oxadiazol-5-yl]-1H-1,2,3-benzotriazole | 306.33 | 307.1 |

-continued

| Structure | Compound Number | Chemical Name | Exact Mass | Actual Peak |
|---|---|---|---|---|
| 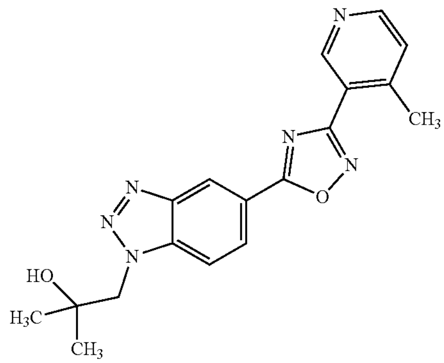 [SMILES: Cc1ccncc1-c1noc(-c2ccc3c(c2)nnn3CC(C)(C)O)n1] | 206 | 2-methyl-1-{5-[3-(4-methylpyridin-3-yl)-1,2,4-oxadiazol-5-yl]-1H-1,2,3-benzotriazol-1-yl}propan-2-ol | 350.38 | 351.1 |
| 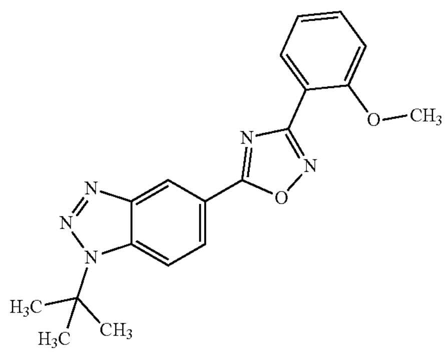 [SMILES: COc1ccccc1-c1noc(-c2ccc3c(c2)nnn3C(C)(C)C)n1] | 207 | 1-tert-butyl-5-[3-(2-methoxyphenyl)-1,2,4-oxadiazol-5-yl]-1H-1,2,3-benzotriazole | 349.39 | 350.2 |
| 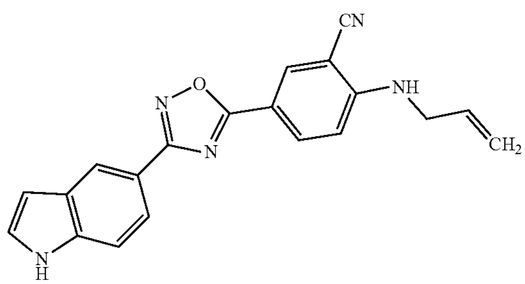 [SMILES: C=CCNc1ccc(-c2nc(-c3ccc4[nH]ccc4c3)no2)cc1C#N] | 208 | 5-(3-(1H-indol-5-yl)-1,2,4-oxadiazol-5-yl)-2-(allylamino)benzonitrile | 341.37 | 342.2 |
| 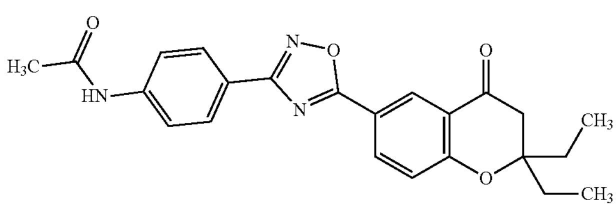 [SMILES: CCC1(CC)CC(=O)c2cc(-c3nc(-c4ccc(NC(C)=O)cc4)no3)ccc2O1] | 209 | N-(4-(5-(2,2-diethyl-4-oxochroman-6-yl)-1,2,4-oxadiazol-3-yl)phenyl)acetamide | 405.45 | 406.2 |
| 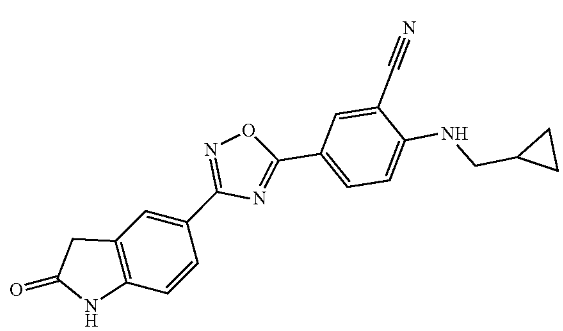 [SMILES: N#Cc1cc(-c2nc(-c3ccc4c(c3)CC(=O)N4)no2)ccc1NCC1CC1] | 210 | 2-((cyclopropylmethyl)amino)-5-(3-(2-oxoindolin-5-yl)-1,2,4-oxadiazol-5-yl)benzonitrile | 371.40 | 372.1 |

-continued

| Structure | Compound Number | Chemical Name | Exact Mass | Actual Peak |
|---|---|---|---|---|
| 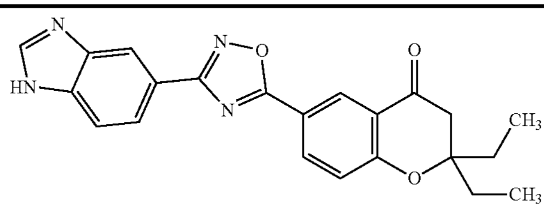 | 211 | 6-(3-(1H-benzo[d]imidazol-5-yl)-1,2,4-oxadiazol-5-yl)-2,2-diethylchroman-4-one | 388.43 | 389.1 |
| 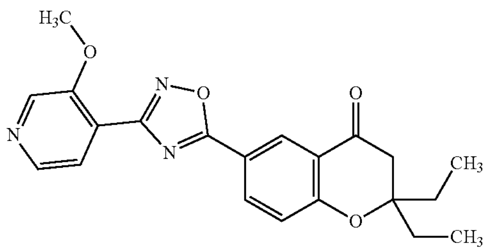 [SMILES: CCC1(CC)CC(=O)c2cc(-c3nc(-c4ccncc4OC)no3)ccc2O1] | 212 | 2,2-diethyl-6-(3-(3-methoxypyridin-4-yl)-1,2,4-oxadiazol-5-yl)chroman-4-one | 379.42 | 380.2 |
| 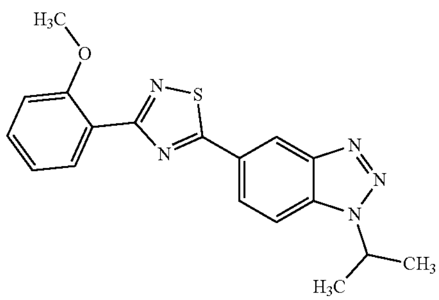 [SMILES: COc1ccccc1-c1nsc(-c2ccc3c(c2)nnn3C(C)C)n1] | 213 | 5-[3-(2-methoxyphenyl)-1,2,4-thiadiazol-5-yl]-1-(propan-2-yl)-1H-1,2,3-benzotriazole | 351.43 | 352 |
| 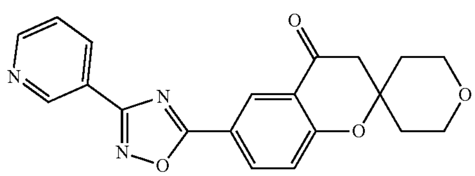 [SMILES: O=C1CC2(CCOCC2)Oc2ccc(-c3nc(-c4cccnc4)no3)cc21] | 214 | 6-[3-(pyridin-3-yl)-1,2,4-oxadiazol-5-yl]-3,4-dihydrospiro[1-benzopyran-2,4'-oxane]-4-one | 363.37 | 364.1 |
| 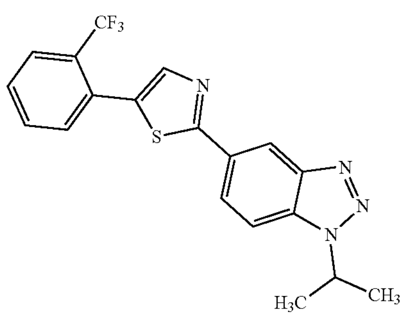 [SMILES: CC(C)n1nnc2cc(-c3ncc(-c4ccccc4C(F)(F)F)s3)ccc21] | 215 | 2-(1-isopropyl-1H-benzo[d][1,2,3]triazol-5-yl)-5-(2-(trifluoromethyl)phenyl)thiazole | 388.41 | 389.2 |
| 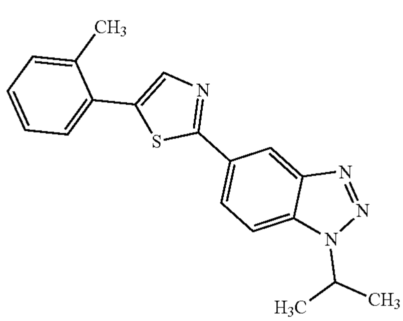 [SMILES: Cc1ccccc1-c1cnc(-c2ccc3c(c2)nnn3C(C)C)s1] | 216 | 2-(1-isopropylbenzotriazol-5-yl)-5-(o-tolyl)thiazole | 334.44 | 335.1 |

-continued

| Structure | Compound Number | Chemical Name | Exact Mass | Actual Peak |
|---|---|---|---|---|
| 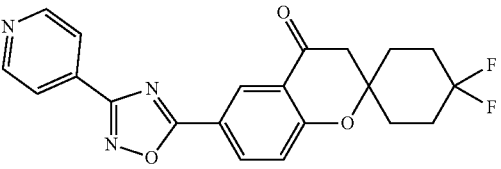 [SMILES: O=C1CC2(CCC(F)(F)CC2)Oc2ccc(-c3nc(-c4ccncc4)no3)cc21] | 217 | 4',4'-difluoro-6-[3-(pyridin-4-yl)-1,2,4-oxadiazol-5-yl]-3,4-dihydrospiro[1-benzopyran-2,1'-cyclohexane]-4-one | 397.38 | 398.2 |
| 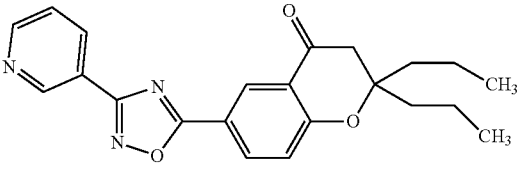 [SMILES: CCCC1(CCC)CC(=O)c2cc(-c3nc(-c4cccnc4)no3)ccc2O1] | 218 | 2,2-dipropyl-6-[3-(pyridin-3-yl)-1,2,4-oxadiazol-5-yl]-3,4-dihydro-2H-1-benzopyran-4-one | 377.44 | 378.2 |
| 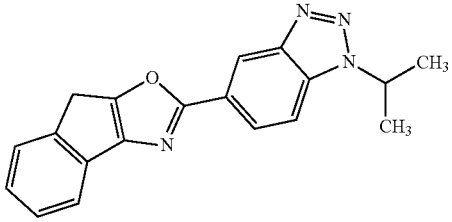 [SMILES: CC(C)n1nnc2cc(-c3nc4c(o3)Cc3ccccc3-4)ccc21] | 219 | 5-{8H-indeno[1,2-d][1,3]oxazol-2-yl}-1-(propan-2-yl)-1H-1,2,3-benzotriazole | 316.36 | 317 |
| 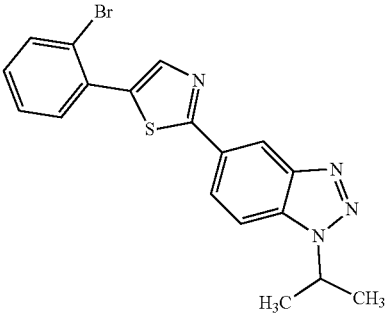 [SMILES: CC(C)n1nnc2cc(-c3ncc(-c4ccccc4Br)s3)ccc21] | 220 | 5-(2-bromophenyl)-2-(1-isopropylbenzotriazol-5-yl)thiazole | 399.31 | 401 |
| 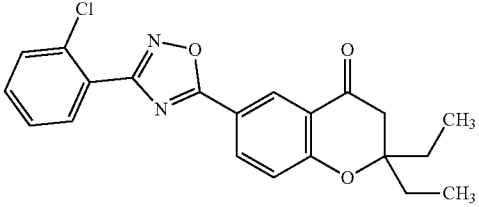 [SMILES: CCC1(CC)CC(=O)c2cc(-c3nc(-c4ccccc4Cl)no3)ccc2O1] | 221 | 6-(3-(2-chlorophenyl)-1,2,4-oxadiazol-5-yl)-2,2-diethylchroman-4-one | 382.84 | 383.1 |
| 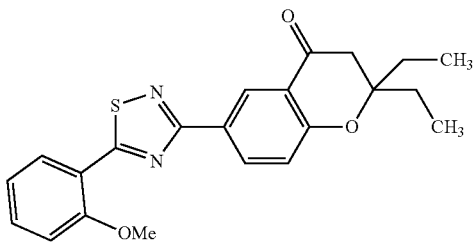 [SMILES: CCC1(CC)CC(=O)c2cc(-c3nsc(-c4ccccc4OC)n3)ccc2O1] | 222 | 2,2-diethyl-6-(5-(2-methoxyphenyl)-1,2,4-thiadiazol-3-yl)chroman-4-one | 394.49 | 395.1 |

-continued

| Structure | Compound Number | Chemical Name | Exact Mass | Actual Peak |
|---|---|---|---|---|
| 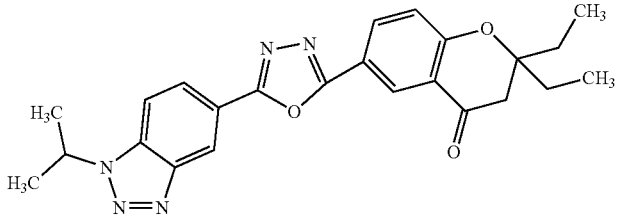 [SMILES: CCC1(CC)CC(=O)c2cc(-c3nnc(-c4ccc5c(c4)nnn5C(C)C)o3)ccc2O1] | 223 | 2,2-diethyl-6-(5-(1-isopropyl-1H-benzo[d][1,2,3]triazol-5-yl)-1,3,4-oxadiazol-2-yl)chroman-4-one | 431.50 | 432.2 |
| 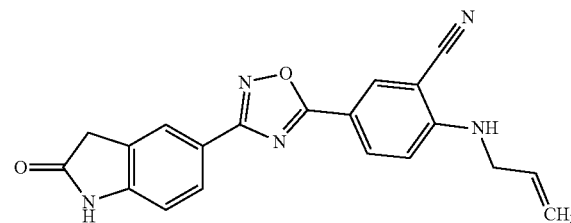 [SMILES: C=CCNc1ccc(-c2nc(-c3ccc4c(c3)CC(=O)N4)no2)cc1C#N] | 224 | 2-(allylamino)-5-(3-(2-oxoindolin-5-yl)-1,2,4-oxadiazol-5-yl)benzonitrile | 357.37 | 358.1 |
| 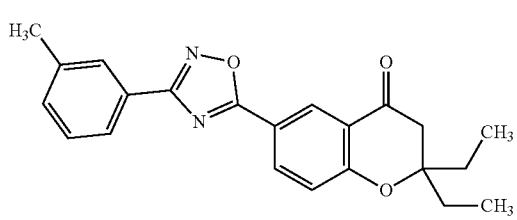 [SMILES: CCC1(CC)CC(=O)c2cc(-c3nc(-c4cccc(C)c4)no3)ccc2O1] | 225 | 2,2-diethyl-6-(3-(m-tolyl)-1,2,4-oxadiazol-5-yl)chroman-4-one | 362.43 | 363.1 |
| 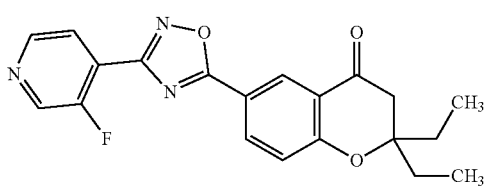 | 226 | 2,2-diethyl-6-(3-(3-fluoropyridin-4-yl)-1,2,4-oxadiazol-5-yl)chroman-4-one | 367.38 | 368.1 |
| 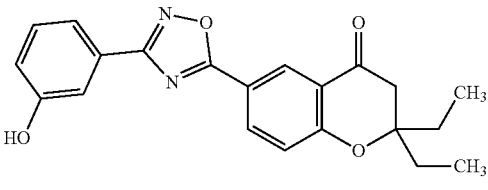 [SMILES: CCC1(CC)CC(=O)c2cc(-c3nc(-c4cccc(O)c4)no3)ccc2O1] | 227 | 2,2-diethyl-6-[3-(3-hydroxyphenyl)-1,2,4-oxadiazol-5-yl]chroman-4-one | 364.40 | 365.1 |
| 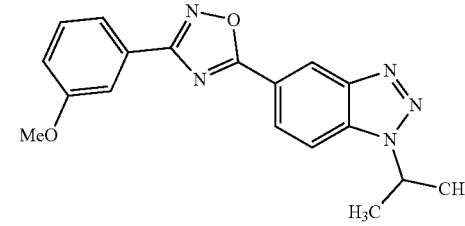 | 228 | 5-(1-isopropyl-1H-benzo[d][1,2,3]triazol-5-yl)-3-(3-methoxyphenyl)-1,2,4-oxadiazole | 335.37 | 336 |
| 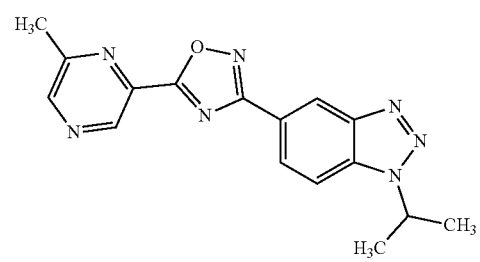 [SMILES: Cc1cncc(-c2nc(-c3ccc4c(c3)nnn4C(C)C)no2)n1] | 229 | 3-(1-isopropyl-1H-benzo[d][1,2,3]triazol-5-yl)-5-(6-methylpyrazin-2-yl)-1,2,4-oxadiazole | 321.34 | 322.1 |

-continued
| Structure | Compound Number | Chemical Name | Exact Mass | Actual Peak |
|---|---|---|---|---|
| 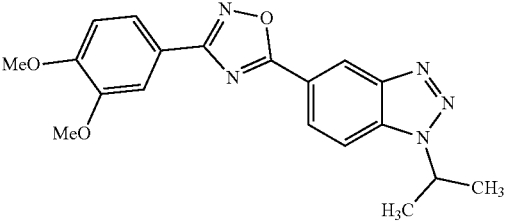 | 230 | 3-(3,4-dimethoxyphenyl)-5-(1-isopropyl-1H-benzo[d][1,2,3]triazol-5-yl)-1,2,4-oxadiazole | 365.39 | 366 |
| 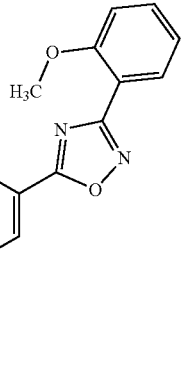 | 231 | 5-[3-(2-methoxyphenyl)-1,2,4-oxadiazol-5-yl]-1-(oxan-4-yl)-1H-1,2,3-benzotriazole | 377.40 | 378.2 |
| 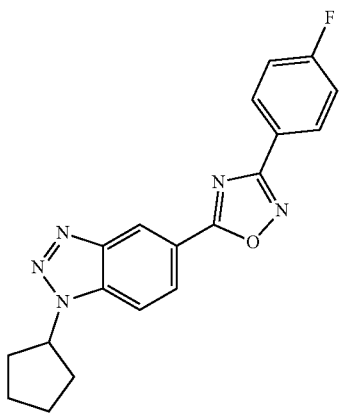 [SMILES: Fc1ccc(-c2noc(-c3ccc4c(c3)nnn4C3CCCC3)n2)cc1] | 232 | 1-cyclopentyl-5-[3-(4-fluorophenyl)-1,2,4-oxadiazol-5-yl]-1H-1,2,3-benzotriazole | 349.37 | 350.2 |
| 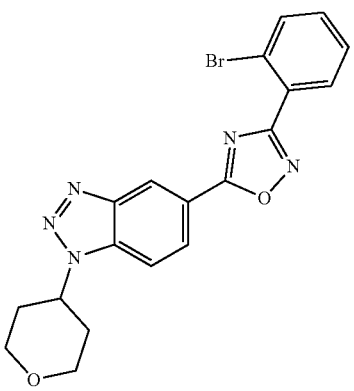 [SMILES: Brc1ccccc1-c1noc(-c2ccc3c(c2)nnn3C2CCOCC2)n1] | 233 | 5-[3-(2-bromophenyl)-1,2,4-oxadiazol-5-yl]-1-(oxan-4-yl)-1H-1,2,3-benzotriazole | 426.27 | 426.1 |

-continued

| Structure | Compound Number | Chemical Name | Exact Mass | Actual Peak |
|---|---|---|---|---|
| 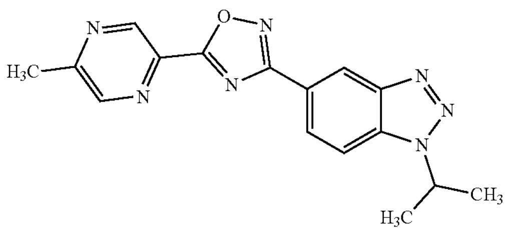 [SMILES: Cc1cnc(-c2nc(-c3ccc4c(c3)nnn4C(C)C)no2)cn1] | 234 | 3-(1-isopropyl-1H-benzo[d][1,2,3]triazol-5-yl)-5-(5-methylpyrazin-2-yl)-1,2,4-oxadiazole | 321.34 | 322.1 |
| 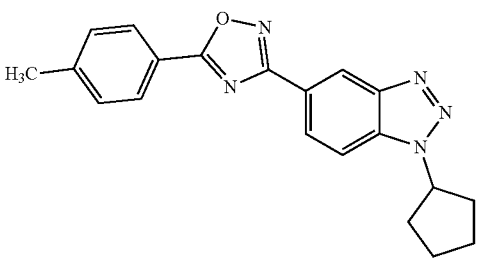 [SMILES: Cc1ccc(-c2nc(-c3ccc4c(c3)nnn4C3CCCC3)no2)cc1] | 235 | 3-(1-cyclopentyl-1H-benzo[d][1,2,3]triazol-5-yl)-5-(p-tolyl)-1,2,4-oxadiazole | 345.41 | 346 |
| 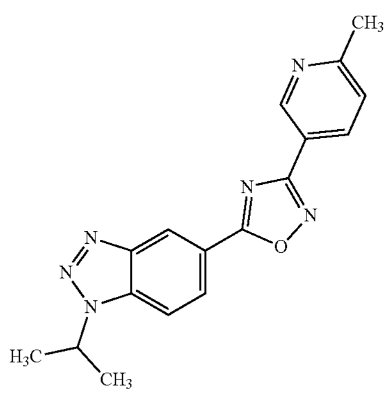 [SMILES: Cc1ccc(-c2noc(-c3ccc4c(c3)nnn4C(C)C)n2)cn1] | 236 | 5-[3-(6-methylpyridin-3-yl)-1,2,4-oxadiazol-5-yl]-1-(propan-2-yl)-1H-1,2,3-benzotriazole | 320.36 | 321.1 |
| 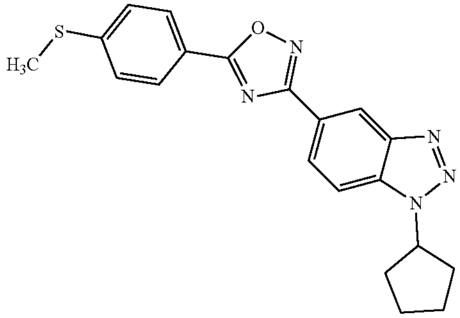 [SMILES: CSc1ccc(-c2nc(-c3ccc4c(c3)nnn4C3CCCC3)no2)cc1] | 237 | 3-(1-cyclopentyl-1H-benzo[d][1,2,3]triazol-5-yl)-5-(4-(methylthio)phenyl)-1,2,4-oxadiazole | 377.47 | 378.1 |
| 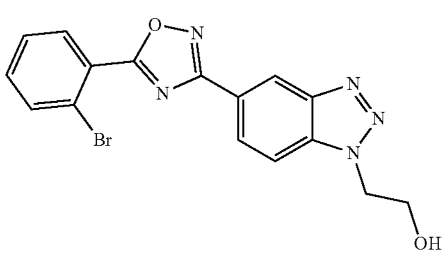 [SMILES: OCCn1nnc2cc(-c3noc(-c4ccccc4Br)n3)ccc21] | 238 | 2-(5-(5-(2-bromophenyl)-1,2,4-oxadiazol-3-yl)-1H-benzo[d][1,2,3]triazol-1-yl)ethanol | 386.21 | 386 |

-continued

| Structure | Compound Number | Chemical Name | Exact Mass | Actual Peak |
|---|---|---|---|---|
| 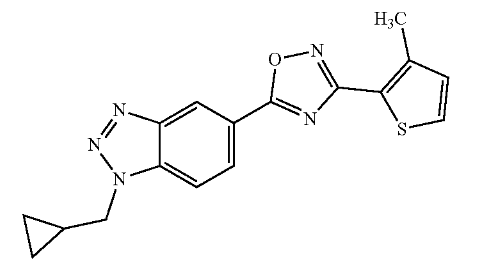 [SMILES: Cc1ccsc1-c1noc(-c2ccc3c(c2)nnn3CC2CC2)n1] | 239 | 1-(cyclopropylmethyl)-5-[3-(3-methylthiophen-2-yl)-1,2,4-oxadiazol-5-yl]-1H-1,2,3-benzotriazole | 337.40 | 338.2 |
| 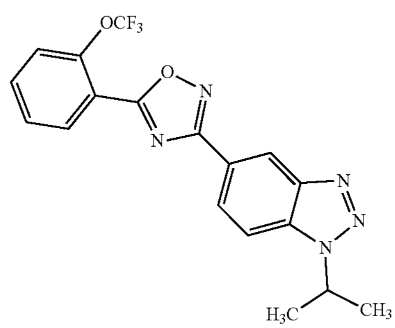 [SMILES: CC(C)n1nnc2cc(-c3noc(-c4ccccc4OC(F)(F)F)n3)ccc21] | 240 | 3-(1-isopropyl-1H-benzo[d][1,2,3]triazol-5-yl)-5-(2-(trifluoromethoxy)phenyl)-1,2,4-oxadiazole | 389.34 | 390 |
| 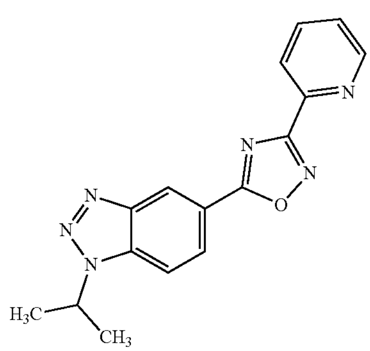 | 241 | 1-(propan-2-yl)-5-[3-(pyridin-2-yl)-1,2,4-oxadiazol-5-yl]-1H-1,2,3-benzotriazole | 306.33 | 307.2 |
| 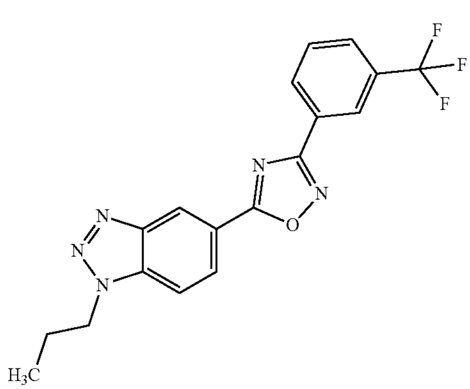 [SMILES: CCCn1nnc2cc(-c3nc(-c4cccc(C(F)(F)F)c4)no3)ccc21] | 242 | 1-propyl-5-{3-[3-(trifluoromethyl)phenyl]-1,2,4-oxadiazol-5-yl}-1H-1,2,3-benzotriazole | 373.34 | 374.3 |

-continued

| Structure | Compound Number | Chemical Name | Exact Mass | Actual Peak |
|---|---|---|---|---|
| 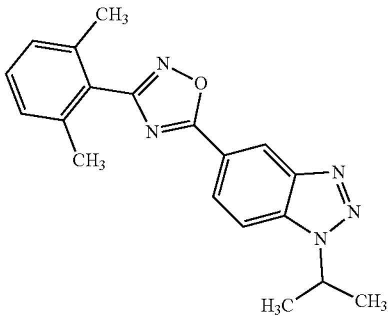 [SMILES: Cc1cccc(C)c1-c1noc(-c2ccc3c(c2)nnn3C(C)C)n1] | 243 | 3-(2,6-dimethylphenyl)-5-(1-isopropyl-1H-benzo[d][1,2,3]triazol-5-yl)-1,2,4-oxadiazole | 333.40 | 334 |
| 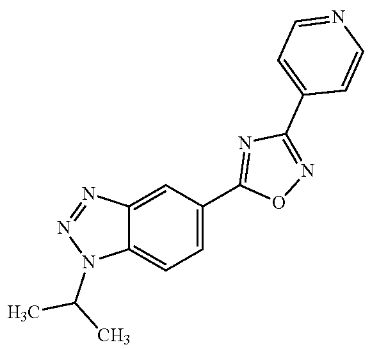 [SMILES: CC(C)n1nnc2cc(-c3nc(-c4ccncc4)no3)ccc21] | 244 | 1-(propan-2-yl)-5-[3-(pyridin-4-yl)-1,2,4-oxadiazol-5-yl]-1H-1,2,3-benzotriazole | 306.33 | 307.1 |
| 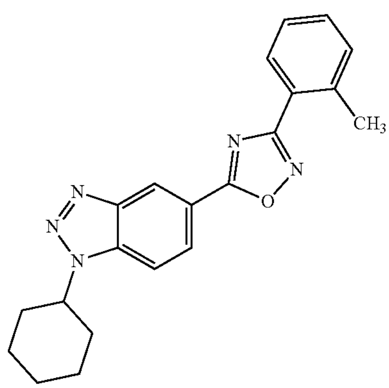 [SMILES: Cc1ccccc1-c1noc(-c2ccc3c(c2)nnn3C2CCCCC2)n1] | 245 | 1-cyclohexyl-5-[3-(2-methylphenyl)-1,2,4-oxadiazol-5-yl]-1H-1,2,3-benzotriazole | 359.43 | 360.2 |
| 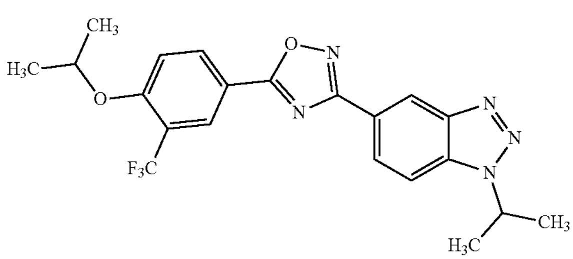 [SMILES: CC(C)Oc1ccc(-c2nc(-c3ccc4c(c3)nnn4C(C)C)no2)cc1C(F)(F)F] | 246 | 5-(4-isopropoxy-3-(trifluoromethyl)phenyl)-3-(1-isopropyl-1H-benzo[d][1,2,3]triazol-5-yl)-1,2,4-oxadiazole | 431.42 | 432 |
| 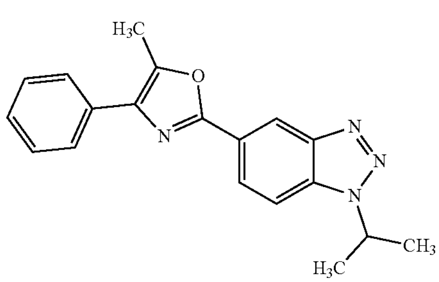 [SMILES: Cc1oc(-c2ccc3c(c2)nnn3C(C)C)nc1-c1ccccc1] | 247 | 5-(5-methyl-4-phenyl-1,3-oxazol-2-yl)-1-(propan-2-yl)-1H-1,2,3-benzotriazole | 318.38 | 319 |

-continued

| Structure | Compound Number | Chemical Name | Exact Mass | Actual Peak |
|---|---|---|---|---|
| 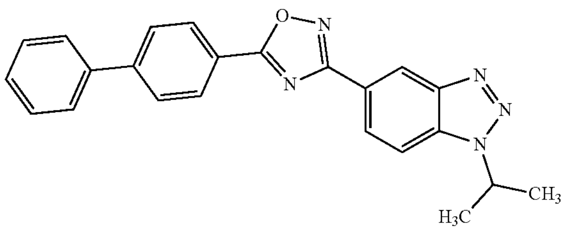 [SMILES: CC(C)n1nnc2cc(-c3noc(-c4ccc(-c5ccccc5)cc4)n3)ccc21] | 248 | 5-([1,1'-biphenyl]-4-yl)-3-(1-isopropyl-1H-benzo[d][1,2,3]triazol-5-yl)-1,2,4-oxadiazole | 381.44 | 382.1 |
| 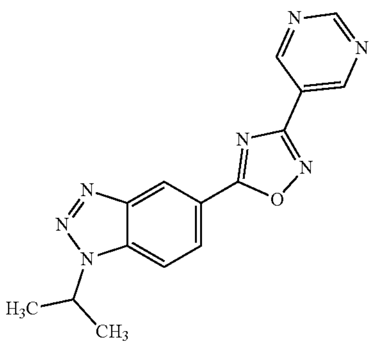 [SMILES: CC(C)n1nnc2cc(-c3nc(-c4cncnc4)no3)ccc21] | 249 | 1-(propan-2-yl)-5-[3-(pyrimidin-5-yl)-1,2,4-oxadiazol-5-yl]-1H-1,2,3-benzotriazole | 307.32 | 308.1 |
| 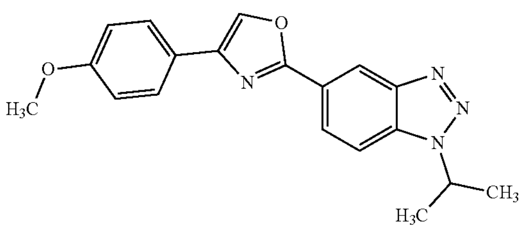 [SMILES: COc1ccc(-c2coc(-c3ccc4c(c3)nnn4C(C)C)n2)cc1] | 250 | 5-[4-(4-methoxyphenyl)-1,3-oxazol-2-yl]-1-(propan-2-yl)-1H-1,2,3-benzotriazole | 334.38 | 335 |
| 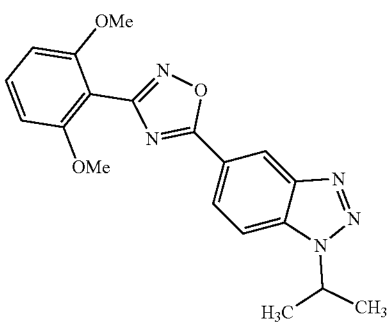 [SMILES: COc1cccc(OC)c1-c1noc(-c2ccc3c(c2)nnn3C(C)C)n1] | 251 | 3-(2,6-dimethoxyphenyl)-5-(1-isopropylbenzotriazol-5-yl)-1,2,4-oxadiazole | 365.39 | 366.1 |
| 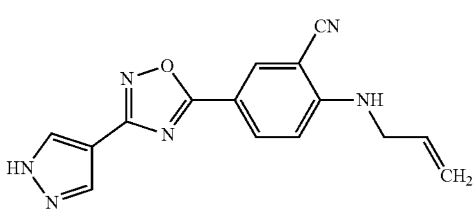 [SMILES: C=CCNc1ccc(-c2nc(-c3cn[nH]c3)no2)cc1C#N] | 252 | 5-(3-(1H-pyrazol-4-yl)-1,2,4-oxadiazol-5-yl)-2-(allylamino)benzonitrile | 292.30 | 293.1 |
| 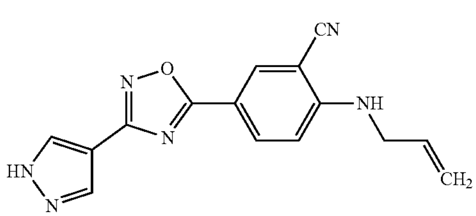 [SMILES: C=CCNc1ccc(-c2nc(-c3cn[nH]c3)no2)cc1C#N] | 253 | 1-tert-butyl-5-[3-(3-methylthiophen-2-yl)-1,2,4-oxadiazol-5-yl]-1H-1,2,3-benzotriazole | 339.42 | 340.1 |

-continued

| Structure | Compound Number | Chemical Name | Exact Mass | Actual Peak |
|---|---|---|---|---|
| 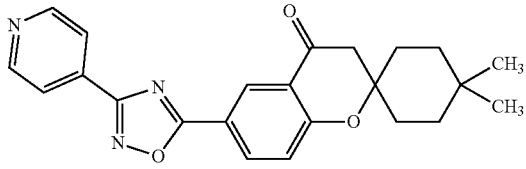 [SMILES: CC1(C)CCC2(CC1)CC(=O)c1cc(-c3nc(-c4ccncc4)no3)ccc1O2] | 254 | 4',4'-dimethyl-6-[3-(pyridin-4-yl)-1,2,4-oxadiazol-5-yl]-3,4-dihydrospiro[1-benzopyran-2,1'-cyclohexane]-4-one | 389.46 | 390.2 |
| 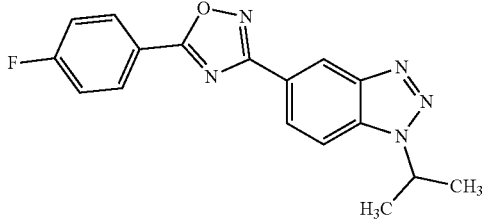 [SMILES: CC(C)n1nnc2cc(-c3noc(-c4ccc(F)cc4)n3)ccc21] | 255 | 5-(4-fluorophenyl)-3-(1-isopropylbenzotriazol-5-yl)-1,2,4-oxadiazole | 323.33 | 324.1 |
| 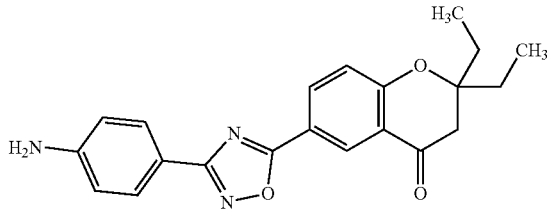 [SMILES: CCC1(CC)CC(=O)c2cc(-c3nc(-c4ccc(N)cc4)no3)ccc2O1] | 256 | 6-(3-(4-aminophenyl)-1,2,4-oxadiazol-5-yl)-2,2-diethylchroman-4-one | 363.42 | 364.2 |
| 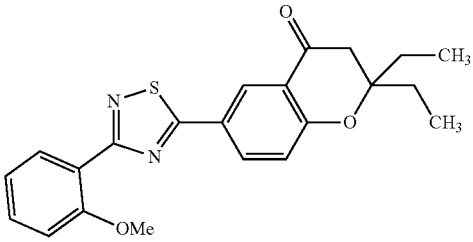 [SMILES: CCC1(CC)CC(=O)c2cc(-c3nc(-c4ccccc4OC)ns3)ccc2O1] | 257 | 2,2-diethyl-6-(3-(2-methoxyphenyl)-1,2,4-thiadiazol-5-yl)chroman-4-one | 394.49 | 395.1 |
| 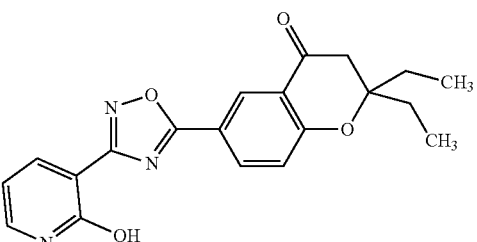 | 258 | 2,2-diethyl-6-(3-(2-hydroxypyridin-3-yl)-1,2,4-oxadiazol-5-yl)chroman-4-one | 365.39 | 366.3 |
| 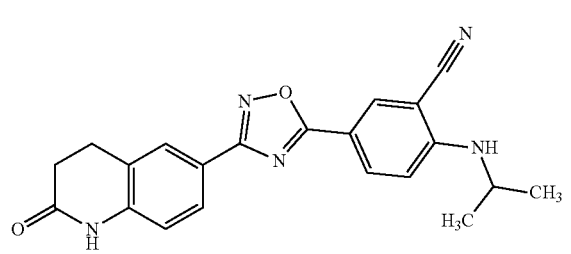 [SMILES: CC(C)Nc1ccc(-c2nc(-c3ccc4c(c3)CCC(=O)N4)no2)cc1C#N] | 259 | 2-(isopropylamino)-5-(3-(2-oxo-1,2,3,4-tetrahydroquinolin-6-yl)-1,2,4-oxadiazol-5-yl)benzonitrile | 373.42 | 374.1 |

-continued

| Structure | Compound Number | Chemical Name | Exact Mass | Actual Peak |
|---|---|---|---|---|
| 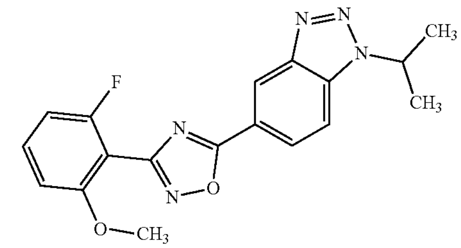 [SMILES: COc1cccc(F)c1-c1noc(-c2ccc3c(c2)nnn3C(C)C)n1] | 260 | 3-(2-fluoro-6-methoxy-phenyl)-5-(1-isopropylbenzotriazol-5-yl)-1,2,4-oxadiazole | 353.36 | 354.1 |
| 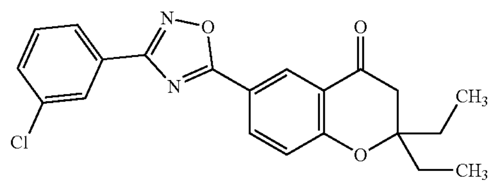 [SMILES: CCC1(CC)CC(=O)c2cc(-c3nc(-c4cccc(Cl)c4)no3)ccc2O1] | 261 | 6-[3-(3-chlorophenyl)-1,2,4-oxadiazol-5-yl]-2,2-diethyl-chroman-4-one | 382.84 | 383.1 |
| 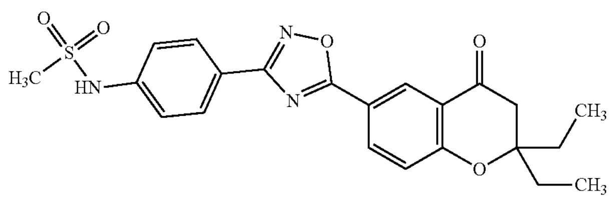 [SMILES: CCC1(CC)CC(=O)c2cc(-c3nc(-c4ccc(NS(C)(=O)=O)cc4)no3)ccc2O1] | 262 | N-(4-(5-(2,2-diethyl-4-oxochroman-6-yl)-1,2,4-oxadiazol-3-yl)phenyl)methanesulfonamide | 441.50 | 442 |
| 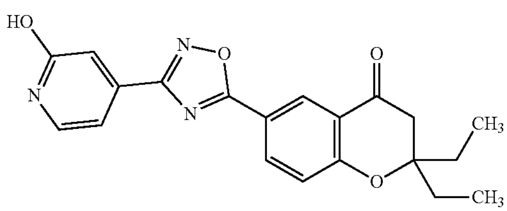 [SMILES: CCC1(CC)CC(=O)c2cc(-c3nc(-c4ccnc(O)c4)no3)ccc2O1] | 263 | 2,2-diethyl-6-[3-(2-hydroxy-4-pyridyl)-1,2,4-oxadiazol-5-yl]chroman-4-one | 365.39 | 366.1 |
| 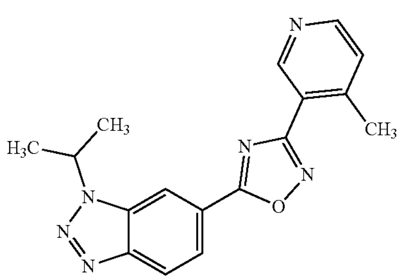 [SMILES: Cc1ccncc1-c1noc(-c2ccc3nnn(C(C)C)c3c2)n1] | 264 | 6-[3-(4-methylpyridin-3-yl)-1,2,4-oxadiazol-5-yl]-1-(propan-2-yl)-1H-1,2,3-benzotriazole | 320.36 | 321.1 |
| 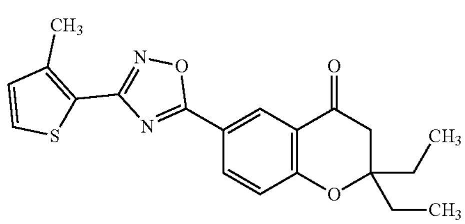 [SMILES: CCC1(CC)CC(=O)c2cc(-c3nc(-c4sccc4C)no3)ccc2O1] | 265 | 2,2-diethyl-6-(3-(3-methylthiophen-2-yl)-1,2,4-oxadiazol-5-yl)chroman-4-one | 368.45 | 369.1 |
| 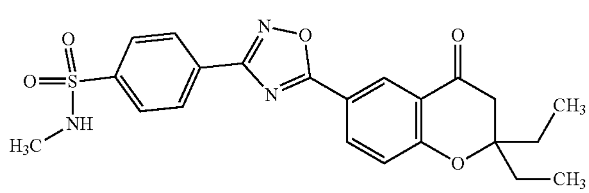 [SMILES: CCC1(CC)CC(=O)c2cc(-c3nc(-c4ccc(S(=O)(=O)NC)cc4)no3)ccc2O1] | 266 | 4-(5-(2,2-diethyl-4-oxochroman-6-yl)-1,2,4-oxadiazol-3-yl)-N-methylbenzene-sulfonamide | 441.50 | 442.1 |

-continued

| Structure | Compound Number | Chemical Name | Exact Mass | Actual Peak |
|---|---|---|---|---|
| 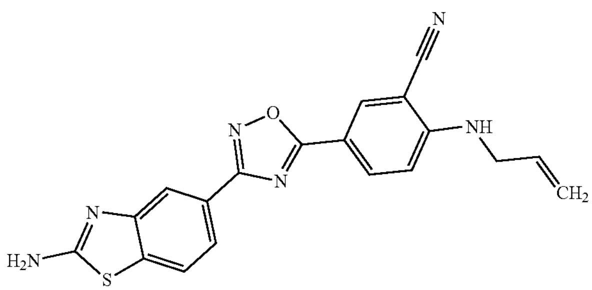 [SMILES: C=CCNc1ccc(-c2nc(-c3ccc4sc(N)nc4c3)no2)cc1C#N] | 267 | 2-(allylamino)-5-(3-(2-aminobenzo[d]thiazol-5-yl)-1,2,4-oxadiazol-5-yl)benzonitrile | 374.42 | 375.3 |
| 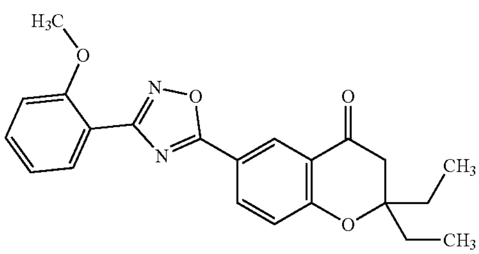 [SMILES: CCC1(CC)CC(=O)c2cc(-c3nc(-c4ccccc4OC)no3)ccc2O1] | 268 | 2,2-diethyl-6-[3-(2-methoxyphenyl)-1,2,4-oxadiazol-5-yl]chroman-4-one | 378.43 | 379.1 |
| 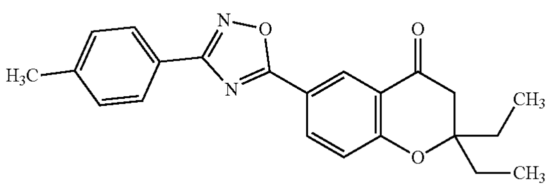 [SMILES: CCC1(CC)CC(=O)c2cc(-c3nc(-c4ccc(C)cc4)no3)ccc2O1] | 269 | 2,2-diethyl-6-[3-(p-tolyl)-1,2,4-oxadiazol-5-yl]chroman-4-one | 362.43 | 363.1 |
| 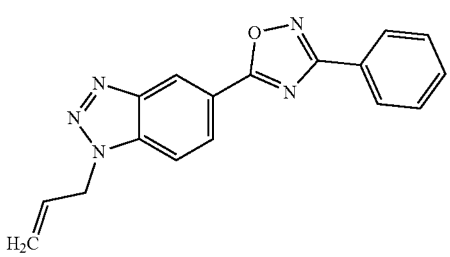 [SMILES: C=CCn1nnc2cc(-c3nc(-c4ccccc4)no3)ccc21] | 270 | 5-(3-phenyl-1,2,4-oxadiazol-5-yl)-1-(prop-2-en-1-yl)-1H-1,2,3-benzotriazole | 303.33 | |
| 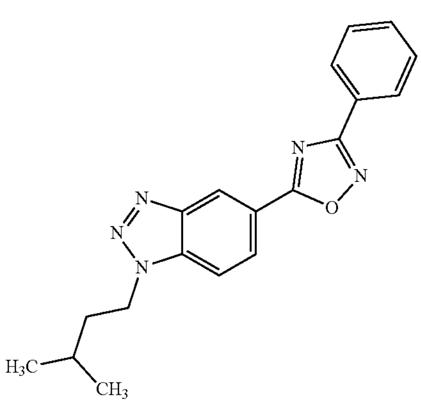 [SMILES: CC(C)CCn1nnc2cc(-c3nc(-c4ccccc4)no3)ccc21] | 271 | 1-(3-methylbutyl)-5-(3-phenyl-1,2,4-oxadiazol-5-yl)-1H-1,2,3-benzotriazole | 333.40 | 334.2 |

-continued

| Structure | Compound Number | Chemical Name | Exact Mass | Actual Peak |
|---|---|---|---|---|
| 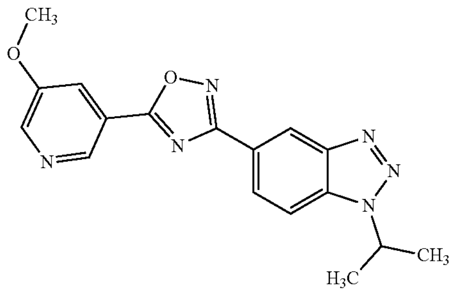 [SMILES: COc1cncc(-c2nc(-c3ccc4c(c3)nnn4C(C)C)no2)c1] | 272 | 3-(1-isopropyl-1H-benzo[d][1,2,3]triazol-5-yl)-5-(5-methoxypyridin-3-yl)-1,2,4-oxadiazole | 336.36 | 337.1 |
| 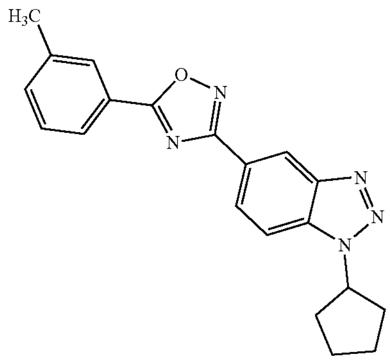 [SMILES: Cc1cccc(-c2nc(-c3ccc4c(c3)nnn4C3CCCC3)no2)c1] | 273 | 3-(1-cyclopentyl-1H-benzo[d][1,2,3]triazol-5-yl)-5-(m-tolyl)-1,2,4-oxadiazole | 345.41 | 346 |
| 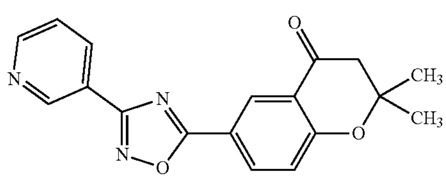 [SMILES: CC1(C)CC(=O)c2cc(-c3nc(-c4cccnc4)no3)ccc2O1] | 274 | 2,2-dimethyl-6-[3-(pyridin-3-yl)-1,2,4-oxadiazol-5-yl]-3,4-dihydro-2H-1-benzopyran-4-one | 321.34 | 322.1 |
| 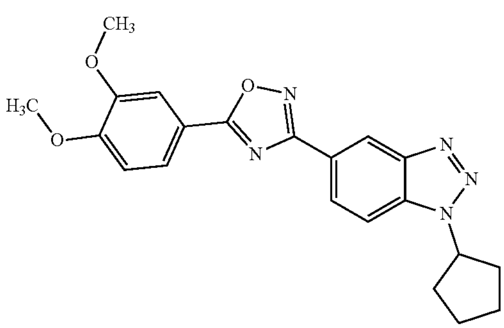 [SMILES: COc1ccc(-c2nc(-c3ccc4c(c3)nnn4C3CCCC3)no2)cc1OC] | 275 | 3-(1-cyclopentyl-1H-benzo[d][1,2,3]triazol-5-yl)-5-(3,4-dimethoxyphenyl)-1,2,4-oxadiazole | 391.43 | 392.1 |
| 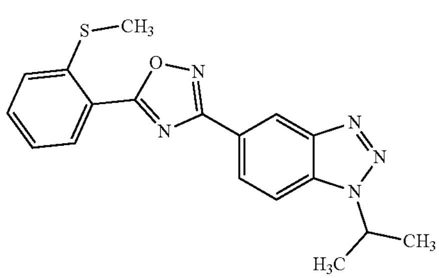 [SMILES: CSc1ccccc1-c1nc(-c2ccc3c(c2)nnn3C(C)C)no1] | 276 | 3-(1-isopropyl-1H-benzo[d][1,2,3]triazol-5-yl)-5-(2-(methylthio)phenyl)-1,2,4-oxadiazole | 351.43 | 352.1 |

-continued

| Structure | Compound Number | Chemical Name | Exact Mass | Actual Peak |
|---|---|---|---|---|
| 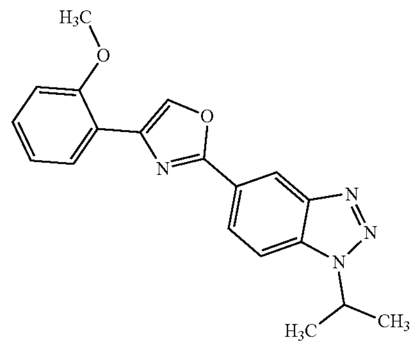 [SMILES: COc1ccccc1-c1coc(-c2ccc3c(c2)nnn3C(C)C)n1] | 277 | 5-[4-(2-methoxyphenyl)-1,3-oxazol-2-yl]-1-(propan-2-yl)-1H-1,2,3-benzotriazole | 334.38 | 335 |
| 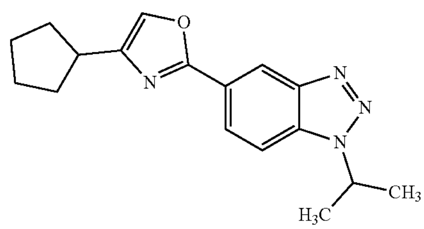 [SMILES: CC(C)n1nnc2cc(-c3nc(C4CCCC4)co3)ccc21] | 278 | 5-(5-cyclopentyl-1,2,4-oxadiazol-3-yl)-1-(propan-2-yl)-1H-1,2,3-benzotriazole5-(5-cyclopentyl-1,2,4-oxadiazol-3-yl)-1-(propan-2-yl)-1H-1,2,3-benzotriazole | 297.36 | 298 |
| 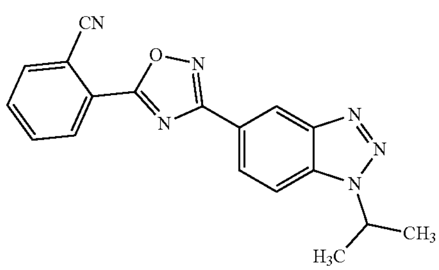 [SMILES: CC(C)n1nnc2cc(-c3noc(-c4ccccc4C#N)n3)ccc21] | 279 | 2-(3-(1-isopropyl-1H-benzo[d][1,2,3]triazol-5-yl)-1,2,4-oxadiazol-5-yl)benzonitrile | 330.35 | 331 |
| 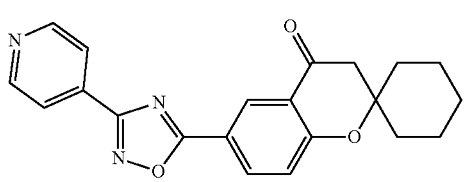 [SMILES: O=C1CC2(CCCCC2)Oc2ccc(-c3nc(-c4ccncc4)no3)cc21] | 280 | 6-[3-(pyridin-4-yl)-1,2,4-oxadiazol-5-yl]-3,4-dihydrospiro[1-benzopyran-2,1'-cyclohexane]-4-one | 361.40 | 362.1 |
| 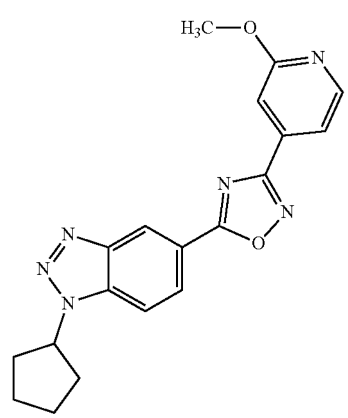 [SMILES: COc1cc(-c2noc(-c3ccc4c(c3)nnn4C3CCCC3)n2)ccn1] | 281 | 1-cyclopentyl-5-[3-(2-methoxypyridin-4-yl)-1,2,4-oxadiazol-5-yl]-1H-1,2,3-benzotriazole | 362.39 | 363.1 |

-continued

| Structure | Compound Number | Chemical Name | Exact Mass | Actual Peak |
|---|---|---|---|---|
| 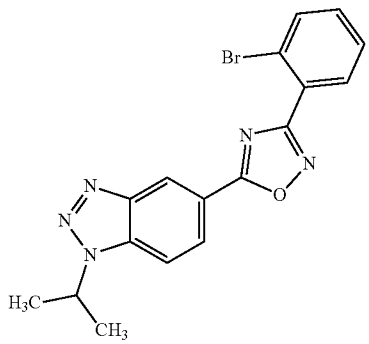 [SMILES: CC(C)n1nnc2cc(-c3nc(-c4ccccc4Br)no3)ccc21] | 282 | 5-[3-(2-bromophenyl)-1,2,4-oxadiazol-5-yl]-1-(propan-2-yl)-1H-1,2,3-benzotriazole | 384.24 | 384.2 |
| 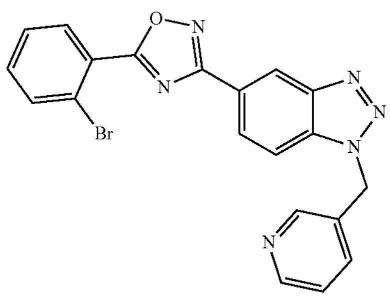 [SMILES: Brc1ccccc1-c1nc(-c2ccc3c(c2)nnn3Cc2cccnc2)no1] | 283 | 5-(2-bromophenyl)-3-(1-(pyridin-3-ylmethyl)-1H-benzo[d][1,2,3]triazol-5-yl)-1,2,4-oxadiazole | 433.27 | 434.9 |
| 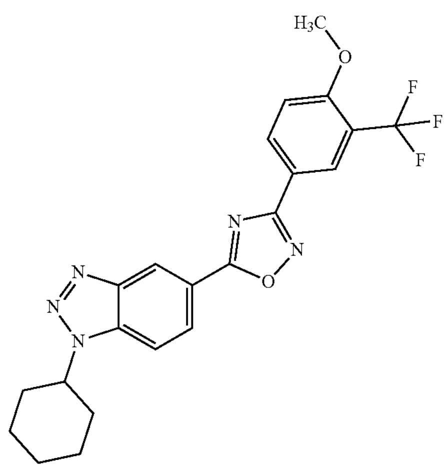 [SMILES: COc1ccc(-c2noc(-c3ccc4c(c3)nnn4C3CCCCC3)n2)cc1C(F)(F)F] | 284 | 1-cyclohexyl-5-{3-[4-methoxy-3-(trifluoromethyl)phenyl]-1,2,4-oxadiazol-5-yl}-1H-1,2,3-benzotriazole | 443.43 | 444.2 |
| 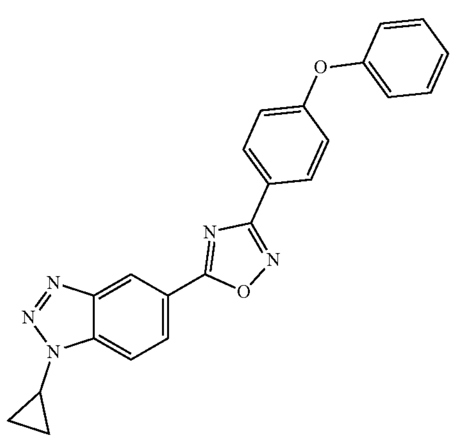 [SMILES: c1ccc(Oc2ccc(-c3noc(-c4ccc5c(c4)nnn5C4CC4)n3)cc2)cc1] | 285 | 1-cyclopropyl-5-[3-(4-phenoxyphenyl)-1,2,4-oxadiazol-5-yl]-1H-1,2,3-benzotriazole | 395.42 | 396.2 |

-continued

| Structure | Compound Number | Chemical Name | Exact Mass | Actual Peak |
|---|---|---|---|---|
| 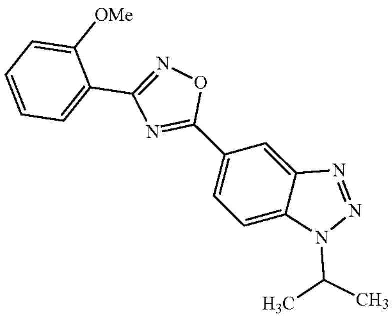 [SMILES: COc1ccccc1-c1noc(-c2ccc3c(c2)nnn3C(C)C)n1] | 286 | 5-(1-isopropyl-1H-benzo[d][1,2,3]triazol-5-yl)-3-(2-methoxyphenyl)-1,2,4-oxadiazole | 335.37 | 356 |
| 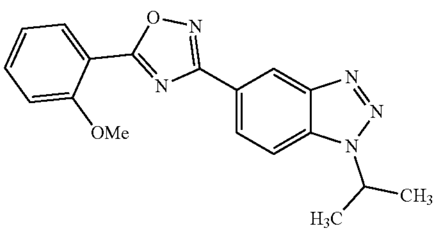 [SMILES: COc1ccccc1-c1nc(-c2ccc3c(c2)nnn3C(C)C)no1] | 287 | 3-(1-isopropyl-1H-benzo[d][1,2,3]triazol-5-yl)-5-(2-methoxyphenyl)-1,2,4-oxadiazole | 335.37 | 356 |
| 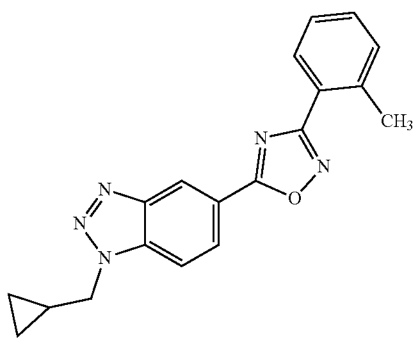 [SMILES: Cc1ccccc1-c1noc(-c2ccc3c(c2)nnn3CC2CC2)n1] | 288 | 1-(cyclopropylmethyl)-5-[3-(2-methylphenyl)-1,2,4-oxadiazol-5-yl]-1H-1,2,3-benzotriazole | 331.38 | 332.2 |
| 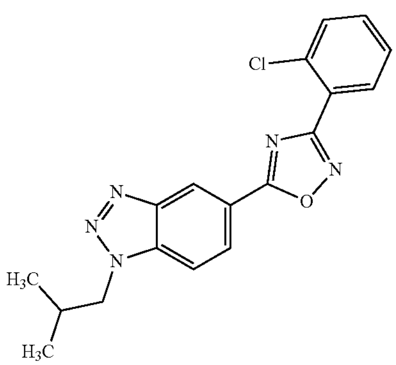 [SMILES: CC(C)Cn1nnc2cc(-c3nc(-c4ccccc4Cl)no3)ccc21] | 289 | 5-[3-(2-chlorophenyl)-1,2,4-oxadiazol-5-yl]-1-(2-methylpropyl)-1H-1,2,3-benzotriazole | 353.81 | 354.2 |
| 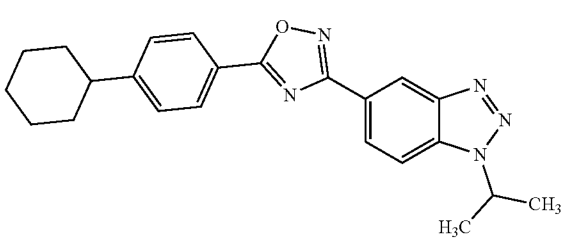 [SMILES: CC(C)n1nnc2cc(-c3noc(-c4ccc(C5CCCCC5)cc4)n3)ccc21] | 290 | 5-(4-cyclohexylphenyl)-3-(1-isopropyl-1H-benzo[d][1,2,3]triazol-5-yl)-1,2,4-oxadiazole | 387.49 | 388.1 |

-continued

| Structure | Compound Number | Chemical Name | Exact Mass | Actual Peak |
|---|---|---|---|---|
| 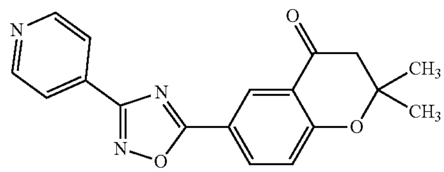 [SMILES: CC1(C)CC(=O)c2cc(-c3nc(-c4ccncc4)no3)ccc2O1] | 291 | 2,2-dimethyl-6-[3-(pyridin-4-yl)-1,2,4-oxadiazol-5-yl]-3,4-dihydro-2H-1-benzopyran-4-one | 321.34 | 322.1 |
| 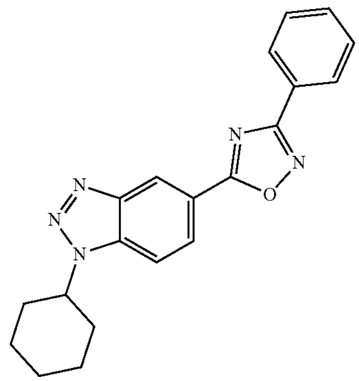 [SMILES: c1ccc(-c2noc(-c3ccc4c(c3)nnn4C3CCCCC3)n2)cc1] | 292 | 1-cyclohexyl-5-(3-phenyl-1,2,4-oxadiazol-5-yl)-1H-1,2,3-benzotriazole | 345.41 | 346.3 |
| 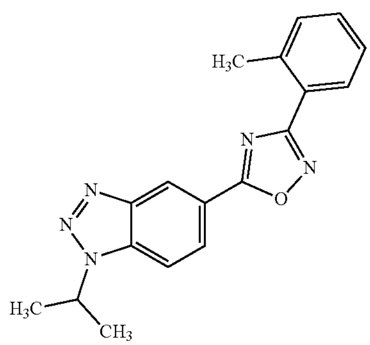 [SMILES: Cc1ccccc1-c1noc(-c2ccc3c(c2)nnn3C(C)C)n1] | 293 | 5-[3-(2-methylphenyl)-1,2,4-oxadiazol-5-yl]-1-(propan-2-yl)-1H-1,2,3-benzotriazole | 319.37 | 320.3 |
| 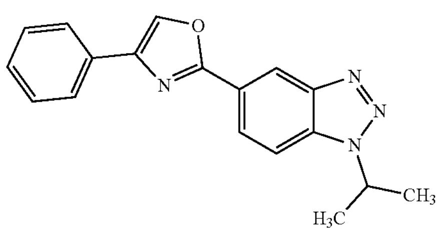 [SMILES: CC(C)n1nnc2cc(-c3nc(-c4ccccc4)co3)ccc21] | 294 | 5-(4-phenyl-1,3-oxazol-2-yl)-1-(propan-2-yl)-1H-1,2,3-benzotriazole | 304.35 | 305 |
| 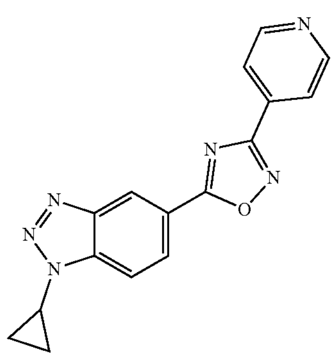 [SMILES: c1cc(-c2noc(-c3ccc4c(c3)nnn4C3CC3)n2)ccn1] | 295 | 1-cyclopropyl-5-[3-(pyridin-4-yl)-1,2,4-oxadiazol-5-yl]-1H-1,2,3-benzotriazole | 304.31 | 305.2 |

-continued

| Structure | Compound Number | Chemical Name | Exact Mass | Actual Peak |
|---|---|---|---|---|
| 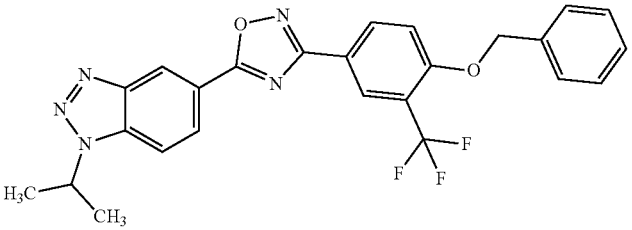 [SMILES: CC(C)n1nnc2cc(-c3nc(-c4ccc(OCc5ccccc5)c(C(F)(F)F)c4)no3)ccc21] | 296 | 5-{3-[4-(benzyloxy)-3-(trifluoromethyl)phenyl]-1,2,4-oxadiazol-5-yl}-1-(propan-2-yl)-1H-1,2,3-benzotriazole | 479.46 | 480.2 |
| 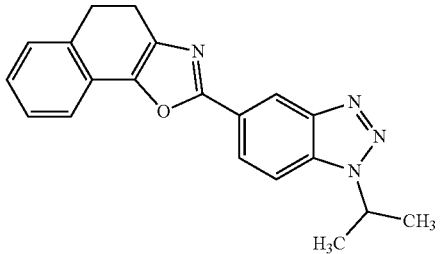 [SMILES: CC(C)n1nnc2cc(-c3nc4c(o3)-c3ccccc3CC4)ccc21] | 297 | 5-{4H,5H-naphtho[2,1-d][1,3]oxazol-2-yl}-1-(propan-2-yl)-1H-1,2,3-benzotriazole | 330.39 | 331 |
| 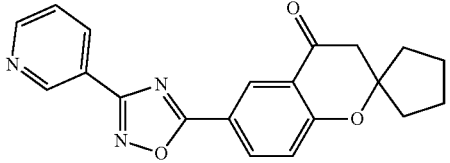 [SMILES: O=C1CC2(CCCC2)Oc2ccc(-c3nc(-c4cccnc4)no3)cc21] | 298 | 6-[3-(pyridin-3-yl)-1,2,4-oxadiazol-5-yl]-3,4-dihydrospiro[1-benzopyran-2,1'-cyclopentane]-4-one | 347.37 | 348.1 |
| 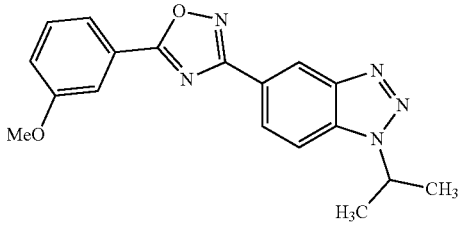 [SMILES: COc1cccc(-c2nc(-c3ccc4c(c3)nnn4C(C)C)no2)c1] | 299 | 3-(1-isopropylbenzotriazol-5-yl)-5-(3-methoxyphenyl)-1,2,4-oxadiazole | 335.37 | 336.1 |
| 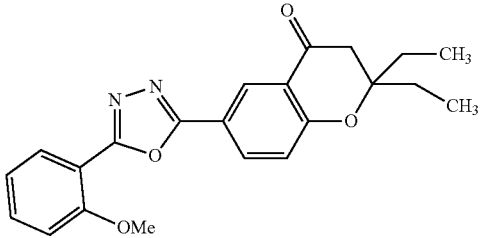 [SMILES: CCC1(CC)CC(=O)c2cc(-c3nnc(-c4ccccc4OC)o3)ccc2O1] | 300 | 2,2-diethyl-6-(5-(2-methoxyphenyl)-1,3,4-oxadiazol-2-yl)chroman-4-one | 378.43 | 379.3 |
| 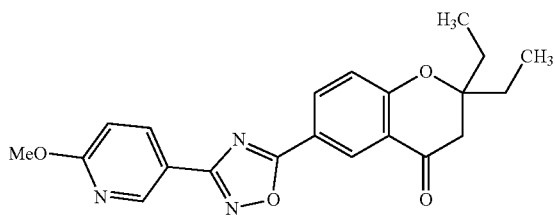 [SMILES: CCC1(CC)CC(=O)c2cc(-c3nc(-c4ccc(OC)nc4)no3)ccc2O1] | 301 | 2,2-diethyl-6-[3-(6-methoxy-3-pyridyl)-1,2,4-oxadiazol-5-yl]chroman-4-one | 379.42 | 380.3 |

-continued

| Structure | Compound Number | Chemical Name | Exact Mass | Actual Peak |
|---|---|---|---|---|
| 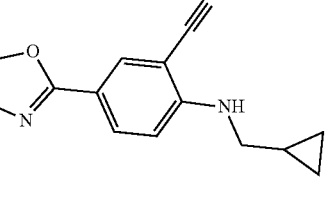 | 302 | 2-((cyclopropylmethyl)amino)-5-(3-(2-oxo-1,2,3,4-tetrahydroquinolin-6-yl)-1,2,4-oxadiazol-5-yl)benzonitrile | 385.43 | 386.2 |
| 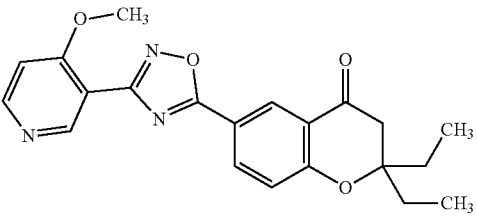 [SMILES: CCC1(CC)CC(=O)c2cc(-c3nc(-c4cnccc4OC)no3)ccc2O1] | 303 | 2,2-diethyl-6-(3-(4-methoxypyridin-3-yl)-1,2,4-oxadiazol-5-yl)chroman-4-one | 379.42 | 380.3 |
| 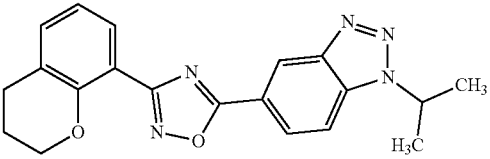 [SMILES: CC(C)n1nnc2cc(-c3nc(-c4cccc5c4OCCC5)no3)ccc21] | 304 | 3-chroman-8-yl-5-(1-isopropylbenzotriazol-5-yl)-1,2,4-oxadiazole | 361.41 | 362.1 |
| 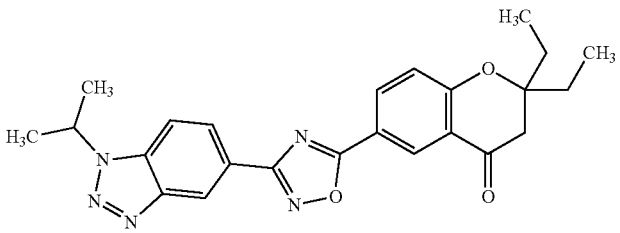 [SMILES: CCC1(CC)CC(=O)c2cc(-c3nc(-c4ccc5c(c4)nnn5C(C)C)no3)ccc2O1] | 305 | 2,2-diethyl-6-(3-(1-isopropyl-1H-benzo[d][1,2,3]triazol-5-yl)-1,2,4-oxadiazol-5-yl)chroman-4-one | 431.50 | 432.2 |
| 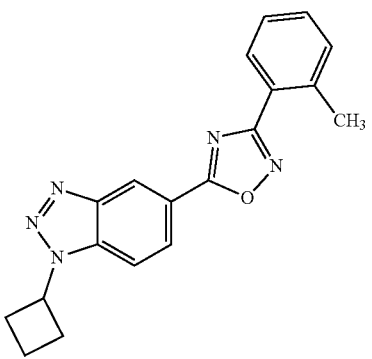 [SMILES: Cc1ccccc1-c1noc(-c2ccc3c(c2)nnn3C2CCC2)n1] | 306 | 1-cyclobutyl-5-[3-(2-methylphenyl)-1,2,4-oxadiazol-5-yl]-1H-1,2,3-benzotriazole | 331.38 | 332.1 |
| 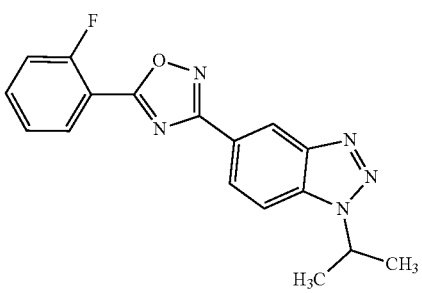 [SMILES: CC(C)n1nnc2cc(-c3noc(-c4ccccc4F)n3)ccc21] | 307 | 5-(2-fluorophenyl)-3-(1-isopropyl-1H-benzo[d][1,2,3]triazol-5-yl)-1,2,4-oxadiazole | 323.33 | 324 |

-continued

| Structure | Compound Number | Chemical Name | Exact Mass | Actual Peak |
|---|---|---|---|---|
| 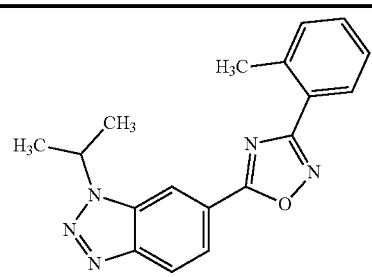 | 308 | 6-[3-(2-methylphenyl)-1,2,4-oxadiazol-5-yl]-1-(propan-2-yl)-1H-1,2,3-benzotriazole | 319.37 | 320.1 |
| 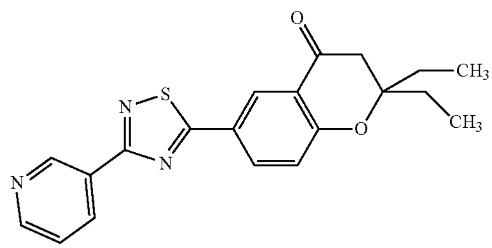 [SMILES: CCC1(CC)CC(=O)c2cc(-c3nc(-c4cccnc4)ns3)ccc2O1] | 309 | 2,2-diethyl-6-(3-(pyridin-3-yl)-1,2,4-thiadiazol-5-yl)chroman-4-one | 365.45 | 366 |
| 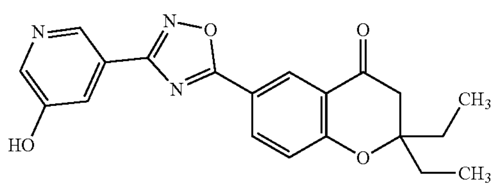 [SMILES: CCC1(CC)CC(=O)c2cc(-c3nc(-c4cncc(O)c4)no3)ccc2O1] | 310 | 2,2-diethyl-6-[3-(5-hydroxy-3-pyridyl)-1,2,4-oxadiazol-5-yl]chroman-4-one | 365.39 | 366.1 |
| 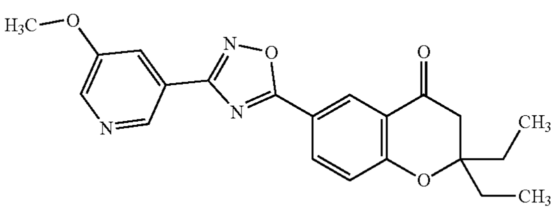 [SMILES: CCC1(CC)CC(=O)c2cc(-c3nc(-c4cncc(OC)c4)no3)ccc2O1] | 311 | 2,2-diethyl-6-(3-(5-methoxypyridin-3-yl)-1,2,4-oxadiazol-5-yl)chroman-4-one | 379.42 | 380.1 |
| 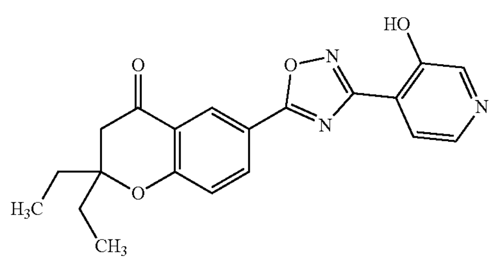 [SMILES: CCC1(CC)CC(=O)c2cc(-c3nc(-c4ccncc4O)no3)ccc2O1] | 312 | 2,2-diethyl-6-(3-(3-hydroxypyridin-4-yl)-1,2,4-oxadiazol-5-yl)chroman-4-one | 365.39 | 366 |
| 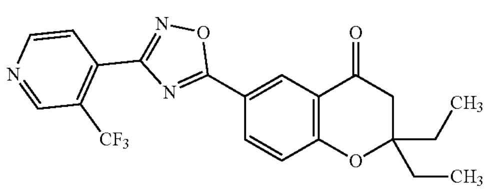 [SMILES: CCC1(CC)CC(=O)c2cc(-c3nc(-c4ccncc4C(F)(F)F)no3)ccc2O1] | 313 | 2,2-diethyl-6-(3-(3-(trifluoromethyl)pyridin-4-yl)-1,2,4-oxadiazol-5-yl)chroman-4-one | 417.39 | 418 |
| 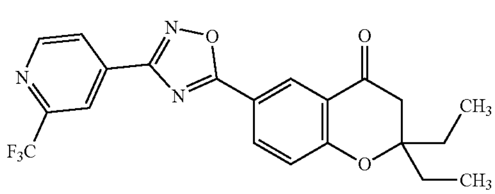 [SMILES: CCC1(CC)CC(=O)c2cc(-c3nc(-c4ccnc(C(F)(F)F)c4)no3)ccc2O1] | 314 | 2,2-diethyl-6-(3-(2-(trifluoromethyl)pyridin-4-yl)-1,2,4-oxadiazol-5-yl)chroman-4-one | 417.39 | 418 |

-continued

| Structure | Compound Number | Chemical Name | Exact Mass | Actual Peak |
|---|---|---|---|---|
| 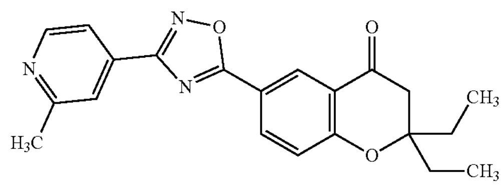 | 315 | 2,2-diethyl-6-(3-(2-methylpyridin-4-yl)-1,2,4-oxadiazol-5-yl)chroman-4-one | 363.42 | 364.1 |
| 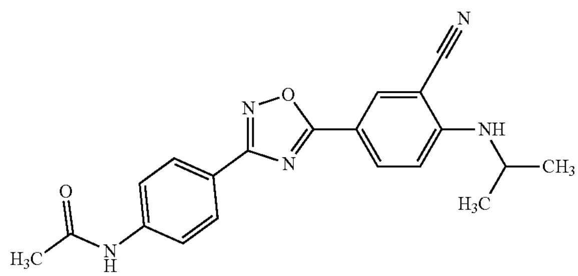 [SMILES: CC(=O)Nc1ccc(-c2noc(-c3ccc(NC(C)C)c(C#N)c3)n2)cc1] | 316 | N-(4-(5-(3-cyano-4-(isopropylamino)phenyl)-1,2,4-oxadiazol-3-yl)phenyl)acetamide | 361.41 | 362.1 |
| 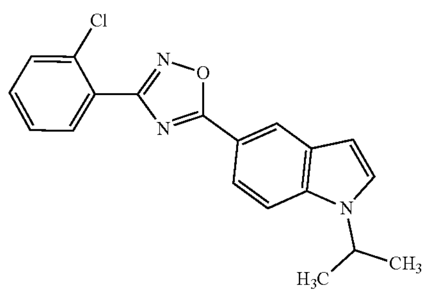 [SMILES: CC(C)n1ccc2cc(-c3nc(-c4ccccc4Cl)no3)ccc21] | 320 | 3-(2-chlorophenyl)-5-(1-isopropyl-1H-indol-5-yl)-1,2,4-oxadiazole | 337.81 | 338 |
| 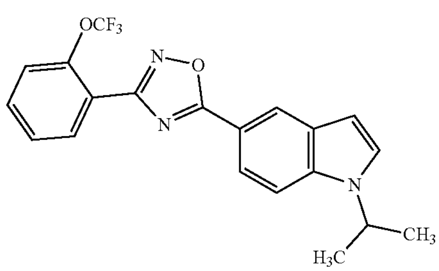 [SMILES: CC(C)n1ccc2cc(-c3nc(-c4ccccc4OC(F)(F)F)no3)ccc21] | 321 | 5-(1-isopropyl-1H-indol-5-yl)-3-(2-(trifluoromethoxy)phenyl)-1,2,4-oxadiazole | 387.36 | 388.1 |
| 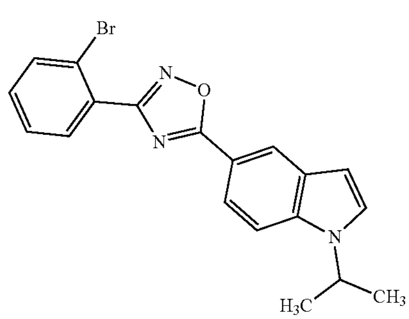 [SMILES: CC(C)n1ccc2cc(-c3nc(-c4ccccc4Br)no3)ccc21] | 322 | 3-(2-bromophenyl)-5-(1-isopropyl-1H-indol-5-yl)-1,2,4-oxadiazole | 382.26 | 384 |

-continued

| Structure | Compound Number | Chemical Name | Exact Mass | Actual Peak |
|---|---|---|---|---|
| 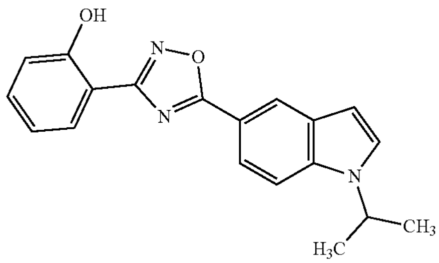 [SMILES: CC(C)n1ccc2cc(-c3nc(-c4ccccc4O)no3)ccc21] | 323 | 2-(5-(1-isopropyl-1H-indol-5-yl)-1,2,4-oxadiazol-3-yl)phenol | 319.36 | 320.1 |
| 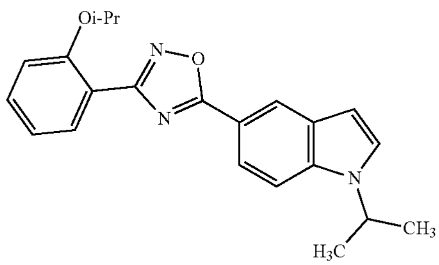 | 324 | 3-(2-isopropoxyphenyl)-5-(1-isopropyl-1H-indol-5-yl)-1,2,4-oxadiazole | 361.45 | 362.1 |
| 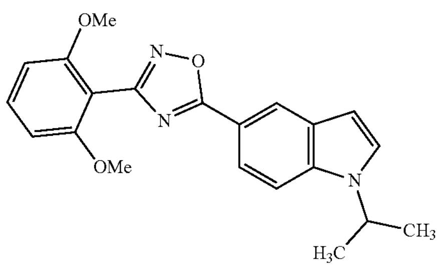 [SMILES: COc1cccc(OC)c1-c1noc(-c2ccc3c(ccn3C(C)C)c2)n1] | 325 | 3-(2,6-dimethoxyphenyl)-5-(1-isopropylindol-5-yl)-1,2,4-oxadiazole | 363.42 | 364.1 |
| 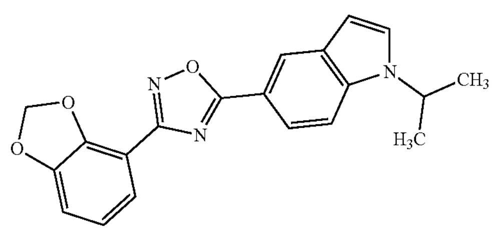 [SMILES: CC(C)n1ccc2cc(-c3nc(-c4cccc5c4OCO5)no3)ccc21] | 326 | 3-(benzo[d][1,3]dioxol-4-yl)-5-(1-isopropyl-1H-indol-5-yl)-1,2,4-oxadiazole | 347.37 | 348.1 |
| 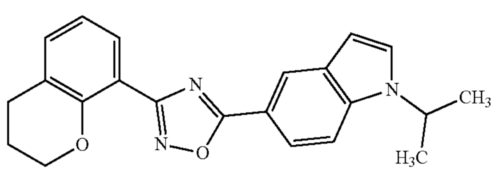 [SMILES: CC(C)n1ccc2cc(-c3nc(-c4cccc5c4OCCC5)no3)ccc21] | 327 | 3-chroman-8-yl-5-(1-isopropylindol-5-yl)-1,2,4-oxadiazole | 359.43 | 360.1 |
| 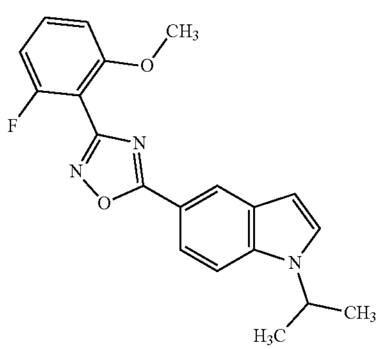 [SMILES: COc1cccc(F)c1-c1noc(-c2ccc3c(ccn3C(C)C)c2)n1] | 328 | 3-(2-fluoro-6-methoxy-phenyl)-5-(1-isopropylindol-5-yl)-1,2,4-oxadiazole | 351.38 | 352.1 |

-continued

| Structure | Compound Number | Chemical Name | Exact Mass | Actual Peak |
|---|---|---|---|---|
| 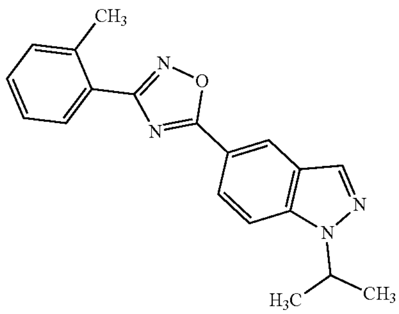 | 329 | 5-(1-isopropyl-1H-indazol-5-yl)-3-(o-tolyl)-1,2,4-oxadiazole | 318.38 | 319.1 |
| 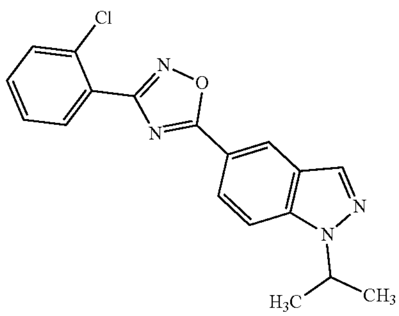 [SMILES: CC(C)n1ncc2cc(-c3nc(-c4ccccc4Cl)no3)ccc21] | 330 | 3-(2-chlorophenyl)-5-(1-isopropyl-1H-indazol-5-yl)-1,2,4-oxadiazole | 338.80 | 339 |
| 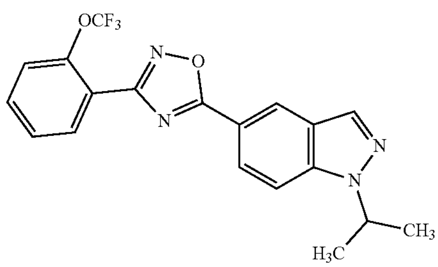 | 331 | 5-(1-isopropyl-1H-indazol-5-yl)-3-(2-(trifluoromethoxy)phenyl)-1,2,4-oxadiazole | 388.35 | 389.1 |
| 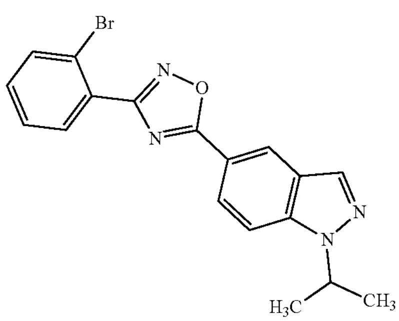 | 332 | 3-(2-bromophenyl)-5-(1-isopropyl-1H-indazol-5-yl)-1,2,4-oxadiazole | 383.25 | 385.1 |
| 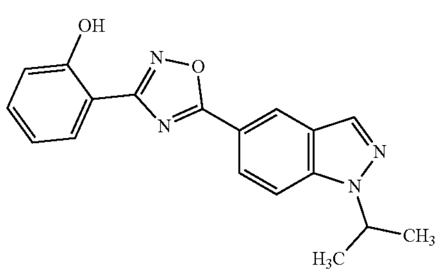 | 333 | 2-(5-(1-isopropyl-1H-indazol-5-yl)-1,2,4-oxadiazol-3-yl)phenol | 320.35 | 321.1 |

-continued

| Structure | Compound Number | Chemical Name | Exact Mass | Actual Peak |
|---|---|---|---|---|
| 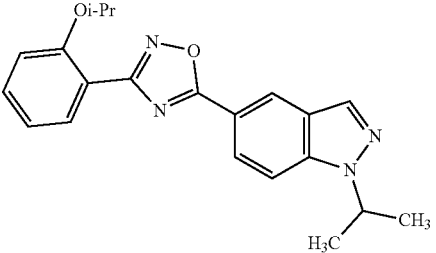 | 334 | 3-(2-isopropoxyphenyl)-5-(1-isopropyl-1H-indazol-5-yl)-1,2,4-oxadiazole | 362.43 | 363.1 |
| 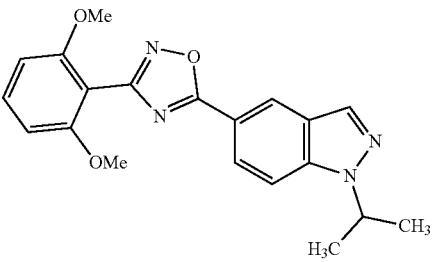 [SMILES: COc1cccc(OC)c1-c1noc(-c2ccc3c(cnn3C(C)C)c2)n1] | 335 | 3-(2,6-dimethoxyphenyl)-5-(1-isopropylindazol-5-yl)-1,2,4-oxadiazole | 364.41 | 365.1 |
| 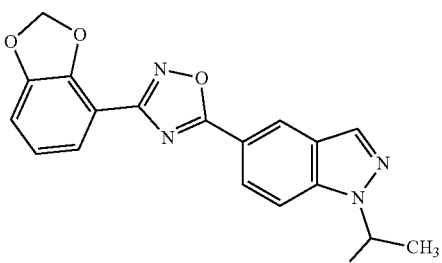 | 336 | 3-(benzo[d][1,3]dioxol-4-yl)-5-(1-isopropyl-1H-indazol-5-yl)-1,2,4-oxadiazole | 348.36 | 349.1 |
| 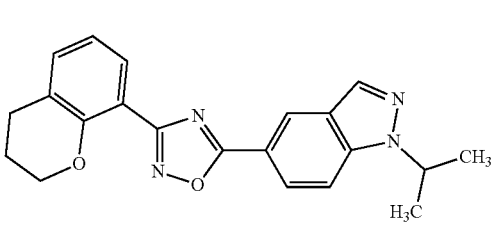 [SMILES: CC(C)n1ncc2cc(-c3nc(-c4cccc5c4OCCC5)no3)ccc21] | 337 | 3-chroman-8-yl-5-(1-isopropylindazol-5-yl)-1,2,4-oxadiazole | 360.42 | 361.1 |
| 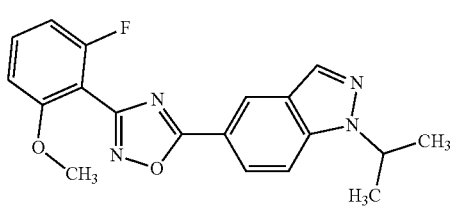 [SMILES: COc1cccc(F)c1-c1noc(-c2ccc3c(cnn3C(C)C)c2)n1] | 338 | 3-(2-fluoro-6-methoxy-phenyl)-5-(1-isopropylindazol-5-yl)-1,2,4-oxadiazole | 352.37 | 353.1 |
| 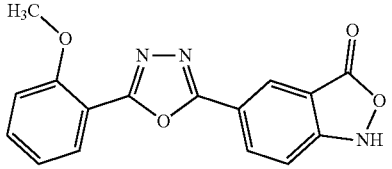 [SMILES: COc1ccccc1-c1nnc(-c2ccc3[nH]oc(=O)c3c2)o1] | 339 | 5-[5-(2-methoxyphenyl)-1,3,4-oxadiazol-2-yl]-1,3-dihydro-2,1-benzoxazol-3-one | 309.28 | 310.2 |

-continued

| Structure | Compound Number | Chemical Name | Exact Mass | Actual Peak |
|---|---|---|---|---|
| 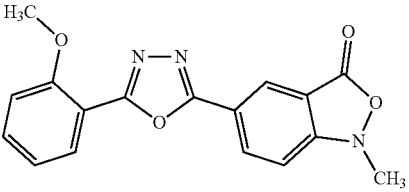 [SMILES: COc1ccccc1-c1nnc(-c2ccc3c(c2)c(=O)on3C)o1] | 340 | 5-[5-(2-methoxyphenyl)-1,3,4-oxadiazol-2-yl]-1-methyl-1,3-dihydro-2,1-benzoxazol-3-one | 323.31 | 324.1 |
| 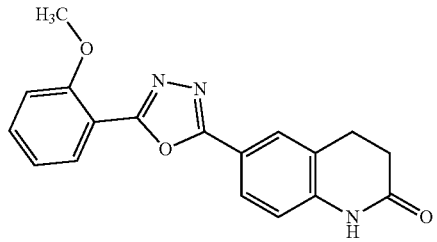 [SMILES: COc1ccccc1-c1nnc(-c2ccc3c(c2)CCC(=O)N3)o1] | 341 | 6-[5-(2-methoxyphenyl)-1,3,4-oxadiazol-2-yl]-1,2,3,4-tetrahydroquinolin-2-one | 321.34 | 322.1 |
| 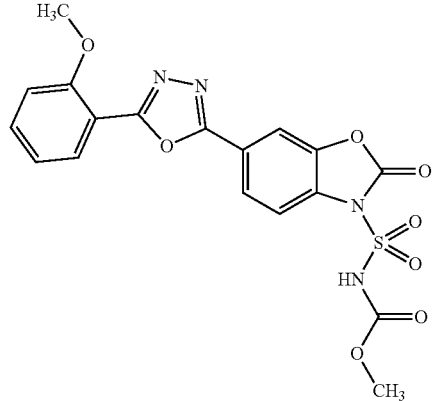 [SMILES: COC(=O)NS(=O)(=O)n1c(=O)oc2cc(-c3nnc(-c4ccccc4OC)o3)ccc21] | 342 | methyl N-({6-[5-(2-methoxyphenyl)-1,3,4-oxadiazol-2-yl]-2-oxo-2,3-dihydro-1,3-benzoxazol-3-yl}sulfonyl)carbamate | 446.39 | 447 |
| 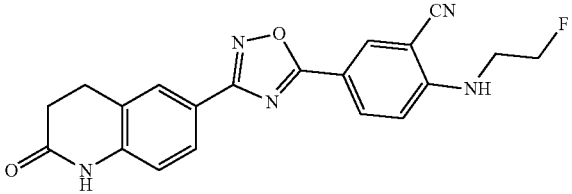 [SMILES: N#Cc1cc(-c2nc(-c3ccc4c(c3)CCC(=O)N4)no2)ccc1NCCF] | 343 | 2-[(2-fluoroethyl)amino]-5-[3-(2-oxo-1,2,3,4-tetrahydroquinolin-6-yl)-1,2,4-oxadiazol-5-yl]benzonitrile | 377.38 | 378.1 |
| 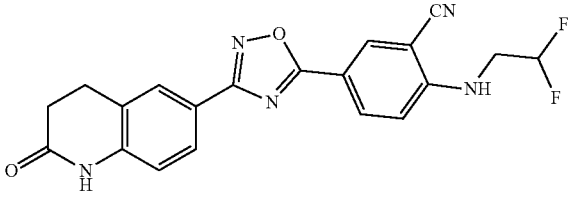 [SMILES: N#Cc1cc(-c2nc(-c3ccc4c(c3)CCC(=O)N4)no2)ccc1NCC(F)F] | 344 | 2-[(2,2-difluoroethyl)amino]-5-[3-(2-oxo-1,2,3,4-tetrahydroquinolin-6-yl)-1,2,4-oxadiazol-5-yl]benzonitrile | 395.37 | 396.1 |
| 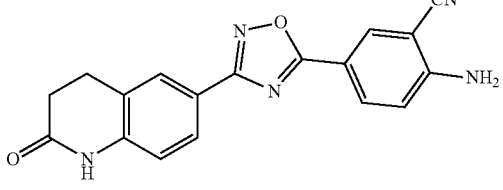 | 345 | 2-amino-5-[3-(2-oxo-1,2,3,4-tetrahydroquinolin-6-yl)-1,2,4-oxadiazol-5-yl]benzonitrile | 331.34 | 332.1 |

| Structure | Compound Number | Chemical Name | Exact Mass | Actual Peak |
|---|---|---|---|---|
| 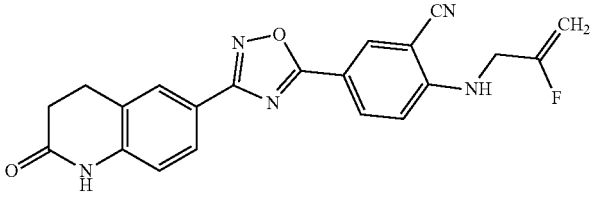 [SMILES: C=C(F)CNc1ccc(-c2nc(-c3ccc4c(c3)CCC(=O)N4)no2)cc1C#N] | 346 | 2-[(2-fluoroprop-2-en-1-yl)amino]-5-[3-(2-oxo-1,2,3,4-tetrahydroquinolin-6-yl)-1,2,4-oxadiazol-5-yl]benzonitrile | 389.39 | 390.1 |
| 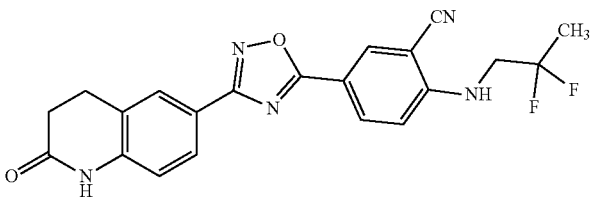 [SMILES: CC(F)(F)CNc1ccc(-c2nc(-c3ccc4c(c3)CCC(=O)N4)no2)cc1C#N] | 347 | 2-[(2,2-difluoropropyl)amino]-5-[3-(2-oxo-1,2,3,4-tetrahydroquinolin-6-yl)-1,2,4-oxadiazol-5-yl]benzonitrile | 409.40 | 410.1 |
| 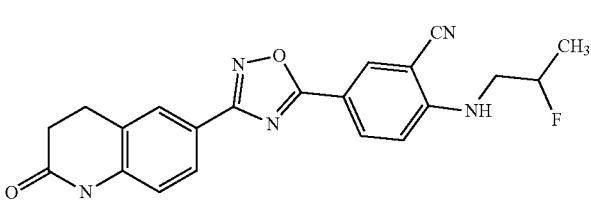 | 348 | 2-[(2-fluoropropyl)amino]-5-[3-(2-oxo-1,2,3,4-tetrahydroquinolin-6-yl)-1,2,4-oxadiazol-5-yl]benzonitrile | 391.41 | 392.1 |
| 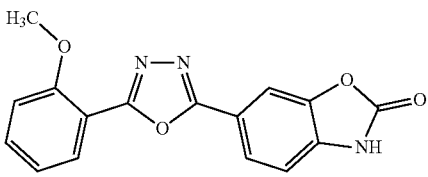 [SMILES: COc1ccccc1-c1nnc(-c2ccc3[nH]c(=O)oc3c2)o1] | 349 | 6-[5-(2-methoxyphenyl)-1,3,4-oxadiazol-2-yl]-2,3-dihydro-1,3-benzoxazol-2-one | 309.28 | 310 |
| 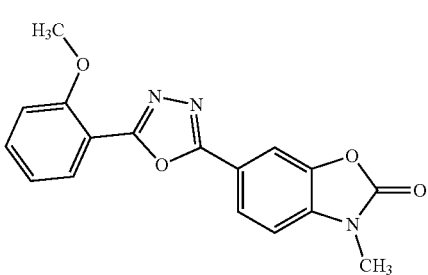 [SMILES: COc1ccccc1-c1nnc(-c2ccc3c(c2)oc(=O)n3C)o1] | 350 | 6-[5-(2-methoxyphenyl)-1,3,4-oxadiazol-2-yl]-3-methyl-2,3-dihydro-1,3-benzoxazol-2-one | 323.31 | 324.1 |
| 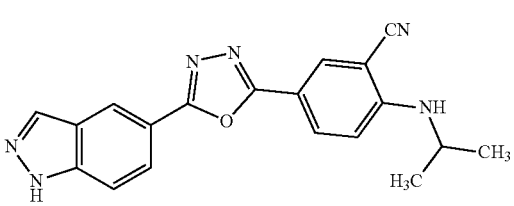 [SMILES: CC(C)Nc1ccc(-c2nnc(-c3ccc4[nH]ncc4c3)o2)cc1C#N] | 351 | 5-[5-(1H-indazol-5-yl)-1,3,4-oxadiazol-2-yl]-2-[(propan-2-yl)amino]benzonitrile | 344.38 | 345.2 |
| 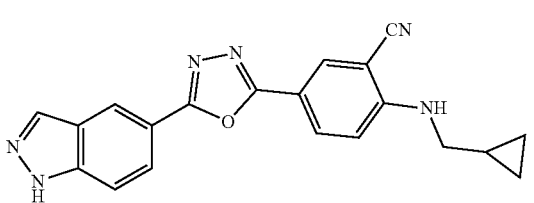 [SMILES: N#Cc1cc(-c2nnc(-c3ccc4[nH]ncc4c3)o2)ccc1NCC1CC1] | 352 | 2-[(cyclopropylmethyl)amino]-5-[5-(1H-indazol-5-yl)-1,3,4-oxadiazol-2-yl]benzonitrile | 356.39 | 357.1 |

-continued

| Structure | Compound Number | Chemical Name | Exact Mass | Actual Peak |
|---|---|---|---|---|
| 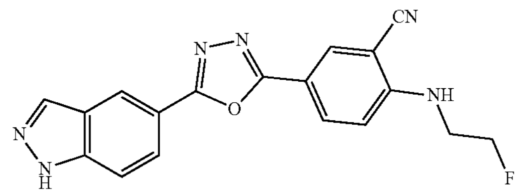 [SMILES: N#Cc1cc(-c2nnc(-c3ccc4[nH]ncc4c3)o2)ccc1NCCF] | 353 | 2-[(2-fluoroethyl)amino]-5-[5-(1H-indazol-5-yl)-1,3,4-oxadiazol-2-yl]benzonitrile | 348.34 | 349.1 |
| 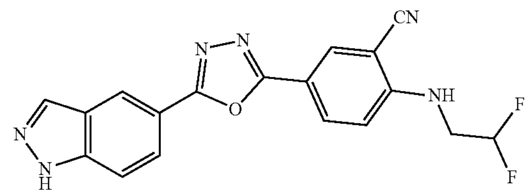 [SMILES: N#Cc1cc(-c2nnc(-c3ccc4[nH]ncc4c3)o2)ccc1NCC(F)F] | 354 | 2-[(2,2-difluoroethyl)amino]-5-[5-(1H-indazol-5-yl)-1,3,4-oxadiazol-2-yl]benzonitrile | 366.33 | 367.1 |
| 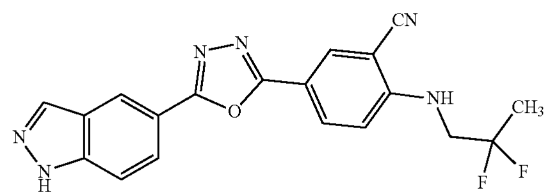 [SMILES: CC(F)(F)CNc1ccc(-c2nnc(-c3ccc4[nH]ncc4c3)o2)cc1C#N] | 355 | 2-[(2,2-difluoropropyl)amino]-5-[5-(1H-indazol-5-yl)-1,3,4-oxadiazol-2-yl]benzonitrile | 380.36 | 381.1 |
| 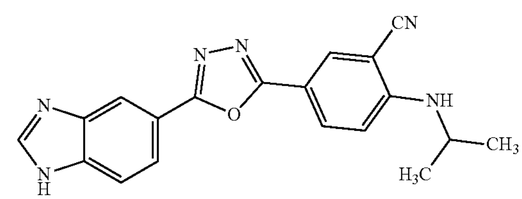 [SMILES: CC(C)Nc1ccc(-c2nnc(-c3ccc4[nH]cnc4c3)o2)cc1C#N] | 356 | 5-[5-(1H-1,3-benzodiazol-5-yl)-1,3,4-oxadiazol-2-yl]-2-[(propan-2-yl)amino]benzonitrile | 344.38 | 345.1 |
| 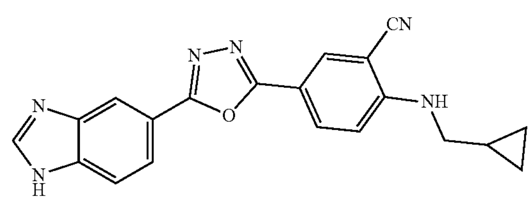 [SMILES: N#Cc1cc(-c2nnc(-c3ccc4[nH]cnc4c3)o2)ccc1NCC1CC1] | 357 | 5-[5-(1H-1,3-benzodiazol-5-yl)-1,3,4-oxadiazol-2-yl]-2-[(cyclopropylmethyl)amino]benzonitrile | 356.39 | 357.1 |
| 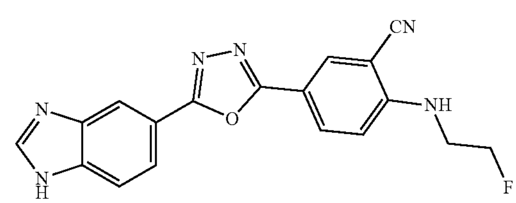 [SMILES: N#Cc1cc(-c2nnc(-c3ccc4[nH]cnc4c3)o2)ccc1NCCF] | 358 | 5-[5-(1H-1,3-benzodiazol-5-yl)-1,3,4-oxadiazol-2-yl]-2-[(2-fluoroethyl)amino]benzonitrile | 348.34 | 349.1 |
| 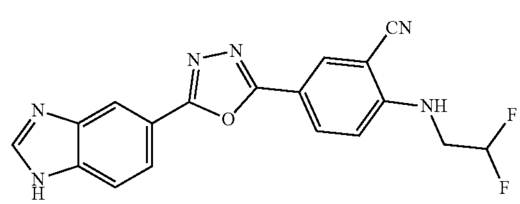 [SMILES: N#Cc1cc(-c2nnc(-c3ccc4[nH]cnc4c3)o2)ccc1NCC(F)F] | 359 | 5-[5-(1H-1,3-benzodiazol-5-yl)-1,3,4-oxadiazol-2-yl]-2-[(2,2-difluoroethyl)amino]benzonitrile | 366.33 | 367.1 |

-continued

| Structure | Compound Number | Chemical Name | Exact Mass | Actual Peak |
|---|---|---|---|---|
| 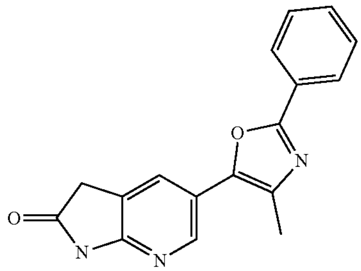 [SMILES: Cc1nc(-c2ccccc2)oc1-c1cnc2c(c1)CC(=O)N2] | 360 | 5-(4-methyl-2-phenyl-1,3-oxazol-5-yl)-1H,2H,3H-pyrrolo[2,3-b]pyridin-2-one | 291.1 | 292.1 |
| 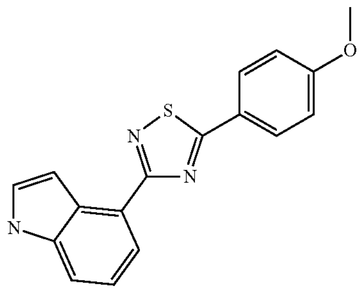 [SMILES: COc1ccc(-c2nc(-c3cccc4[nH]ccc34)ns2)cc1] | 361 | 4-[5-(4-methoxyphenyl)-1,2,4-thiadiazol-3-yl]-1H-indole | 307.08 | 308 |
| 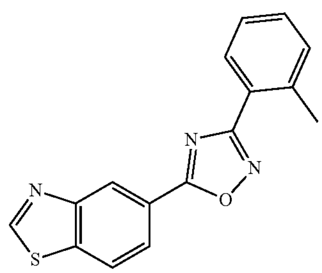 [SMILES: Cc1ccccc1-c1noc(-c2ccc3scnc3c2)n1] | 362 | 5-[3-(2-methylphenyl)-1,2,4-oxadiazol-5-yl]-1,3-benzothiazole | 293.06 | 294.2 |
| 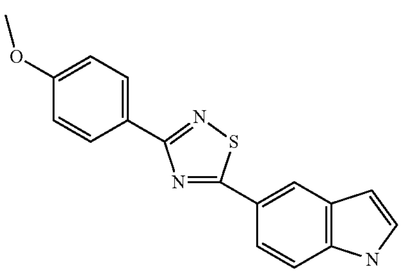 [SMILES: COc1ccc(-c2nsc(-c3ccc4[nH]ccc4c3)n2)cc1] | 363 | 5-[3-(4-methoxyphenyl)-1,2,4-thiadiazol-5-yl]-1H-indole | 307.08 | 308 |
| 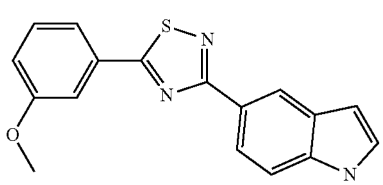 [SMILES: COc1cccc(-c2nc(-c3ccc4[nH]ccc4c3)ns2)c1] | 364 | 5-[5-(3-methoxyphenyl)-1,2,4-thiadiazol-3-yl]-1H-indole | 307.08 | 308 |
| 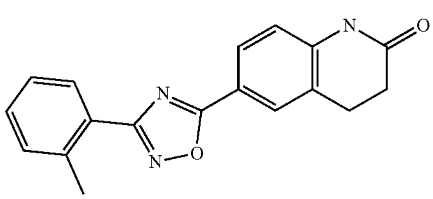 [SMILES: Cc1ccccc1-c1noc(-c2ccc3c(c2)CCC(=O)N3)n1] | 365 | 6-[3-(2-methylphenyl)-1,2,4-oxadiazol-5-yl]-1,2,3,4-tetrahydroquinolin-2-one | 305.12 | 306.1 |

-continued
| Structure | Compound Number | Chemical Name | Exact Mass | Actual Peak |
|---|---|---|---|---|
| 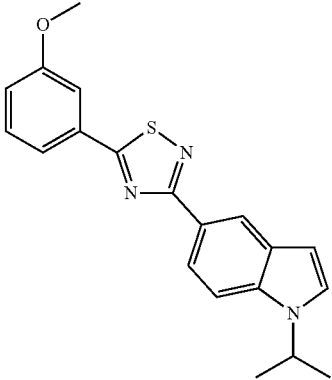 [SMILES: COc1cccc(-c2nc(-c3ccc4c(ccn4C(C)C)c3)ns2)c1] | 366 | 5-[5-(3-methoxyphenyl)-1,2,4-thiadiazol-3-yl]-1-(propan-2-yl)-1H-indole | 349.12 | 350 |
| 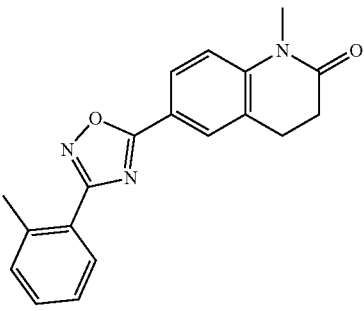 [SMILES: Cc1ccccc1-c1noc(-c2ccc3c(c2)CCC(=O)N3C)n1] | 367 | 1-methyl-6-[3-(2-methylphenyl)-1,2,4-oxadiazol-5-yl]-1,2,3,4-tetrahydroquinolin-2-one | 319.13 | 320.2 |
| 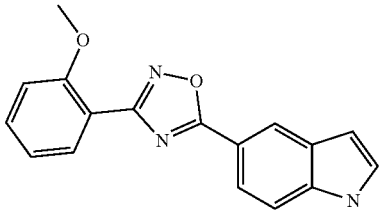 [SMILES: COc1ccccc1-c1noc(-c2ccc3[nH]ccc3c2)n1] | 368 | 5-(1H-indol-5-yl)-3-(2-methoxyphenyl)-1,2,4-oxadiazole | 291.1 | 292 |
| 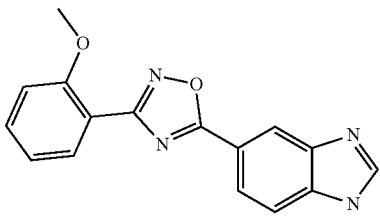 [SMILES: COc1ccccc1-c1noc(-c2ccc3[nH]cnc3c2)n1] | 369 | 5-(1H-benzo[d]imidazol-5-yl)-3-(2-methoxyphenyl)-1,2,4-oxadiazole | 292.1 | 293.2 |
| 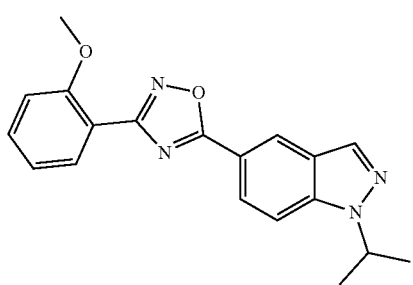 [SMILES: COc1ccccc1-c1noc(-c2ccc3c(cnn3C(C)C)c2)n1] | 370 | 5-(1-isopropyl-1H-indazol-5-yl)-3-(2-methoxyphenyl)-1,2,4-oxadiazole | 334.14 | 335.3 |

-continued

| Structure | Compound Number | Chemical Name | Exact Mass | Actual Peak |
|---|---|---|---|---|
| 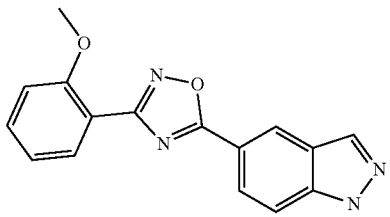 [SMILES: COc1ccccc1-c1noc(-c2ccc3[nH]ncc3c2)n1] | 371 | 5-(1H-indazol-5-yl)-3-(2-methoxyphenyl)-1,2,4-oxadiazole | 292.1 | 293.2 |
| 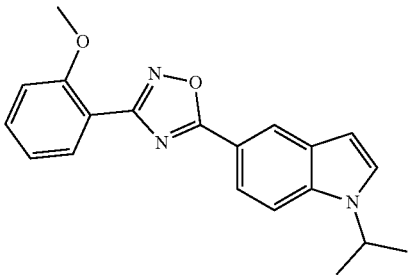 [SMILES: COc1ccccc1-c1noc(-c2ccc3c(ccn3C(C)C)c2)n1] | 372 | 5-(1-isopropyl-1H-indol-5-yl)-3-(2-methoxyphenyl)-1,2,4-oxadiazole | 333.15 | 334.1 |
| 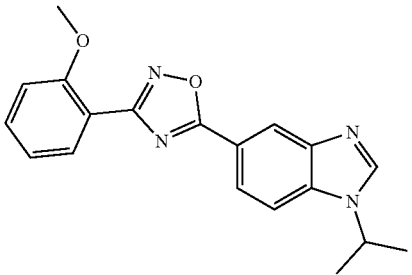 [SMILES: COc1ccccc1-c1noc(-c2ccc3c(c2)ncn3C(C)C)n1] | 373 | 5-(1-isopropyl-1H-benzo[d]imidazol-5-yl)-3-(2-methoxyphenyl)-1,2,4-oxadiazole | 334.14 | 335.2 |
| 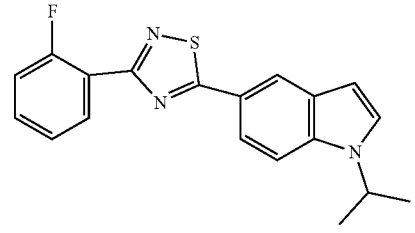 [SMILES: CC(C)n1ccc2cc(-c3nc(-c4ccccc4F)ns3)ccc21] | 374 | 5-[3-(2-fluorophenyl)-1,2,4-thiadiazol-5-yl]-1-(propan-2-yl)-1H-indole | 337.1 | 338 |
| 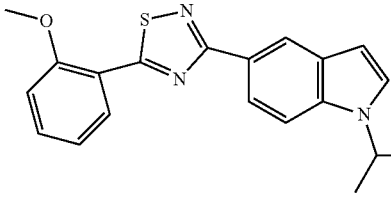 | 375 | 5-[5-(2-methoxyphenyl)-1,2,4-thiadiazol-3-yl]-1-(propan-2-yl)-1H-indole | 349.12 | 350 |
| 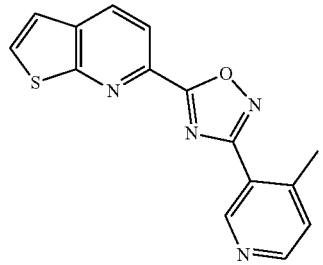 [SMILES: Cc1ccncc1-c1noc(-c2ccc3ccsc3n2)n1] | 376 | 4-methyl-3-(5-{thieno[2,3-b]pyridin-6-yl}-1,2,4-oxadiazol-3-yl)pyridine | 294.06 | 295 |

-continued

| Structure | Compound Number | Chemical Name | Exact Mass | Actual Peak |
|---|---|---|---|---|
| 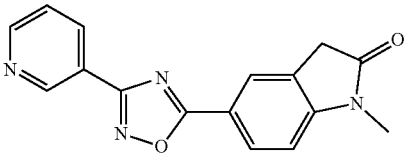 [SMILES: CN1C(=O)Cc2cc(-c3nc(-c4cccnc4)no3)ccc21] | 377 | 1-methyl-5-[3-(pyridin-3-yl)-1,2,4-oxadiazol-5-yl]-2,3-dihydro-1H-indol-2-one | 292.1 | 293.1 |
| 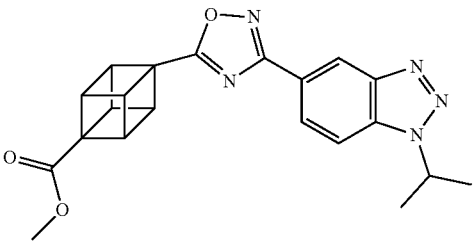 [SMILES: COC(=O)C12C3C4C1C1C2C3C41c1nc(-c2ccc3c(c2)nnn3C(C)C)no1] | 378 | 8-{3-[1-(propan-2-yl)-1H-1,2,3-benzotriazol-5-yl]-1,2,4-oxadiazol-5-yl}cubane-1-carboxylate | 389.15 | 390 |
| 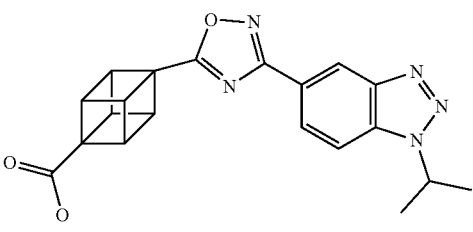 [SMILES: CC(C)n1nnc2cc(-c3noc(C45C6C7C4C4C5C6C74C(=O)O)n3)ccc21] | 379 | 8-{3-[1-(propan-2-yl)-1H-1,2,3-benzotriazol-5-yl]-1,2,4-oxadiazol-5-yl}cubane-1-carboxylic acid | 375.13 | 376 |
| 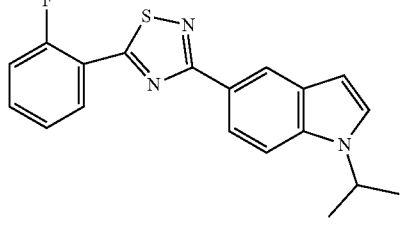 | 380 | 5-[5-(2-fluorophenyl)-1,2,4-thiadiazol-3-yl]-1-(propan-2-yl)-1H-indole | 337.1 | 338 |
| 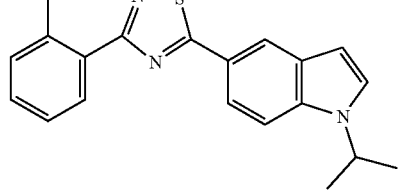 | 381 | 5-[3-(2-methylphenyl)-1,2,4-thiadiazol-5-yl]-1-(propan-2-yl)-1H-indole | 333.13 | 334 |
| 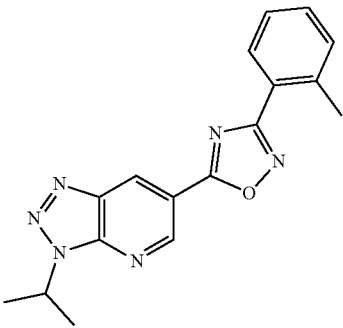 [SMILES: Cc1ccccc1-c1noc(-c2cnc3c(c2)nnn3C(C)C)n1] | 382 | 3-(2-methylphenyl)-5-[3-(propan-2-yl)-3H-[1,2,3]triazolo[4,5-b]pyridin-6-yl]-1,2,4-oxadiazole | 320.14 | 321.2 |

-continued

| Structure | Compound Number | Chemical Name | Exact Mass | Actual Peak |
|---|---|---|---|---|
| 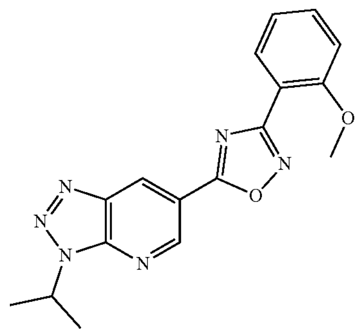 [SMILES: COc1ccccc1-c1noc(-c2cnc3c(c2)nnn3C(C)C)n1] | 383 | 3-(2-methoxyphenyl)-5-[3-(propan-2-yl)-3H-[1,2,3]triazolo[4,5-b]pyridin-6-yl]-1,2,4-oxadiazole | 336.13 | 337.1 |
| 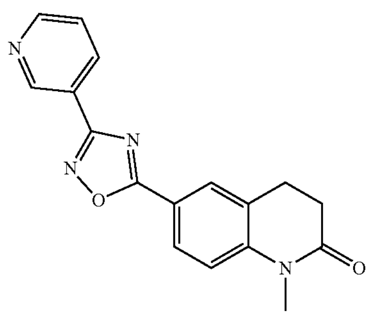 [SMILES: CN1C(=O)CCc2cc(-c3nc(-c4cccnc4)no3)ccc21] | 384 | 1-methyl-6-[3-(pyridin-3-yl)-1,2,4-oxadiazol-5-yl]-1,2,3,4-tetrahydroquinolin-2-one | 306.11 | 307.1 |
| 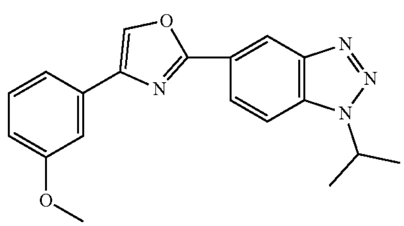 [SMILES: COc1cccc(-c2coc(-c3ccc4c(c3)nnn4C(C)C)n2)c1] | 385 | 5-[4-(3-methoxyphenyl)-1,3-oxazol-2-yl]-1-(propan-2-yl)-1H-1,2,3-benzotriazole | 334.14 | 335 |
| 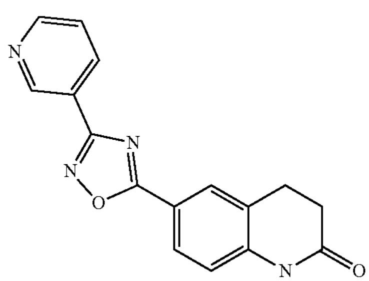 [SMILES: O=C1CCc2cc(-c3nc(-c4cccnc4)no3)ccc2N1] | 386 | 6-[3-(pyridin-3-yl)-1,2,4-oxadiazol-5-yl]-1,2,3,4-tetrahydroquinolin-2-one | 292.1 | 293.1 |
| 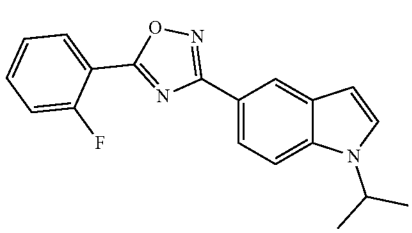 | 387 | 5-(2-fluorophenyl)-3-(1-isopropyl-1H-indol-5-yl)-1,2,4-oxadiazole | 321.13 | 322.3 |

-continued

| Structure | Compound Number | Chemical Name | Exact Mass | Actual Peak |
|---|---|---|---|---|
| 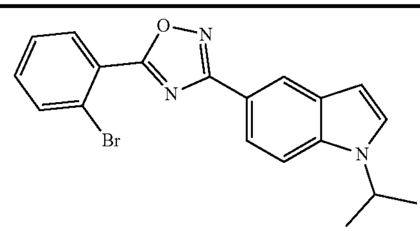 | 388 | 5-(2-bromophenyl)-3-(1-isopropyl-1H-indol-5-yl)-1,2,4-oxadiazole | 381.05 | 382.2 |
| 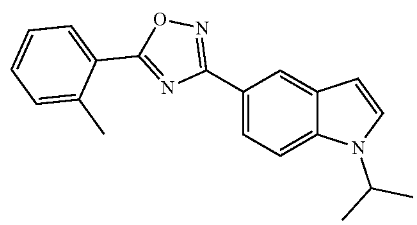 [SMILES: Cc1ccccc1-c1nc(-c2ccc3c(ccn3C(C)C)c2)no1] | 389 | 3-(1-isopropyl-1H-indol-5-yl)-5-(o-tolyl)-1,2,4-oxadiazole | 317.15 | 318.3 |
| 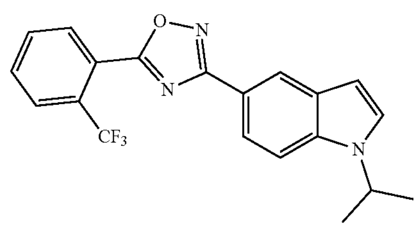 | 390 | 3-(1-isopropyl-1H-indol-5-yl)-5-(2-(trifluoromethyl)phenyl)-1,2,4-oxadiazole | 371.12 | 372.3 |
| 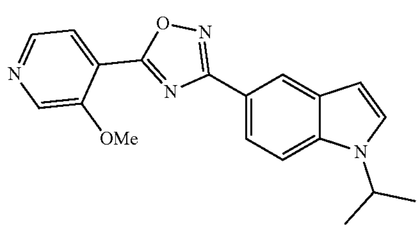 [SMILES: COc1cnccc1-c1nc(-c2ccc3c(ccn3C(C)C)c2)no1] | 391 | 3-(1-isopropyl-1H-indol-5-yl)-5-(3-methoxypyridin-4-yl)-1,2,4-oxadiazole | 334.14 | 335.3 |
| 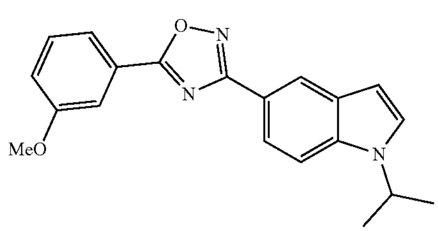 [SMILES: COc1cccc(-c2nc(-c3ccc4c(ccn4C(C)C)c3)no2)c1] | 392 | 3-(1-isopropyl-1H-indol-5-yl)-5-(3-methoxyphenyl)-1,2,4-oxadiazole | 333.15 | 334.3 |
| 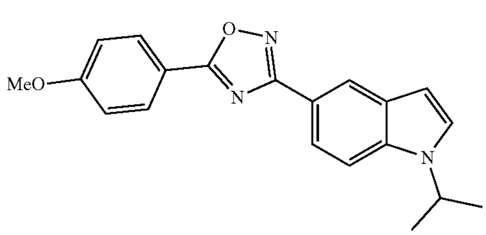 [SMILES: COc1ccc(-c2nc(-c3ccc4c(ccn4C(C)C)c3)no2)cc1] | 393 | 3-(1-isopropyl-1H-indol-5-yl)-5-(4-methoxyphenyl)-1,2,4-oxadiazole | 333.15 | 334.2 |
| 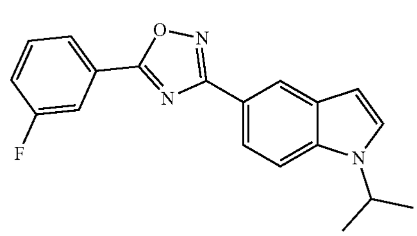 [SMILES: CC(C)n1ccc2cc(-c3noc(-c4cccc(F)c4)n3)ccc21] | 394 | 5-(3-fluorophenyl)-3-(1-isopropyl-1H-indol-5-yl)-1,2,4-oxadiazole | 321.13 | 322.1 |

-continued

| Structure | Compound Number | Chemical Name | Exact Mass | Actual Peak |
|---|---|---|---|---|
| 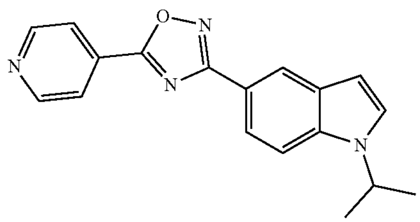 [SMILES: CC(C)n1ccc2cc(-c3noc(-c4ccncc4)n3)ccc21] | 395 | 3-(1-isopropyl-1H-indol-5-yl)-5-(pyridin-4-yl)-1,2,4-oxadiazole | 304.13 | 305.1 |
| 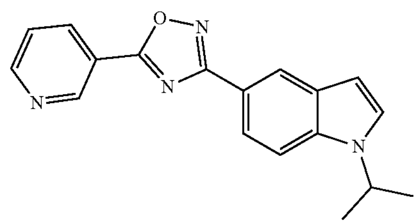 [SMILES: CC(C)n1ccc2cc(-c3noc(-c4cccnc4)n3)ccc21] | 396 | 3-(1-isopropyl-1H-indol-5-yl)-5-(pyridin-3-yl)-1,2,4-oxadiazole | 304.13 | 305.1 |
| 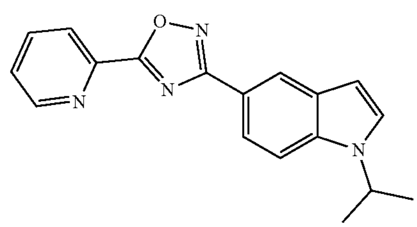 [SMILES: CC(C)n1ccc2cc(-c3noc(-c4ccccn4)n3)ccc21] | 397 | 3-(1-isopropyl-1H-indol-5-yl)-5-(pyridin-2-yl)-1,2,4-oxadiazole | 304.13 | 305.1 |
| 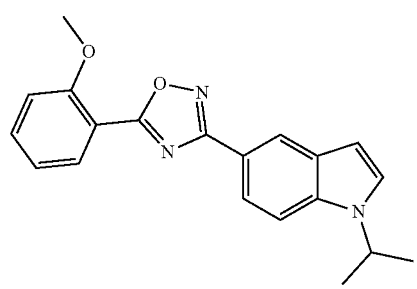 [SMILES: COc1ccccc1-c1nc(-c2ccc3c(ccn3C(C)C)c2)no1] | 398 | 3-(1-isopropyl-1H-indol-5-yl)-5-(2-methoxyphenyl)-1,2,4-oxadiazole | 333.15 | 334.2 |
| 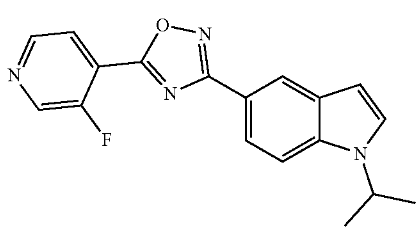 [SMILES: CC(C)n1ccc2cc(-c3noc(-c4ccncc4F)n3)ccc21] | 399 | 5-(3-fluoropyridin-4-yl)-3-(1-isopropyl-1H-indol-5-yl)-1,2,4-oxadiazole | 322.12 | 323 |
| 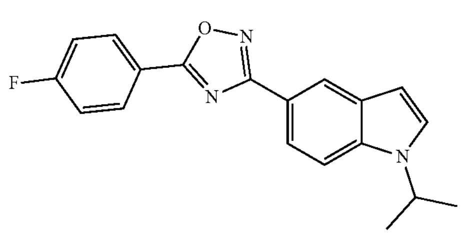 [SMILES: CC(C)n1ccc2cc(-c3noc(-c4ccc(F)cc4)n3)ccc21] | 400 | 5-(4-fluorophenyl)-3-(1-isopropyl-1H-indol-5-yl)-1,2,4-oxadiazole | 321.13 | 322.1 |

-continued

| Structure | Compound Number | Chemical Name | Exact Mass | Actual Peak |
|---|---|---|---|---|
| 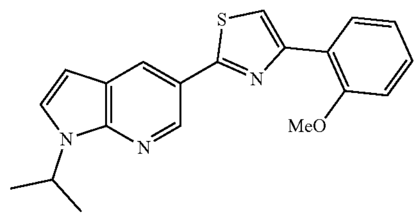 [SMILES: COc1ccccc1-c1csc(-c2cnc3c(ccn3C(C)C)c2)n1] | 401 | 2-(1-isopropyl-1H-pyrrolo[2,3-b]pyridin-5-yl)-4-(2-methoxyphenyl)thiazole | 349.12 | 350 |
| 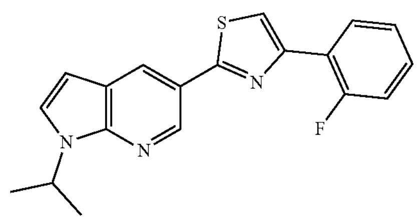 [SMILES: CC(C)n1ccc2cc(-c3nc(-c4ccccc4F)cs3)cnc21] | 402 | 4-(2-fluorophenyl)-2-(1-isopropyl-1H-pyrrolo[2,3-b]pyridin-5-yl)thiazole | 337.1 | 338.1 |
| 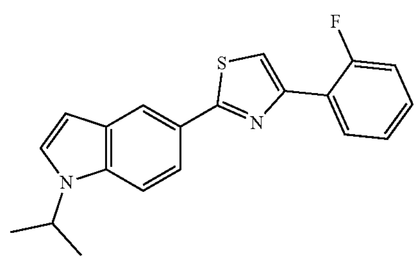 [SMILES: CC(C)n1ccc2cc(-c3nc(-c4ccccc4F)cs3)ccc21] | 403 | 4-(2-fluorophenyl)-2-(1-isopropylindol-5-yl)thiazole | 336.11 | 337.1 |
| 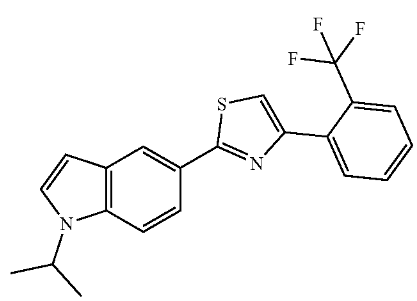 [SMILES: CC(C)n1ccc2cc(-c3nc(-c4ccccc4C(F)(F)F)cs3)ccc21] | 404 | 2-(1-isopropylindol-5-yl)-4-[2-(trifluoromethyl)phenyl]thiazole | 386.11 | 387.1 |
| 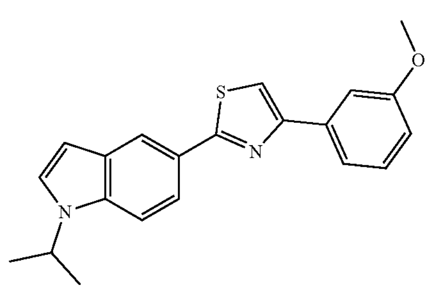 [SMILES: COc1cccc(-c2csc(-c3ccc4c(ccn4C(C)C)c3)n2)c1] | 405 | 2-(1-isopropylindol-5-yl)-4-(3-methoxyphenyl)thiazole | 348.13 | 349.1 |
| 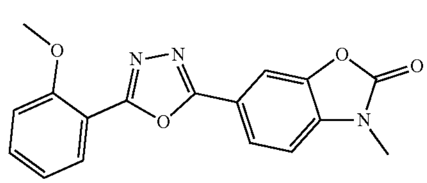 [SMILES: COc1ccccc1-c1nnc(-c2ccc3c(c2)oc(=O)n3C)o1] | 406 | 6-[5-(2-methoxyphenyl)-1,3,4-oxadiazol-2-yl]-3-methyl-2,3-dihydro-1,3-benzoxazol-2-one | 323.09 | 324.1 |

-continued

| Structure | Compound Number | Chemical Name | Exact Mass | Actual Peak |
|---|---|---|---|---|
| 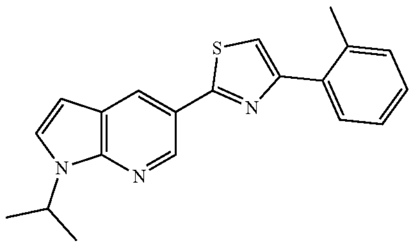 [SMILES: Cc1ccccc1-c1csc(-c2cnc3c(ccn3C(C)C)c2)n1] | 407 | 2-(1-isopropylpyrrolo[2,3-b]pyridin-5-yl)-4-(o-tolyl)thiazole | 333.13 | 334.1 |
| 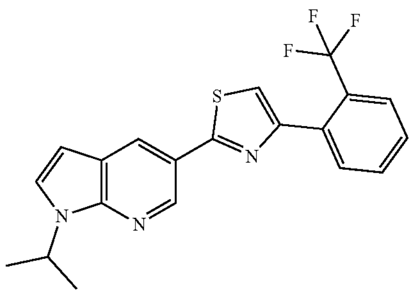 [SMILES: CC(C)n1ccc2cc(-c3nc(-c4ccccc4C(F)(F)F)cs3)cnc21] | 408 | 2-(1-isopropylpyrrolo[2,3-b]pyridin-5-yl)-4-[2-(trifluoromethyl)phenyl]thiazole | 387.1 | 388.1 |
| 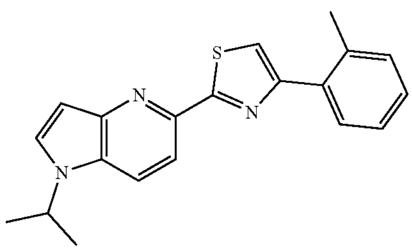 [SMILES: Cc1ccccc1-c1csc(-c2ccc3c(ccn3C(C)C)n2)n1] | 409 | 2-(1-isopropylpyrrolo[3,2-b]pyridin-5-yl)-4-(o-tolyl)thiazole | 333.13 | 334.1 |
| 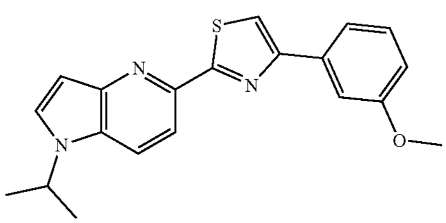 [SMILES: COc1cccc(-c2csc(-c3ccc4c(ccn4C(C)C)n3)n2)c1] | 410 | 2-(1-isopropylpyrrolo[3,2-b]pyridin-5-yl)-4-(3-methoxyphenyl)thiazole | 349.12 | 350.1 |
| 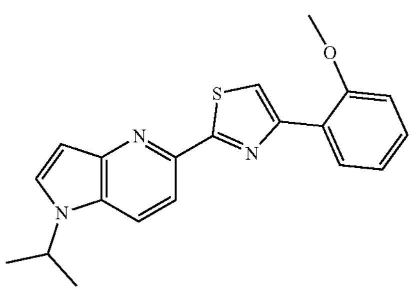 [SMILES: COc1ccccc1-c1csc(-c2ccc3c(ccn3C(C)C)n2)n1] | 411 | 2-(1-isopropyl-1H-pyrrolo[3,2-b]pyridin-5-yl)-4-(2-methoxyphenyl)thiazole | 349.12 | 350.1 |
| 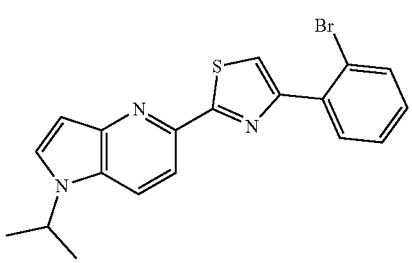 [SMILES: CC(C)n1ccc2nc(-c3nc(-c4ccccc4Br)cs3)ccc21] | 412 | 4-(2-bromophenyl)-2-(1-isopropyl-1H-pyrrolo[3,2-b]pyridin-5-yl)thiazole | 397.02 | 400 |

-continued

| Structure | Compound Number | Chemical Name | Exact Mass | Actual Peak |
|---|---|---|---|---|
| 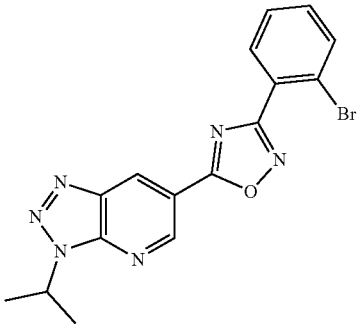 [SMILES: CC(C)n1nnc2cc(-c3nc(-c4ccccc4Br)no3)cnc21] | 413 | 3-(2-bromophenyl)-5-[3-(propan-2-yl)-3H-[1,2,3]triazolo[4,5-b]pyridin-6-yl]-1,2,4-oxadiazole | 384.03 | 385.1 |
| 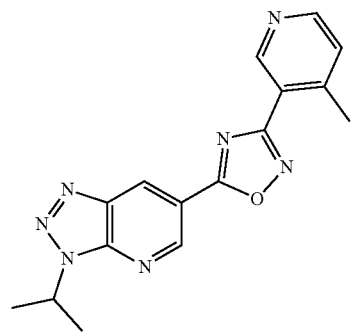 [SMILES: Cc1ccncc1-c1noc(-c2cnc3c(c2)nnn3C(C)C)n1] | 414 | 4-methyl-3-{5-[3-(propan-2-yl)-3H-[1,2,3]triazolo[4,5-b]pyridin-6-yl]-1,2,4-oxadiazol-3-yl}pyridine | 321.13 | 322.1 |
| 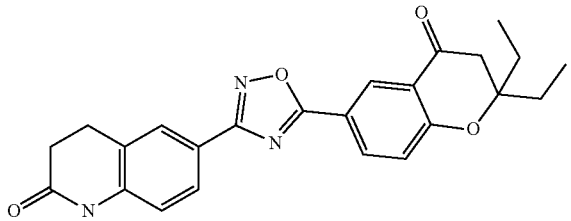 [SMILES: CCC1(CC)CC(=O)c2cc(-c3nc(-c4ccc5c(c4)CCC(=O)N5)no3)ccc2O1] | 415 | 6-(5-(2,2-diethyl-4-oxochroman-6-yl)-1,2,4-oxadiazol-3-yl)-3,4-dihydroquinolin-2(1H)-one | 417.17 | 418.2 |
| 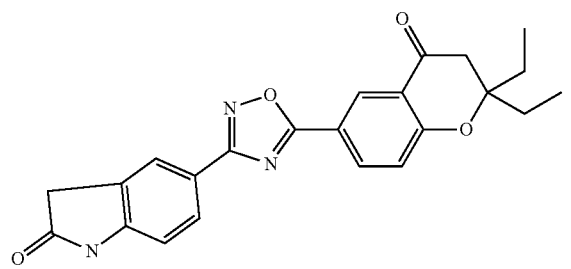 [SMILES: CCC1(CC)CC(=O)c2cc(-c3nc(-c4ccc5c(c4)CC(=O)N5)no3)ccc2O1] | 416 | 5-(5-(2,2-diethyl-4-oxochroman-6-yl)-1,2,4-oxadiazol-3-yl)indolin-2-one | 403.15 | 404.1 |
| 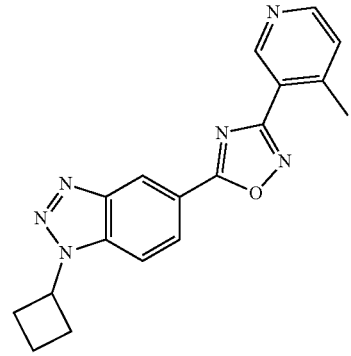 [SMILES: Cc1ccncc1-c1noc(-c2ccc3c(c2)nnn3C2CCC2)n1] | 417 | 1-cyclobutyl-5-[3-(4-methylpyridin-3-yl)-1,2,4-oxadiazol-5-yl]-1H-1,2,3-benzotriazole | 332.14 | 333.1 |

-continued

| Structure | Compound Number | Chemical Name | Exact Mass | Actual Peak |
|---|---|---|---|---|
| 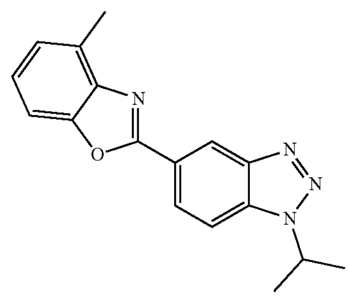 [SMILES: Cc1cccc2oc(-c3ccc4c(c3)nnn4C(C)C)nc12] | 418 | 2-(1-isopropyl-1H-benzo[d][1,2,3]triazol-5-yl)-4-methylbenzo[d]oxazole | 292.13 | 293.1 |
| 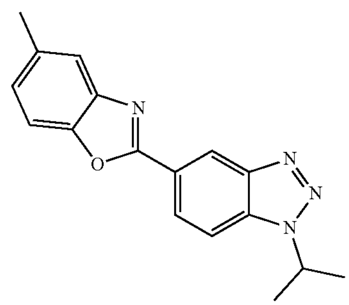 [SMILES: Cc1ccc2oc(-c3ccc4c(c3)nnn4C(C)C)nc2c1] | 419 | 2-(1-isopropyl-1H-benzo[d][1,2,3]triazol-5-yl)-5-methylbenzo[d]oxazole | 292.13 | 293.1 |
| 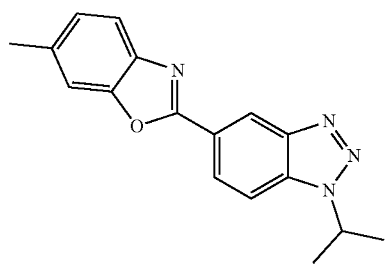 [SMILES: Cc1ccc2nc(-c3ccc4c(c3)nnn4C(C)C)oc2c1] | 420 | 2-(1-isopropyl-1H-benzo[d][1,2,3]triazol-5-yl)-6-methylbenzo[d]oxazole | 292.13 | 293.1 |
| 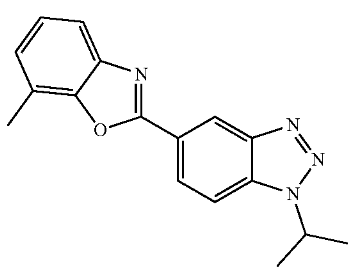 [SMILES: Cc1cccc2nc(-c3ccc4c(c3)nnn4C(C)C)oc12] | 421 | 2-(1-isopropyl-1H-benzo[d][1,2,3]triazol-5-yl)-7-methylbenzo[d]oxazole | 292.13 | 293.1 |
| 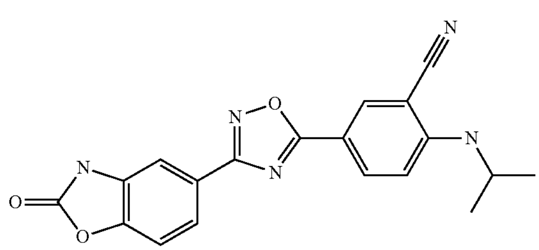 [SMILES: CC(C)Nc1ccc(-c2nc(-c3ccc4oc(=O)[nH]c4c3)no2)cc1C#N] | 422 | 2-(isopropylamino)-5-(3-(2-oxo-2,3-dihydrobenzo[d]oxazol-5-yl)-1,2,4-oxadiazol-5-yl)benzonitrile | 361.12 | 362.1 |

-continued

| Structure | Compound Number | Chemical Name | Exact Mass | Actual Peak |
|---|---|---|---|---|
| 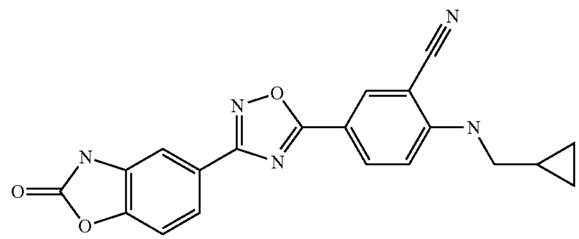 | 423 | 2-((cyclopropylmethyl)amino)-5-(3-(2-oxo-2,3-dihydrobenzo[d]oxazol-5-yl)-1,2,4-oxadiazol-5-yl)benzonitrile | 373.12 | 374.2 |
| 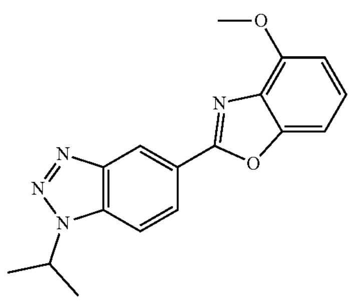 [SMILES: COc1cccc2oc(-c3ccc4c(c3)nnn4C(C)C)nc12] | 424 | 2-(1-isopropyl-1H-benzo[d][1,2,3]triazol-5-yl)-4-methoxybenzo[d]oxazole | 308.13 | 309 |
| 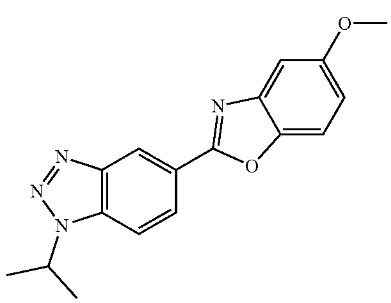 [SMILES: COc1ccc2oc(-c3ccc4c(c3)nnn4C(C)C)nc2c1] | 425 | 2-(1-isopropyl-1H-benzo[d][1,2,3]triazol-5-yl)-5-methoxybenzo[d]oxazole | 308.13 | 309.1 |
| 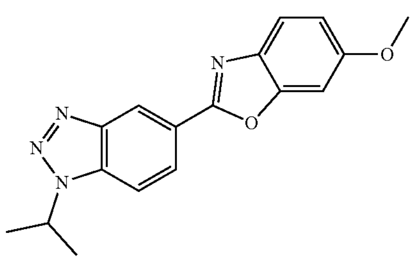 [SMILES: COc1ccc2nc(-c3ccc4c(c3)nnn4C(C)C)oc2c1] | 426 | 2-(1-isopropyl-1H-benzo[d][1,2,3]triazol-5-yl)-6-methoxybenzo[d]oxazole | 308.13 | 309 |
| 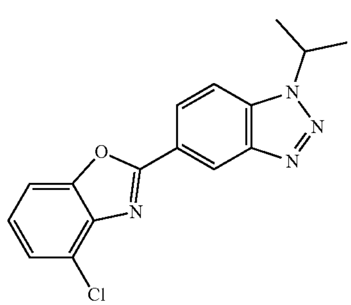 [SMILES: CC(C)n1nnc2cc(-c3nc4c(Cl)cccc4o3)ccc21] | 427 | 4-chloro-2-(1-isopropyl-1H-benzo[d][1,2,3]triazol-5-yl)benzo[d]oxazole | 312.08 | 313 |

-continued

| Structure | Compound Number | Chemical Name | Exact Mass | Actual Peak |
|---|---|---|---|---|
| 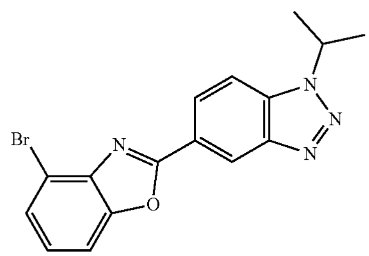 [SMILES: CC(C)n1nnc2cc(-c3nc4c(Br)cccc4o3)ccc21] | 428 | 4-bromo-2-(1-isopropylbenzotriazol-5-yl)-1,3-benzoxazole | 356.03 | 357 |
| 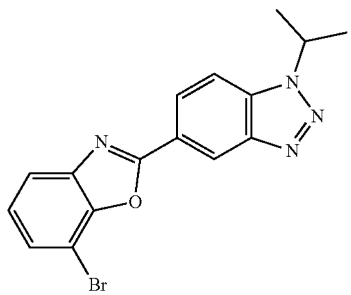 [SMILES: CC(C)n1nnc2cc(-c3nc4cccc(Br)c4o3)ccc21] | 429 | 7-bromo-2-(1-isopropyl-1H-benzo[d][1,2,3]triazol-5-yl)benzo[d]oxazole | 356.03 | 359 |
| 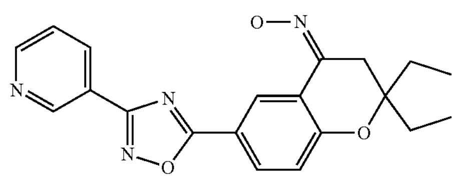 [SMILES: CCC1(CC)C/C(=N/O)c2cc(-c3nc(-c4cccnc4)no3)ccc2O1] | 430 | N-[(4Z)-2,2-diethyl-6-[3-(pyridin-3-yl)-1,2,4-oxadiazol-5-yl]-3,4-dihydro-2H-1-benzopyran-4-ylidene]hydroxylamine | 364.15 | 365.1 |
| 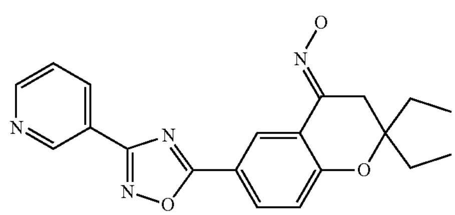 [SMILES: CCC1(CC)C/C(=N\O)c2cc(-c3nc(-c4cccnc4)no3)ccc2O1] | 431 | N-[(4E)-2,2-diethyl-6-[3-(pyridin-3-yl)-1,2,4-oxadiazol-5-yl]-3,4-dihydro-2H-1-benzopyran-4-ylidene]hydroxylamine | 364.15 | 365.1 |
| 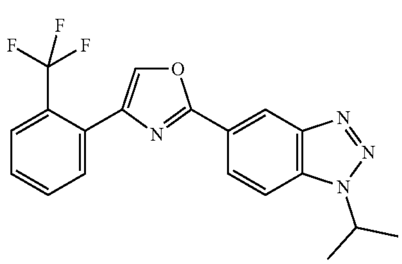 [SMILES: CC(C)n1nnc2cc(-c3nc(-c4ccccc4C(F)(F)F)co3)ccc21] | 432 | 1-(propan-2-yl)-5-(4-[2-(trifluoromethyl)phenyl]-1,3-oxazol-2-yl}-1H-1,2,3-benzotriazole | 372.12 | 373 |
| 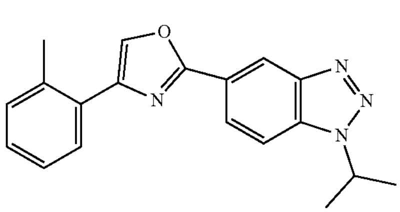 [SMILES: Cc1ccccc1-c1coc(-c2ccc3c(c2)nnn3C(C)C)n1] | 433 | 5-[4-(2-methylphenyl)-1,3-oxazol-2-yl]-1-(propan-2-yl)-1H-1,2,3-benzotriazole | 318.15 | 319 |

-continued

| Structure | Compound Number | Chemical Name | Exact Mass | Actual Peak |
|---|---|---|---|---|
| 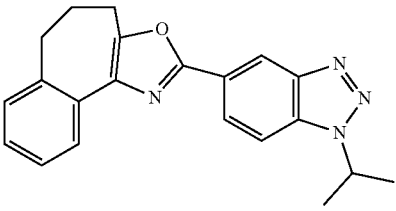 [SMILES: CC(C)n1nnc2cc(-c3nc4c(o3)CCCc3ccccc3-4)ccc21] | 434 | 4-[1-(propan-2-yl)-1H-1,2,3-benzotriazol-5-yl]-5-oxa-3-azatricyclo[8.4.0.0²,⁶]tetradeca-1(14),2(6),3,10,12-pentaene | 344.16 | 345 |
| 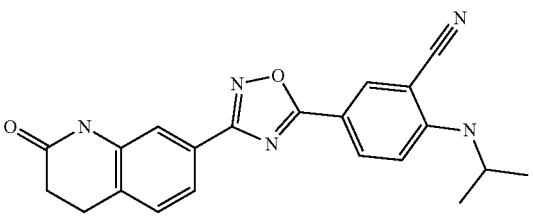 [SMILES: CC(C)Nc1ccc(-c2nc(-c3ccc4c(c3)NC(=O)CC4)no2)cc1C#N] | 435 | 2-(isopropylamino)-5-(3-(2-oxo-1,2,3,4-tetrahydroquinolin-7-yl)-1,2,4-oxadiazol-5-yl)benzonitrile | 373.15 | 374 |
| 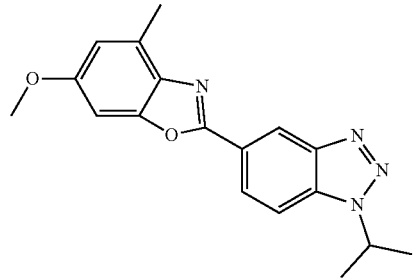 [SMILES: COc1cc(C)c2nc(-c3ccc4c(c3)nnn4C(C)C)oc2c1] | 436 | 2-(1-isopropyl-1H-benzo[d][1,2,3]triazol-5-yl)-6-methoxy-4-methylbenzo[d]oxazole | 322.14 | 323 |
| 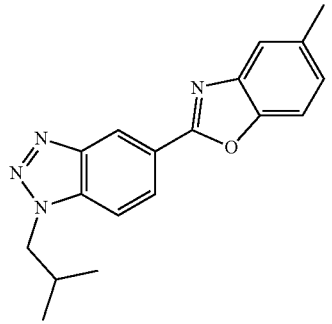 [SMILES: Cc1ccc2oc(-c3ccc4c(c3)nnn4CC(C)C)nc2c1] | 437 | 2-(1-isobutyl-1H-benzo[d][1,2,3]triazol-5-yl)-5-methylbenzo[d]oxazole | 306.15 | 307.2 |
| 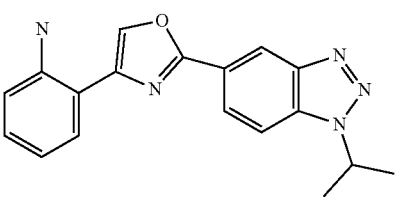 [SMILES: CC(C)n1nnc2cc(-c3nc(-c4ccccc4N)co3)ccc21] | 438 | 2-{2-[1-(propan-2-yl)-1H-1,2,3-benzotriazol-5-yl]-1,3-oxazol-4-yl}aniline | 319.14 | 320 |

-continued

| Structure | Compound Number | Chemical Name | Exact Mass | Actual Peak |
|---|---|---|---|---|
| 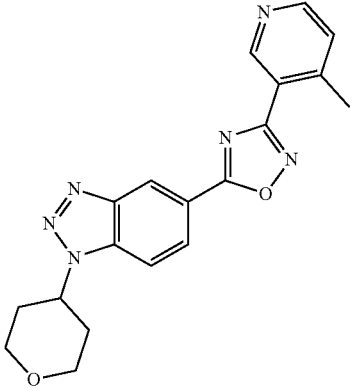 [SMILES: Cc1ccncc1-c1noc(-c2ccc3c(c2)nnn3C2CCOCC2)n1] | 439 | 5-[3-(4-methylpyridin-3-yl)-1,2,4-oxadiazol-5-yl]-1-(oxan-4-yl)-1H-1,2,3-benzotriazole | 362.15 | 363.1 |
| 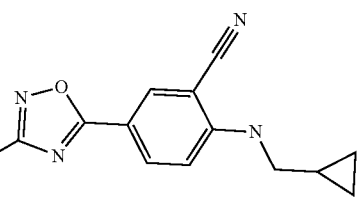 | 440 | 5-(3-(2-aminobenzo[d]thiazol-5-yl)-1,2,4-oxadiazol-5-yl)-2-((cyclopropylmethyl)amino)benzonitrile | 388.11 | 389 |
| 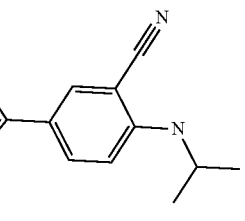 | 441 | 5-(3-(2-aminobenzo[d]thiazol-5-yl)-1,2,4-oxadiazol-5-yl)-2-(isopropylamino)benzonitrile | 376.11 | 377 |
| 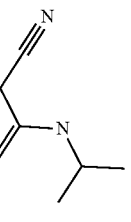 | 442 | 2-(isopropylamino)-5-(3-(1-oxo-1,2,3,4-tetrahydroisoquinolin-6-yl)-1,2,4-oxadiazol-5-yl)benzonitrile | 373.15 | 374 |
| 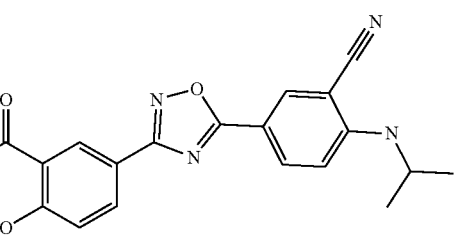 | 443 | 5-(3-(2,2-diethyl-4-oxochroman-6-yl)-1,2,4-oxadiazol-5-yl)-2-(isopropylamino)benzonitrile | 430.2 | 431 |

-continued

| Structure | Compound Number | Chemical Name | Exact Mass | Actual Peak |
|---|---|---|---|---|
| 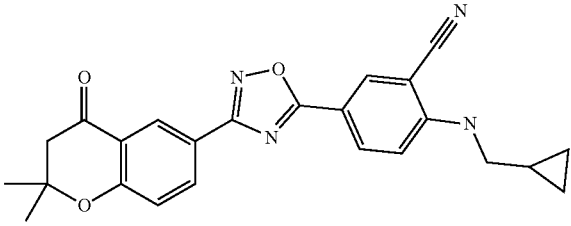 [SMILES: CC1(C)CC(=O)c2cc(-c3noc(-c4ccc(NCC5CC5)c(C#N)c4)n3)ccc2O1] | 444 | 2-((cyclopropylmethyl)amino)-5-(3-(2,2-diethyl-4-oxochroman-6-yl)-1,2,4-oxadiazol-5-yl)benzonitrile | 442.2 | 443.3 |
| 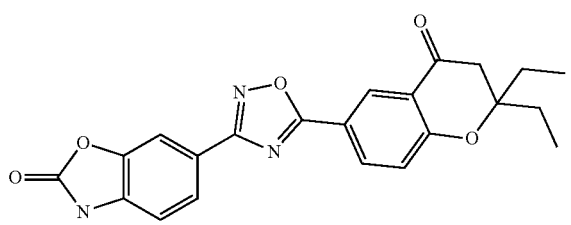 [SMILES: CCC1(CC)CC(=O)c2cc(-c3nc(-c4ccc5[nH]c(=O)oc5c4)no3)ccc2O1] | 445 | 6-(5-(2,2-diethyl-4-oxochroman-6-yl)-1,2,4-oxadiazol-3-yl)benzo[d]oxazol-2(3H)-one | 405.13 | 406 |
| 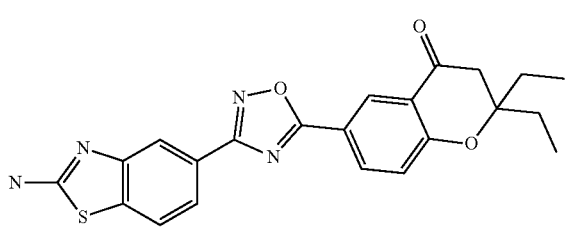 [SMILES: CCC1(CC)CC(=O)c2cc(-c3nc(-c4ccc5sc(N)nc5c4)no3)ccc2O1] | 446 | 6-(3-(2-aminobenzo[d]thiazol-5-yl)-1,2,4-oxadiazol-5-yl)-2,2-diethylchroman-4-one | 420.13 | 421 |
| 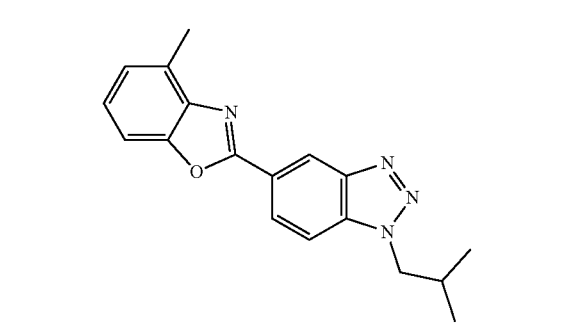 [SMILES: Cc1cccc2oc(-c3ccc4c(c3)nnn4CC(C)C)nc12] | 447 | 2-(1-isobutyl-1H-benzo[d][1,2,3]triazol-5-yl)-4-methylbenzo[d]oxazole | 306.15 | 307 |
| 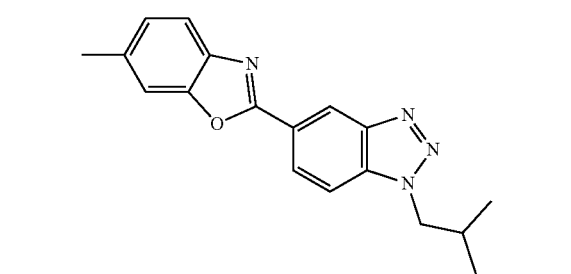 [SMILES: Cc1ccc2nc(-c3ccc4c(c3)nnn4CC(C)C)oc2c1] | 448 | 2-(1-isobutyl-1H-benzo[d][1,2,3]triazol-5-yl)-6-methylbenzo[d]oxazole | 306.15 | 307 |
| 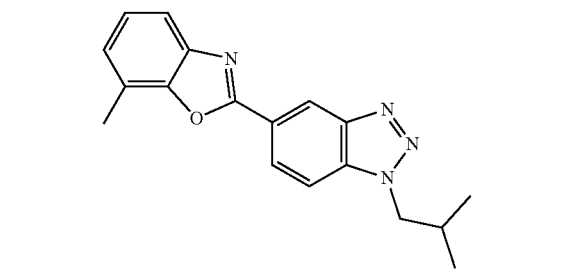 [SMILES: Cc1cccc2nc(-c3ccc4c(c3)nnn4CC(C)C)oc12] | 449 | 2-(1-isobutyl-1H-benzo[d][1,2,3]triazol-5-yl)-7-methylbenzo[d]oxazole | 306.15 | 307 |

-continued

| Structure | Compound Number | Chemical Name | Exact Mass | Actual Peak |
|---|---|---|---|---|
| 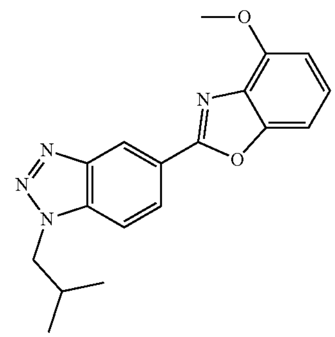 [SMILES: COc1cccc2oc(-c3ccc4c(c3)nnn4CC(C)C)nc12] | 450 | 2-(1-isobutyl-1H-benzo[d][1,2,3]triazol-5-yl)-4-methoxybenzo[d]oxazole | 322.14 | 323 |
| 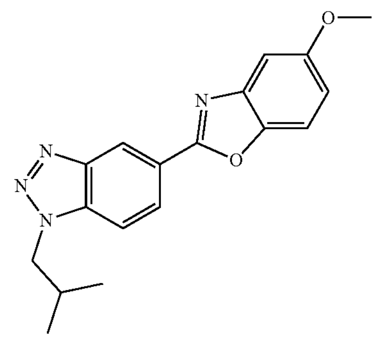 [SMILES: COc1ccc2oc(-c3ccc4c(c3)nnn4CC(C)C)nc2c1] | 451 | 2-(1-isobutyl-1H-benzo[d][1,2,3]triazol-5-yl)-5-methoxybenzo[d]oxazole | 322.14 | 323 |
| 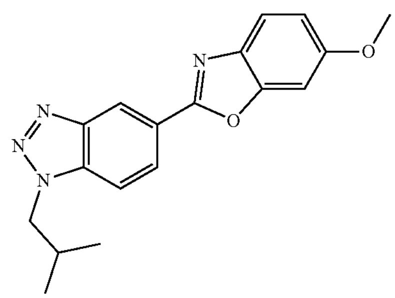 [SMILES: COc1ccc2nc(-c3ccc4c(c3)nnn4CC(C)C)oc2c1] | 452 | 2-(1-isobutyl-1H-benzo[d][1,2,3]triazol-5-yl)-6-methoxybenzo[d]oxazole | 322.14 | 323 |
| 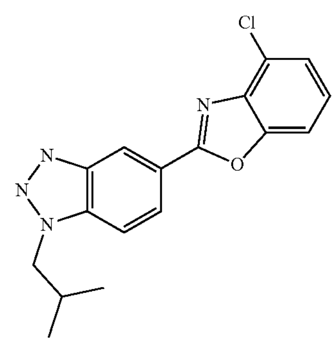 [SMILES: CC(C)CN1NNc2cc(-c3nc4c(Cl)cccc4o3)ccc21] | 453 | 4-chloro-2-(1-isobutyl-1H-benzo[d][1,2,3]triazol-5-yl)benzo[d]oxazole | 326.09 | 326.9 |

-continued

| Structure | Compound Number | Chemical Name | Exact Mass | Actual Peak |
|---|---|---|---|---|
| 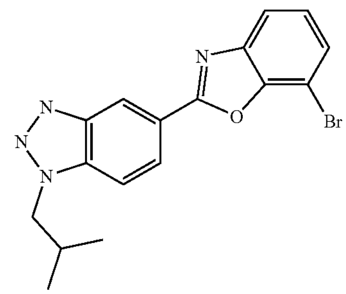 [SMILES: CC(C)CN1NNc2cc(-c3nc4cccc(Br)c4o3)ccc21] | 454 | 7-bromo-2-(1-isobutyl-1H-benzo[d][1,2,3]triazol-5-yl)benzo[d]oxazole | 370.04 | 371.1 |
| 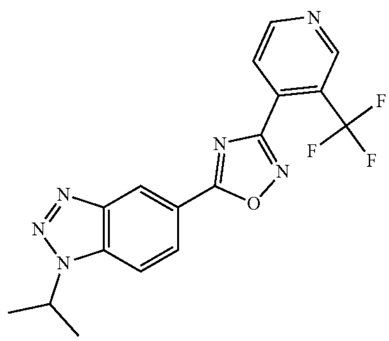 [SMILES: CC(C)n1nnc2cc(-c3nc(-c4ccncc4C(F)(F)F)no3)ccc21] | 455 | 1-(propan-2-yl)-5-{3-[3-(trifluoromethyl)pyridin-4-yl]-1,2,4-oxadiazol-5-yl}-1H-1,2,3-benzotriazole | 374.11 | 375.1 |
| 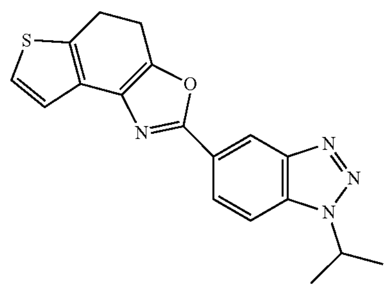 [SMILES: CC(C)n1nnc2cc(-c3nc4c(o3)CCc3sccc3-4)ccc21] | 456 | 4-[1-(propan-2-yl)-1H-1,2,3-benzotriazol-5-yl]-5-oxa-10-thia-3-azatricyclo[7.3.0.0²,⁶]dodeca-1(9),2(6),3,11-tetraene | 336.1 | 337 |
| 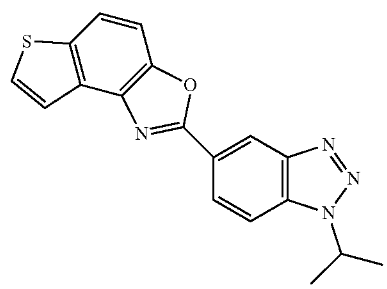 [SMILES: CC(C)n1nnc2cc(-c3nc4c(ccc5sccc54)o3)ccc21] | 457 | 4-[1-(propan-2-yl)-1H-1,2,3-benzotriazol-5-yl]-5-oxa-10-thia-3-azatricyclo[7.3.0.0²,⁶]dodeca-1(9),2(6),3,7,11-pentaene | 334.09 | 335 |
| 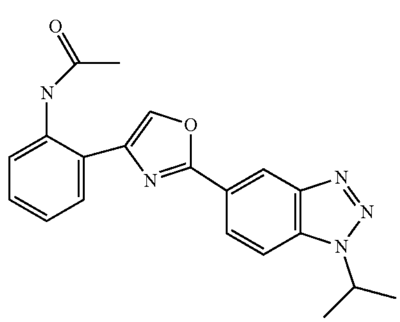 [SMILES: CC(=O)Nc1ccccc1-c1coc(-c2ccc3c(c2)nnn3C(C)C)n1] | 458 | N-(2-{2-[1-(propan-2-yl)-1H-1,2,3-benzotriazol-5-yl]-1,3-oxazol-4-yl}phenyl)acetamide | 361.15 | 362 |

-continued

| Structure | Compound Number | Chemical Name | Exact Mass | Actual Peak |
|---|---|---|---|---|
| 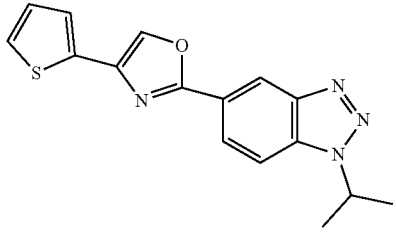 [SMILES: CC(C)n1nnc2cc(-c3nc(-c4cccs4)co3)ccc21] | 459 | 1-(propan-2-yl)-5-[4-(thiophen-2-yl)-1,3-oxazol-2-yl]-1H-1,2,3-benzotriazole | 310.09 | 311 |
| 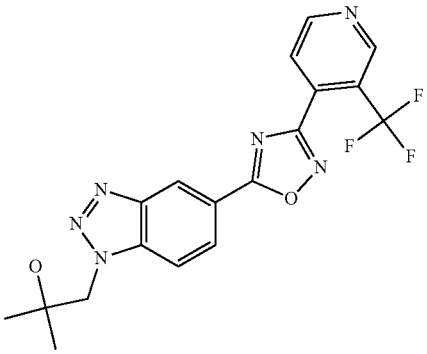 [SMILES: CC(C)(O)Cn1nnc2cc(-c3nc(-c4ccncc4C(F)(F)F)no3)ccc21] | 460 | 2-methyl-1-(5-{3-[3-(trifluoromethyl)pyridin-4-yl]-1,2,4-oxadiazol-5-yl}-1H-1,2,3-benzotriazol-1-yl)propan-2-ol | 404.12 | 405.1 |
| 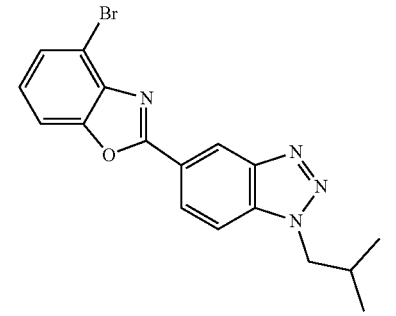 [SMILES: CC(C)Cn1nnc2cc(-c3nc4c(Br)cccc4o3)ccc21] | 461 | 4-bromo-2-(1-isobutyl-1H-benzo[d][1,2,3]triazol-5-yl)benzo[d]oxazole | 370.04 | 372.9 |
| 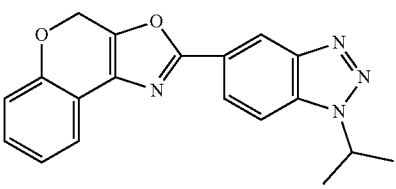 [SMILES: CC(C)n1nnc2cc(-c3nc4c(o3)COc3ccccc3-4)ccc21] | 462 | 5-{4H-chromeno[4,3-d][1,3]oxazol-2-yl}-1-(propan-2-yl)-1H-1,2,3-benzotriazole | 332.13 | 333 |
| 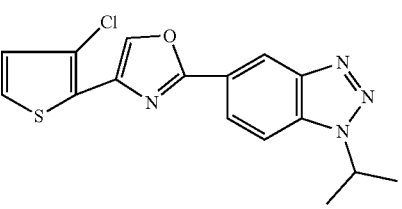 [SMILES: CC(C)n1nnc2cc(-c3nc(-c4sccc4Cl)co3)ccc21] | 463 | 5-[4-(3-chlorothiophen-2-yl)-1,3-oxazol-2-yl]-1-(propan-2-yl)-1H-1,2,3-benzotriazole | 344.05 | 345 |
| 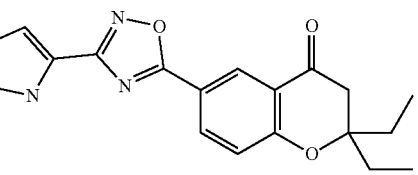 | 464 | 6-(3-(1H-pyrrol-2-yl)-1,2,4-oxadiazol-5-yl)-2,2-diethylchroman-4-one | 337.14 | 338.2 |

-continued

| Structure | Compound Number | Chemical Name | Exact Mass | Actual Peak |
|---|---|---|---|---|
| 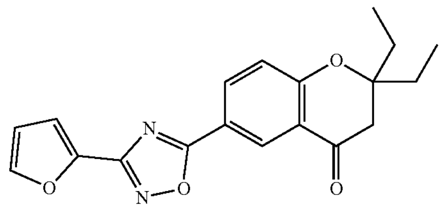 [SMILES: CCC1(CC)CC(=O)c2cc(-c3nc(-c4ccco4)no3)ccc2O1] | 465 | 2,2-diethyl-6-(3-(furan-2-yl)-1,2,4-oxadiazol-5-yl)chroman-4-one | 338.13 | 339.2 |
| 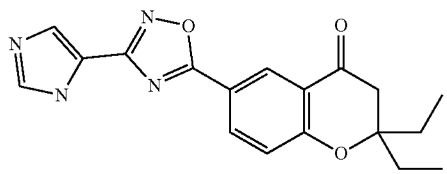 [SMILES: CCC1(CC)CC(=O)c2cc(-c3nc(-c4cnc[nH]4)no3)ccc2O1] | 466 | 6-(3-(1H-imidazol-5-yl)-1,2,4-oxadiazol-5-yl)-2,2-diethylchroman-4-one | 338.14 | 339.2 |
| 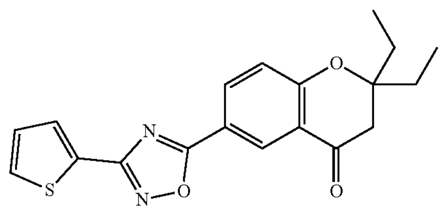 [SMILES: CCC1(CC)CC(=O)c2cc(-c3nc(-c4cccs4)no3)ccc2O1] | 467 | 2,2-diethyl-6-(3-(thiophen-2-yl)-1,2,4-oxadiazol-5-yl)chroman-4-one | 354.1 | 355.2 |
| 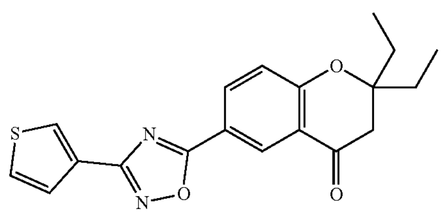 [SMILES: CCC1(CC)CC(=O)c2cc(-c3nc(-c4ccsc4)no3)ccc2O1] | 468 | 2,2-diethyl-6-(3-(thiophen-3-yl)-1,2,4-oxadiazol-5-yl)chroman-4-one | 354.1 | 354.9 |
| 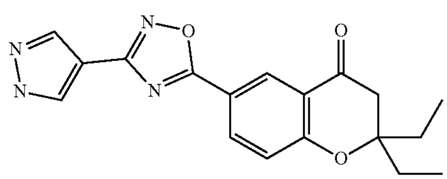 [SMILES: CCC1(CC)CC(=O)c2cc(-c3nc(-c4cn[nH]c4)no3)ccc2O1] | 469 | 6-(3-(1H-pyrazol-4-yl)-1,2,4-oxadiazol-5-yl)-2,2-diethylchroman-4-one | 338.14 | 339.1 |
| 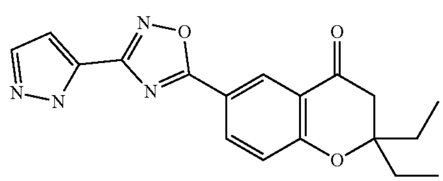 [SMILES: CCC1(CC)CC(=O)c2cc(-c3nc(-c4ccn[nH]4)no3)ccc2O1] | 470 | 6-(3-(1H-pyrazol-5-yl)-1,2,4-oxadiazol-5-yl)-2,2-diethylchroman-4-one | 338.14 | 339.1 |
| 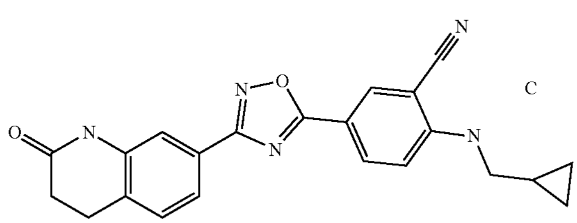 | 471 | 2-((cyclopropylmethyl)amino)-5-(3-(2-oxo-1,2,3,4-tetrahydroquinolin-7-yl)-1,2,4-oxadiazol-5-yl)benzonitrile | | 385.43 |
| 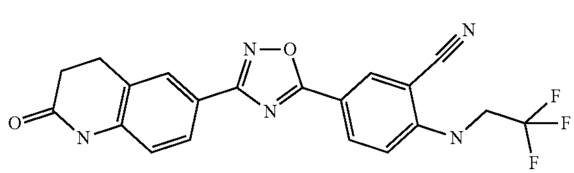 [SMILES: N#Cc1cc(-c2nc(-c3ccc4c(c3)CCC(=O)N4)no2)ccc1NCC(F)(F)F] | 472 | 5-[3-(2-oxo-1,2,3,4-tetrahydroquinolin-6-yl)-1,2,4-oxadiazol-5-yl]-2-[(2,2,2-trifluoroethyl)amino]benzonitrile | 413.11 | 414.1 |

-continued

| Structure | Compound Number | Chemical Name | Exact Mass | Actual Peak |
|---|---|---|---|---|
| 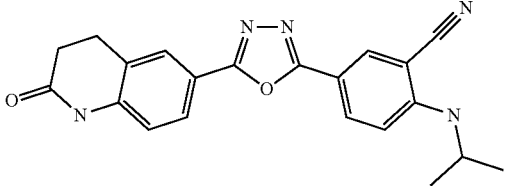 [SMILES: CC(C)Nc1ccc(-c2nnc(-c3ccc4c(c3)CCC(=O)N4)o2)cc1C#N] | 473 | 5-[5-(2-oxo-1,2,3,4-tetrahydroquinolin-6-yl)-1,3,4-oxadiazol-2-yl]-2-[(propan-2-yl)amino]benzonitrile | 373.15 | 374.1 |
| 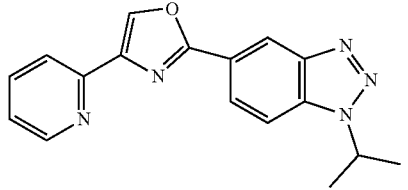 [SMILES: CC(C)n1nnc2cc(-c3nc(-c4ccccn4)co3)ccc21] | 474 | 1-(propan-2-yl)-5-[4-(pyridin-2-yl)-1,3-oxazol-2-yl]-1H-1,2,3-benzotriazole | 305.13 | 306 |
| 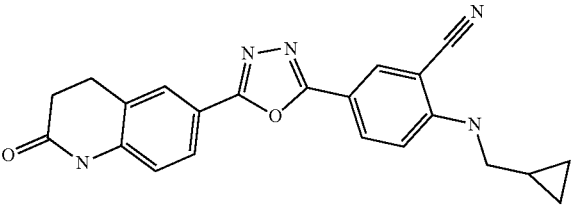 [SMILES: N#Cc1cc(-c2nnc(-c3ccc4c(c3)CCC(=O)N4)o2)ccc1NCC1CC1] | 475 | 2-[(cyclopropylmethyl)amino]-5-[5-(2-oxo-1,2,3,4-tetrahydroquinolin-6-yl)-1,3,4-oxadiazol-2-yl]benzonitrile | 385.15 | 386.1 |
| 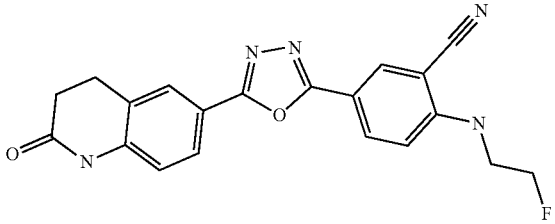 [SMILES: N#Cc1cc(-c2nnc(-c3ccc4c(c3)CCC(=O)N4)o2)ccc1NCCF] | 476 | 2-[(2-fluoroethyl)amino]-5-[5-(2-oxo-1,2,3,4-tetrahydroquinolin-6-yl)-1,3,4-oxadiazol-2-yl]benzonitrile | 377.13 | 378.1 |
| 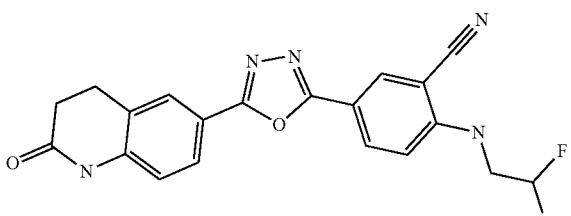 | 477 | 2-[(2,2-difluoroethyl)amino]-5-[5-(2-oxo-1,2,3,4-tetrahydroquinolin-6-yl)-1,3,4-oxadiazol-2-yl]benzonitrile | 395.12 | 396.1 |
| 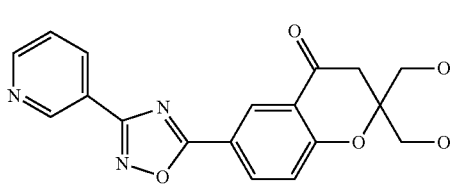 [SMILES: O=C1CC(CO)(CO)Oc2ccc(-c3nc(-c4cccnc4)no3)cc21] | 478 | 2,2-bis(hydroxymethyl)-6-[3-(pyridin-3-yl)-1,2,4-oxadiazol-5-yl]-3,4-dihydro-2H-1-benzopyran-4-one | 353.1 | 354.1 |
| 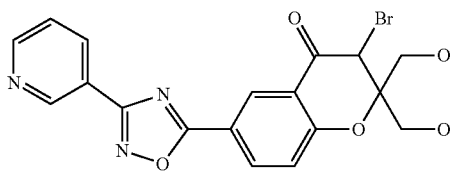 [SMILES: O=C1c2cc(-c3nc(-c4cccnc4)no3)ccc2OC(CO)(CO)C1Br] | 479 | 3-bromo-2,2-bis(hydroxymethyl)-6-[3-(pyridin-3-yl)-1,2,4-oxadiazol-5-yl]-3,4-dihydro-2H-1-benzopyran-4-one | 431.01 | 432 |

-continued

| Structure | Compound Number | Chemical Name | Exact Mass | Actual Peak |
|---|---|---|---|---|
| 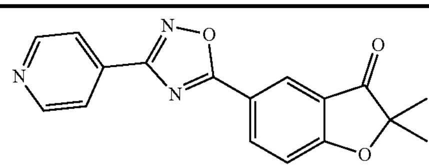 | 480 | 2,2-dimethyl-5-[3-(pyridin-4-yl)-1,2,4-oxadiazol-5-yl]-2,3-dihydro-1-benzofuran-3-one | 307.1 | 308.1 |
| 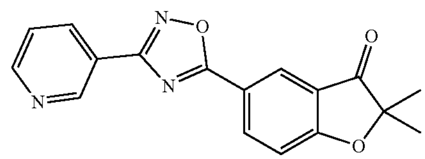 [SMILES: CC1(C)Oc2ccc(-c3nc(-c4cccnc4)no3)cc2C1=O] | 481 | 2,2-dimethyl-5-[3-(pyridin-3-yl)-1,2,4-oxadiazol-5-yl]-2,3-dihydro-1-benzofuran-3-one | 307.1 | 308.1 |
| 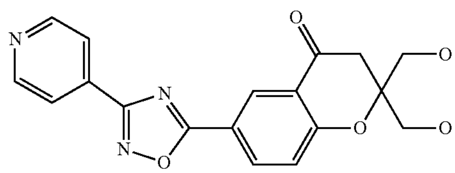 | 482 | 2,2-bis(hydroxymethyl)-6-[3-(pyridin-4-yl)-1,2,4-oxadiazol-5-yl]-3,4-dihydro-2H-1-benzopyran-4-one | 353.1 | 354.1 |
| 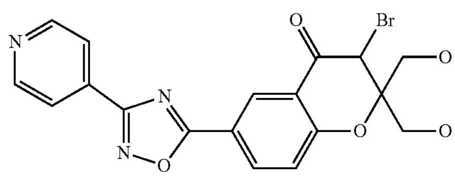 [SMILES: O=C1c2cc(-c3nc(-c4ccncc4)no3)ccc2OC(CO)(CO)C1Br] | 483 | 3-bromo-2,2-bis(hydroxymethyl)-6-[3-(pyridin-4-yl)-1,2,4-oxadiazol-5-yl]-3,4-dihydro-2H-1-benzopyran-4-one | 431.01 | 432 |
| 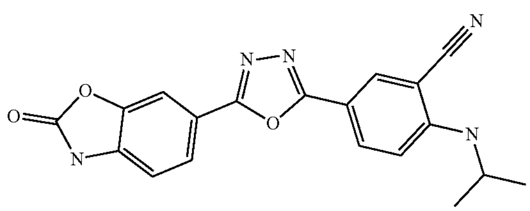 [SMILES: CC(C)Nc1ccc(-c2nnc(-c3ccc4[nH]c(=O)oc4c3)o2)cc1C#N] | 484 | 5-[5-(2-oxo-2,3-dihydro-1,3-benzoxazol-6-yl)-1,3,4-oxadiazol-2-yl]-2-[(propan-2-yl)amino]benzonitrile | 361.12 | 362.1 |
| 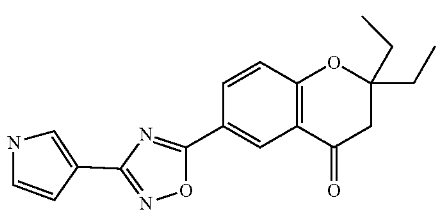 [SMILES: CCC1(CC)CC(=O)c2cc(-c3nc(-c4cc[nH]c4)no3)ccc2O1] | 485 | 6-(3-(1H-pyrrol-3-yl)-1,2,4-oxadiazol-5-yl)-2,2-diethylchroman-4-one | 337.14 | 338 |
| 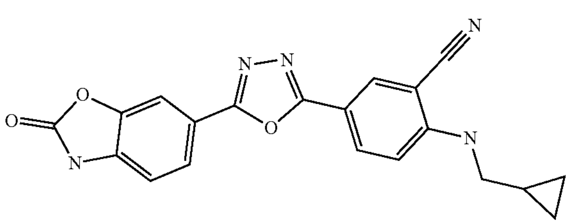 [SMILES: N#Cc1cc(-c2nnc(-c3ccc4[nH]c(=O)oc4c3)o2)ccc1NCC1CC1] | 486 | 2-[(cyclopropylmethyl)amino]-5-[5-(2-oxo-2,3-dihydro-1,3-benzoxazol-6-yl)-1,3,4-oxadiazol-2-yl]benzonitrile | 373.12 | 374.1 |
| 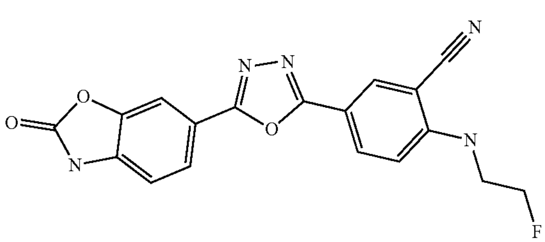 [SMILES: N#Cc1cc(-c2nnc(-c3ccc4[nH]c(=O)oc4c3)o2)ccc1NCCF] | 487 | 2-[(2-fluoroethyl)amino]-5-[5-(2-oxo-2,3-dihydro-1,3-benzoxazol-6-yl)-1,3,4-oxadiazol-2-yl]benzonitrile | 365.09 | 366.1 |

-continued

| Structure | Compound Number | Chemical Name | Exact Mass | Actual Peak |
|---|---|---|---|---|
| 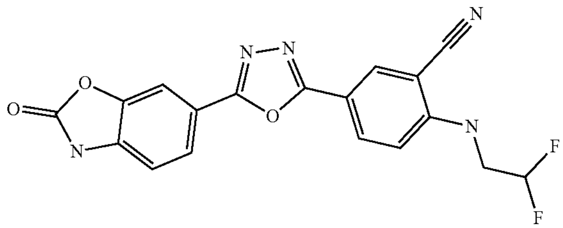 [SMILES: N#Cc1cc(-c2nnc(-c3ccc4[nH]c(=O)oc4c3)o2)ccc1NCC(F)F] | 488 | 2-[(2,2-difluoroethyl)amino]-5-[5-(2-oxo-2,3-dihydro-1,3-benzoxazol-6-yl)-1,3,4-oxadiazol-2-yl]benzonitrile | 383.08 | 384 |
| 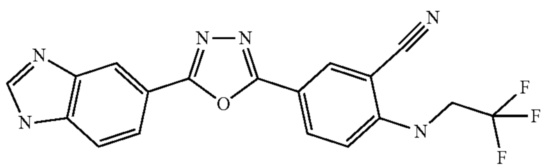 [SMILES: N#Cc1cc(-c2nnc(-c3ccc4[nH]cnc4c3)o2)ccc1NCC(F)(F)F] | 489 | 5-[3-(1H-1,3-benzodiazol-5-yl)-1,2,4-oxadiazol-5-yl]-2-[(2,2,2-trifluoroethyl)amino]benzonitrile | 384.09 | 385.2 |
| 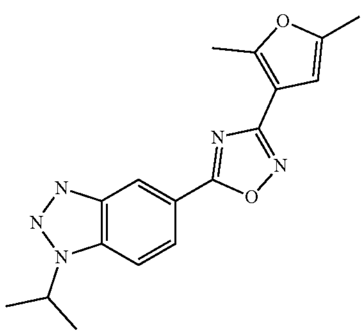 [SMILES: Cc1cc(-c2noc(-c3ccc4c(c3)NNN4C(C)C)n2)c(C)o1] | 490 | 5-[3-(2,5-dimethylfuran-3-yl)-1,2,4-oxadiazol-5-yl]-1-(propan-2-yl)-1H-1,2,3-benzotriazole | 323.14 | 324.1 |
| 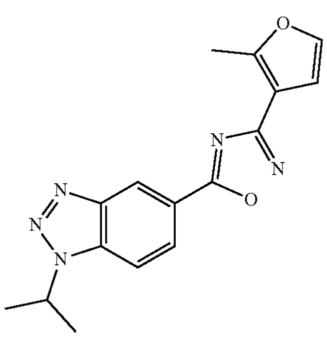 [SMILES: Cc1occc1C(=N)/N=C(\O)c1ccc2c(c1)nnn2C(C)C] | 491 | 5-[3-(2-methylfuran-3-yl)-1,2,4-oxadiazol-5-yl]-1-(propan-2-yl)-1H-1,2,3-benzotriazole | 309.12 | 310.1 |
| 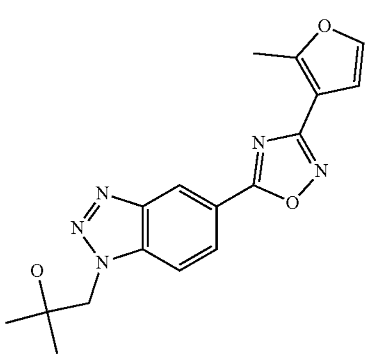 [SMILES: Cc1occc1-c1noc(-c2ccc3c(c2)nnn3CC(C)(C)O)n1] | 492 | 2-methyl-1-{5-[3-(2-methylfuran-3-yl)-1,2,4-oxadiazol-5-yl]-1H-1,2,3-benzotriazol-1-yl}propan-2-ol | 339.13 | 340.1 |

| Structure | Compound Number | Chemical Name | Exact Mass | Actual Peak |
|---|---|---|---|---|
| 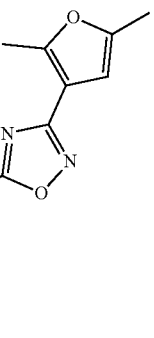 | 493 | 1-{5-[3-(2,5-dimethylfuran-3-yl)-1,2,4-oxadiazol-5-yl]-1H-1,2,3-benzotriazol-1-yl}-2-methylpropan-2-ol | 353.15 | 354.1 |
| 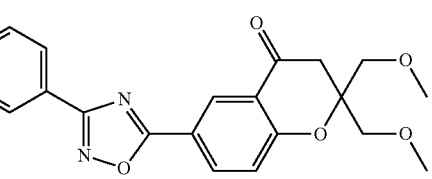 | 494 | 2,2-bis(methoxymethyl)-6-[3-(pyridin-4-yl)-1,2,4-oxadiazol-5-yl]-3,4-dihydro-2H-1-benzopyran-4-one | 381.13 | 382.1 |
| 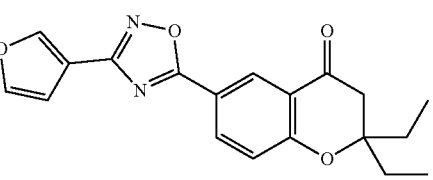 | 495 | 2,2-diethyl-6-(3-(furan-3-yl)-1,2,4-oxadiazol-5-yl)chroman-4-one | 338.13 | 339 |
| 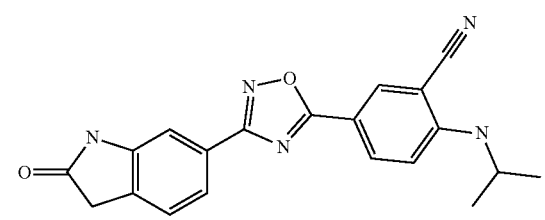 [SMILES: CC(C)Nc1ccc(-c2nc(-c3ccc4c(c3)NC(=O)C4)no2)cc1C#N] | 496 | 2-(isopropylamino)-5-(3-(2-oxoindolin-6-yl)-1,2,4-oxadiazol-5-yl)benzonitrile | 359.14 | 360.2 |
| 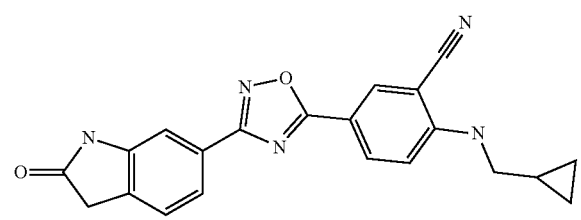 [SMILES: N#Cc1cc(-c2nc(-c3ccc4c(c3)NC(=O)C4)no2)ccc1NCC1CC1] | 497 | 2-((cyclopropylmethyl)amino)-5-(3-(2-oxoindolin-6-yl)-1,2,4-oxadiazol-5-yl)benzonitrile | 371.14 | 372.3 |
| 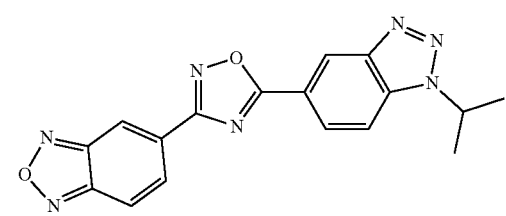 [SMILES: CC(C)n1nnc2cc(-c3nc(-c4ccc5nonc5c4)no3)ccc21] | 498 | 5-{5-[1-(propan-2-yl)-1H-1,2,3-benzotriazol-5-yl]-1,2,4-oxadiazol-3-yl}-2,1,3-benzoxadiazole | 347.11 | 348.1 |
| 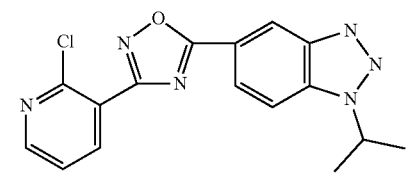 | 499 | 5-[3-(2-chloropyridin-3-yl)-1,2,4-oxadiazol-5-yl]-1-(propan-2-yl)-1H-1,2,3-benzotriazole | 340.08 | 341 |

-continued

| Structure | Compound Number | Chemical Name | Exact Mass | Actual Peak |
|---|---|---|---|---|
| 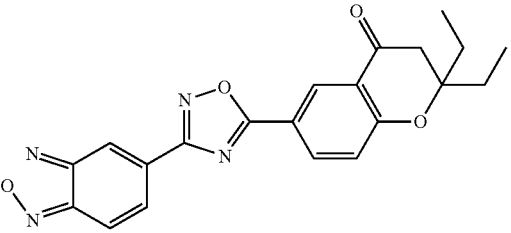 [SMILES: CCC1(CC)CC(=O)c2cc(-c3nc(C4=CC(=N)/C(=N\O)C=C4)no3)ccc2O1] | 500 | 6-[3-(2,1,3-benzoxadiazol-5-yl)-1,2,4-oxadiazol-5-yl]-2,2-diethyl-3,4-dihydro-2H-1-benzopyran-4-one | 390.13 | 391.1 |
| 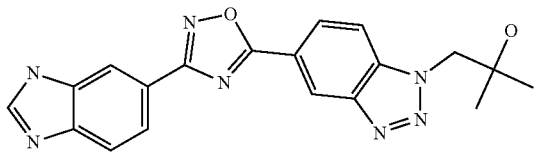 [SMILES: CC(C)(O)Cn1nnc2cc(-c3nc(-c4ccc5nc[nH]c5c4)no3)ccc21] | 501 | 1-{5-[3-(1H-1,3-benzodiazol-6-yl)-1,2,4-oxadiazol-5-yl]-1H-1,2,3-benzotriazol-1-yl}-2-methylpropan-2-ol | 375.14 | 376.1 |
| 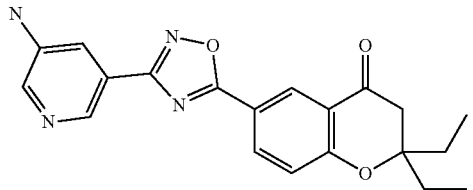 [SMILES: CCC1(CC)CC(=O)c2cc(-c3nc(-c4cncc(N)c4)no3)ccc2O1] | 502 | 6-(3-(5-aminopyridin-3-yl)-1,2,4-oxadiazol-5-yl)-2,2-diethylchroman-4-one | 364.15 | 365.2 |
| 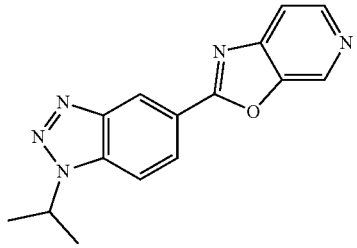 [SMILES: CC(C)n1nnc2cc(-c3nc4ccncc4o3)ccc21] | 503 | 2-(1-isopropyl-1H-benzo[d][1,2,3]triazol-5-yl)oxazolo[5,4-c]pyridine | 279.11 | 280.2 |
| 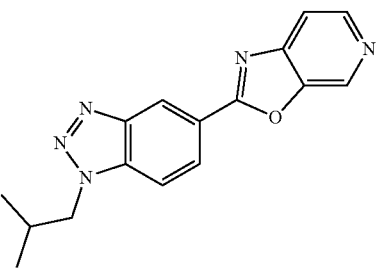 [SMILES: CC(C)Cn1nnc2cc(-c3nc4ccncc4o3)ccc21] | 504 | 2-(1-isobutyl-1H-benzo[d][1,2,3]triazol-5-yl)oxazolo[5,4-c]pyridine | 293.13 | 294.3 |
| 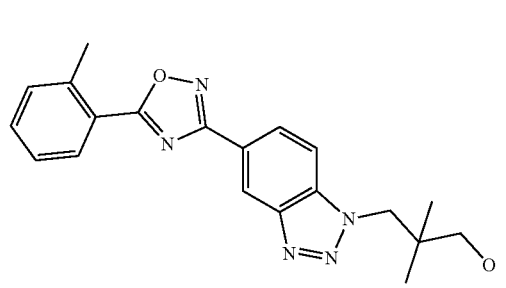 [SMILES: Cc1ccccc1-c1nc(-c2ccc3c(c2)nnn3CC(C)(C)CO)no1] | 505 | 2,2-dimethyl-3-(5-(5-(o-tolyl)-1,2,4-oxadiazol-3-yl)-1H-benzo[d][1,2,3]triazol-1-yl)propan-1-ol | 363.17 | 364.1 |

-continued

| Structure | Compound Number | Chemical Name | Exact Mass | Actual Peak |
|---|---|---|---|---|
| 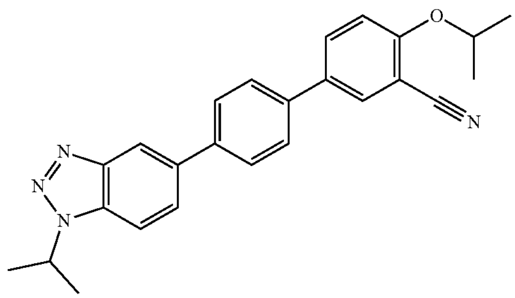 [SMILES: CC(C)Oc1ccc(-c2ccc(-c3ccc4c(c3)nnn4C(C)C)cc2)cc1C#N] | 506 | 4-isopropoxy-4'-(1-isopropyl-1H-benzo[d][1,2,3]triazol-5-yl)-[1,1'-biphenyl]-3-carbonitrile | 396.2 | 397.1 |
| 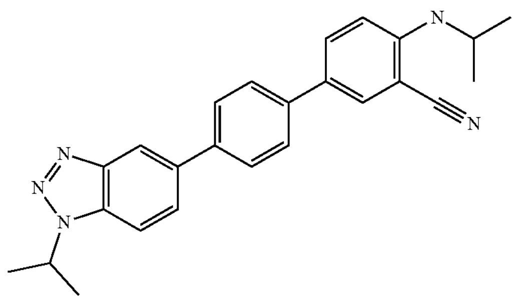 [SMILES: CC(C)Nc1ccc(-c2ccc(-c3ccc4c(c3)nnn4C(C)C)cc2)cc1C#N] | 507 | 4'-(1-isopropyl-1H-benzo[d][1,2,3]triazol-5-yl)-4-(isopropylamino)-[1,1'-biphenyl]-3-carbonitrile | 395.21 | 396.1 |
| 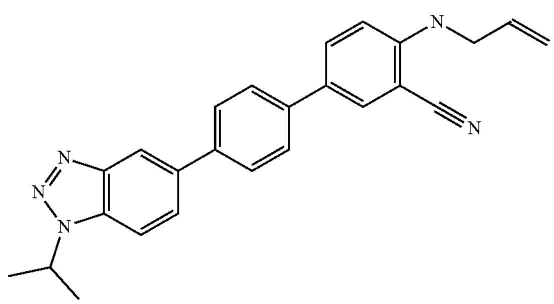 [SMILES: C=CCNc1ccc(-c2ccc(-c3ccc4c(c3)nnn4C(C)C)cc2)cc1C#N] | 508 | 4-(allylamino)-4'-(1-isopropyl-1H-benzo[d][1,2,3]triazol-5-yl)-[1,1'-biphenyl]-3-carbonitrile | 393.2 | 394.1 |
| 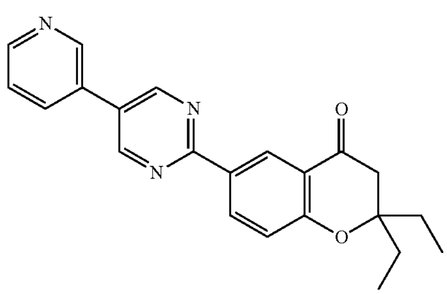 [SMILES: CCC1(CC)CC(=O)c2cc(-c3ncc(-c4cccnc4)cn3)ccc2O1] | 509 | 2,2-diethyl-6-(5-(pyridin-3-yl)pyrimidin-2-yl)chroman-4-one | 359.16 | 360.3 |
| 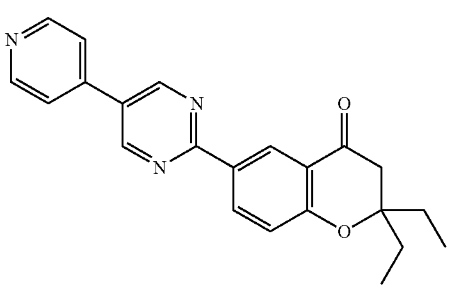 [SMILES: CCC1(CC)CC(=O)c2cc(-c3ncc(-c4ccncc4)cn3)ccc2O1] | 510 | 2,2-diethyl-6-(5-(pyridin-4-yl)pyrimidin-2-yl)chroman-4-one | 359.16 | 360.3 |

-continued

| Structure | Compound Number | Chemical Name | Exact Mass | Actual Peak |
|---|---|---|---|---|
| 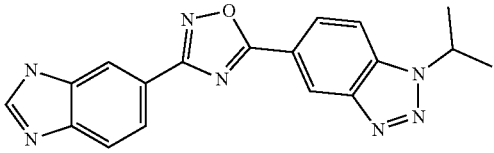 [SMILES: CC(C)n1nnc2cc(-c3nc(-c4ccc5nc[nH]c5c4)no3)ccc21] | 511 | 5-[3-(1H-1,3-benzodiazol-6-yl)-1,2,4-oxadiazol-5-yl]-1-(propan-2-yl)-1H-1,2,3-benzotriazole | 345.13 | 346.1 |
| 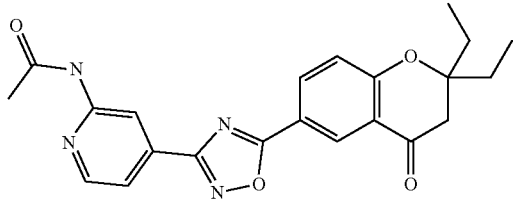 [SMILES: CCC1(CC)CC(=O)c2cc(-c3nc(-c4ccnc(NC(C)=O)c4)no3)ccc2O1] | 512 | N-(4-(5-(2,2-diethyl-4-oxochroman-6-yl)-1,2,4-oxadiazol-3-yl)pyridin-2-yl)acetamide | 406.16 | 407.3 |
| 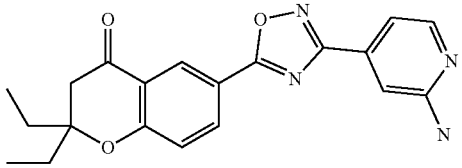 [SMILES: CCC1(CC)CC(=O)c2cc(-c3nc(-c4ccnc(N)c4)no3)ccc2O1] | 513 | 6-(3-(2-aminopyridin-4-yl)-1,2,4-oxadiazol-5-yl)-2,2-diethylchroman-4-one | 364.15 | 365.4 |
| 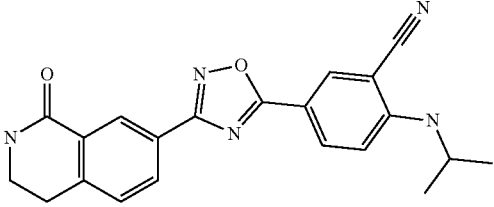 [SMILES: CC(C)Nc1ccc(-c2nc(-c3ccc4c(c3)C(=O)NCC4)no2)cc1C#N] | 514 | 2-(isopropylamino)-5-(3-(1-oxo-1,2,3,4-tetrahydroisoquinolin-7-yl)-1,2,4-oxadiazol-5-yl)benzonitrile | 373.15 | 374.3 |
| 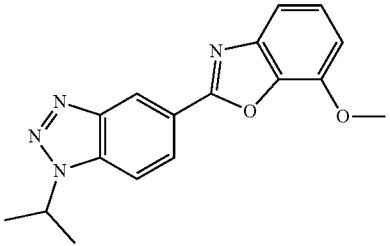 [SMILES: COc1cccc2nc(-c3ccc4c(c3)nnn4C(C)C)oc12] | 515 | 2-(1-isopropyl-1H-benzo[d][1,2,3]triazol-5-yl)-7-methoxybenzo[d]oxazole | 308.13 | 309.2 |
| 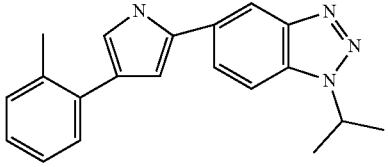 [SMILES: Cc1ccccc1-c1c[nH]c(-c2ccc3c(c2)nnn3C(C)C)c1] | 516 | 5-[4-(2-methylphenyl)-1H-pyrrol-2-yl]-1-(propan-2-yl)-1H-1,2,3-benzotriazole | 316.17 | 317 |
| 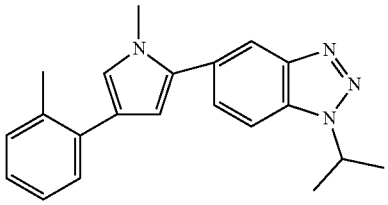 [SMILES: Cc1ccccc1-c1cc(-c2ccc3c(c2)nnn3C(C)C)n(C)c1] | 517 | 5-[1-methyl-4-(2-methylphenyl)-1H-pyrrol-2-yl]-1-(propan-2-yl)-1H-1,2,3-benzotriazole | 330.18 | 331 |

-continued

| Structure | Compound Number | Chemical Name | Exact Mass | Actual Peak |
|---|---|---|---|---|
| 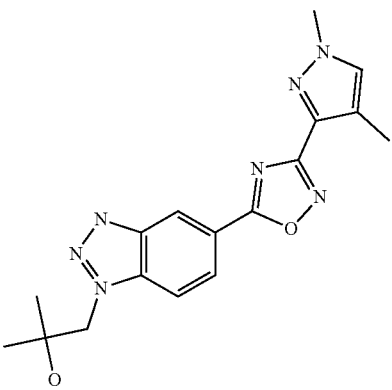 | 518 | 1-{5-[3-(1,4-dimethyl-1H-pyrazol-3-yl)-1,2,4-oxadiazol-5-yl]-1H-1,2,3-benzotriazol-1-yl}-2-methylpropan-2-ol | 353.16 | 354.1 |
| 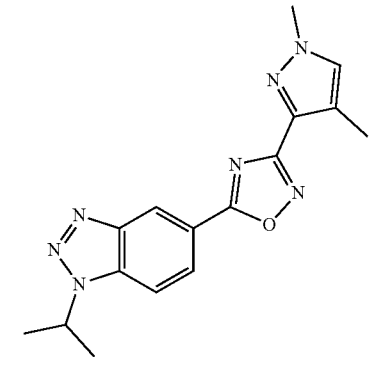 [SMILES: Cc1cn(C)nc1-c1noc(-c2ccc3c(c2)nnn3C(C)C)n1] | 519 | 5-[3-(1,4-dimethyl-1H-pyrazol-3-yl)-1,2,4-oxadiazol-5-yl]-1-(propan-2-yl)-1H-1,2,3-benzotriazole | 323.15 | 324.1 |
| 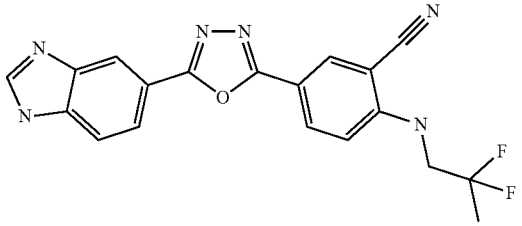 [SMILES: CC(F)(F)CNc1ccc(-c2nnc(-c3ccc4[nH]cnc4c3)o2)cc1C#N] | 520 | 5-[5-(1H-1,3-benzodiazol-5-yl)-1,3,4-oxadiazol-2-yl]-2-[(2,2-difluoropropyl)amino]benzonitrile | 380.12 | 381.2 |
| 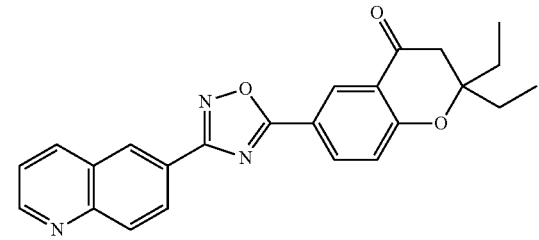 [SMILES: CCC1(CC)CC(=O)c2cc(-c3nc(-c4ccc5ncccc5c4)no3)ccc2O1] | 521 | 2,2-diethyl-6-(3-(quinolin-6-yl)-1,2,4-oxadiazol-5-yl)chroman-4-one | 399.16 | 400.4 |
| 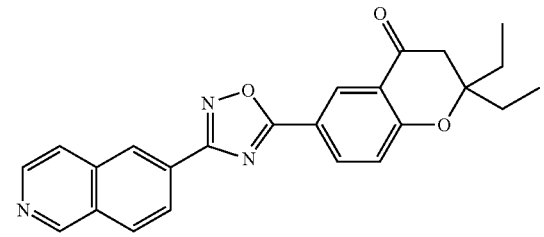 [SMILES: CCC1(CC)CC(=O)c2cc(-c3nc(-c4ccc5cnccc5c4)no3)ccc2O1] | 522 | 2,2-diethyl-6-(3-(isoquinolin-6-yl)-1,2,4-oxadiazol-5-yl)chroman-4-one | 399.16 | 400.3 |

-continued

| Structure | Compound Number | Chemical Name | Exact Mass | Actual Peak |
|---|---|---|---|---|
| 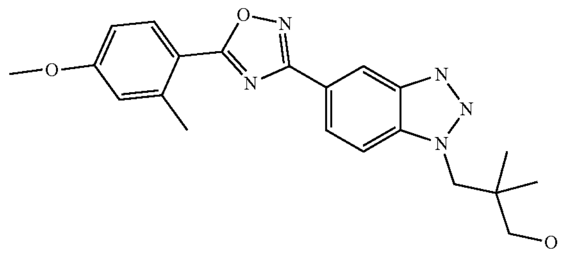 [SMILES: COc1ccc(-c2nc(-c3ccc4c(c3)NNN4CC(C)(C)CO)no2)c(C)c1] | 523 | 3-(5-(5-(4-methoxy-2-methylphenyl)-1,2,4-oxadiazol-3-yl)-1H-benzo[d][1,2,3]triazol-1-yl)-2,2-dimethylpropan-1-ol | 393.18 | 394.3 |
| 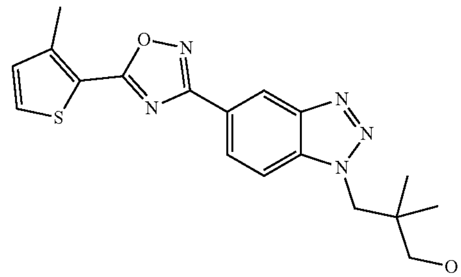 [SMILES: Cc1ccsc1-c1nc(-c2ccc3c(c2)nnn3CC(C)(C)CO)no1] | 524 | 2,2-dimethyl-3-(5-(5-(3-methylthiophen-2-yl)-1,2,4-oxadiazol-3-yl)-1H-benzo[d][1,2,3]triazol-1-yl)propan-1-ol | 369.13 | 370.2 |
| 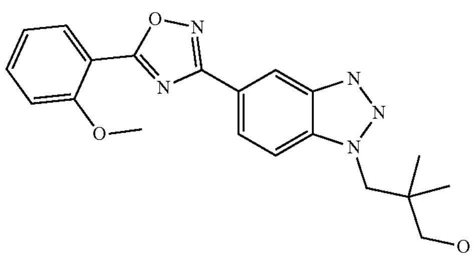 [SMILES: COc1ccccc1-c1nc(-c2ccc3c(c2)NNN3CC(C)(C)CO)no1] | 525 | 3-(5-(5-(2-methoxyphenyl)-1,2,4-oxadiazol-3-yl)-1H-benzo[d][1,2,3]triazol-1-yl)-2,2-dimethylpropan-1-ol | 379.16 | 380 |
| 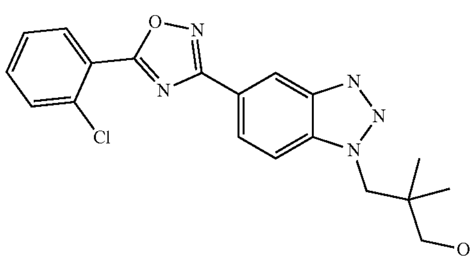 [SMILES: CC(C)(CO)CN1NNc2cc(-c3noc(-c4ccccc4Cl)n3)ccc21] | 526 | 3-(5-(5-(2-chlorophenyl)-1,2,4-oxadiazol-3-yl)-1H-benzo[d][1,2,3]triazol-1-yl)-2,2-dimethylpropan-1-ol | 383.11 | 384 |
| 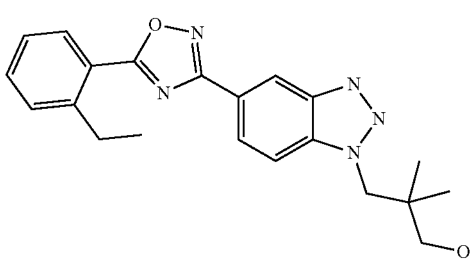 [SMILES: CCc1ccccc1-c1nc(-c2ccc3c(c2)NNN3CC(C)(C)CO)no1] | 527 | 3-(5-(5-(2-ethylphenyl)-1,2,4-oxadiazol-3-yl)-1H-benzo[d][1,2,3]triazol-1-yl)-2,2-dimethylpropan-1-ol | 377.19 | 378.1 |
| 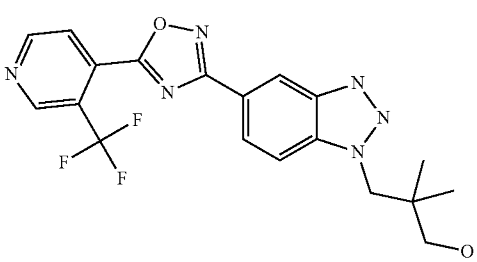 [SMILES: CC(C)(CO)CN1NNc2cc(-c3noc(-c4ccncc4C(F)(F)F)n3)ccc21] | 528 | 2,2-dimethyl-3-(5-(5-(3-(trifluoromethyl)pyridin-4-yl)-1,2,4-oxadiazol-3-yl)-1H-benzo[d][1,2,3]triazol-1-yl)propan-1-ol | 418.14 | 419 |

-continued

| Structure | Compound Number | Chemical Name | Exact Mass | Actual Peak |
|---|---|---|---|---|
| 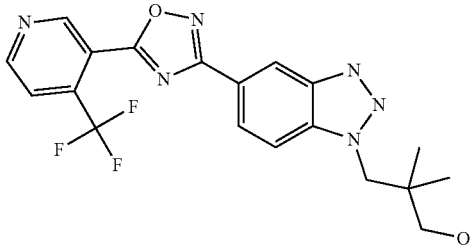 [SMILES: CC(C)(CO)CN1NNc2cc(-c3noc(-c4cnccc4C(F)(F)F)n3)ccc21] | 529 | 2,2-dimethyl-3-(5-(5-(4-(trifluoromethyl)pyridin-3-yl)-1,2,4-oxadiazol-3-yl)-1H-benzo[d][1,2,3]triazol-1-yl)propan-1-ol | 418.14 | 419 |
| 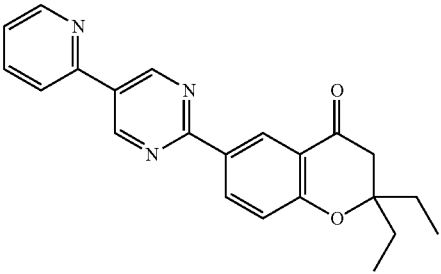 [SMILES: CCC1(CC)CC(=O)c2cc(-c3ncc(-c4ccccn4)cn3)ccc2O1] | 530 | 2,2-diethyl-6-(5-(pyridin-2-yl)pyrimidin-2-yl)chroman-4-one | 359.16 | 360.3 |
| 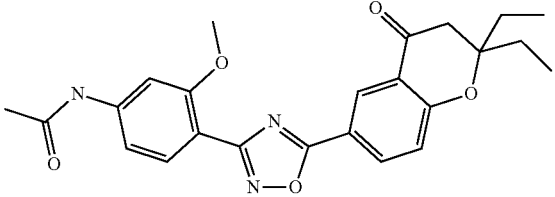 [SMILES: CCC1(CC)CC(=O)c2cc(-c3nc(-c4ccc(NC(C)=O)cc4OC)no3)ccc2O1] | 531 | N-{4-[5-(2,2-diethyl-4-oxo-3,4-dihydro-2H-1-benzopyran-6-yl)-1,2,4-oxadiazol-3-yl]-3-methoxyphenyl}acetamide | 435.18 | 436.2 |
| 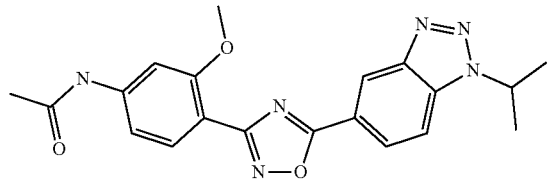 [SMILES: COc1cc(NC(C)=O)ccc1-c1noc(-c2ccc3c(c2)nnn3C(C)C)n1] | 532 | N-(3-methoxy-4-{5-[1-(propan-2-yl)-1H-1,2,3-benzotriazol-5-yl]-1,2,4-oxadiazol-3-yl}phenyl)acetamide | 392.16 | 393.1 |
| 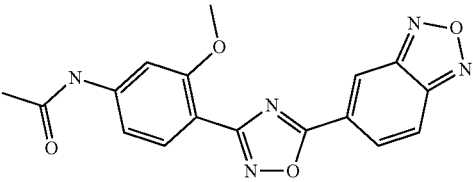 [SMILES: COc1cc(NC(C)=O)ccc1-c1noc(-c2ccc3nonc3c2)n1] | 533 | N-{4-[5-(2,1,3-benzoxadiazol-5-yl)-1,2,4-oxadiazol-3-yl]-3-methoxyphenyl}acetamide | 351.1 | 352 |
| 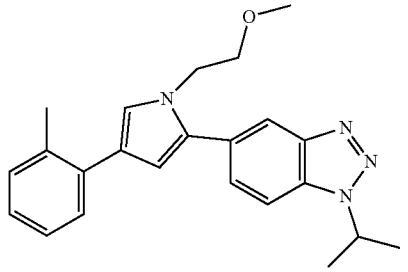 [SMILES: COCCn1cc(-c2ccccc2C)cc1-c1ccc2c(c1)nnn2C(C)C] | 534 | 5-[1-(2-methoxyethyl)-4-(2-methylphenyl)-1H-pyrrol-2-yl]-1-(propan-2-yl)-1H-1,2,3-benzotriazole | 374.21 | 375 |

-continued

| Structure | Compound Number | Chemical Name | Exact Mass | Actual Peak |
|---|---|---|---|---|
| 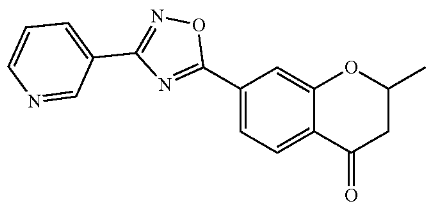 [SMILES: CC1CC(=O)c2ccc(-c3nc(-c4cccnc4)no3)cc2O1] | 535 | 2-methyl-7-[3-(pyridin-3-yl)-1,2,4-oxadiazol-5-yl]-3,4-dihydro-2H-1-benzopyran-4-one | 307.1 | 308 |
| 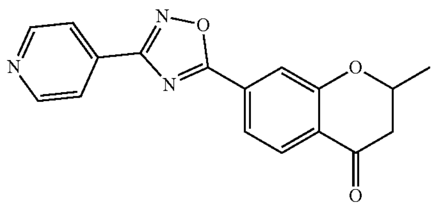 [SMILES: CC1CC(=O)c2ccc(-c3nc(-c4ccncc4)no3)cc2O1] | 536 | 2-methyl-7-[3-(pyridin-4-yl)-1,2,4-oxadiazol-5-yl]-3,4-dihydro-2H-1-benzopyran-4-one | 307.1 | 308.1 |
| 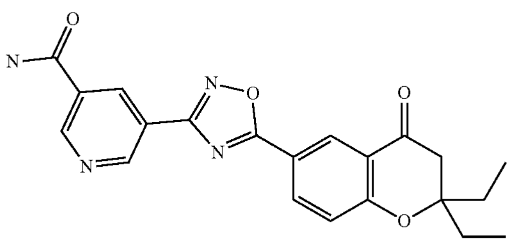 [SMILES: CCC1(CC)CC(=O)c2cc(-c3nc(-c4cncc(C(N)=O)c4)no3)ccc2O1] | 537 | 5-(5-(2,2-diethyl-4-oxochroman-6-yl)-1,2,4-oxadiazol-3-yl)nicotinamide | 392.15 | 393.2 |
| 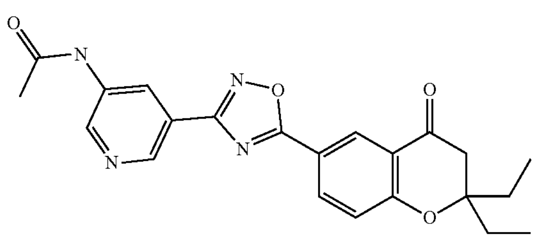 [SMILES: CCC1(CC)CC(=O)c2cc(-c3nc(-c4cncc(NC(C)=O)c4)no3)ccc2O1] | 538 | N-(5-(5-(2,2-diethyl-4-oxochroman-6-yl)-1,2,4-oxadiazol-3-yl)pyridin-3-yl)acetamide | 406.16 | 407.3 |
| 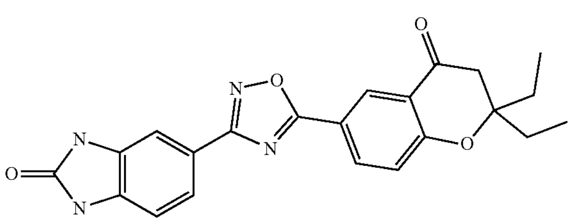 [SMILES: CCC1(CC)CC(=O)c2cc(-c3nc(-c4ccc5[nH]c(=O)[nH]c5c4)no3)ccc2O1] | 539 | 5-(5-(2,2-diethyl-4-oxochroman-6-yl)-1,2,4-oxadiazol-3-yl)-1H-benzo[d]imidazol-2(3H)-one | 404.15 | 405 |
| 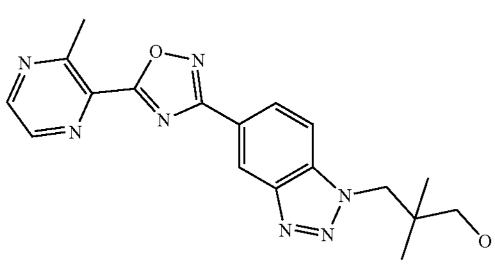 [SMILES: Cc1nccnc1-c1nc(-c2ccc3c(c2)nnn3CC(C)(C)CO)no1] | 540 | 2,2-dimethyl-3-(5-(5-(3-methylpyrazin-2-yl)-1,2,4-oxadiazol-3-yl)-1H-benzo[d][1,2,3]triazol-1-yl)propan-1-ol | 365.16 | 366.3 |

-continued

| Structure | Compound Number | Chemical Name | Exact Mass | Actual Peak |
|---|---|---|---|---|
| 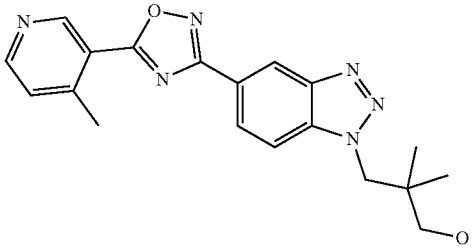 [SMILES: Cc1ccncc1-c1nc(-c2ccc3c(c2)nnn3CC(C)(C)CO)no1] | 541 | 2,2-dimethyl-3-(5-(5-(4-methylpyridin-3-yl)-1,2,4-oxadiazol-3-yl)-1H-benzo[d][1,2,3]triazol-1-yl)propan-1-ol | 364.16 | 365 |
| 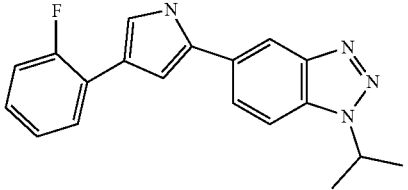 [SMILES: CC(C)n1nnc2cc(-c3cc(-c4ccccc4F)c[nH]3)ccc21] | 542 | 5-[4-(2-fluorophenyl)-1H-pyrrol-2-yl]-1-(propan-2-yl)-1H-1,2,3-benzotriazole | 320.14 | 321.2 |
| 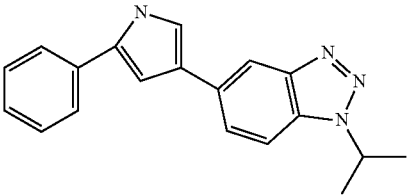 [SMILES: CC(C)n1nnc2cc(-c3c[nH]c(-c4ccccc4)c3)ccc21] | 543 | 5-(5-phenyl-1H-pyrrol-3-yl)-1-(propan-2-yl)-1H-1,2,3-benzotriazole | 302.15 | 303 |
| 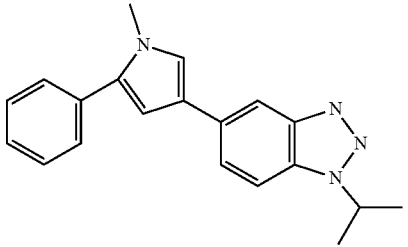 [SMILES: CC(C)N1NNc2cc(-c3cc(-c4ccccc4)n(C)c3)ccc21] | 544 | 5-(1-methyl-5-phenyl-1H-pyrrol-3-yl)-1-(propan-2-yl)-1H-1,2,3-benzotriazole | 316.17 | 317 |
| 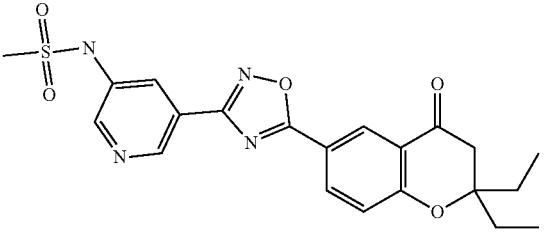 [SMILES: CCC1(CC)CC(=O)c2cc(-c3nc(-c4cncc(NS(C)(=O)=O)c4)no3)ccc2O1] | 545 | N-(5-(5-(2,2-diethyl-4-oxochroman-6-yl)-1,2,4-oxadiazol-3-yl)pyridin-3-yl)methanesulfonamide | 442.13 | 443.3 |
| 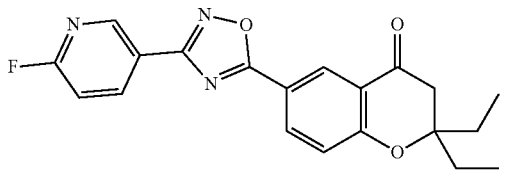 [SMILES: CCC1(CC)CC(=O)c2cc(-c3nc(-c4ccc(F)nc4)no3)ccc2O1] | 546 | 2,2-diethyl-6-(3-(6-fluoropyridin-3-yl)-1,2,4-oxadiazol-5-yl)chroman-4-one | 367.13 | 368.3 |
| 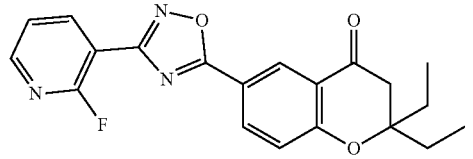 [SMILES: CCC1(CC)CC(=O)c2cc(-c3nc(-c4cccnc4F)no3)ccc2O1] | 547 | 2,2-diethyl-6-(3-(2-fluoropyridin-3-yl)-1,2,4-oxadiazol-5-yl)chroman-4-one | 367.13 | 368.2 |

-continued

| Structure | Compound Number | Chemical Name | Exact Mass | Actual Peak |
|---|---|---|---|---|
| 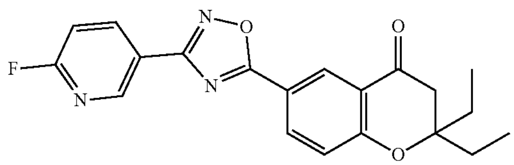 [SMILES: CCC1(CC)CC(=O)c2cc(-c3nc(-c4ccc(F)nc4)no3)ccc2O1] | 548 | 2,2-diethyl-6-(3-(6-(trifluoromethyl)pyridin-3-yl)-1,2,4-oxadiazol-5-yl)chroman-4-one | 417.13 | 418.2 |
| 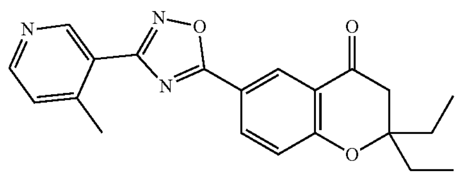 [SMILES: CCC1(CC)CC(=O)c2cc(-c3nc(-c4cnccc4C)no3)ccc2O1] | 549 | 2,2-diethyl-6-(3-(4-methylpyridin-3-yl)-1,2,4-oxadiazol-5-yl)chroman-4-one | 363.16 | 364.3 |
| 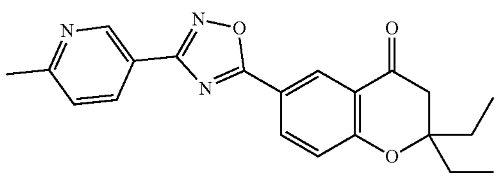 [SMILES: CCC1(CC)CC(=O)c2cc(-c3nc(-c4ccc(C)nc4)no3)ccc2O1] | 550 | 2,2-diethyl-6-(3-(6-methylpyridin-3-yl)-1,2,4-oxadiazol-5-yl)chroman-4-one | 363.16 | 364.3 |
| 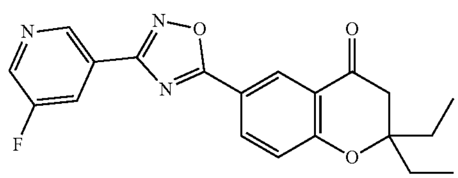 [SMILES: CCC1(CC)CC(=O)c2cc(-c3nc(-c4cncc(F)c4)no3)ccc2O1] | 551 | 2,2-diethyl-6-(3-(5-fluoropyridin-3-yl)-1,2,4-oxadiazol-5-yl)chroman-4-one | 367.13 | 368.2 |
| 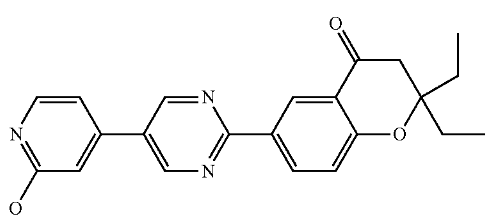 [SMILES: CCC1(CC)CC(=O)c2cc(-c3ncc(-c4ccnc(O)c4)cn3)ccc2O1] | 552 | 2,2-diethyl-6-(5-(2-hydroxypyridin-4-yl)pyrimidin-2-yl)chroman-4-one | 375.16 | 376.3 |
| 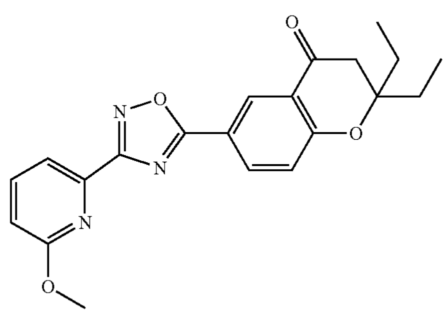 [SMILES: CCC1(CC)CC(=O)c2cc(-c3nc(-c4cccc(OC)n4)no3)ccc2O1] | 553 | 2,2-diethyl-6-[3-(6-methoxypyridin-2-yl)-1,2,4-oxadiazol-5-yl]-3,4-dihydro-2H-1-benzopyran-4-one | 379.15 | 380.1 |
| 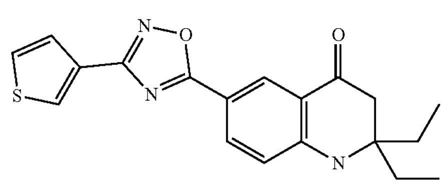 [SMILES: CCC1(CC)CC(=O)c2cc(-c3nc(-c4ccsc4)no3)ccc2N1] | 554 | 2,2-diethyl-6-(3-(thiophen-3-yl)-1,2,4-oxadiazol-5-yl)-2,3-dihydroquinolin-4(1H)-one | 353.12 | 354.2 |

-continued

| Structure | Compound Number | Chemical Name | Exact Mass | Actual Peak |
|---|---|---|---|---|
| 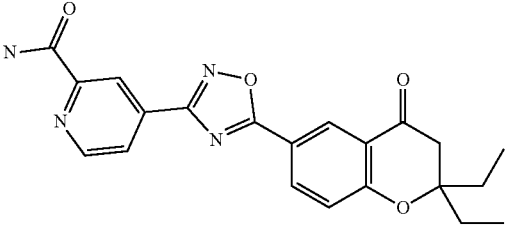 [SMILES: CCC1(CC)CC(=O)c2cc(-c3nc(-c4ccnc(C(N)=O)c4)no3)ccc2O1] | 555 | 4-(5-(2,2-diethyl-4-oxochroman-6-yl)-1,2,4-oxadiazol-3-yl)picolinamide | 392.15 | 393 |
| 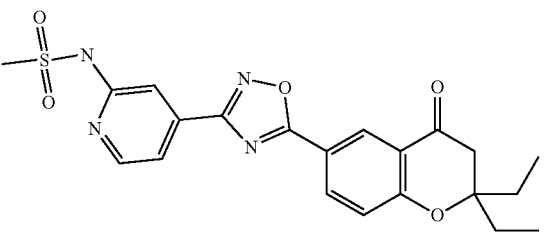 [SMILES: CCC1(CC)CC(=O)c2cc(-c3nc(-c4ccnc(NS(C)(=O)=O)c4)no3)ccc2O1] | 556 | N-(4-(5-(2,2-diethyl-4-oxochroman-6-yl)-1,2,4-oxadiazol-3-yl)pyridin-2-yl)methanesulfonamide | 442.13 | 443.3 |
| 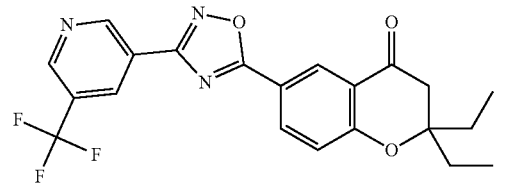 [SMILES: CCC1(CC)CC(=O)c2cc(-c3nc(-c4cncc(C(F)(F)F)c4)no3)ccc2O1] | 557 | 2,2-diethyl-6-(3-(5-(trifluoromethyl)pyridin-3-yl)-1,2,4-oxadiazol-5-yl)chroman-4-one | 417.13 | 418 |
| 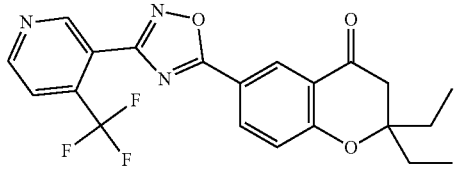 [SMILES: CCC1(CC)CC(=O)c2cc(-c3nc(-c4cnccc4C(F)(F)F)no3)ccc2O1] | 558 | 2,2-diethyl-6-(3-(4-(trifluoromethyl)pyridin-3-yl)-1,2,4-oxadiazol-5-yl)chroman-4-one | 417.13 | 418 |
| 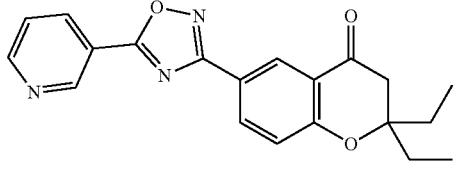 [SMILES: CCC1(CC)CC(=O)c2cc(-c3noc(-c4cccnc4)n3)ccc2O1] | 559 | 2,2-diethyl-6-(5-(pyridin-3-yl)-1,2,4-oxadiazol-3-yl)chroman-4-one | 349.14 | 350 |
| 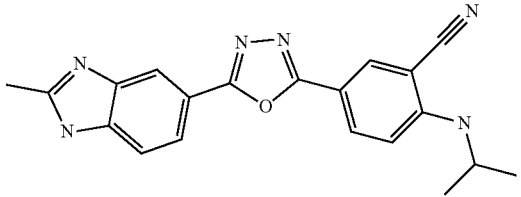 [SMILES: Cc1nc2cc(-c3nnc(-c4ccc(NC(C)C)c(C#N)c4)o3)ccc2[nH]1] | 560 | 5-[5-(2-methyl-1H-1,3-benzodiazol-5-yl)-1,3,4-oxadiazol-2-yl]-2-[(propan-2-yl)amino]benzonitrile | 358.15 | 359.2 |
| 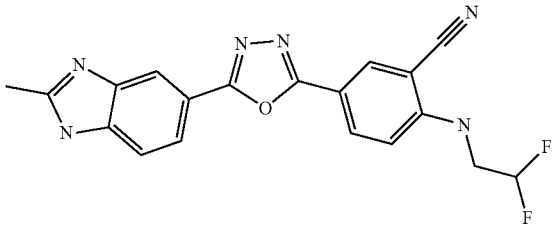 [SMILES: Cc1nc2cc(-c3nnc(-c4ccc(NCC(F)F)c(C#N)c4)o3)ccc2[nH]1] | 561 | 2-[(2,2-difluoroethyl)amino]-5-[5-(2-methyl-1H-1,3-benzodiazol-5-yl)-1,3,4-oxadiazol-2-yl]benzonitrile | 380.12 | 381.2 |

-continued

| Structure | Compound Number | Chemical Name | Exact Mass | Actual Peak |
|---|---|---|---|---|
| 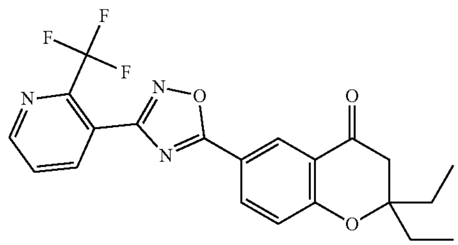 [SMILES: CCC1(CC)CC(=O)c2cc(-c3nc(-c4cccnc4C(F)(F)F)no3)ccc2O1] | 562 | 2,2-diethyl-6-(3-(2-(trifluoromethyl)pyridin-3-yl)-1,2,4-oxadiazol-5-yl)chroman-4-one | 417.13 | 418 |
| 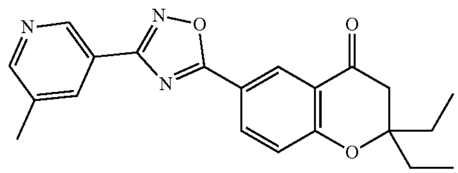 [SMILES: CCC1(CC)CC(=O)c2cc(-c3nc(-c4cncc(C)c4)no3)ccc2O1] | 563 | 2,2-diethyl-6-(3-(5-methylpyridin-3-yl)-1,2,4-oxadiazol-5-yl)chroman-4-one | 363.16 | 364 |
| 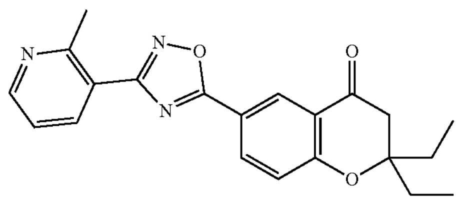 [SMILES: CCC1(CC)CC(=O)c2cc(-c3nc(-c4cccnc4C)no3)ccc2O1] | 564 | 2,2-diethyl-6-(3-(2-methylpyridin-3-yl)-1,2,4-oxadiazol-5-yl)chroman-4-one | 363.16 | 364 |
| 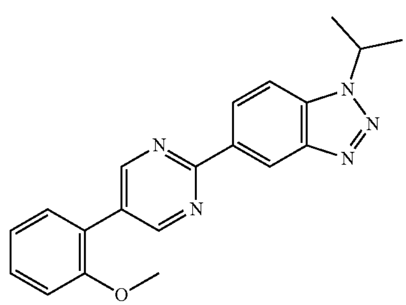 [SMILES: COc1ccccc1-c1cnc(-c2ccc3c(c2)nnn3C(C)C)nc1] | 565 | 1-isopropyl-5-(5-(2-methoxyphenyl)pyrimidin-2-yl)-1H-benzo[d][1,2,3]triazole | 345.16 | 346.1 |
| 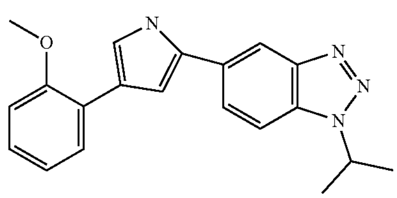 [SMILES: COc1ccccc1-c1c[nH]c(-c2ccc3c(c2)nnn3C(C)C)c1] | 566 | 5-[4-(2-methoxyphenyl)-1H-pyrrol-2-yl]-1-(propan-2-yl)-1H-1,2,3-benzotriazole | 332.16 | 333.2 |
| 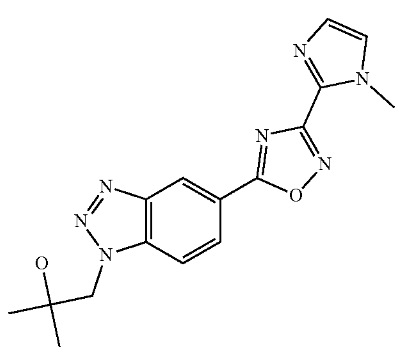 [SMILES: Cn1ccnc1-c1noc(-c2ccc3c(c2)nnn3CC(C)(C)O)n1] | 567 | 2-methyl-1-{5-[3-(1-methyl-1H-imidazol-2-yl)-1,2,4-oxadiazol-5-yl]-1H-1,2,3-benzotriazol-1-yl}propan-2-ol | 339.14 | 340.1 |

-continued

| Structure | Compound Number | Chemical Name | Exact Mass | Actual Peak |
|---|---|---|---|---|
| 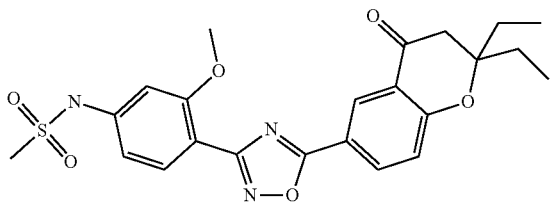 [SMILES: CCC1(CC)CC(=O)c2cc(-c3nc(-c4ccc(NS(C)(=O)=O)cc4OC)no3)ccc2O1] | 568 | N-{4-[5-(2,2-diethyl-4-oxo-3,4-dihydro-2H-1-benzopyran-6-yl)-1,2,4-oxadiazol-3-yl]-3-methoxyphenyl}methanesulfonamide | 471.15 | 472.1 |
| 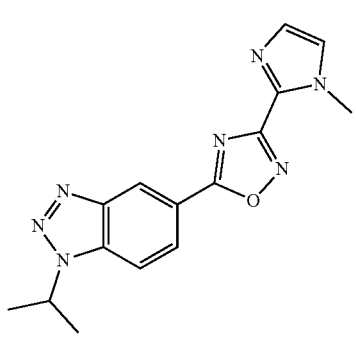 [SMILES: CC(C)n1nnc2cc(-c3nc(-c4nccn4C)no3)ccc21] | 569 | 5-[3-(1-methyl-1H-imidazol-2-yl)-1,2,4-oxadiazol-5-yl]-1-(propan-2-yl)-1H-1,2,3-benzotriazole | 309.13 | 310.1 |
| 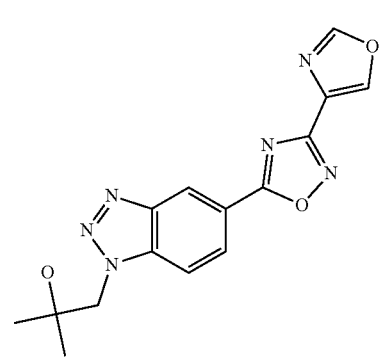 [SMILES: CC(C)(O)Cn1nnc2cc(-c3nc(-c4cocn4)no3)ccc21] | 570 | 2-methyl-1-{5-[3-(1,3-oxazol-4-yl)-1,2,4-oxadiazol-5-yl]-1H-1,2,3-benzotriazol-1-yl}propan-2-ol | 326.11 | 327 |
| 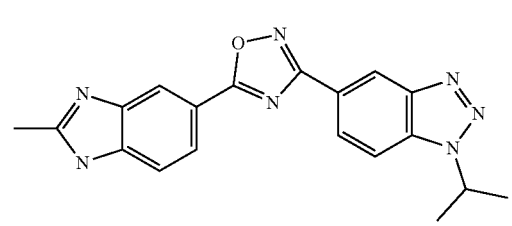 [SMILES: Cc1nc2cc(-c3nc(-c4ccc5c(c4)nnn5C(C)C)no3)ccc2[nH]1] | 571 | 5-[5-(2-methyl-1H-1,3-benzodiazol-5-yl)-1,2,4-oxadiazol-3-yl]-1-(propan-2-yl)-1H-1,2,3-benzotriazole | 359.15 | 360 |
| 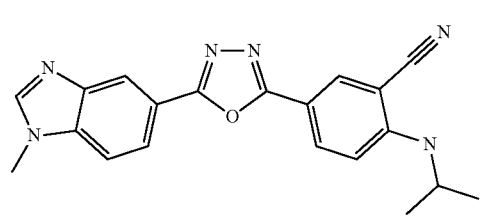 [SMILES: CC(C)Nc1ccc(-c2nnc(-c3ccc4c(c3)ncn4C)o2)cc1C#N] | 572 | 5-[5-(1-methyl-1H-1,3-benzodiazol-5-yl)-1,3,4-oxadiazol-2-yl]-2-[(propan-2-yl)amino]benzonitrile | 358.15 | 359.1 |
| 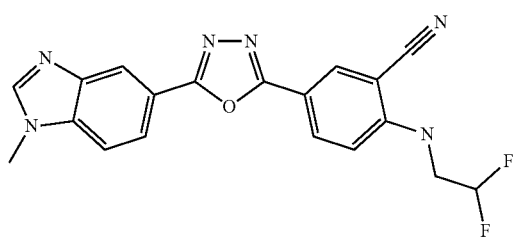 [SMILES: Cn1cnc2cc(-c3nnc(-c4ccc(NCC(F)F)c(C#N)c4)o3)ccc21] | 573 | 2-[(2,2-difluoroethyl)amino]-5-[5-(1-methyl-1H-1,3-benzodiazol-5-yl)-1,3,4-oxadiazol-2-yl]benzonitrile | 380.12 | 381.1 |

-continued

| Structure | Compound Number | Chemical Name | Exact Mass | Actual Peak |
|---|---|---|---|---|
| 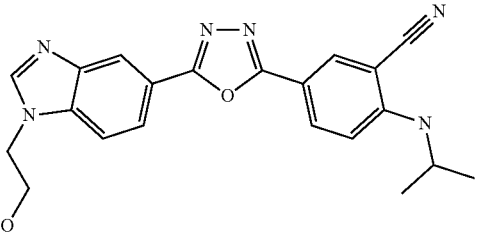 [SMILES: CC(C)Nc1ccc(-c2nnc(-c3ccc4c(c3)ncn4CCO)o2)cc1C#N] | 574 | 5-{5-[1-(2-hydroxyethyl)-1H-1,3-benzodiazol-5-yl]-1,3,4-oxadiazol-2-yl}-2-[(propan-2-yl)amino]benzonitrile | 388.16 | 389.1 |
| 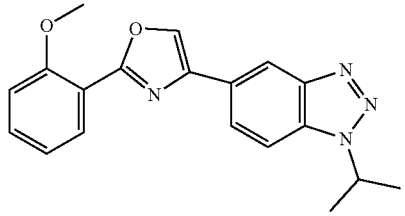 [SMILES: COc1ccccc1-c1nc(-c2ccc3c(c2)nnn3C(C)C)co1] | 575 | 5-[2-(2-methoxyphenyl)-1,3-oxazol-4-yl]-1-(propan-2-yl)-1H-1,2,3-benzotriazole | 334.14 | 335 |
| 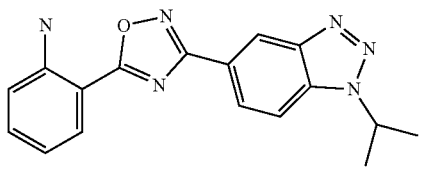 | 576 | 2-{3-[1-(propan-2-yl)-1H-1,2,3-benzotriazol-5-yl]-1,2,4-oxadiazol-5-yl}aniline | 320.14 | 321.2 |
| 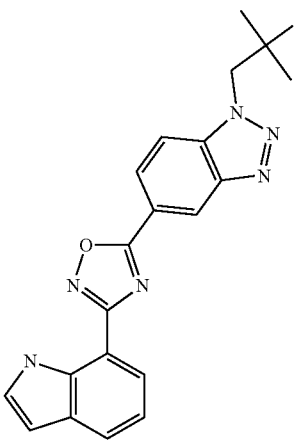 | 577 | 1-{5-[3-(1H-indol-7-yl)-1,2,4-oxadiazol-5-yl]-1H-1,2,3-benzotriazol-1-yl}-2-methylpropan-2-ol | 374.15 | 375.2 |
| 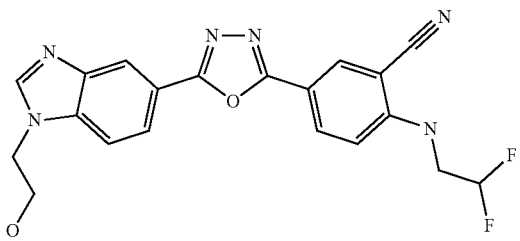 [SMILES: N#Cc1cc(-c2nnc(-c3ccc4c(c3)ncn4CCO)o2)ccc1NCC(F)F] | 578 | 2-[(2,2-difluoroethyl)amino]-5-{5-[1-(2-hydroxyethyl)-1H-1,3-benzodiazol-5-yl]-1,3,4-oxadiazol-2-yl}benzonitrile | 410.13 | 411.1 |
| 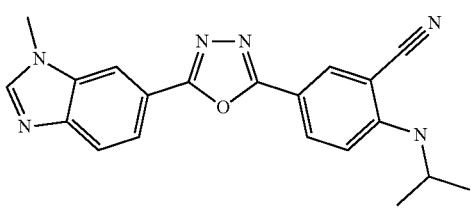 [SMILES: CC(C)Nc1ccc(-c2nnc(-c3ccc4ncn(C)c4c3)o2)cc1C#N] | 579 | 5-[5-(1-methyl-1H-1,3-benzodiazol-6-yl)-1,3,4-oxadiazol-2-yl]-2-[(propan-2-yl)amino]benzonitrile | 358.15 | 359.2 |

-continued

| Structure | Compound Number | Chemical Name | Exact Mass | Actual Peak |
|---|---|---|---|---|
| 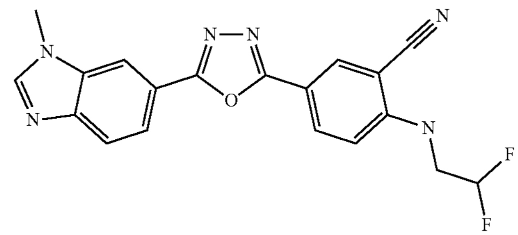 [SMILES: Cn1cnc2ccc(-c3nnc(-c4ccc(NCC(F)F)c(C#N)c4)o3)cc21] | 580 | 2-[(2,2-difluoroethyl)amino]-5-[5-(1-methyl-1H-1,3-benzodiazol-6-yl)-1,3,4-oxadiazol-2-yl]benzonitrile | 380.12 | 381.1 |
| 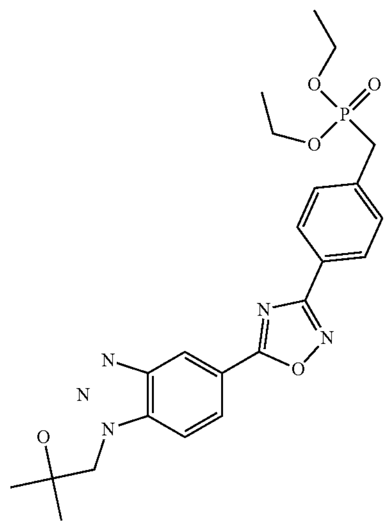 | 581 | [(4-{5-[1-(2-hydroxy-2-methylpropyl)-1H-1,2,3-benzotriazol-5-yl]-1,2,4-oxadiazol-3-yl}phenyl)methyl] phosphonate | 485.18 | 486.2 |
| 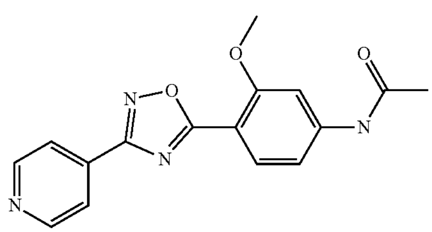 [SMILES: COc1cc(NC(C)=O)ccc1-c1nc(-c2ccncc2)no1] | 582 | N-{3-methoxy-4-[3-(pyridin-4-yl)-1,2,4-oxadiazol-5-yl]phenyl}acetamide | 310.11 | 311.2 |
| 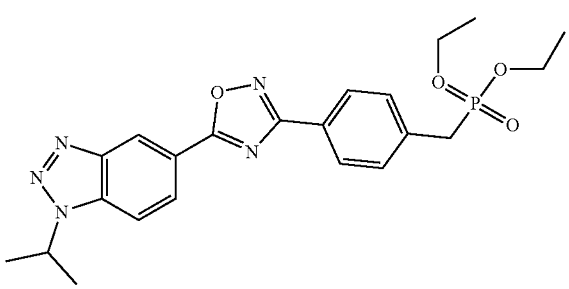 | 583 | diethyl [(4-{5-[1-(propan-2-yl)-1H-1,2,3-benzotriazol-5-yl]-1,2,4-oxadiazol-3-yl}phenyl)methyl] phosphonate | 455.17 | 456.1 |
| 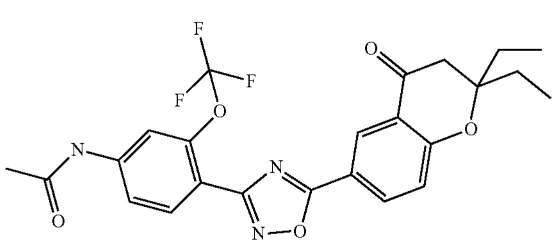 [SMILES: CCC1(CC)CC(=O)c2cc(-c3nc(-c4ccc(NC(C)=O)cc4OC(F)(F)F)no3)ccc2O1] | 584 | N-{4-[5-(2,2-diethyl-4-oxo-3,4-dihydro-2H-1-benzopyran-6-yl)-1,2,4-oxadiazol-3-yl]-3-(trifluoromethoxy)phenyl}acetamide | 489.15 | 490.1 |

-continued

| Structure | Compound Number | Chemical Name | Exact Mass | Actual Peak |
|---|---|---|---|---|
| 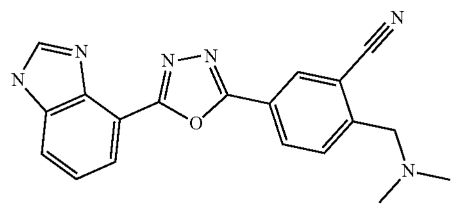 [SMILES: CN(C)Cc1ccc(-c2nnc(-c3cccc4[nH]cnc34)o2)cc1C#N] | 585 | 5-[5-(1H-1,3-benzodiazol-4-yl)-1,3,4-oxadiazol-2-yl]-2-[(propan-2-yl)amino]benzonitrile | 344.14 | 345.1 |
| 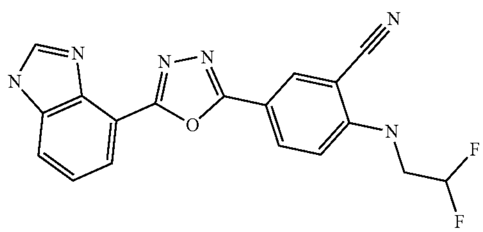 [SMILES: N#Cc1cc(-c2nnc(-c3cccc4[nH]cnc34)o2)ccc1NCC(F)F] | 586 | 5-[5-(1H-1,3-benzodiazol-4-yl)-1,3,4-oxadiazol-2-yl]-2-[(2,2-difluoroethyl)amino]benzonitrile | 366.1 | 367.1 |
| 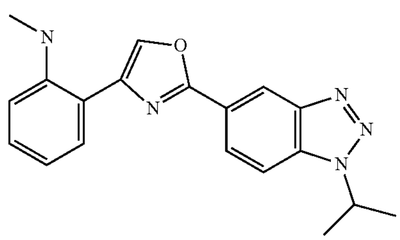 [SMILES: CNc1ccccc1-c1coc(-c2ccc3c(c2)nnn3C(C)C)n1] | 587 | N-methyl-2-{2-[1-(propan-2-yl)-1H-1,2,3-benzotriazol-5-yl]-1,3-oxazol-4-yl}aniline | 333.16 | 334 |
| 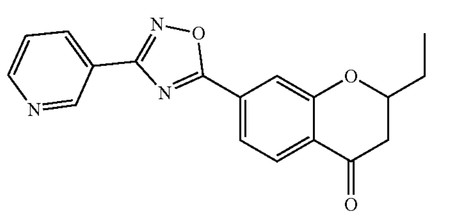 [SMILES: CCC1CC(=O)c2ccc(-c3nc(-c4cccnc4)no3)cc2O1] | 588 | 2-ethyl-7-[3-(pyridin-3-yl)-1,2,4-oxadiazol-5-yl]-3,4-dihydro-2H-1-benzopyran-4-one | 321.11 | 322.1 |
| 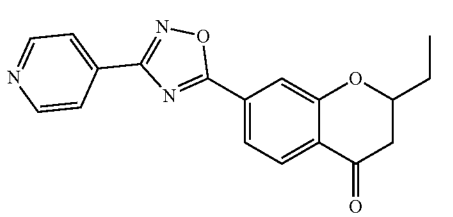 [SMILES: CCC1CC(=O)c2ccc(-c3nc(-c4ccncc4)no3)cc2O1] | 589 | 2-ethyl-7-[3-(pyridin-4-yl)-1,2,4-oxadiazol-5-yl]-3,4-dihydro-2H-1-benzopyran-4-one | 321.11 | 322.1 |
| 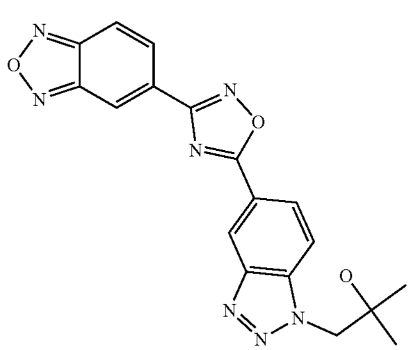 [SMILES: CC(C)(O)Cn1nnc2cc(-c3nc(-c4ccc5nonc5c4)no3)ccc21] | 590 | 1-{5-[3-(2,1,3-benzoxadiazol-5-yl)-1,2,4-oxadiazol-5-yl]-1H-1,2,3-benzotriazol-1-yl}-2-methylpropan-2-ol | 377.12 | 378.1 |

-continued

| Structure | Compound Number | Chemical Name | Exact Mass | Actual Peak |
|---|---|---|---|---|
| 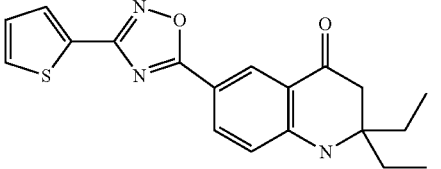 [SMILES: CCC1(CC)CC(=O)c2cc(-c3nc(-c4cccs4)no3)ccc2N1] | 591 | 2,2-diethyl-6-(3-(thiophen-2-yl)-1,2,4-oxadiazol-5-yl)-2,3-dihydroquinolin-4(1H)-one | 353.12 | 353.9 |
| 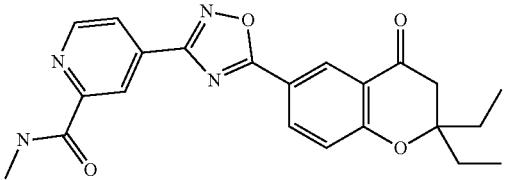 [SMILES: CCC1(CC)CC(=O)c2cc(-c3nc(-c4ccnc(C(=O)NC)c4)no3)ccc2O1] | 592 | 4-(5-(2,2-diethyl-4-oxochroman-6-yl)-1,2,4-oxadiazol-3-yl)-N-methylpicolinamide | 406.16 | 407 |
| 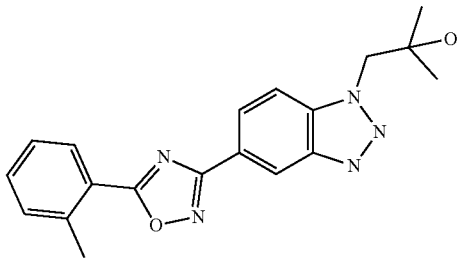 [SMILES: Cc1ccccc1-c1nc(-c2ccc3c(c2)NNN3CC(C)(C)O)no1] | 593 | 2-methyl-1-(5-(5-(o-tolyl)-1,2,4-oxadiazol-3-yl)-1H-benzo[d][1,2,3]triazol-1-yl)propan-2-ol | 349.15 | 350 |
| 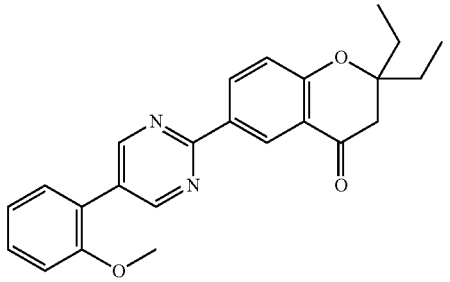 [SMILES: CCC1(CC)CC(=O)c2cc(-c3ncc(-c4ccccc4OC)cn3)ccc2O1] | 594 | 2,2-diethyl-6-(5-(2-methoxyphenyl)pyrimidin-2-yl)chroman-4-one | 388.18 | 389 |
| 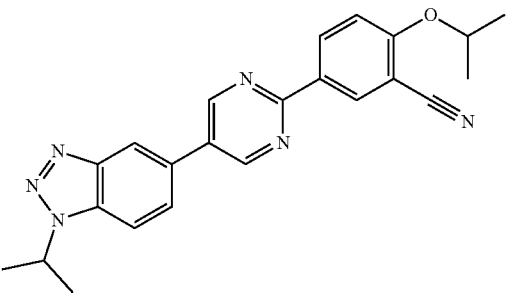 | 595 | 2-isopropoxy-5-(5-(1-isopropyl-1H-benzo[d][1,2,3]triazol-5-yl)pyrimidin-2-yl)benzonitrile | 398.19 | 399.2 |
| 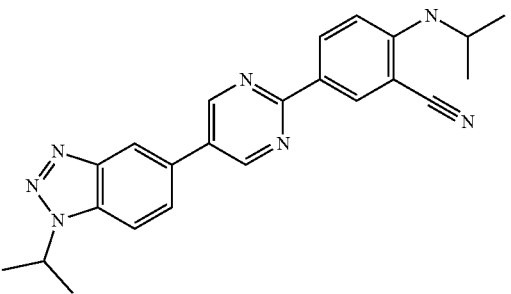 [SMILES: CC(C)Nc1ccc(-c2ncc(-c3ccc4c(c3)nnn4C(C)C)cn2)cc1C#N] | 596 | 5-(5-(1-isopropyl-1H-benzo[d][1,2,3]triazol-5-yl)pyrimidin-2-yl)-2-(isopropylamino)benzonitrile | 397.2 | 398.1 |

-continued

| Structure | Compound Number | Chemical Name | Exact Mass | Actual Peak |
|---|---|---|---|---|
| 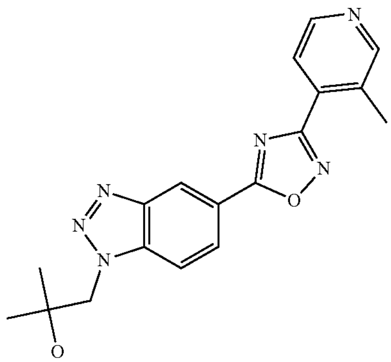 [SMILES: Cc1cnccc1-c1noc(-c2ccc3c(c2)nnn3CC(C)(C)O)n1] | 597 | 2-methyl-1-{5-[3-(3-methylpyridin-4-yl)-1,2,4-oxadiazol-5-yl]-1H-1,2,3-benzotriazol-1-yl}propan-2-ol | 350.15 | 351.1 |
| 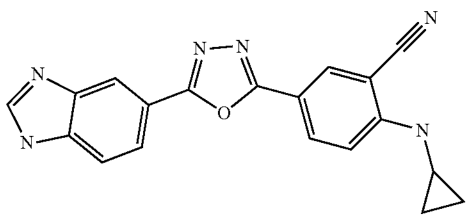 [SMILES: N#Cc1cc(-c2nnc(-c3ccc4[nH]cnc4c3)o2)ccc1NC1CC1] | 598 | 5-[5-(1H-1,3-benzodiazol-5-yl)-1,3,4-oxadiazol-2-yl]-2-(cyclopropylamino)benzonitrile | 342.12 | 343.1 |
| 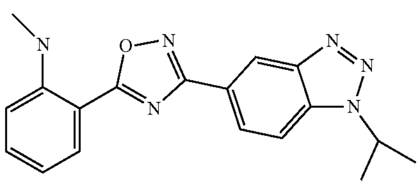 [SMILES: CNc1ccccc1-c1nc(-c2ccc3c(c2)nnn3C(C)C)no1] | 599 | N-methyl-2-{3-[1-(propan-2-yl)-1H-1,2,3-benzotriazol-5-yl]-1,2,4-oxadiazol-5-yl}aniline | 334.15 | 335.2 |
| 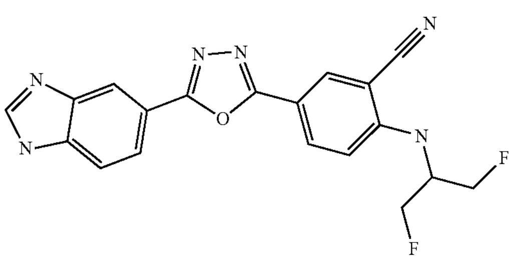 [SMILES: N#Cc1cc(-c2nnc(-c3ccc4[nH]cnc4c3)o2)ccc1NC(CF)CF] | 600 | 5-[5-(1H-1,3-benzodiazol-5-yl)-1,3,4-oxadiazol-2-yl]-2-[(1,3-difluoropropan-2-yl)amino]benzonitrile | 380.12 | 381.1 |
| 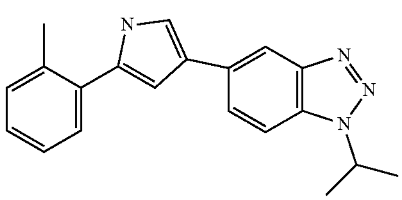 [SMILES: Cc1ccccc1-c1cc(-c2ccc3c(c2)nnn3C(C)C)c[nH]1] | 601 | 5-[5-(2-methylphenyl)-1H-pyrrol-3-yl]-1-(propan-2-yl)-1H-1,2,3-benzotriazole | 316.17 | 317 |
| 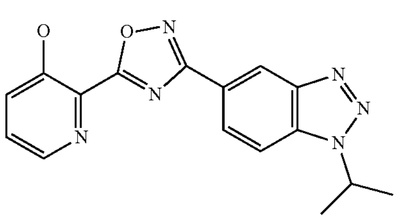 [SMILES: CC(C)n1nnc2cc(-c3noc(-c4ncccc4O)n3)ccc21] | 602 | 2-{3-[1-(propan-2-yl)-1H-1,2,3-benzotriazol-5-yl]-1,2,4-oxadiazol-5-yl}pyridin-3-ol | 322.12 | 323 |

-continued

| Structure | Compound Number | Chemical Name | Exact Mass | Actual Peak |
|---|---|---|---|---|
| 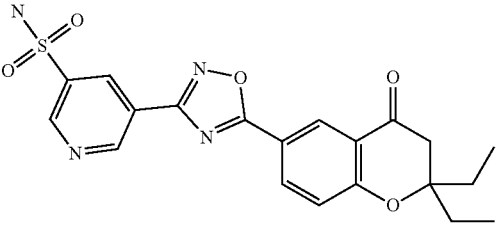 [SMILES: CCC1(CC)CC(=O)c2cc(-c3nc(-c4cncc(S(N)(=O)=O)c4)no3)ccc2O1] | 603 | 5-(5-(2,2-diethyl-4-oxochroman-6-yl)-1,2,4-oxadiazol-3-yl)pyridine-3-sulfonamide | 428.12 | 428.9 |
| 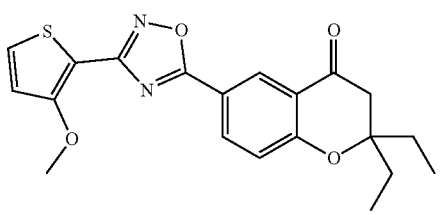 [SMILES: CCC1(CC)CC(=O)c2cc(-c3nc(-c4sccc4OC)no3)ccc2O1] | 604 | 2,2-diethyl-6-(3-(3-methoxythiophen-2-yl)-1,2,4-oxadiazol-5-yl)chroman-4-one | 384.11 | 385.2 |
| 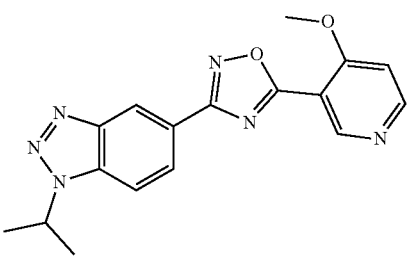 [SMILES: COc1ccncc1-c1nc(-c2ccc3c(c2)nnn3C(C)C)no1] | 605 | 3-(1-isopropyl-1H-benzo[d][1,2,3]triazol-5-yl)-5-(4-methoxypyridin-3-yl)-1,2,4-oxadiazole | 336.13 | 337.2 |
| 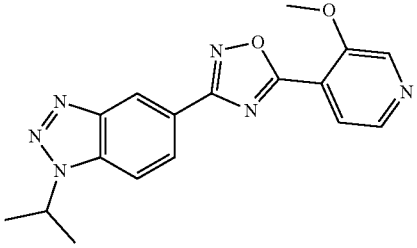 [SMILES: COc1cnccc1-c1nc(-c2ccc3c(c2)nnn3C(C)C)no1] | 606 | 3-(1-isopropyl-1H-benzo[d][1,2,3]triazol-5-yl)-5-(3-methoxypyridin-4-yl)-1,2,4-oxadiazole | 336.13 | 337.2 |
| 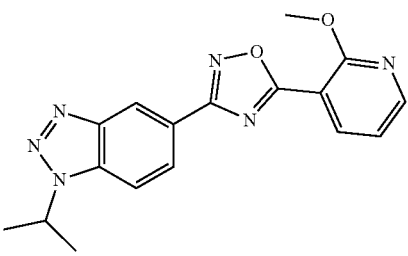 | 607 | 3-(1-isopropyl-1H-benzo[d][1,2,3]triazol-5-yl)-5-(2-methoxypyridin-3-yl)-1,2,4-oxadiazole | 336.13 | 337.2 |
| 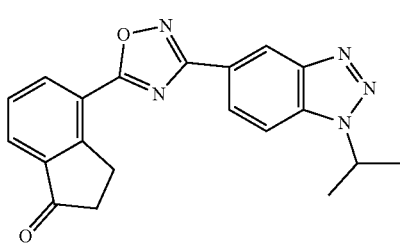 [SMILES: CC(C)n1nnc2cc(-c3noc(-c4cccc5c4CCC5=O)n3)ccc21] | 608 | 4-{3-[1-(propan-2-yl)-1H-1,2,3-benzotriazol-5-yl]-1,2,4-oxadiazol-5-yl}-2,3-dihydro-1H-inden-1-one | 359.14 | 360 |

-continued

| Structure | Compound Number | Chemical Name | Exact Mass | Actual Peak |
|---|---|---|---|---|
| 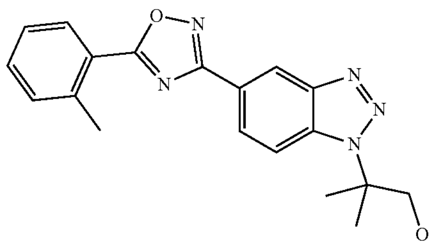 [SMILES: Cc1ccccc1-c1nc(-c2ccc3c(c2)nnn3C(C)(C)CO)no1] | 609 | 2-methyl-2-(5-(5-(o-tolyl)-1,2,4-oxadiazol-3-yl)-1H-benzo[d][1,2,3]triazol-1-yl)propan-1-ol | 349.15 | 350.1 |
| 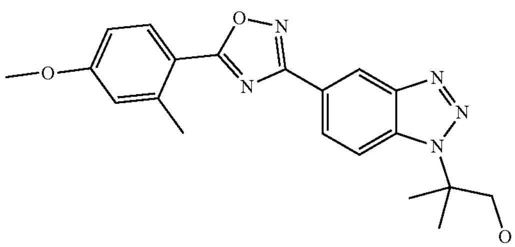 [SMILES: COc1ccc(-c2nc(-c3ccc4c(c3)nnn4C(C)(C)CO)no2)c(C)c1] | 610 | 2-(5-(5-(4-methoxy-2-methylphenyl)-1,2,4-oxadiazol-3-yl)-1H-benzo[d][1,2,3]triazol-1-yl)-2-methylpropan-1-ol | 379.16 | 380 |
| 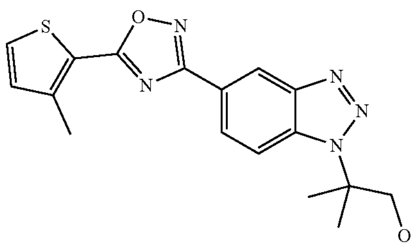 [SMILES: Cc1ccsc1-c1nc(-c2ccc3c(c2)nnn3C(C)(C)CO)no1] | 611 | 2-methyl-2-(5-(5-(3-methylthiophen-2-yl)-1,2,4-oxadiazol-3-yl)-1H-benzo[d][1,2,3]triazol-1-yl)propan-1-ol | 355.11 | 355.9 |
| 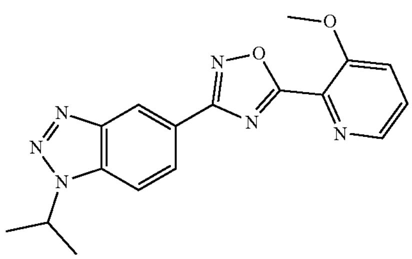 [SMILES: COc1cccnc1-c1nc(-c2ccc3c(c2)nnn3C(C)C)no1] | 612 | 3-(1-isopropyl-1H-benzo[d][1,2,3]triazol-5-yl)-5-(3-methoxypyridin-2-yl)-1,2,4-oxadiazole | 336.13 | 337.2 |
| 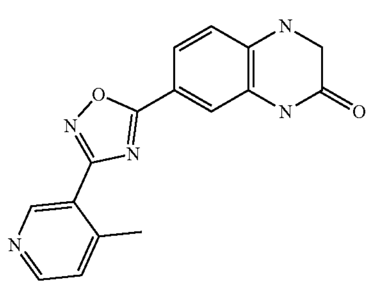 [SMILES: Cc1ccncc1-c1noc(-c2ccc3c(c2)NC(=O)CN3)n1] | 613 | 7-[3-(4-methylpyridin-3-yl)-1,2,4-oxadiazol-5-yl]-1,2,3,4-tetrahydroquinoxalin-2-one | 307.11 | 307.1 |
| 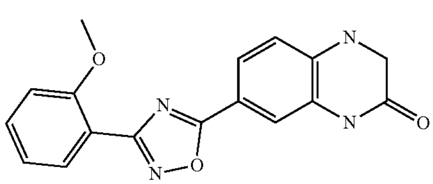 [SMILES: COc1ccccc1-c1noc(-c2ccc3c(c2)NC(=O)CN3)n1] | 614 | 7-[3-(2-methoxyphenyl)-1,2,4-oxadiazol-5-yl]-1,2,3,4-tetrahydroquinoxalin-2-one | 322.11 | 322.1 |

-continued

| Structure | Compound Number | Chemical Name | Exact Mass | Actual Peak |
|---|---|---|---|---|
| 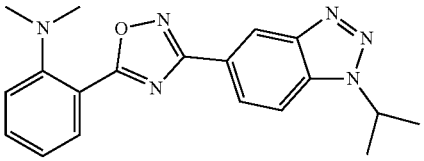 [SMILES: CC(C)n1nnc2cc(-c3noc(-c4ccccc4N(C)C)n3)ccc21] | 615 | N,N-dimethyl-2-{3-[1-(propan-2-yl)-1H-1,2,3-benzotriazol-5-yl]-1,2,4-oxadiazol-5-yl}aniline | 348.17 | 349.1 |
| 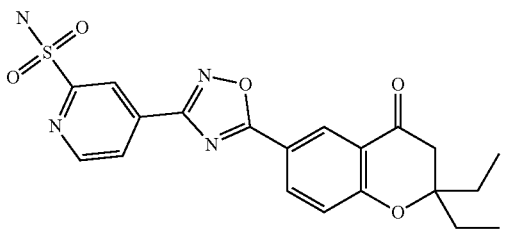 [SMILES: CCC1(CC)CC(=O)c2cc(-c3nc(-c4ccnc(S(N)(=O)=O)c4)no3)ccc2O1] | 616 | 4-(5-(2,2-diethyl-4-oxochroman-6-yl)-1,2,4-oxadiazol-3-yl)pyridine-2-sulfonamide | 428.12 | 428.9 |
| 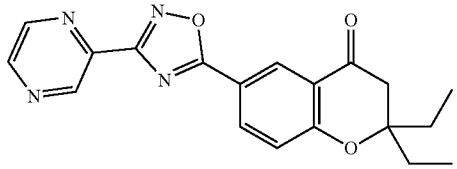 [SMILES: CCC1(CC)CC(=O)c2cc(-c3nc(-c4cnccn4)no3)ccc2O1] | 617 | 2,2-diethyl-6-(3-(pyrazin-2-yl)-1,2,4-oxadiazol-5-yl)chroman-4-one | 350.14 | 351.1 |
| 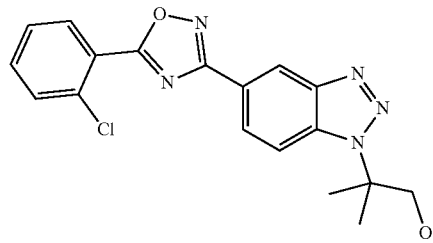 | 618 | 2-(5-(5-(2-chlorophenyl)-1,2,4-oxadiazol-3-yl)-1H-benzo[d][1,2,3]triazol-1-yl)-2-methylpropan-1-ol | 369.1 | 369.9 |
| 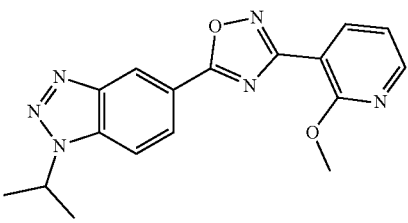 | 619 | 5-(1-isopropyl-1H-benzo[d][1,2,3]triazol-5-yl)-3-(2-methoxypyridin-3-yl)-1,2,4-oxadiazole | 336.13 | 337.2 |
| 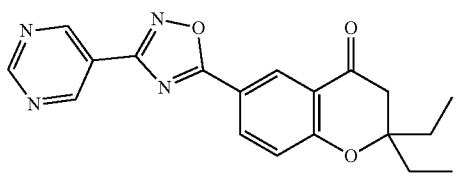 [SMILES: CCC1(CC)CC(=O)c2cc(-c3nc(-c4cncnc4)no3)ccc2O1] | 620 | 2,2-diethyl-6-(3-(pyrimidin-5-yl)-1,2,4-oxadiazol-5-yl)chroman-4-one | 350.14 | 351.1 |
| 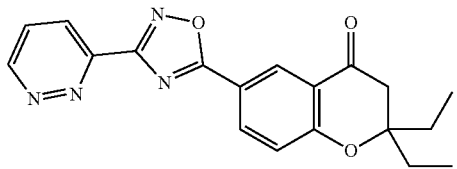 [SMILES: CCC1(CC)CC(=O)c2cc(-c3nc(-c4cccnn4)no3)ccc2O1] | 621 | 2,2-diethyl-6-(3-(pyridazin-3-yl)-1,2,4-oxadiazol-5-yl)chroman-4-one | 350.14 | 351.1 |

-continued

| Structure | Compound Number | Chemical Name | Exact Mass | Actual Peak |
|---|---|---|---|---|
| 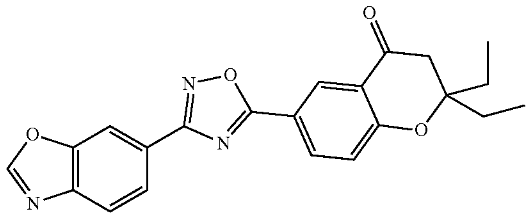 [SMILES: CCC1(CC)CC(=O)c2cc(-c3nc(-c4ccc5ncoc5c4)no3)ccc2O1] | 622 | 6-(3-(benzo[d]oxazol-6-yl)-1,2,4-oxadiazol-5-yl)-2,2-diethylchroman-4-one | 389.14 | 390 |
| 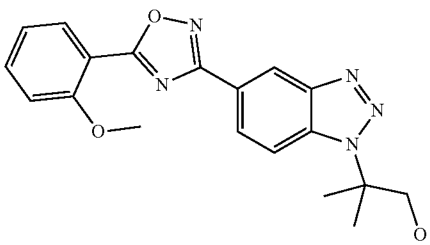 [SMILES: COc1ccccc1-c1nc(-c2ccc3c(c2)nnn3C(C)(C)CO)no1] | 623 | 2-(5-(5-(2-methoxyphenyl)-1,2,4-oxadiazol-3-yl)-1H-benzo[d][1,2,3]triazol-1-yl)-2-methylpropan-1-ol | 365.15 | 365.9 |
| 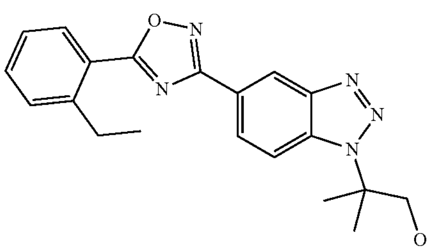 | 624 | 2-(5-(5-(2-ethylphenyl)-1,2,4-oxadiazol-3-yl)-1H-benzo[d][1,2,3]triazol-1-yl)-2-methylpropan-1-ol | 363.17 | 364.1 |
| 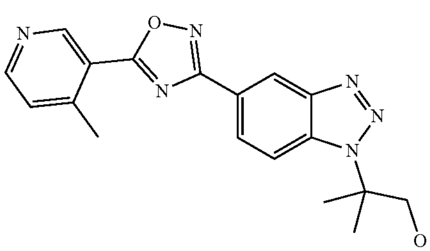 [SMILES: Cc1ccncc1-c1nc(-c2ccc3c(c2)nnn3C(C)(C)CO)no1] | 625 | 2-methyl-2-(5-(5-(4-methylpyridin-3-yl)-1,2,4-oxadiazol-3-yl)-1H-benzo[d][1,2,3]triazol-1-yl)propan-1-ol | 350.15 | 351.1 |
| 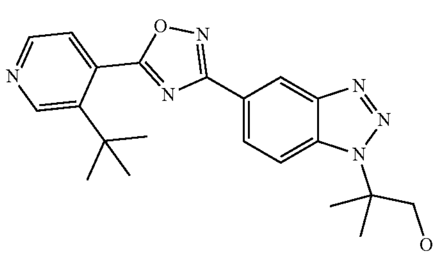 [SMILES: CC(C)(C)c1cnccc1-c1nc(-c2ccc3c(c2)nnn3C(C)(C)CO)no1] | 626 | 2-methyl-2-(5-(5-(3-(trifluoromethyl)pyridin-4-yl)-1,2,4-oxadiazol-3-yl)-1H-benzo[d][1,2,3]triazol-1-yl)propan-1-ol | 404.12 | 405.1 |
| 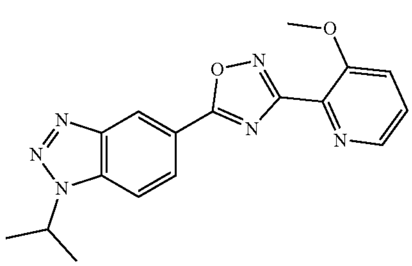 | 627 | 5-(1-isopropyl-1H-benzo[d][1,2,3]triazol-5-yl)-3-(3-methoxypyridin-2-yl)-1,2,4-oxadiazole | 336.13 | 337.1 |

-continued

| Structure | Compound Number | Chemical Name | Exact Mass | Actual Peak |
|---|---|---|---|---|
| 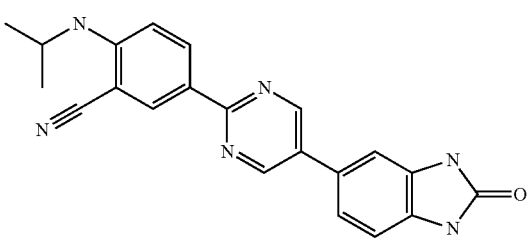 [SMILES: CC(C)Nc1ccc(-c2ncc(-c3ccc4[nH]c(=O)[nH]c4c3)cn2)cc1C#N] | 628 | 2-(isopropylamino)-5-(5-(2-oxo-2,3-dihydro-1H-benzo[d]imidazol-5-yl)pyrimidin-2-yl)benzonitrile | 370.15 | 371.1 |
| 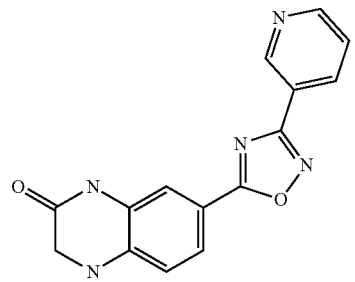 [SMILES: O=C1CNc2ccc(-c3nc(-c4cccnc4)no3)cc2N1] | 629 | 7-[3-(pyridin-3-yl)-1,2,4-oxadiazol-5-yl]-1,2,3,4-tetrahydroquinoxalin-2-one | 293.09 | 292.1 |
| 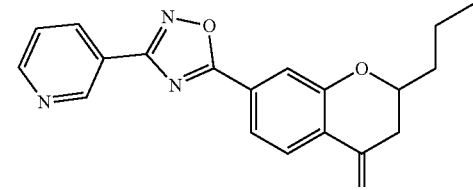 | 630 | 2-propyl-7-[3-(pyridin-3-yl)-1,2,4-oxadiazol-5-yl]-3,4-dihydro-2H-1-benzopyran-4-one | 335.13 | 336.1 |
| 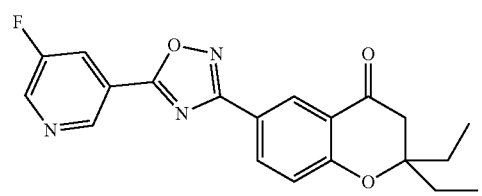 [SMILES: CCC1(CC)CC(=O)c2cc(-c3noc(-c4cncc(F)c4)n3)ccc2O1] | 631 | 2,2-diethyl-6-[5-(5-fluoropyridin-3-yl)-1,2,4-oxadiazol-3-yl]-3,4-dihydro-2H-1-benzopyran-4-one | 367.13 | 368.1 |
| 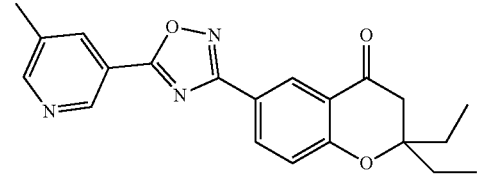 [SMILES: CCC1(CC)CC(=O)c2cc(-c3noc(-c4cncc(C)c4)n3)ccc2O1] | 632 | 2,2-diethyl-6-[5-(5-methylpyridin-3-yl)-1,2,4-oxadiazol-3-yl]-3,4-dihydro-2H-1-benzopyran-4-one | 363.16 | 364.1 |
| 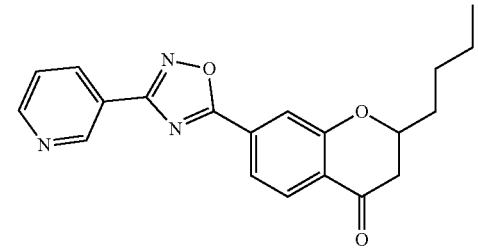 [SMILES: CCCCC1CC(=O)c2ccc(-c3nc(-c4cccnc4)no3)cc2O1] | 633 | 2-butyl-7-[3-(pyridin-3-yl)-1,2,4-oxadiazol-5-yl]-3,4-dihydro-2H-1-benzopyran-4-one | 349.14 | 350.1 |

-continued

| Structure | Compound Number | Chemical Name | Exact Mass | Actual Peak |
|---|---|---|---|---|
| 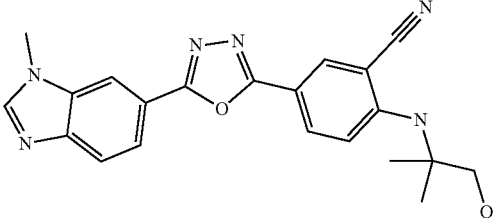 [SMILES: Cn1cnc2ccc(-c3nnc(-c4ccc(NC(C)(C)CO)c(C#N)c4)o3)cc21] | 634 | 2-[(1-hydroxy-2-methylpropan-2-yl)amino]-5-[5-(1-methyl-1H-1,3-benzodiazol-6-yl)-1,3,4-oxadiazol-2-yl]benzonitrile | 388.16 | 389.2 |
| 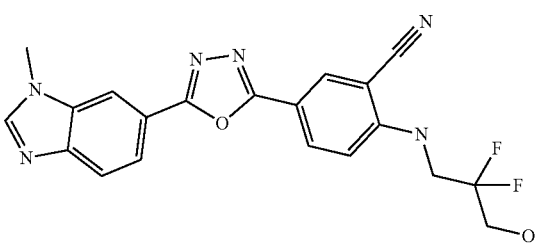 [SMILES: Cn1cnc2ccc(-c3nnc(-c4ccc(NCC(F)(F)CO)c(C#N)c4)o3)cc21] | 635 | 2-[(2,2-difluoro-3-hydroxypropyl)amino]-5-[5-(1-methyl-1H-1,3-benzodiazol-6-yl)-1,3,4-oxadiazol-2-yl]benzonitrile | 410.13 | 411.2 |
| 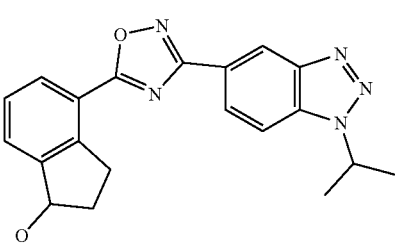 [SMILES: CC(C)n1nnc2cc(-c3noc(-c4cccc5c4CCC5O)n3)ccc21] | 636 | 4-{3-[1-(propan-2-yl)-1H-1,2,3-benzotriazol-5-yl]-1,2,4-oxadiazol-5-yl}-2,3-dihydro-1H-inden-1-ol | 361.15 | 362 |
| 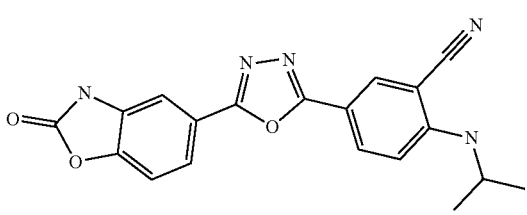 [SMILES: CC(C)Nc1ccc(-c2nnc(-c3ccc4oc(=O)[nH]c4c3)o2)cc1C#N] | 637 | 5-[5-(2-oxo-2,3-dihydro-1,3-benzoxazol-5-yl)-1,3,4-oxadiazol-2-yl]-2-[(propan-2-yl)amino]benzonitrile | 361.12 | 362.2 |
| 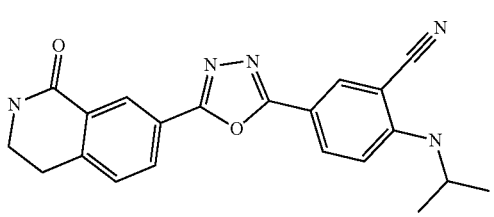 [SMILES: CC(C)Nc1ccc(-c2nnc(-c3ccc4c(c3)C(=O)NCC4)o2)cc1C#N] | 638 | 5-[5-(1-oxo-1,2,3,4-tetrahydroisoquinolin-7-yl)-1,3,4-oxadiazol-2-yl]-2-[(propan-2-yl)amino]benzonitrile | 373.15 | 374.2 |
| 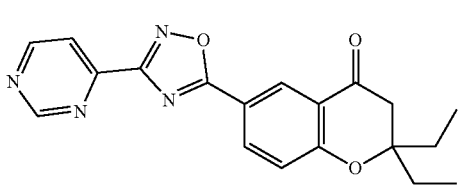 [SMILES: CCC1(CC)CC(=O)c2cc(-c3nc(-c4ccncn4)no3)ccc2O1] | 639 | 2,2-diethyl-6-(3-(pyrimidin-4-yl)-1,2,4-oxadiazol-5-yl)chroman-4-one | 350.14 | 351.1 |
| 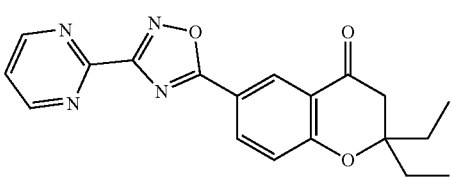 [SMILES: CCC1(CC)CC(=O)c2cc(-c3nc(-c4ncccn4)no3)ccc2O1] | 640 | 2,2-diethyl-6-(3-(pyrimidin-2-yl)-1,2,4-oxadiazol-5-yl)chroman-4-one | 350.14 | 351.1 |

-continued

| Structure | Compound Number | Chemical Name | Exact Mass | Actual Peak |
|---|---|---|---|---|
| 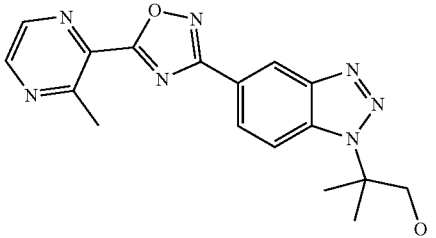 [SMILES: Cc1nccnc1-c1nc(-c2ccc3c(c2)nnn3C(C)(C)CO)no1] | 641 | 2-methyl-2-(5-(5-(3-methylpyrazin-2-yl)-1,2,4-oxadiazol-3-yl)-1H-benzo[d][1,2,3]triazol-1-yl)propan-1-ol | 351.14 | 352.2 |
| 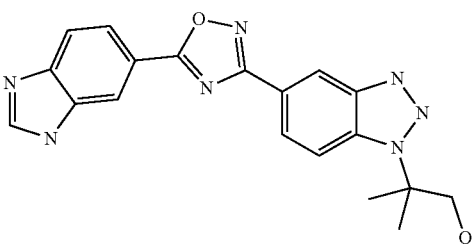 [SMILES: CC(C)(CO)N1NNc2cc(-c3noc(-c4ccc5nc[nH]c5c4)n3)ccc21] | 642 | 2-(5-(5-(1H-benzo[d]imidazol-6-yl)-1,2,4-oxadiazol-3-yl)-1H-benzo[d][1,2,3]triazol-1-yl)-2-methylpropan-1-ol | 375.14 | 376.1 |
| 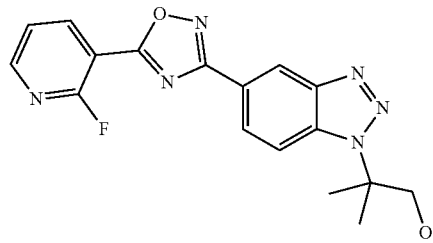 [SMILES: CC(C)(CO)n1nnc2cc(-c3noc(-c4cccnc4F)n3)ccc21] | 643 | 2-(5-(5-(2-fluoropyridin-3-yl)-1,2,4-oxadiazol-3-yl)-1H-benzo[d][1,2,3]triazol-1-yl)-2-methylpropan-1-ol | 354.12 | 355.1 |
| 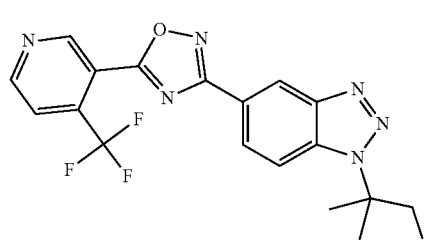 | 644 | 2-methyl-2-(5-(5-(4-(trifluoromethyl)pyridin-3-yl)-1,2,4-oxadiazol-3-yl)-1H-benzo[d][1,2,3]triazol-1-yl)propan-1-ol | 404.12 | 405.2 |
| 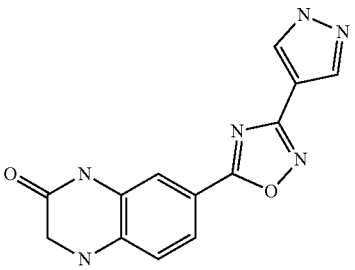 [SMILES: O=C1CNc2ccc(-c3nc(-c4cn[nH]c4)no3)cc2N1] | 645 | 7-[3-(1H-pyrazol-4-yl)-1,2,4-oxadiazol-5-yl]-1,2,3,4-tetrahydroquinoxalin-2-one | 282.09 | 281.1 |

-continued

| Structure | Compound Number | Chemical Name | Exact Mass | Actual Peak |
|---|---|---|---|---|
| 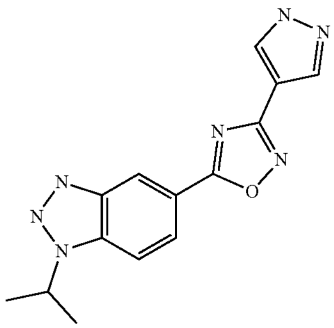 [SMILES: CC(C)N1NNc2cc(-c3nc(-c4cn[nH]c4)no3)ccc21] | 646 | 1-(propan-2-yl)-5-[3-(1H-pyrazol-4-yl)-1,2,4-oxadiazol-5-yl]-1H-1,2,3-benzotriazole | 295.12 | 296.2 |
| 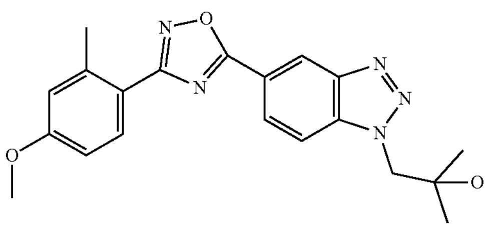 [SMILES: COc1ccc(-c2noc(-c3ccc4c(c3)nnn4CC(C)(C)O)n2)c(C)c1] | 647 | 1-{5-[3-(4-methoxy-2-methylphenyl)-1,2,4-oxadiazol-5-yl]-1H-1,2,3-benzotriazol-1-yl}-2-methylpropan-2-ol | 379.16 | 380.1 |
| 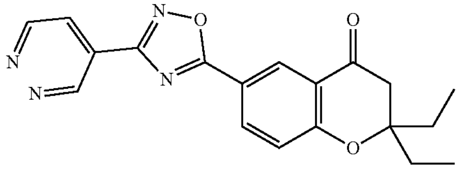 [SMILES: CCC1(CC)CC(=O)c2cc(-c3nc(/C(C=N)=C/C=N)no3)ccc2O1] | 648 | 2,2-diethyl-6-(3-(pyridazin-4-yl)-1,2,4-oxadiazol-5-yl)chroman-4-one | 350.14 | 351 |
| 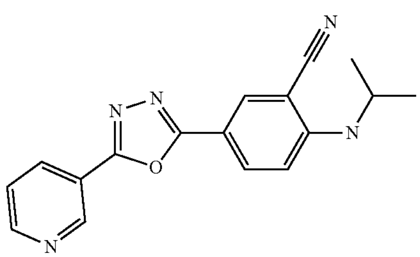 [SMILES: CC(C)Nc1ccc(-c2nnc(-c3cccnc3)o2)cc1C#N] | 649 | 2-(isopropylamino)-5-(5-(pyridin-3-yl)-1,3,4-oxadiazol-2-yl)benzonitrile | 305.13 | 306.3 |
| 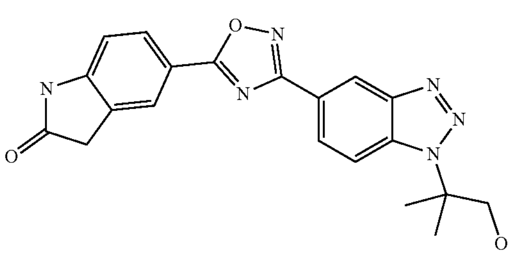 [SMILES: CC(C)(CO)n1nnc2cc(-c3noc(-c4ccc5c(c4)CC(=O)N5)n3)ccc21] | 650 | 5-(3-(1-(1-hydroxy-2-methylpropan-2-yl)-1H-benzo[d][1,2,3]triazol-5-yl)-1,2,4-oxadiazol-5-yl)indolin-2-one | 390.14 | 391.1 |
| 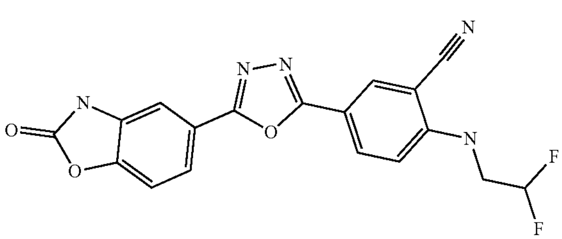 [SMILES: N#Cc1cc(-c2nnc(-c3ccc4oc(=O)[nH]c4c3)o2)ccc1NCC(F)F] | 651 | 2-[(2,2-difluoroethyl)amino]-5-[5-(2-oxo-2,3-dihydro-1,3-benzoxazol-5-yl)-1,3,4-oxadiazol-2-yl]benzonitrile | 383.08 | 384 |

-continued

| Structure | Compound Number | Chemical Name | Exact Mass | Actual Peak |
|---|---|---|---|---|
| 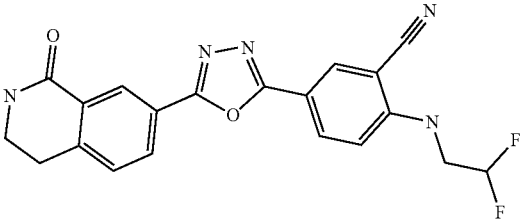 [SMILES: N#Cc1cc(-c2nnc(-c3ccc4c(c3)C(=O)NCC4)o2)ccc1NCC(F)F] | 652 | 2-[(2,2-difluoroethyl)amino]-5-[5-(1-oxo-1,2,3,4-tetrahydroisoquinolin-7-yl)-1,3,4-oxadiazol-2-yl]benzonitrile | 395.12 | 396.1 |
| 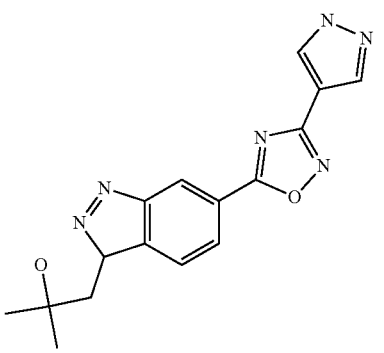 [SMILES: CC(C)(O)CC1N=Nc2cc(-c3nc(-c4cn[nH]c4)no3)ccc21] | 653 | 2-methyl-1-{6-[3-(1H-pyrazol-4-yl)-1,2,4-oxadiazol-5-yl]-3H-indazol-3-yl}propan-2-ol | 324.13 | 326.2 |
| 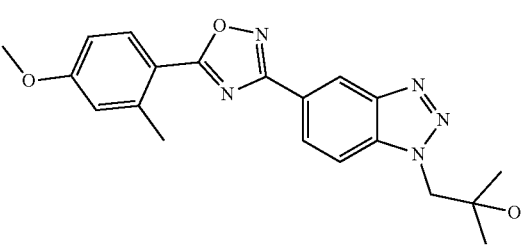 [SMILES: COc1ccc(-c2nc(-c3ccc4c(c3)nnn4CC(C)(C)O)no2)c(C)c1] | 654 | 1-(5-(5-(4-methoxy-2-methylphenyl)-1,2,4-oxadiazol-3-yl)-1H-benzo[d][1,2,3]triazol-1-yl)-2-methylpropan-2-ol | 379.16 | 380.3 |
| 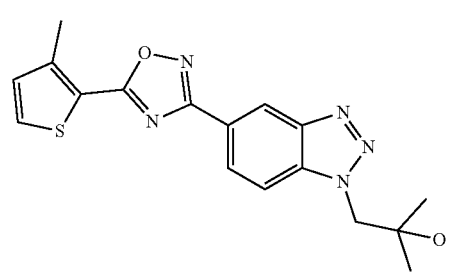 [SMILES: Cc1ccsc1-c1nc(-c2ccc3c(c2)nnn3CC(C)(C)O)no1] | 655 | 2-methyl-1-(5-(5-(3-methylthiophen-2-yl)-1,2,4-oxadiazol-3-yl)-1H-benzo[d][1,2,3]triazol-1-yl)propan-2-ol | 355.11 | 356.2 |
| 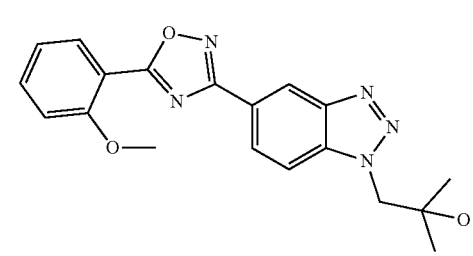 [SMILES: COc1ccccc1-c1nc(-c2ccc3c(c2)nnn3CC(C)(C)O)no1] | 656 | 1-(5-(5-(2-methoxyphenyl)-1,2,4-oxadiazol-3-yl)-1H-benzo[d][1,2,3]triazol-1-yl)-2-methylpropan-2-ol | 365.15 | 366.2 |

-continued

| Structure | Compound Number | Chemical Name | Exact Mass | Actual Peak |
|---|---|---|---|---|
| 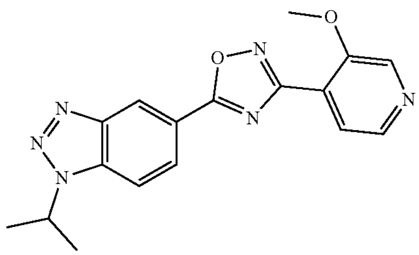 [SMILES: COc1cnccc1-c1noc(-c2ccc3c(c2)nnn3C(C)C)n1] | 657 | 5-(1-isopropyl-1H-benzo[d][1,2,3]triazol-5-yl)-3-(3-methoxypyridin-4-yl)-1,2,4-oxadiazole | 336.13 | 337.1 |
| 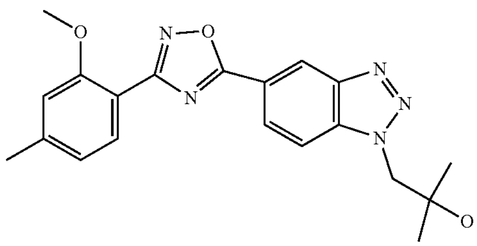 [SMILES: COc1cc(C)ccc1-c1noc(-c2ccc3c(c2)nnn3CC(C)(C)O)n1] | 662 | 1-{5-[3-(2-methoxy-4-methylphenyl)-1,2,4-oxadiazol-5-yl]-1H-1,2,3-benzotriazol-1-yl}-2-methylpropan-2-ol | 379.16 | 380 |
| 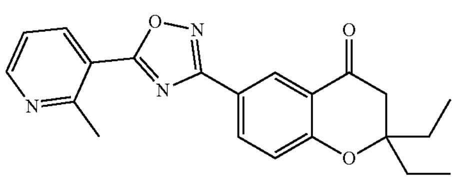 | 663 | 2,2-diethyl-6-[5-(2-methylpyridin-3-yl)-1,2,4-oxadiazol-3-yl]-3,4-dihydro-2H-1-benzopyran-4-one | 363.16 | 364.1 |
| 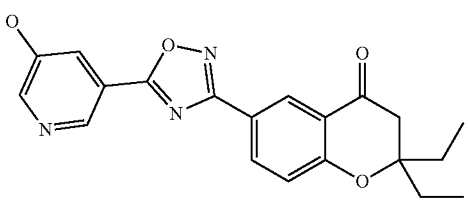 [SMILES: CCC1(CC)CC(=O)c2cc(-c3noc(-c4cncc(O)c4)n3)ccc2O1] | 664 | 2,2-diethyl-6-[5-(5-hydroxypyridin-3-yl)-1,2,4-oxadiazol-3-yl]-3,4-dihydro-2H-1-benzopyran-4-one | 365.14 | 366.1 |
| 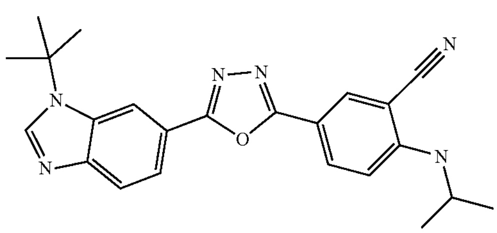 [SMILES: CC(C)Nc1ccc(-c2nnc(-c3ccc4ncn(C(C)(C)C)c4c3)o2)cc1C#N] | 665 | 5-[5-(1-tert-butyl-1H-1,3-benzodiazol-6-yl)-1,3,4-oxadiazol-2-yl]-2-[(propan-2-yl)amino]benzonitrile | 400.2 | 401.3 |
| 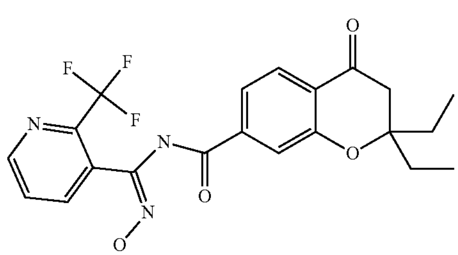 [SMILES: CCC1(CC)CC(=O)c2ccc(C(=O)N/C(=N/O)c3cccnc3C(F)(F)F)cc2O1] | 666 | 2,2-diethyl-N-[(1E)-(hydroxyimino)[2-(trifluoromethyl)pyridin-3-yl]methyl]-4-oxo-3,4-dihydro-2H-1-benzopyran-7-carboxamide | 435.14 | 436.2 |

-continued

| Structure | Compound Number | Chemical Name | Exact Mass | Actual Peak |
|---|---|---|---|---|
| 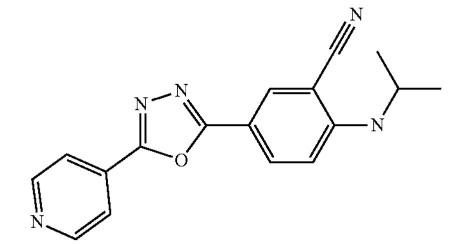 [SMILES: CC(C)Nc1ccc(-c2nnc(-c3ccncc3)o2)cc1C#N] | 667 | 2-(isopropylamino)-5-(5-(pyridin-4-yl)-1,3,4-oxadiazol-2-yl)benzonitrile | 305.13 | 306.3 |
| 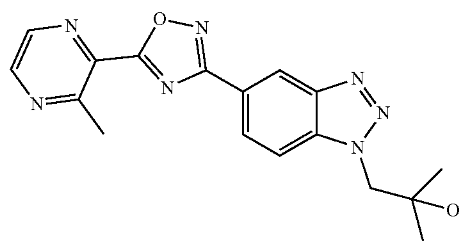 [SMILES: Cc1nccnc1-c1nc(-c2ccc3c(c2)nnn3CC(C)(C)O)no1] | 668 | 2-methyl-1-(5-(5-(3-methylpyrazin-2-yl)-1,2,4-oxadiazol-3-yl)-1H-benzo[d][1,2,3]triazol-1-yl)propan-2-ol | 351.14 | 352.2 |
| 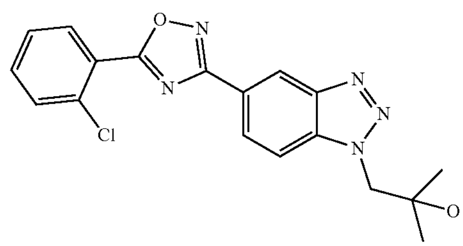 [SMILES: CC(C)(O)Cn1nnc2cc(-c3noc(-c4ccccc4Cl)n3)ccc21] | 669 | 1-(5-(5-(2-chlorophenyl)-1,2,4-oxadiazol-3-yl)-1H-benzo[d][1,2,3]triazol-1-yl)-2-methylpropan-2-ol | 369.1 | 369.9 |
| 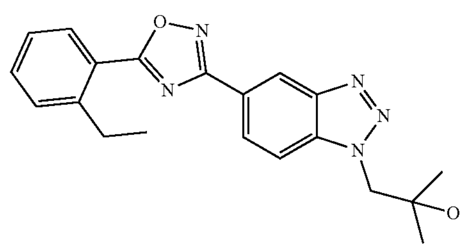 [SMILES: CCc1ccccc1-c1nc(-c2ccc3c(c2)nnn3CC(C)(C)O)no1] | 670 | 1-(5-(5-(2-ethylphenyl)-1,2,4-oxadiazol-3-yl)-1H-benzo[d][1,2,3]triazol-1-yl)-2-methylpropan-2-ol | 363.17 | 364 |
| 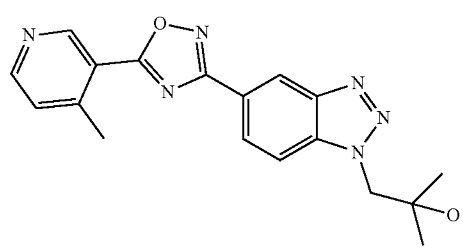 [SMILES: Cc1ccncc1-c1nc(-c2ccc3c(c2)nnn3CC(C)(C)O)no1] | 671 | 2-methyl-1-(5-(5-(4-methylpyridin-3-yl)-1,2,4-oxadiazol-3-yl)-1H-benzo[d][1,2,3]triazol-1-yl)propan-2-ol | 350.15 | 351.2 |
| 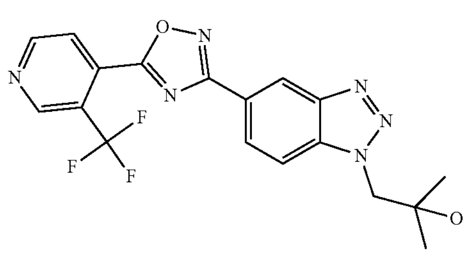 [SMILES: CC(C)(O)Cn1nnc2cc(-c3noc(-c4ccncc4C(F)(F)F)n3)ccc21] | 672 | 2-methyl-1-(5-(5-(3-(trifluoromethyl)pyridin-4-yl)-1,2,4-oxadiazol-3-yl)-1H-benzo[d][1,2,3]triazol-1-yl)propan-2-ol | 404.12 | 405.2 |

| Structure | Compound Number | Chemical Name | Exact Mass | Actual Peak |
|---|---|---|---|---|
| 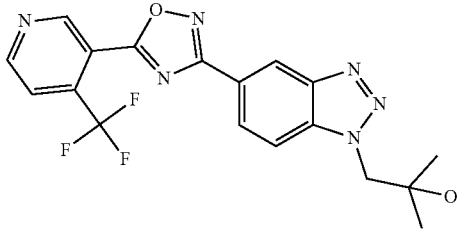 [SMILES: CC(C)(O)Cn1nnc2cc(-c3noc(-c4cnccc4C(F)(F)F)n3)ccc21] | 673 | 2-methyl-1-(5-(5-(4-(trifluoromethyl)pyridin-3-yl)-1,2,4-oxadiazol-3-yl)-1H-benzo[d][1,2,3]triazol-1-yl)propan-2-ol | 404.12 | 405.2 |
| 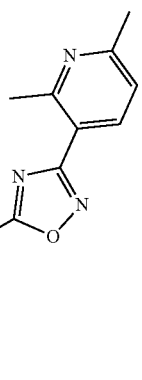 | 675 | 1-{5-[3-(2,6-dimethylpyridin-3-yl)-1,2,4-oxadiazol-5-yl]-1H-1,2,3-benzotriazol-1-yl}-2-methylpropan-2-ol | 364.16 | 365.1 |
| 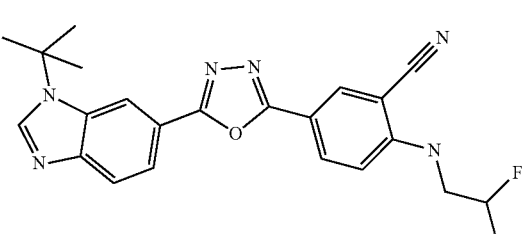 | 676 | 5-[5-(1-tert-butyl-1H-1,3-benzodiazol-6-yl)-1,3,4-oxadiazol-2-yl]-2-[(2,2-difluoroethyl)amino]benzonitrile | 422.17 | 423.1 |
| 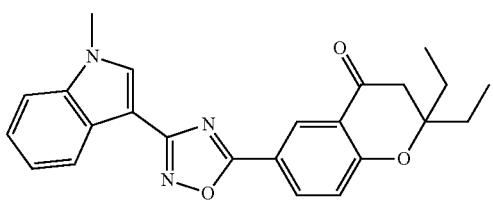 [SMILES: CCC1(CC)CC(=O)c2cc(-c3nc(-c4cn(C)c5ccccc45)no3)ccc2O1] | 677 | 2,2-diethyl-6-[3-(1-methyl-1H-indol-3-yl)-1,2,4-oxadiazol-5-yl]-3,4-dihydro-2H-1-benzopyran-4-one | 401.17 | 402.1 |
| 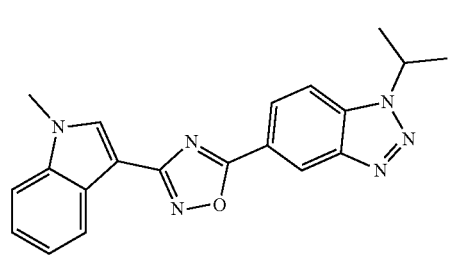 [SMILES: CC(C)n1nnc2cc(-c3nc(-c4cn(C)c5ccccc45)no3)ccc21] | 678 | 5-[3-(1-methyl-1H-indol-3-yl)-1,2,4-oxadiazol-5-yl]-1-(propan-2-yl)-1H-1,2,3-benzotriazole | 358.15 | 359.1 |

-continued

| Structure | Compound Number | Chemical Name | Exact Mass | Actual Peak |
|---|---|---|---|---|
| 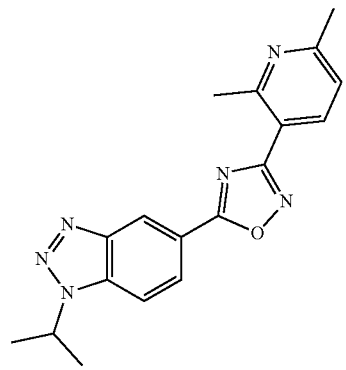 [SMILES: Cc1ccc(-c2noc(-c3ccc4c(c3)nnn4C(C)C)n2)c(C)n1] | 679 | 5-[3-(2,6-dimethylpyridin-3-yl)-1,2,4-oxadiazol-5-yl]-1-(propan-2-yl)-1H-1,2,3-benzotriazole | 334.15 | 335.1 |
| 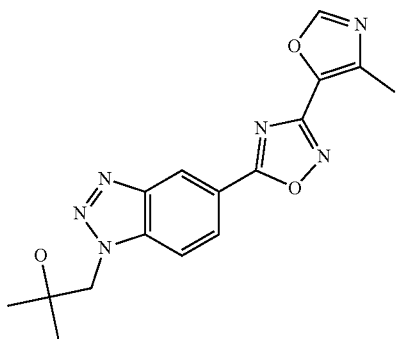 [SMILES: Cc1ncoc1-c1noc(-c2ccc3c(c2)nnn3CC(C)(C)O)n1] | 680 | 2-methyl-1-(5-[3-(4-methyl-1,3-oxazol-5-yl)-1,2,4-oxadiazol-5-yl]-1H-1,2,3-benzotriazol-1-yl}propan-2-ol | 340.13 | 341.1 |
| 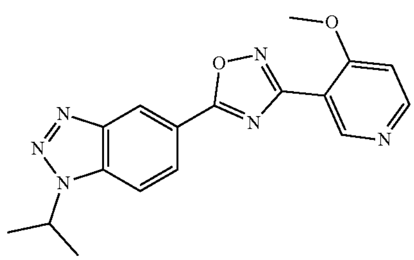 [SMILES: COc1ccncc1-c1noc(-c2ccc3c(c2)nnn3C(C)C)n1] | 681 | 5-(1-isopropyl-1H-benzo[d][1,2,3]triazol-5-yl)-3-(4-methoxypyridin-3-yl)-1,2,4-oxadiazole | 336.13 | 337.3 |
| 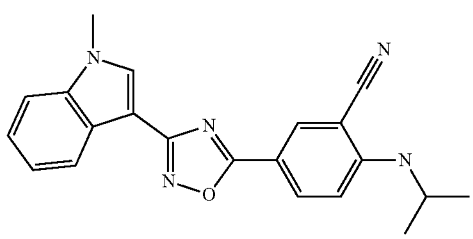 [SMILES: CC(C)Nc1ccc(-c2nc(-c3cn(C)c4ccccc34)no2)cc1C#N] | 682 | 5-[3-(1-methyl-1H-indol-3-yl)-1,2,4-oxadiazol-5-yl]-2-[(propan-2-yl)amino]benzonitrile | 357.16 | 358.2 |
| 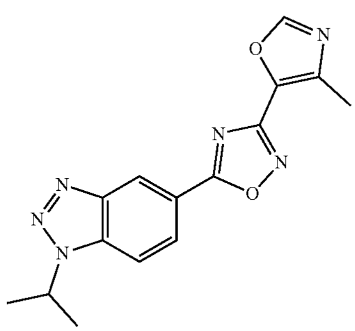 [SMILES: Cc1ncoc1-c1noc(-c2ccc3c(c2)nnn3C(C)C)n1] | 683 | 5-[3-(4-methyl-1,3-oxazol-5-yl)-1,2,4-oxadiazol-5-yl]-1-(propan-2-yl)-1H-1,2,3-benzotriazole | 310.12 | 311.1 |

-continued

| Structure | Compound Number | Chemical Name | Exact Mass | Actual Peak |
|---|---|---|---|---|
| 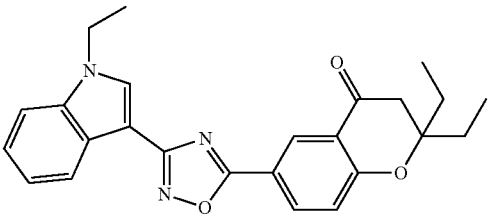 [SMILES: CCn1cc(-c2noc(-c3ccc4c(c3)C(=O)CC(CC)(CC)O4)n2)c2ccccc21] | 684 | 2,2-diethyl-6-[3-(1-ethyl-1H-indol-3-yl)-1,2,4-oxadiazol-5-yl]-3,4-dihydro-2H-1-benzopyran-4-one | 415.19 | 416.2 |
| 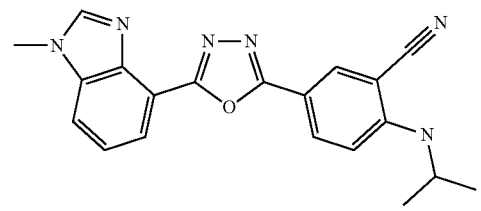 [SMILES: CC(C)Nc1ccc(-c2nnc(-c3cccc4c3ncn4C)o2)cc1C#N] | 685 | 5-[5-(1-methyl-1H-1,3-benzodiazol-4-yl)-1,3,4-oxadiazol-2-yl]-2-[(propan-2-yl)amino]benzonitrile | 358.15 | 359.2 |
| 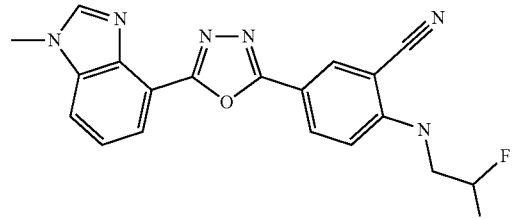 | 686 | 2-[(2,2-difluoroethyl)amino]-5-[5-(1-methyl-1H-1,3-benzodiazol-4-yl)-1,3,4-oxadiazol-2-yl]benzonitrile | 380.12 | 381.2 |
| 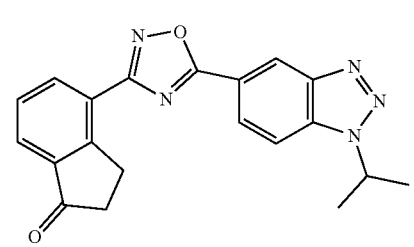 [SMILES: CC(C)n1nnc2cc(-c3nc(-c4cccc5c4CCC5=O)no3)ccc21] | 687 | 4-{5-[1-(propan-2-yl)-1H-1,2,3-benzotriazol-5-yl]-1,2,4-oxadiazol-3-yl}-2,3-dihydro-1H-inden-1-one | 359.14 | 360 |
| 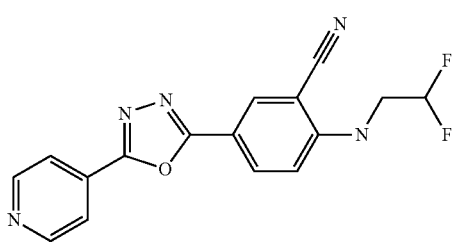 [SMILES: N#Cc1cc(-c2nnc(-c3ccncc3)o2)ccc1NCC(F)F] | 688 | 2-((2,2-difluoroethyl)amino)-5-(5-(pyridin-4-yl)-1,3,4-oxadiazol-2-yl)benzonitrile | 327.09 | 328.3 |
| 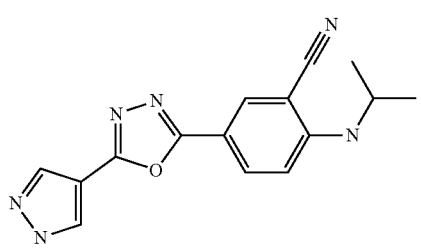 [SMILES: CC(C)Nc1ccc(-c2nnc(-c3cn[nH]c3)o2)cc1C#N] | 689 | 5-(5-(1H-pyrazol-4-yl)-1,3,4-oxadiazol-2-yl)-2-(isopropylamino)benzonitrile | 294.12 | 295.3 |

| Structure | Compound Number | Chemical Name | Exact Mass | Actual Peak |
|---|---|---|---|---|
| 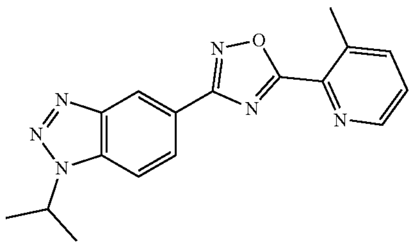 [SMILES: Cc1cccnc1-c1nc(-c2ccc3c(c2)nnn3C(C)C)no1] | 690 | 3-(1-isopropyl-1H-benzo[d][1,2,3]triazol-5-yl)-5-(3-methylpyridin-2-yl)-1,2,4-oxadiazole | 320.14 | 321.3 |
| 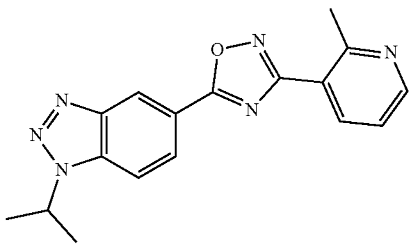 [SMILES: Cc1ncccc1-c1noc(-c2ccc3c(c2)nnn3C(C)C)n1] | 691 | 5-(1-isopropyl-1H-benzo[d][1,2,3]triazol-5-yl)-3-(2-methylpyridin-3-yl)-1,2,4-oxadiazole | 320.14 | 321.2<br>321.2 |
| 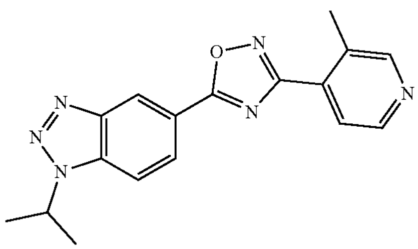 [SMILES: Cc1cnccc1-c1noc(-c2ccc3c(c2)nnn3C(C)C)n1] | 692 | 5-(1-isopropyl-1H-benzo[d][1,2,3]triazol-5-yl)-3-(3-methylpyridin-4-yl)-1,2,4-oxadiazole | 320.14 | 321.2 |
| 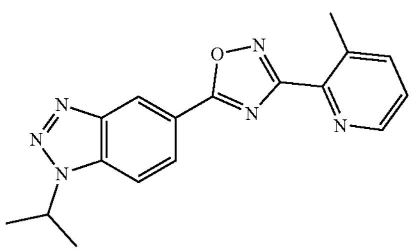 [SMILES: Cc1cccnc1-c1noc(-c2ccc3c(c2)nnn3C(C)C)n1] | 693 | 5-(1-isopropyl-1H-benzo[d][1,2,3]triazol-5-yl)-3-(3-methylpyridin-2-yl)-1,2,4-oxadiazole | 320.14 | 321.1 |
| 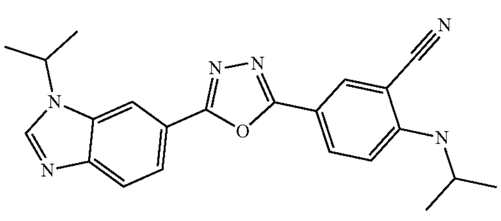 [SMILES: CC(C)Nc1ccc(-c2nnc(-c3ccc4ncn(C(C)C)c4c3)o2)cc1C#N] | 694 | 5-{5-[1-(propan-2-yl)-1H-1,3-benzodiazol-6-yl]-1,3,4-oxadiazol-2-yl}-2-[(propan-2-yl)amino]benzonitrile | 386.19 | 387.2 |
| 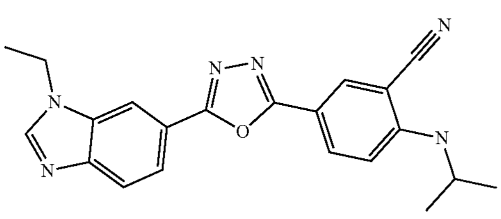 [SMILES: CCn1cnc2ccc(-c3nnc(-c4ccc(NC(C)C)c(C#N)c4)o3)cc21] | 695 | 5-[5-(1-ethyl-1H-1,3-benzodiazol-6-yl)-1,3,4-oxadiazol-2-yl]-2-[(propan-2-yl)amino]benzonitrile | 372.17 | 373.1 |

-continued

| Structure | Compound Number | Chemical Name | Exact Mass | Actual Peak |
|---|---|---|---|---|
| 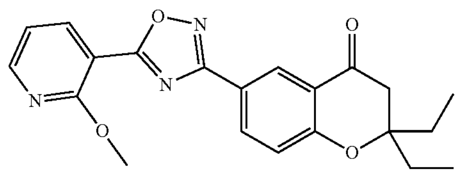 [SMILES: CCC1(CC)CC(=O)c2cc(-c3noc(-c4cccnc4OC)n3)ccc2O1] | 696 | 2,2-diethyl-6-[5-(2-methoxypyridin-3-yl)-1,2,4-oxadiazol-3-yl]-3,4-dihydro-2H-1-benzopyran-4-one | 379.15 | 380.2 |
| 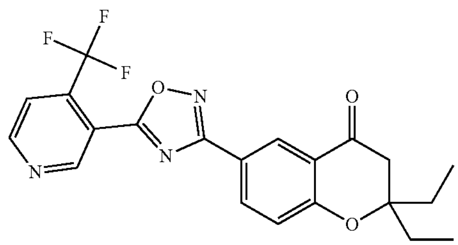 [SMILES: CCC1(CC)CC(=O)c2cc(-c3noc(-c4cnccc4C(F)(F)F)n3)ccc2O1] | 697 | 2,2-diethyl-6-{5-[4-(trifluoromethyl)pyridin-3-yl]-1,2,4-oxadiazol-3-yl}-3,4-dihydro-2H-1-benzopyran-4-one | 417.13 | 418.2 |
| 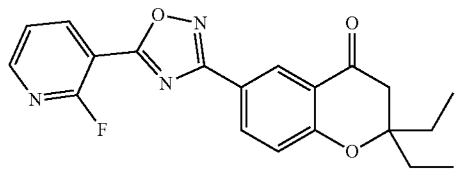 | 698 | 2,2-diethyl-6-[5-(2-fluoropyridin-3-yl)-1,2,4-oxadiazol-3-yl]-3,4-dihydro-2H-1-benzopyran-4-one | 367.13 | 368.1 |
| 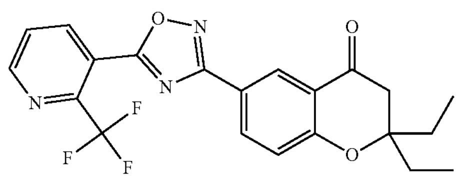 [SMILES: CCC1(CC)CC(=O)c2cc(-c3noc(-c4cccnc4C(F)(F)F)n3)ccc2O1] | 699 | 2,2-diethyl-6-{5-[2-(trifluoromethyl)pyridin-3-yl]-1,2,4-oxadiazol-3-yl}-3,4-dihydro-2H-1-benzopyran-4-one | 417.13 | 418.1 |
| 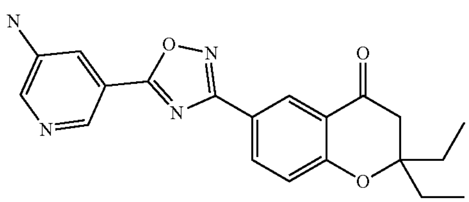 | 700 | 6-[5-(5-aminopyridin-3-yl)-1,2,4-oxadiazol-3-yl]-2,2-diethyl-3,4-dihydro-2H-1-benzopyran-4-one | 364.15 | 365.1 |
| 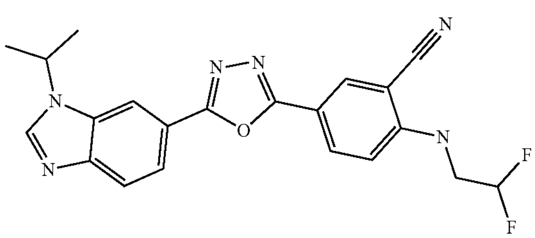 [SMILES: CC(C)n1cnc2ccc(-c3nnc(-c4ccc(NCC(F)F)c(C#N)c4)o3)cc21] | 701 | 2-{(2,2-difluoroethyl)amino]-5-{5-[1-(propan-2-yl)-1H-1,3-benzodiazol-6-yl]-1,3,4-oxadiazol-2-yl}benzonitrile | 408.15 | 409.1 |
| 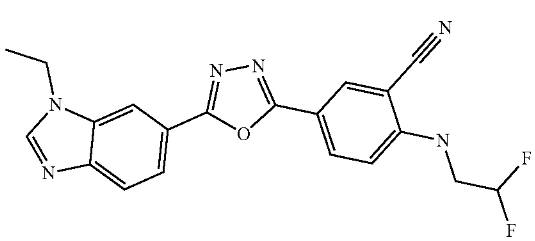 [SMILES: CCn1cnc2ccc(-c3nnc(-c4ccc(NCC(F)F)c(C#N)c4)o3)cc21] | 702 | 2-[(2,2-difluoroethyl)amino]-5-[5-(1-ethyl-1H-1,3-benzodiazol-6-yl)-1,3,4-oxadiazol-2-yl]benzonitrile | 394.14 | 395.1 |

-continued

| Structure | Compound Number | Chemical Name | Exact Mass | Actual Peak |
|---|---|---|---|---|
| 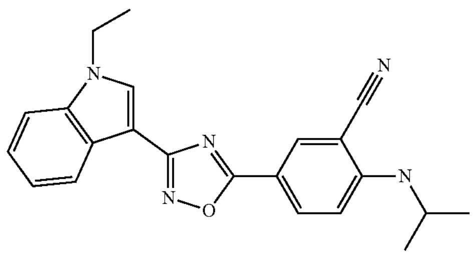 [SMILES: CCn1cc(-c2noc(-c3ccc(NC(C)C)c(C#N)c3)n2)c2ccccc21] | 703 | 5-[3-(1-ethyl-1H-indol-3-yl)-1,2,4-oxadiazol-5-yl]-2-[(propan-2-yl)amino]benzonitrile | 371.17 | 372.1 |
| 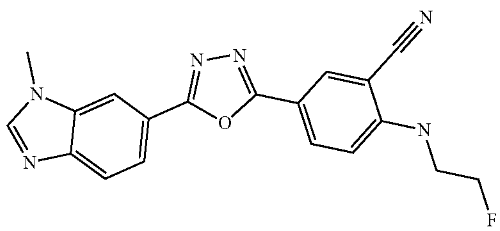 [SMILES: Cn1cnc2ccc(-c3nnc(-c4ccc(NCCF)c(C#N)c4)o3)cc21] | 704 | 2-[(2-fluoroethyl)amino]-5-[5-(1-methyl-1H-1,3-benzodiazol-6-yl)-1,3,4-oxadiazol-2-yl]benzonitrile | 362.13 | 363.1 |
| 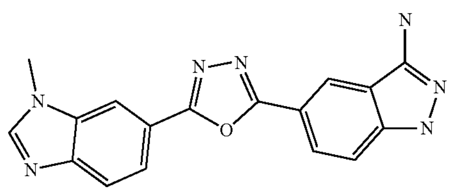 [SMILES: Cn1cnc2ccc(-c3nnc(-c4ccc5[nH]nc(N)c5c4)o3)cc21] | 705 | 5-[5-(1-methyl-1H-1,3-benzodiazol-6-yl)-1,3,4-oxadiazol-2-yl]-1H-indazol-3-amine | 331.12 | 332 |
| 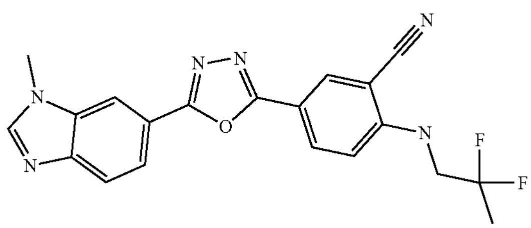 [SMILES: Cn1cnc2ccc(-c3nnc(-c4ccc(NCC(C)(F)F)c(C#N)c4)o3)cc21] | 706 | 2-[(2,2-difluoropropyl)amino]-5-[5-(1-methyl-1H-1,3-benzodiazol-6-yl)-1,3,4-oxadiazol-2-yl]benzonitrile | 394.14 | 395.1 |
| 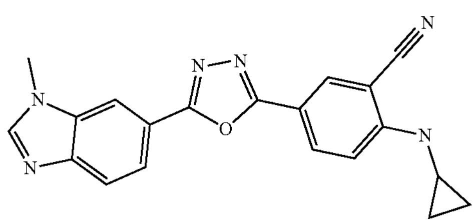 [SMILES: Cn1cnc2ccc(-c3nnc(-c4ccc(NC5CC5)c(C#N)c4)o3)cc21] | 707 | 2-(cyclopropylamino)-5-[5-(1-methyl-1H-1,3-benzodiazol-6-yl)-1,3,4-oxadiazol-2-yl]benzonitrile | 356.14 | 357.1 |
| 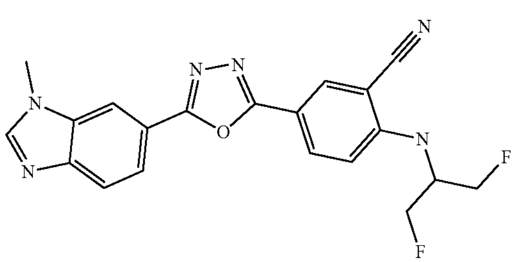 [SMILES: Cn1cnc2ccc(-c3nnc(-c4ccc(NC(CF)CF)c(C#N)c4)o3)cc21] | 708 | 2-[(1,3-difluoropropan-2-yl)amino]-5-[5-(1-methyl-1H-1,3-benzodiazol-6-yl)-1,3,4-oxadiazol-2-yl]benzonitrile | 394.14 | 395.1 |

-continued

| Structure | Compound Number | Chemical Name | Exact Mass | Actual Peak |
|---|---|---|---|---|
| 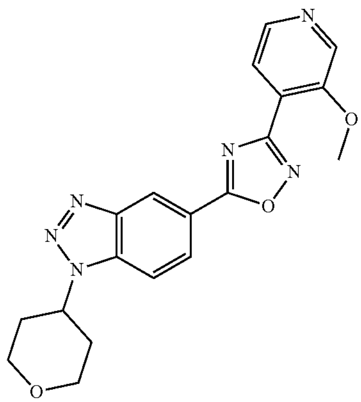 [SMILES: COc1cnccc1-c1noc(-c2ccc3c(c2)nnn3C2CCOCC2)n1] | 709 | 5-[3-(3-methoxypyridin-4-yl)-1,2,4-oxadiazol-5-yl]-1-(oxan-4-yl)-1H-1,2,3-benzotriazole | 378.14 | 379.1 |
| 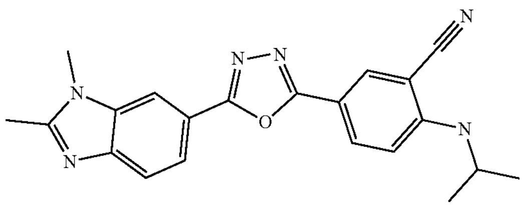 [SMILES: Cc1nc2ccc(-c3nnc(-c4ccc(NC(C)C)c(C#N)c4)o3)cc2n1C] | 710 | 5-[5-(1,2-dimethyl-1H-1,3-benzodiazol-6-yl)-1,3,4-oxadiazol-2-yl]-2-[(propan-2-yl)amino]benzonitrile | 372.17 | 373.1 |
| 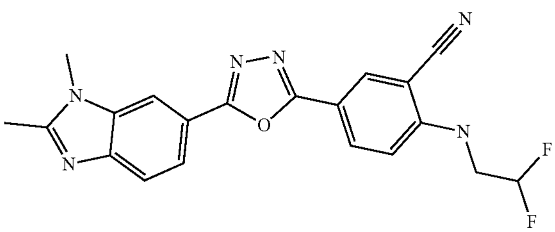 [SMILES: Cc1nc2ccc(-c3nnc(-c4ccc(NCC(F)F)c(C#N)c4)o3)cc2n1C] | 711 | 2-[(2,2-difluoroethyl)amino]-5-[5-(1,2-dimethyl-1H-1,3-benzodiazol-6-yl)-1,3,4-oxadiazol-2-yl]benzonitrile | 394.14 | 395.1 |
| 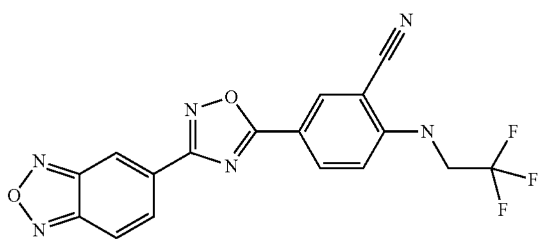 [SMILES: N#Cc1cc(-c2nc(-c3ccc4nonc4c3)no2)ccc1NCC(F)(F)F] | 712 | 5-[3-(2,1,3-benzoxadiazol-5-yl)-1,2,4-oxadiazol-5-yl]-2-[(2,2,2-trifluoroethyl)amino]benzonitrile | 386.07 | 387 |
| 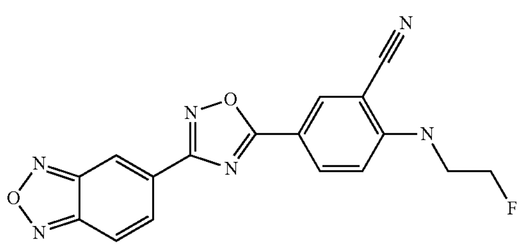 [SMILES: N#Cc1cc(-c2nc(-c3ccc4nonc4c3)no2)ccc1NCCF] | 713 | 5-[3-(2,1,3-benzoxadiazol-5-yl)-1,2,4-oxadiazol-5-yl]-2-[(2-fluoroethyl)amino]benzonitrile | 350.09 | 351 |
| 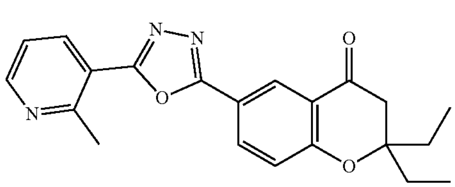 [SMILES: CCC1(CC)CC(=O)c2cc(-c3nnc(-c4cccnc4C)o3)ccc2O1] | 718 | 2,2-diethyl-6-(5-(2-methylpyridin-3-yl)-1,3,4-oxadiazol-2-yl)chroman-4-one | 363.16 | 364.4 |

-continued

| Structure | Compound Number | Chemical Name | Exact Mass | Actual Peak |
|---|---|---|---|---|
| 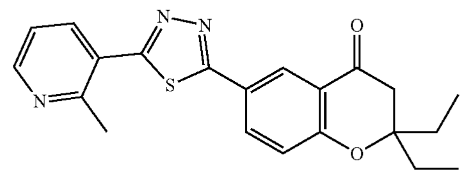 [SMILES: CCC1(CC)CC(=O)c2cc(-c3nnc(-c4cccnc4C)s3)ccc2O1] | 719 | 2,2-diethyl-6-(5-(2-methylpyridin-3-yl)-1,3,4-thiadiazol-2-yl)chroman-4-one | 379.14 | 380.2 |
| 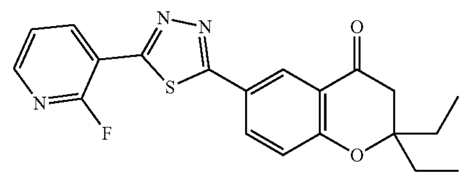 [SMILES: CCC1(CC)CC(=O)c2cc(-c3nnc(-c4cccnc4F)s3)ccc2O1] | 720 | 2,2-diethyl-6-(5-(2-fluoropyridin-3-yl)-1,3,4-thiadiazol-2-yl)chroman-4-one | 383.11 | 384.2 |
| 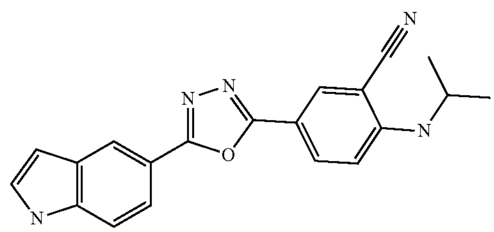 [SMILES: CC(C)Nc1ccc(-c2nnc(-c3ccc4[nH]ccc4c3)o2)cc1C#N] | 721 | 5-(5-(1H-indol-5-yl)-1,3,4-oxadiazol-2-yl)-2-(isopropylamino)benzonitrile | 343.14 | 344.4 |
| 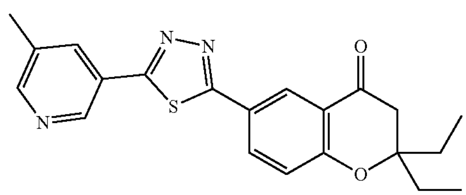 [SMILES: CCC1(CC)CC(=O)c2cc(-c3nnc(-c4cncc(C)c4)s3)ccc2O1] | 724 | 2,2-diethyl-6-(5-(5-methylpyridin-3-yl)-1,3,4-thiadiazol-2-yl)chroman-4-one | 379.14 | 380.3 |
| 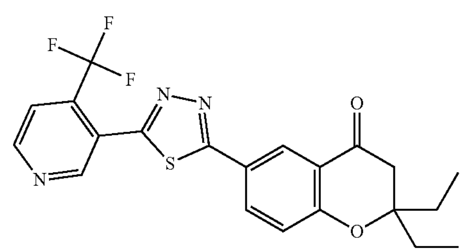 [SMILES: CCC1(CC)CC(=O)c2cc(-c3nnc(-c4cnccc4C(F)(F)F)s3)ccc2O1] | 725 | 2,2-diethyl-6-(5-(4-(trifluoromethyl)pyridin-3-yl)-1,3,4-thiadiazol-2-yl)chroman-4-one | 433.11 | 434.3 |
| 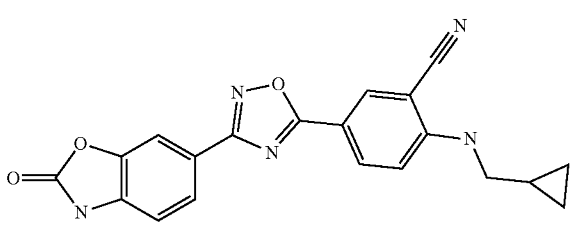 [SMILES: N#Cc1cc(-c2nc(-c3ccc4[nH]c(=O)oc4c3)no2)ccc1NCC1CC1] | 726 | 2-(cyclopropylmethylamino)-5-[3-(2-oxo-3H-1,3-benzoxazol-6-yl)-1,2,4-oxadiazol-5-yl]benzonitrile | 373.12 | 374.1 |
| 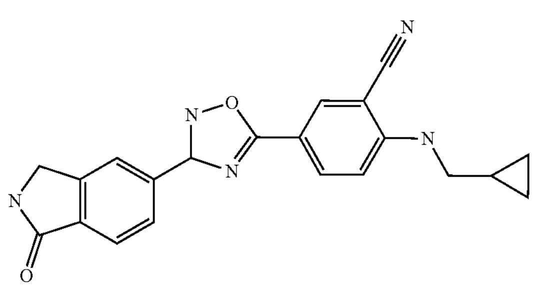 [SMILES: N#Cc1cc(C2=NC(c3ccc4c(c3)CNC4=O)NO2)ccc1NCC1CC1] | 727 | 2-((cyclopropylmethyl)amino)-5-(3-(1-oxoisoindolin-5-yl)-1,2,4-oxadiazol-5-yl)benzonitrile | 371.14 | 372.1 |

-continued

| Structure | Compound Number | Chemical Name | Exact Mass | Actual Peak |
|---|---|---|---|---|
| 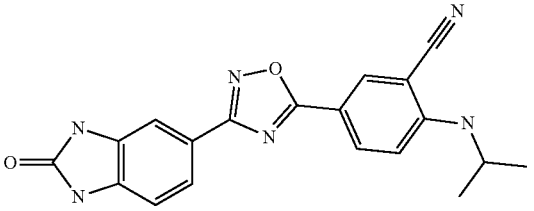 [SMILES: CC(C)Nc1ccc(-c2nc(-c3ccc4[nH]c(=O)[nH]c4c3)no2)cc1C#N] | 728 | 2-(isopropylamino)-5-(3-(2-oxo-2,3-dihydro-1H-benzo[d]imidazol-5-yl)-1,2,4-oxadiazol-5-yl)benzonitrile | 360.13 | 361.1 |
| 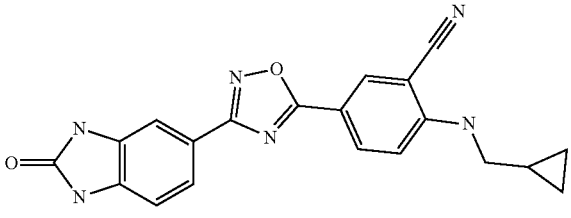 [SMILES: N#Cc1cc(-c2nc(-c3ccc4[nH]c(=O)[nH]c4c3)no2)ccc1NCC1CC1] | 729 | 2-((cyclopropylmethyl)amino)-5-(3-(2-oxo-2,3-dihydro-1H-benzo[d]imidazol-5-yl)-1,2,4-oxadiazol-5-yl)benzonitrile | 372.13 | 373.1 |
| 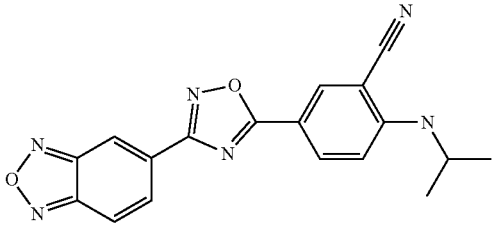 [SMILES: CC(C)Nc1ccc(-c2nc(-c3ccc4nonc4c3)no2)cc1C#N] | 730 | 5-[3-(2,1,3-benzoxadiazol-5-yl)-1,2,4-oxadiazol-5-yl]-2-[(propan-2-yl)amino]benzonitrile | 346.12 | 347.1 |
| 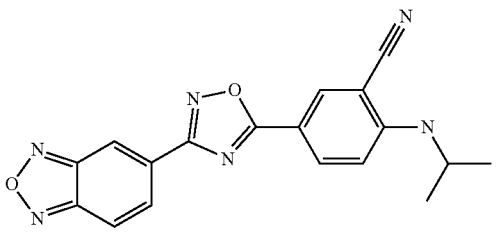 [SMILES: CC(C)Nc1ccc(-c2nc(-c3ccc4nonc4c3)no2)cc1C#N] | 730 | 5-[3-(2,1,3-benzoxadiazol-5-yl)-1,2,4-oxadiazol-5-yl]-2-[(propan-2-yl)amino]benzonitrile | 346.12 | 347.1 |
| 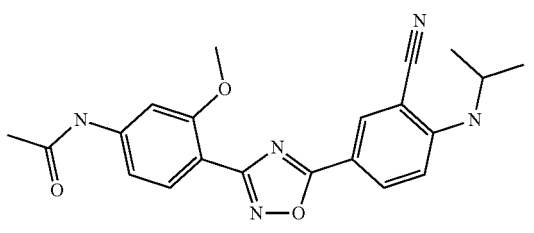 [SMILES: COc1cc(NC(C)=O)ccc1-c1noc(-c2ccc(NC(C)C)c(C#N)c2)n1] | 731 | N-[4-(5-{3-cyano-4-[(propan-2-yl)amino]phenyl}-1,2,4-oxadiazol-3-yl)-3-methoxyphenyl]acetamide | 391.16 | 392.1 |
| 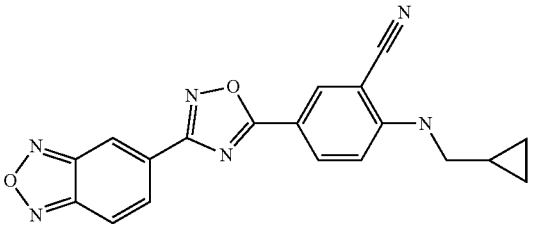 [SMILES: N#Cc1cc(-c2nc(-c3ccc4nonc4c3)no2)ccc1NCC1CC1] | 732 | 5-[3-(2,1,3-benzoxadiazol-5-yl)-1,2,4-oxadiazol-5-yl]-2-[(2,2-difluoroethyl)amino]benzonitrile | 358.12 | 369 |

-continued

| Structure | Compound Number | Chemical Name | Exact Mass | Actual Peak |
|---|---|---|---|---|
| 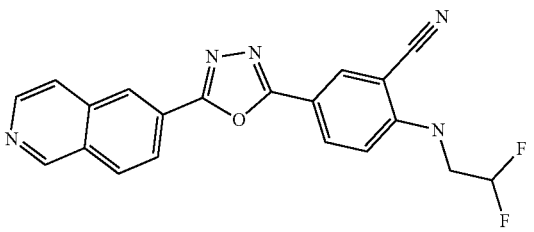 [SMILES: N#Cc1cc(-c2nnc(-c3ccc4cnccc4c3)o2)ccc1NCC(F)F] | 733 | 2-[(2,2-difluoroethyl)amino]-5-[5-(isoquinolin-6-yl)-1,3,4-oxadiazol-2-yl]benzonitrile | 377.11 | 378.1 |
| 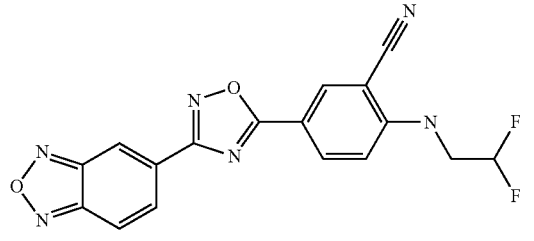 [SMILES: N#Cc1cc(-c2nc(-c3ccc4nonc4c3)no2)ccc1NCC(F)F] | 734 | 5-[3-(2,1,3-benzoxadiazol-5-yl)-1,2,4-oxadiazol-5-yl]-2-[(cyclopropylmethyl)amino]benzonitrile | 368.08 | 359 |
| 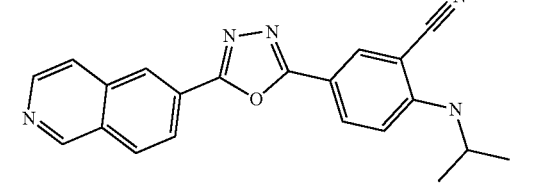 | 735 | 5-[5-(isoquinolin-6-yl)-1,3,4-oxadiazol-2-yl]-2-[(propan-2-yl)amino]benzonitrile | 355.14 | 356.1 |
| 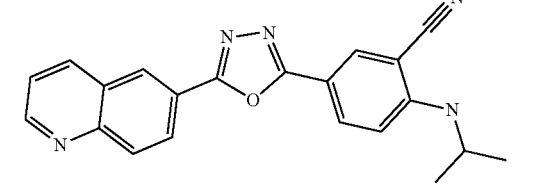 | 736 | 2-[(propan-2-yl)amino]-5-[5-(quinolin-6-yl)-1,3,4-oxadiazol-2-yl]benzonitrile | 355.14 | 356.1 |
| 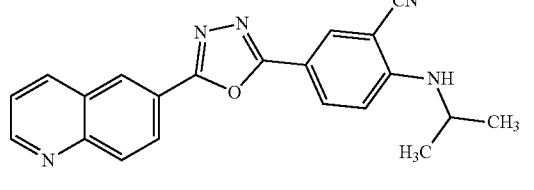 | 736 | 2-[(propan-2-yl)amino]-5-[5-(quinolin-6-yl)-1,3,4-oxadiazol-2-yl]benzonitrile | 355.14 | 356.1 |
| 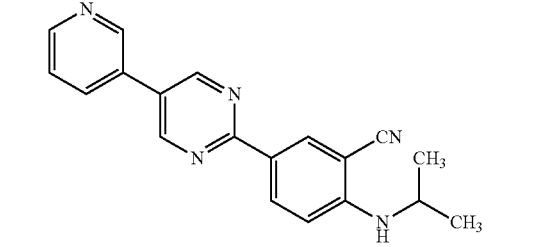 [SMILES: CC(C)Nc1ccc(-c2ncc(-c3cccnc3)cn2)cc1C#N] | 737 | 2-(isopropylamino)-5-(5-(pyridin-3-yl)pyrimidin-2-yl)benzonitrile | 315.15 | 316 |

-continued

| Structure | Compound Number | Chemical Name | Exact Mass | Actual Peak |
|---|---|---|---|---|
| 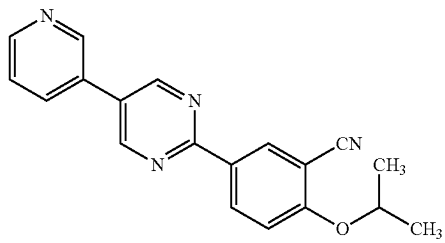 [SMILES: CC(C)Oc1ccc(-c2ncc(-c3cccnc3)cn2)cc1C#N] | 738 | 2-isopropoxy-5-(5-(pyridin-3-yl)pyrimidin-2-yl)benzonitrile | 316.13 | 317 |
| 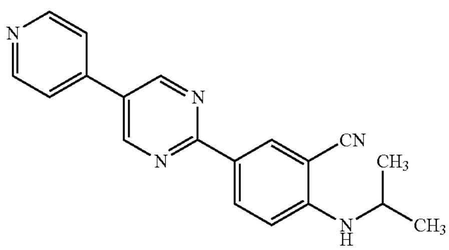 [SMILES: CC(C)Nc1ccc(-c2ncc(-c3ccncc3)cn2)cc1C#N] | 739 | 2-(isopropylamino)-5-(5-(pyridin-4-yl)pyrimidin-2-yl)benzonitrile | 315.15 | 316 |
| 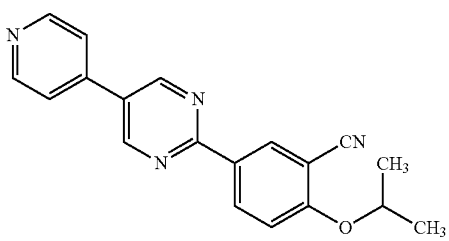 | 740 | 2-isopropoxy-5-(5-(pyridin-4-yl)pyrimidin-2-yl)benzonitrile | 316.13 | 317 |
| 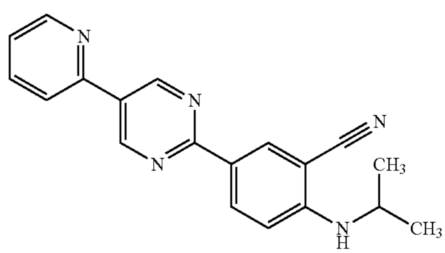 [SMILES: CC(C)Nc1ccc(-c2ncc(-c3ccccn3)cn2)cc1C#N] | 741 | 2-(isopropylamino)-5-(5-(pyridin-2-yl)pyrimidin-2-yl)benzonitrile | 315.15 | 316 |
| 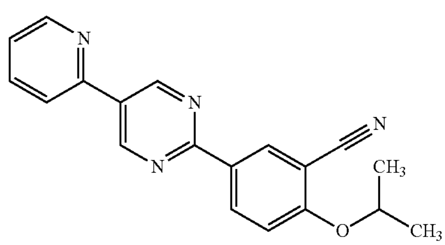 [SMILES: CC(C)Oc1ccc(-c2ncc(-c3ccccn3)cn2)cc1C#N] | 742 | 2-isopropoxy-5-(5-(pyridin-2-yl)pyrimidin-2-yl)benzonitrile | 316.15 | 317 |
| 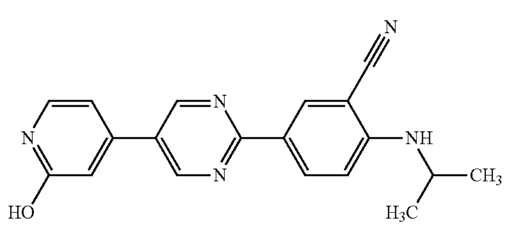 [SMILES: CC(C)Nc1ccc(-c2ncc(-c3ccnc(O)c3)cn2)cc1C#N] | 743 | 5-(5-(2-hydroxypyridin-4-yl)pyrimidin-2-yl)-2-(isopropylamino)benzonitrile | 331.14 | 332 |

-continued

| Structure | Compound Number | Chemical Name | Exact Mass | Actual Peak |
|---|---|---|---|---|
| 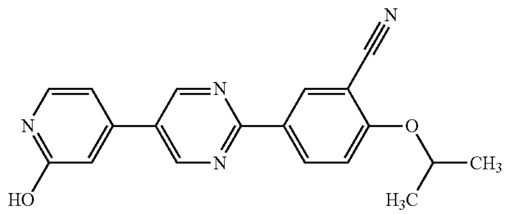 [SMILES: CC(C)Oc1ccc(-c2ncc(-c3ccnc(O)c3)cn2)cc1C#N] | 744 | 5-(5-(2-hydroxypyridin-4-yl)pyrimidin-2-yl)-2-isopropoxybenzonitrile | 332.13 | 333 |
| 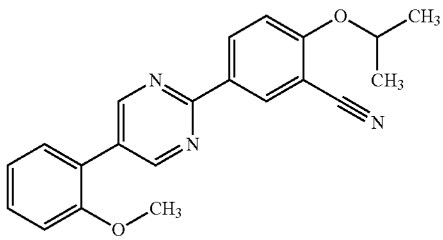 [SMILES: COc1ccccc1-c1cnc(-c2ccc(OC(C)C)c(C#N)c2)nc1] | 745 | 2-isopropoxy-5-(5-(2-methoxyphenyl)pyrimidin-2-yl)benzonitrile | 345.15 | 346 |
| 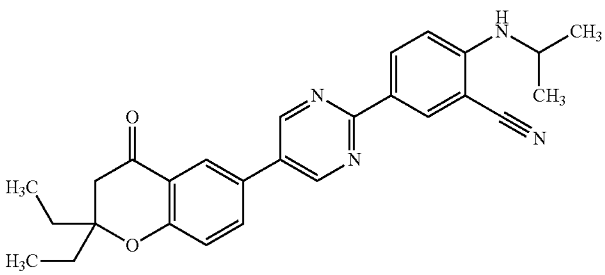 [SMILES: CCC1(CC)CC(=O)c2cc(-c3cnc(-c4ccc(NC(C)C)c(C#N)c4)nc3)ccc2O1] | 746 | 5-(5-(2,2-diethyl-4-oxochroman-6-yl)pyrimidin-2-yl)-2-(isopropylamino)benzonitrile | 440.22 | 441.4 |
| 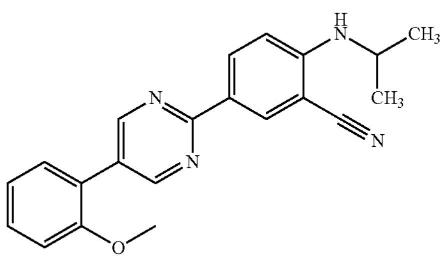 [SMILES: COc1ccccc1-c1cnc(-c2ccc(NC(C)C)c(C#N)c2)nc1] | 747 | 2-(isopropylamino)-5-(5-(2-methoxyphenyl)pyrimidin-2-yl)benzonitrile | 344.16 | 345.3 |
| 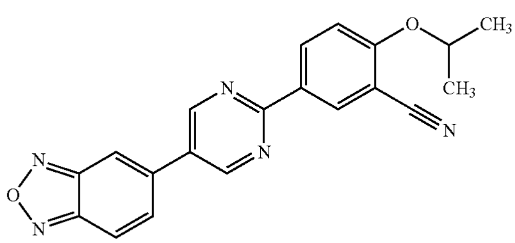 [SMILES: CC(C)Oc1ccc(-c2ncc(-c3ccc4nonc4c3)cn2)cc1C#N] | 748 | 5-(5-(benzo[c][1,2,5]oxadiazol-5-yl)pyrimidin-2-yl)-2-isopropoxybenzonitrile | 357.12 | 357.9 |
| 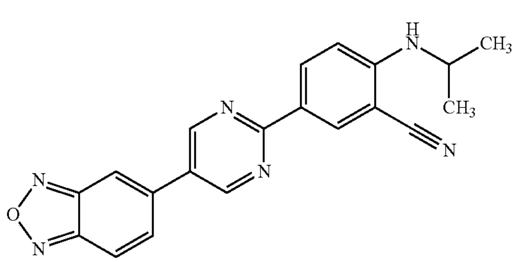 [SMILES: CC(C)Nc1ccc(-c2ncc(-c3ccc4nonc4c3)cn2)cc1C#N] | 749 | 5-(5-(benzo[c][1,2,5]oxadiazol-5-yl)pyrimidin-2-yl)-2-(isopropylamino)benzonitrile | 356.14 | 356.9 |

-continued
| Structure | Compound Number | Chemical Name | Exact Mass | Actual Peak |
|---|---|---|---|---|
| 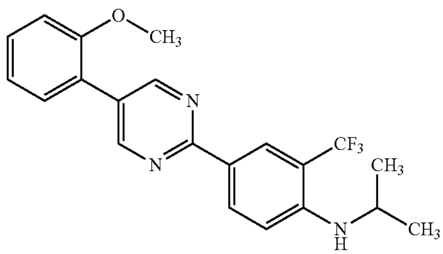 [SMILES: COc1ccccc1-c1cnc(-c2ccc(NC(C)C)c(C(F)(F)F)c2)nc1] | 750 | N-isopropyl-4-(5-(2-methoxyphenyl)pyrimidin-2-yl)-2-(trifluoromethyl)aniline | 387.16 | 388 |
| 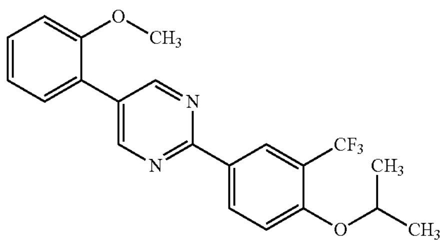 [SMILES: COc1ccccc1-c1cnc(-c2ccc(OC(C)C)c(C(F)(F)F)c2)nc1] | 751 | 2-(4-isopropoxy-3-(trifluoromethyl)phenyl)-5-(2-methoxyphenyl)pyrimidine | 388.14 | 389 |
| 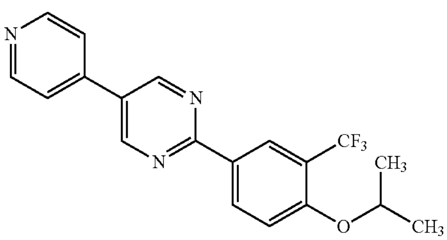 [SMILES: CC(C)Oc1ccc(-c2ncc(-c3ccncc3)cn2)cc1C(F)(F)F] | 752 | 2-(4-isopropoxy-3-(trifluoromethyl)phenyl)-5-(pyridin-4-yl)pyrimidine | 359.13 | 360 |
General Procedure A:
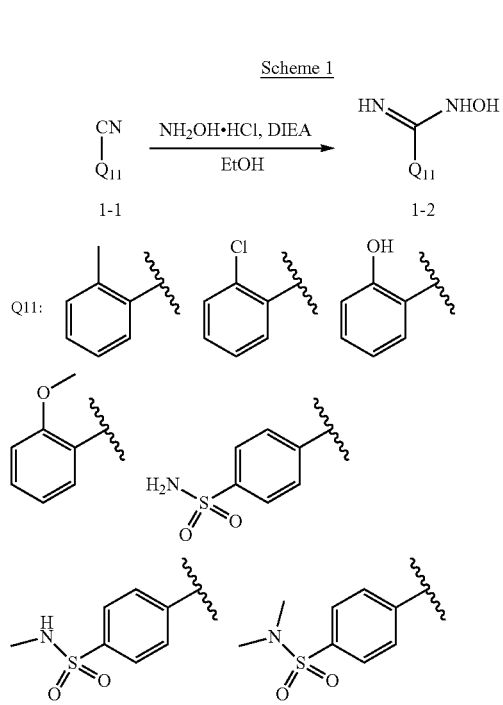
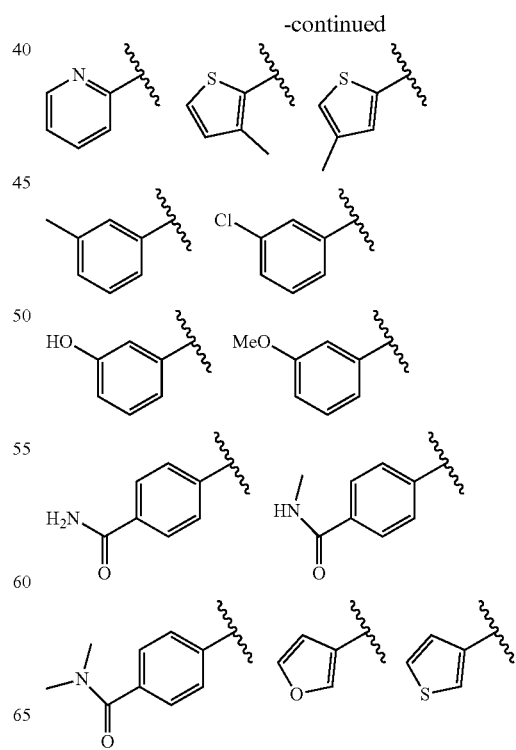

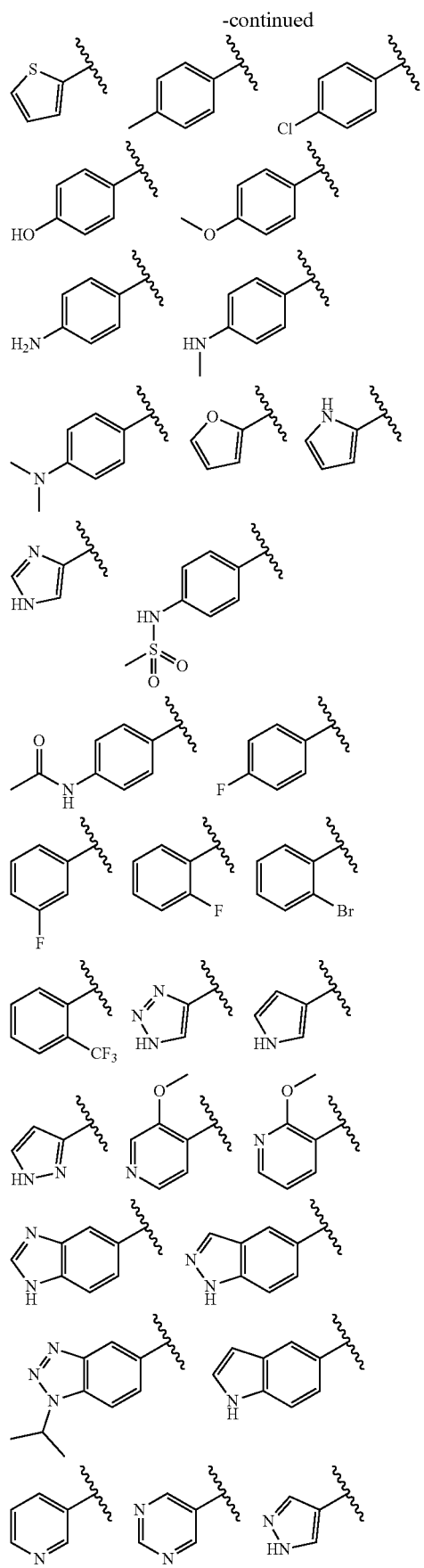
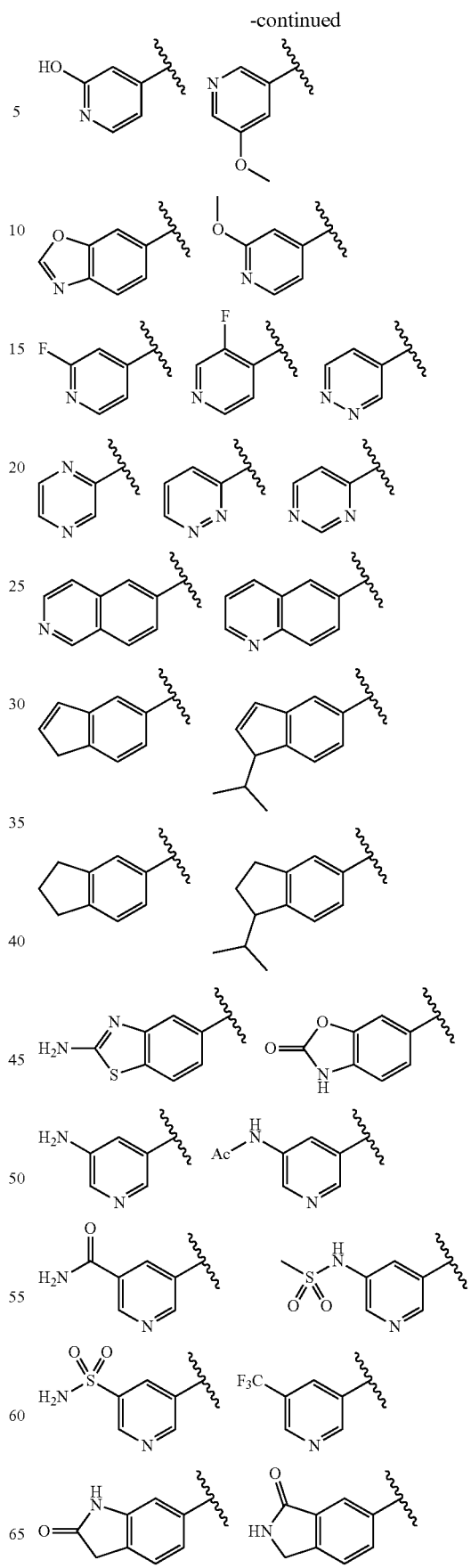

-continued

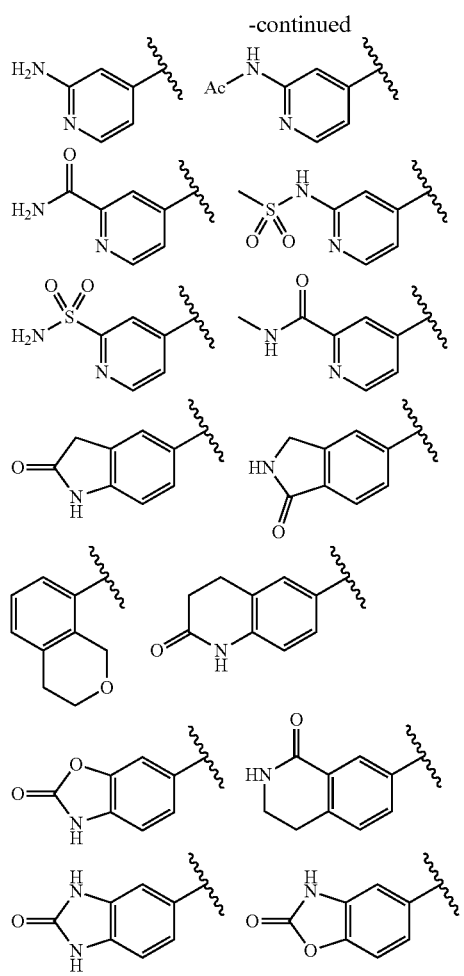

Example 2

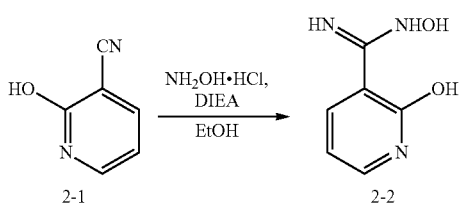

Synthesis of Intermediate 2-2:
N,2-dihydroxypyridine-3-carboximidamide

To a mixture of 2-1 (2-hydroxypyridine-3-carbonitrile)(200 mg, 1.67 mmol) in ethanol (10 mL) was added hydrochloride salt of hydroxylamine (174 mg, 2.50 mmol), diisopropylethylamine (430 mg, 3.33 mmol) at 20° C. The mixture was then heated to 90° C. and stirred for 16 hrs. The mixture was concentrated in vacuum to remove part of ethanol, the resulting mixture was filtered, and the solid was dried in vacuum which was used as the product in next step without further purification (185 mg, 69% yield).

$^1$H NMR (400 MHz, DMSO-$d_6$) δ=12.06 (br, s, 1H), 9.50 (br, s, 1H), 7.95 (dd, J=7.2, 2.4 Hz, 1H), 7.51 (dd, J=6.0, 2.0 Hz, 1H), 6.3-6.30 (m, 3H).

General Procedure B

Synthesis of Intermediate 3-2: 2,2-diethyl-4-oxo-3,4-dihydro-2H-1-benzopyran-6-carboxylic acid

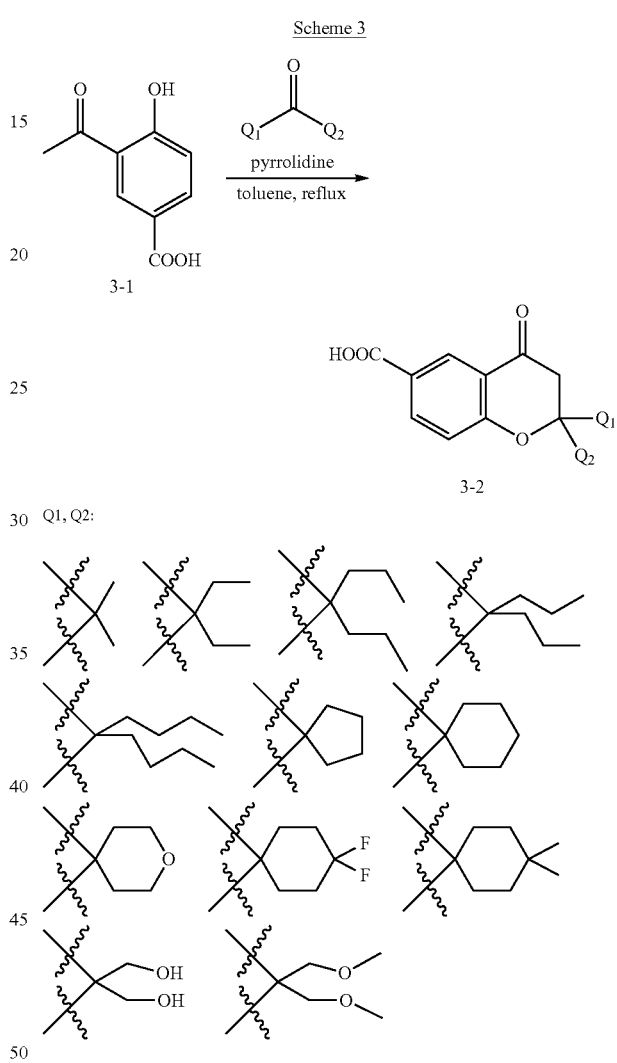

Alternative Synthesis of Intermediate 4-4: 2,2-diethyl-4-oxo-3,4-dihydro-2H-1-benzopyran-6-carboxylic acid Scheme 4

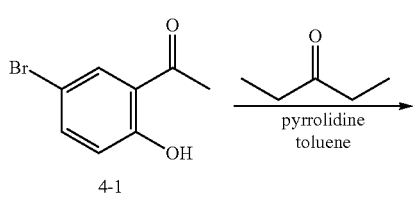

Synthesis of 4-2: 6-bromo-2,2-diethyl-3,4-dihydro-2H-1-benzopyran-4-one

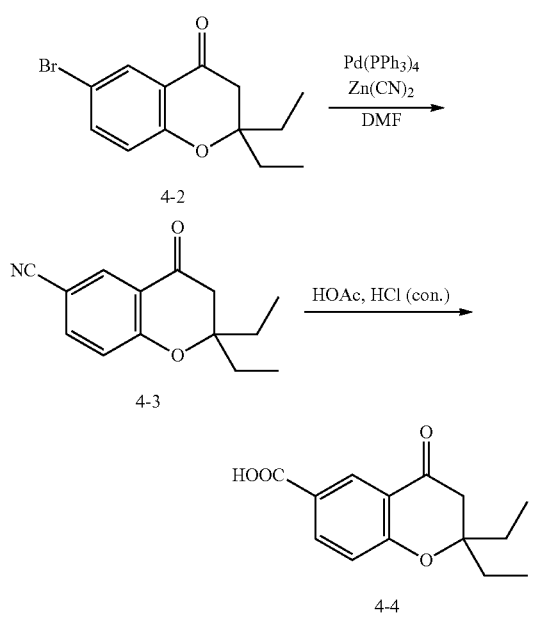

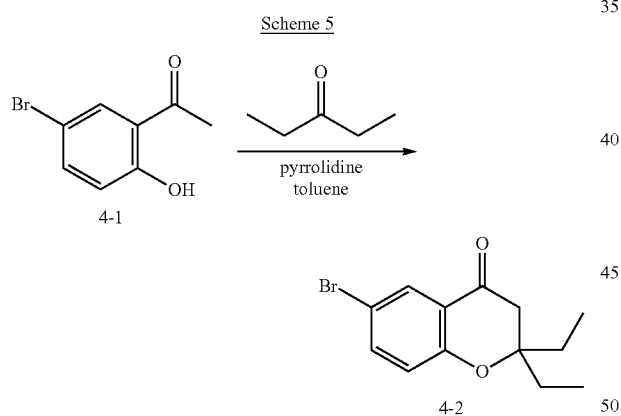

To a solution of 1-(5-bromo-2-hydroxy-phenyl)ethanone (20 g, 93.0 mmol, 1 eq) in methanol (400 mL) was added pyrrolidine (7.94 g, 112 mmol, 1.2 eq) and pentan-3-one (9.61 g, 112 mmol, 1.2 eq). The mixture was stirred at 80° C. for 16 hr. The reaction mixture diluted with water (200 mL) and extracted with ethyl acetate (200 mL×2), the combined organic layers were washed with brine (500 mL), dried over sodium sulfate, filtered and concentrated under reduced pressure to give a residue which was purified by column chromatography to give the desired product 4-2 (12 g, 46% yield) as a yellow oil.

$^1$H NMR (400 MHz, CDCl$_3$) δ=7.93 (d, J=2.5 Hz, 1H), 7.52 (dd, J=8.8, 2.6 Hz, 1H), 6.84 (d, J=8.8 Hz, 1H), 2.70 (s, 2H), 1.86-1.62 (m, 4H), 0.92 (t, J=7.5 Hz, 6H).

Synthesis of Intermediate 4-3: 2,2-diethyl-4-oxo-3,4-dihydro-2H-1-benzopyran-6-carbonitrile

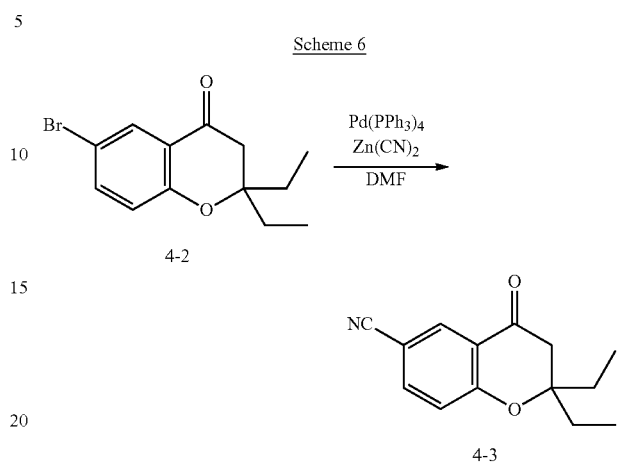

To a solution of 6-bromo-2,2-diethyl-chroman-4-one (10 g, 35.3 mmol, 1 eq) in DMF (100 mL) was added zinc cyanide (6.22 g, 53.0 mmol, 1.5 eq) and tetratriphenylphosphine palladium (4.08 g, 3.53 mmol, 0.1 eq). The mixture was stirred at 130° C. for 2 hr. The reaction mixture was diluted with water (100 mL) and extracted with ethyl acetate (100 mL×3). The combined organic layers were washed with brine (200 mL), dried over sodium sulfate, filtered and concentrated under reduced pressure to give a residue which was purified by flash silica gel chromatography (petroleum ether/ethyl acetate=100/1 to 1/1) to give the desired product 4-3 (8 g, 99% yield).

$^1$H NMR (400 MHz, DMSO-d$_6$) δ=8.08 (d, J=1.9 Hz, 1H), 7.96 (dd, J=8.7, 2.0 Hz, 1H), 7.20 (d, J=8.7 Hz, 1H), 2.88 (s, 2H), 1.86-1.59 (m, 4H), 0.86 (br, t, J=7.4 Hz, 6H).

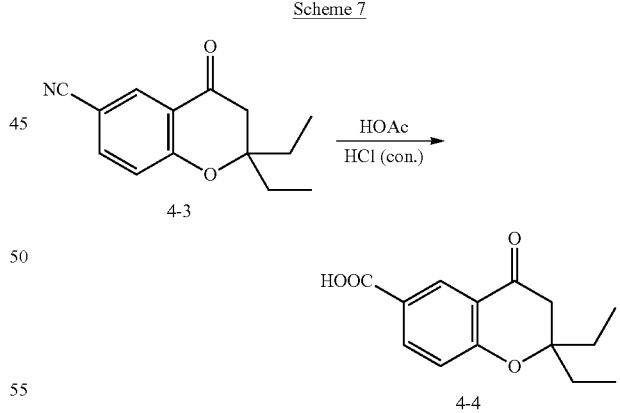

Synthesis of Intermediate 4-4: 2,2-diethyl-4-oxo-3,4-dihydro-2H-1-benzopyran-6-carboxylic acid A suspension of 2,2-diethyl-4-oxo-chromane-6-carbonitrile (6.05 g, 26.4 mmol, 1 eq) in acetic acid (60 mL) and concentrated hydrochloride solution (60 mL) was stirred at 120° C. for 16 hr, The residue was triturated with water (500 mL), filtered and dried under vacuum to give the titled product 4-4 (5.8 g, 89% yield).

$^1$H NMR (400 MHz, DMSO-d$_6$) δ=8.27 (d, J=1.9 Hz, 1H), 8.06 (dd, J=8.7, 2.0 Hz, 1H), 7.11 (d, J=8.7 Hz, 1H), 2.85 (s, 2H), 1.77-1.68 (m, 4H), 0.87 (t, J=7.4 Hz, 6H).

General Procedure C

Scheme 8

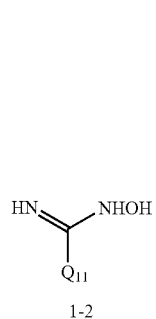

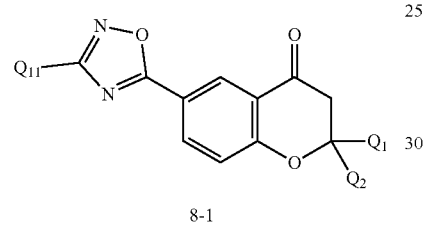

Scheme 8

Synthesis of Compound 9a-1: 2,2-diethyl-6-(3-(2-hydroxypyridin-3-yl)-1,2,4-oxadiazol-5-yl)chroman-4-one

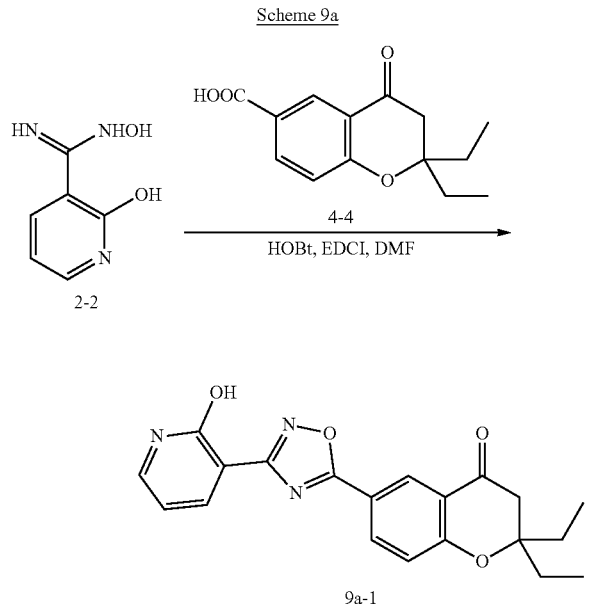

To a mixture of 4-4 (268 mg, 1.08 mmol) in N,N-dimethylformamide (6 mL) was added HOBt (159 mg, 1.18 mmol, 1.2 eq), EDCI (225 mg, 1.18 mmol, 1.2 eq) at 20° C. under nitrogen atmosphere. The mixture was stirred for 30 min, then, 2-2 (150 mg, 980 umol, 1 eq) was added, and the resultant mixture was then heated to 120° C. and stirred for 2 hrs. The mixture was diluted with water (20 mL), extracted with ethyl acetate (20 mL×3). The combined organic phase was washed by brine (50 mL), dried over sodium sulfate, concentrated in vacuum. The residue was purified by prep-HPLC (column: Phenomenex Gemini 150×25 mm×10 um; mobile phase: [water (0.05% ammonia hydroxide v/v)-ACN]; B %: 35%-65%, 12 min) to give the product 9-1 as a white solid (20 mg, 6% yield).

$^1$H NMR (400 MHz, DMSO-d$_6$) δ=12.23 (br, s, 1H), 8.44 (d, J=2.0 Hz, 1H), 8.33 (dd, J=7.2, 2.0 Hz, 1H), 8.28 (dd, J=8.8, 2.4 Hz, 1H), 7.68 (dd, J=6.0, 2.0 Hz, 1H), 7.29 (d, J=8.8 Hz, 1H), 6.42 (t, J=6.8 Hz, 1H), 2.93 (s, 2H), 1.81-1.70 (m, 4H), 0.90 (t, J=7.2 Hz, 6H).

Synthesis of Compound: 2,2-diethyl-6-[3-(1H-pyrazol-4-yl)-1,2,4-oxadiazol-5-yl]-3H-1-benzopyran-4-one

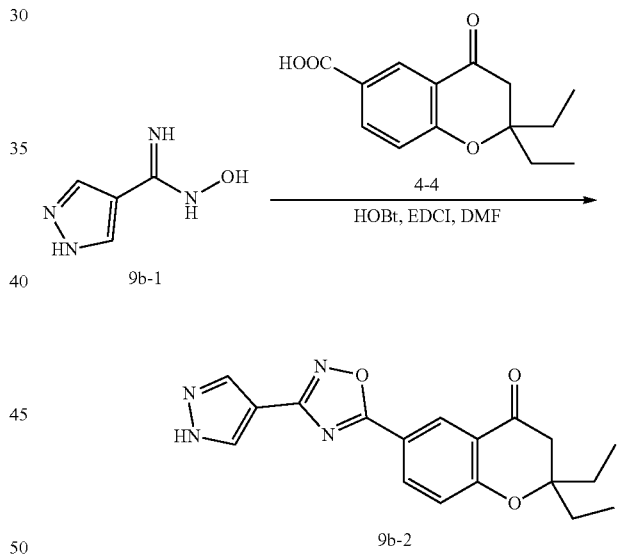

To a solution of compound 4-4 (16.41 g, 66.08 mmol, 1 eq.) in DMF (50 mL) was added EDCI (15.20 g, 79.29 mmol, 1.2 eq.) and HOBt (8.93 g, 66.08 mmol, 1.0 eq.), stirred at 20° C. for 0.5 hour. Then compound 9b-1 (10 g, 79.29 mmol, 1.2 eq.) was added. The mixture was stirred at 20° C. for 0.5 hour, then heated to 120° C. and stirred for 2 hours. The mixture was diluted with water (100 mL), extracted with EtOAc (150 mL*3), dried with sodium sulfate, filtered and concentrated. The residue was purified by silica gel column chromatography (PE:EA=3:1) to give 9b-2 (7.2 g, yield: 30%) as white solid.

$^1$H NMR (400 MHz, DMSO-d$_6$) δ=13.49 (br. s, 1H), 8.47 (s, 1H), 8.42 (d, J=2.3 Hz, 1H), 8.26 (dd, J=2.3, 8.8 Hz, 1H), 8.06 (s, 1H), 7.26 (d, J=8.7 Hz, 1H), 2.91 (s, 2H), 1.79-1.69 (m, 4H), 0.89 (t, J=7.4 Hz, 6H).

General Procedure D

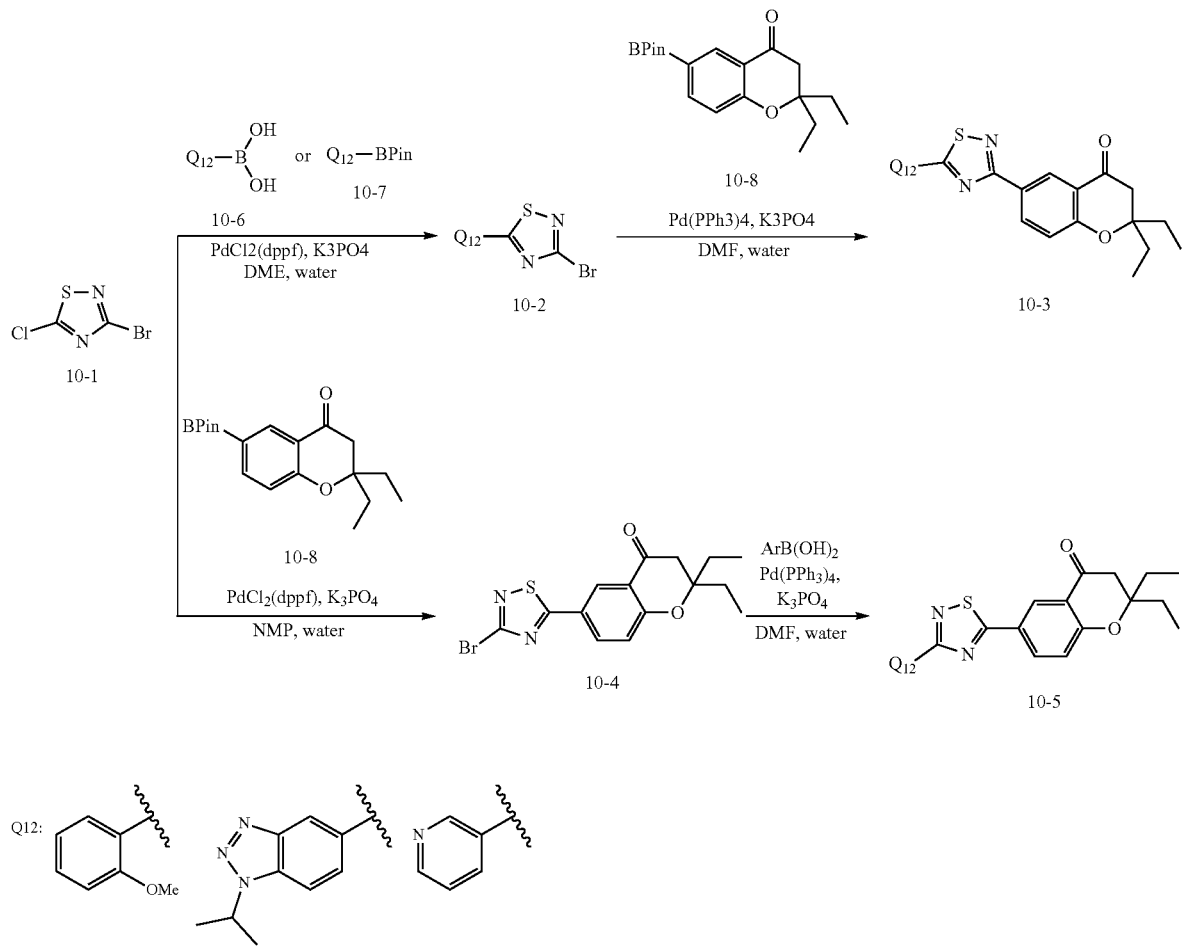

Synthesis of 11-1:
3-bromo-5-(3-methoxyphenyl)-1,2,4-thiadiazole

Scheme 11

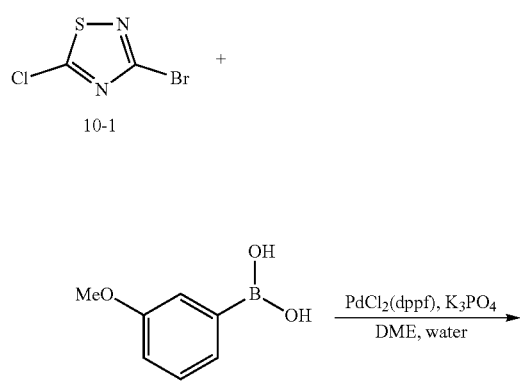

-continued

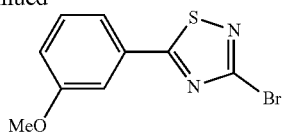

To a solution of (3-methoxyphenyl)boronic acid (247.25 mg, 1.63 mmol, 1 eq) in DME (5 mL) was added Pd(dppf)Cl$_2$ (119.06 mg, 162.71 umol, 0.1 eq), K$_3$PO$_4$ (1.04 g, 4.88 mmol, 3 eq) and 10-1, 3-bromo-5-chloro-1,2,4-thiadiazole (649.07 mg, 3.25 mmol, 2 eq). The mixture was stirred at 80° C. for 0.5 h. The reaction mixture was diluted with water (50 mL) and extracted with EA (50 mL×3). The combined organic layers were dried over Na$_2$SO$_4$, filtered and concentrated under reduced pressure to give a residue. The residue was purified by flash silica gel chromatography (PE/EA 10/1) to give 11-1 (3-bromo-5-(3-methoxyphenyl)-1,2,4-thiadiazole) (200 mg, 737.64 umol, 45% yield) as a white solid.

$^1$H NMR (400 MHz, DMSO-d$_6$) δ=8.23 (dd, J=1.6, 7.8 Hz, 1H), 7.78-7.57 (m, 1H), 7.38 (d, J=8.4 Hz, 1H), 7.21 (t, J=7.6 Hz, 1H), 4.13 (s, 3H).

593

Synthesis of 12-1: 2,2-diethyl-6-[5-(2-methoxyphenyl)-1,2,4-thiadiazol-3-yl]-3,4-ihydro-2H-1-benzopyran-4-one Scheme 12

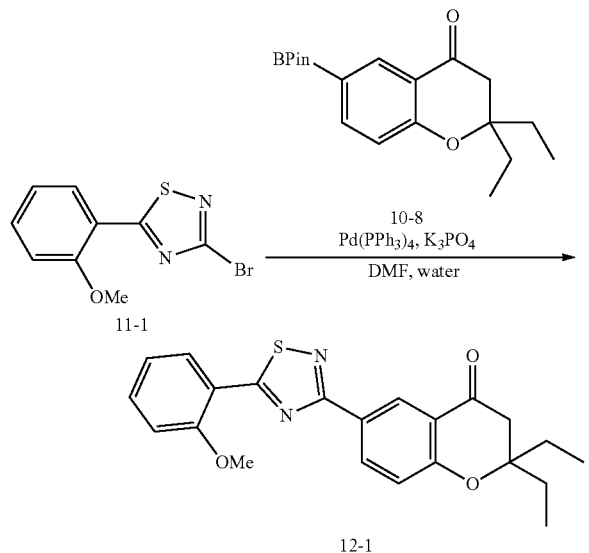

To a solution of 3-bromo-5-(2-methoxyphenyl)-1,2,4-thiadiazole (100 mg, 368.82 umol, 1 eq) and 2,2-diethyl-6-(4,4,5,5-tetramethyl-1,3,2-dioxaborolan-2-yl)chroman-4-one (146.15 mg, 442.59 umol, 1.2 eq) in DMF (1 mL) and H$_2$O (0.5 mL) was added K$_3$PO$_4$ (234.87 mg, 1.11 mmol, 3 eq) and Pd(PPh$_3$)$_4$ (42.62 mg, 36.88 umol, 0.1 eq) and stirred at 120° C. for 0.25 h. The residue was purified by prep-HPLC (column: Phenomenex Synergi C18 150×25×10 um; mobile phase: [water(0.225% FA)-ACN]; B %: 70%-100%, 10 min) to give 2,2-diethyl-6-[5-(2-methoxyphenyl)-1,2,4-thiadiazol-3-yl]chroman-4-one (34.5 mg, 87.46 umol, 23.71% yield, 100% purity) as a yellow solid.

$^1$H NMR (400 MHz, DMSO-d$_6$) δ=8.66 (d, J=2.1 Hz, 1H), 8.52-8.41 (m, 2H), 7.71-7.62 (m, 1H), 7.39 (d, J=8.3 Hz, 1H), 7.26 (t, J=7.5 Hz, 1H), 7.19 (d, J=8.7 Hz, 1H), 4.14 (s, 3H), 2.88 (s, 2H), 1.76 (quint, J=7.2, 14.4 Hz, 4H), 0.90 (t, J=7.4 Hz, 6H).

Synthesis of 10-8: 2,2-diethyl-6-(tetramethyl-1,3,2-dioxaborolan-2-yl)-3,4-dihydro-2H-1-benzopyran-4-one Scheme 13

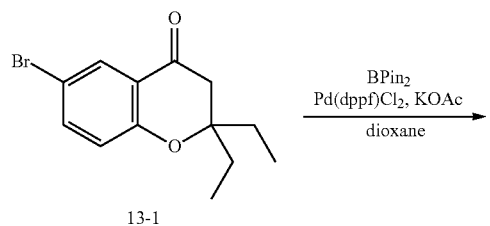

594

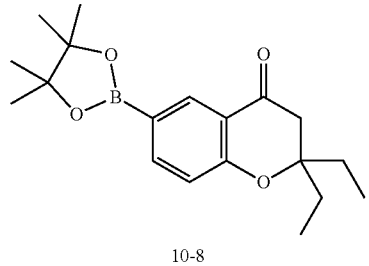

To a solution of 6-bromo-2,2-diethyl-chroman-4-one (1 g, 3.53 mmol, 1 eq) in dioxane (10 mL) was added 4,4,5,5-tetramethyl-2-(4,4,5,5-tetramethyl-1,3,2-dioxaborolan-2-yl)-1,3,2-dioxaborolane (986.48 mg, 3.88 mmol, 1.1 eq), DPPF (195.78 mg, 353.16 umol, 0.1 eq), Pd(dppf)Cl$_2$ (258.41 mg, 353.16 umol, 0.1 eq) and KOAc (415.92 mg, 4.24 mmol, 1.2 eq), the mixture was stirred at 100° C. for 4 h, The reaction mixture was diluted with water (100 mL) and extracted with (EA 100 mL×2). The combined organic layers were dried over Na$_2$SO$_4$, filtered and concentrated under reduced pressure to give a residue. The residue was purified by flash silica gel chromatography (PE/EA=1/1) to give 2,2-diethyl-6-(4,4,5,5-tetramethyl-1,3,2-dioxaborolan-2-yl)chroman-4-one (1 g, 3.03 mmol, 85.75% yield) as a white solid.

$^1$H NMR (400 MHz, CHLOROFORM-d) δ=8.26 (d, J=1.6 Hz, 1H), 7.86-7.75 (m, 1H), 6.85 (d, J=8.3 Hz, 1H), 2.64 (s, 2H), 1.82-1.58 (m, 4H), 1.32-1.21 (m, 12H), 0.85 (t, J=7.5 Hz, 6H).

Synthesis of 14-5: 1-(propan-2-yl)-5-(tetramethyl-1,3,2-dioxaborolan-2-yl)-1H-1,2,3-benzotriazole Scheme 14

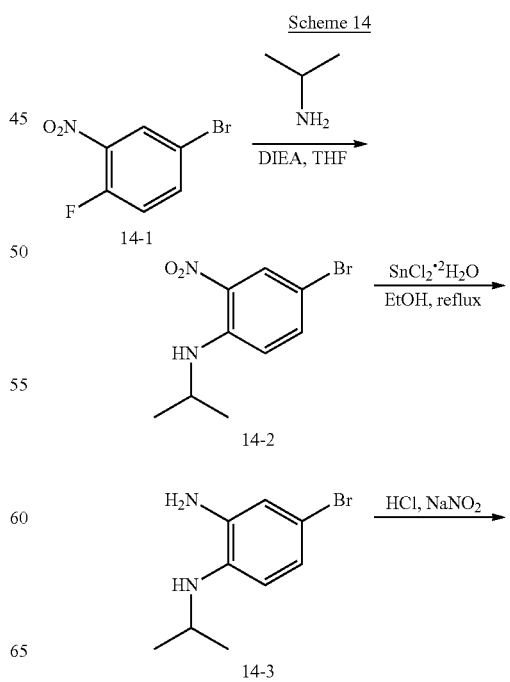

596

Synthesis of 14-3: 4-bromo-1-N-(propan-2-yl)benzene-1,2-diamine Scheme 16

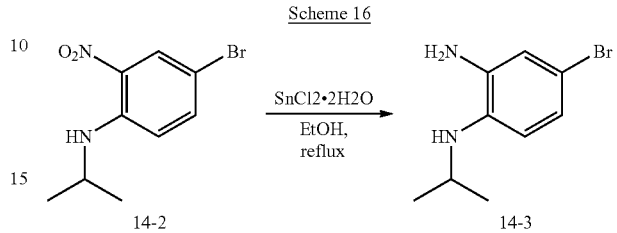

Scheme 16

To a solution of 4-bromo-N-isopropyl-2-nitro-aniline (2 g, 7.72 mmol, 1 eq) in EtOH (20 mL) was added SnCl$_2$.2H$_2$O (5.23 g, 23.16 mmol, 1.93 mL, 3 eq) and stirred at 80° C. for 16 h. The reaction mixture was quenched with aqueous NaOH (4 M, 50 mL), and then diluted with water (50 mL) and extracted with EA (100 mL×2). The combined organic layers were dried over Na$_2$SO$_4$, filtered and concentrated under reduced pressure to give a residue. The residue was purified by flash silica gel chromatography (PE/EA=100/1 to 1/1) to give 4-bromo-N-isopropyl-benzene-1,2-diamine (850 mg, 3.71 mmol, 48.06% yield) as a black-brown solid.

$^1$H NMR (400 MHz, CHLOROFORM-d) δ=6.82 (dd, J=2.1, 8.4 Hz, 1H), 6.76 (d, J=2.2 Hz, 1H), 6.44 (d, J=8.3 Hz, 1H), 3.56-3.40 (m, 1H), 1.14 (d, J=6.4 Hz, 6H).

Synthesis of 14-4: 5-bromo-1-(propan-2-yl)-1H-1,2,3-benzotriazole

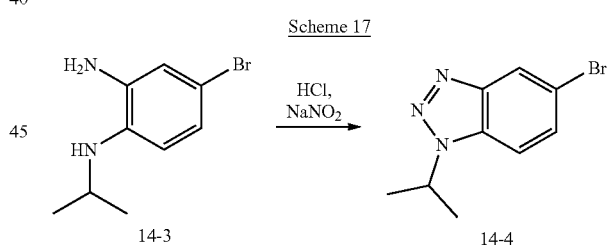

To a solution of 4-bromo-N-isopropyl-benzene-1,2-diamine (750 mg, 3.27 mmol, 1.00 eq) in HCl (5 mL, 6 M) was added NaNO$_2$ (271.04 mg, 3.93 mmol, 213.42 uL, 1.20 eq) in H$_2$O (2 mL) dropwise at 5° C. and stirred for 0.5 h. The reaction mixture was diluted with water (200 mL) and extracted with EA (200 mL×2). The combined organic layers were dried over Na$_2$SO$_4$, filtered and concentrated under reduced pressure to give a residue. The residue was purified by flash silica gel chromatography (1/1) to give 5-bromo-1-isopropyl-benzotriazole (700 mg, 2.92 mmol, 89.06% yield) black-brown solid.

$^1$H NMR (400 MHz, DMSO-d$_6$) δ=8.32 (d, J=1.7 Hz, 1H), 7.94 (d, J=8.8 Hz, 1H), 7.60-7.60 (m, 1H), 7.67 (dd, J=1.8, 8.9 Hz, 1H), 5.32-5.16 (m, 1H), 1.62 (d, J=6.7 Hz, 6H).

595

-continued

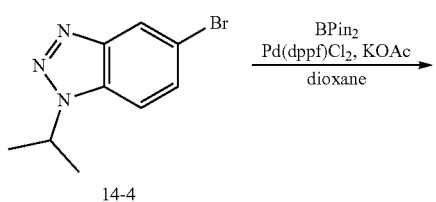

14-4

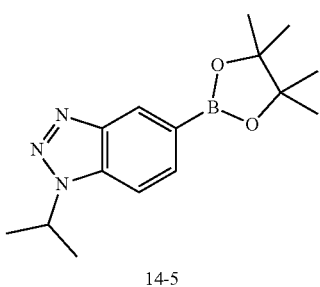

14-5

Synthesis of 14-2: 4-bromo-2-nitro-N-(propan-2-yl)aniline

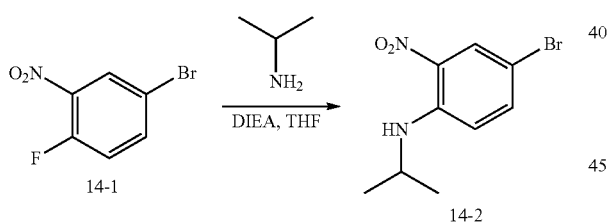

To a solution of 4-bromo-1-fluoro-2-nitro-benzene (5 g, 22.73 mmol, 2.79 mL, 1.00 eq) and propan-2-amine (2.02 g, 34.09 mmol, 2.92 mL, 1.50 eq) in THF (250.00 mL) was added DIEA (7.34 g, 56.82 mmol, 9.90 mL, 2.50 eq) at 10° C. and stirred for 1 h, The reaction mixture was diluted with water (500 mL) and extracted with EA (500 mL×2). The combined organic layers were washed with NaHCO$_3$(500 mL), dried over Na$_2$SO$_4$, filtered and concentrated under reduced pressure to give a residue. The residue was purified by flash silica gel chromatography to give 4-bromo-N-isopropyl-2-nitro-aniline (3.2 g, 12.35 mmol, 54.34% yield) as yellow oil.

$^1$H NMR (400 MHz, DMSO-d$_6$) δ=8.14 (d, J=2.4 Hz, 1H), 7.88 (br d, J=7.5 Hz, 1H), 7.63 (dd, J=2.3, 9.3 Hz, 1H), 7.07 (d, J=9.4 Hz, 1H), 3.92 (sxtd, J=6.5, 13.2 Hz, 1H), 1.25 (d, J=6.4 Hz, 6H).

Synthesis of 14-5: 1-(propan-2-yl)-5-(tetramethyl-1,3,2-dioxaborolan-2-yl)-1H-1,2,3-benzotriazole

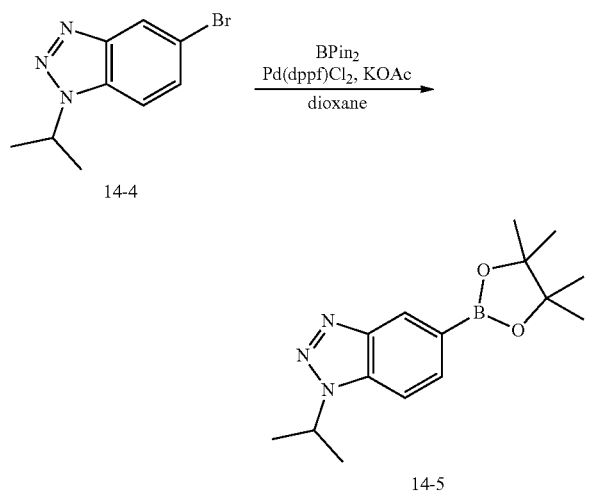

To a solution of 5-bromo-1-isopropyl-benzotriazole (700 mg, 2.92 mmol, 1 eq) in dioxane (10 mL) was added 4,4,5,5-tetramethyl-2-(4,4,5,5-tetramethyl-1,3,2-dioxaborolan-2-yl)-1,3,2-dioxaborolane (814.38 mg, 3.21 mmol, 1.1 eq), DPPF (161.63 mg, 291.55 umol, 0.1 eq), Pd(dppf)Cl$_2$ (213.33 mg, 291.55 umol, 0.1 eq) and KOAc (343.35 mg, 3.50 mmol, 1.2 eq), The mixture was stirred at 100° C. for 1 h, the mixture was diluted with water (100 mL) and extracted with (EA 100 mL×2). The combined organic layers were dried over Na$_2$SO$_4$, filtered and concentrated under reduced pressure to give a residue. The residue was purified by flash silica gel chromatography (PE/EA=1001 to 1/1) to give 1-isopropyl-5-(4,4,5,5-tetramethyl-1,3,2-dioxaborolan-2-yl)benzotriazole (300 mg, 1.04 mmol, 35.83% yield) as a yellow solid.

$^1$H NMR (400 MHz, CHLOROFORM-d) δ=8.57 (s, 1H), 7.89 (dd, J=0.7, 8.3 Hz, 1H), 7.55 (dd, J=0.8, 8.4 Hz, 1H), 5.11 (spt, J=6.8 Hz, 1H), 1.75 (d, J=6.8 Hz, 6H), 1.47-1.34 (m, 12H).

General Procedure E

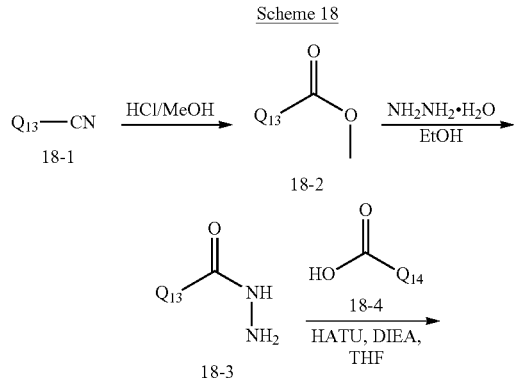

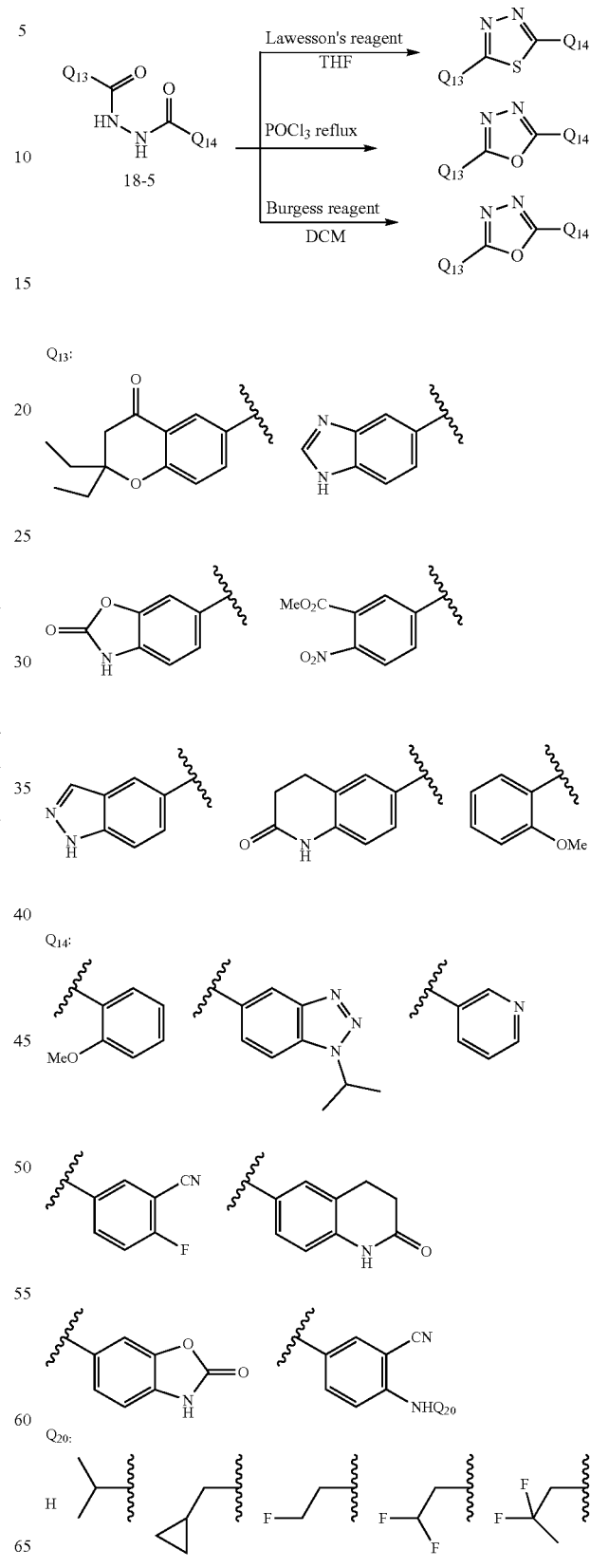

Synthesis of 19-6 and 19-7: 2,2-diethyl-6-{5-[1-(propan-2-yl)-1H-1,2,3-benzotriazol-5-yl]-1,3,4-thiadiazol-2-yl}-3,4-dihydro-2H-1-benzopyran-4-one; 2,2-diethyl-6-{5-[1-(propan-2-yl)-1H-1,2,3-benzotriazol-5-yl]-1,3,4-oxadiazol-2-yl}-3,4-dihydro-2H-1-benzopyran-4-one
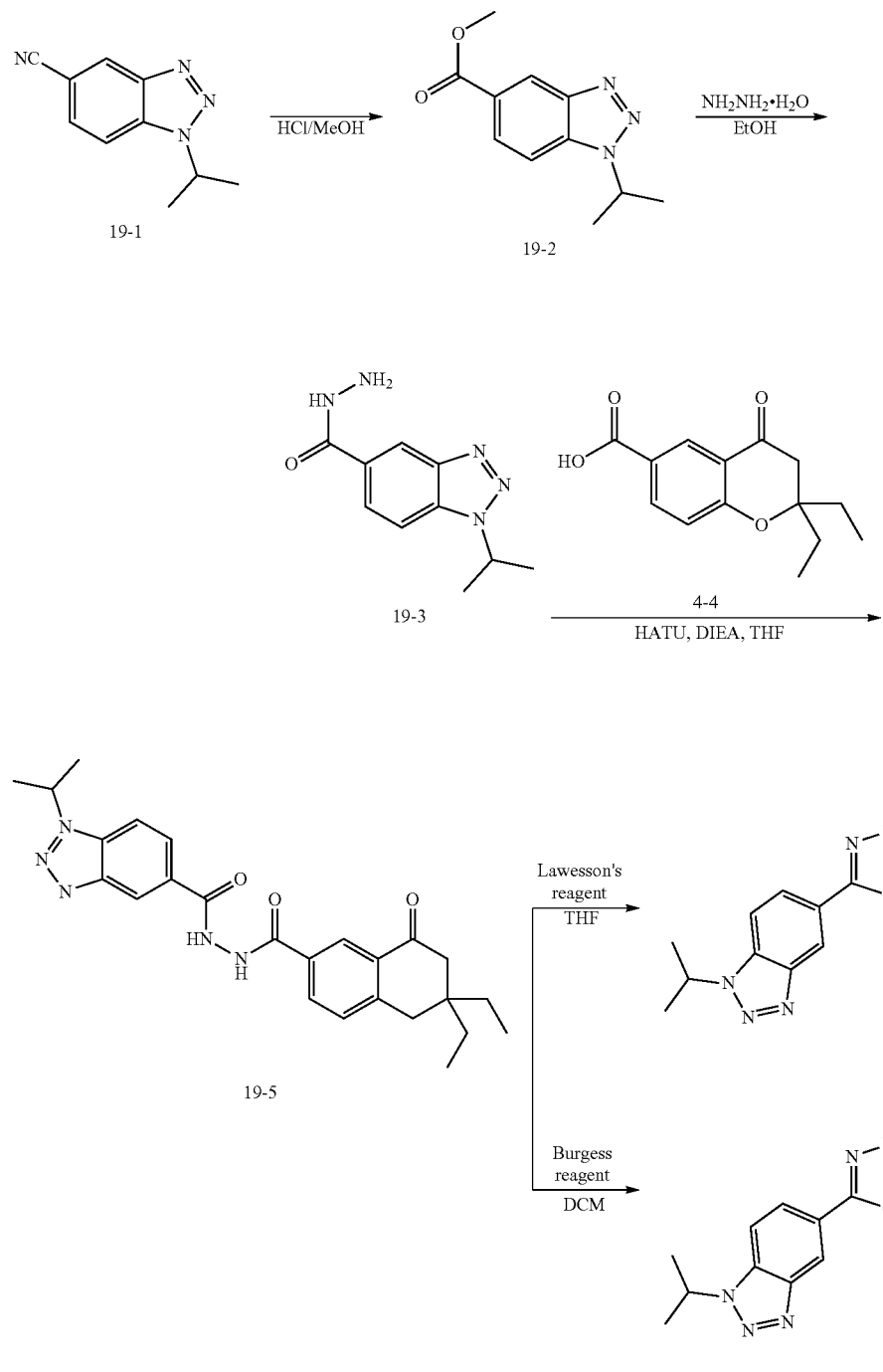

Synthesis of 19-2: methyl 1-(propan-2-yl)-1H-1,2,3-benzotriazole-5-carboxylate Scheme 20

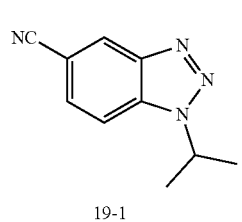

A mixture of 1-isopropylbenzotriazole-5-carbonitrile (1 g, 5.37 mmol, 1 eq.) in HCl/MeOH (20 mL, 4 M) was stirred at 80° C. for 2 h. The mixture was concentrated, diluted with water (20 mL), extracted with EA (20 mL×2), dried over Na₂SO₄ and concentrated to dry. The crude product methyl 1-isopropylbenzotriazole-5-carboxylate (0.9 g, 4.11 mmol, 76.44% yield) was used into the next step without further purification.

Synthesis of 19-3: 1-(propan-2-yl)-1H-1,2,3-benzotriazole-5-carbohydrazide

Scheme 21

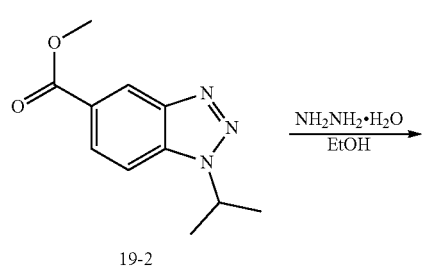

A mixture of methyl 1-isopropylbenzotriazole-5-carboxylate (0.5 g, 2.28 mmol, 1 eq.) and NH₂NH₂H₂O (1.14 g, 22.81 mmol, 1.11 mL, 10 eq.) in EtOH (10 mL) was stirred at 80° C. for 2 h. The mixture was concentrated to dry. The residue was purified by column chromatography (SiO₂, Petroleum ether/Ethyl acetate=1:1) to give 1-isopropyl Benzotriazole-5-carbohydrazide (0.38 g, 1.73 mmol, 76.00% yield) as a white solid.

Synthesis of 19-5: 2,2-diethyl-4-oxo-N'-[1-(propan-2-yl)-1H-1,2,3-benzotriazole-5-carbonyl]-3,4-dihydro-2H-1-benzopyran-6-carbohydrazide Scheme 22

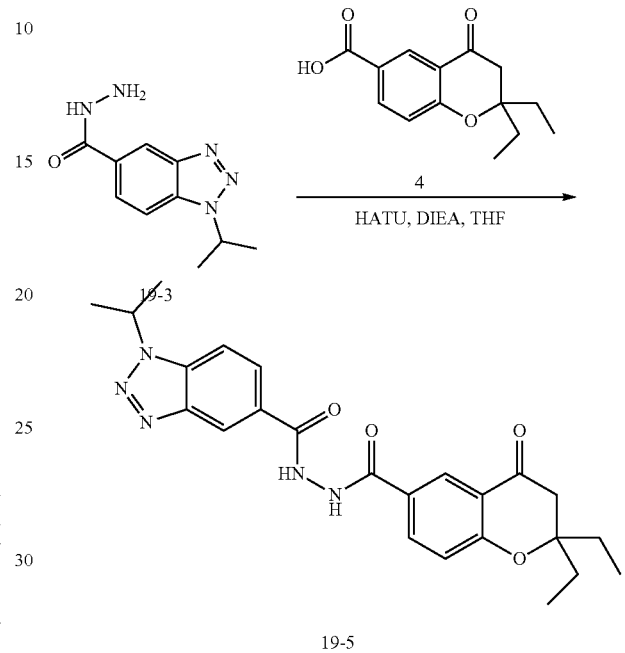

To a mixture of 2,2-diethyl-4-oxo-chromane-6-carboxylic acid (274.04 mg, 1.10 mmol, 1.1 eq.) and 1-isopropylbenzotriazole-5-carbohydrazide (220 mg, 1.00 mmol, 1 eq.) in THF (10 mL) was added HATU (419.70 mg, 1.10 mmol, 1.1 eq.) and DIEA (142.66 mg, 1.10 mmol, 192.26 uL, 1.1 eq.), the mixture was stirred at 15° C. for 2 hr. The mixture was diluted with water (50 mL), extracted with EA (50 mL×2), dried over Na₂SO₄ and concentrated in vacuum. N'-(2,2-diethyl-4-oxo-chromane-6-carbonyl)-1-isopropyl-benzotriazole-5-carbohydrazide (420 mg, 934.37 umol, 93.12% yield) was obtained as yellow solid without further purification.

Synthesis of 19-7: 2,2-diethyl-6-{5-[1-(propan-2-yl)-1H-1,2,3-benzotriazol-5-yl]-1,3,4-thiadiazol-2-yl}-3,4-dihydro-2H-1-benzopyran-4-one Scheme 23

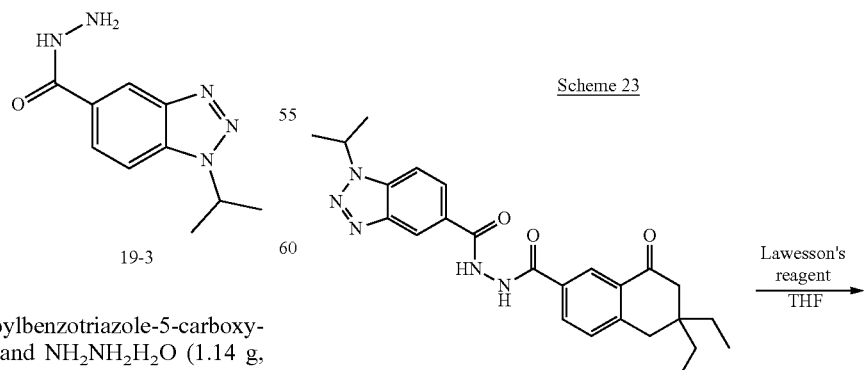

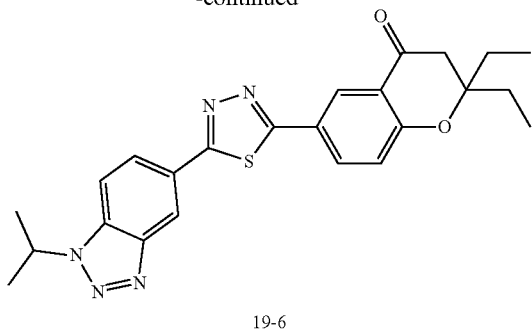

19-6

A mixture of N'-(2,2-diethyl-4-oxo-chromane-6-carbonyl)-1-isopropyl-benzotriazole-5-carbohydrazide (200 mg, 444.94 umol, 1 eq.) and Lawesson's reagent (359.93 mg, 889.88 umol, 2 eq.) in THF (2 mL) was stirred at 80° C. for 2 h. The mixture was diluted with water (20 mL), extracted with EA (20 mL×2), dried over $Na_2SO_4$ and concentrated to dry. The residue was purified by prep-HPLC (column: Phenomenex Synergi C18 150×25×10 um; mobile phase: [water(0.1% TFA)-ACN]; B %: 62%-92%, 13 min) to give 2,2-diethyl-6-[5-(1-isopropylbenzotriazol-5-yl)-1,3,4-thiadiazol-2-yl]chroman-4-one (61 mg, 29.99 umol, 6.74% yield, 22% purity) as a white solid.

$^1$H NMR (400 MHz, CHLOROFORM-d) δ=8.62 (d, J=0.6 Hz, 1H), 8.38-8.36 (m, 1H), 8.36-8.33 (m, 1H), 8.33-8.30 (m, 1H), 7.72 (d, J=8.8 Hz, 1H), 7.13 (d, J=8.7 Hz, 1H), 5.22-5.11 (m, 1H), 2.82 (s, 2H), 1.95-1.83 (m, 4H), 1.82-1.80 (m, 6H), 0.99 (t, J=7.5 Hz, 6H).

Synthesis of 19-7: 2,2-diethyl-6-{5-[1-(propan-2-yl)-1H-1,2,3-benzotriazol-5-yl]-1,3,4-oxadiazol-2-yl}-3,4-dihydro-2H-1-benzopyran-4-one

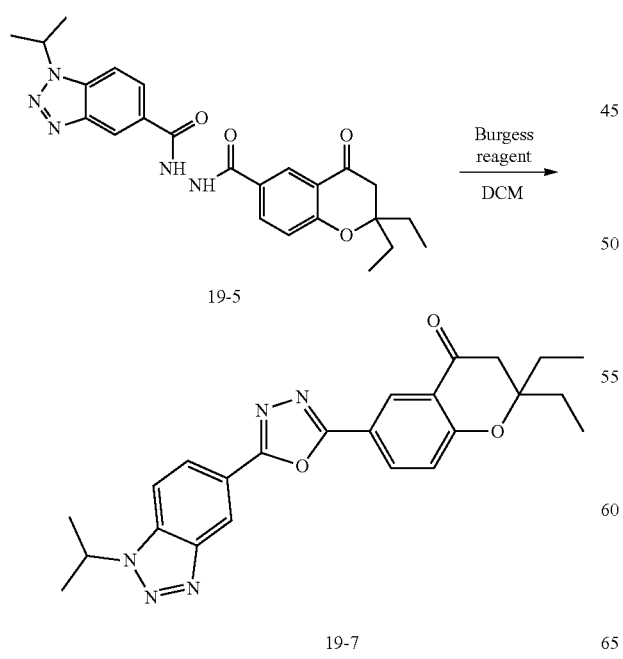

A mixture of N'-(2,2-diethyl-4-oxo-chromane-6-carbonyl)-1-isopropyl-benzotriazole-5-carbohydrazide (200 mg, 444.94 umol, 1 eq.) and Burgess reagent (530.17 mg, 2.22 mmol, 5 eq.) in DCM (2 mL) was stirred at 15° C. for 2 h. The mixture was diluted with water (20 mL), extracted with EA (20 mL×2), dried over $Na_2SO_4$ and concentrated to dry. The residue was purified by prep-HPLC (column: Phenomenex Synergi C18 150×25×10 um; mobile phase: [water (0.1% TFA)-ACN]; B %: 55%-85%, 12 min) to give 2,2-diethyl-6-[5-(1-isopropylbenzotriazol-5-yl)-1,3,4-oxadiazol-2-yl]chroman-4-one (56 mg, 129.78 umol, 29.17% yield, 100% purity) as a white solid.

$^1$H NMR (400 MHz, CHLOROFORM-d) δ=8.85 (s, 1H), 8.61 (d, J=2.3 Hz, 1H), 8.35 (t, J=2.1 Hz, 1H), 8.33 (t, J=2.1 Hz, 1H), 7.75 (d, J=8.7 Hz, 1H), 7.16 (d, J=8.8 Hz, 1H), 5.24-5.11 (m, 1H), 2.84 (s, 2H), 1.94-1.85 (m, 2H), 1.82 (d, J=6.8 Hz, 5H), 1.80-1.75 (m, 2H), 1.00 (t, J=7.5 Hz, 6H)

Synthesis of 25-2: 5-[5-(1H-1,3-benzodiazol-5-yl)-1,3,4-oxadiazol-2-yl]-2-fluorobenzonitrile

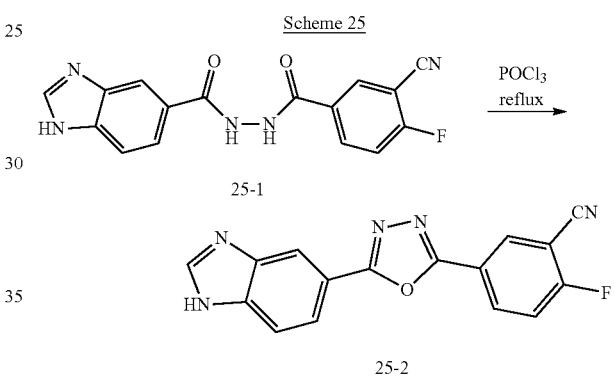

A suspension of 1 (N'-(1H-1,3-benzodiazole-5-carbonyl)-3-cyano-4-fluorobenzohydrazide, 541 mg, 1.67 mmol) in phosphorus oxychloride (10 mL, excess) was heated at 105° C. for 3 hours. The mixture was concentrated, and the residue was suspended in water with sonication/stirring. The resulting solid was collected, washed with sat'd $NaHCO_3$ and water, then dried under $N_2$/vac in the filter funnel. The tan solid was suspended in MeCN and concentrated twice to remove residual water and dried under high vacuum to yield 25-2 (0.55 g, 107%). MH+=306.1.

Synthesis of 26-2: 6-[5-(2-methoxyphenyl)-1,3,4-oxadiazol-2-yl]-3-methyl-2,3-dihydro-1,3-benzoxazol-2-one

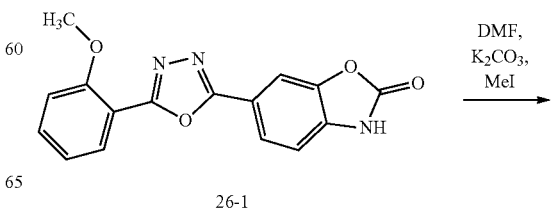

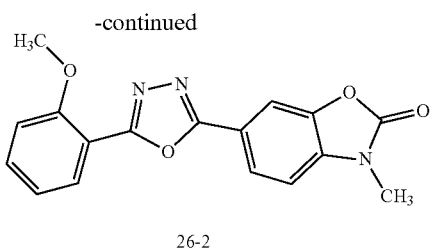

26-2

To a suspension of 3 (6-[5-(2-methoxyphenyl)-1,3,4-oxadiazol-2-yl]-2,3-dihydro-1,3-benzoxazol-2-one trifluoroacetate, 13 mg, 0.031 mmol) in DMF (1 mL) was added potassium carbonate (8.6 mg, 0.062 mmol) followed by methyl iodide (5.2 mg, 0.037 mmol) and the resulting white suspension heated to 100° C. for 45 min. The reaction was cooled to room temperature, filtered, and purified by reverse phase chromatography, 25%-75% MeCN/water/0.1% TFA. The product fractions lyophilized to yield 26-2 (1.6 mg, 12%). MH+=324.1. $^1$H NMR (400 MHz, DMSO) 7.93-7.91 (3H, m), 7.59-7.54 (1H, m), 7.44-7.41 (1H, m), 7.25-7.22 (1H, m), 7.11-7.07 (1H, m), 3.88 (3H, s); 3.45 (3H, s)

Synthesis of 27-3: methyl N-({6-[5-(2-methoxyphenyl)-1,3,4-oxadiazol-2-yl]-2-oxo-2,3-dihydro-1,3-benzoxazol-3-yl}sulfonyl)carbamate

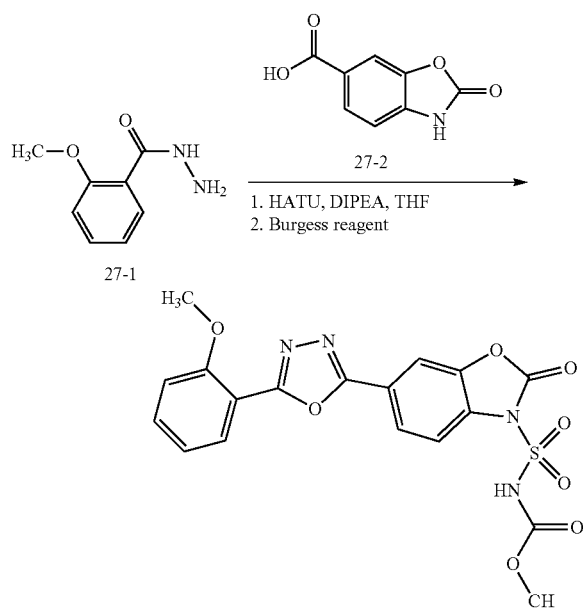

To a dry mixture of 27-1 (2-methoxyphenylhydrazide, 139 mg, 0.837 mmol), 27-2 (benzoxazol-2-one-6-carboxylic acid, 150 mg, 0.837 mmol), and HATU (318 mg, 0.837 mmol) was added THF (10 mL) to yield a hazy reddish solution. DIPEA (0.29 mL, 1.67 mmol) was added and the reaction was stirred at rt for 2 hr. Burgess reagent (499 mg, 2.09 mmol) was added one portion, and the reaction was heated to 60° C. overnight. An additional 499 mg Burgess reagent was added. and continued heating. After 4 hr, 2N KHSO₄ (10 mL) was added and the resulting oily mixture was extracted 3× EtOAc. The combined organics were washed once with water, once with brine, filtered through cotton and concentrated to an orange solid which was purified by reverse phase chromatography, 20%-60% MeCN/water/0.1% TFA to yield 67 mg 27-3(18%) MH+=447.0. $^1$H NMR (400 MHz, DMSO) 8.02-7.97 (3H, m), 7.74 (1H, d, J=8.4 Hz), 7.64 (1H, t, J=8.2 Hz), 7.30 (1H, d, J=8.4 Hz), 7.18 (1H, t, J=7.4 Hz), 3.95 (3H, s), 3.39 (3H, s).

Synthesis of 28-2: 2-[(2-fluoropropyl)amino]-5-[5-(2-oxo-1,2,3,4-tetrahydroquinolin-6-yl)-1,3,4-oxadiazol-2-yl]benzonitrile

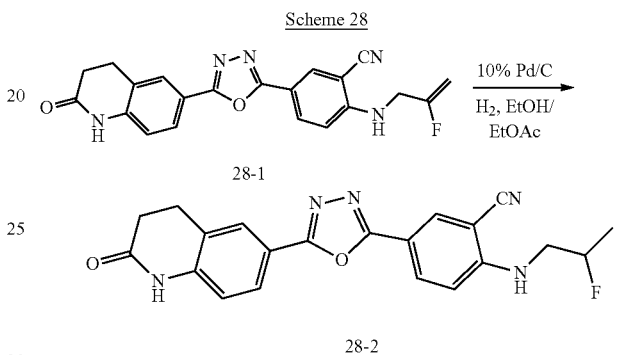

To a nitrogen purged small Parr hydrogenation bottle was added 10% Pd/C (14 mg) and moistened with a small volume of EtOH. To 28-1 (2-[(2-fluoroprop-2-en-1-yl)amino]-5-[5-(2-oxo-1,2,3,4-tetrahydroquinolin-6-yl)-1,3,4-oxadiazol-2-yl]benzonitrile trifluoroacetate, 70 mg, 0.139 mmol) was added EtOH (10 mL) and EtOAc (90 mL) to yield a milky mixture which was added to the hydrogenation bottle. The mixture was hydrogenated under 50 psi H₂ for 24 hr. MeCN was added until the milky mixture clears, then filtered through Celite and concentrated. The residue was heated in a small volume of DMF, cooled, filtered, and purified by reverse phase chromatography, 30%-75% MeCN/water/0.1% TFA. The product fractions were lyophilized to yield 28-2 as a fluffy white solid (12.8 mg, 18%). MH+=392.1. $^1$H NMR (400 MHz, DMSO) 10.40 (1H, s), 8.25 (1H, d, J=2.1 Hz), 8.11 (1H, dd, J=2.0, 9.2 Hz), 7.92-7.81 (2H, m), 7.22 (1H, t, J=6.3 Hz), 7.11 (1H, d, J=9.2 Hz), 7.11 (1H, d, J=9.4 Hz), 7.02 (1H, d, J=8.7 Hz), 7.04-7.00 (1H, m), 5.00-4.80 (1H, m), 3.60-3.51 (2H, m), 3.01 (2H, t, J=7.4 Hz), 1.35 (3H, dd, J=6.2, 24.0 Hz).

Synthesis of 29-3: 5-[5-(2-methoxyphenyl)-1,3,4-oxadiazol-2-yl]-1,3-dihydro-2,1-benzoxazol-3-one Scheme 29

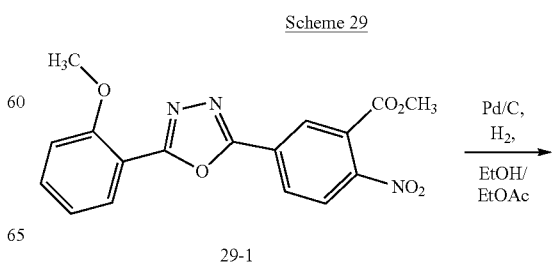

29-1

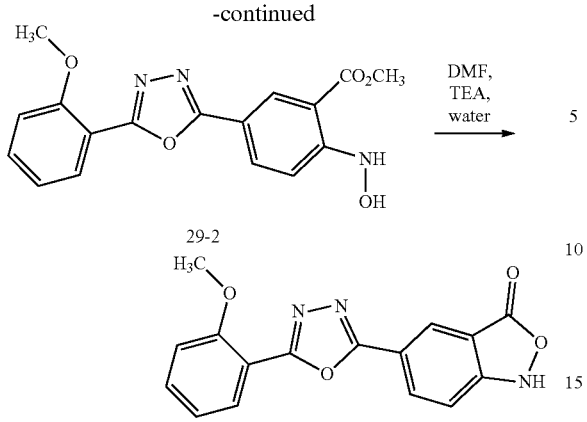

29-2

29-3

To a nitrogen purged hydrogenation bottle was added 10% Pd/C (12 mg), which was moistened with EtOH. A suspension of 29-1 (methyl 5-[5-(2-methoxyphenyl)-1,3,4-oxadiazol-2-yl]-2-nitrobenzoate, prepared according to Wuxi 1,3,4-oxadiazole experimental, 112 mg, 0.281) in EtOH (25 mL) and EtOAc (20 mL) was hydrogenated at 48 psi $H_2$. After 30 minutes the reaction was filtered and concentrated to solid 29-2 (113 mg, 105%), which was used without further purification. MH+=342.1.

To a solution of 29-2 (47 mg, 0.132 mmol) in DMF (2 mL) was added triethylamine (0.1 mL) then water (0.2 mL) and the resulting solution stirred at rt for 60 hr. The reaction mixture was purified directly by reverse phase chromatography, 20%-65% MeCN/water/0.1% TFA to yield 8 mg 29-3 (14%). MH+=310.1. $^1$H NMR (400 MHz, DMSO) 12.52 (1H, s), 8.42-8.38 (2H, m), 8.03 (1H, d, J=6.9 Hz), 7.65 (1H, t, J=8.3 Hz), 7.57 (1H, d, J=7.6 Hz), 7.32 (1H, d, J=8.3 Hz), 7.17 (1H, t, J=6.9 Hz), 3.96 (3H, s).

Synthesis of 30-1: 5-[5-(2-methoxyphenyl)-1,3,4-oxadiazol-2-yl]-1-methyl-1,3-dihydro-2,1-benzoxazol-3-one Scheme 30

Scheme 30

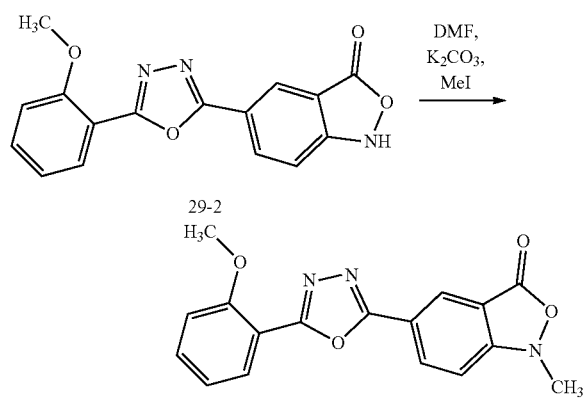

To a solution of 29-2 (8 mg, 0.019 mmol) in DMF (0.5 mL) was added potassium carbonate (2.6 mg, 0.019 mmol) followed by methyl iodide (4.0 mg, 0.028 mmol) and the resulting solution heated to 100° C. for 15 minutes. The reaction was cooled to rt, filtered, and purified directly by reverse phase chromatography, 25%-75% MeCN/water/0.1% TFA to yield 5.3 mg 30-1 (64%) as a white solid.

MH+=324.1. $^1$H NMR (400 MHz, DMSO) 8.40 (1H, d, J=8.7 Hz), 8.32 (1H, s), 7.97 (1H, d, J=8.0 Hz), 7.73 (1H, d, J=8.7 Hz), 7.58 (1H, t, J=8.3 Hz), 7.25 (1H, d, J=8.0 Hz), 7.10 (1H, t, J=7.7 Hz), 3.89 (3H, s), 3.49 (3H, s).

General Procedure F

Scheme 31

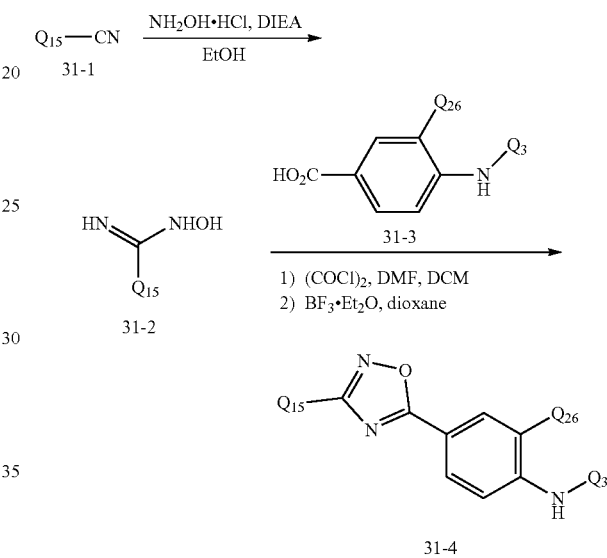

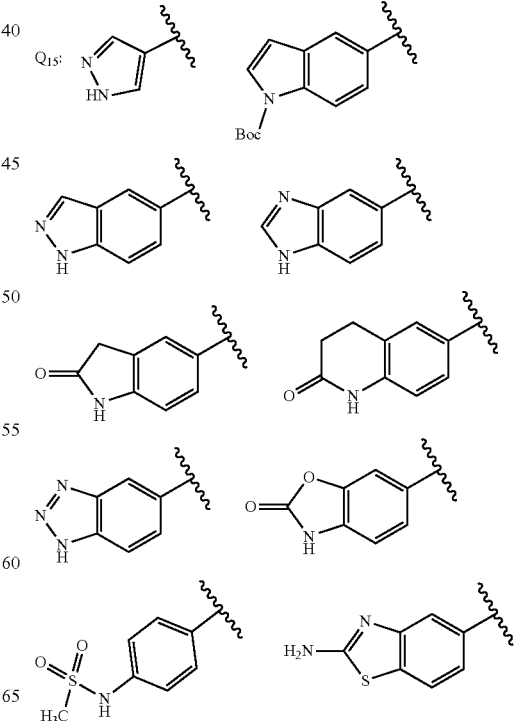

-continued

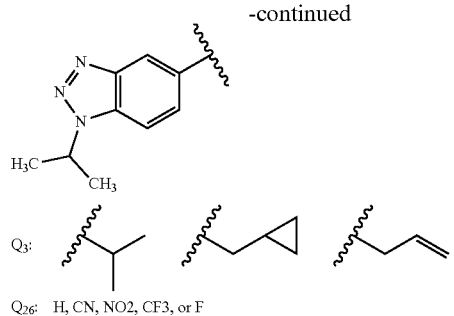

Q<sub>26</sub>: H, CN, NO2, CF3, or F

Synthesis of 32-2: N-hydroxy-2-oxo-2,3-dihydro-1H-indole-5-carboximidamide

Scheme 32

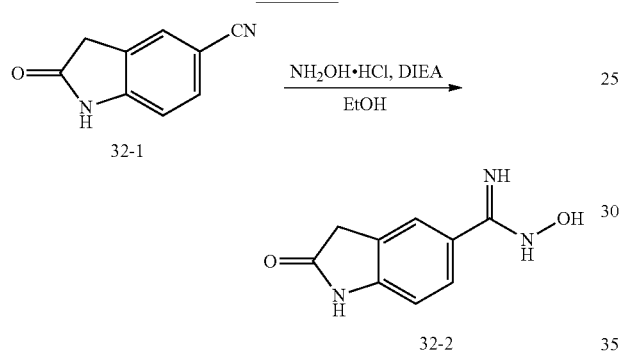

To a mixture of 2-oxoindoline-5-carbonitrile (200 mg, 1.26 mmol, 1 eq) in ethanol (5 mL) was added hydrochloride salt of hydroxylamine (176 mg, 2.53 mmol, 2.0 eq), diisopropylethylamine (327 mg, 2.53 mmol, 2.0 eq) at 20° C. under nitrogen atmosphere. The mixture was then heated to 90° C. and stirred for 16 hrs. The mixture was concentrated in vacuum, and a white solid was precipitated out. The suspension was filtered, and the white solid was dried in vacuum to give the product 32-2 (210 mg, 83% yield).

$^1$H NMR (400 MHz, DMSO-d$_6$) δ=10.46 (br, s, 1H), 9.45 (br, s, 1H), 7.51 (s, 1H), 7.50 (d, J=10.8 Hz, 1H), 6.79 (d, J=8.0 Hz, 1H), 5.70 (br, s, 2H), 3.49 (s, 2H).

Synthesis of 33-1: 2-[(cyclopropylmethyl)amino]-5-[3-(2-oxo-2,3-dihydro-1H-indol-5-yl)-1,2,4-oxadiazol-5-yl]benzonitrile Scheme 33

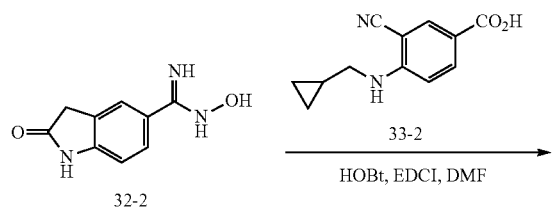

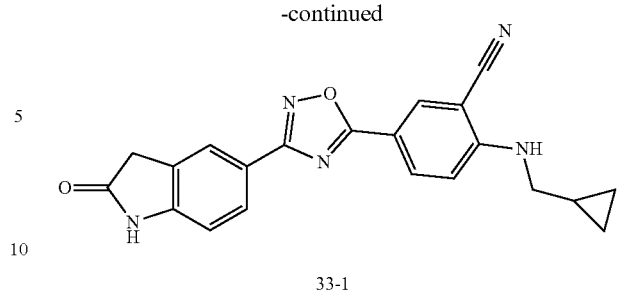

33-1

To a mixture of 3-cyano-4-(cyclopropylmethylamino)benzoic acid (107 mg, 496 umol, 1.2 eq) in N,N-dimethylformamide (1 mL) was added HOBt (67.0 mg, 496 umol, 1.2 eq), EDCI (95.1 mg, 496 umol, 1.2 eq) at 20° C. The mixture was stirred for 30 min, then N-hydroxy-2-oxo-indoline-5-carboxamidine (79 mg, 413 umol, 1 eq) was added, and the resultant mixture then heated to 150° C. and stirred for 1 hour. The cooled reaction mixture was directly purified by prep-HPLC (column: Boston Green ODS 150×30 5u; mobile phase: [water(0.225% FA)-ACN]; B %: 47%-77%, 10 min) to give the product 33-1 (20 mg, 12% yield).

$^1$H NMR (400 MHz, DMSO-d$_6$) δ=10.73 (br, s, 1H), 8.23 (d, J=2.4 Hz, 1H), 8.11 (dd, J=9.2, 2.0 Hz, 1H), 7.93 (d, J=8.0 Hz, 1H), 7.89 (s, 1H), 7.17 (t, J=6.4 Hz, 1H), 7.07 (d, J=9.2 Hz, 1H), 7.00 (d, J=8.0 Hz, 1H), 3.61 (s, 2H), 3.20 (t, J=6.4 Hz, 2H), 1.16-1.13 (m, 1H), 0.52-0.47 (m, 2H), 0.33-0.29 (m, 2H).

General Procedure G

Scheme 34

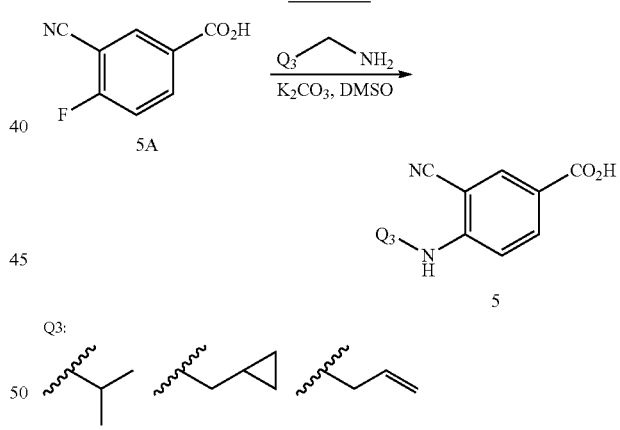

Synthesis of 35-2: 3-cyano-4-[(cyclopropylmethyl)amino]benzoic acid

Scheme 35

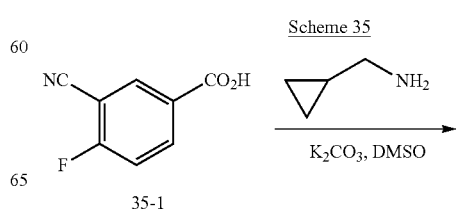

35-1

611
-continued

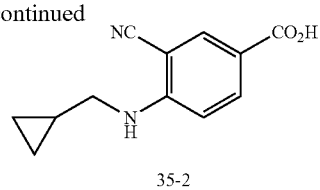

35-2

To a mixture of 3-cyano-4-fluoro-benzoic acid (5 g, 30.3 mmol, 1 eq) and cyclopropylmethanamine (5.38 g, 75.7 mmol, 2.5 eq) in dimethylsulfoxide (30 mL) was added potassium carbonate (12.6 g, 90.8 mmol, 3 eq) at 20° C. The mixture was then heated to 100° C. and stirred for 16 hours. The mixture was filtered, and the filtrate was diluted with water (50 mL), acidified by hydrochloride solution (2N) to pH=4-5. A yellow solid was precipitated out, the suspension was filtered, and the solid was washed by water (50 mL×3). The solid was dried in vacuum to give the desired product 35-2 (5 g, 73% yield).

1H NMR (400 MHz, DMSO-$d_6$) δ=7.95 (d, J=1.2 Hz, 1H), 7.90 (d, J=9.2 Hz, 1H), 6.88 (d, J=9.2 Hz, 1H), 6.85-6.82 (m, 1H), 3.13 (t, J=6.0, 2H), 1.16-1.06 (m, 1H), 0.49-0.44 (m, 2H), 0.29-0.25 (m, 2H).

Synthesis of 36-2: 5-[3-(1H-indol-5-yl)-1,2,4-oxadi-azol-5-yl]-2-[(prop-2-en-1-yl)amino]benzonitrile Scheme 36

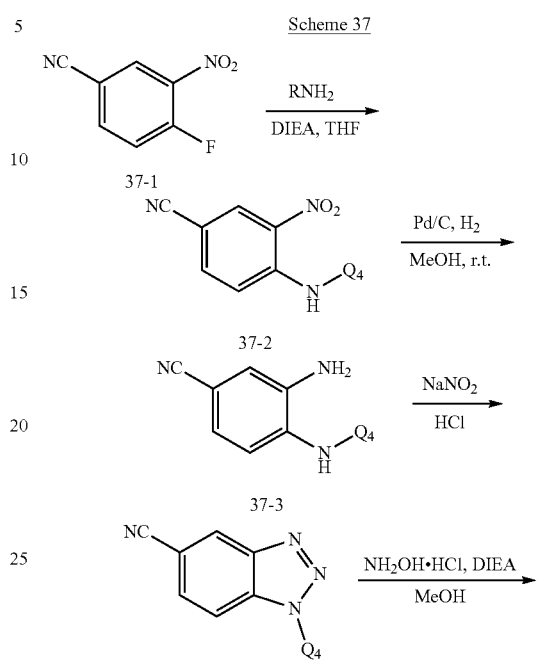

36-21

36-2

To a mixture of tert-butyl 5-[5-[4-(allylamino)-3-cyano-phenyl]-1,2,4-oxadiazol-3-yl]indole-1-carboxylate (60.0 mg, 136 umol, 1.00 eq) in dichloromethane (10.0 mL) was added trifluoroacetic acid (770 mg, 6.75 mmol, 50 eq) at 20° C. under nitrogen atmosphere. The mixture was stirred at 20° C. for 16 h. The mixture was concentrated in vacuum and the residue was purified by prep-HPLC (column: Gemini 150×25 5u; mobile phase: [water (0.05% ammonia hydroxide v/v)-ACN]; B %: 47%-77%, 12 min) to give the product 36-2 (15 mg, 30% yield) as a white solid.

$^1$H NMR (400 MHz, DMSO-$d_6$) δ=8.33 (s, 1H), 8.27 (d, J=2.0 Hz, 1H), 8.14 (dd, J=8.8, 2.0 Hz, 1H), 7.80 (dd, J=8.4, 1.2 Hz, 1H), 7.56 (d, J=8.8 Hz, 1H), 7.48 (t, J=2.4 Hz, 1H), 7.39 (t, J=5.6 Hz, 1H), 6.91 (d, J=8.8 Hz, 1H), 6.61 (s, 1H), 5.94-5.85 (m, 1H), 5.24-5.16 (m, 2H), 3.97 (s, 1H).

612
General Procedure H

Scheme 37

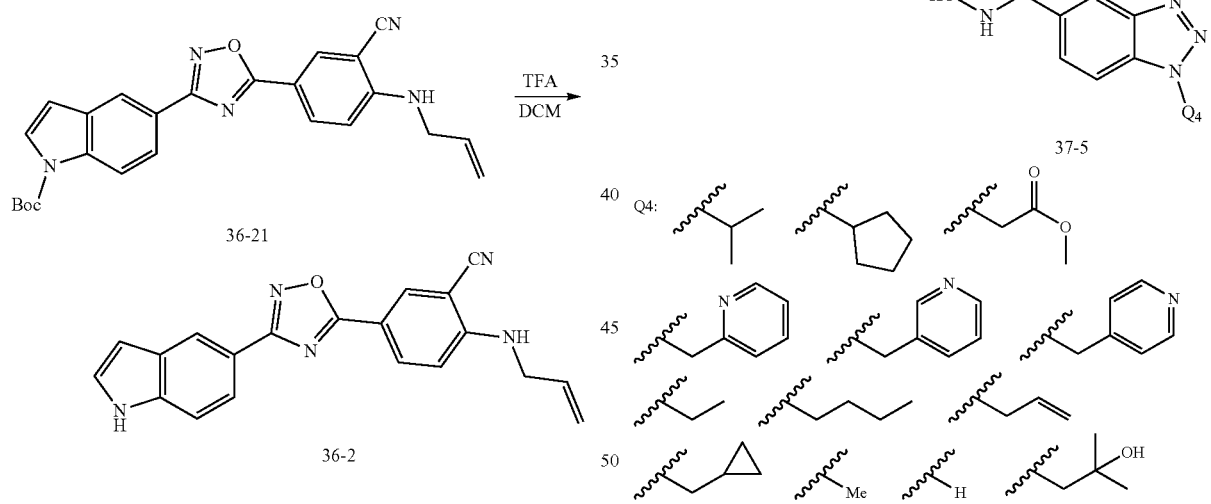

Synthesis of 38-4: 1-cyclopentyl-N-hydroxy-1H-1,2,3-benzotriazole-5-carboximidamide Scheme 38

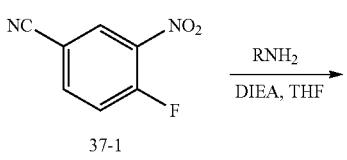

37-1

-continued

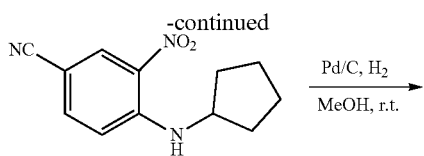

38-1

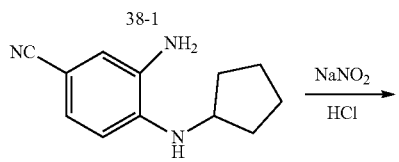

38-2

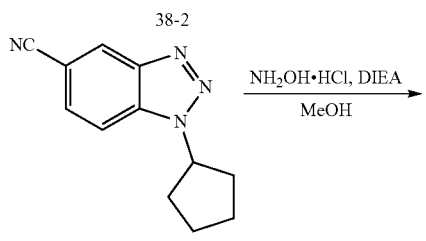

38-3

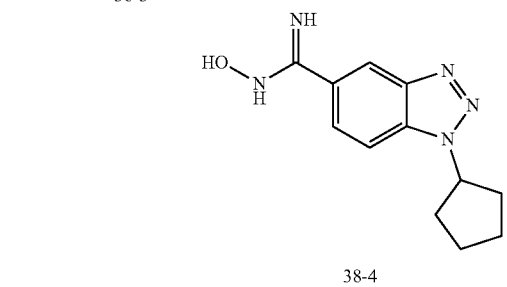

38-4

Synthesis of 38-1:
4-(cyclopentylamino)-3-nitrobenzonitrile

Scheme 39

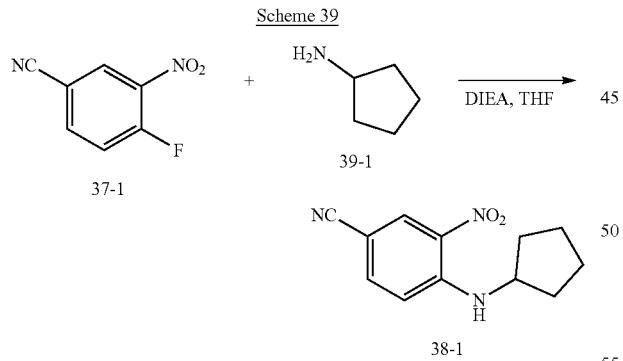

Preparation of 1: To a solution of 4-fluoro-3-nitro-benzonitrile (1.00 g, 6.02 mmol, 1.00 eq) and cyclopentanamine (767 mg, 9.03 mmol, 1.50 eq) in THF (20.00 mL) was added DIEA (1.95 g, 15.05 mmol, 2.63 mL, 2.50 eq) and the mixture was stirred at 10° C. for 16 hour. The mixture was evaporated to dry and diluted with H$_2$O (50 mL), extracted with DCM (50 mL×2), dried over Na$_2$SO$_4$, filtered and concentrated to dry. Compound 4-(cyclopentylamino)-3-nitrobenzonitrile (1.36 g, 5.91 mmol, 98.10% yield) was obtained as a yellow solid which was used directly in next step.

Synthesis of 38-2:
3-amino-4-(cyclopentylamino)benzonitrile

Scheme 40

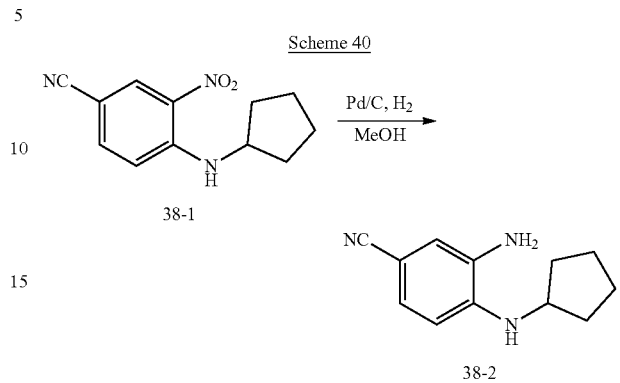

Preparation of 2: To a solution of 4-(cyclopentylamino)-3-nitro-benzonitrile (5.00 g, 21.62 mmol, 1.00 eq) in MeOH (150.00 mL) was added Pd/C (1.00 g, 4.32 mmol, 10% purity, 0.20 eq). Then the mixture was stirred for 12 hours at 20° C. under H$_2$ (50 psi). The mixture was filtered and the filtrate was concentrated to dry to get 3-amino-4-(cyclopentylamino)benzonitrile (4.20 g, 20.87 mmol, 96.52% yield) as black solid, which was used directly in the next step. $^1$H NMR (400 MHz, DMSO-d6) δ=8.77 (s, 1H), 8.12 (d, J=8.7 Hz, 1H), 7.91 (d, J=8.7 Hz, 1H), 5.43 (m, 1H), 2.37-2.21 (m, 2H), 2.18-2.06 (m, 2H), 1.99-1.85 (m, 2H), 1.81-1.67 (m, 2H).

Synthesis of 38-4: 1-cyclopentyl-N-hydroxy-1H-1,2,3-benzotriazole-5-carboximidamide Scheme 41

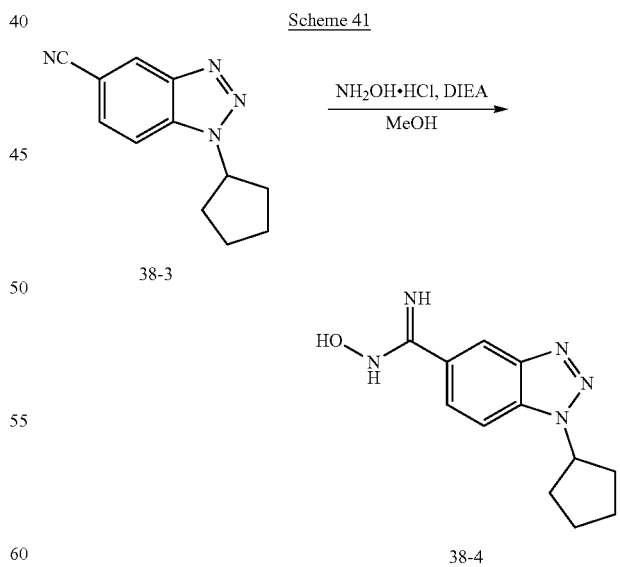

Preparation of 3: To a solution of 1-cyclopentylbenzotriazole-5-carbonitrile (1.50 g, 7.07 mmol) in ethanol (15.00 mL) was added hydroxylamine hydrochloride (736.64 mg, 10.60 mmol) and DIPEA (2.01 g, 15.55 mmol, 2.72 mL). Then the mixture was stirred at 70° C. for 4 hours. The mixture was filtered to get 1-cyclopentyl-N-hydroxy-benzotriazole-5-carboxamidine (1.20 g, 4.89 mmol, 69.20% yield) as a white solid.

$^1$H NMR (400 MHz, DMSO-d6) δ=9.77 (s, 1H), 8.31 (s, 1H), 7.97-7.89 (m, 1H), 7.87-7.79 (m, 1H), 5.98 (s, 2H), 5.34 (q, J=7.0 Hz, 1H), 2.36-2.21 (m, 2H), 2.19-2.07 (m, 2H), 1.99-1.84 (m, 2H), 1.81-1.67 (m, 2H).

General Procedure I

Scheme 42

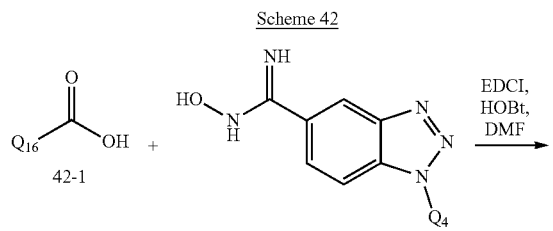

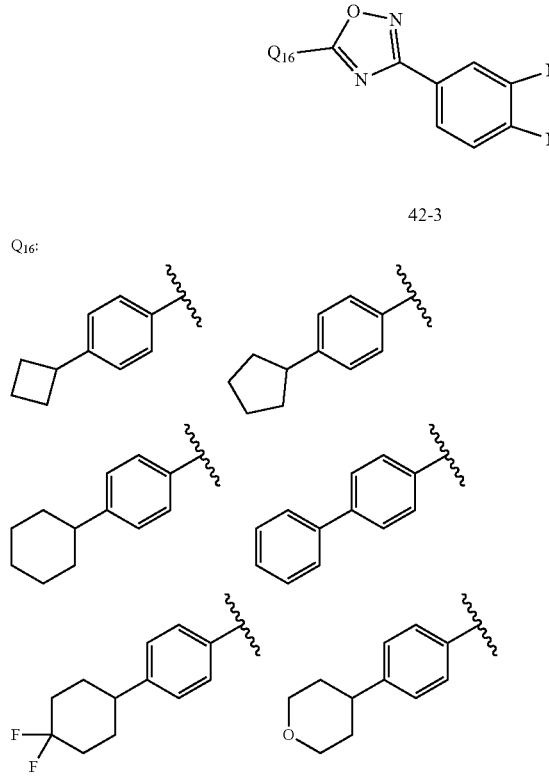

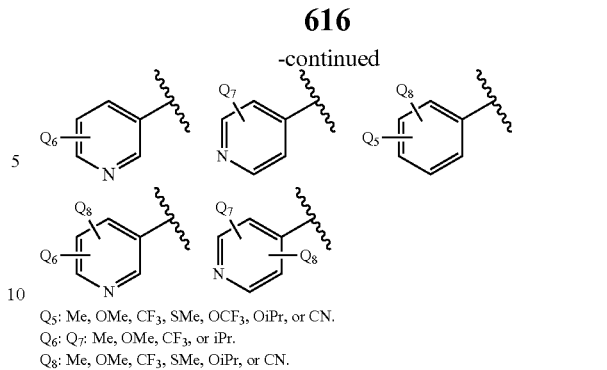

Q$_5$: Me, OMe, CF$_3$, SMe, OCF$_3$, OiPr, or CN.
Q$_6$: Q$_7$: Me, OMe, CF$_3$, or iPr.
Q$_8$: Me, OMe, CF$_3$, SMe, OiPr, or CN.

Synthesis of 42-2 5-[5-(2-bromophenyl)-1,2,4-oxadiazol-3-yl-1-cyclopentyl-1H-1,2,3-benzotriazole Scheme 43

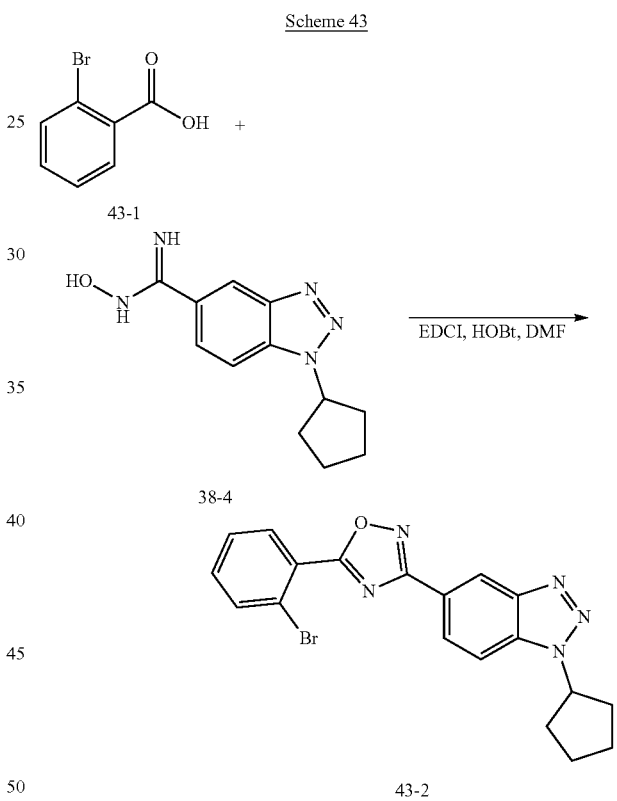

To a solution of 3-methylbenzoic acid (66.61 mg, 489.24 umol) in DMF (4.00 mL) was added EDCI (93.79 mg, 489.24 umol) and HOBt (66.11 mg, 489.24 umol). The mixture was stirred at 20° C. for 1 hour and 1-cyclopentyl-N-hydroxy-benzotriazole-5-carboxamidine (100.00 mg, 407.70 umol) was added to the mixture. Then the mixture was stirred at 120° C. for 12 hours under N$_2$. The mixture was quenched with water (30 mL) and extracted with ethyl acetate (30 mL×2). The organic layers were washed with brine (40 mL), dried over Na$_2$SO$_4$ and concentrated to dryness. The residue was purified by prep-HPLC (TFA) to get t 3-(1-cyclopentylbenzotriazol-5-yl)-5-(m-tolyl)-1,2,4-oxadiazole (96.00 mg, 277.94 umol, 68.17% yield) as a white solid. $^1$H NMR (400 MHz, CDCl$_3$) δ=8.93 (s, 1H), 8.30 (dd, J=1.3, 8.7 Hz, 1H), 8.08 (s, 1H), 8.06 (br d, J=6.8

Hz, 1H), 7.68 (d, J=8.8 Hz, 1H), 7.51-7.42 (m, 2H), 5.22 (quin, J=7.0 Hz, 1H), 2.50 (s, 3H), 2.43-2.32 (m, 4H), 2.15-2.01 (m, 2H), 1.92-1.81 (m, 2H).

Synthesis of 44-2: 2-{5-[5-(2-bromophenyl)-1,2,4-oxadiazol-3-yl]-1H-1,2,3-benzotriazol-1-yl}acetic acid Scheme 44

Scheme 44

44-1

44-2

To a solution of methyl 2-[5-[5-(2-bromophenyl)-1,2,4-oxadiazol-3-yl]benzotriazol-1-yl] acetate (40.00 mg, 96.57 umol, 1.00 eq) in dioxane (2.00 mL) and H₂O (2.00 mL) was added NaOH (15.45 mg, 386.28 umol, 4.00 eq). Then the mixture was stirred at 20° C. for 12 hours. The mixture was adjust to pH=2-3 with HCl (1N) and extracted with ethyl acetate (15 mL×2). The organic layers were dried over Na₂SO₄ and concentrated to give 2-[5-[5-(2-bromophenyl)-1,2, 4-oxadiazol-3-yl]benzotriazol-1-yl]acetic acid(17.30 mg, 43.23 umol, 44.76% yield) as a white solid.

¹H NMR (400 MHz, DMSO-d₆) δ=8.70 (s, 1H), 8.26 (m, 3H), 7.93 (m, 2H), 7.66 (m, 2H), 5.24 (br s, 2H)

Synthesis of 45-1: 2-{5-[5-(2-bromophenyl)-1,2,4-oxadiazol-3-yl]-1H-1,2,3-benzotriazol-1-yl}ethan-1-ol Scheme 45

44-1

45-1

To a solution of methyl 2-[5-[5-(2-bromophenyl)-1,2,4-oxadiazol-3-yl]benzotriazol-1-yl] acetate (50.00 mg, 120.71 umol, 1.00 eq) in THF (1.00 mL) was added LiBH₄ (5.26 mg, 241.42 umol, 2.00 eq) and stirred at 10° C. for 16 h. The mixture was diluted with H₂O (20 mL) and extracted with EA (30 mL×2), the combined organic layers were dried over Na₂SO₄, filtered and concentrated to dry. The residue was purified by prep-HPLC (TFA condition) to give 2-[5-[5-(2-bromophenyl)-1,2,4-oxadiazol-3-yl]benzotriazol-1-yl]ethanol (10.00 mg, 25.89 umol, 21.45% yield) as a white solid.

¹H NMR (400 MHz, DMSO-d₆) δ=8.74 (s, 1H), 8.43 (br s, 1H), 8.25 (dd, J=1.1, 8.8 Hz, 1H), 8.17 (dd, J=1.9, 7.4 Hz, 1H), 8.12 (d, J=8.7 Hz, 1H), 8.01-7.92 (m, 1H), 7.74-7.60 (m, 2H), 4.84 (t, J=5.1 Hz, 2H), 3.93 (t, J=5.1 Hz, 2H).

General Procedure J

Scheme 46

46-1

46-2

Q9:

-continued

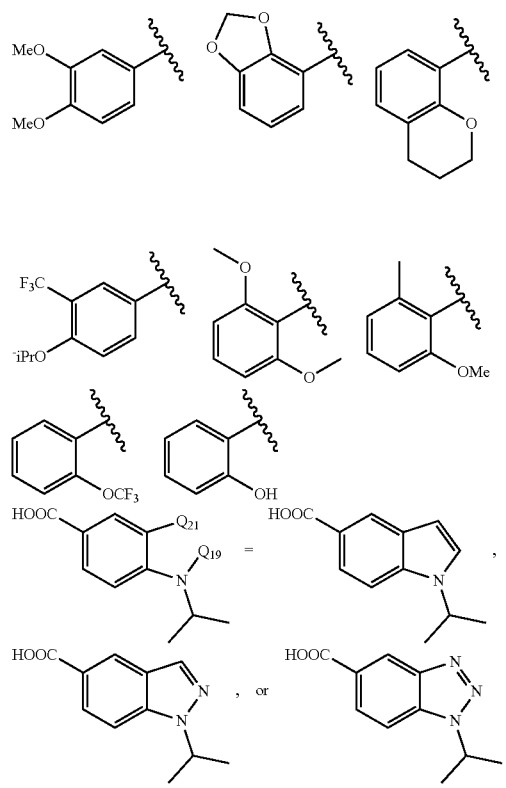

Synthesis of 46-1: 3-(2-isopropoxyphenyl)-5-(1-isopropylindol-5-yl)-1,2,4-oxadiazole Scheme 47

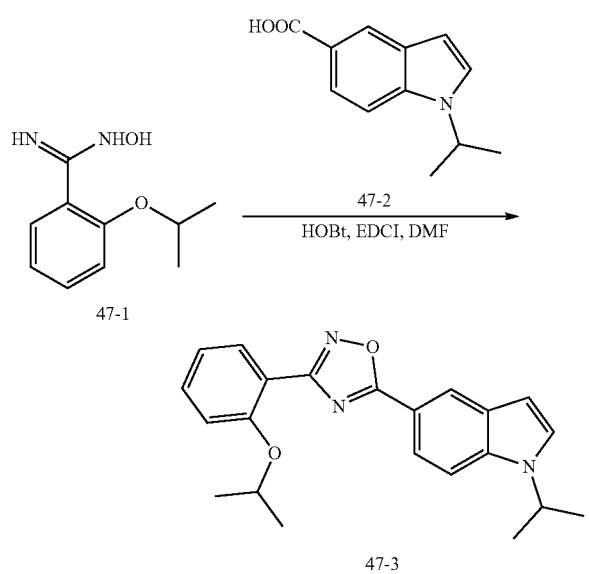

To a solution of N-hydroxy-2-isopropoxy-benzamidine (90.00 mg, 393.86 umol, 1.00 eq) in DMF (2.00 mL) was added 1-isopropylindole-5-carboxylic acid (80.05 mg, 393.86 umol, 1.00 eq), HOBt (63.86 mg, 472.63 umol, 1.20 eq) and EDCI (90.60 mg, 472.63 umol, 1.20 eq), the reaction was stirred at 120° C. for 12h. The mixture was filtered and concentrated. The residue was purified by prep-HPLC to give 3-(2-isopropoxyphenyl)-5-(1-isopropylindol-5-yl)-1,2,4-oxadiazole (26.00 mg, 71.93 umol, 18.26% yield, 98.9% purity) as a yellow oil.

$^1$H NMR (400 MHz, CHLOROFORM-d) δ=8.56 (d, J=1.1 Hz, 1H), 8.10 (dt, J=1.7, 8.6 Hz, 2H), 7.53-7.43 (m, 2H), 7.35 (d, J=3.3 Hz, 1H), 7.14-7.07 (m, 2H), 6.69 (d, J=3.3 Hz, 1H), 4.81-4.65 (m, 2H), 1.60 (d, J=6.7 Hz, 7H), 1.46 (d, J=6.1 Hz, 6H).

Synthesis of 48-2: 5-[3-(2-methoxyphenyl)-1,2,4-oxadiazol-5-yl]-1-(propan-2-yl)-1H-1,2,3-benzotriazole Scheme 48

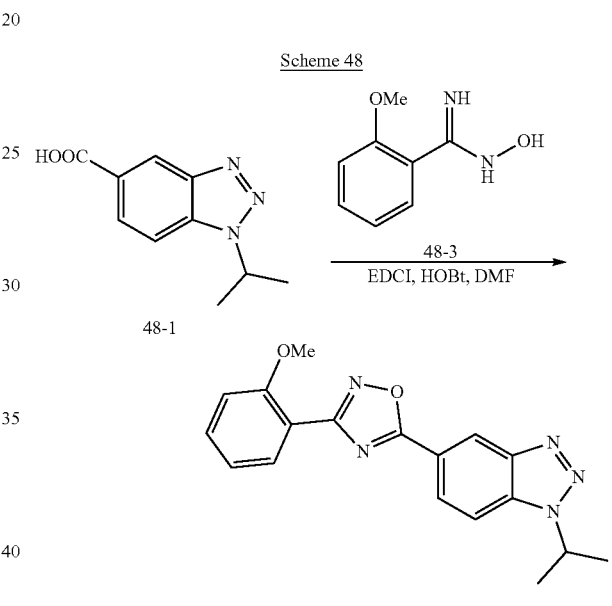

To a solution of 1-isopropylbenzotriazole-5-carboxylic acid (100.00 mg, 487.31 umol, 1.00 eq) in DMF (1.00 mL) was added HOBt (79.01 mg, 584.77 umol, 1.20 eq) and EDCI (112.10 mg, 584.77 umol, 1.20 eq). The mixture was stirred at 10° C. for 0.5 h, then N-hydroxy-2-methoxy-benzamidine (80.98 mg, 487.31 umol, 1.00 eq) was added and stirred at 120° C. for 12 h. The mixture was diluted with H$_2$O (20 mL) and extracted with EA (30 mL×2), the combined organic layers were dried over Na$_2$SO$_4$, filtered and concentrated to dry. The residue was purified by prep-HPLC (column: Welch Ultimate AQ-C18 150×30 mm×5 um; mobile phase: [water (0.1% TFA)-ACN]; B %: 50%-80%, 13 min) to give 5-(1-isopropylbenzotriazol-5-yl)-3-(2-methoxyphenyl)-1,2,4-oxadiazole (110.00 mg, 328.01 umol, 67.31% yield) as a white solid.

$^1$H NMR (400 MHz, CHLOROFORM-d) δ=8.99 (s, 1H), 8.36 (dd, J=1.2, 8.7 Hz, 1H), 8.17 (dd, J=1.6, 7.7 Hz, 1H), 7.74 (d, J=8.7 Hz, 1H), 7.59-7.48 (m, 1H), 7.20-7.05 (m, 2H), 5.16 (spt, J=6.8 Hz, 1H), 4.03 (s, 3H), 1.81 (d, J=6.8 Hz, 6H).

621
General Procedure K

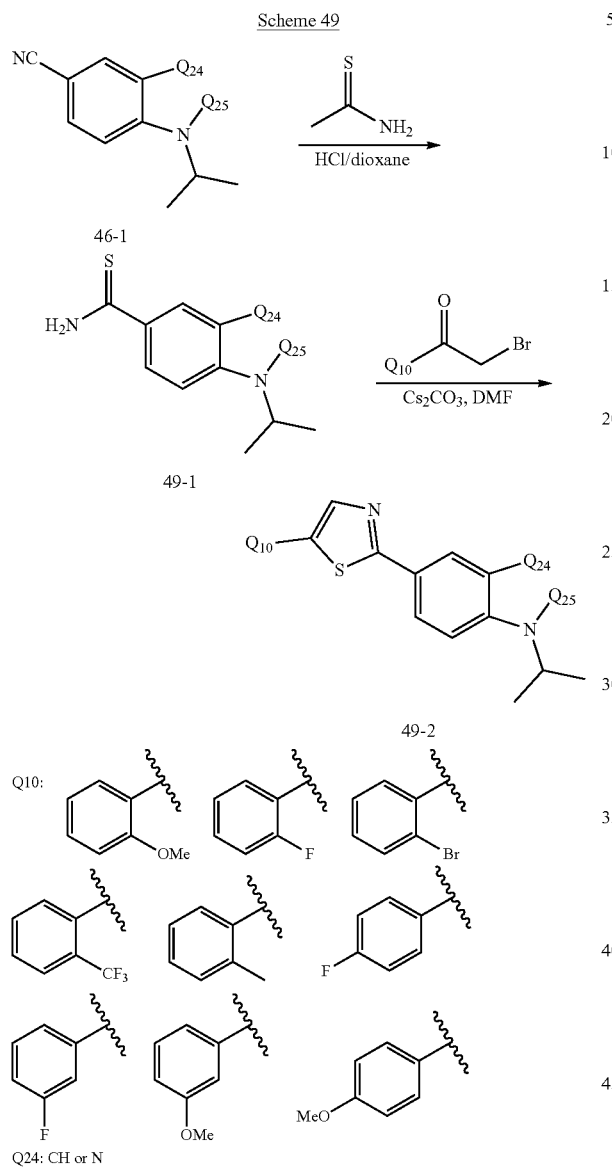

Q24: CH or N
Q25: CH or N

Synthesis of 49-1: 1-(propan-2-yl)-1H-1,2,3-benzotriazole-5-carbothioamide

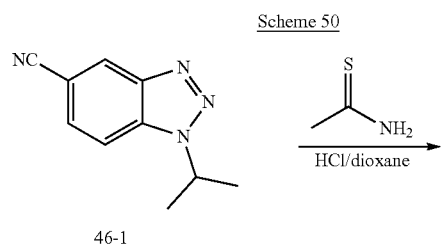

622
-continued

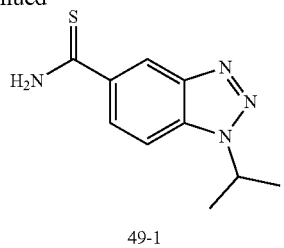

To a solution of 1-isopropylbenzotriazole-5-carbonitrile (2 g, 10.74 mmol, 1 eq) in HCl/dioxane (100 mL, 4 M) was added thioacetamide (1.61 g, 21.48 mmol, 2 eq) and stirred at 110° C. for 2 h. The reaction mixture was concentrated under reduced pressure and purified by flash silica gel chromatography (PE/EA=2/1 to 1/1) to give 1-isopropyl-benzotriazole-5-carbothioamide (2.1 g, 9.53 mmol, 88.76% yield) as a yellow solid.

Synthesis of 51-2 : 5-{5-[2-(methyl-λ³-oxy)phenyl]-1,3-thiazol-2-yl}-1-(propan-2-yl)-1H-1,2,3-benzotriazole

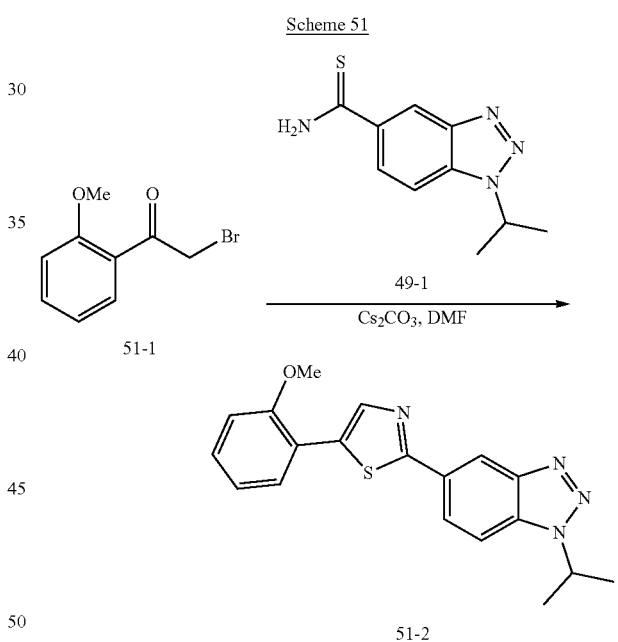

To a solution of 1-isopropylbenzotriazole-5-carbothioamide (300 mg, 1.36 mmol, 1 eq) in DMF (3 mL) was added Cs$_2$CO$_3$ (443.71 mg, 1.36 mmol, 1.00 eq) and 2-bromo-1-(2-methoxyphenyl)ethanone (311.95 mg, 1.36 mmol, 1 eq). The mixture was stirred at 100° C. for 12 h. The residue was purified by prep-HPLC (column: Waters Xbridge 150×25 5u; mobile phase: [water(10 mM NH$_4$HCO$_3$)-ACN]; B %: 60%-90%, 10 min) to give 2-(1-isopropylbenzotriazol-5-yl)-5-(2-methoxyphenyl)thiazole (190 mg, 509.65 umol, 37.42% yield, 94% purity) as a yellow solid.

$^1$H NMR (400 MHz, CHLOROFORM-d) δ=8.60 (s, 1H), 8.37 (dd, J=1.7, 7.8 Hz, 1H), 8.22 (dd, J=1.1, 8.8 Hz, 1H), 7.91 (s, 1H), 7.55 (d, J=8.8 Hz, 1H), 7.31-7.23 (m, 1H), 7.05 (t, J=7.5 Hz, 1H), 6.96 (d, J=8.3 Hz, 1H), 5.04 (spt, J=6.8 Hz, 1H), 3.92 (s, 3H), 1.70 (d, J=6.7 Hz, 6H).

General Procedure L

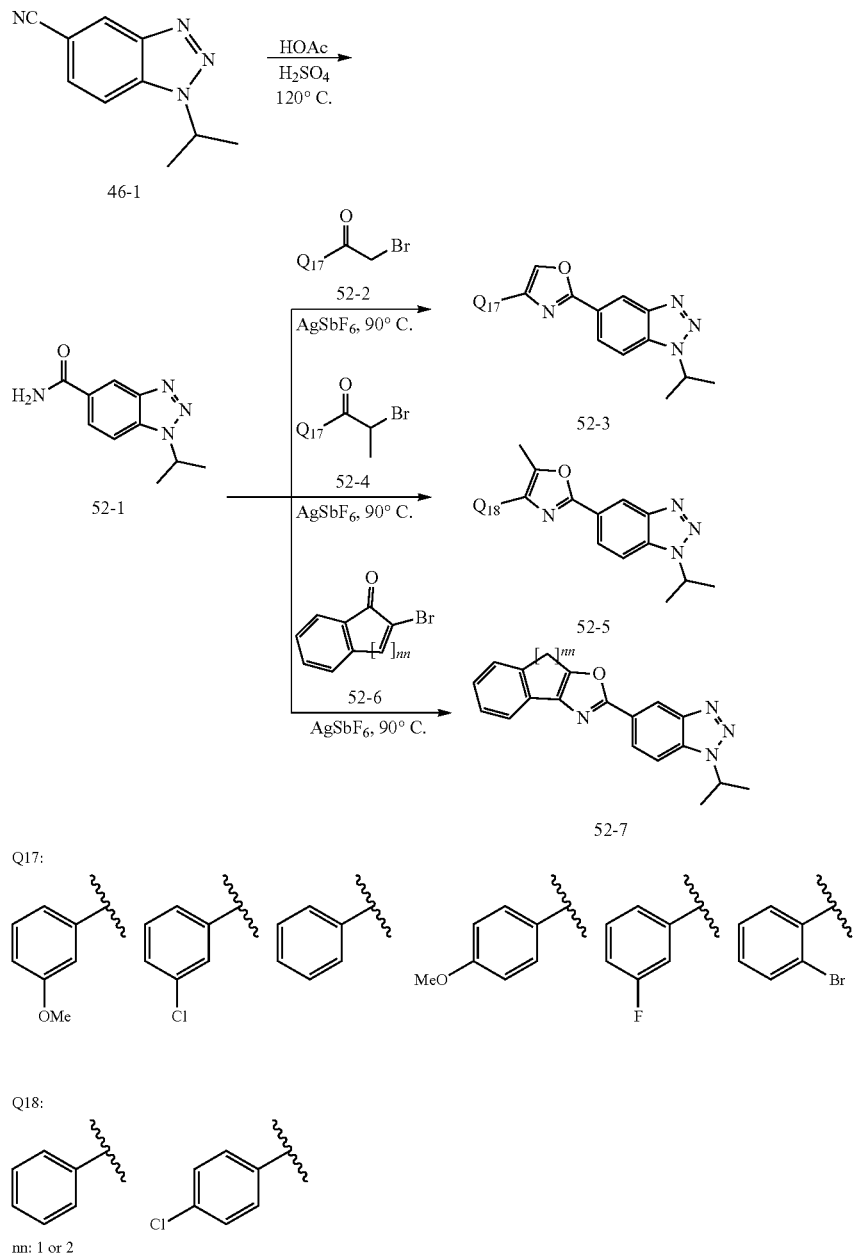

Scheme 52 nn: 1 or 2

Synthesis of 52-1: 1-(propan-2-yl)-1H-1,2,3-benzotriazole-5-carboxamide

To a solution of 46-1 (1.0 g, 5.4 mmol) in HOAc (10 mL) was added $H_2SO_4$ (0.5 mL) and reaction heated in MW 90 min at 120° C. Let cool overnight. Reaction mixture poured onto ice, neutralized and extracted with EtOAc. Solvent evaporated to give a dark solid. Silica gel chromatography (10-50% acetone in hexane) gave a residue which was triturated with a small amount of acetone and an off-white solid was collected by filtration to give the title compound (52-1) (0.5 g, 45%).

Synthesis of 52-3: 5-(4-phenyl-1,3-oxazol-2-yl)-1-(propan-2-yl)-1H-1,2,3-benzotriazole: To a mixture of 52-1 (50 mg, 0.25 mmol), 52-2 (51 mg, 0.25 mmol) was added AgSbF6 (86 0.25 mmol) and the mixture was heated to 90° C. for about 3 hrs then cool to rt. Reaction worked up with $NaHCO_3$ and $CH_2C_{12}$. Organic layer separated and evaporated to give a dark oil. Residue was chromatographed (0 to 5% MeOH in $CH_2Cl_2$) to give a residue which was further purified by reverse phase HPLC. Appropriate fractions combined and lyophilized to give the title compound as an off-white solid. (7 mg, 10%).

General Procedure M

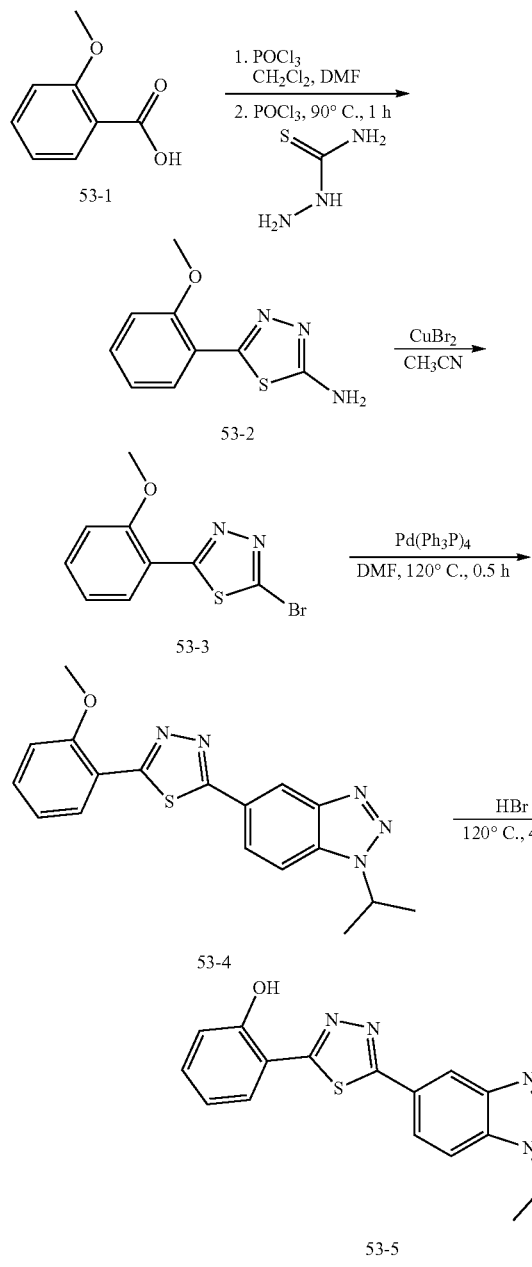

Synthesis of 5-(2-methoxyphenyl)-1,3,4-thiadiazol-2-amine 53-2: To a solution of 53-1 (1.9 g, 10.0 mmol) in CH₂Cl₂ (50 mL) was added DMF (0.2 mL) followed by portion wise addition of oxalyl chloride (1.7 mL, 20.0 mmol) and the solution was stirred overnight at rt. Reaction mixture was evaporated in vacuum. To residue was added thiosemicarbazide (1.1 g, 15 mmol) followed by POCl3 (2.8 mL, 30 mmol) and the reaction mixture was heated to 90° C. After about 45 min to 1 hr, heat was turned off and allowed to cool overnight. Quench with ice and worked up with K2CO3 and EtOAc. Organic layer washed with sat'd NaHCO3 and dried over Na2SO4. Filtered and evaporated to give a yellow residue which was triturated with CH2Cl2 and the title compound was collected as a beige solid (0.9 g, 43%). This material was used directly in the next step.

Synthesis of 2-bromo-5-(2-methoxyphenyl)-1,3,4-thiadiazole 53-3: A mixture of t-Bu-nitrite (0.9 mL, 9.6 mmol) and CuBr2 (2.2 g, 9.6 mmol) in MeCN (30 mL) was stirred for 10 min and then 53-2 (0.9 g, 1.76 mmol) was added in 2 portions. Stirred ~ 1 hr and then solvent removed in vacuum. Residue was suspended in EtOAc, washed 2x with 1 N HCl, then brine and dried over Na₂SO₄. Filtered and evaporated to give the title compound as a yellow-orange solid (1 g, 86%).

Synthesis of 5-[5-(2-methoxyphenyl)-1,3,4-thiadiazol-2-yl]-1-(propan-2-yl)-1H-1,2,3-benzotriazole 53-4: Combined 52-3 (95 mg, 0.25 mmol), 14-5 (45 mg, 0.3 mmol), K₃PO₄ (132 mg, 0.625 mmol) and Pd(Ph3P)4 (58 mg, 0.05 mmol) in a mixture of DMF (4 mL) and water (1 mL). Heated to 120° C. for 30 min in MW. Evap sol to give a residue which was chromatographed on silica (0 to 30% EtOAc in hex). Appropriate fraction were combined and solvent evaporated. This residue was further purified by reverse phase HPLC to give the title compound (30 mg, 20%) as an off-white solid.

Synthesis of 2-{3-[1-(propan-2-yl)-1H-1,2,3-benzotriazol-5-yl]-1,2,4-thiadiazol-5-yl}phenol 53-5: 53-4 (40 mg, 0.11 mmol) was dissolved in HR and heated to 120° C. After ~ 48 hrs starting material was gone. Neutralize with NaHCO₃. Residue purified by reverse phase HPLC to give the title compound (10 mg, 22%). [M+H]⁺ 0.338.0

General Procedure N

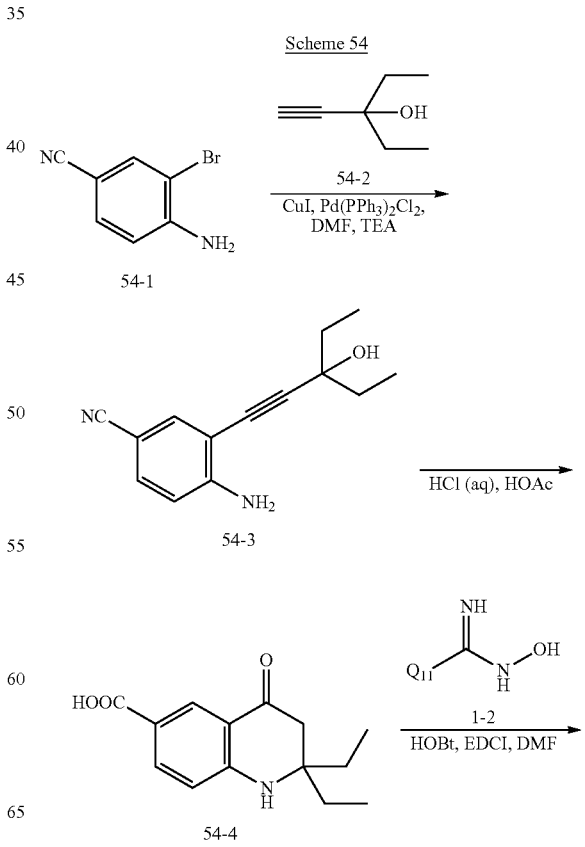

627

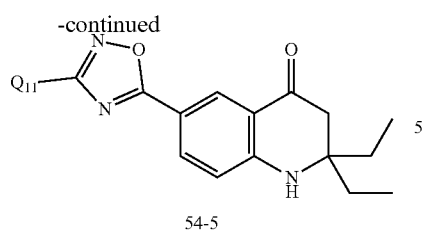

54-5

Synthesis of 54-3: 4-amino-3-(3-ethyl-3-hydroxy-pent-1-yn-1-yl)benzonitrile

To a solution of compound 54-1 (1 g, 5.08 mmol, 1 eq.) in DMF (7 mL) and TEA (2.18 g, 21.55 mmol, 3 mL, 4.25 eq.) was added compound 54-2 (683.15 mg, 6.09 mmol, 783.43 uL, 1.2 eq.), CuI (48.33 mg, 253.77 umol, 0.05 eq.) and Pd(PPh$_3$)$_2$C$_{12}$ (178.12 mg, 253.77 umol, 0.05 eq.). The mixture was stirred at 90° C. under nitrogen atmosphere for 3 hours. TLC showed a new one spot formed. The reaction mixture was diluted with water (20 mL), extracted with EtOAc (20 mL×2), washed with brine (20 mL), dried with sodium sulfate, filtered and concentrated. The residue was purified by flash silica gel column chromatography (PE: EA=5:1) to give compound 3 (1 g, yield: 86%) as a yellow oil. $^1$H NMR (400 MHz, CDCl$_3$) δ=7.52 (d, J=1.6 Hz, 1H), 7.34 (dd, J=8.6, 1.8 Hz, 1H), 6.68 (d, J=8.4 Hz, 1H), 4.76 (s, 2H), 2.95 (s, 1H), 2.88 (s, 1H), 2.32 (s, 1H), 1.85-1.70 (m, 4H), 1.10 (t, J=7.4 Hz, 6H).

Synthesis of 54-4: 2,2-diethyl-4-oxo-1,3-dihydroquinoline-6-carboxylic acid

A mixture of compound 54-3 (300 mg, 1.31 mmol) in concentrated hydrochloric acid solution (1 mL) and acetic acid (1 mL) was stirred at 115° C. for 3 hours. The mixture was basified with 1 N sodium hydroxide solution to pH=10, washed with EtOAc (20 mL×3), the aqueous phase was acidized with 1 N hydrochloric acid solution to pH=3, filtered, the filtrate cake was washed with water (10 mL), dried under vacuum to give compound 54-4 (35 mg, yield: 11%) as white solid. $^1$H NMR (400 MHz, DMSO-d$_6$) δ=12.08 (br. s, 1H), 7.90 (d, J=2.0 Hz, 1H), 7.52 (dd, J=2.0, 8.7 Hz, 1H), 7.14 (s, 1H), 6.58 (d, J=8.7 Hz, 1H), 1.73 (s, 1H), 1.36-1.19 (m, 4H), 0.58 (t, J=7.4 Hz, 6H).

628

Synthesis of 55-1: 2,2-diethyl-6-[3-(thiophen-3-yl)-1,2,4-oxadiazol-5-yl]-1,3-dihydroquinolin-4-one Scheme 55

Scheme 55

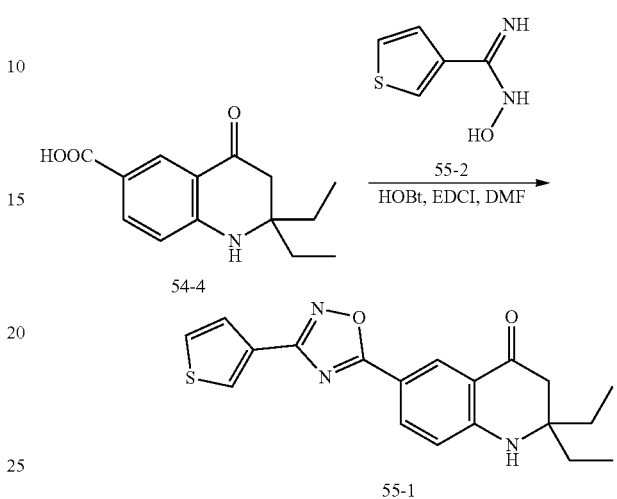

To a solution of compound 54-4 (100 mg, 404.39 umol, 1 eq.) in DMF (1 mL) was added HOBt (65.57 mg, 485.26 umol, 1.2 eq.) and EDCI (93.02 mg, 485.26 umol, 1.2 eq.). After stirring at 20° C. for 30 mins, compound 55-2 (63.24 mg, 444.82 umol, 1.1 eq.) was added, and stirred for another 30 mins. Then the mixture was heated to 120° C. and stirred for 2 hours. The mixture was triturated with EA (20 mL), filtered, washed with EA (10 mL), the residue was purified by prep-HPLC (column: Phenomenex Synergi C18 150× 25×10 um; mobile phase: [water(0.1% TFA)-ACN]; B %: 50%-80%, 13 min) to give 55-1 (45 mg, yield: 29%) as orange solid. $^1$H NMR (400 MHz, DMSO-d$_6$) δ =8.36-8.27 (m, 2H), 7.96 (dd, J=2.0, 8.8 Hz, 1H), 7.79 (dd, J=3.0, 5.0 Hz, 1H), 7.71 (s, 1H), 7.62 (d, J=5.0 Hz, 1H), 6.99 (d, J=8.9 Hz, 1H), 2.59 (s, 2H), 1.67-1.48 (m, 4H), 0.86 (t, J=7.3 Hz, 6H).

General Procedure O

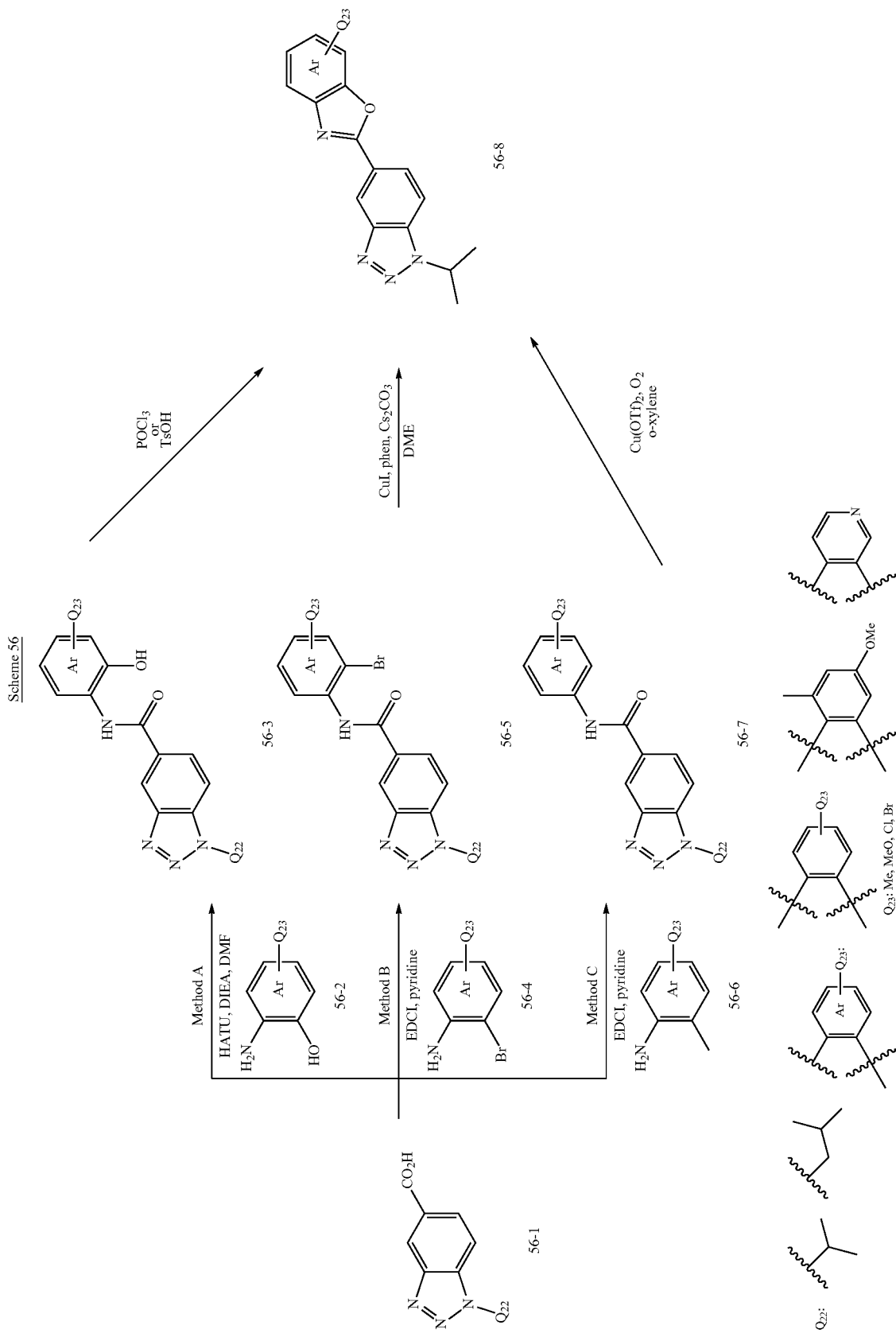

631

Synthesis of 57-3: 5-(4-methoxy-1,3-benzoxazol-2-yl)-1-(2-methylpropyl)-1,2,3-benzotriazole

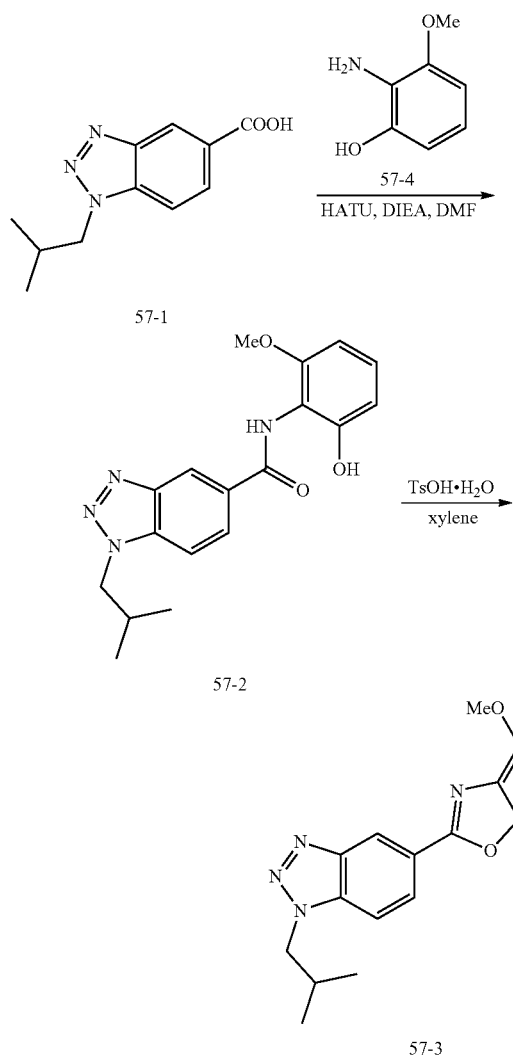

Scheme 57

Synthesis of 57-2: N-(2-hydroxy-6-methoxyphenyl)-1-(2-methylpropyl)-1,2,3-benzotriazole-5-carboxamide To a solution of compound 57-1 (100 mg, 487.30 umol, 1 eq.) in DMF (3 mL) was added HOBt (65.85 mg, 487.30 umol, 1 eq.) and EDCI (112.10 mg, 584.76 umol, 1.2 eq.). After addition, the mixture was stirred at 20° C. for 0.5 hour, then compound 57-4 (81.37 mg, 584.76 umol, 1.2 eq.) was added, the mixture was stirred at 20° C. for further 12 hours. LCMS showed compound 57-1 consumed, and a major peak with desired MS detected. The mixture was diluted with water (20 mL), extracted with EtOAc (15 mL*2), washed with brine (20 mL), dried with sodium sulfate, filtered and concentrated, to give compound 57-2 (159 mg, crude) as brown oil, which was used in next step directly without further purification. LCMS: 327.2[M+1]

632

Synthesis of 57-3: 5-(4-methoxy-1,3-benzoxazol-2-yl)-1-(2-methylpropyl)-1,2,3-benzotriazole To a solution of compound 57-2 (159 mg, crude) in xylene (10 mL) was added TsOH-H$_2$O (370.70 mg, 1.95 mmol, 4 eq.). After addition, the mixture was stirred at 120° C. for 2 hours. LCMS showed compound 57-2 consumed, and a major peak with desired Ms detected. The mixture was concentrated, diluted with saturated sodium bicarbonate solution (20 mL), extracted with EtOAc (20 mL*2), dried with sodium sulfate, filtered and concentrated. The residue was purified by prep-HPLC (column: Phenomenex Synergi C18 150*25*10 um; mobile phase: [water(0.1% TFA)-ACN]; B %: 42%-72%, 10 min) to give 57-3 (53 mg, yield: 35%) as grey solids.

$^1$H NMR (400 MHz, CDCl$_3$) δ=8.95 (s, 1H), 8.51 (dd, J=1.1, 8.8 Hz, 1H), 7.69 (d, J=8.8 Hz, 1H), 7.37-7.31 (m, 1H), 7.28-7.27 (m, 1H), 6.85 (d, J=7.9 Hz, 1H), 5.18-5.08 (m, 1H), 4.10 (s, 3H), 1.80 (s, 3H), 1.78 (s, 3H)

Synthesis of 58-3: 1-isopropyl-5-(7-methoxy-1,3-benzoxazol-2-yl)-1,2,3-benzotriazole

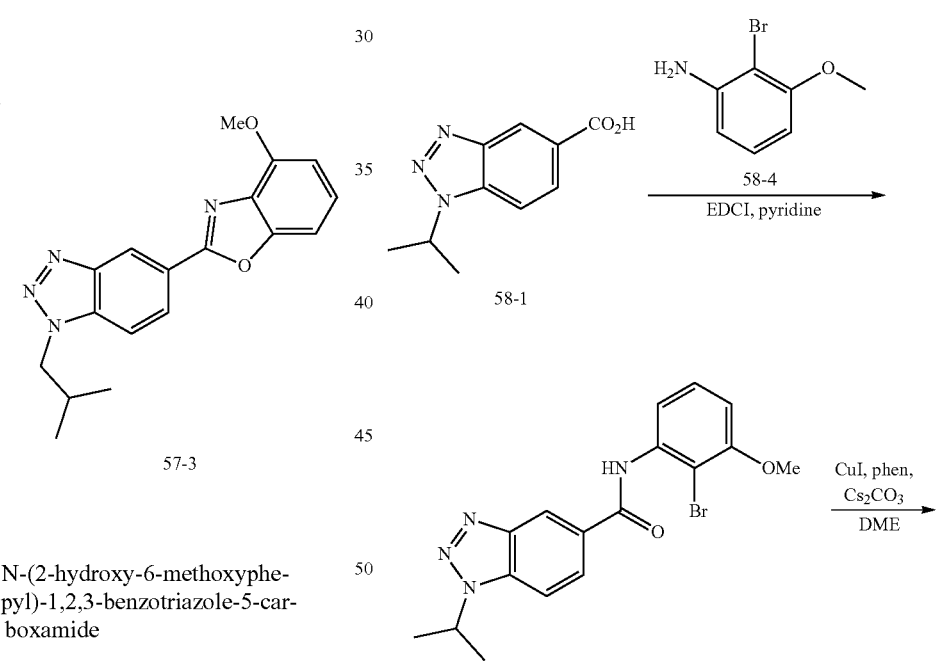

Scheme 58

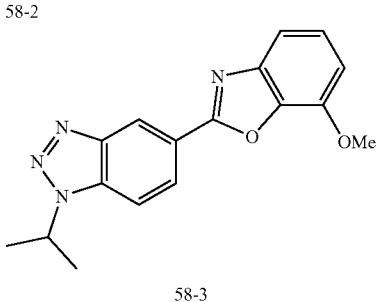

58-3

Synthesis of 58-2: N-(2-bromo-3-methoxyphenyl)-1-isopropyl-1,2,3-benzotriazole-5-carboxamide A mixture of compound 58-1 (200 mg, 989.86 umol, 1 eq.), compound 58-1 (243.76 mg, 1.19 mmol, 1.2 eq.) and EDCI (284.64 mg, 1.48 mmol, 1.5 eq.) in pyridine (3 mL) was stirred at 20° C. for 12 hours. The mixture was diluted with EtOAc (30 mL), washed with 1 N hydrochloric acid solution (20 mL*3), dried with sodium sulfate, filtered and concentrated. The residue was purified by prep-TLC (PE:EA=3:1) to give compound 58-2 (150 mg, yield: 38%) as brown oil. LCMS: 391.1 [M+1]

Synthesis of 58-3: 1-isopropyl-5-(7-methoxy-1,3-benzoxazol-2-yl)-1,2,3-benzotriazole A mixture of compound 58-2 (50 mg, 128.45 umol, 1 eq.), 1,10-phenanthroline (2.31 mg, 12.85 umol, 0.1 eq.), $Cs_2CO_3$ (62.78 mg, 192.68 umol, 1.5 eq.) and CuI (1.22 mg, 6.42 umol, 0.05 eq.) in DME (2 mL) was heated to 85° C. and stirred for 12 hours under nitrogen atmosphere. The mixture was diluted with EtOAc (20 mL), washed with water (10 mL), dried with sodium sulfate, filtered and concentrated. The residue was purified by prep-HPLC (column: Phenomenex Synergi C18 150*25*10 um; mobile phase: [water (0.1% TFA)-ACN]; B %: 45%-75%, 12 min) to give 58-3 (8 mg, yield: 19%) as gray solid.

$^1$H NMR (400 MHz, DMSO-d$_6$) δ=8.76 (s, 1H), 8.32 (dd, J=1.3, 8.8 Hz, 1H), 8.13 (d, J=8.7 Hz, 1H), 7.44-7.28 (m, 2H), 7.07 (d, J=7.8 Hz, 1H), 5.29 (spt, J=6.7 Hz, 1H), 4.02 (s, 3H), 1.66 (d, J=6.6 Hz, 6H).

Synthesis of 59-3: 1-isopropyl-5-(6-methoxy-4-methyl-1,3-benzoxazol-2-yl)-1,2,3-benzotriazole

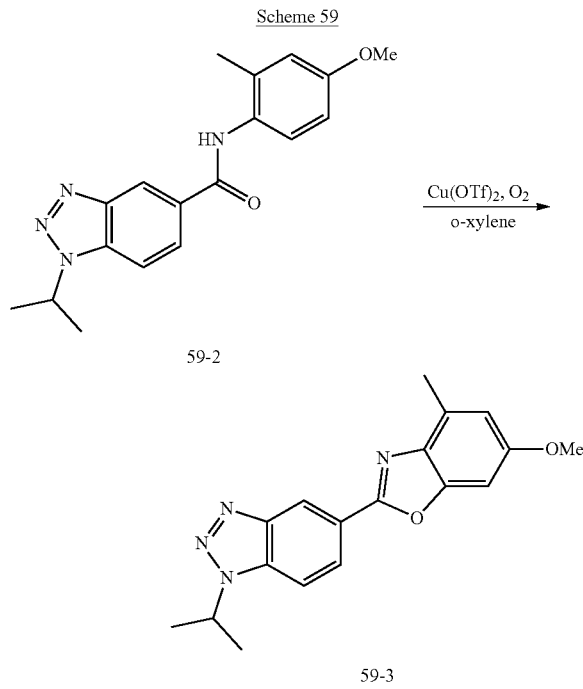

Scheme 59

59-2

59-3

Synthesis of 59-3: 1-isopropyl-5-(6-methoxy-4-methyl-1,3-benzoxazol-2-yl)-1,2,3-benzotriazole To a solution of compound 59-2 (1-isopropyl-N-(4-methoxy-2-methylphenyl)-1,2,3-benzotriazole-5-carboxamide) prepared according to the procedure to prepare 58-2, (50 mg, 154.14 umol, 1 eq.) in o-xylene (2 mL) was added Cu(OTf)$_2$ (11.12 mg, 30.83 umol, 0.2 eq.). The reaction was stirred at 130° C. under oxygen atmosphere for 16 hours. The mixture was diluted with water (20 mL), extracted with EtOAc (30 mL*3), dried with sodium sulfate, filtered and concentrated. The residue was purified by prep-TLC (PE:EA=4:1) to give 59-3 (1.1 mg, yield: 2%) as yellow solid.

$^1$H NMR (400 MHz, CDCl$_3$) δ=8.80 (s, 1H), 8.33 (dd, J=1.4, 8.7 Hz, 1H), 7.59 (d, J=8.8 Hz, 1H), 6.91 (d, J=2.2 Hz, 1H), 6.72 (d, J=1.5 Hz, 1H), 5.16-4.93 (m, 1H), 3.81 (s, 3H), 2.58 (s, 3H), 1.72 (d, J=6.8 Hz, 6H)

Example 2: In Vitro Activity of Compounds

Stable clonal Chinese hamster ovary K1 (CHO-K1) cells co-expressing EA-β-arrestin2 and the human sphingosine-1-phosphate receptor 1 (NM_001400, S$_1$P$_1$) with a C-terminal Prolink™ tag were purchased from DiscoverX corporation (Cat #: 93-0207C2).

Cell Culturing and Assay Plating

Cell lines were cultured in AssayComplete™ Media 6 (DiscoverX Corporation, Cat #: 920018GF2) at 37° C. and 5% CO$_2$ in a humidified CO$_2$ and temperature-controlled incubator. To begin assay plating, cells were washed with dulbecco's phosphate buffered saline (CellGro, Cat #: 21-031-CV) and lifted from the culturing flask by incubation (37° C., 5 min) with CellStripper (Cellgro, Cat #: 25-056-CI). Lifted cells were resuspended to 250,000 cells per milliliter in AssayComplete™ Cell Plating 11 Reagent (DiscoverX Corporation, Cat #: 93-0563R11B) and plated at 5,000 cells per well in white-opaque 384 well plates (Greiner Bio-One Item #: 20-784080). Plated cells were incubated overnight at 37° C. and 5% CO$_2$ in a humidified CO$_2$ and temperature-controlled incubator.

Detecting Inhibition of cAMP Production

Agonist-promoted G-protein responses were determined by measuring changes in intracellular cAMP using the HTRF® cAMP HiRange kit (CisBio, Cat #: 62AM6PEJ) based on time-resolved fluorescence resonance energy transfer (TR-FRET) technology. AssayComplete™ Cell Plating 11 Reagent was removed and replaced with Ham's F-12 (CellGro, Cat #: 10-080-CM) containing isobutyl-methylxanthine (IBMX; 500 µM; Tocris Bioscience, Cat #: 2845), and NKH-477 (1.5 µM; Tocris Bioscience, Cat #: 1603) along with test or control compounds at the desired concentrations. Following a 30-minute incubation at 37° C. and 5% CO$_2$ in a humidified CO$_2$ and temperature-controlled incubator, the components of the cAMP HiRange kit were added as per the manufacturer's instructions. After an hour incubation at room temperature, plates were analyzed by a BMG PheraStar microplate reader. Responses were measured as the ratio of fluorescence emission at 665 nm to fluorescence emission at 620 nm.

β-Arrestin2 Recruitment Assay

Agonist-promoted β-arrestin2 recruitment to the sphingosine-1-phosphate 1 receptor was determined using the β-arrestin PathHunter®) Detection kit (DiscoverX Corporation, Cat #: 93-0001). In this system, β-arrestin2 is fused to an N-terminal deletion mutant of β-galactosidase (termed the enzyme acceptor or EA) and the C-terminus of the GPCR of interest is fused to a smaller (42 amino acids), weakly-complementing fragment 15 termed ProLink™. In cells that stably express these fusion proteins, stimulation with a cognate agonist results in the interaction of β-arrestin2 and the Prolink™-tagged GPCR. This allows the complementation of the two β-galactosidase fragments and results in the formation of a functional enzyme with β-galactosidase activity. AssayComplete™ Cell Plating Reagent was removed and replaced with Ham's F-12 containing IBMX (500 μM), and NKH-477 (1.5 μM) along with test or control compounds at the desired concentrations. Following a 60 minute incubation at 37° C. and 5% $CO_2$ in a humidified $CO_2$ and temperature-controlled incubator, the components of the β-arrestin PathHunter® Detection kit were added as per the manufacturer's instructions. After an hour incubation at room temperature, plates were analyzed by a BMG PheraStar microplate reader.

Activity Table

The compounds as indicated herein were able to modulate the activities (inhibition of cAMP production and β-arrestin2 recruitment) of the sphingosine-1-phosphate 1 receptor as indicated herein. The tables below include the efficacy of the compound as compared to a positive control, referred to as "SPAN". These values are normalized to fingolimod, a known agonist of the sphingosine-1-phosphate 1 receptor. The tables also include potency values (pEC50) for modulating discrete receptor-mediated activities (inhibition of cAMP production and $P_3$-arrestin2 recruitment). This value represents the estimated concentration to promote half of the maximal efficacy (or SPAN) observed for each compound.

| Compound Number | hS1P1 cAMP $pEC_{50}$ | hS1P1 cAMP SPAN | hS1P1 B-arrestin2 $pEC_{50}$ | hS1P1 B-arrestin2 SPAN |
|---|---|---|---|---|
| 1 | <6.5 | <75 | <5 | <75 |
| 2 | <6.5 | >75 | >5 | <75 |
| 3 | >6.5 | >75 | >5 | >75 |
| 4 | <6.5 | <75 | <5 | <75 |
| 5 | <6.5 | <75 | <5 | <75 |
| 6 | <6.5 | <75 | <5 | <75 |
| 7 | <6.5 | >75 | <5 | >75 |
| 8 | <6.5 | <75 | <5 | <75 |
| 9 | <6.5 | <75 | <5 | <75 |
| 10 | <6.5 | <75 | <5 | <75 |
| 11 | <6.5 | <75 | <5 | <75 |
| 12 | <6.5 | <75 | <5 | <75 |
| 13 | >6.5 | <75 | >5 | <75 |
| 14 | >6.5 | <75 | >5 | <75 |
| 15 | <6.5 | >75 | <5 | <75 |
| 16 | <6.5 | <75 | >5 | >75 |
| 17 | >6.5 | >75 | >5 | >75 |
| 18 | <6.5 | <75 | <5 | <75 |
| 19 | <6.5 | <75 | >5 | <75 |
| 20 | >6.5 | >75 | >5 | >75 |
| 21 | <6.5 | >75 | >5 | >75 |
| 22 | >6.5 | >75 | >5 | >75 |
| 23 | <6.5 | <75 | <5 | <75 |
| 24 | <6.5 | >75 | <5 | <75 |
| 25 | <6.5 | <75 | <5 | <75 |
| 26 | >6.5 | >75 | >5 | >75 |
| 26 | >6.5 | >75 | >5 | <75 |
| 27 | <6.5 | >75 | >5 | <75 |
| 28 | <6.5 | >75 | <5 | >75 |
| 29 | <6.5 | <75 | <5 | <75 |
| 30 | <6.5 | <75 | <5 | <75 |
| 31 | >6.5 | >75 | >5 | >75 |
| 32 | >6.5 | >75 | >5 | >75 |
| 33 | >6.5 | >75 | >5 | >75 |
| 34 | <6.5 | >75 | <5 | >75 |
| 35 | <6.5 | >75 | <5 | >75 |
| 36 | <6.5 | <75 | <5 | <75 |
| 37 | <6.5 | <75 | <5 | <75 |
| 38 | <6.5 | <75 | <5 | >75 |
| 39 | <6.5 | <75 | <5 | <75 |
| 40 | >6.5 | >75 | >5 | >75 |
| 41 | <6.5 | <75 | <5 | <75 |
| 41 | <6.5 | <75 | <5 | <75 |
| 42 | <6.5 | >75 | <5 | >75 |
| 43 | >6.5 | >75 | >5 | >75 |
| 44 | <6.5 | <75 | <5 | <75 |
| 45 | <6.5 | <75 | <5 | <75 |
| 46 | >6.5 | >75 | >5 | >75 |
| 47 | <6.5 | <75 | <5 | <75 |
| 48 | <6.5 | <75 | <5 | <75 |
| 49 | <6.5 | <75 | <5 | <75 |
| 50 | <6.5 | <75 | <5 | <75 |
| 51 | <6.5 | <75 | <5 | <75 |
| 52 | <6.5 | <75 | <5 | <75 |
| 53 | <6.5 | <75 | <5 | <75 |
| 54 | <6.5 | <75 | <5 | >75 |
| 55 | >6.5 | >75 | >5 | >75 |
| 56 | <6.5 | <75 | <5 | <75 |
| 57 | <6.5 | <75 | <5 | <75 |
| 58 | <6.5 | <75 | <5 | <75 |
| 59 | >6.5 | >75 | >5 | >75 |
| 60 | <6.5 | <75 | <5 | <75 |
| 61 | >6.5 | >75 | >5 | >75 |
| 62 | <6.5 | <75 | <5 | >75 |
| 63 | >6.5 | <75 | <5 | <75 |
| 64 | >6.5 | >75 | <5 | >75 |
| 65 | <6.5 | <75 | <5 | <75 |
| 66 | <6.5 | <75 | >5 | >75 |
| 67 | <6.5 | >75 | >5 | >75 |
| 68 | <6.5 | <75 | <5 | <75 |
| 69 | <6.5 | <75 | >5 | <75 |
| 70 | >6.5 | <75 | >5 | <75 |
| 71 | <6.5 | >75 | <5 | <75 |
| 72 | >6.5 | >75 | >5 | >75 |
| 73 | <6.5 | <75 | >5 | <75 |
| 74 | <6.5 | <75 | <5 | <75 |
| 75 | >6.5 | <75 | >5 | >75 |
| 76 | <6.5 | <75 | <5 | <75 |
| 77 | <6.5 | <75 | <5 | <75 |
| 78 | <6.5 | <75 | <5 | <75 |
| 79 | >6.5 | >75 | >5 | >75 |
| 80 | >6.5 | <75 | <5 | <75 |
| 81 | <6.5 | >75 | <5 | <75 |
| 82 | <6.5 | <75 | <5 | <75 |
| 83 | >6.5 | >75 | >5 | >75 |
| 84 | <6.5 | <75 | >5 | <75 |
| 85 | <6.5 | <75 | <5 | <75 |
| 86 | <6.5 | <75 | <5 | >75 |
| 87 | <6.5 | <75 | <5 | <75 |
| 88 | <6.5 | <75 | <5 | <75 |
| 89 | <6.5 | <75 | <5 | <75 |
| 90 | <6.5 | >75 | >5 | >75 |
| 91 | <6.5 | <75 | <5 | <75 |
| 92 | <6.5 | <75 | <5 | <75 |
| 93 | <6.5 | <75 | <5 | >75 |
| 94 | <6.5 | <75 | <5 | <75 |
| 95 | <6.5 | <75 | <5 | <75 |
| 96 | >6.5 | >75 | >5 | >75 |
| 97 | <6.5 | <75 | <5 | <75 |
| 98 | <6.5 | >75 | >5 | >75 |
| 99 | >6.5 | >75 | >5 | >75 |
| 100 | <6.5 | <75 | <5 | <75 |
| 101 | >6.5 | >75 | >5 | >75 |
| 102 | <6.5 | <75 | <5 | <75 |
| 103 | >6.5 | >75 | >5 | >75 |
| 103 | >6.5 | >75 | >5 | >75 |
| 103 | >6.5 | >75 | >5 | >75 |
| 104 | >6.5 | >75 | <5 | <75 |
| 105 | <6.5 | <75 | <5 | <75 |
| 106 | >6.5 | >75 | >5 | >75 |
| 107 | >6.5 | >75 | >5 | >75 |
| 108 | >6.5 | <75 | <5 | <75 |
| 109 | <6.5 | <75 | >5 | <75 |
| 110 | <6.5 | <75 | <5 | <75 |

| Compound Number | hS1P1 cAMP pEC$_{50}$ | hS1P1 cAMP SPAN | hS1P1 B-arrestin2 pEC$_{50}$ | hS1P1 B-arrestin2 SPAN |
|---|---|---|---|---|
| 111 | <6.5 | >75 | <5 | >75 |
| 112 | >6.5 | >75 | <5 | >75 |
| 113 | <6.5 | <75 | <5 | <75 |
| 114 | <6.5 | <75 | <5 | <75 |
| 115 | >6.5 | >75 | >5 | >75 |
| 116 | <6.5 | <75 | <5 | <75 |
| 117 | <6.5 | <75 | <5 | <75 |
| 118 | <6.5 | <75 | <5 | <75 |
| 119 | <6.5 | <75 | <5 | <75 |
| 120 | >6.5 | >75 | >5 | >75 |
| 121 | <6.5 | <75 | <5 | <75 |
| 122 | <6.5 | <75 | <5 | <75 |
| 123 | >6.5 | >75 | >5 | >75 |
| 124 | <6.5 | <75 | <5 | <75 |
| 125 | <6.5 | <75 | <5 | <75 |
| 126 | <6.5 | <75 | <5 | <75 |
| 127 | <6.5 | <75 | <5 | <75 |
| 128 | <6.5 | <75 | <5 | <75 |
| 129 | <6.5 | <75 | <5 | <75 |
| 130 | <6.5 | <75 | <5 | <75 |
| 131 | <6.5 | <75 | <5 | <75 |
| 132 | >6.5 | >75 | >5 | >75 |
| 133 | <6.5 | <75 | <5 | <75 |
| 134 | <6.5 | <75 | <5 | <75 |
| 135 | <6.5 | <75 | <5 | <75 |
| 136 | <6.5 | <75 | <5 | <75 |
| 137 | >6.5 | >75 | <5 | >75 |
| 138 | >6.5 | >75 | >5 | >75 |
| 139 | >6.5 | >75 | >5 | >75 |
| 140 | >6.5 | >75 | >5 | >75 |
| 141 | >6.5 | >75 | >5 | >75 |
| 142 | >6.5 | >75 | >5 | >75 |
| 143 | <6.5 | <75 | <5 | <75 |
| 144 | <6.5 | >75 | >5 | >75 |
| 145 | >6.5 | >75 | >5 | <75 |
| 146 | >6.5 | >75 | >5 | <75 |
| 147 | >6.5 | >75 | >5 | >75 |
| 148 | <6.5 | <75 | <5 | <75 |
| 149 | >6.5 | >75 | >5 | >75 |
| 150 | >6.5 | >75 | >5 | >75 |
| 151 | >6.5 | >75 | <5 | >75 |
| 152 | <6.5 | >75 | >5 | >75 |
| 153 | >6.5 | >75 | >5 | <75 |
| 154 | <6.5 | <75 | <5 | <75 |
| 155 | <6.5 | <75 | <5 | <75 |
| 156 | >6.5 | >75 | >5 | <75 |
| 157 | <6.5 | <75 | <5 | <75 |
| 158 | <6.5 | <75 | <5 | <75 |
| 159 | <6.5 | <75 | <5 | <75 |
| 160 | <6.5 | <75 | <5 | <75 |
| 161 | <6.5 | <75 | <5 | <75 |
| 162 | <6.5 | >75 | >5 | >75 |
| 163 | >6.5 | >75 | >5 | >75 |
| 164 | <6.5 | <75 | <5 | <75 |
| 165 | <6.5 | >75 | <5 | <75 |
| 166 | <6.5 | <75 | <5 | >75 |
| 167 | <6.5 | <75 | <5 | <75 |
| 168 | <6.5 | <75 | <5 | <75 |
| 169 | >6.5 | >75 | >5 | >75 |
| 170 | <6.5 | <75 | <5 | <75 |
| 171 | >6.5 | >75 | >5 | >75 |
| 172 | <6.5 | <75 | <5 | <75 |
| 173 | >6.5 | >75 | >5 | >75 |
| 174 | >6.5 | >75 | <5 | >75 |
| 175 | >6.5 | >75 | >5 | >75 |
| 176 | >6.5 | >75 | <5 | >75 |
| 177 | >6.5 | >75 | >5 | >75 |
| 178 | <6.5 | >75 | <5 | <75 |
| 179 | >6.5 | >75 | <5 | <75 |
| 180 | <6.5 | >75 | <5 | <75 |
| 181 | <6.5 | >75 | <5 | <75 |
| 182 | >6.5 | >75 | <5 | <75 |
| 183 | >6.5 | >75 | <5 | <75 |
| 184 | <6.5 | >75 | <5 | <75 |
| 185 | >6.5 | >75 | >5 | >75 |
| 186 | <6.5 | <75 | <5 | <75 |
| 187 | <6.5 | <75 | <5 | >75 |
| 188 | <6.5 | <75 | <5 | <75 |
| 189 | >6.5 | >75 | >5 | >75 |
| 190 | <6.5 | <75 | <5 | <75 |
| 192 | <6.5 | <75 | <5 | <75 |
| 193 | <6.5 | <75 | <5 | <75 |
| 194 | <6.5 | <75 | <5 | <75 |
| 195 | <6.5 | <75 | <5 | <75 |
| 196 | <6.5 | <75 | <5 | <75 |
| 197 | <6.5 | <75 | <5 | <75 |
| 198 | >6.5 | >75 | >5 | <75 |
| 199 | <6.5 | <75 | <5 | <75 |
| 200 | <6.5 | <75 | <5 | <75 |
| 201 | <6.5 | <75 | <5 | >75 |
| 202 | <6.5 | <75 | <5 | <75 |
| 203 | <6.5 | <75 | <5 | >75 |
| 204 | <6.5 | >75 | >5 | >75 |
| 205 | >6.5 | >75 | <5 | <75 |
| 206 | <6.5 | >75 | <5 | <75 |
| 207 | >6.5 | >75 | >5 | >75 |
| 208 | >6.5 | >75 | >5 | >75 |
| 209 | >6.5 | >75 | >5 | >75 |
| 210 | >6.5 | >75 | >5 | >75 |
| 211 | <6.5 | <75 | >5 | >75 |
| 212 | <6.5 | >75 | >5 | >75 |
| 213 | <6.5 | <75 | <5 | >75 |
| 214 | <6.5 | <75 | <5 | <75 |
| 215 | <6.5 | <75 | <5 | <75 |
| 216 | <6.5 | <75 | <5 | <75 |
| 217 | <6.5 | <75 | <5 | <75 |
| 218 | <6.5 | <75 | <5 | >75 |
| 219 | >6.5 | <75 | >5 | >75 |
| 220 | <6.5 | <75 | <5 | <75 |
| 221 | >6.5 | >75 | >5 | >75 |
| 222 | <6.5 | >75 | >5 | >75 |
| 223 | <6.5 | <75 | <5 | >75 |
| 224 | >6.5 | >75 | >5 | >75 |
| 225 | >6.5 | >75 | >5 | >75 |
| 226 | <6.5 | <75 | <5 | >75 |
| 227 | >6.5 | <75 | <5 | >75 |
| 228 | <6.5 | <75 | <5 | <75 |
| 229 | <6.5 | <75 | >5 | >75 |
| 230 | <6.5 | <75 | <5 | <75 |
| 231 | <6.5 | <75 | <5 | <75 |
| 232 | <6.5 | <75 | <5 | <75 |
| 233 | <6.5 | <75 | <5 | <75 |
| 234 | <6.5 | <75 | <5 | <75 |
| 235 | <6.5 | <75 | <5 | <75 |
| 236 | <6.5 | <75 | <5 | >75 |
| 237 | <6.5 | <75 | <5 | <75 |
| 238 | <6.5 | <75 | <5 | <75 |
| 239 | <6.5 | <75 | <5 | <75 |
| 240 | <6.5 | >75 | <5 | >75 |
| 241 | <6.5 | <75 | <5 | <75 |
| 242 | <6.5 | <75 | <5 | >75 |
| 243 | <6.5 | <75 | <5 | >75 |
| 244 | >6.5 | >75 | >5 | >75 |
| 245 | <6.5 | >75 | >5 | >75 |
| 246 | >6.5 | >75 | >5 | >75 |
| 247 | <6.5 | <75 | <5 | <75 |
| 248 | <6.5 | <75 | <5 | <75 |
| 249 | >6.5 | >75 | >5 | >75 |
| 250 | <6.5 | <75 | <5 | <75 |
| 251 | <6.5 | <75 | <5 | <75 |
| 252 | >6.5 | >75 | >5 | >75 |
| 253 | >6.5 | >75 | >5 | >75 |
| 254 | >6.5 | >75 | <5 | <75 |
| 255 | <6.5 | >75 | <5 | <75 |
| 256 | >6.5 | >75 | >5 | <75 |
| 257 | <6.5 | <75 | <5 | <75 |
| 258 | <6.5 | <75 | <5 | <75 |
| 259 | >6.5 | >75 | >5 | <75 |
| 260 | <6.5 | >75 | <5 | >75 |
| 261 | >6.5 | >75 | >5 | <75 |

-continued

| Compound Number | hS1P1 cAMP pEC$_{50}$ | hS1P1 cAMP SPAN | hS1P1 B-arrestin2 pEC$_{50}$ | hS1P1 B-arrestin2 SPAN |
|---|---|---|---|---|
| 262 | >6.5 | >75 | >5 | >75 |
| 263 | >6.5 | >75 | >5 | >75 |
| 264 | <6.5 | <75 | <5 | <75 |
| 265 | >6.5 | >75 | >5 | <75 |
| 266 | <6.5 | >75 | >5 | >75 |
| 267 | >6.5 | <75 | >5 | <75 |
| 268 | >6.5 | >75 | >5 | >75 |
| 269 | <6.5 | <75 | <5 | <75 |
| 270 | <6.5 | <75 | <5 | <75 |
| 271 | <6.5 | <75 | <5 | <75 |
| 272 | <6.5 | <75 | <5 | <75 |
| 273 | <6.5 | <75 | <5 | <75 |
| 274 | <6.5 | >75 | >5 | <75 |
| 275 | <6.5 | <75 | <5 | <75 |
| 276 | >6.5 | >75 | >5 | >75 |
| 277 | >6.5 | >75 | >5 | >75 |
| 278 | <6.5 | <75 | <5 | <75 |
| 279 | <6.5 | >75 | <5 | >75 |
| 280 | <6.5 | <75 | <5 | <75 |
| 281 | <6.5 | <75 | <5 | <75 |
| 282 | >6.5 | >75 | >5 | >75 |
| 283 | <6.5 | <75 | <5 | <75 |
| 284 | <6.5 | <75 | <5 | <75 |
| 285 | <6.5 | <75 | <5 | <75 |
| 286 | >6.5 | >75 | >5 | >75 |
| 287 | >6.5 | >75 | >5 | >75 |
| 288 | <6.5 | <75 | <5 | <75 |
| 289 | <6.5 | <75 | <5 | <75 |
| 290 | <6.5 | <75 | <5 | <75 |
| 291 | <6.5 | <75 | <5 | <75 |
| 292 | <6.5 | <75 | <5 | >75 |
| 293 | >6.5 | >75 | >5 | >75 |
| 294 | <6.5 | <75 | <5 | >75 |
| 295 | <6.5 | >75 | <5 | <75 |
| 296 | <6.5 | <75 | <5 | <75 |
| 297 | <6.5 | >75 | <5 | >75 |
| 298 | <6.5 | >75 | >5 | <75 |
| 299 | <6.5 | <75 | <5 | <75 |
| 300 | <6.5 | >75 | <5 | >75 |
| 301 | <6.5 | <75 | <5 | <75 |
| 302 | >6.5 | >75 | >5 | >75 |
| 303 | <6.5 | >75 | <5 | >75 |
| 304 | <6.5 | <75 | <5 | >75 |
| 305 | <6.5 | >75 | <5 | <75 |
| 306 | >6.5 | >75 | >5 | <75 |
| 307 | >6.5 | >75 | >5 | <75 |
| 308 | <6.5 | <75 | <5 | <75 |
| 309 | <6.5 | >75 | <5 | >75 |
| 310 | >6.5 | >75 | >5 | >75 |
| 311 | <6.5 | <75 | <5 | >75 |
| 312 | <6.5 | >75 | <5 | <75 |
| 313 | >6.5 | >75 | <5 | <75 |
| 314 | <6.5 | <75 | <5 | <75 |
| 315 | >6.5 | >75 | >5 | <75 |
| 316 | <6.5 | >75 | <5 | <75 |
| 320 | >6.5 | >75 | >5 | >75 |
| 321 | <6.5 | <75 | <5 | <75 |
| 322 | >6.5 | >75 | >5 | <75 |
| 323 | <6.5 | >75 | <5 | <75 |
| 324 | <6.5 | <75 | <5 | <75 |
| 325 | <6.5 | <75 | <5 | <75 |
| 326 | <6.5 | >75 | >5 | >75 |
| 327 | <6.5 | >75 | >5 | <75 |
| 328 | <6.5 | >75 | >5 | <75 |
| 329 | >6.5 | >75 | >5 | >75 |
| 330 | >6.5 | >75 | >5 | >75 |
| 331 | >6.5 | >75 | >5 | >75 |
| 332 | >6.5 | >75 | >5 | >75 |
| 333 | >6.5 | >75 | >5 | <75 |
| 334 | <6.5 | <75 | <5 | <75 |
| 335 | <6.5 | <75 | <5 | <75 |
| 336 | <6.5 | <75 | <5 | <75 |
| 337 | >6.5 | >75 | >5 | <75 |
| 338 | <6.5 | >75 | <5 | >75 |
| 339 | <6.5 | <75 | <5 | <75 |
| 340 | <6.5 | <75 | <5 | <75 |
| 341 | <6.5 | <75 | <5 | <75 |
| 342 | <6.5 | <75 | <5 | <75 |
| 343 | >6.5 | >75 | >5 | >75 |
| 344 | >6.5 | >75 | >5 | >75 |
| 345 | <6.5 | <75 | <5 | <75 |
| 346 | >6.5 | >75 | >5 | >75 |
| 347 | >6.5 | >75 | >5 | >75 |
| 348 | >6.5 | >75 | >5 | >75 |
| 349 | <6.5 | <75 | <5 | <75 |
| 350 | <6.5 | <75 | <5 | <75 |
| 351 | >6.5 | >75 | >5 | >75 |
| 352 | >6.5 | >75 | >5 | >75 |
| 353 | >6.5 | >75 | >5 | >75 |
| 354 | >6.5 | >75 | >5 | >75 |
| 355 | >6.5 | >75 | >5 | >75 |
| 356 | >6.5 | >75 | >5 | >75 |
| 357 | >6.5 | >75 | >5 | >75 |
| 358 | >6.5 | >75 | >5 | >75 |
| 359 | >6.5 | >75 | >5 | >75 |
| 360 | <6.5 | <75 | <5 | <75 |
| 361 | <6.5 | <75 | <5 | <75 |
| 362 | <6.5 | <75 | <5 | <75 |
| 363 | <6.5 | <75 | <5 | <75 |
| 364 | <6.5 | >75 | <5 | <75 |
| 365 | <6.5 | >75 | >5 | <75 |
| 366 | <6.5 | <75 | <5 | <75 |
| 367 | <6.5 | <75 | <5 | <75 |
| 368 | <6.5 | <75 | <5 | <75 |
| 369 | <6.5 | <75 | <5 | <75 |
| 370 | >6.5 | >75 | >5 | >75 |
| 371 | <6.5 | <75 | <5 | <75 |
| 372 | >6.5 | >75 | >5 | >75 |
| 373 | <6.5 | <75 | <5 | <75 |
| 374 | <6.5 | <75 | <5 | <75 |
| 375 | >6.5 | >75 | >5 | <75 |
| 376 | <6.5 | <75 | <5 | <75 |
| 377 | <6.5 | <75 | <5 | <75 |
| 378 | <6.5 | <75 | <5 | <75 |
| 379 | <6.5 | <75 | <5 | <75 |
| 380 | <6.5 | <75 | <5 | <75 |
| 381 | <6.5 | <75 | >5 | <75 |
| 382 | >6.5 | >75 | >5 | >75 |
| 383 | >6.5 | >75 | >5 | >75 |
| 384 | <6.5 | >75 | <5 | <75 |
| 385 | <6.5 | <75 | <5 | >75 |
| 386 | <6.5 | <75 | <5 | <75 |
| 387 | >6.5 | >75 | >5 | >75 |
| 388 | >6.5 | >75 | >5 | >75 |
| 389 | >6.5 | >75 | >5 | >75 |
| 390 | >6.5 | >75 | >5 | >75 |
| 391 | >6.5 | >75 | >5 | >75 |
| 392 | <6.5 | <75 | <5 | <75 |
| 393 | <6.5 | <75 | <5 | <75 |
| 394 | <6.5 | <75 | >5 | <75 |
| 395 | >6.5 | >75 | >5 | >75 |
| 396 | <6.5 | <75 | <5 | >75 |
| 397 | <6.5 | <75 | <5 | >75 |
| 398 | >6.5 | >75 | >5 | >75 |
| 399 | >6.5 | >75 | >5 | >75 |
| 400 | <6.5 | <75 | <5 | <75 |
| 401 | <6.5 | <75 | <5 | <75 |
| 402 | >6.5 | >75 | <5 | <75 |
| 403 | <6.5 | <75 | <5 | <75 |
| 404 | <6.5 | >75 | <5 | <75 |
| 405 | <6.5 | >75 | <5 | <75 |
| 406 | >6.5 | >75 | >5 | >75 |
| 407 | >6.5 | >75 | <5 | <75 |
| 408 | <6.5 | >75 | <5 | <75 |
| 409 | <6.5 | <75 | <5 | <75 |
| 410 | <6.5 | <75 | <5 | <75 |
| 411 | <6.5 | <75 | <5 | <75 |
| 412 | <6.5 | >75 | <5 | <75 |
| 413 | >6.5 | >75 | >5 | >75 |
| 414 | >6.5 | >75 | <5 | >75 |

| Compound Number | hS1P1 cAMP pEC$_{50}$ | hS1P1 cAMP SPAN | hS1P1 B-arrestin2 pEC$_{50}$ | hS1P1 B-arrestin2 SPAN | Compound Number | hS1P1 cAMP pEC$_{50}$ | hS1P1 cAMP SPAN | hS1P1 B-arrestin2 pEC$_{50}$ | hS1P1 B-arrestin2 SPAN |
|---|---|---|---|---|---|---|---|---|---|
| 415 | >6.5 | <75 | <5 | >75 | 490 | >6.5 | >75 | >5 | >75 |
| 416 | >6.5 | >75 | >5 | >75 | 491 | >6.5 | >75 | >5 | >75 |
| 417 | >6.5 | >75 | >5 | >75 | 492 | <6.5 | >75 | <5 | >75 |
| 418 | >6.5 | >75 | >5 | >75 | 493 | <6.5 | >75 | <5 | >75 |
| 419 | >6.5 | >75 | >5 | <75 | 494 | <6.5 | >75 | >5 | <75 |
| 420 | >6.5 | >75 | <5 | >75 | 495 | >6.5 | >75 | >5 | >75 |
| 421 | <6.5 | >75 | <5 | <75 | 496 | >6.5 | >75 | >5 | >75 |
| 422 | >6.5 | >75 | >5 | >75 | 497 | >6.5 | >75 | >5 | >75 |
| 423 | >6.5 | >75 | >5 | >75 | 498 | >6.5 | >75 | <5 | <75 |
| 424 | >6.5 | >75 | <5 | >75 | 499 | >6.5 | >75 | >5 | >75 |
| 425 | >6.5 | >75 | >5 | >75 | 500 | <6.5 | <75 | <5 | <75 |
| 426 | >6.5 | >75 | <5 | >75 | 501 | <6.5 | <75 | <5 | >75 |
| 427 | <6.5 | >75 | <5 | >75 | 502 | >6.5 | >75 | >5 | >75 |
| 428 | <6.5 | >75 | <5 | >75 | 503 | <6.5 | >75 | <5 | >75 |
| 429 | <6.5 | >75 | <5 | >75 | 504 | <6.5 | >75 | <5 | >75 |
| 430 | <6.5 | >75 | <5 | >75 | 505 | <6.5 | <75 | <5 | >75 |
| 431 | <6.5 | >75 | <5 | >75 | 506 | >6.5 | >75 | >5 | <75 |
| 432 | >6.5 | >75 | >5 | >75 | 507 | >6.5 | <75 | <5 | <75 |
| 433 | >6.5 | >75 | >5 | >75 | 508 | <6.5 | >75 | <5 | <75 |
| 434 | >6.5 | <75 | <5 | >75 | 509 | <6.5 | <75 | <5 | >75 |
| 435 | >6.5 | >75 | >5 | >75 | 510 | >6.5 | >75 | >5 | >75 |
| 436 | >6.5 | >75 | >5 | >75 | 511 | >6.5 | <75 | >5 | <75 |
| 437 | >6.5 | >75 | >5 | <75 | 512 | >6.5 | >75 | >5 | <75 |
| 438 | >6.5 | >75 | >5 | >75 | 513 | >6.5 | >75 | >5 | >75 |
| 439 | <6.5 | >75 | <5 | >75 | 514 | >6.5 | >75 | >5 | <75 |
| 440 | >6.5 | >75 | >5 | >75 | 515 | >6.5 | >75 | >5 | >75 |
| 441 | >6.5 | >75 | >5 | >75 | 516 | <6.5 | <75 | <5 | <75 |
| 442 | >6.5 | >75 | >5 | >75 | 517 | <6.5 | >75 | <5 | >75 |
| 443 | >6.5 | >75 | >5 | <75 | 518 | <6.5 | >75 | <5 | <75 |
| 444 | <6.5 | <75 | <5 | <75 | 519 | >6.5 | >75 | >5 | >75 |
| 445 | >6.5 | >75 | >5 | >75 | 520 | >6.5 | >75 | >5 | >75 |
| 446 | <6.5 | <75 | <5 | <75 | 521 | <6.5 | <75 | <5 | >75 |
| 447 | >6.5 | >75 | >5 | <75 | 522 | >6.5 | >75 | >5 | >75 |
| 448 | >6.5 | >75 | <5 | <75 | 523 | <6.5 | >75 | <5 | >75 |
| 449 | <6.5 | >75 | <5 | >75 | 524 | >6.5 | >75 | >5 | >75 |
| 450 | >6.5 | >75 | >5 | >75 | 525 | <6.5 | >75 | <5 | >75 |
| 451 | >6.5 | <75 | >5 | <75 | 526 | <6.5 | >75 | <5 | >75 |
| 452 | <6.5 | >75 | >5 | <75 | 527 | <6.5 | <75 | <5 | >75 |
| 453 | >6.5 | >75 | >5 | <75 | 528 | <6.5 | >75 | <5 | >75 |
| 454 | >6.5 | >75 | >5 | >75 | 529 | <6.5 | >75 | >5 | <75 |
| 455 | >6.5 | >75 | >5 | >75 | 530 | <6.5 | >75 | <5 | >75 |
| 456 | >6.5 | >75 | <5 | >75 | 531 | >6.5 | >75 | >5 | >75 |
| 457 | >6.5 | >75 | <5 | >75 | 532 | >6.5 | >75 | >5 | >75 |
| 458 | <6.5 | <75 | <5 | <75 | 533 | <6.5 | <75 | <5 | <75 |
| 459 | <6.5 | >75 | <5 | >75 | 534 | <6.5 | <75 | <5 | >75 |
| 460 | >6.5 | >75 | <5 | >75 | 535 | <6.5 | >75 | >5 | <75 |
| 461 | <6.5 | >75 | <5 | >75 | 536 | <6.5 | <75 | <5 | <75 |
| 462 | >6.5 | >75 | <5 | >75 | 537 | >6.5 | >75 | >5 | >75 |
| 463 | >6.5 | >75 | >5 | >75 | 538 | >6.5 | <75 | >5 | <75 |
| 464 | >6.5 | <75 | <5 | <75 | 539 | >6.5 | >75 | >5 | <75 |
| 465 | >6.5 | >75 | >5 | >75 | 540 | <6.5 | <75 | <5 | <75 |
| 466 | <6.5 | >75 | <5 | >75 | 541 | <6.5 | <75 | <5 | <75 |
| 467 | >6.5 | >75 | >5 | >75 | 542 | >6.5 | <75 | >5 | <75 |
| 468 | >6.5 | >75 | >5 | >75 | 543 | >6.5 | <75 | <5 | <75 |
| 469 | >6.5 | >75 | >5 | >75 | 544 | <6.5 | <75 | <5 | <75 |
| 470 | <6.5 | >75 | <5 | >75 | 545 | >6.5 | >75 | >5 | >75 |
| 471 | >6.5 | >75 | >5 | >75 | 546 | <6.5 | <75 | <5 | <75 |
| 472 | >6.5 | >75 | >5 | >75 | 547 | >6.5 | >75 | >5 | >75 |
| 473 | >6.5 | >75 | >5 | >75 | 548 | <6.5 | >75 | <5 | <75 |
| 474 | <6.5 | >75 | <5 | >75 | 549 | >6.5 | >75 | >5 | >75 |
| 475 | >6.5 | >75 | >5 | <75 | 550 | <6.5 | >75 | >5 | >75 |
| 476 | >6.5 | >75 | >5 | <75 | 551 | >6.5 | >75 | >5 | >75 |
| 477 | >6.5 | >75 | >5 | <75 | 552 | <6.5 | <75 | <5 | <75 |
| 478 | <6.5 | <75 | <5 | <75 | 553 | <6.5 | >75 | >5 | >75 |
| 479 | <6.5 | <75 | <5 | <75 | 554 | >6.5 | >75 | >5 | >75 |
| 480 | >6.5 | >75 | >5 | >75 | 555 | <6.5 | >75 | >5 | >75 |
| 481 | <6.5 | >75 | <5 | <75 | 556 | >6.5 | >75 | >5 | >75 |
| 482 | >6.5 | <75 | <5 | >75 | 557 | <6.5 | >75 | >5 | >75 |
| 483 | <6.5 | >75 | <5 | <75 | 558 | >6.5 | >75 | >5 | >75 |
| 484 | >6.5 | >75 | >5 | <75 | 559 | >6.5 | >75 | >5 | >75 |
| 485 | >6.5 | >75 | <5 | >75 | 560 | >6.5 | >75 | >5 | >75 |
| 486 | >6.5 | >75 | <5 | >75 | 561 | >6.5 | >75 | >5 | >75 |
| 487 | <6.5 | >75 | >5 | >75 | 562 | >6.5 | >75 | >5 | >75 |
| 488 | >6.5 | <75 | >5 | >75 | 563 | >6.5 | >75 | >5 | <75 |
| 489 | >6.5 | >75 | >5 | >75 | 564 | >6.5 | >75 | >5 | >75 |

| Compound Number | hS1P1 cAMP pEC$_{50}$ | hS1P1 cAMP SPAN | hS1P1 B-arrestin2 pEC$_{50}$ | hS1P1 B-arrestin2 SPAN |
|---|---|---|---|---|
| 565 | >6.5 | >75 | >5 | >75 |
| 566 | <6.5 | <75 | <5 | <75 |
| 567 | <6.5 | >75 | <5 | <75 |
| 568 | >6.5 | >75 | >5 | >75 |
| 569 | <6.5 | >75 | <5 | <75 |
| 570 | <6.5 | <75 | <5 | <75 |
| 571 | >6.5 | >75 | >5 | <75 |
| 572 | <6.5 | <75 | <5 | <75 |
| 573 | <6.5 | <75 | <5 | <75 |
| 574 | <6.5 | >75 | <5 | <75 |
| 575 | >6.5 | >75 | >5 | >75 |
| 576 | >6.5 | >75 | >5 | <75 |
| 577 | <6.5 | <75 | <5 | <75 |
| 578 | <6.5 | >75 | <5 | <75 |
| 579 | >6.5 | >75 | >5 | >75 |
| 580 | >6.5 | >75 | >5 | >75 |
| 581 | <6.5 | >75 | <5 | <75 |
| 582 | <6.5 | >75 | <5 | <75 |
| 583 | <6.5 | <75 | <5 | <75 |
| 584 | >6.5 | >75 | >5 | >75 |
| 585 | >6.5 | >75 | >5 | >75 |
| 586 | >6.5 | >75 | >5 | >75 |
| 587 | <6.5 | <75 | <5 | <75 |
| 588 | <6.5 | <75 | <5 | <75 |
| 589 | <6.5 | <75 | <5 | >75 |
| 590 | <6.5 | <75 | <5 | <75 |
| 591 | >6.5 | <75 | >5 | >75 |
| 592 | <6.5 | <75 | <5 | >75 |
| 593 | >6.5 | >75 | >5 | >75 |
| 594 | >6.5 | >75 | >5 | >75 |
| 595 | >6.5 | >75 | >5 | >75 |
| 596 | >6.5 | <75 | >5 | >75 |
| 597 | >6.5 | >75 | >5 | >75 |
| 598 | >6.5 | >75 | >5 | >75 |
| 599 | >6.5 | <75 | >5 | >75 |
| 600 | >6.5 | >75 | >5 | >75 |
| 601 | >6.5 | >75 | >5 | <75 |
| 602 | <6.5 | <75 | <5 | >75 |
| 603 | >6.5 | >75 | >5 | >75 |
| 604 | >6.5 | >75 | >5 | >75 |
| 605 | >6.5 | >75 | >5 | >75 |
| 606 | >6.5 | >75 | >5 | >75 |
| 607 | >6.5 | >75 | >5 | >75 |
| 608 | >6.5 | >75 | >5 | >75 |
| 609 | <6.5 | <75 | <5 | <75 |
| 610 | >6.5 | >75 | >5 | >75 |
| 611 | >6.5 | >75 | >5 | >75 |
| 612 | >6.5 | <75 | >5 | >75 |
| 613 | <6.5 | <75 | <5 | >75 |
| 614 | >6.5 | >75 | <5 | >75 |
| 615 | >6.5 | >75 | >5 | >75 |
| 616 | >6.5 | >75 | >5 | >75 |
| 617 | <6.5 | <75 | <5 | >75 |
| 618 | >6.5 | >75 | >5 | >75 |
| 619 | >6.5 | >75 | >5 | >75 |
| 620 | >6.5 | >75 | >5 | >75 |
| 621 | >6.5 | <75 | <5 | >75 |
| 622 | >6.5 | >75 | <5 | >75 |
| 623 | <6.5 | >75 | <5 | >75 |
| 624 | <6.5 | >75 | <5 | >75 |
| 625 | <6.5 | <75 | <5 | >75 |
| 626 | <6.5 | <75 | <5 | >75 |
| 627 | <6.5 | >75 | <5 | >75 |
| 628 | >6.5 | >75 | >5 | >75 |
| 629 | <6.5 | >75 | <5 | <75 |
| 630 | <6.5 | <75 | <5 | <75 |
| 633 | <6.5 | <75 | <5 | <75 |
| 634 | <6.5 | <75 | <5 | <75 |
| 635 | >6.5 | <75 | >5 | <75 |
| 636 | >6.5 | >75 | >5 | <75 |
| 637 | >6.5 | >75 | >5 | >75 |
| 638 | >6.5 | <75 | <5 | <75 |
| 639 | <6.5 | <75 | <5 | <75 |
| 640 | >6.5 | >75 | <5 | <75 |
| 641 | <6.5 | <75 | <5 | <75 |
| 642 | <6.5 | <75 | <5 | <75 |
| 643 | <6.5 | >75 | <5 | <75 |
| 644 | <6.5 | >75 | <5 | >75 |
| 645 | <6.5 | >75 | <5 | <75 |
| 646 | <6.5 | <75 | <5 | >75 |
| 647 | >6.5 | >75 | >5 | >75 |

Example 3: S$_1$P$_1$ Receptor are Effective to Treat Chemotherapeutic Induced Peripheral Neuropathy Compounds were tested for efficacy in mouse models of chemotherapy induced peripheral neuropathy. The intraperitoneal (i.p.) injection of chemotherapeutics in rodents has been shown to induce sensory impairment and pain, similar to what is seen in humans where these sensations begin within days and last for several weeks. For these studies c57bl/6 mice are habituated to the test environment and baseline measurements of pain sensitivity are assessed. To determine mechanical responses, the threshold for responses to punctate mechanical stimuli (mechanical hyperalgesia) was tested according to the frequency method. In brief, the plantar surface of the animal hindpaw was stimulated with a single von Frey monofilament (0.4 g) for approximately 1-2 seconds. If there was a withdrawal response, it was recorded as a positive response. A response was defined as a lifting or shaking of the paw upon stimulation. This was repeated ten times for each mouse. The final measurement for each mouse is the % non-response to stimulation for the ten trials.

The % non-response to stimulation is converted to a % MPE. For paclitaxel induced peripheral neuropathy, a series of injections of PAC (6 mg/kg, i.p.) on days 1, 3, 5 and 7 is used to induce peripheral neuropathy. After approximately 14 days from the initiation of PAC injections, animals are re-assessed for mechanical sensitivity. Animals that exhibit a 50% response rate and lower can be included in studies with test compounds. On test day animals are dosed with compounds either subcutaneously or orally and tested for mechanical response by the frequency method either 30 min (s.c.) or 60 min (p.o.) after drug administration. Data is presented as a % MPE. For oxaliplatin induced peripheral neuropathy, a series of injections of OXA (4 mg/kg, i.p.) on days 1-5 is used to induce peripheral neuropathy. After approximately 14 days from the initiation of PAC injections, animals are re-assessed for mechanical sensitivity. Animals that exhibit a 50% response rate and lower can be included in studies with test compounds. On test day animals are dosed with compounds subcutaneously and tested for mechanical response by the frequency method 30 min after drug administration. Data is presented as a % MPE. One or more of the compounds show reversal of chemotherapeutic induced peripheral neuropathy.

A compound was tested for the ability to prevent the development of OXA induced peripheral neuropathy. A concurrent with the OXA injections on Day 1-5, a compound was dosed (3 mg/kg, sc) every day for 15 days. On Day 16 animals were tested for mechanical allodynia. Animals treated with a test compound did not exhibit peripheral neuropathy. The data for exemplary compounds is provided below.

Reversal of Allodynia Induced by Oxaliplatin in Mice

| Compound Number | Screen @ 3 mg/kg sc (% MPE) |
|---|---|
| 142 | >50 |
| 287 | >50 |
| 55 | >50 |
| 169 | >50 |

Reversal of Allodynia Induced by Paclitaxel in Mice (s.c.)
Compound Screen® 1 mg/kg se

| Compound Number | Screen @ 1 mg/kg sc (% MPE) |
|---|---|
| 293 | >50 |
| 287 | <50 |
| 99 | >50 |
| 55 | <50 |
| 142 | >50 |
| 8 | <50 |
| 169 | >50 |
| 96 | >50 |
| 277 | >50 |
| 142 | >50 |
| 103 | >50 |
| 177 | >50 |
| 26 | <50 |
| 252 | <50 |
| 304 | >50 |
| 221 | >50 |
| 33 | <50 |
| 149 | <50 |
| 263 | >50 |
| 147 | >50 |
| 212 | >50 |
| 267 | >50 |
| 262 | >50 |
| 305 | >50 |
| 224 | >50 |
| 179 | >50 |
| 185 | >50 |
| 106 | <50 |
| 306 | <50 |
| 259 | <50 |
| 107 | <50 |
| 210 | <50 |

Reversal of Allodynia Induced by paclitaxel in Mice(p.o.)

| Compound Number | Screen @ 3 mg/kg po (% MPE) |
|---|---|
| 26 | <50 |
| 99 | >50 |
| 103 | >50 |
| 142 | >50 |
| 179 | >50 |
| 262 | >50 |
| 263 | >50 |
| 348 | >50 |
| 354 | >50 |
| 355 | >50 |
| 356 | >50 |
| 358 | >50 |
| 359 | >50 |
| 415 | <50 |
| 423 | >50 |
| 435 | >50 |
| 442 | >50 |
| 455 | >50 |
| 469 | >50 |
| 471 | <50 |
| 472 | >50 |
| 489 | >50 |
| 497 | <50 |
| 502 | >50 |
| 513 | <50 |
| 514 | >50 |
| 519 | <50 |
| 520 | >50 |
| 531 | >50 |
| 547 | >50 |
| 558 | >50 |
| 560 | >50 |
| 562 | >50 |
| 563 | <50 |
| 564 | >50 |
| 568 | <50 |
| 579 | >50 |
| 580 | >50 |
| 584 | >50 |
| 585 | <50 |
| 586 | <50 |
| 598 | <50 |
| 600 | <50 |
| 606 | >50 |
| 607 | >50 |
| 608 | <50 |
| 615 | >50 |
| 636 | <50 |
| 637 | >50 |
| 726 | >50 |
| 727 | >50 |
| 728 | >50 |
| 729 | >50 |
| 730 | >50 |
| 731 | >50 |
| 732 | >50 |
| 733 | >50 |
| 734 | >50 |
| 735 | <50 |
| 736 | >50 |

Example 4: The $S_1P_1$ Receptor Compounds can be Used to Treat Inflammation and Pain Assessment of Tactile Allodynia Produced by Intraplantar Freund's Complete Adjuvant in Rats:

Animals were acclimated to the vivarium for at least 48 hr prior to behavioral testing. Inflammation was induced with the administration of an intraplantar (subcutaneous injection into the plantar surface of the hind paw, i.pl.) injection of 0.10 ml Freund's Complete Adjuvant (FCA).

The experiments were conducted 24 hours after CFA administration. Rats are tested for mechanical allodynia in a Randall-Selitto apparatus. The inflamed paw is put on a pedestal and a pointed force of increasing intensity (0 to 250 grams) is applied to the paw. When the animal struggles to withdraw from the force the test is stopped and the force to induce that struggle is recorded. Data is presented as mean grams of force to withdrawal or a percentage of the maximum possible effect.

Exemplary Compounds in the CFA Model are Shown Below.

| Compound Number | Active Doses, mg/kg sc (>50% MPE) |
|---|---|
| 103 | ≥0.03 |
| 293 | ≥0.1 |
| 142 | ≥0.1 |
| 26 | ≥0.1 |
| 212 | ≥0.1 |
| 469 | ≥0.01 |

Example 5: Compounds Selective for $S_1P_1$ Receptor

In Vitro Selectivity Assays

Stable clonal Chinese hamster ovary K1 (CHO-K1) cells co-expressing EA-β-arrestin2 and the human sphingosine-1-phosphate receptor 2 (NM_004230.3, $S_1P_2$), human sphingosine-1-phosphate receptor 3 (NM_005226, $S_1P_3$) and sphingosine-1-phosphate receptor 5 (NM_001166215.1, $S_1P_5$) with a C-terminal Prolink™ tag were purchased from DiscoverX corporation (S1P2: Cat #93-0256C2, S1P3: Cat #93-0217C2, S1P5: Cat #93-0583C2).

Cell Culturing and Assay Plating

Cell lines were cultured in AssayComplete™ Media 6 (DiscoverX Corporation, Cat #: 920018GF2) at 37° C. and 5% $CO_2$ in a humidified $CO_2$ and temperature-controlled incubator. To begin assay plating, cells were washed with dulbecco's phosphate buffered saline (CellGro, Cat #: 21-031-CV) and lifted from the culturing flask by incubation (37° C., 5 min) with CellStripper (Cellgro, Cat #: 25-056-CI). Lifted cells were resuspended to 250,000 cells per milliliter in either AssayComplete™ Cell Plating 11 Reagent (S1P5 cell line) (DiscoverX Corporation, Cat #: 93-0563R11B) or AssayComplete™ Cell Plating 2 Reagent (S1P2 and S1P3 cell line) (DiscoverX Corporation, Cat #: 93-0563R2B) and plated at 5000 cells per well (S1P3 cell line) or 7500 cells per well (S1P2 and $S_1P_5$ cell line) in white-opaque 384 well plates (Greiner Bio-One Item #: 20-784080). Plated cells were incubated overnight at 37° C. and 5% $CO_2$ in a humidified $CO_2$ and temperature-controlled incubator.

Detecting Inhibition of cAMP Production $S_1P_3$ and $S_1P_5$ Agonist-promoted G-protein responses were determined by measuring changes in intracellular cAMP using the HTRF® cAMP HiRange kit (CisBio, Cat #: 62AM6PEJ) based on time-resolved fluorescence resonance energy transfer (TR-FRET) technology. AssayComplete™ Cell Plating 11 Reagent was removed and replaced with Ham's F-12 (CellGro, Cat #: 10-080-CM) containing isobutyl-methyl-xanthine (IBMX; 500 µM; Tocris Bioscience, Cat #: 2845), and NKH-477 (1.5 µM; Tocris Bioscience, Cat #: 1603) along with test or control compounds at the desired concentrations. Following a 30-minute room temperature incubation the components of the cAMP HiRange kit were added as per the manufacturer's instructions. After an hour incubation at room temperature, plates were analyzed by a BMG PheraStar microplate reader. Responses were measured as the ratio of signal over background, fluorescence emission at 665 nm to fluorescence emission at 620 nm.

Detecting inositol monophosphate production

S1P2 Agonist-promoted G-protein responses were determined by measuring changes in intracellular inositol monophosphate using the IP-one TB kit (CisBio, Cat #: 62IPA-PEJ) based on time-resolved fluorescence resonance energy transfer (TR-FRET) technology. AssayComplete™ Cell Plating 2 Reagent was removed and replaced with 1× IP-one stimulation buffer (as per manufacturer's instructions) along with test or control compounds at the desired concentrations. Following a 60-minute incubation at 37° C. and 5% $CO_2$ in a humidified $CO_2$ and temperature-controlled incubator, the components of the IP-one TB kit were added as per the manufacturer's instructions. After an hour incubation at room temperature, plates were analyzed by a BMG PheraStar microplate reader. Responses were measured as the ratio of signal over background, fluorescence emission at 665 nm to fluorescence emission at 620 nm.

Activity Table

The compounds were able to modulate the activities (inhibition of cAMP production or accumulation of inositol monophosphate) of the sphingosine-1-phosphate 2, sphingosine-1-phosphate 3, sphingosine-1-phosphate 5 receptor as indicated herein. The tables below include the efficacy of the compound as compared to a positive control, referred to as "SPAN". These values are normalized to fingolimod, a known agonist of the sphingosine-1-phosphate 3 and 5 receptor or CYM5520, a known agonist of the sphingosine-1-phosphate 2 receptor. The tables also include potency values (pEC50) for modulating discrete receptor-mediated activities (inhibition of cAMP production or inositol monophosphate accumulation). This value represents the estimated concentration to promote half of the maximal efficacy (or SPAN) observed for each compound. Exemplary compounds that were found to be selective are shown below.

| Compound number | hS1P2 IP-one $pEC_{50}$ | hS1P2 IP-one SPAN | hS1P3 cAMP $pEC_{50}$ | hS1P3 cAMP SPAN | hS1P5 cAMP $pEC_{50}$ | hS1P5 cAMP SPAN |
|---|---|---|---|---|---|---|
| 22 | >5.0 | <50 | <5.0 | <50 | >5.0 | <50 |
| 26 | <5.0 | <50 | <5.0 | <50 | <5.0 | <50 |
| 32 | <5.0 | <50 | <5.0 | <50 | <5.0 | <50 |
| 99 | <5.0 | <50 | <5.0 | <50 | <5.0 | >50 |
| 103 | <5.0 | <50 | <5.0 | <50 | <5.0 | <50 |
| 141 | <5.0 | <50 | >5.0 | >50 | >5.0 | >50 |
| 147 | <5.0 | <50 | <5.0 | <50 | >5.0 | <50 |
| 149 | <5.0 | <50 | >5.0 | >50 | >5.0 | >50 |
| 152 | <5.0 | <50 | <5.0 | <50 | <5.0 | <50 |
| 177 | <5.0 | <50 | >5.0 | >50 | >5.0 | >50 |
| 185 | <5.0 | <50 | <5.0 | <50 | <5.0 | >50 |
| 212 | <5.0 | <50 | <5.0 | <50 | <5.0 | <50 |
| 219 | >5.0 | <50 | <5.0 | <50 | <5.0 | <50 |
| 221 | <5.0 | <50 | >5.0 | <50 | >5.0 | <50 |
| 252 | >5.0 | <50 | >5.0 | <50 | >5.0 | >50 |
| 259 | <5.0 | <50 | <5.0 | <50 | <5.0 | <50 |
| 262 | <5.0 | >50 | <5.0 | <50 | <5.0 | <50 |
| 263 | <5.0 | <50 | <5.0 | <50 | <5.0 | <50 |
| 267 | <5.0 | <50 | <5.0 | <50 | <5.0 | <50 |
| 277 | <5.0 | >50 | <5.0 | <50 | <5.0 | <50 |
| 287 | <5.0 | <50 | <5.0 | <50 | <5.0 | <50 |
| 293 | <5.0 | <50 | <5.0 | <50 | <5.0 | >50 |
| 304 | <5.0 | <50 | >5.0 | <50 | <5.0 | <50 |
| 391 | >5.0 | <50 | >5.0 | >50 | >5.0 | <50 |
| 398 | <5.0 | <50 | <5.0 | <50 | <5.0 | <50 |
| 406 | <5.0 | <50 | <5.0 | <50 | <5.0 | <50 |
| 417 | >5.0 | <50 | <5.0 | <50 | <5.0 | <50 |
| 422 | >5.0 | <50 | >5.0 | <50 | | |
| 423 | >5.0 | <50 | >5.0 | <50 | | |
| 445 | >5.0 | <50 | <5.0 | <50 | | |
| 455 | <5.0 | <50 | <5.0 | <50 | | |
| 496 | <5.0 | <50 | <5.0 | <50 | | |

Thus, the compounds were found to be sufficiently selective for S1P1.

Example 6: The $S_1P_1$ Receptor Compounds can be Used to Treat Diabetic Neuropathy Assessment of Tactile Allodynia and Thermal Hyperalgesia in a Rodent Model of Diabetic Neuropathy-Streptozotocin-Induced (STZ)

A cohort of 48 male Sprague Dawley rats, weighing 225-250 g at arrival, was group housed under constant temperature, humidity and a 12-hour light-dark cycle. Following acclimation to the animal colony, the animals were tested for baseline withdrawal responses to mechanical allodynia and thermal hyperalgesia using the methods described below in Chaplan, S. R., Bach, F. W., Pogrel, J. W., Chung, J. M. and Yaksh, T. L. Quantitative assessment of tactile allodynia in the rat paw. J. Neurosci. Methods 53: 55-63, 1994; Joris, J. L., Dubner, R. and Hargreaves, K. M. Opioid analgesia at Peripheral Sites: a Target for Opioids Released during Stress and Inflammation? Anesthesia and Analgesia 66(12), 1277-81, 1987; and Morrow, T. J. Animal Models of Painful Diabetic Neuropathy: The STZ rat model. Current Protocols in Neuroscience, November; Chapter 9, Unit 9.18, 2004..

A diabetic-like state was induced with a single intraperitoneal (IP) injection of streptozotocin STZ (50 mg/kg) freshly dissolved in 10 mM citric acid buffer was injected intraperitoneally (IP) on Day 1. Two days later (on Day 3), hyperglycermia was confirmed by existence of blood glucose >350 mg/dL as measured by glucometer, and the animal health was monitored biweekly for 12 days.

For measures of mechanical allodynia, rats were preselected for experimentation only if the pain threshold 7-14 days after STZ injection (pre-treatment) was reduced by 10 grams of force relative to the response of the individual paw before STZ challenge (pre-induction), namely, with clear presence of allodynia. The rats were randomized based on pre-dose mechanical allodynia scores to balanced treatment groups. The animals were tested prior to study inclusion for mechanical allodynia by the manual von Frey test on Day 20 (Chaplan up/down method using von Frey filaments on the plantar surface of the paw). The manual von Frey test was repeated at 0.5 or 1 hr following administrations of test articles, vehicle, and reference compound via the specified route(s) and on Day 21 post-surgery.

For measures of thermal hyperalgesia, rats were preselected for experimentation only if the pain threshold 7-14 days after STZ injection (pre-treatment) was reduced by 75% relative to the response of the individual paw before STZ challenge (pre-induction), namely, with clear presence of hyperalgesia. The rats were randomized based on pre-dose thermal hyperalgesia scores to balanced treatment groups. Rats were preselected (with clear presence of thermal hyperalgesia) on Day 20. Thermal hyperalgesia was measured at 1 or 1.5 hr after dosing of test articles, vehicle, and reference compound via the specified route(s) on Day 21. Each rat was placed within a plastic box atop a glass floor for 20 to 30 minutes. A light beam under the floor was aimed at the plantar surface of the left hind paw. The time was measured automatically when the paw was withdrawn away from the thermal stimulus. A cut-off latency of 23 sec was imposed. The latency to withdrawal was obtained for each rat and defined as the heat pain threshold.

Mean thresholds and withdrawal latencies were analyzed via Two Way ANOVA followed by Dunnett's Multiple Comparison tests to STZ+VEH group with differences considered significant at $p<0.05$.

Exemplary compounds, but not limited to these, that were effective in this animal model are described below. For example, compounds 103 and 293 were tested and found to have active doses between 50 and 100 mg/kg in both mechanical allodynia and thermal hyperalgesia.

| Compound # | Active Doses in STZ Diabetic Neuropathy Model (mg/kg, po) ($p < 0.05$ compared to STZ + VEH treated mice) MECHANICAL | Active Doses in STZ Diabetic Neuropathy Model (mg/kg, po) ($p < 0.05$ compared to STZ + VEH treated mice) THERMAL |
|---|---|---|
| 103 | <100 | <100 |
| 293 | <100 | <100 |
| 469 | <100 | <100 |

Example 7: The $S_1P_1$ Receptor Compounds Can Be Used To Treat Peripheral Neuropathy Assessment of Tactile Allodynia and Thermal Hyperalgesia in a Rodent Model of Peripheral Neuropathy-Spinal Nerve Ligation (SNL)

A cohort of 48 male Sprague Dawley rats, weighing 225-250 g at arrival, was group housed under constant temperature, humidity and a 12-hour light-dark cycle. Following acclimation to the animal colony, the animals were tested for baseline withdrawal responses to mechanical allodynia and thermal hyperalgesia using the methods described in. Chaplan, S. R., Bach, F. W., Pogrel, J. W., Chung, J. M. and Yaksh, T. L. Quantitative assessment of tactile allodynia in the rat paw. J. Neurosci. Methods 53: 55-63, 1994; Joris, J. L., Dubner, R. and Hargreaves, K. M. Opioid analgesia at Peripheral Sites: a Target for Opioids Released during Stress and Inflammation? Anesthesia and Analgesia 66(12), 1277-81, 1987; and Kim, S. H. and Chung, J. M. An experimental model of peripheral neuropathy produced by segmental spinal nerve ligation in the rat. Pain 50: 335-63, 1992.

Animals (n=40) were anesthetized with an intraperitoneal (IP) injection of Pentobarbital (50 mg/kg). Spinal nerve ligation (SNL) was performed by first separating the left paraspinal muscles from the spinous processes (L4- S2). The L6-S1 facet joint was nipped. The transverse process of L6 was removed to identify the locations of the L5 and L6 spinal nerve. The left L5 and L6 spinal nerves were isolated and tightly ligated with 6.0 silk sutures. Another 8 animals were underwent sham surgery only (anesthesia, surgical opening and skin suture).

For measures of mechanical allodynia, rats were preselected for experimentation only if the pain threshold 7-14 days after SNL surgery (pre-treatment) was reduced by 10 grams of force relative to the response of the individual paw before surgery (pre-induction), namely, with clear presence of allodynia. The rats were randomized based on pre-dose mechanical allodynia scores to balanced treatment groups. The animals were tested prior to study inclusion for mechanical allodynia by the manual von Frey test on Day 20 (Chaplan up/down method using von Frey filaments on the plantar surface of the paw). The manual von Frey test was repeated at 0.5 or 1 hr following administrations of test articles, vehicle, and reference compound via the specified route(s) and on Day 21 post-surgery.

For measures of thermal hyperalgesia, rats were pre-selected for experimentation only if the pain threshold 7-14 days after spinal surgery (pre-treatment) was reduced by 75% relative to the response of the individual paw before surgery (pre-induction), namely, with clear presence of hyperalgesia. The rats were randomized based on pre-dose thermal hyperalgesia scores to balanced treatment groups. Rats were preselected (with clear presence of thermal hyperalgesia) on Day 20. Thermal hyperalgesia was measured at 1 or 1.5 hr after dosing of test articles, vehicle, and reference compound via the specified route(s) on Day 21. Each rat was placed within a plastic box atop a glass floor for 20 to 30 minutes. A light beam under the floor was aimed at the plantar surface of the left hind paw. The time was measured automatically when the paw was withdrawn away from the thermal stimulus. A cut-off latency of 23 sec was imposed. The latency to withdrawal was obtained for each rat and defined as the heat pain threshold.

Mean thresholds and withdrawal latencies were analyzed via Two Way ANOVA followed by Dunnett's Multiple Comparison tests to SNL+VEH group with differences considered significant at $p<0.05$.

Exemplary compounds, but not limited to these, that were effective in this animal model are described below. For example, compound 103 was tested and found to have active doses between 50 and 100 mg/kg.

| Compound # | Active Doses in SNL Neuropathy Model (mg/kg) ($p < 0.05$ compared to SNL + VEH treated mice) MECHANICAL | Active Doses in SNL Neuropathy Model (mg/kg) ($p < 0.05$ compared to SNL + VEH treated mice) THERMAL |
|---|---|---|
| 103 | <100 | <100 |

Example 8: Compounds do not Inhibit hERG Channel Activity

The standard Automated Qpatch patch-clamp assay have been used and the selective hERG inhibitor E4031, serves as a positive control.

| Compound number | $IC_{50}$ ($\mu M$) |
|---|---|
| E4031 | 0.013 |
| 26 | >10 |
| 304 | >10 |
| 469 | >10 |
| 497 | >10 |
| 520 | >10 |
| 730 | >10 |
| 738 | >10 |
| 742 | >10 |
| 743 | >10 |
| 744 | >10 |

Example 9: Compounds do not Cause Lymphopenia

Compounds were tested for changes in peripheral blood lymphocytes in c57bl/6 mice. In acute studies, animals (n=5/group) were dosed subcutaneously with test compound at a dose of 3 mg/kg. Animals were sacrificed at specific time points and 500 µl of whole blood was collected in EDTA (K2) Eppendorf tubes. Blood was stored on ice and shipped immediately overnight delivery to Charles River Laboratories for analysis. CRL ran samples through their WBC/differential panel on an Advia 120 instrument. We received peripheral lymphocyte counts ($10^3$ cells/µl) for each blood sample. Treatment group means were compared to a vehicle treatment group for statistical significance. In chronic studies, animals (n=6-8/group) were dosed subcutaneously with test compound either in a dose response paradigm (highest dose of 3 mg/kg) or in a screening paradigm at 6 mg/kg for seven days. On the seventh day, animals were sacrificed 45 minutes after the final dose. Whole blood was collected and analyzed as described for acute studies. None of the compounds showed statistically significant decreases in peripheral blood lymphocytes in acute or chronic studies. Non-limiting exemplary data is provided below.

Lymphopenia —c57bl/6 Mice

| Compound Number | Effect and Doses, mg/kg, sc |
|---|---|
| 8 | no change: 6 mg/kg, 7 days |
| 19 | no change: 6 mg/kg, 7 days |
| 22 | no change: 3 mg/kg, 7 days |
| 32 | no change: 6 mg/kg, 7 days |
| 55 | no change: 6 mg/kg, 7 days |
| 59 | no change: 6 mg/kg, 7 days |
| 96 | no change: 6 mg/kg, 7 days |
| 99 | no change: 6 mg/kg, 7 days |
| 103 | no change: 6 mg/kg, 7 days |
| 142 | no change: 6 mg/kg, 7 days |
| 147 | no change: 6 mg/kg, 7 days |
| 169 | no change: 6 mg/kg, 7 days |
| 234 | no change: 6 mg/kg, 7 days |
| 287 | no change: 6 mg/kg, 7 days |
| 293 | no change: 6 mg/kg, 7 days |
| 304 | no change: 6 mg/kg, 7 days |
| 355 | no change: 6 mg/kg, 7 days |
| 356 | no change: 6 mg/kg, 7 days |
| 384 | no change: 3 mg/kg; 45 min and 2 hr |
| 423 | no change: 6 mg/kg, 7 days |
| 455 | no change: 6 mg/kg, 7 days |
| 469 | −28% not stat sig: 6 mg/kg, 7 days |
| 520 | no change: 6 mg/kg, 7 days |
| 531 | no change: 6 mg/kg, 7 days |
| 730 | no change: 6 mg/kg, 7 days |
| 731 | −78% stat sig: 6 mg/kg, 7 days |
| 737 | −40% not stat sig: 6 mg/kg, 7 days |

Example 10: Compounds Inhibit Tumor Growth and Prolong Survival in Tumor Model Female athymic nude mice (Crl:NU(NCr)-Foxnlnu, Charles River Laboratories) were implanted with A2780 human ovarian carcinoma cells to initiate tumor growth.

Each mouse received $1\times10_7$ cells (0.1 mL cell suspension) subcutaneously in the right flank, and tumors were monitored as their volumes approached the target range of 100 to 150 $mm_3$. Fourteen days later, designated as Day 1 of the study, mice were sorted into six groups of ten each. The individual tumor volumes ranged from 108 to 196 $mm_3$ and group mean tumor volumes were 148 $mm_3$. Tumors were measured twice weekly for the study duration.

Paclitaxel dosing solutions were prepared in 5% ethanol, 5% Cremophor EL in $D_5W$ (Vehicle 1). Ozanimod and Compound 103 dosing solutions were prepared in 10% dimethylacetamide, 10% Cremophor EL, 80% sterile water with 10% β-cyclodextrin (Vehicle 2). Starting on Day 1 of the study, six groups (n=10) of female athymic nude mice with established A2780 tumors were treated according to the following plan. Treatments were administered either by intravenous injection (i.v.) or oral gavage (p.o.) and were adjusted to the body weight of the individual animal. Group 1 received Vehicle 1, i.v., once every other day for five doses (qod×5) and Vehicle 2, p.o., once daily to the end of the study (qd to end), and served as the control group for efficacy analysis. Group 2, the paclitaxel monotherapy group, received paclitaxel i.v., qod×5 plus Vehicle 2, p.o., qd to end. Group 3, the ozanimod monotherapy group, received ozanimod p.o., qd to end plus Vehicle 1, i.v., qod×5. Combination Group 4 received ozanimod p.o., qd to end plus paclitaxel i.v., qod×5. Group 5, the Compound 103 monotherapy group, received Compound 103 p.o., qd to end plus Vehicle 1, i.v., qod×5. Combination Group 6 received Compound 103 p.o., qd to end plus paclitaxel i.v., qod×5.

Animals were monitored individually, and each mouse was euthanized when its tumor reached the endpoint volume of 2000 mm$_3$ or on the final day, whichever came first. The time to endpoint (TTE) was calculated for each mouse. Treatment outcome was determined from percent tumor growth delay (% TGD), defined as the percent increase in median TTE for treated versus control mice, with differences in TTE values between groups deemed statistically significant at $P<0.05$ using logrank survival analysis. Mice were also monitored for complete regression (CR) and partial regression (PR) responses. An animal with a CR at the end of the study was additionally classified as a tumor-free survivor (TFS). Treatment tolerability was assessed by body weight measurements and frequent observation for clinical signs of treatment-related side effects.

All regimens were acceptably-tolerated based. Control tumors exhibited progressive growth, attaining the 2000 mm$_3$ endpoint in a median 9.8 days, establishing a maximum possible TGD of 50.2 days (512%) for the 60-day study. Paclitaxel as monotherapy provided significant ($P<0.001$) survival benefit (128% TGD) compared to controls, whereas the ozanimod and Compound 103 monotherapy regimens were associated with non-significant ($P>0.05$) TGD of 31% and 15%, respectively, compared with the control. One animal receiving Compound 103 monotherapy survived the study with a sub-endpoint tumor. The combination of paclitaxel and ozanimod was associated with 185% TGD, providing statistically significant survival benefit over either of the corresponding monotherapies, and one study survivor with a CR/TFS tumor regression response. The combination of paclitaxel and Compound 103 provided 193% TGD, a significant result compared with paclitaxel monotherapy, but not statistically different ($P>0.05$) from the result for ozanimod monotherapy.

SUMMARY

The present example evaluated test agents ozanimod and Compound 103 each in combination with paclitaxel for efficacy in the A2780 human ovarian carcinoma model in female athymic mice. All regimens were acceptably-tolerated. Control tumors exhibited progressive growth, attaining the 2000 mm$_3$ endpoint in a median 9.8 days, establishing a maximum possible TGD of 50.2 days (512%) for the 60-day study. Paclitaxel as monotherapy provided significant ($P<0.05$) survival benefit (128% TGD) compared to controls, whereas the ozanimod and Compound 103 monotherapy regimens were associated with non-significant ($P>0.05$) TGD of 31% and 15%, respectively, compared with the control. One animal receiving Compound 103 monotherapy survived the study with a sub-endpoint tumor. The combination of paclitaxel and ozanimod was associated with 185% TGD, providing statistically significant survival benefit over either of the corresponding monotherapies, and one study survivor with a CR/TFS tumor regression response. The combination of paclitaxel and Compound 103 provided 193% TGD, a significant result compared with paclitaxel monotherapy and more than additive as compared with the corresponding monotherapies..

Thus, these results demonstrate that the compounds provided herein can be used to treat cancers, such as breast or ovarian cancer.

The examples and data provided herein demonstrate the unexpected properties and advantages of the compounds and pharmaceutical compositions provided herein. These properties could not have been predicted.

What is claimed is:
1. A compound having the formula of:

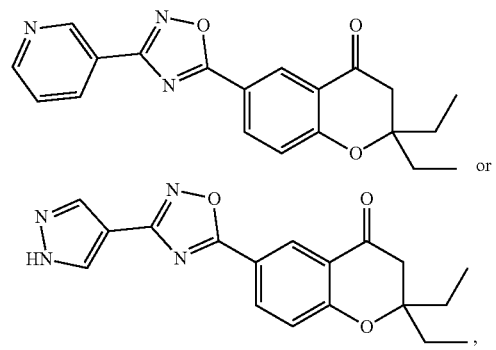

or a pharmaceutically acceptable salt thereof.

2. A pharmaceutical composition comprising a compound of claim 1, or a pharmaceutically acceptable salt thereof.

3. A method of ameliorating neuropathy, chemotherapy induced neuropathic pain, chemotherapy induced peripheral neuropathy, diabetic neuropathy or pain associated with diabetic neuropathy in a subject in need thereof, the method comprising administering to the subject a compound of claim 1 or a pharmaceutically acceptable salt thereof, or a pharmaceutical composition thereof.

4. The compound of claim 1 having the formula of:

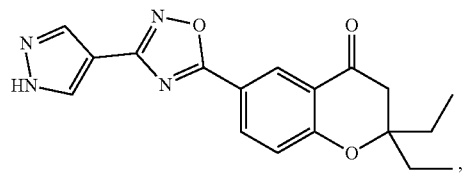 [SMILES: CCC1(CC)CC(=O)c2cc(-c3nc(-c4cn[nH]c4)no3)ccc2O1]

or a pharmaceutically acceptable salt thereof.

5. A pharmaceutical composition comprising a compound of claim 4, or a pharmaceutically acceptable salt thereof.

6. A method of ameliorating chemotherapy induced neuropathic pain in a subject in need thereof, the method comprising administering to the subject a compound of claim 1 or a pharmaceutically acceptable salt thereof, or a pharmaceutical composition thereof.

7. A method of ameliorating chemotherapy induced neuropathic pain in a subject in need thereof, the method comprising administering to the subject a compound of claim 4 or a pharmaceutically acceptable salt thereof, or a pharmaceutical composition thereof.

8. A method of ameliorating neuropathy, chemotherapy induced neuropathic pain, chemotherapy induced peripheral neuropathy, diabetic neuropathy or pain associated with diabetic neuropathy in a subject in need thereof, the method comprising administering to the subject a compound of claim 4 or a pharmaceutically acceptable salt thereof, or a pharmaceutical composition thereof.

* * * * *